United States Patent
Duffy et al.

(10) Patent No.: US 12,098,141 B2
(45) Date of Patent: Sep. 24, 2024

(54) BICYCLIC INDAZOLE GLUCOCORTICOID RECEPTOR ANTAGONISTS

(71) Applicant: Corcept Therapeutics Incorporated, Menlo Park, CA (US)

(72) Inventors: Lorna Duffy, Nottingham (GB); Thomas Hornsby, Nottingham (GB); Morgan Jouanneau, Nottingham (GB); Mark Mills, Nottingham (GB); Andrew William Phillips, Nottingham (GB); Andrew James Smith, Nottingham (GB); Hazel Joan Hunt, West Sussex (GB); Peter Hunt, West Sussex (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

(21) Appl. No.: 18/068,857

(22) Filed: Dec. 20, 2022

(65) Prior Publication Data
US 2023/0242514 A1  Aug. 3, 2023

Related U.S. Application Data

(60) Provisional application No. 63/368,409, filed on Jul. 14, 2022, provisional application No. 63/292,089, filed on Dec. 21, 2021.

(51) Int. Cl.
C07D 403/04 (2006.01)
C07D 401/14 (2006.01)

(52) U.S. Cl.
CPC ......... *C07D 403/04* (2013.01); *C07D 401/14* (2013.01)

(58) Field of Classification Search
CPC .... A61K 31/4155; A61P 37/06; C07K 16/241
See application file for complete search history.

(56) References Cited

U.S. PATENT DOCUMENTS

| | | | |
|---|---|---|---|
| 7,238,696 B2 | 7/2007 | Bernotas | |
| 7,678,813 B2 | 3/2010 | Clark et al. | |
| 7,928,237 B2 | 4/2011 | Clark et al. | |
| 8,324,203 B2 | 12/2012 | Clark et al. | |
| 8,557,839 B2 | 10/2013 | Williams et al. | |
| 8,598,154 B2 | 12/2013 | Clark et al. | |
| 8,658,637 B2 | 2/2014 | Kuzmich | |
| 8,859,774 B2 | 10/2014 | Hunt et al. | |
| 9,273,047 B2 | 3/2016 | Hunt et al. | |
| 9,707,223 B2 | 7/2017 | Hunt et al. | |
| 9,956,216 B2 | 5/2018 | Hunt et al. | |
| 10,047,082 B2 | 8/2018 | Hunt et al. | |
| 10,323,034 B2 | 6/2019 | Hunt et al. | |
| 10,456,392 B2 | 10/2019 | Hunt et al. | |
| 10,464,927 B2 | 11/2019 | Zheng | |
| 10,787,449 B2 | 9/2020 | Hunt et al. | |
| 10,793,576 B2 | 10/2020 | Li | |
| 10,973,813 B2 | 4/2021 | Hunt et al. | |
| 11,370,789 B2 | 6/2022 | Hunt et al. | |
| 11,787,780 B2 | 10/2023 | Hunt | |
| 2004/0138286 A1 | 7/2004 | Imazaki et al. | |
| 2007/0142438 A1 | 6/2007 | Arista | |
| 2011/0021556 A1 | 1/2011 | Lucas et al. | |
| 2012/0165320 A1 | 6/2012 | Jain | |
| 2015/0291604 A1 | 12/2015 | Chen | |
| 2018/0093991 A1 | 4/2018 | Thompson et al. | |
| 2018/0228776 A1 | 8/2018 | Saitoh et al. | |
| 2019/0016721 A1 | 1/2019 | Chen et al. | |
| 2019/0185470 A1* | 6/2019 | Jakob | C07D 401/14 |
| 2021/0169872 A1 | 6/2021 | Hunt et al. | |
| 2021/0369701 A1 | 12/2021 | Hunt et al. | |
| 2023/0032612 A1 | 2/2023 | Hunt et al. | |
| 2023/0192666 A1 | 6/2023 | Mills | |

FOREIGN PATENT DOCUMENTS

| | | |
|---|---|---|
| WO | 2019121611 | 6/2019 |
| WO | 2020254552 A2 | 12/2020 |
| WO | 2021262587 | 12/2021 |
| WO | 2022072512 A1 | 4/2022 |
| WO | 2023122600 | 6/2022 |

OTHER PUBLICATIONS

Clark et al. (Feb. 15, 2008) "1H-Pyrazolo[3,4-g]Hexahydro-Isoguinolines as Selective Glucocorticoid Receptor Antagonists with High Functional Activity", Bioorganic & Medicinal Chemistry Letters, 18(4):1312-1317.
Clark et al. (Nov. 2007) "2-benzenesulfonyl-8a-benzyl-hexahydro-2h-isoquinolin-6-ones as Selective Glucocorticoid Receptor Antagonists", Bioorganic & Medicinal Chemistry Letters, 17(20):5704-5708.
Hunt et al. (2015) "1H-Pyrazolo[3,4-g]hexahydro-isoquinolines as Potent GR antagonists with Reduced hERG Inhibition and an Improved Pharmacokinetic Profile", Bioorganic & Medicinal Chemistry Letters, 25(24):5720-5725.
Hunt et al. (Apr. 27, 2017) "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]Isoquinolin-4a-yl)(4-(Trifluoromethyl)Pyridin-2-yl)Methanone (CORT125134): A Selective Glucocorticoid Receptor", Journal of Medicinal Chemistry, 60(8):3405-3421.
"International Search Report and Written Opinion for PCT/US2021/038218", mailed on Oct. 12, 2021, 10 Pages.

(Continued)

*Primary Examiner* — Matthew P Coughlin
*Assistant Examiner* — Meghan C Heasley
(74) *Attorney, Agent, or Firm* — Mintz, Levin, Cohn, Ferris, Glovsky and Popeo, P.C.

(57) ABSTRACT

The present disclosure provides compounds of Formula I, Ia, Ib, Ib-1, Ib-2, Ic, Ic-1, Id-1, and Id-2. Compounds of Formula I, Ia, Ib, Ib-1, Ib-2, Ic, Ic-1, Id-1, and Id-2 may be used in pharmaceutical formulations, and may be used for modulating glucocorticoid receptors.

27 Claims, No Drawings

(56) References Cited

OTHER PUBLICATIONS

Zhang et al., "Recent Advances in Indazole-Containing Derivatives: Synthesis and Biological Perspectives", Molecules 2018, 23(11):2783.
Clark et al., "Glucocorticoid Receptor Antagonists", Curr Top Med Chem 2008; 8(9), 813-838.
International Search Report and Written Opinion for PCT/US2022/082027, mailed Apr. 17, 2023, 14 pages.
International Search Report and Written Opinion for PCT/US2022/082034, mailed Apr. 26, 2023, 12 pages.

* cited by examiner

BICYCLIC INDAZOLE GLUCOCORTICOID RECEPTOR ANTAGONISTS

CROSS-REFERENCES TO RELATED APPLICATIONS

This application claims priority to U.S. Provisional Application Nos. 63/368,409, filed Jul. 14, 2022, and 63/292,089, filed Dec. 21, 2021, each of which is incorporated herein in its entirety for all purposes.

BACKGROUND OF THE INVENTION

In most species, including man, the physiological glucocorticoid is cortisol (hydrocortisone). In rodents, the physiological glucocorticoid is corticosterone. Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) Annu. Rev. Med. 48:129).

Cortisol (and corticosterone) also bind to the mineralocorticoid receptor, MR. Cortisol has higher affinity for MR than it does for GR, and MR is usually considered to be fully occupied under normal physiological conditions. Under conditions of stress, cortisol concentrations are increased and GR becomes occupied. MR also binds to the mineralocorticoid aldosterone, and aldosterone and cortisol have similar affinity for MR. However, glucocorticoids circulate at roughly 100 times the level of mineralocorticoids. An enzyme (11-β hydroxsteroid dehydrogenase 1), which deactivates cortisol (and corticosterone) exists in mineralocorticoid target tissues to prevent overstimulation by glucocorticoids.

When administered to subjects in need thereof, steroids can provide both intended therapeutic effects as well as negative side effects. What is needed in the art are new compositions and methods for selectively modulating GR. Surprisingly, the present invention meets these and other needs.

BRIEF SUMMARY OF THE INVENTION

In one embodiment, the present invention provides a compound of Formula I:

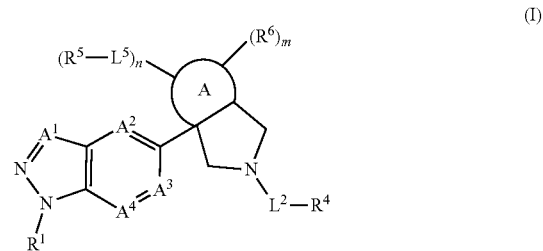

(I)

or a pharmaceutically acceptable salt thereof, wherein
$R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;
each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =CR$^2$— or =N—;
each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN;
Ring A is a $C_{3-6}$ cycloalkyl;
$L^2$ is absent, —C(O)—, —C(O)O—, —C(O)N($R^3$)—, —S(O)$_2$— or —S(O)$_2$N($R^3$)—;
$R^3$ is hydrogen or $C_{1-6}$ alkyl;
$R^4$ is $C_{1-6}$ alkyl, $C_{2-6}$ alkenyl, $C_{2-6}$ alkynyl, $C_{2-6}$ alkoxyalkyl, —(CH$_2$CH$_2$O)$_{2-6}$CH$_3$, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)R$^{4b}$, —C(O)OR$^{4b}$, —OC(O)R$^{4b}$, —OC(O)OR$^{4b}$, —C(O)N(R$^{4b}$)(R$^{4c}$), —N(R$^{4b}$)C(O)R$^{4c}$, —OC(O)N(R$^{4b}$)(R$^{4c}$), —N(R$^{4b}$)C(O)OR$^{4c}$, —S(O)$_2$R$^{4b}$, —S(O)$_2$N(R$^{4b}$)(R$^{4c}$), —N(R$^{4b}$)S(O)$_2$R$^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OR$^{5a}$, —C(O)R$^{5a}$, —C(O)OR$^{5a}$, —OC(O)R$^{5a}$, —C(O)N(R$^{5a}$)(R$^{5b}$), —N(R$^{5a}$)C(O)R$^{5b}$, —OC(O)N(R$^{5a}$)(R$^{5b}$), —N(R$^{5a}$)C(O)OR$^{5b}$, —S(O)$_2$R$^{5a}$, —S(O)$_2$N(R$^{5a}$)(R$^{5b}$), —N(R$^{5a}$)S(O)$_2$R$^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)R$^{5c1}$, —C(O)OR$^{5c1}$, —OC(O)R$^{5c1}$, —OC(O)OR$^{5c1}$, —C(O)N(R$^{5c1}$)(R$^{5c2}$), —N(R$^{5c1}$)C(O)R$^{5c2}$, —OC(O)N(R$^{5c1}$)(R$^{5c2}$), —N(R$^{5c1}$)C(O)OR$^{5c2}$, —S(O)$_2$R$^{5c1}$, —S(O)$_2$N(R$^{5c1}$)(R$^{5c2}$), —N(R$^{5c1}$)S(O)$_2$R$^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy;

subscript m is 0, 1, 2, 3, 4 or 5; and subscript n is 1 or 2.

In another embodiment, the present invention provides a compound of Formula I:

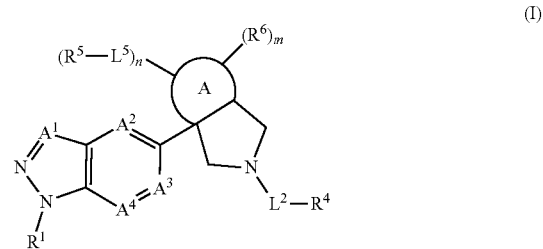

(I)

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N(R$^{1b}$)(R$^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR$^2$— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN;

Ring A is a $C_{3-6}$ cycloalkyl;

$L^2$ is —C(O)—, —C(O)O—, —C(O)N(R$^3$)—, —S(O)$_2$— or —S(O)$_2$N(R$^3$)—;

$R^3$ is hydrogen or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2R^{4b}$, —S(O)$_2$N($R^{4b}$)($R^{4c}$), —N($R^{4b}$)S(O)$_2R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —O$R^{5a}$, —C(O)$R^{5a}$, —C(O)O$R^{5a}$, —OC(O)$R^{5a}$, —C(O)N($R^{5a}$)($R^{5b}$), —N($R^{5a}$)C(O)$R^{5b}$, —OC(O)N($R^{5a}$)($R^{5b}$), —N($R^{5a}$)C(O)O$R^{5b}$, —S(O)$_2R^{5a}$, —S(O)$_2$N($R^{5a}$)($R^{5b}$), —N($R^{5a}$)S(O)$_2R^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2R^{5c1}$, —S(O)$_2$N($R^{5c1}$)($R^{5c2}$), —N($R^{5c1}$)S(O)$_2R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy;

subscript m is 0, 1, 2, 3, 4 or 5; and subscript n is 1 or 2.

In another embodiment, the present invention provides a pharmaceutical composition comprising a compound of the present invention and a pharmaceutically acceptable excipient.

In another embodiment, the present invention provides a method of treating a disorder or condition through modulating a glucocorticoid receptor, the method comprising administering to a subject in need of such treatment, a therapeutically effective amount of a compound or a pharmaceutical composition of the present invention, thereby treating the disorder or condition.

In another embodiment, the present invention provides a method of treating a disorder or condition through antagonizing a glucocorticoid receptor, the method comprising administering to a subject in need of such treatment, an effective amount of the compound or a pharmaceutical composition of the present invention.

In another embodiment, the present invention provides a compound or pharmaceutical composition for use in a method of treating a disorder or condition through modulating a glucocorticoid receptor.

In another embodiment, the present invention provides a compound or pharmaceutical composition for use in a method of treating a disorder or condition through antagonizing the glucocorticoid receptor.

In another embodiment, the present invention provides use of a compound or pharmaceutical composition of the present invention in the manufacture of a medicament for treating a disorder or condition through modulating a glucocorticoid receptor.

In another embodiment, the present invention provides a use of a compound or pharmaceutical composition of the present invention in the manufacture of a medicament for treating a disorder or condition through antagonizing a glucocorticoid receptor.

DETAILED DESCRIPTION OF THE INVENTION

I. General

The present invention provides compounds of Formula I, Ia, Ib, Ib-1, Ib-2, Ic, Ic-1, Id-1, and Id-2 capable of modulating and/or antagonizing a glucocorticoid receptor, and thereby providing beneficial therapeutic effects. The present invention also provides methods of treating disorders and conditions by modulating a glucocorticoid receptor or by antagonizing a glucocorticoid receptor. The present invention also provides use of a compound of the present invention in the manufacture of a medicament for treating a disorder or condition through modulating a glucocorticoid receptor, agonizing a glucocorticoid receptor or antagonizing a glucocorticoid receptor.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated (i.e., $C_{1-6}$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative $C_{1-4}$ alkylene groups include, but are not limited to, methylene, ethylene, propylene, isopropylene, butylene, isobutylene, and sec-butylene.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Deuteroalkyl" refers to an alkyl group, as defined above, where at least one of the hydrogen atoms is replaced with a deuterium. As for the alkyl group, deuteroalkyl groups can have any suitable number of carbon atoms, such as $C_{1-6}$. Exemplary $C_{1-4}$ deuteroalkyl groups include, but are not limited to, $-CH_2D$, $-CHD_2$, $-CD_3$, $-CH_2CH_2D$, $-CH_2CHD_2$, $-CH_2CD_3$, and the like.

"Alkoxy" refers to an alkyl group having an oxygen atom that connects the alkyl group to the point of attachment: alkyl-O—. As for alkyl groups, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The alkoxy component is as defined above. Examples of the alkyl-alkoxy group include, but are not limited to, 2-ethoxy-ethyl and methoxymethyl.

"Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_1$-6. Exemplary $C_{1-4}$ hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxyethyl, and the like.

"Halogen" refers to fluorine, chlorine, bromine and iodine.

"Haloalkyl" refers to alkyl, as defined above, where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Oxo" refers to a carbonyl group, =O.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycloalkyl" or "heterocyclyl" refers to a saturated ring system having from 3 to 12 ring members and from 1 to 5 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. The heterocycloalkyl groups can also form spiro structures such as, but not limited to, diazabicycloheptane, diazabicyclooctane, diazaspirooctane or diazaspirononane. Heterocycloalkyl groups can be unsubstituted or substituted. For example, heterocycloalkyl groups can be substituted with $C_{1-6}$ alkyl or oxo (=O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 12 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined above. Alkyl-heterocycloalkyl groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of alkyl-aryl groups include, but are not limited to, benzyl and ethyl-benzene. Alkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, —N(O)—, —S(O)— and —S(O)$_2$—. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 10 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_2$-3, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined within. Alkyl-heteroaryl groups can be substituted or unsubstituted.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount" refers to a dose that produces therapeutic effects for which it is administered. The exact dose will depend on the purpose of the treatment, and will be ascertainable by one skilled in the art using known techniques (see, e.g., Lieberman, *Pharmaceutical*

*Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an $IC_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulators of the present invention. In some embodiments, examples of disorders or conditions include, but are not limited to, Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the disorders or conditions include nonalcoholic liver disease and/or nonalcoholic steatohepatitis. In some embodiments, the disorders or conditions include cancer.

"Medicament" refers to a composition or substance used for treatment of a disease or condition.

"Subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

III. Compounds

The present invention provides a compound of Formula I, Ia, Ib, Ib-1, Ib-2, Ic, Ic-1, Id-1, or Id-2, or a pharmaceutically acceptable salt thereof. In some embodiments, the present invention provides a compound of Formula I:

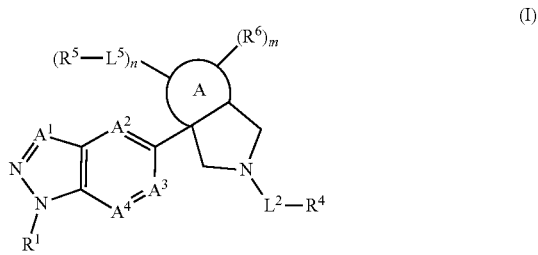

or a pharmaceutically acceptable salt thereof, wherein
$R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;
each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =$CR^2$— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN;

Ring A is a $C_{3-6}$ cycloalkyl;

$L^2$ is absent, —C(O)—, —C(O)O—, —C(O)N($R^3$)—, —S(O)$_2$— or —S(O)$_2$N($R^3$)—.

$R^3$ is hydrogen or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, —(CH$_2$CH$_2$O)$_{2-6}$CH$_3$, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2$$R^{4b}$, —S(O)$_2$N($R^{4b}$)($R^{4c}$), —N($R^{4b}$)S(O)$_2$$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —O$R^{5a}$, —C(O)$R^{5a}$, —C(O)O$R^{5a}$, —OC(O)$R^{5a}$, —C(O)N($R^{5a}$)($R^{5b}$), —N($R^{5a}$)C(O)$R^{5b}$, —OC(O)N($R^{5a}$)($R^{5b}$), —N($R^{5a}$)C(O)O$R^{5b}$, —S(O)$_2$$R^{5a}$, —S(O)$_2$N($R^{5a}$)($R^{5b}$), —N($R^{5a}$)S(O)$_2$$R^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2$$R^{5c1}$, —S(O)$_2$N($R^{5c1}$)($R^{5c2}$), —N($R^{5c1}$)S(O)$_2$$R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy;

subscript m is 0, 1, 2, 3, 4 or 5; and subscript n is 1 or 2.

In some embodiments, the present invention provides a compound of Formula I:

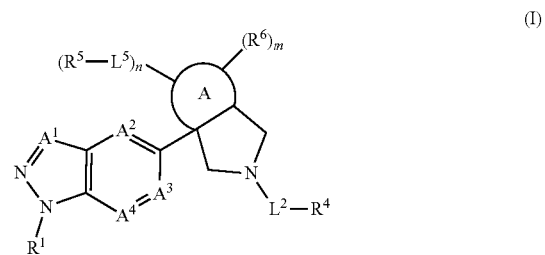

or a pharmaceutically acceptable salt thereof, wherein
$R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN;

Ring A is a $C_{3-6}$ cycloalkyl;

$L^2$ is —C(O)—, —C(O)O—, —C(O)N($R^3$)—, —S(O)₂— or —S(O)₂N($R^3$)—;

$R^3$ is hydrogen or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups; alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)₂$R^{4b}$, —S(O)₂N($R^{4b}$)($R^{4c}$), —N($R^{4b}$)S(O)₂$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —O$R^{5a}$, —C(O)$R^{5a}$, —C(O)O$R^{5a}$, —OC(O)$R^{5a}$, —C(O)N($R^{5a}$)($R^{5b}$), —N($R^{5a}$)C(O)$R^{5b}$, —OC(O)N($R^{5a}$)($R^{5b}$), —N($R^{5a}$)C(O)O$R^{5b}$, —S(O)₂$R^{5a}$, —S(O)₂N($R^{5a}$)($R^{5b}$), —N($R^{5a}$)S(O)₂$R^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)₂$R^{5c1}$, —S(O)₂N($R^{5c1}$)($R^{5c2}$), —N($R^{5c1}$)S(O)₂$R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy;

subscript m is 0, 1, 2, 3, 4 or 5; and
subscript n is 1 or 2.

In some embodiments, the compound of Formula I, Ia, Ib, Ib-1, Ib-2, Ic, or Ic-1, or a pharmaceutically acceptable salt thereof, is the compound wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups; each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S; and each $R^{1b}$ and $R^{1c}$ is independently hydrogen, $C_{1-6}$ alkyl or a 3 to 8 membered heterocycloalkyl having 1 to 3 heteroatoms each independently N, O or S.

In some embodiments, the compound of Formula I, Ia, Ib, Ib-1, Ib-2, Ic, or Ic-1, or a pharmaceutically acceptable salt thereof, is the compound wherein $R^1$ is phenyl substituted with halogen. In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro. In some embodiments, the compound of Formula I, Ia, Ib, Ib-1, Ib-2, Ic, or Ic-1, or a pharmaceutically acceptable salt thereof, is the compound wherein $R^1$ is

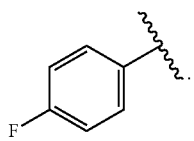

In some embodiments, the compound of Formula I, or a pharmaceutically acceptable salt thereof, is the compound wherein $A^1$, $A^2$, $A^3$ and $A^4$ are each independently =$CR^2$— or =N—; and each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN. In some embodiments, the compound of Formula I, or a pharmaceutically acceptable salt thereof, is the compound wherein each of $A^1$, $A^2$, $A^3$, and $A^4$ is =$CR^2$—.

In some embodiments, the compound of Formula I, Ia, Ib, Ib-1, Ib-2, or Ic, or a pharmaceutically acceptable salt thereof, is the compound wherein each $R^2$ is independently hydrogen or $C_{1-6}$ alkyl. In some embodiments, the compound of Formula I, Ia, Ib, Ib-1, Ib-2, or Ic, or a pharmaceutically acceptable salt thereof, is the compound wherein each $R^2$ is independently hydrogen, methyl, ethyl, n-propyl, or iso-propyl. In some embodiments, the compound of Formula I, Ia, Ib, Ib-1, Ib-2, or Ic, or a pharmaceutically acceptable salt thereof, is the compound wherein each $R^2$ is independently hydrogen, or methyl. In some embodiments, the compound of Formula Ia, Ib, Ib-1, Ib-2, or Ic, or a pharmaceutically acceptable salt thereof, is the compound wherein each $R^2$ is methyl.

In some embodiments, the compound of Formula I, or a pharmaceutically acceptable salt thereof, is the compound wherein $A^1$, $A^2$ and $A^4$ are each =CH—; and $A^3$ is =CH— or =C(Me)-. In some embodiments, the compound of Formula I, or a pharmaceutically acceptable salt thereof, is the compound wherein $A^1$, $A^2$ and $A^4$ are each =CH—; and $A^3$ is =C(Me)-.

Each embodiment of $A^1$, $A^2$, $A^3$, $A^4$ and $R^2$ described herein can be combined with each embodiment of $R^1$ described herein.

In some embodiments, the compound of Formula I, or a pharmaceutically acceptable salt thereof, is the compound having the structure of Formula Ia:

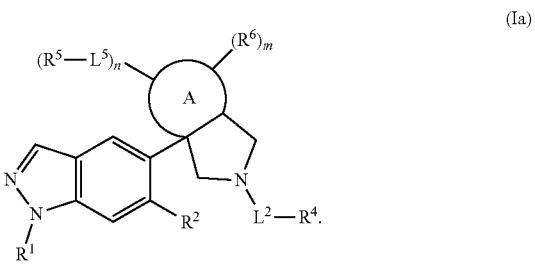

(Ia)

In some embodiments, the compound of Formula I or Ia, or a pharmaceutically acceptable salt thereof, is the compound wherein Ring A is a $C_{3-6}$ cycloalkyl. In some embodiments, the compound of Formula I or Ia, or a pharmaceutically acceptable salt thereof, is the compound wherein Ring A is a $C_{3-5}$ cycloalkyl. In some embodiments, the compound of Formula I or Ia, or a pharmaceutically acceptable salt thereof, is the compound wherein Ring A is a $C_3$ cycloalkyl or a $C_5$ cycloalkyl.

Each embodiment of Ring A described herein can be combined with each embodiment of $R^1$, $A^1$, $A^2$, $A^3$, $A^4$ and $R^2$ described herein.

In some embodiments, the compound of Formula I or Ia, or a pharmaceutically acceptable salt thereof, is the compound having the structure of Formula Ib:

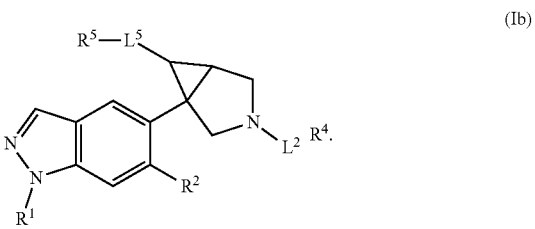

(Ib)

In some embodiments, the compound of Formula I, Ia, or Ib, or a pharmaceutically acceptable salt thereof, is the compound having the structure of Formula Ib-1:

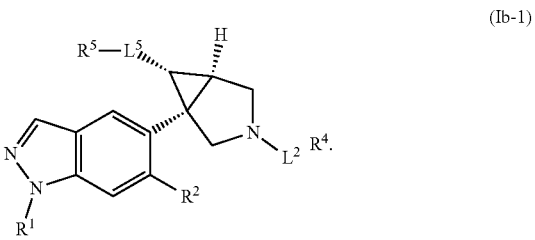

(Ib-1)

In some embodiments, the compound of Formula I, Ia, or Ib, or a pharmaceutically acceptable salt thereof, is the compound having the structure of Formula Ib-2:

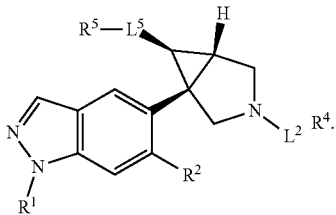
(Ib-2)

In some embodiments, the compound of Formula I or Ia, or a pharmaceutically acceptable salt thereof, is the compound having the structure of Formula Ic:

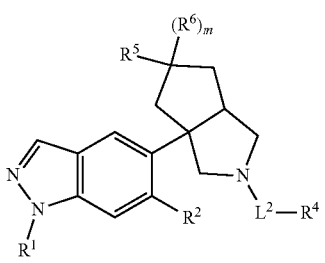
(Ic)

wherein subscript m is 0 or 1.

In some embodiments, the compound of Formula I Ia, or Ic, or a pharmaceutically acceptable salt thereof, is the compound having the structure of Formula Ic-1:

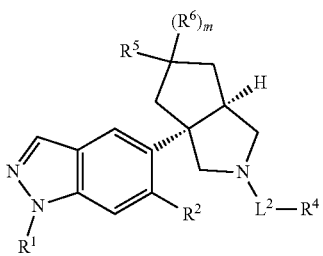
(Ic-1)

wherein subscript m is 0 or 1.

In some embodiments, the compound of Formula I, Ia, Ib, Ib-1, Ib-2, Ic, or Ic-1, or a pharmaceutically acceptable salt thereof, is the compound wherein $L^2$ is absent —C(O)—, —C(O)O—, —C(O)N($R^3$)—, —S(O)$_2$— or —S(O)$_2$N($R^3$)—; and $R^3$ is hydrogen or $C_{1-6}$ alkyl. In some embodiments, the compound of Formula I, Ia, Ib, Ib-1, Ib-2, Ic, or Ic-1, or a pharmaceutically acceptable salt thereof, is the compound wherein $L^2$ is absent, —C(O)—, —C(O)O—, —S(O)$_2$— or —S(O)$_2$N($R^3$)—; and $R^3$ is hydrogen or $C_{1-6}$ alkyl. In some embodiments, the compound of Formula I, Ia, Ib, Ib-1, Ib-2, Ic, or Ic-1, or a pharmaceutically acceptable salt thereof, is the compound wherein $L^2$ is absent, —C(O)—, —C(O)O—, —S(O)$_2$— or —S(O)$_2$N($R^3$)—; and $R^3$ is hydrogen or methyl. In some embodiments, the compound of Formula I, Ia, Ib, Ib-1, Ib-2, Ic, or Ic-1, or a pharmaceutically acceptable salt thereof, is the compound wherein $L^2$ is —C(O)—, —C(O)O—, —S(O)$_2$— or —S(O)$_2$N($R^3$)—; and $R^3$ is hydrogen or methyl. In some embodiments, the compound of Formula I, Ia, Ib, Ib-1, Ib-2, Ic, or Ic-1, or a pharmaceutically acceptable salt thereof, is the compound wherein $L^2$ is absent, —C(O)— or —S(O)$_2$—. In some embodiments, the compound of Formula I, Ia, Ib, Ib-1, Ib-2, Ic, or Ic-1, or a pharmaceutically acceptable salt thereof, is the compound wherein $L^2$ is —C(O)— or —S(O)$_2$—. In some embodiments, the compound of Formula I, Ia, Ib, Ib-1, Ib-2, Ic, or Ic-1, or a pharmaceutically acceptable salt thereof, is the compound wherein $L^2$ is —C(O)—. In some embodiments, the compound of Formula I, Ia, Ib, Ib-1, Ib-2, Ic, or Ic-1, or a pharmaceutically acceptable salt thereof, is the compound wherein $L^2$ is —S(O)$_2$—.

Each embodiment of $L^2$ and $R^3$ described herein can be combined with each embodiment of $R^1$, $A^1$, $A^2$, $A^3$, $A^4$, $R^2$ and Ring A described herein.

In some embodiments, the compound of Formula I, Ia, Ib, Ib-1, Ib-2, Ic, Ic-1, Id-1, or Id-2, or a pharmaceutically acceptable salt thereof, is the compound wherein
$R^4$ is $C_{1-6}$ alkyl, $C_{2-6}$ alkenyl, $C_{2-6}$ alkynyl, $C_{2-6}$ alkoxyalkyl, —(CH$_2$CH$_2$O)$_{2-4}$CH$_3$, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2$$R^{4b}$, —S(O)$_2$N($R^{4b}$)($R^{4c}$), —N($R^{4b}$)S(O)$_2$$R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups; and
each $R^{4t}$ and $R^{4c}$ is hydrogen or $C_{1-6}$ alkyl.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is $C_{1-6}$ alkyl, $C_{2-6}$ alkoxyalkyl, —(CH$_2$CH$_2$O)$_{2-4}$CH$_3$, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, —S(O)$_2$R$^{4b}$, $C_{3-6}$ cycloalkyl, and heterocycloalkyl, wherein each heterocycloalkyl independently has 3 to 12 ring members and 1 to 3 heteroatoms each independently N, O or S; and each $R^{4b}$ is $C_{1-6}$ alkyl.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is $C_{1-6}$ alkyl, $C_{2-6}$ alkoxyalkyl, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups; and each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, or —OH.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is $C_{1-4}$ alkyl, $C_{2-4}$ alkoxyalkyl, —(CH$_2$CH$_2$O)$_{2-4}$CH$_3$, $C_{3-6}$ cycloalkyl, $C_{1-2}$ alkyl-$C_{3-6}$ cycloalkyl, heterocycloalkyl, $C_{1-6}$ alkyl-heterocycloalkyl, $C_{6-12}$ aryl, or heteroaryl, wherein each heterocycloalkyl independently has 3 to 6 ring members and 1 to 3 heteroatoms each independently N or, O, wherein each heteroaryl independently has 5 to 6 ring members and 1 to 4 heteroatoms each independently N, O or S, and wherein each cycloalkyl, heterocycloalkyl, aryl and heteroaryl is independently substituted with 0 to 3 $R^{4a}$ groups; and each $R^{4a}$ is independently $C_{1-3}$ alkyl, $C_{1-3}$ alkoxy, $C_{2-3}$ alkoxyalkyl, halogen, —CN, —S(O)$_2$R$^{4b}$, $C_{3-6}$ cycloalkyl, and heterocycloalkyl, wherein each heterocycloalkyl independently has 3 to 12 ring members and 1 to 3 heteroatoms each independently N, O or S; and each $R^{4b}$ is $C_{1-6}$ alkyl.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is methyl, ethyl, n-propyl, iso-propyl, n-butyl, iso-butyl, sec-butyl, methoxymethyl, methoxyethyl, —(CH$_2$CH$_2$O)$_2$CH$_3$, $C_{3-6}$ cycloalkyl, $C_{1-2}$ alkyl-$C_{3-6}$ cycloalkyl, heterocycloalkyl, $C_{1-6}$ alkyl-heterocycloalkyl, $C_{6-12}$ aryl, or heteroaryl, wherein each cycloalkyl is cyclopropyl, cyclobutyl, cyclopentyl, or cyclohexyl, where each heterocycloalkyl is azetidine, oxetane, pyrrolidine, tetrahydrofuran, piperidine, tetrahydropyran, or morpholine, wherein each heteroaryl is pyrrole, pyridine, pyrazole, imidazole, pyridazine, pyrimidine, pyrazine, isoxazole, oxazole, isothiazole, thiazole, or triazole, and wherein each cycloalkyl, heterocycloalkyl, aryl and heteroaryl is independently substituted with 0 to 2 $R^{4a}$ groups; and each $R^{4a}$ is independently methyl, ethyl, n-propyl, iso-propyl, methoxy, ethoxy, n-propoxy, iso-propoxy, methoxymethyl, methoxyethyl, fluoro, chloro, bromo, —CH$_2$F, —CHF$_2$, —CF$_3$, —CN, —S(O)$_2$Me, —S(O)$_2$Et, cyclopropyl, cyclobutyl, cyclopentyl, piperidine, tetrahydropyran, or morpholine.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is methyl, ethyl, n-propyl, iso-propyl, n-butyl, iso-butyl, sec-butyl, methoxymethyl, methoxyethyl, $C_{3-6}$ cycloalkyl, $C_{1-2}$ alkyl-$C_{3-6}$ cycloalkyl, heterocycloalkyl, $C_{1-6}$ alkyl-heterocycloalkyl, $C_{6-12}$ aryl, or heteroaryl, wherein each cycloalkyl is cyclopropyl, cyclobutyl, cyclopentyl, or cyclohexyl, where each heterocycloalkyl is azetidine, pyrrolidine, tetrahydrofuran, piperidine, tetrahydropyran, or morpholine, wherein each heteroaryl is pyrrole, pyridine, pyrazole, imidazole, pyridazine, pyrimidine, pyrazine, isoxazole, oxazole, isothiazole, thiazole, or triazole, and wherein each cycloalkyl, heterocycloalkyl, aryl and heteroaryl is independently substituted with 0 to 2 $R^{4a}$ groups; and each $R^{4a}$ is independently methyl, ethyl, n-propyl, iso-propyl, methoxy, ethoxy, n-propoxy, iso-propoxy, methoxymethyl, methoxyethyl, fluoro, chloro, bromo, or —CN.

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is methyl, ethyl, iso-propyl, iso-butyl, t-butyl, methoxymethyl, methoxyethyl, —(CH$_2$CH$_2$O)$_2$CH$_3$,

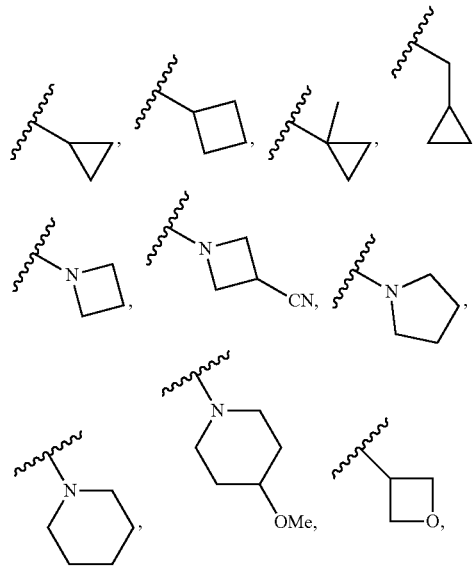

-continued
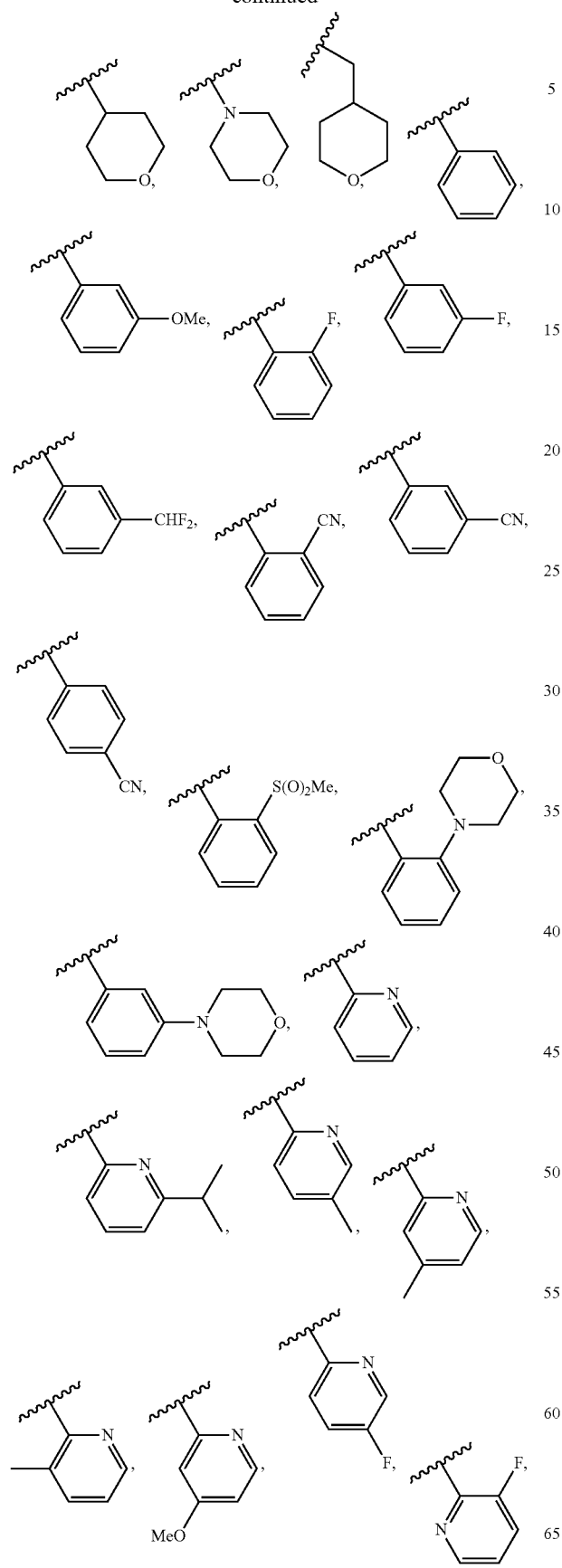
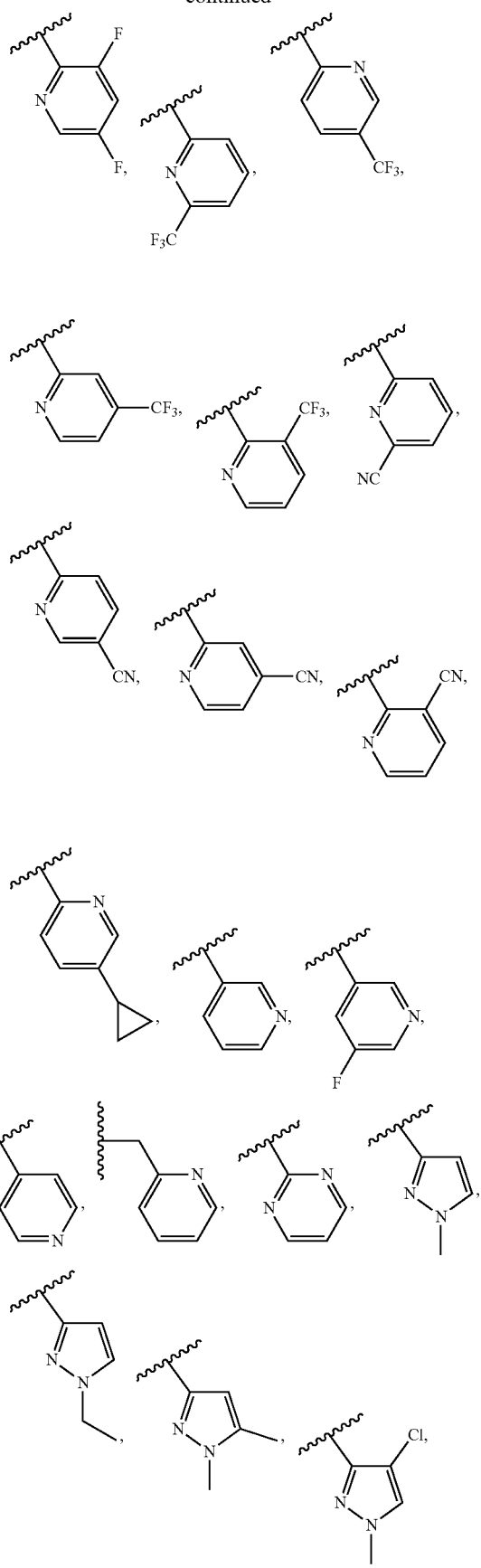

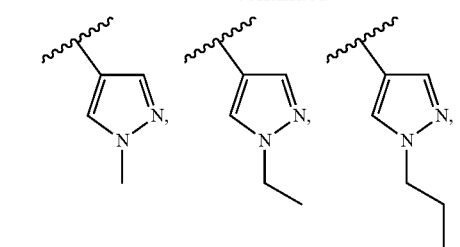
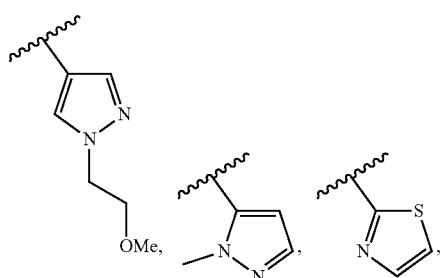
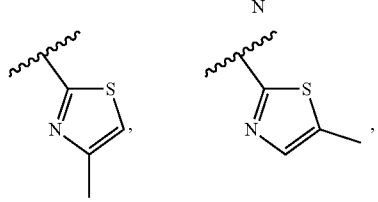
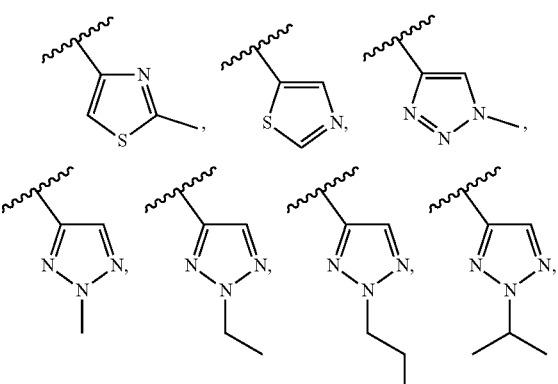
In some embodiments, the compound of Formula I, Ia, Ib, Ib-1, Ib-2, Ic, Ic-1, Id-1, or Id-2, or a pharmaceutically acceptable salt thereof, is the compound wherein R⁴ is methyl, ethyl, iso-propyl, iso-butyl, t-butyl, methoxymethyl, methoxyethyl,
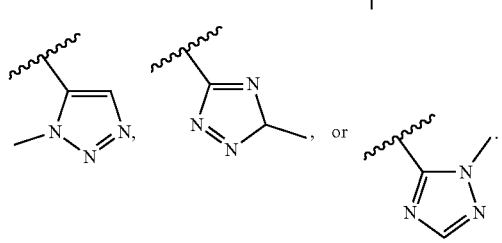
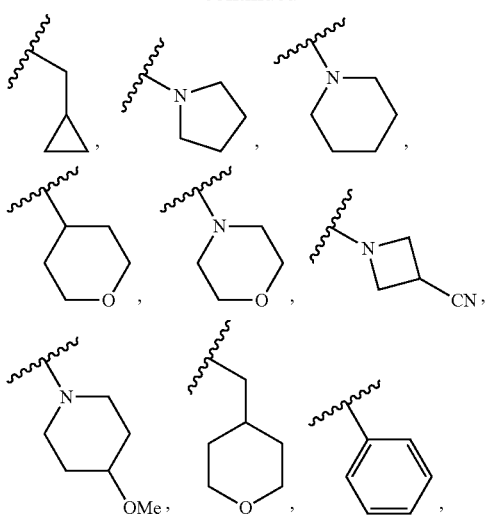
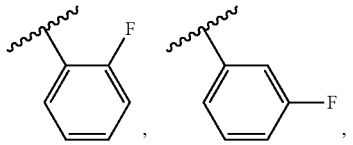
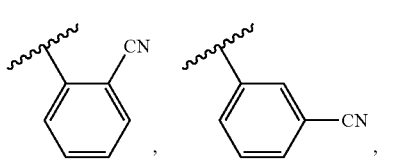
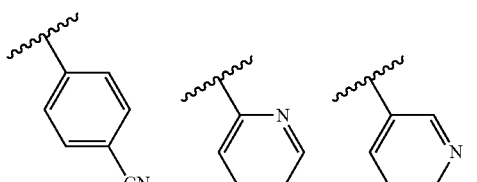
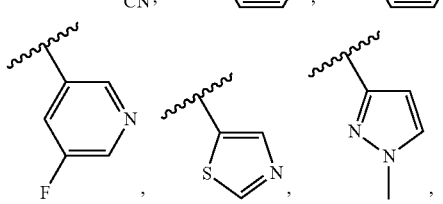
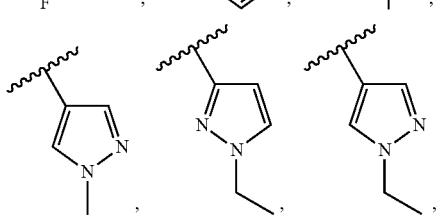
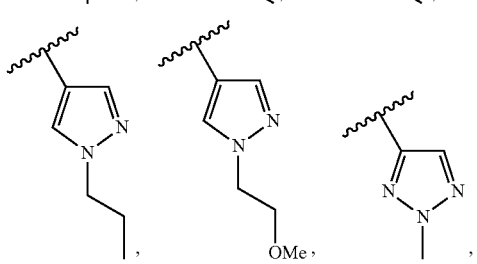

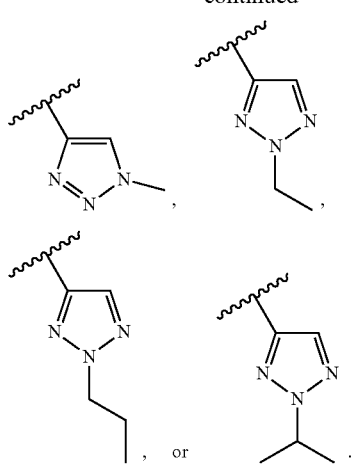
In some embodiments, the compound of Formula I, Ia, Ib, Ib-1, Ib-2, Ic, Ic-1, Id-1, or Id-2, or a pharmaceutically acceptable salt thereof, is the compound wherein R⁴ is methyl, ethyl, iso-propyl, iso-butyl, methoxymethyl, methoxyethyl, $CH_2(CH_2OCH_2)_2H$,
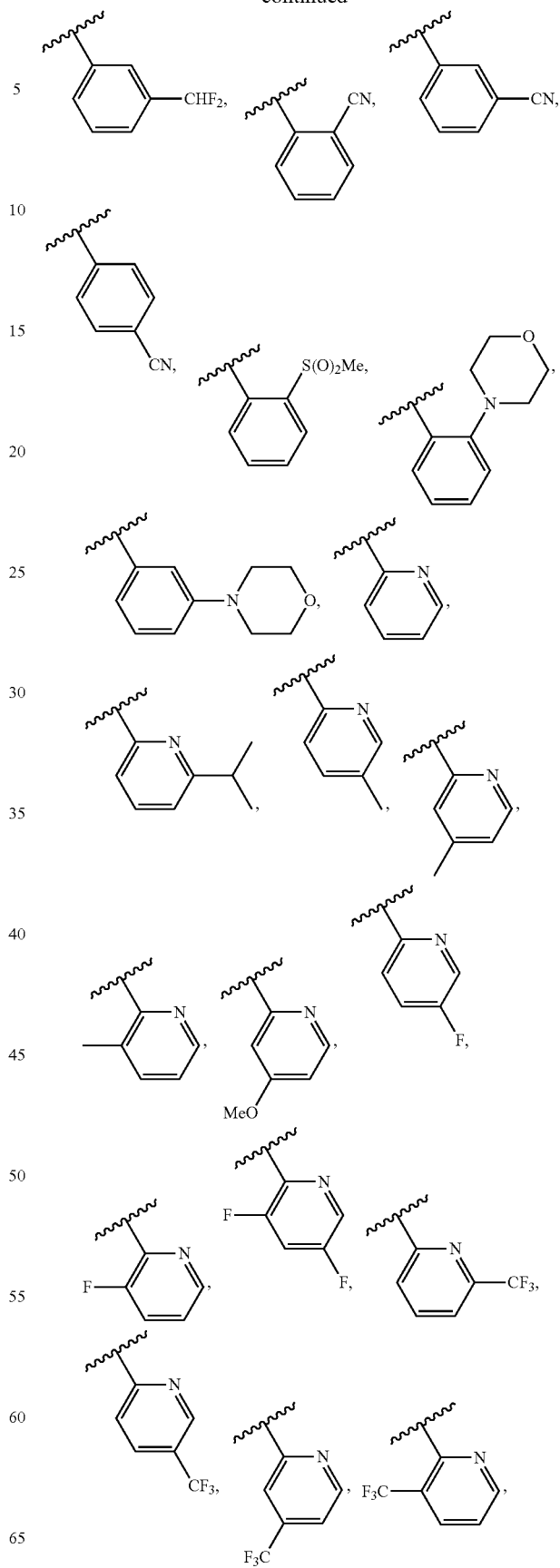

-continued
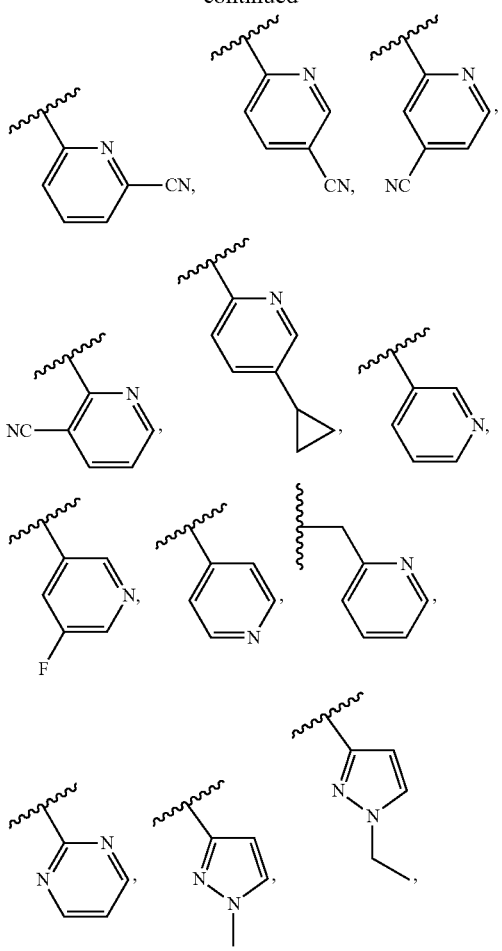
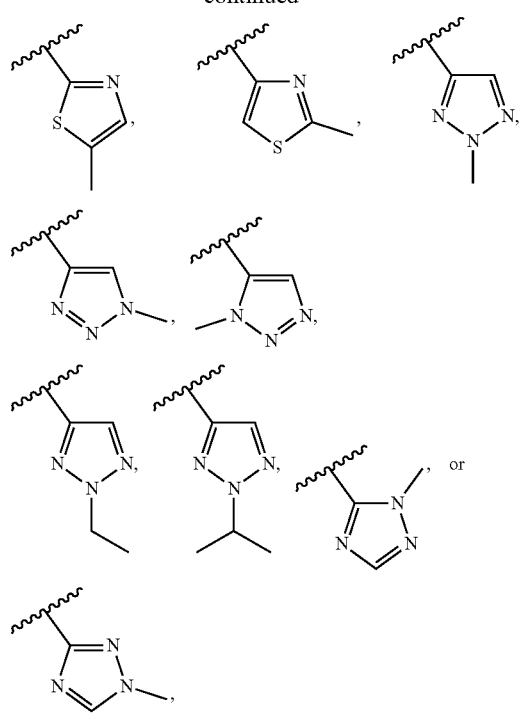
In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is methyl, ethyl, iso-propyl, iso-butyl, methoxymethyl, methoxyethyl,
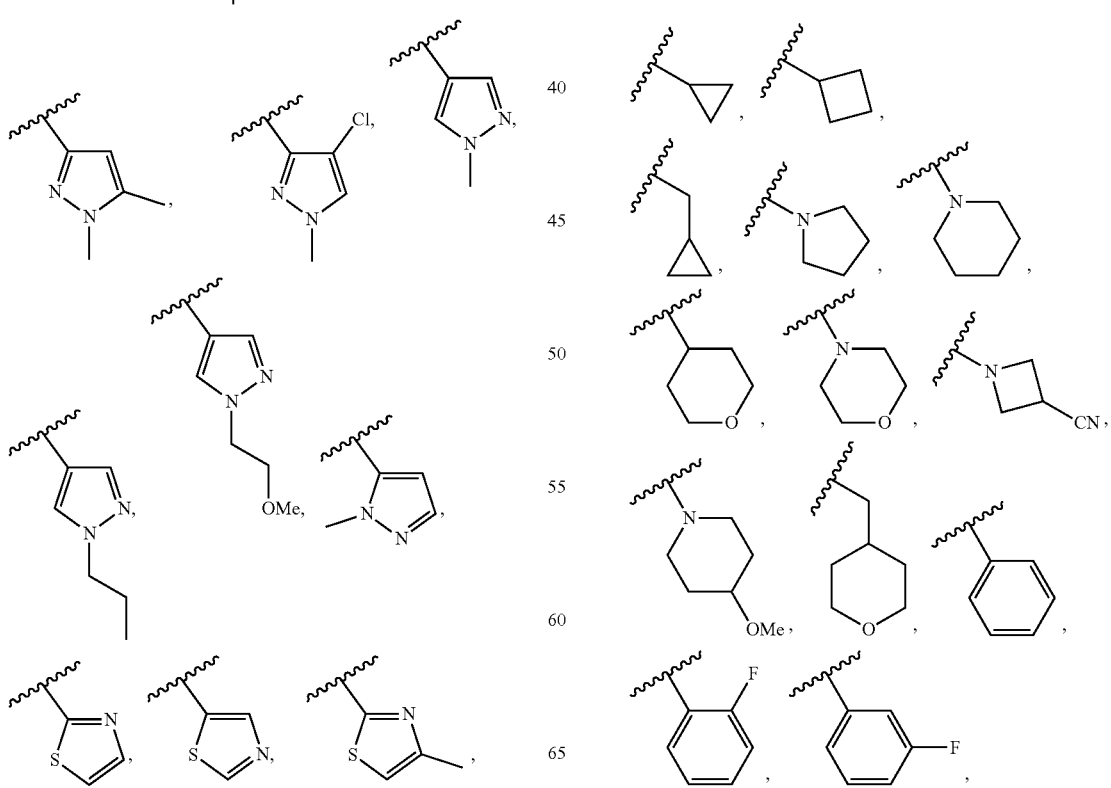

-continued

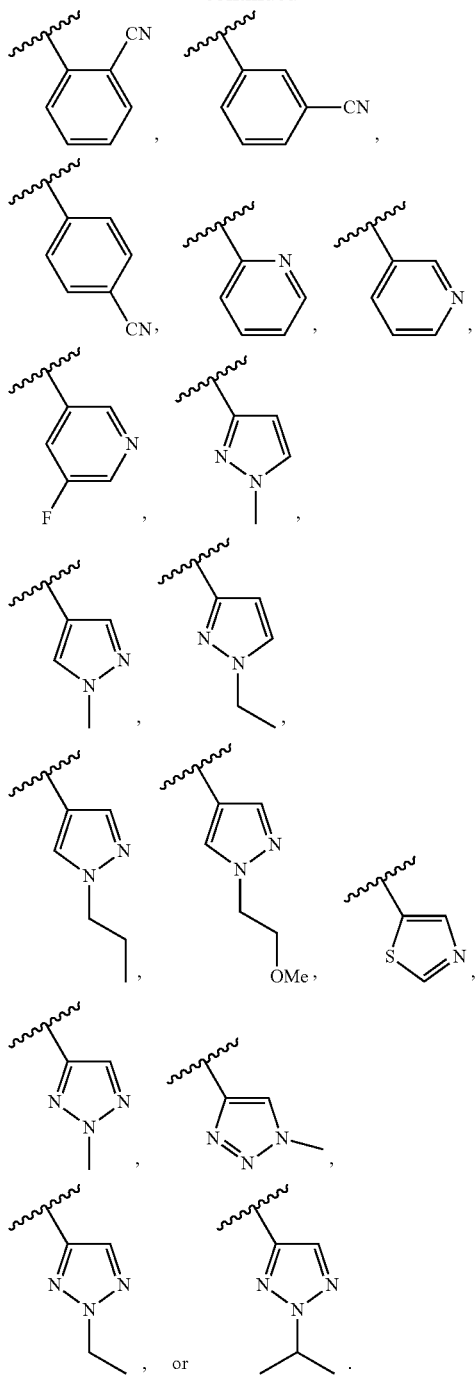

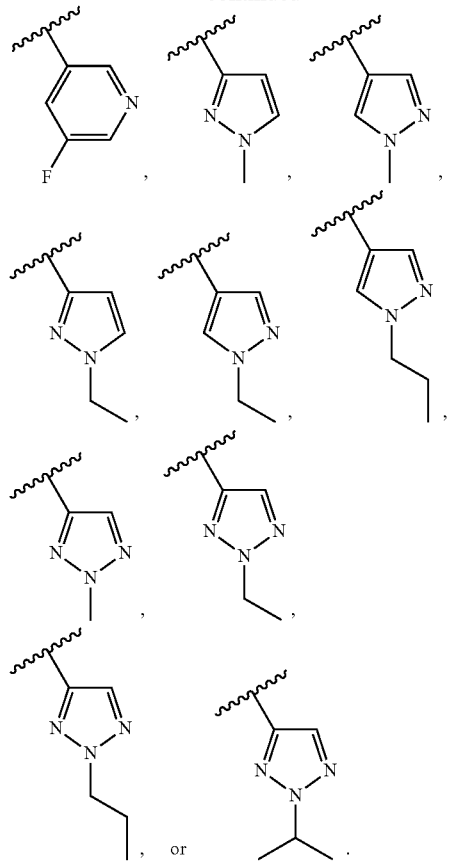

In some embodiments, the compound of Formula I, Ia, Ib, Ib-1, Ib-2, Ic, Ic-1, Id-1, or Id-2, or a pharmaceutically acceptable salt thereof, is the compound wherein $R^4$ is methyl, iso-propyl, t-butyl, methoxyethyl,

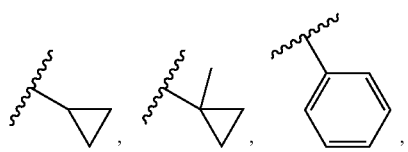

Each embodiment of $R^4$, $R^{4a}$, $R^{4b}$, and $R^{4c}$ described herein can be combined with each embodiment of $R^1$, $A^1$, $A^2$, $A^3$, $A^4$, $R^2$, Ring A, $L^2$ and $R^3$ described herein.

In some embodiments, the compound of Formula I, Ia, Ib, Ib-1, Ib-2, Ic, or Ic-1, or a pharmaceutically acceptable salt thereof, is the compound wherein each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OR$^{5a}$, —C(O)R$^{5a}$, —C(O)OR$^{5a}$, —OC(O)R$^{5a}$, —C(O)N(R$^{5a}$)(R$^{5b}$), —N(R$^{5a}$)C(O)R$^{5b}$, —OC(O)N(R$^{5a}$)(R$^{5b}$), —N(R$^{5a}$)C(O)OR$^{5b}$, —S(O)$_2$R$^{5a}$, —S(O)$_2$N(R$^{5a}$)(R$^{5b}$), —N(R$^{5a}$)S(O)$_2$R$^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)$R^{5c1}$, —C(O)O$R^{5c1}$, —OC(O)$R^{5c1}$, —OC(O)O$R^{5c1}$, —C(O)N($R^{5c1}$)($R^{5c2}$), —N($R^{5c1}$)C(O)$R^{5c2}$, —OC(O)N($R^{5c1}$)($R^{5c2}$), —N($R^{5c1}$)C(O)O$R^{5c2}$, —S(O)$_2R^{5c1}$, —S(O)$_2$N($R^{5c1}$)($R^{5c2}$), —N($R^{5c1}$)S(O)$_2R^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups; and each $R^{5d}$ is independently $C_{1-6}$ alkyl or halogen.

In some embodiments, the compound of Formula I, Ia, Ib, Ib-1, Ib-2, Ic, or Ic-1, or a pharmaceutically acceptable salt thereof, is the compound wherein each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, oxo, —O$R^{5a}$, —C(O)$R^{5a}$, —C(O)O$R^{5a}$, —OC(O)$R^{5a}$, —C(O)N($R^{5a}$)($R^{5b}$), —N($R^{5a}$)C(O)$R^{5b}$, —OC(O)N($R^{5a}$)($R^{5b}$), —N($R^{5a}$)C(O)O$R^{5b}$, —S(O)$_2R^{5a}$, —S(O)$_2$N($R^{5a}$)($R^{5b}$), —N($R^{5a}$)S(O)$_2R^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, halogen, or $C_{1-6}$ haloalkyl; and each $R^{5d}$ is independently $C_{1-6}$ alkyl or halogen.

In some embodiments, the compound of Formula I, Ia, Ib, Ib-1, Ib-2, Ic, or Ic-1, or a pharmaceutically acceptable salt thereof, is the compound wherein each $L^5$ is independently absent or $C_{1-2}$ alkylene;

each $R^5$ is independently $C_{1-3}$ alkyl, $C_{2-4}$ alkynyl, $C_{1-3}$ alkoxy, $C_{1-3}$ hydroxyalkyl, oxo, —O$R^{5a}$, —C(O)N($R^{5a}$)($R^{5b}$), —N($R^{5a}$)C(O)$R^{5b}$, heterocycloalkyl, $C_{6-12}$ aryl, or heteroaryl, wherein each heterocycloalkyl independently has 3 to 8 ring members and 1 to 3 heteroatoms each independently N, O or S, wherein each heteroaryl independently has 5 to 10 ring members and 1 to 4 heteroatoms each independently N, O or S, and wherein each heterocycloalkyl, aryl and heteroaryl is independently substituted with 0 to 4 $R^{5d}$ groups;

each $R^{5a}$ and $R^{5b}$ is independently hydrogen, $C_{1-6}$ alkyl, $C_{3-6}$ cycloalkyl, $C_{6-12}$ aryl, $C_{1-2}$ alkyl-$C_{6-12}$ aryl, or heteroaryl, wherein each heteroaryl independently has 5 to 10 ring members and 1 to 4 heteroatoms each independently N, O or S, and wherein each cycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 6 ring members and 1 additional heteroatom of N or O, wherein the heterocycloalkyl is substituted with 0, 1 or 2 $C_{1-3}$ alkyl groups;

each $R^{5c}$ is independently $C_{1-3}$ alkyl, halogen, or $C_{1-3}$ haloalkyl; and each $R^{5d}$ is independently $C_{1-3}$ alkyl or halogen.

In some embodiments, the compound of Formula I, Ia, Ib, Ib-1, Ib-2, Ic, or Ic-1, or a pharmaceutically acceptable salt thereof, is the compound wherein each $L^5$ is independently absent or $C_{1-2}$ alkylene;

each $R^5$ is independently $C_{1-3}$ alkyl, $C_{2-4}$ alkynyl, $C_{1-3}$ alkoxy, $C_{1-3}$ hydroxyalkyl, oxo, —O$R^{5a}$, —C(O)N($R^{5a}$)($R^{5b}$), —N($R^{5a}$)C(O)$R^{5b}$, $C_{6-12}$ aryl, or heteroaryl, wherein each heteroaryl independently has 5 to 10 ring members and 1 to 4 heteroatoms each independently N, O or S, and wherein each aryl and heteroaryl is independently substituted with 0 to 4 $R^{5c}$ groups;

each $R^{5a}$ and $R^{5b}$ is independently hydrogen, $C_{1-6}$ alkyl, $C_{3-6}$ cycloalkyl, $C_{6-12}$ aryl, $C_{1-2}$ alkyl-$C_{6-12}$ aryl, or heteroaryl, wherein each heteroaryl independently has 5 to 10 ring members and 1 to 4 heteroatoms each independently N, O or S, and wherein each cycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 6 ring members and 1 additional heteroatom of N or O, wherein the heterocycloalkyl is substituted with 0, 1 or 2 $C_{1-3}$ alkyl groups;

each $R^{5c}$ is independently $C_{1-3}$ alkyl, or $C_{1-3}$ haloalkyl; and each $R^{5d}$ is independently halogen.

In some embodiments, the compound of Formula I, Ia, Ib, Ib-1, Ib-2, Ic, or Ic-1, or a pharmaceutically acceptable salt thereof, is the compound wherein each $L^5$ is independently absent or —CH$_2$—;

each $R^5$ is independently methyl, —C≡CH, —C≡CCH$_3$, —CH$_2$C≡CCH$_3$, methoxy, ethoxy, n-propoxy, iso-propoxy, —CH$_2$OH, —CH$_2$CH$_2$OH, —CH$_2$CH$_2$CH$_2$OH, oxo, —OR$^{5a}$, —C(O)N(R$^{5a}$)(R$^{5b}$), —N(R$^{5a}$)C(O)R$^{5b}$, heterocycloalkyl, $C_{6-12}$ aryl, or heteroaryl, wherein each heterocycloalkyl is azetidine, pyrrolidine, piperidine, or morpholine, wherein the aryl is phenyl, wherein each heteroaryl is pyrrole, pyridine, pyrazole, imidazole, pyridazine, pyrimidine, pyrazine, isoxazole, oxazole, benzoxazole, isothiazole, thiazole, benzothiazole, triazole, oxadiazole, or thiadiazole, and wherein each heterocycloalkyl, aryl and heteroaryl is independently substituted with 0 to 2 $R^{5c}$ groups;

each $R^{5a}$ and $R^{5b}$ is independently hydrogen, methyl, ethyl, n-propyl, iso-propyl, n-butyl, iso-butyl, sec-butyl, t-butyl, $C_{3-6}$ cycloalkyl, $C_{6-12}$ aryl, $C_{1-2}$ alkyl-$C_{6-12}$ aryl, or heteroaryl, wherein each cycloalkyl is cyclopropyl, cyclobutyl, cyclopentyl or cyclohexyl, wherein each aryl is phenyl, wherein each heteroaryl is pyrrole, pyridine, pyrazole, imidazole, pyridazine, pyrimidine, or pyrazine, and wherein each cycloalkyl, aryl and heteroaryl is substituted with 0 to 2 $R^{5d}$ groups; alternatively, $R^{5a}$ and $R^{5b}$ are combined with the atoms to which they are attached to form a heterocycloalkyl of azetidine, pyrrolidine or piperidine, wherein the heterocycloalkyl is substituted with 0, 1 or 2 $C_{1-3}$ alkyl groups;

each $R^{5c}$ is independently methyl, ethyl, n-propyl, iso-propyl, fluoro, chloro, —CH$_2$F, —CHF$_2$, —CF$_3$, or —CH$_2$CF$_3$; and each $R^{5d}$ is independently methyl, ethyl, n-propyl, iso-propyl, fluoro, chloro or bromo.

In some embodiments, the compound of Formula I, Ia, Ib, Ib-1, Ib-2, Ic, or Ic-1, or a pharmaceutically acceptable salt thereof, is the compound wherein each $L^5$ is independently absent or —CH$_2$—;

each $R^5$ is independently —C≡CH, —C≡CCH$_3$, —CH$_2$C≡CCH$_3$, methoxy, ethoxy, n-propoxy, iso-propoxy, —CH$_2$OH, —CH$_2$CH$_2$OH, —CH$_2$CH$_2$CH$_2$OH, oxo, —OR$^{5a}$, —C(O)N(R$^{5a}$)(R$^{5b}$), —N(R$^{5a}$)C(O)R$^{5b}$, $C_{6-12}$ aryl, or heteroaryl, wherein the aryl is phenyl, wherein each heteroaryl is pyrrole, pyridine, pyrazole, imidazole, pyridazine, pyrimidine, pyrazine, isoxazole, oxazole, benzoxazole, isothiazole, thiazole, benzothiazole, triazole, oxadiazole, or thiadiazole, and wherein each aryl and heteroaryl is independently substituted with 0 to 2 $R^{5c}$ groups;

each $R^{5a}$ and $R^{5b}$ is independently hydrogen, methyl, ethyl, n-propyl, iso-propyl, n-butyl, iso-butyl, sec-butyl, t-butyl, $C_{3-6}$ cycloalkyl, $C_{6-12}$ aryl, $C_{1-2}$ alkyl-$C_{6-12}$ aryl, or heteroaryl, wherein each cycloalkyl is cyclopropyl, cyclobutyl, cyclopentyl or cyclohexyl, wherein each aryl is phenyl, wherein each heteroaryl is pyrrole, pyridine, pyrazole, imidazole, pyridazine, pyrimidine, or pyrazine, and wherein each cycloalkyl, aryl and heteroaryl is substituted with 0 to 2 $R^{5d}$ groups; alternatively, $R^{5a}$ and $R^{5b}$ are combined with the atoms to which they are attached to form a heterocycloalkyl of azetidine, pyrrolidine or piperidine, wherein the heterocycloalkyl is substituted with 0, 1 or 2 $C_{1-3}$ alkyl groups;

each $R^{5c}$ is independently methyl, ethyl, n-propyl, iso-propyl, —CH$_2$F, —CHF$_2$, —CF$_3$, or —CH$_2$CF$_3$; and each $R^{5d}$ is independently fluoro, chloro or bromo.

In some embodiments, the compound of Formula I, Ia, Ib, Ib-1, Ib-2, Ic, or Ic-1, or a pharmaceutically acceptable salt thereof, is the compound wherein each $R^5$-$L^5$-group is methyl, —C≡CCH$_3$, methoxy, —CH$_2$OH, oxo,

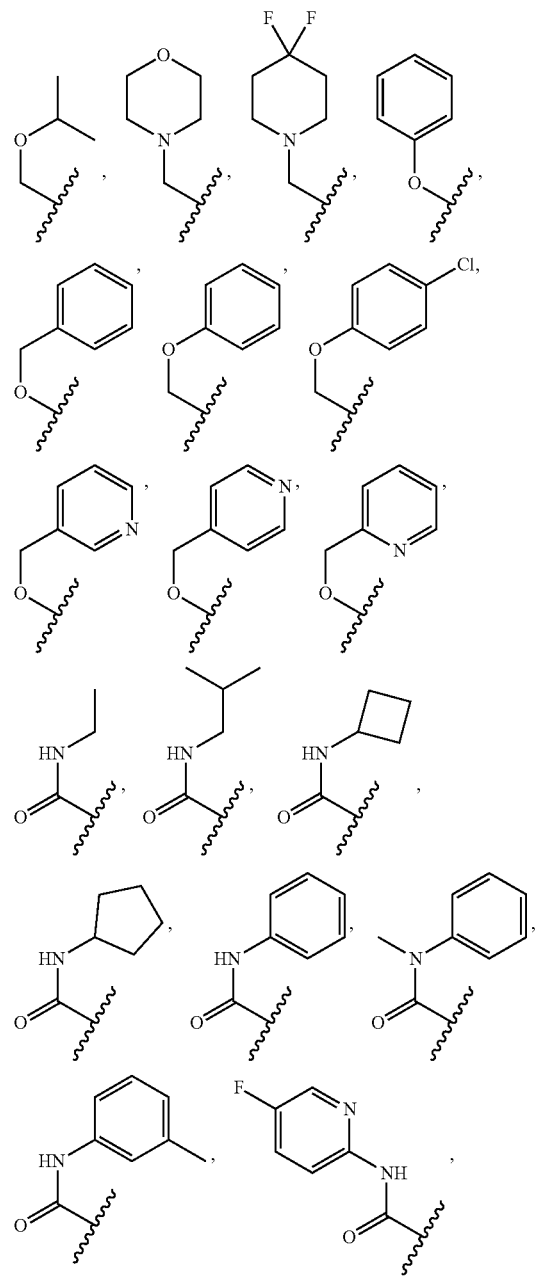

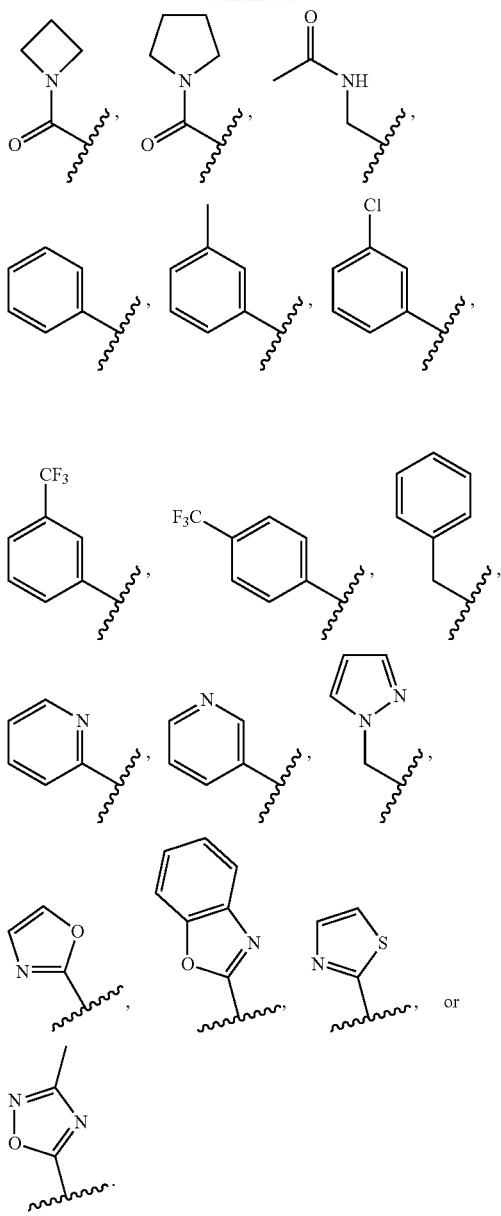
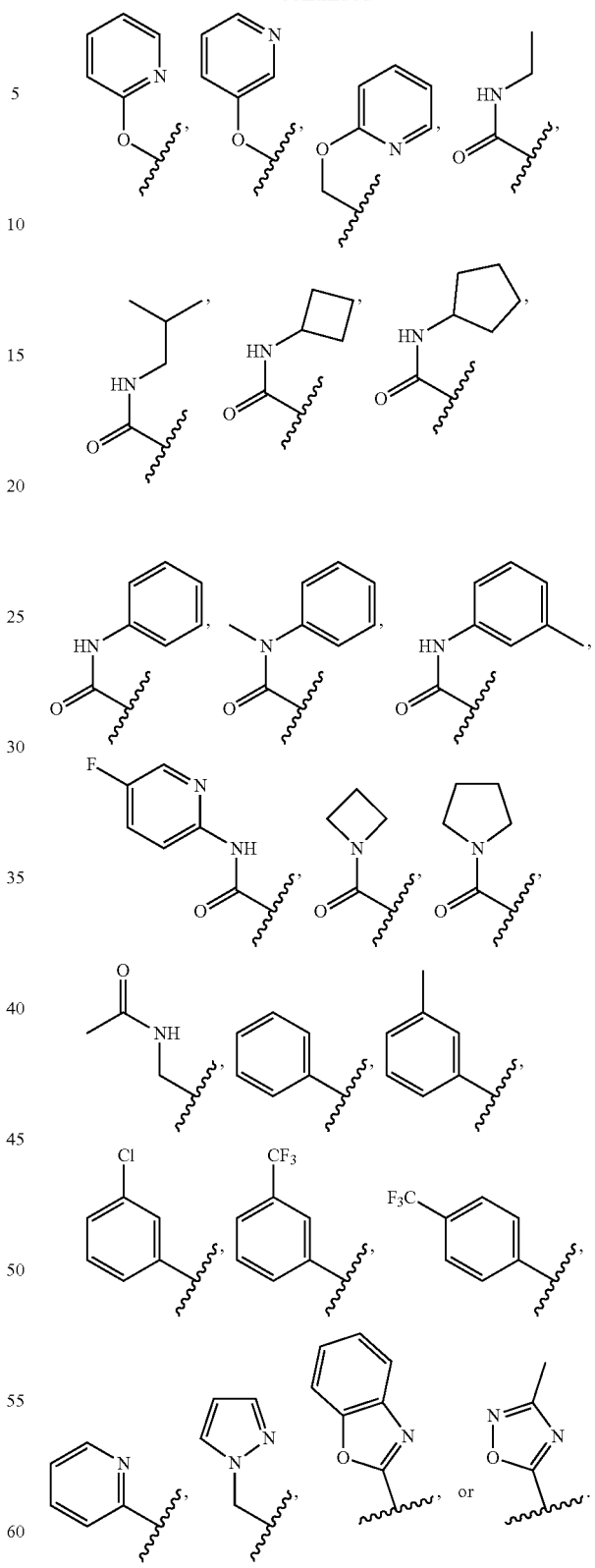
In some embodiments, the compound of Formula I, Ia, Ib, Ib-1, Ib-2, Ic, or Ic-1, or a pharmaceutically acceptable salt thereof, is the compound wherein each $R^5$-$L^5$-group is —C≡CCH$_3$, methoxy, —CH$_2$OH, oxo,
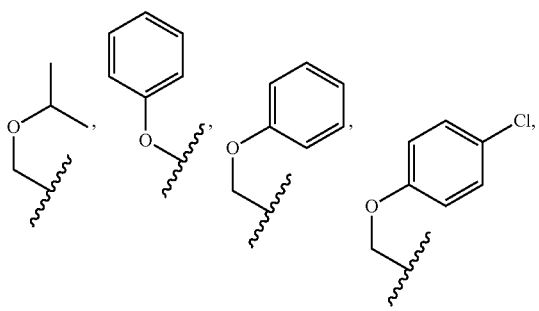
In some embodiments, the compound of Formula I, Ia, Ib, Ib-1, Ib-2, Ic, or Ic-1, or a pharmaceutically acceptable salt thereof, is the compound wherein each $R^5$-$L^5$-group is methyl, —CH$_2$OH,

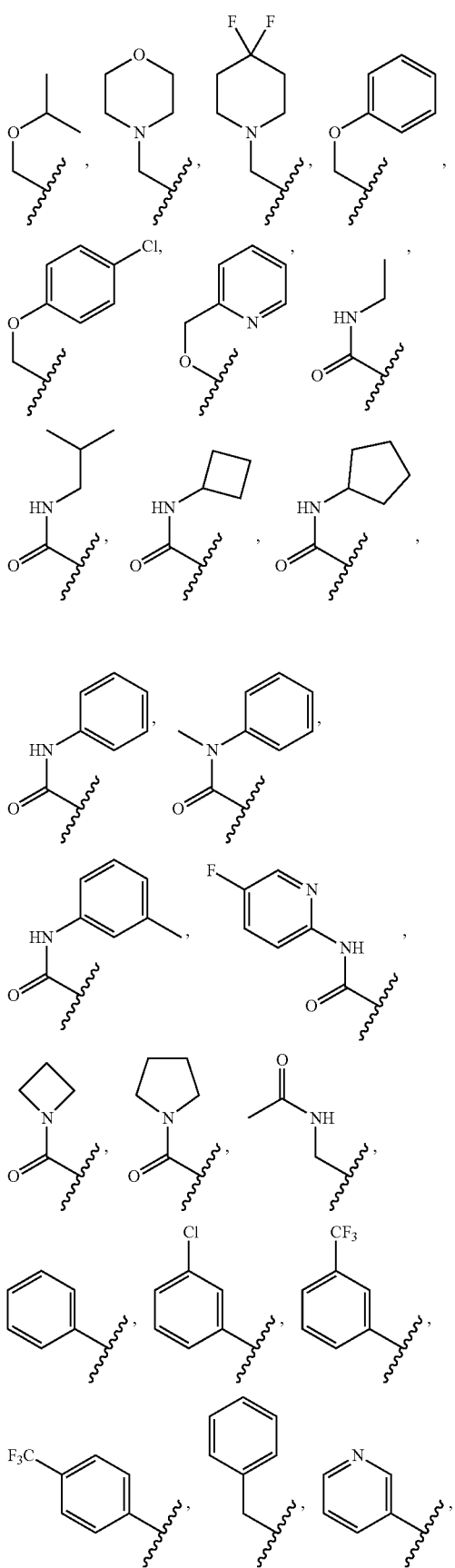
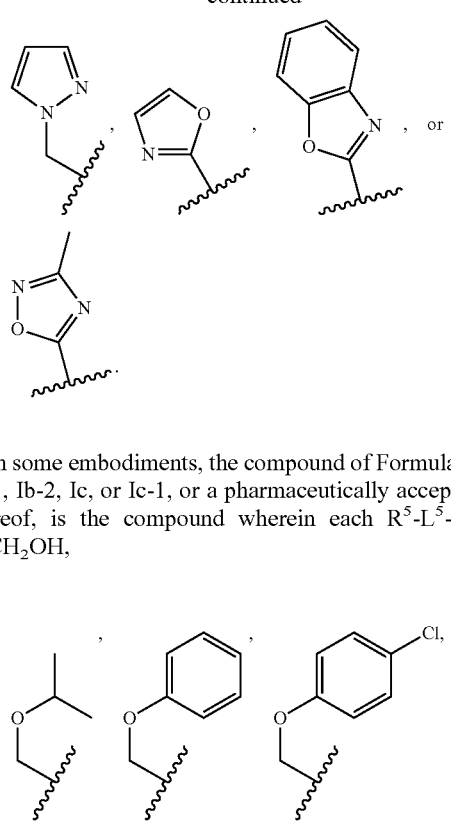
In some embodiments, the compound of Formula I, Ia, Ib, Ib-1, Ib-2, Ic, or Ic-1, or a pharmaceutically acceptable salt thereof, is the compound wherein each $R^5$-$L^5$-group is —CH$_2$OH, -continued

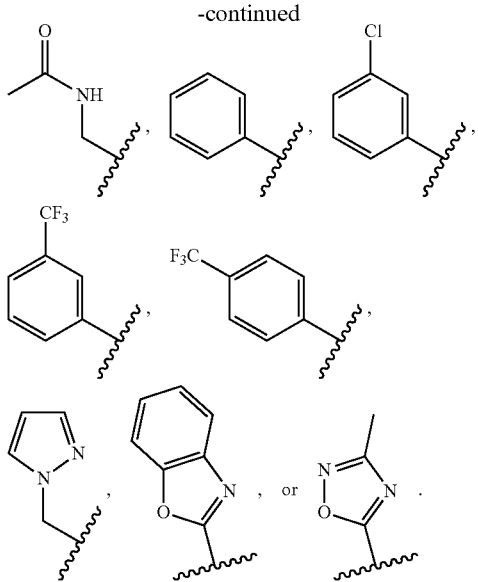

In some embodiments, the compound of Formula I, Ia, Ib, Ib-1, Ib-2, Ic, or Ic-1, or a pharmaceutically acceptable salt thereof, is the compound wherein each $R^5$-$L^5$-group is methoxy, —C≡CCH$_3$, oxo,

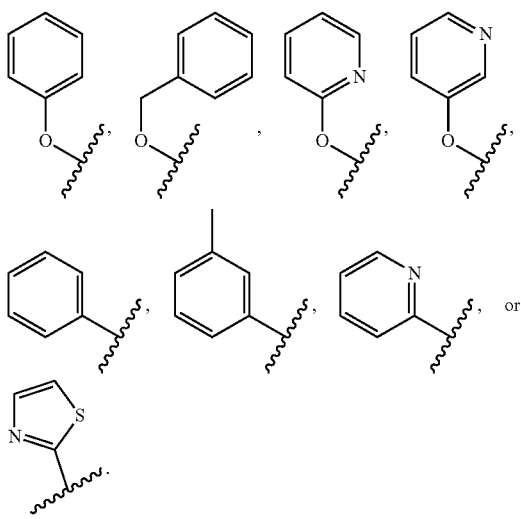

Each embodiment of $L^5$, $R^5$, $R^{5a}$, $R^{5b}$, $R^{5c}$, $R^{5c1}$, $R^{5c2}$, and $R^{5d}$ described herein can be combined with each embodiment of $R^1$, $A^1$, $A^2$, $A^3$, $A^4$, $R^2$, Ring A, $L^2$, $R^3$, $R^4$, $R^{4a}$, $R^{4b}$, and $R^{4c}$ described herein.

In some embodiments, the compound of Formula I, Ia, Ic, or Ic-1, or a pharmaceutically acceptable salt thereof, is the compound wherein each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy; and subscript m is 0, 1, 2, 3, 4 or 5. In some embodiments, the compound of Formula I, Ia, Ic, or Ic-1, or a pharmaceutically acceptable salt thereof, is the compound wherein each $R^6$ is independently $C_{1-6}$ alkoxy, hydroxy, or halogen; and subscript m is 0, or 1.

In some embodiments, the compound of Formula I, Ia, Ic, or Ic-1, or a pharmaceutically acceptable salt thereof, is the compound wherein subscript m is 0 or 1. In some embodiments, the compound of Formula I, Ia, Ic, or Ic-1, or a pharmaceutically acceptable salt thereof, is the compound wherein each $R^6$ is independently —OMe, —OEt, —OPr, —OiPr, hydroxy, F, Cl or Br; and subscript m is 0 or 1. In some embodiments, the compound of Formula I, Ia, Ic, or Ic-1, or a pharmaceutically acceptable salt thereof, is the compound wherein each $R^6$ is independently —OMe, —OEt, hydroxy, or F; and subscript m is 0 or 1.

In some embodiments, the compound of Formula I, Ia, Ic, or Ic-1, or a pharmaceutically acceptable salt thereof, is the compound wherein subscript m is 0.

Each embodiment of $R^6$ and subscript m described herein can be combined with each embodiment of $R^1$, $A^1$, $A^2$, $A^3$, $A^4$, $R^2$, Ring A, $L^2$, $R^3$, $R^4$, $R^{4a}$, $R^{4b}$, $R^{4c}$, $L^5$, $R^5$, $R^{5a}$, $R^{5b}$, $R^{5c}$, $R^{5c1}$, $R^{5c2}$, and $R^{5d}$ described herein.

In some embodiments, the compound of Formula I, Ia, Ib, Ib-1, Ib-2, Ic, or Ic-1, or a pharmaceutically acceptable salt thereof, is the compound wherein subscript n is 1 or 2. In some embodiments, the compound of Formula I, Ia, Ib, Ib-1, Ib-2, Ic, or Ic-1, or a pharmaceutically acceptable salt thereof, is the compound wherein subscript n is 1.

Each embodiment of subscript n described herein can be combined with each embodiment of $R^1$, $A^1$, $A^2$, $A^3$, $A^4$, $R^2$, Ring A, $L^2$, $R^3$, $R^4$, $R^{4a}$, $R^{4b}$, $R^{4C}$, $L^5$, $R^5$, $R^{5a}$, $R^{5b}$, $R^{5c}$, $R^{5c1}$, $R^{5c2}$, $R^{5d}$, $R^6$ and subscript m described herein.

In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro; $A^1$, $A^2$ and $A^4$ are each =CH—; and $A^3$ is =C(Me)-.

In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro; $A^1$, $A^2$ and $A^4$ are each =CH—; $A^3$ is =C(Me)-; and Ring A is a $C_3$ cycloalkyl or a $C_5$ cycloalkyl.

In some embodiments, the compound of Formula I, Ia, Ib, Ib-1, Ib-2, Ic, or Ic-1, or a pharmaceutically acceptable salt thereof, is the compound wherein
  $R^1$ is phenyl substituted with fluoro;
  $A^1$, $A^2$ and $A^4$ are each =CH—;
  $A^3$ is =C(Me)-;
  Ring A is a $C_3$ cycloalkyl or a $C_5$ cycloalkyl;
  $L^2$ is absent, —C(O)—, —C(O)O—, —S(O)$_2$— or —S(O)$_2$N(R$^3$)—; and $R^3$ is hydrogen or $C_{1-6}$ alkyl;
  $R^4$ is $C_{1-6}$ alkyl, $C_{2-6}$ alkoxyalkyl, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;
  alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups; and
  each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, or —OH.

In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro;
$A^1$, $A^2$ and $A^4$ are each =CH—;
$A^3$ is =C(Me)-;
Ring A is a $C_3$ cycloalkyl or a $C_5$ cycloalkyl;
$L^2$ is absent, —C(O)—, —C(O)O—, —S(O)$_2$— or —S(O)$_2$N($R^3$)—; and $R^3$ is hydrogen or $C_{1-6}$ alkyl;
$R^4$ is $C_{1-6}$ alkyl, $C_{2-6}$ alkoxyalkyl, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, or —OH;
each $L^5$ is independently absent or $C_{1-2}$ alkylene;
each $R^5$ is independently $C_{1-3}$ alkyl, $C_{2-4}$ alkynyl, $C_{1-3}$ alkoxy, $C_{1-3}$ hydroxyalkyl, oxo, —$OR^{5a}$, —C(O)N($R^{5a}$)($R^{5b}$), —N($R^{5a}$)C(O)$R^{5b}$, heterocycloalkyl, $C_{6-12}$ aryl, or heteroaryl, wherein each heterocycloalkyl independently has 3 to 8 ring members and 1 to 3 heteroatoms each independently N, O or S, wherein each heteroaryl independently has 5 to 10 ring members and 1 to 4 heteroatoms each independently N, O or S, and wherein each heterocycloalkyl, aryl and heteroaryl is independently substituted with 0 to 4 $R^{5c}$ groups;
each $R^{5a}$ and $R^{5b}$ is independently hydrogen, $C_{1-6}$ alkyl, $C_{3-6}$ cycloalkyl, $C_{6-12}$ aryl, $C_{1-2}$ alkyl-$C_{6-12}$ aryl, or heteroaryl, wherein each heteroaryl independently has 5 to 10 ring members and 1 to 4 heteroatoms each independently N, O or S, and wherein each cycloalkyl, aryl and heteroaryl is substituted with 0 to 4 $R^{5d}$ groups;
alternatively, $R^{5a}$ and $R^{5b}$ are combined with the atoms to which they are attached to form a heterocycloalkyl having 3 to 6 ring members and 1 additional heteroatom of N or O, wherein the heterocycloalkyl is substituted with 0, 1 or 2 $C_{1-3}$ alkyl groups;
each $R^{5c}$ is independently $C_{1-3}$ alkyl, halogen, or $C_{1-3}$ haloalkyl; and
each $R^{5d}$ is independently $C_{1-3}$ alkyl or halogen.

In some embodiments, the compound of Formula I, Ia, Ib, Ib-1, Ib-2, Ic, or Ic-1, or a pharmaceutically acceptable salt thereof, is the compound wherein
$R^1$ is phenyl substituted with fluoro;
$A^1$, $A^2$ and $A^4$ are each =CH—;
$A^3$ is =C(Me)-;
Ring A is a $C_3$ cycloalkyl or a $C_5$ cycloalkyl;
$L^2$ is absent, —C(O)—, —C(O)O—, —S(O)$_2$— or —S(O)$_2$N($R^3$)—; and $R^3$ is hydrogen or $C_{1-6}$ alkyl;
$R^4$ is $C_{1-6}$ alkyl, $C_{2-6}$ alkoxyalkyl, $C_{1-6}$ hydroxyalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;
alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;
each $R^{4a}$ is independently $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, or —OH;
each $L^5$ is independently absent or $C_{1-2}$ alkylene;
each $R^5$ is independently $C_{1-3}$ alkyl, $C_{2-4}$ alkynyl, $C_{1-3}$ alkoxy, $C_{1-3}$ hydroxyalkyl, oxo, —$OR^{5a}$, —C(O)N($R^{5a}$)($R^{5b}$), —N($R^{5a}$)C(O)$R^{5b}$, heterocycloalkyl, $C_{6-12}$ aryl, or heteroaryl, wherein each heterocycloalkyl independently has 3 to 8 ring members and 1 to 3 heteroatoms each independently N, O or S, wherein each heteroaryl independently has 5 to 10 ring members and 1 to 4 heteroatoms each independently N, O or S, and wherein each heterocycloalkyl, aryl and heteroaryl is independently substituted with 0 to 4 $R^{5c}$ groups;
each $R^{5a}$ and $R^{5b}$ is independently hydrogen, $C_{1-6}$ alkyl, $C_{3-6}$ cycloalkyl, $C_{6-12}$ aryl, $C_{1-2}$ alkyl-$C_{6-12}$ aryl, or heteroaryl, wherein each heteroaryl independently has 5 to 10 ring members and 1 to 4 heteroatoms each independently N, O or S, and wherein each cycloalkyl, aryl and heteroaryl is substituted with 0 to 4 $R^{5d}$ groups;
alternatively, $R^{5a}$ and $R^{5b}$ are combined with the atoms to which they are attached to form a heterocycloalkyl having 3 to 6 ring members and 1 additional heteroatom of N or O, wherein the heterocycloalkyl is substituted with 0, 1 or 2 $C_{1-3}$ alkyl groups;
each $R^{5c}$ is independently $C_{1-3}$ alkyl, halogen, or $C_{1-3}$ haloalkyl;
each $R^{5d}$ is independently $C_{1-3}$ alkyl or halogen;
each $R^6$ is independently $C_{1-6}$ alkoxy, hydroxy, or halogen; and
subscript m is 0, or 1.

In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro; $A^1$, $A^2$ and $A^4$ are each =CH—; $A^3$ is =C(Me)-; and Ring A is a $C_3$ cycloalkyl.

In some embodiments, the compound of Formula I, Ia, Ib, Ib-1, Ib-2, Ic, or Ic-1, or a pharmaceutically acceptable salt thereof, is the compound wherein
$R^1$ is phenyl substituted with fluoro;
$A^1$, $A^2$ and $A^4$ are each =CH—;
$A^3$ is =C(Me)-;
Ring A is a $C_3$ cycloalkyl;
$L^2$ is absent, —C(O)—, —C(O)O—, —S(O)$_2$— or —S(O)$_2$N($R^3$)—; and
$R^3$ is hydrogen or methyl.

In some embodiments, the compound of Formula I, Ia, Ib, Ib-1, Ib-2, Ic, or Ic-1, or a pharmaceutically acceptable salt thereof, is the compound wherein
$R^1$ is phenyl substituted with fluoro;
$A^1$, $A^2$ and $A^4$ are each =CH—;
$A^3$ is =C(Me)-;
Ring A is a $C_3$ cycloalkyl;
$L^2$ is absent, —C(O)—, —C(O)O—, —S(O)$_2$— or —S(O)$_2$N($R^3$)—;
$R^3$ is hydrogen or methyl;

$R^4$ is methyl, ethyl, iso-propyl, iso-butyl, t-butyl, methoxymethyl, methoxyethyl, —(CH₂CH₂O)₂CH₃,
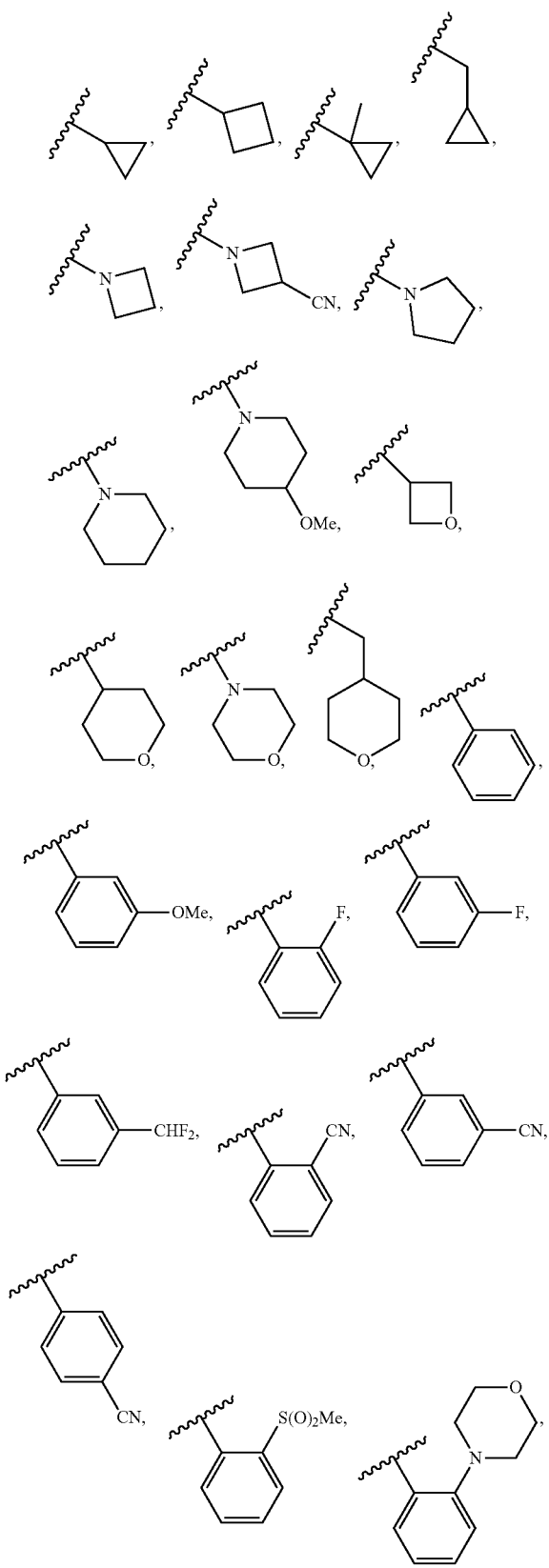
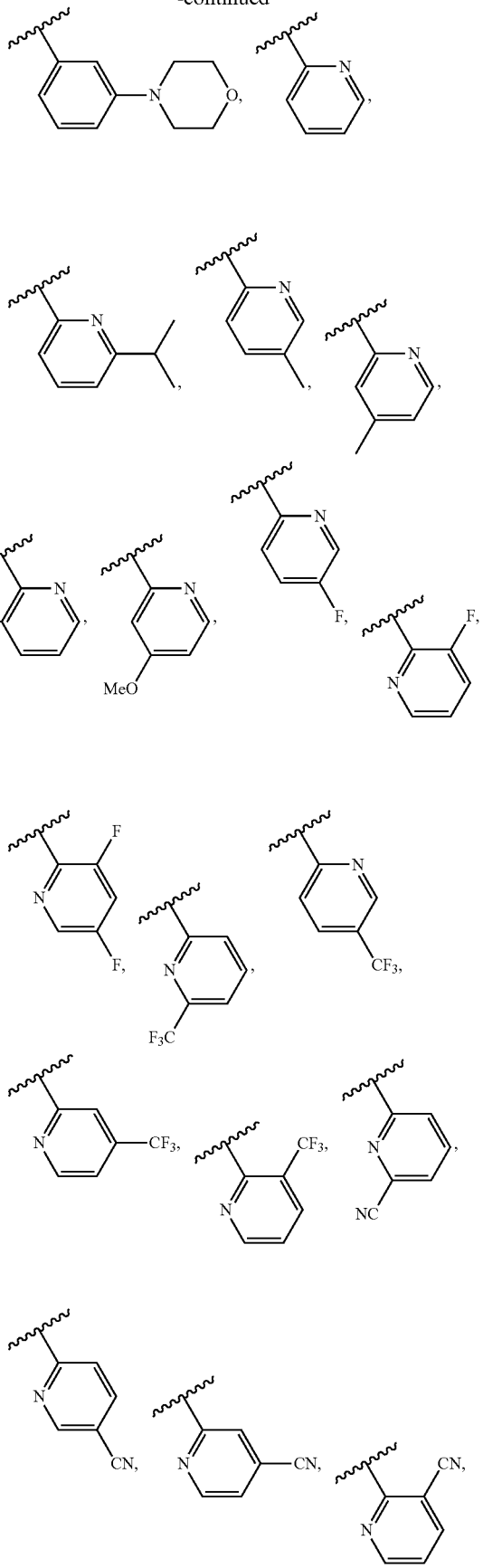

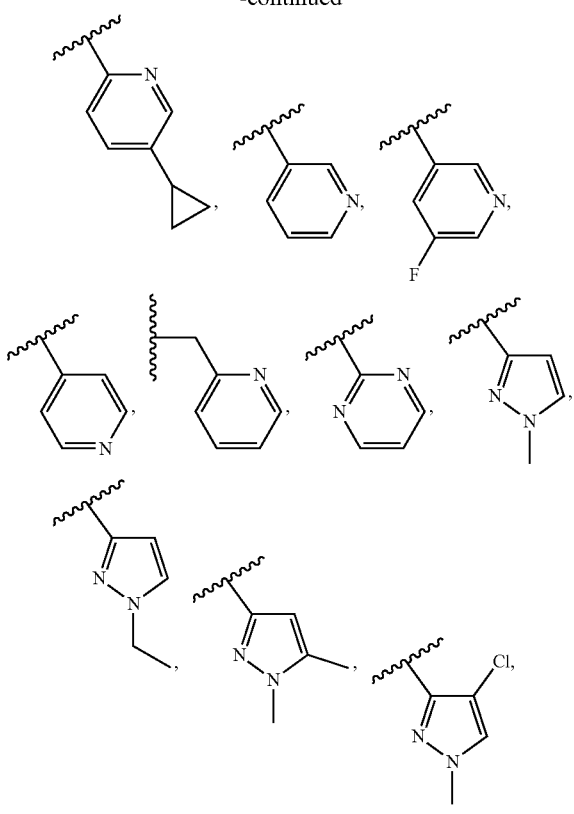

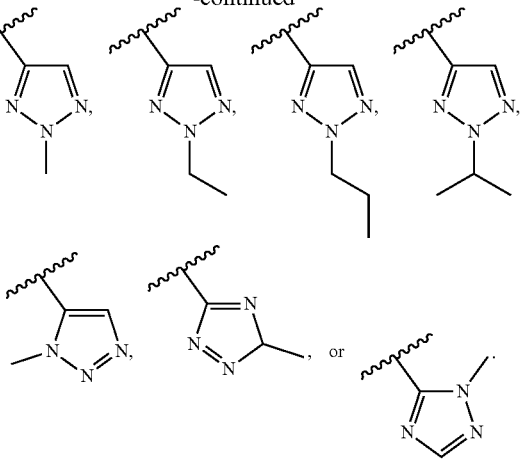

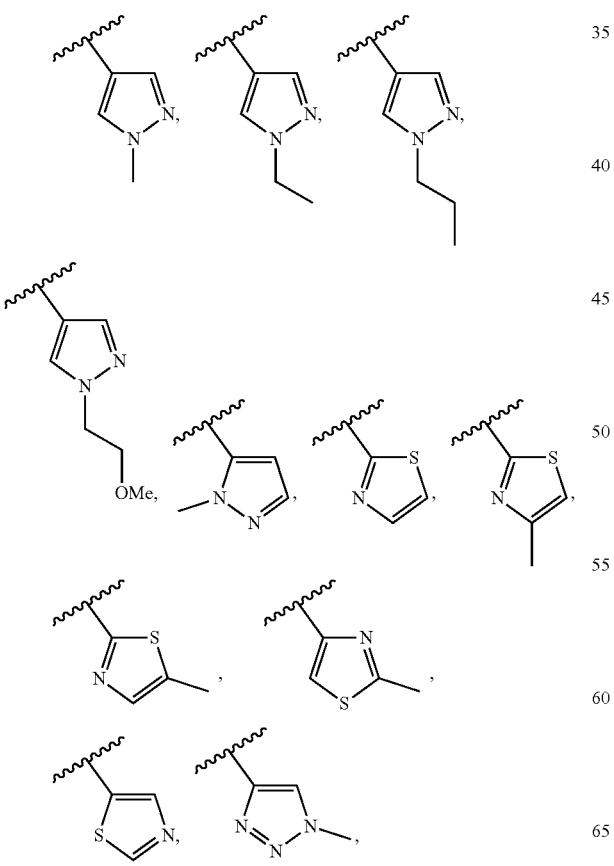

In some embodiments, the compound of Formula I, Ia, Ib, Ib-1, Ib-2, Ic, or Ic-1, or a pharmaceutically acceptable salt thereof, is the compound wherein $R^1$ is phenyl substituted with fluoro;

$A^1$, $A^2$ and $A^4$ are each =CH—;

$A^3$ is =C(Me)-;

Ring A is a $C_3$ cycloalkyl;

$L^2$ is absent, —C(O)—, —C(O)O—, —S(O)$_2$— or —S(O)$_2$N(R$^3$)—;

$R^3$ is hydrogen or methyl;

$R^4$ is methyl, ethyl, iso-propyl, iso-butyl, t-butyl, methoxymethyl, methoxyethyl, —(CH$_2$CH$_2$O)$_2$CH$_3$,

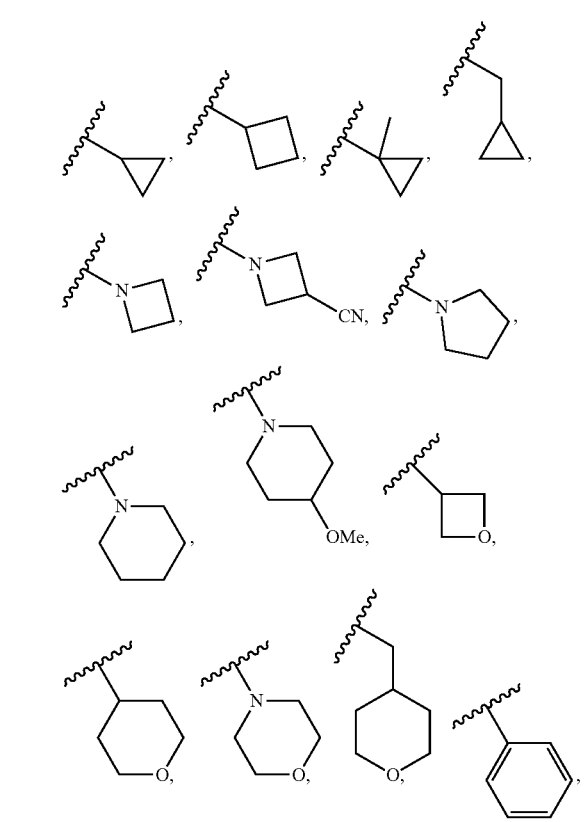

51
-continued
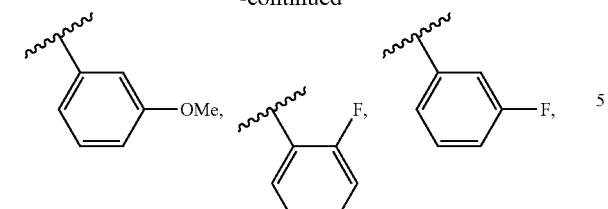
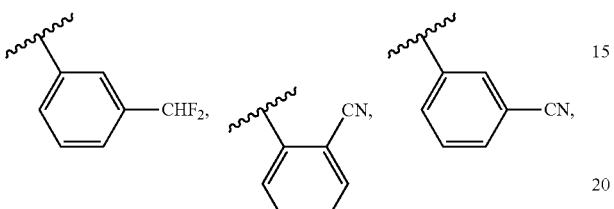
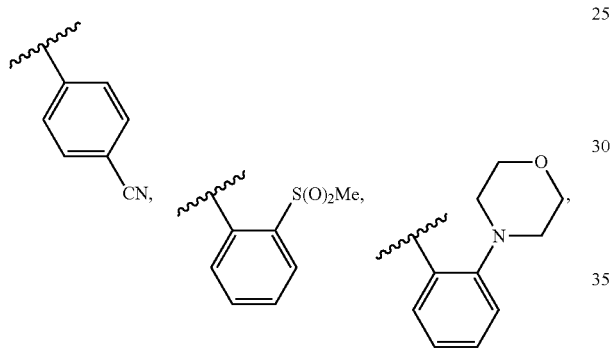
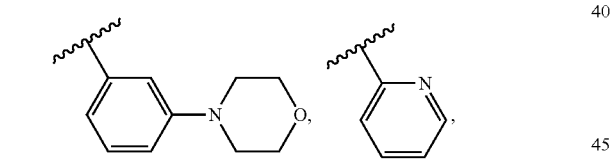
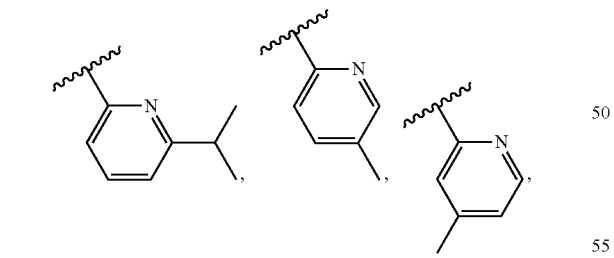
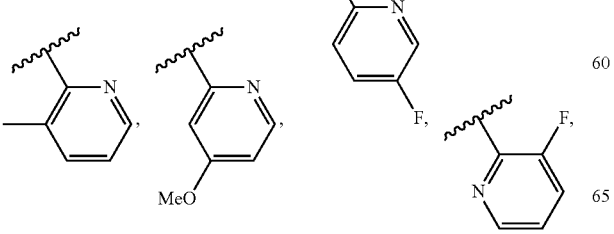
52
-continued
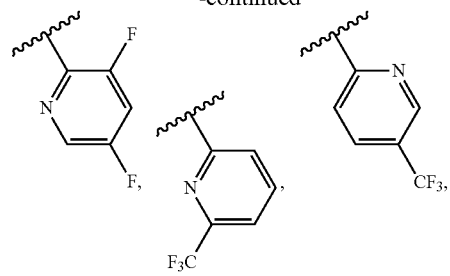
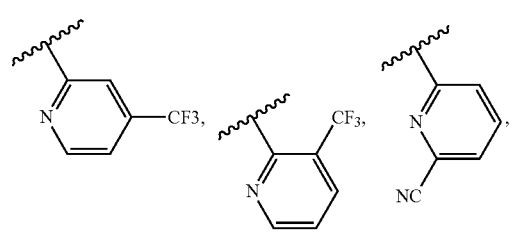
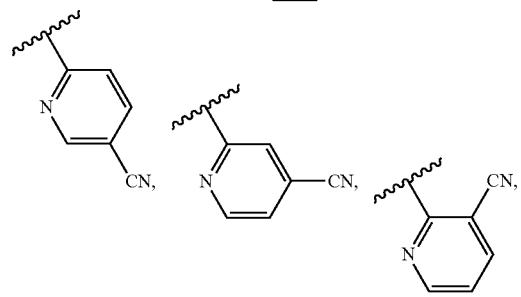
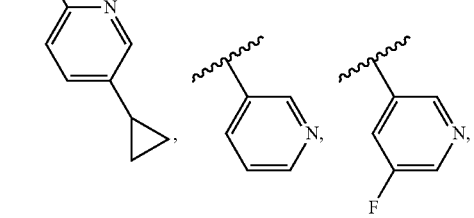
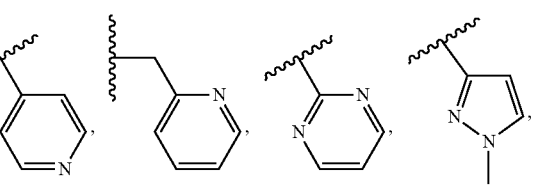
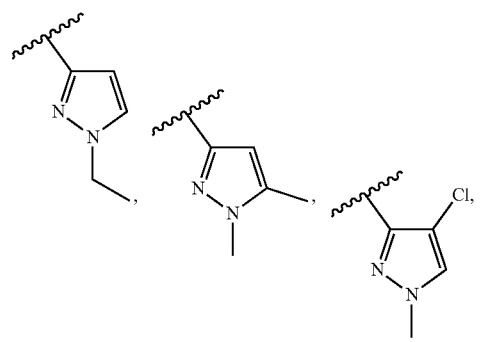

-continued

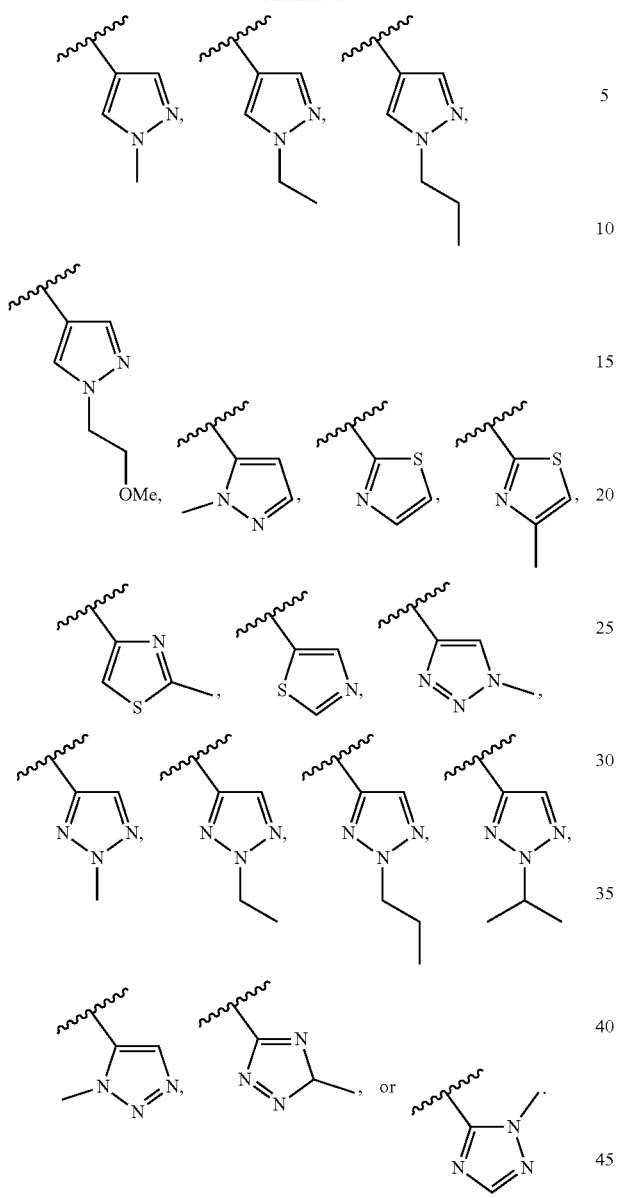

each R⁵-L⁵-group is —CH₂OH,

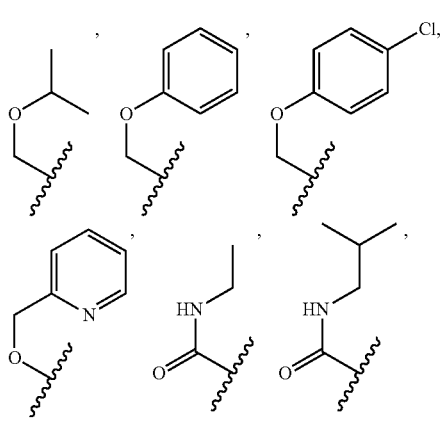

-continued

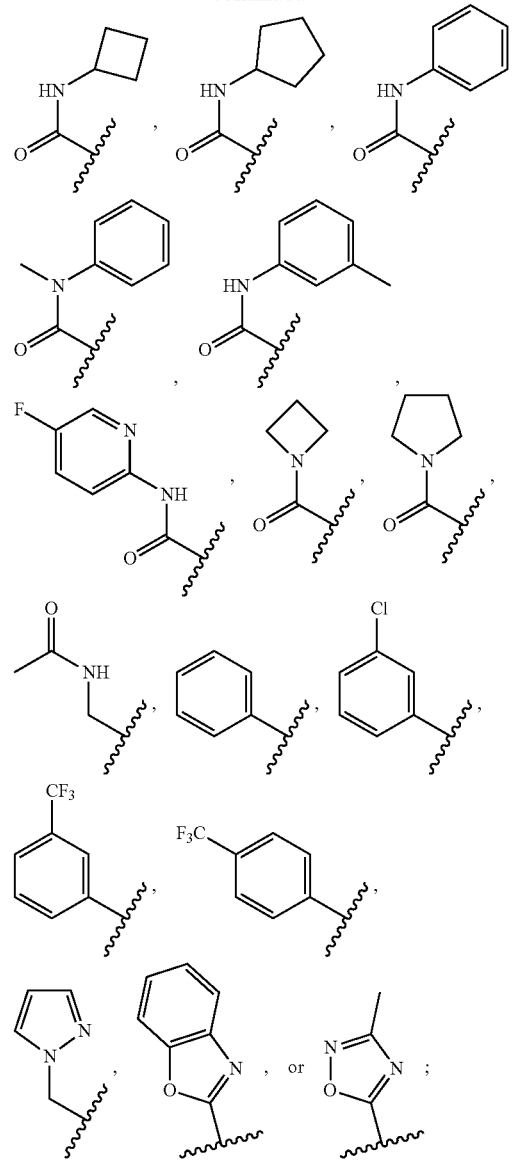

subscript m is 0.

In some embodiments, the compound of Formula I, Ia, Ib, Ib-1, Ib-2, Ic, or Ic-1, or a pharmaceutically acceptable salt thereof, is the compound wherein
  R¹ is phenyl substituted with halogen;
  A¹, A² and A⁴ are each =CH—;
  A³ is =CH— or =C(Me)-;
  Ring A is a C₃₋₅ cycloalkyl;
  L² is absent, —C(O)—, —C(O)O—, —S(O)₂— or —S(O)₂N(R³)—;
  R³ is hydrogen or C₁₋₃ alkyl;
  R⁴ is C₁₋₄ alkyl, C₂₋₄ alkoxyalkyl, —(CH₂CH₂O)₂₋₄CH₃, C₃₋₆ cycloalkyl, C₁₋₂ alkyl-C₃₋₆ cycloalkyl, heterocycloalkyl, C₁₋₆ alkyl-heterocycloalkyl, C₆₋₁₂ aryl, or heteroaryl,
    wherein each heterocycloalkyl independently has 3 to 6 ring members and 1 to 3 heteroatoms each independently N or, O, wherein each heteroaryl independently has 5 to 6 ring members and 1 to 4 heteroatoms each independently N, O or S, and wherein each cycloalkyl, heterocycloalkyl, aryl and heteroaryl is independently substituted with 0 to 3 $R^{4a}$ groups;

each $R^{4a}$ is independently $C_{1-3}$ alkyl, $C_{1-3}$ alkoxy, $C_{2-3}$ alkoxyalkyl, halogen, —CN, —S(O)$_2$R$^{4b}$, $C_{3-6}$ cycloalkyl, and heterocycloalkyl, wherein each heterocycloalkyl independently has 3 to 12 ring members and 1 to 3 heteroatoms each independently N, O or S;

each $R^{4I}$ is $C_{1-6}$ alkyl;

each $L^5$ is independently absent or $C_{1-2}$ alkylene;

each $R^5$ is independently $C_{2-4}$ alkynyl, $C_{1-3}$ alkoxy, $C_{1-3}$ hydroxyalkyl, oxo, —OR$^{5a}$, —C(O)N(R$^{5a}$)(R$^{5b}$), —N(R$^{5a}$)C(O)R$^{5b}$, heterocycloalkyl, $C_{6-12}$ aryl, or heteroaryl, wherein each heterocycloalkyl independently has 3 to 8 ring members and 1 to 3 heteroatoms each independently N, O or S, wherein each heteroaryl independently has 5 to 10 ring members and 1 to 4 heteroatoms each independently N, O or S, and wherein each heterocycloalkyl, aryl and heteroaryl is independently substituted with 0 to 4 R$^5$, groups;

each $R^{5a}$ and $R^{5b}$ is independently hydrogen, $C_{1-6}$ alkyl, $C_{3-6}$ cycloalkyl, $C_{6-12}$ aryl, $C_{1-2}$ alkyl-$C_{6-12}$ aryl, or heteroaryl, wherein each heteroaryl independently has 5 to 10 ring members and 1 to 4 heteroatoms each independently N, O or S, and wherein each cycloalkyl, aryl and heteroaryl is substituted with 0 to 4 R$^{5d}$ groups;

alternatively, $R^{5a}$ and $R^{5b}$ are combined with the atoms to which they are attached to form a heterocycloalkyl having 3 to 6 ring members and 1 additional heteroatom of N or O, wherein the heterocycloalkyl is substituted with 0, 1 or 2 $C_{1-3}$ alkyl groups;

each $R^{5c}$ is independently $C_{1-3}$ alkyl, halogen, or $C_{1-3}$ haloalkyl;

each $R^{5d}$ is independently $C_{1-3}$ alkyl or halogen;

each $R^6$ is independently $C_{1-6}$ alkoxy, hydroxy, or halogen;

subscript m is 0, or 1; and subscript n is 1.

In some embodiments, the compound of Formula I, Ia, Ib, Ib-1, Ib-2, Ic, or Ic-1, or a pharmaceutically acceptable salt thereof, is the compound wherein $R^1$ is

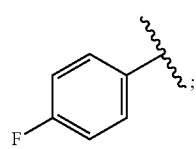

$A^1$, $A^2$ and $A^4$ are each =CH—;

$A^3$ is =CH— or =C(Me)-;

Ring A is a $C_3$ cycloalkyl or a $C_5$ cycloalkyl;

$L^2$ is absent, —C(O)—, —C(O)O—, —S(O)$_2$— or —S(O)$_2$N(R$^3$)—;

$R^3$ is hydrogen or methyl;

$R^4$ is methyl, ethyl, iso-propyl, iso-butyl, t-butyl, methoxymethyl, methoxyethyl, CH$_2$(CH$_2$OCH$_2$)$_2$H,

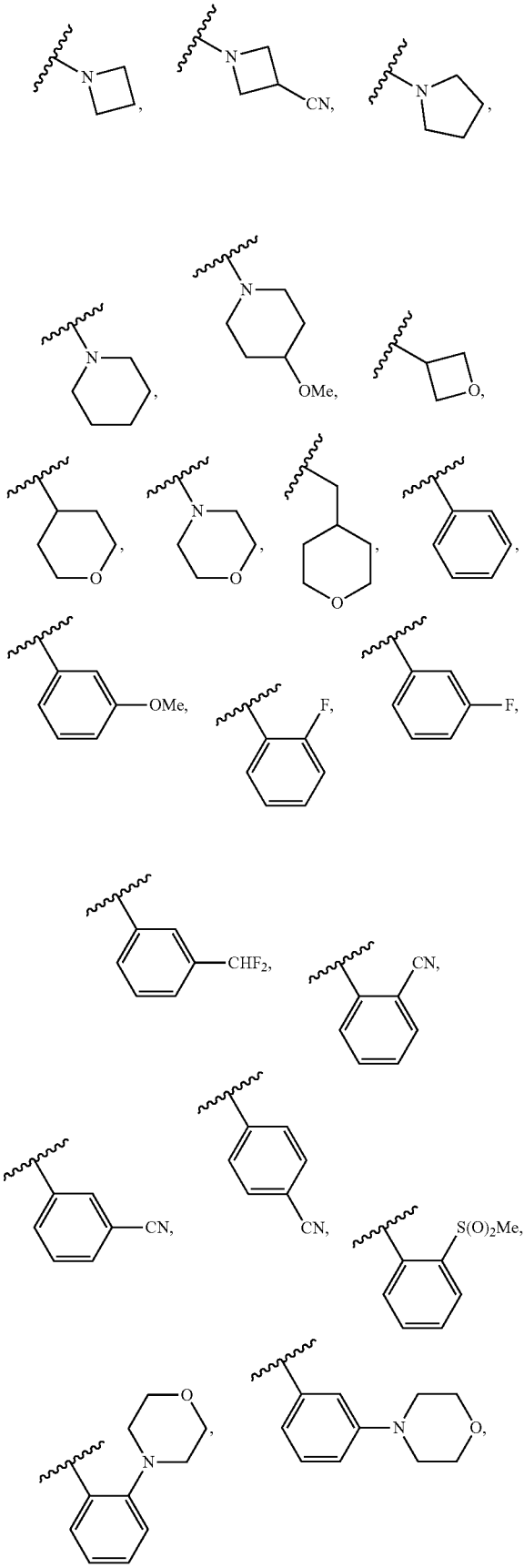

-continued
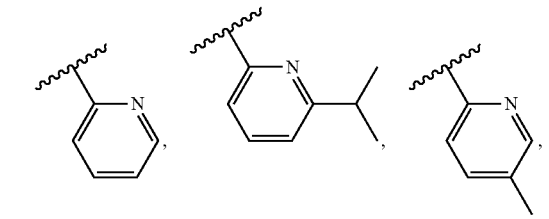
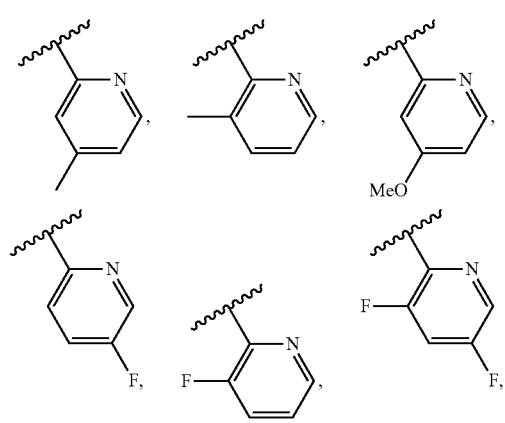
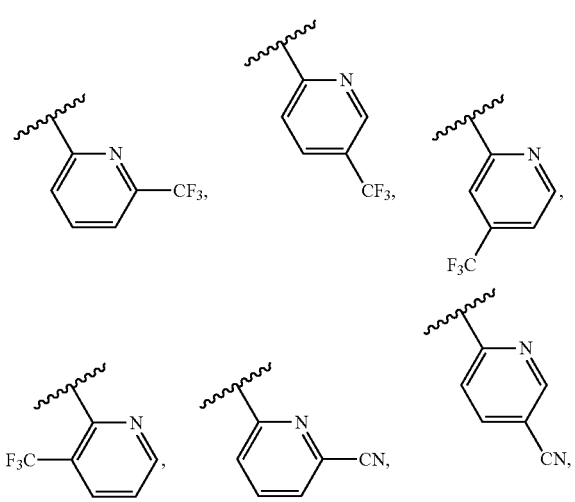
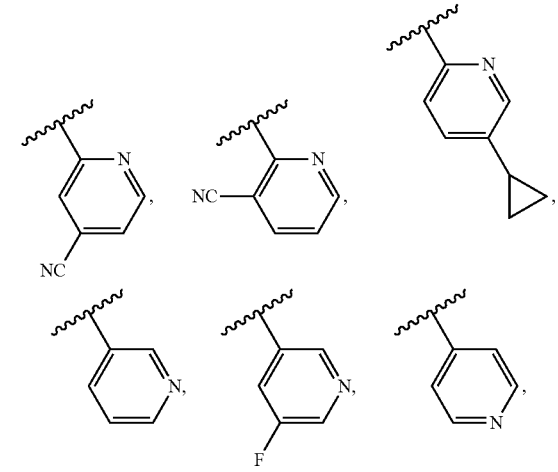
-continued
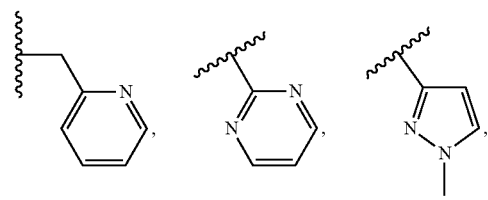
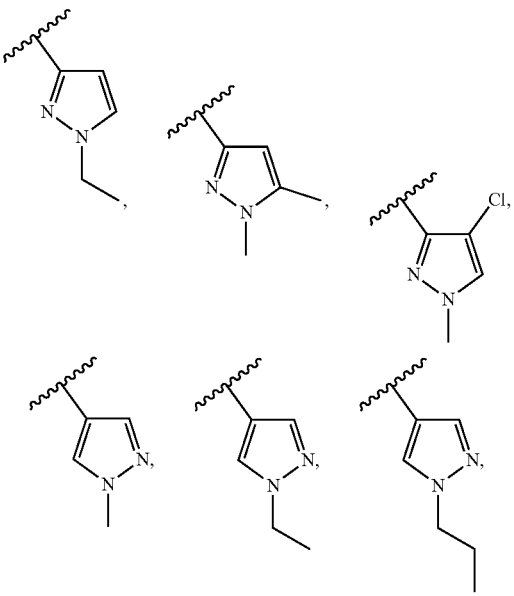
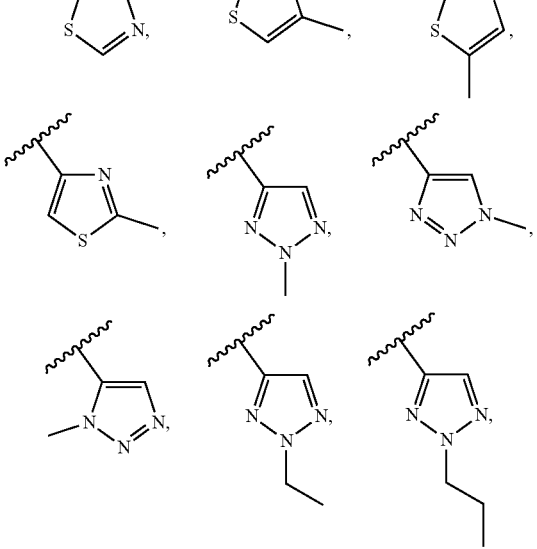

-continued

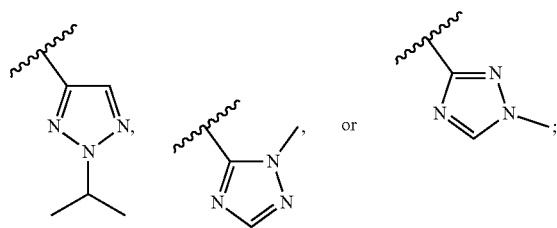

each $R^5$-$L^5$-group is methyl, —C≡CCH$_3$, methoxy, —CH$_2$OH, oxo,

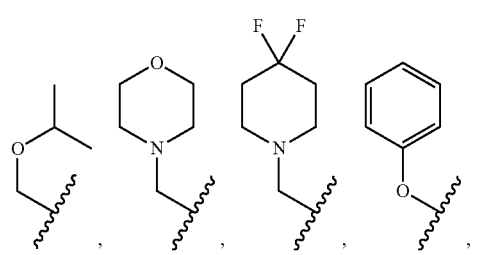

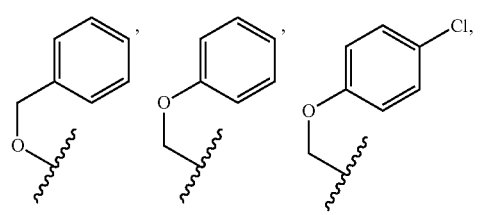

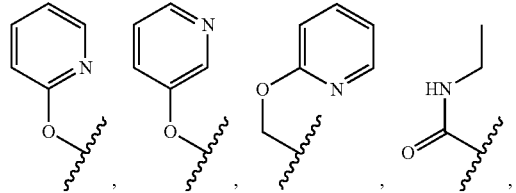

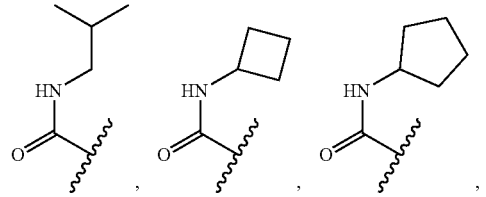

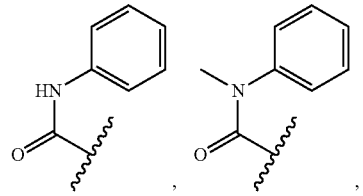

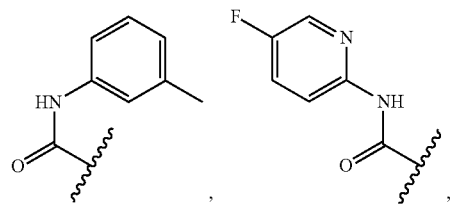

-continued

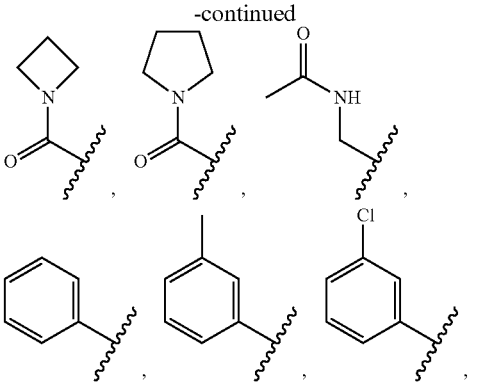

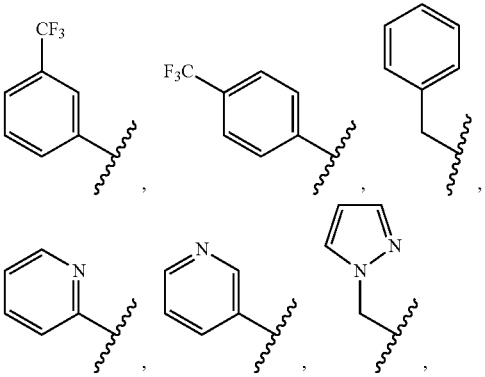

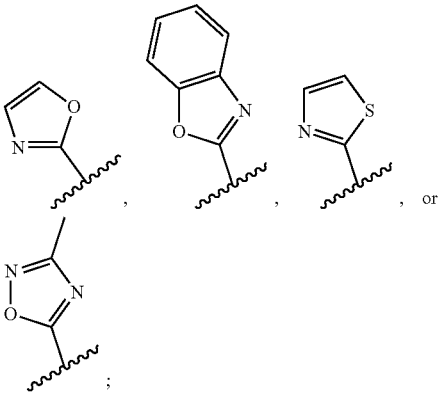

each $R^6$ is independently —OMe, —OEt, hydroxy, or F;
subscript m is 0 or 1; and
subscript n is 1.

In some embodiments, the compound of Formula I, Ia, Ib, Ib-1, Ib-2, Ic, or Ic-1, or a pharmaceutically acceptable salt thereof, is the compound wherein
$R^1$ is

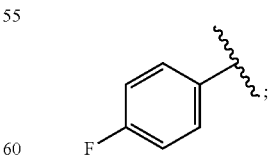

$A^1$, $A^2$ and $A^4$ are each =CH—;
$A^3$ is =CH— or =C(Me)-;
Ring A is a C$_3$ cycloalkyl or a C$_5$ cycloalkyl;
$L^2$ is —C(O)—, —C(O)O—, —S(O)$_2$— or —S(O)$_2$N(R$^3$)—.

$R^3$ is hydrogen or methyl;
$R^4$ is methyl, ethyl, iso-propyl, iso-butyl, t-butyl, methoxymethyl, methoxyethyl,
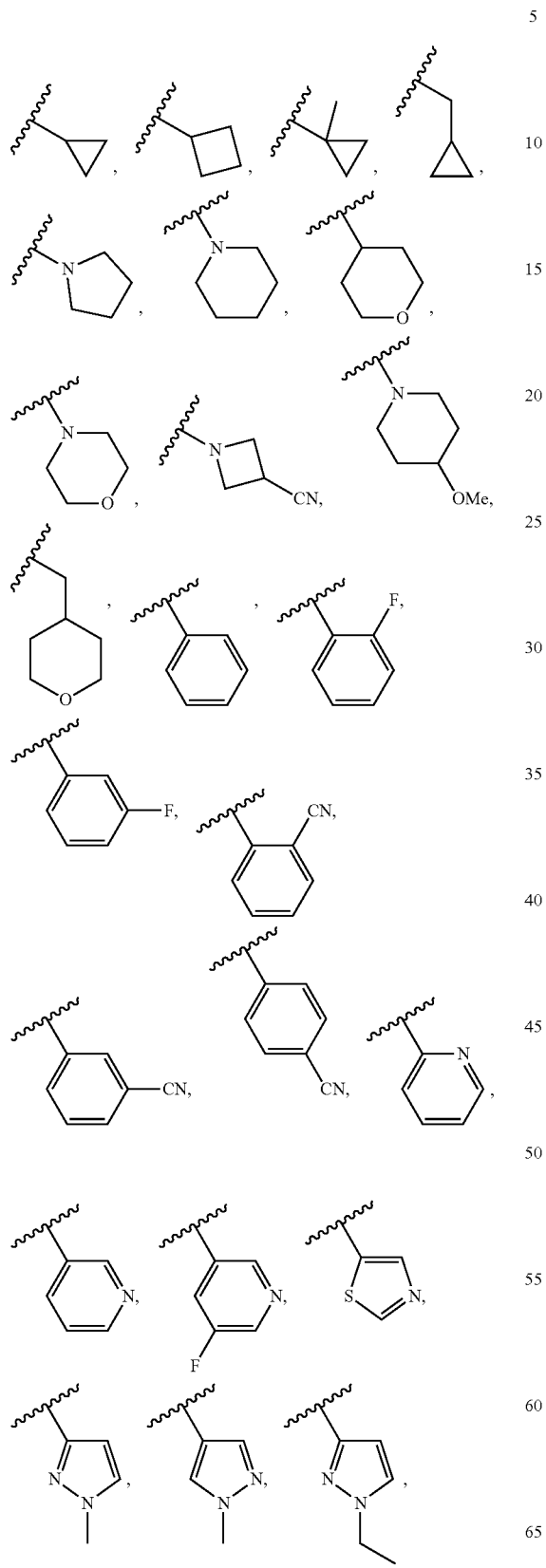
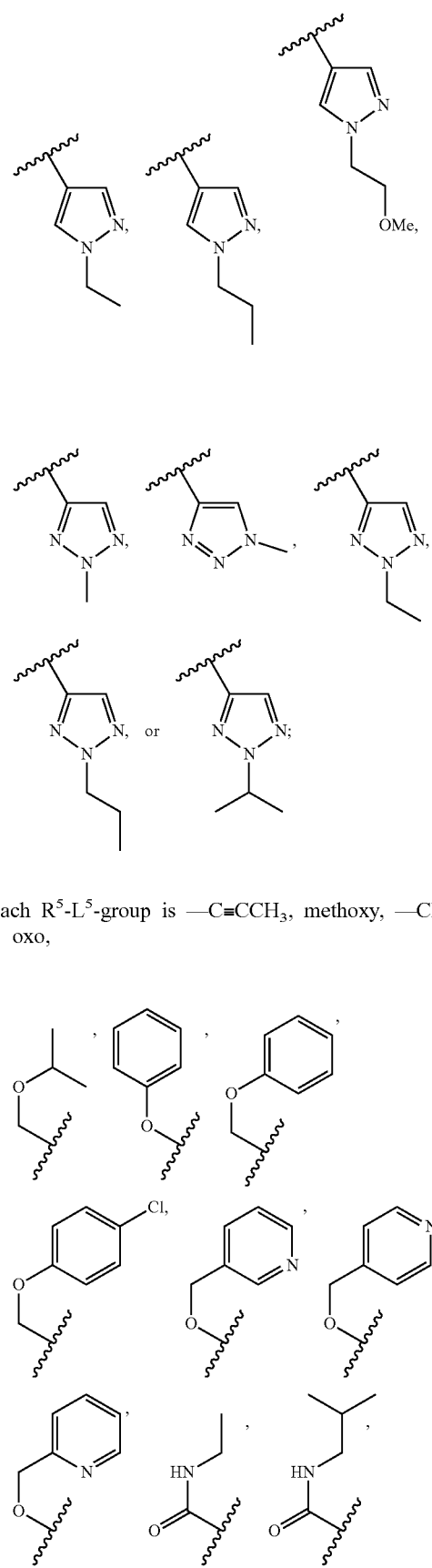
each $R^5$-$L^5$-group is —C≡CCH$_3$, methoxy, —CH$_2$OH, oxo,

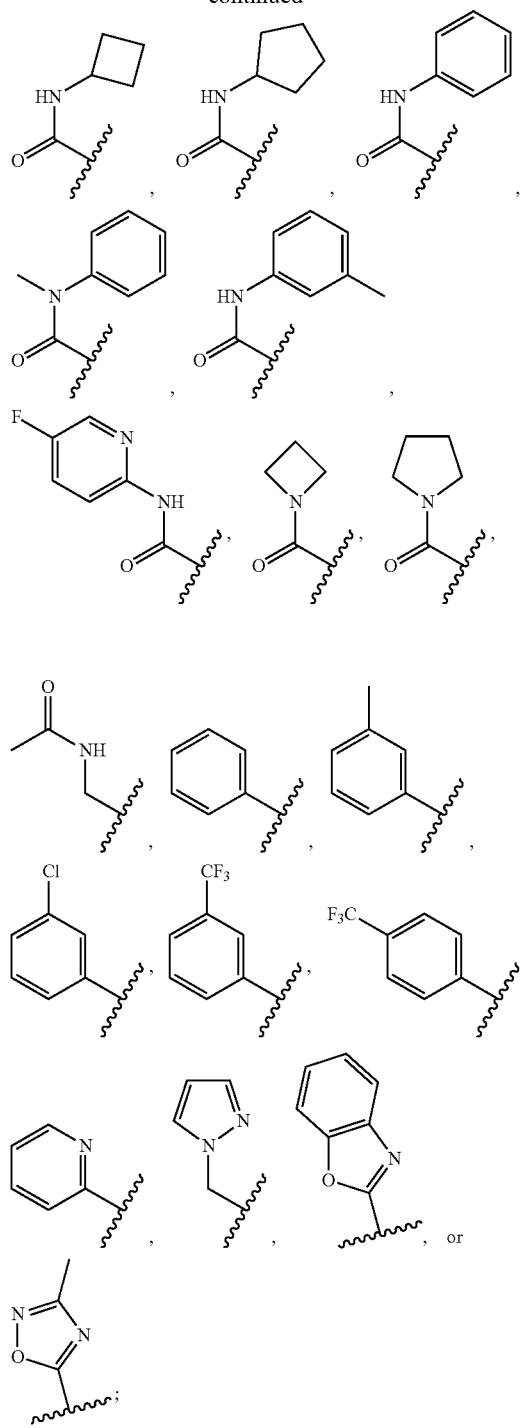
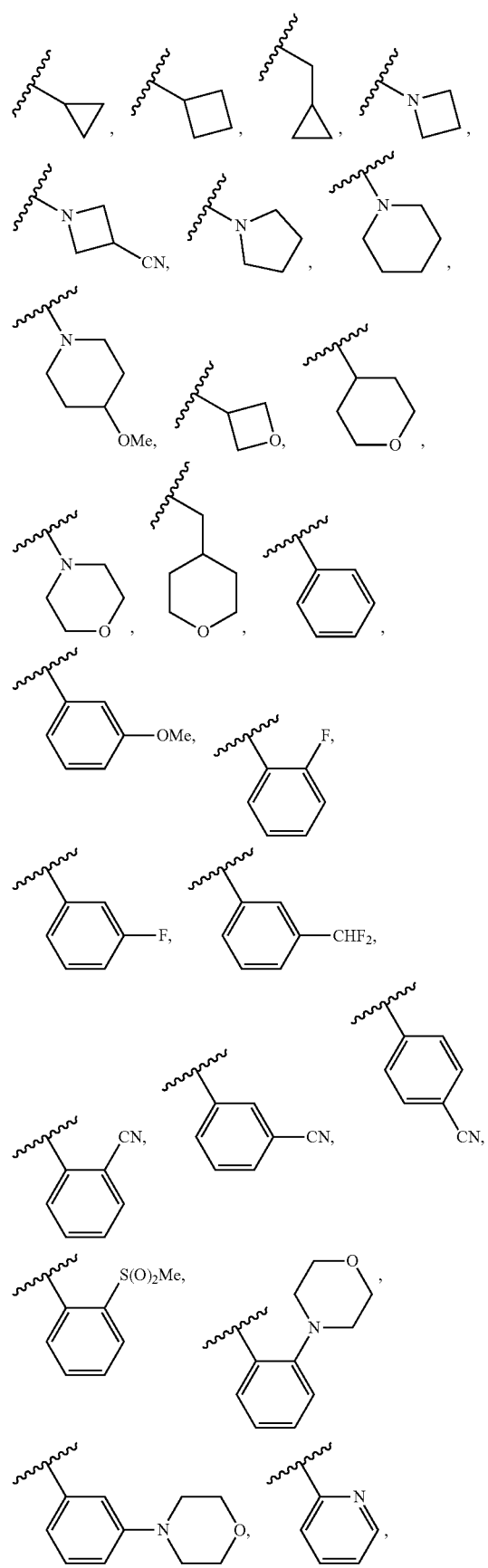
each R is independently —OMe, —OEt, hydroxy, or F; and
subscript m is 0 or 1; and
subscript n is 1.
In some embodiments, the compound of Formula I, Ia, Ib, Ib-1, Ib-2, Ic, or Ic-1, or a pharmaceutically acceptable salt thereof, is the compound wherein
$R^4$ is methyl, ethyl, iso-propyl, iso-butyl, methoxymethyl, methoxyethyl, $CH_2(CH_2OCH_2)_2H$, -continued
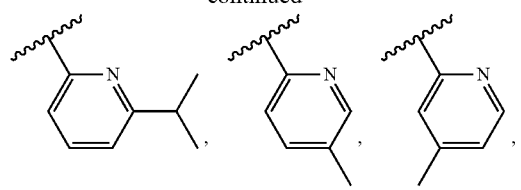
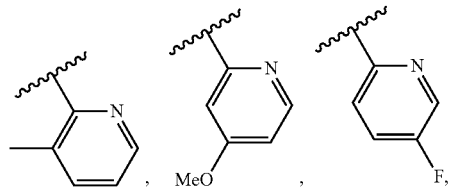
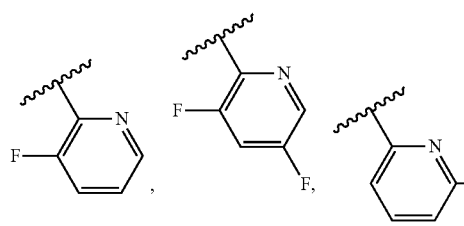
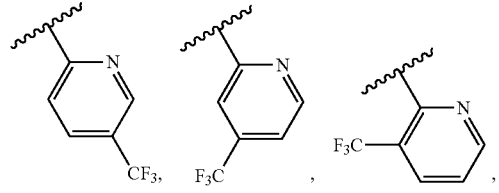
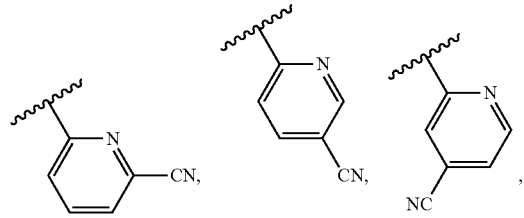
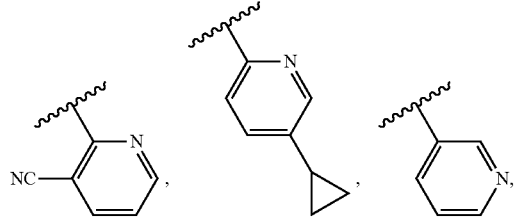
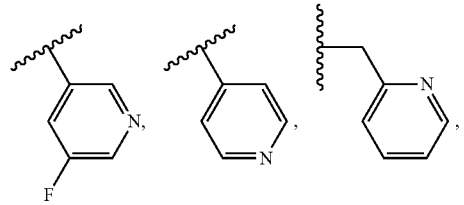
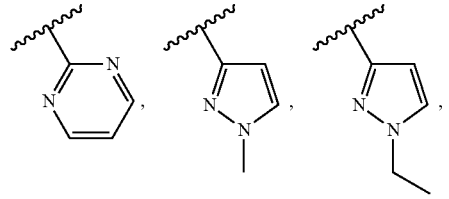
-continued
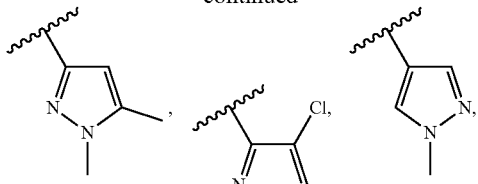
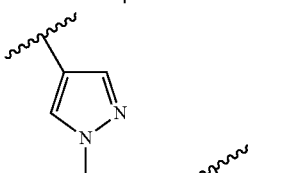
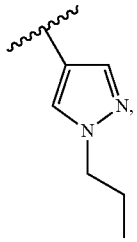
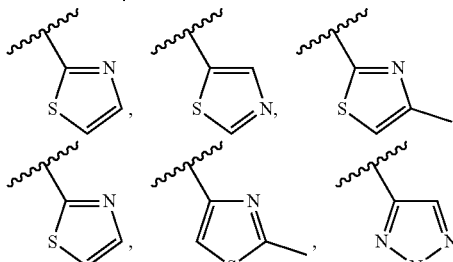
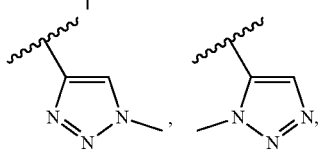
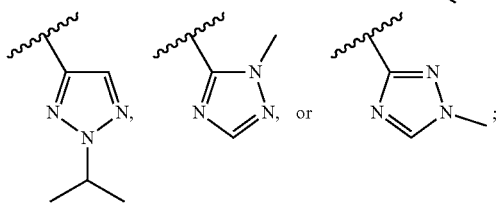
and
each R⁵-L⁵-group is methyl, —CH₂OH,
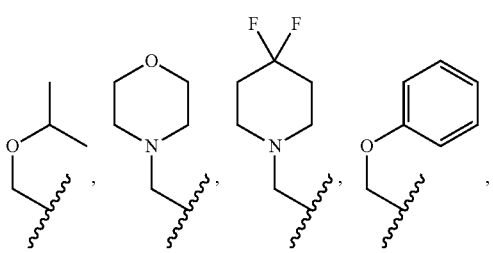

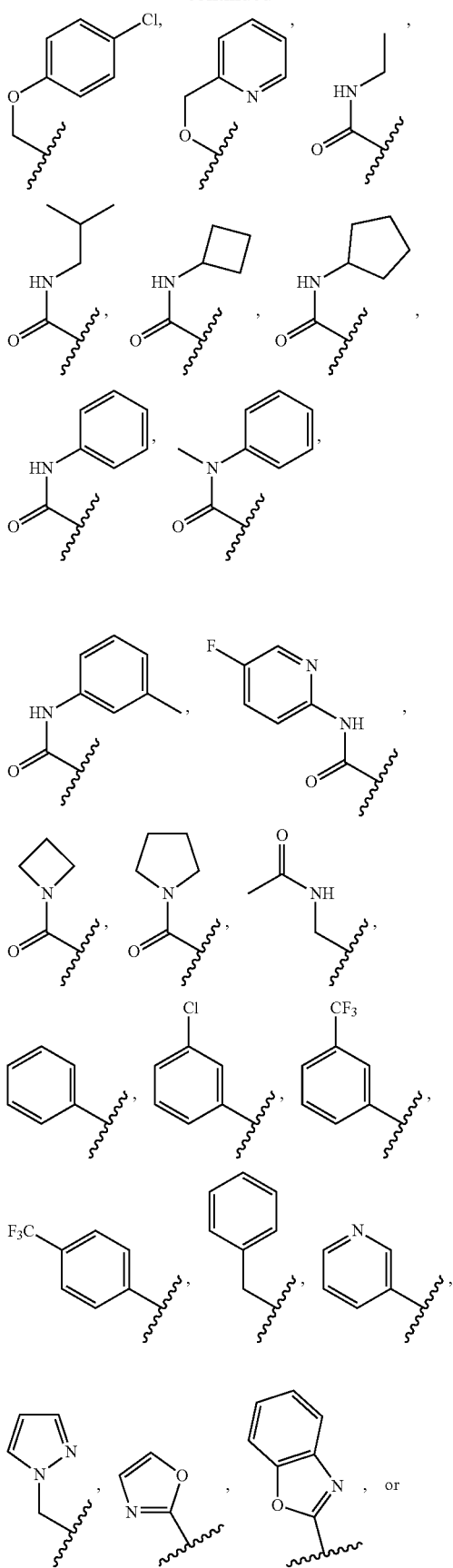
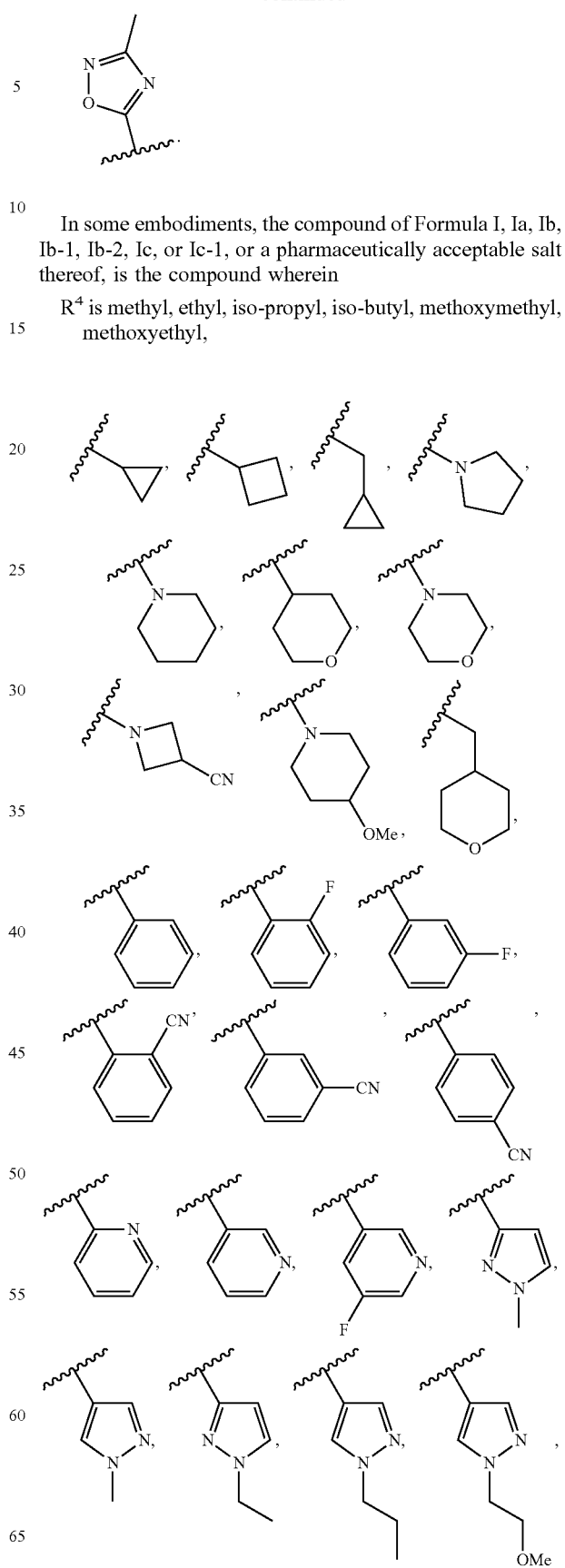
In some embodiments, the compound of Formula I, Ia, Ib, Ib-1, Ib-2, Ic, or Ic-1, or a pharmaceutically acceptable salt thereof, is the compound wherein
$R^4$ is methyl, ethyl, iso-propyl, iso-butyl, methoxymethyl, methoxyethyl, -continued
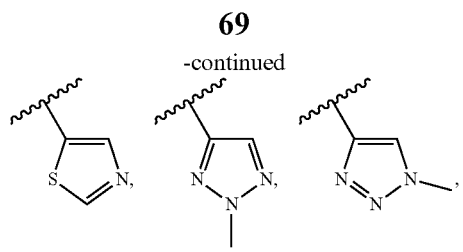
and
each $R^5$-$L^5$-group is —$CH_2OH$,
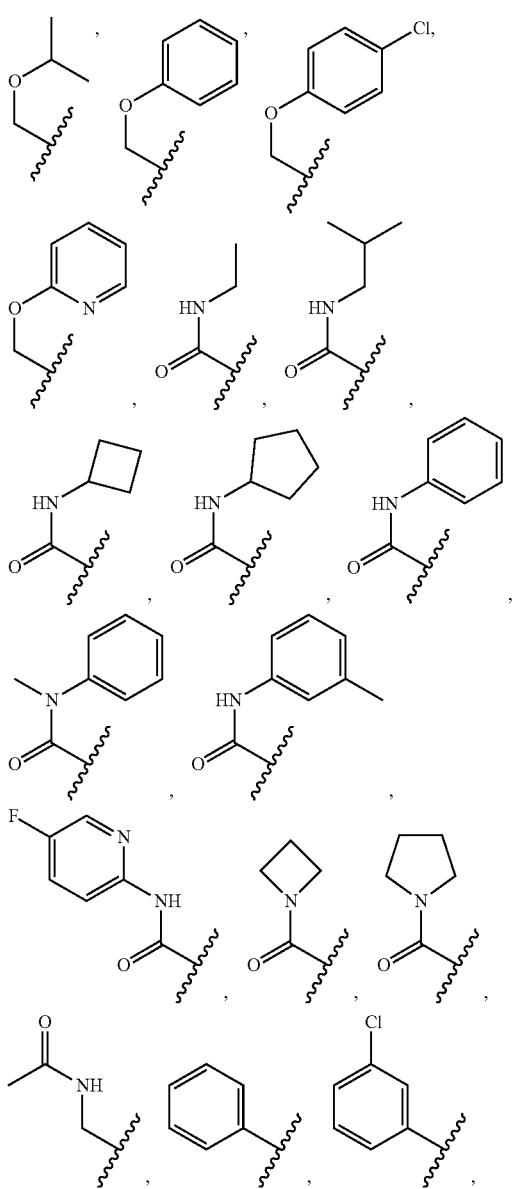
-continued
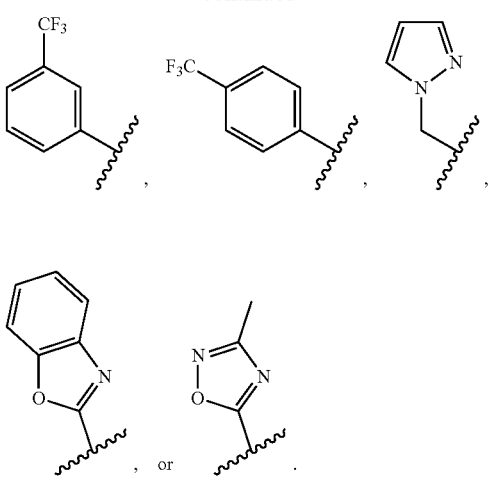
In some embodiments, the compound of Formula I, Ia, Ib, Ib-1, Ib-2, Ic, or Ic-1, or a pharmaceutically acceptable salt thereof, is the compound wherein
$R^4$ is methyl, iso-propyl, t-butyl, methoxyethyl,
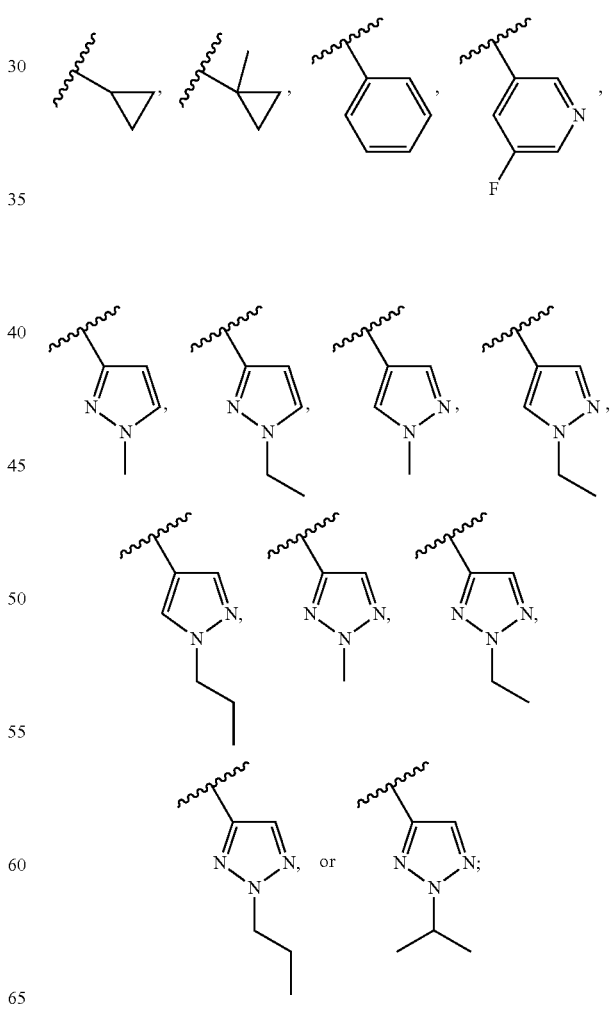

and each $R^5$-$L^5$-group is methoxy, —C≡CCH$_3$, oxo,

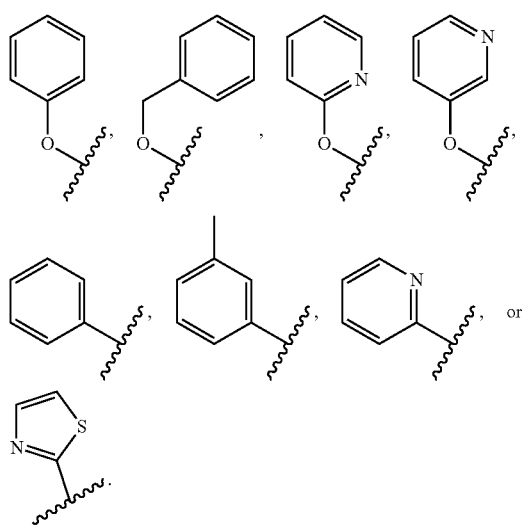

In some embodiments, the compound of Formula I, Ia, Ib, Ib-1, Ib-2, Ic, or Ic-1, or a pharmaceutically acceptable salt thereof, is the compound wherein $R^4$ is methyl, iso-propyl, t-butyl, methoxyethyl,

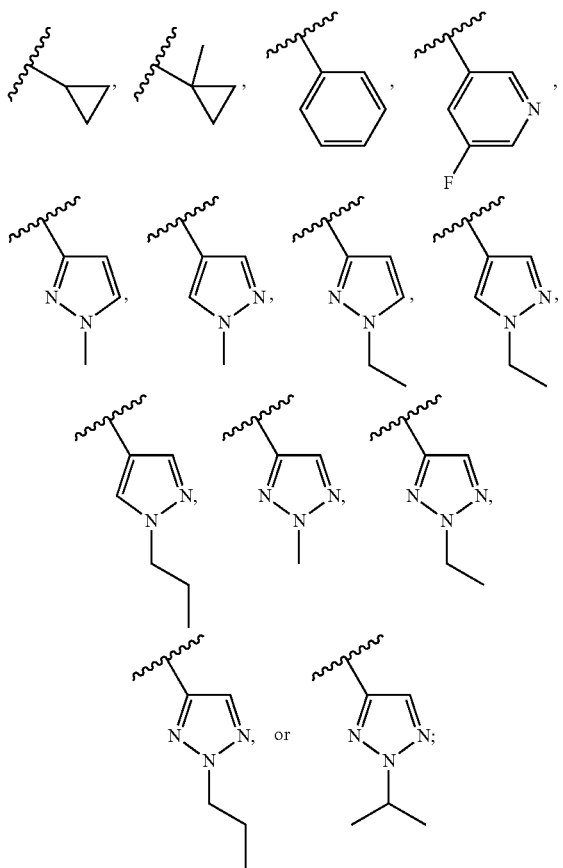

and each $R^5$-$L^5$-group is methoxy, —C≡CCH$_3$, oxo,

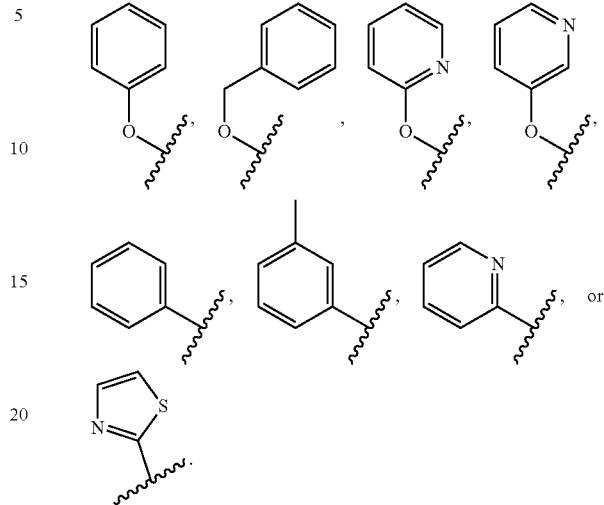

In some embodiments, the compound of Formula I, Ia, Ib, Ib-1, or Ib-2, or a pharmaceutically acceptable salt thereof, is a compound having the structure of Formula Id-1 or Id-2:

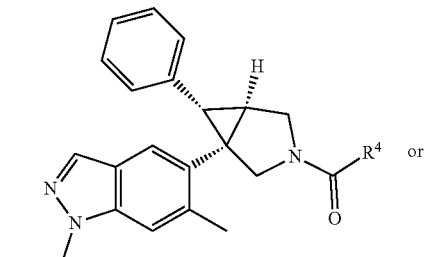

(Id-1)

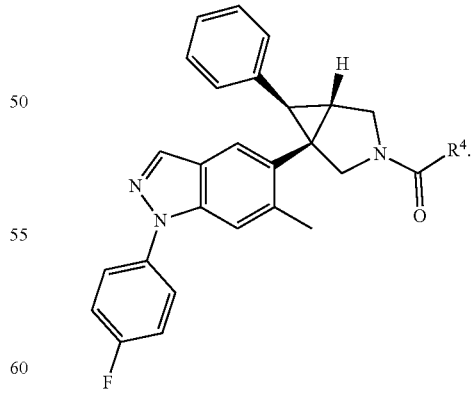

(Id-2)

In some embodiments, the compound of Formula I, Ia, Ib, Ib-1, Ib-2, Ic, Ic-1, Id-1, or Id-2, or a pharmaceutically acceptable salt thereof, is a compound wherein $R^4$ is $C_{6-12}$ aryl, or heteroaryl having 5 to 6 ring members and 1 to 4 heteroatoms each independently N, O or S, and wherein aryl and heteroaryl are independently substituted with 0 to 3 $R^{4a}$ groups; each $R^{4a}$ is independently $C_{1-3}$ alkyl, $C_{1-3}$ alkoxy, halogen, $C_{1-3}$ haloalkyl, —CN, —S(O)$_2R^{4b}$, $C_{3-6}$ cycloalkyl, and heterocycloalkyl, wherein each heterocycloalkyl independently has 5 to 6 ring members and 1 to 2 heteroatoms each independently N, O or S; and each $R^{4b}$ is $C_{1-3}$ alkyl.

In some embodiments, the compound of Formula I, Ia, Ib, Ib-1, Ib-2, Ic, Ic-1, Id-1, or Id-2, or a pharmaceutically acceptable salt thereof, is a compound wherein $R^4$ is phenyl, pyridine, pyridazine, pyrimidine, or pyrazine, substituted with 0 to 2 $R^{4a}$ groups; and each $R^{4a}$ is independently methyl, iso-propyl, methoxy, fluoro, —CHF$_2$, —CF$_3$, —CN, —S(O)$_2$Me, cyclopropyl, or morpholine.

In some embodiments, the compound of Formula I, Ia, Ib, Ib-1, Ib-2, Ic, Ic-1, Id-1, or Id-2, or a pharmaceutically acceptable salt thereof, is a compound wherein $R^4$ is phenyl or pyridine, substituted with 0 to 1 $R^{4a}$ groups; and $R^{4a}$ is —CN.

In some embodiments, the compound of Formula I, Ia, Ib, Ib-1, Ib-2, Ic, Ic-1, Id-1, or Id-2, or a pharmaceutically acceptable salt thereof, is a compound wherein $R^4$ is

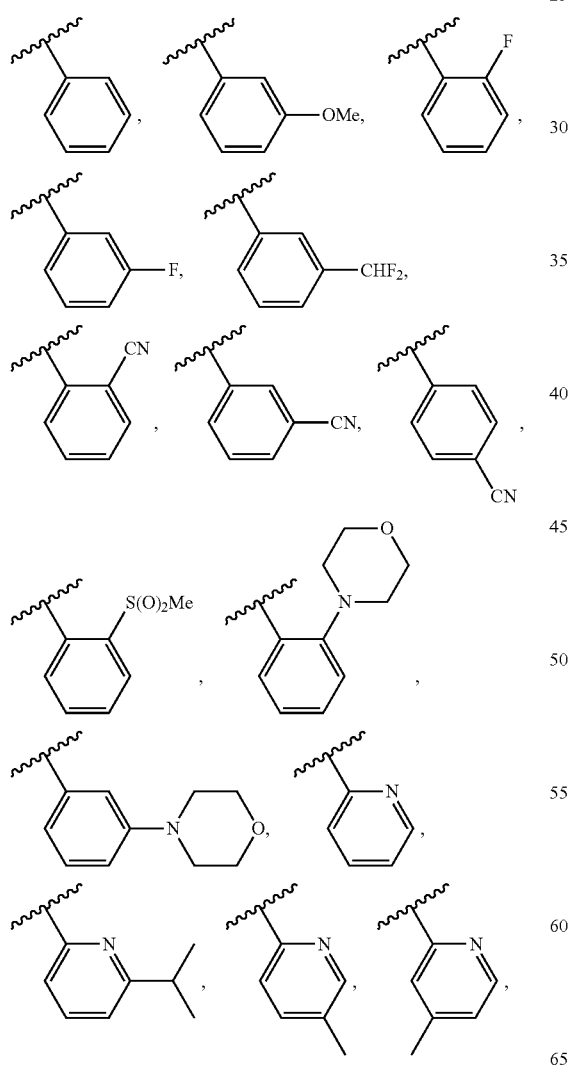

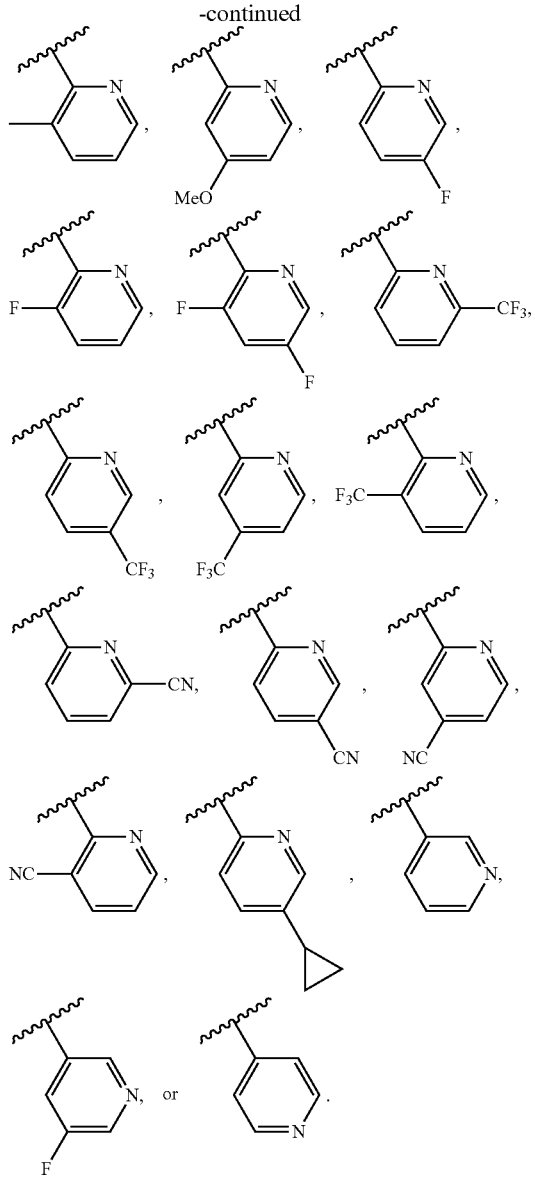

In some embodiments, the compound of Formula I, Ia, Ib, Ib-1, Ib-2, Ic, or Ic-1, or a pharmaceutically acceptable salt thereof, is a compound of Table 1A.

TABLE 1A

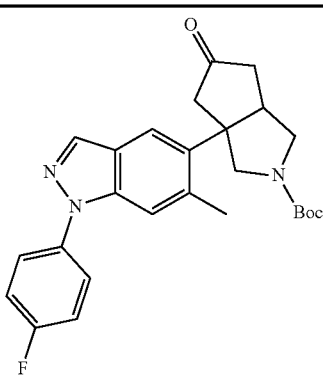

TABLE 1A-continued
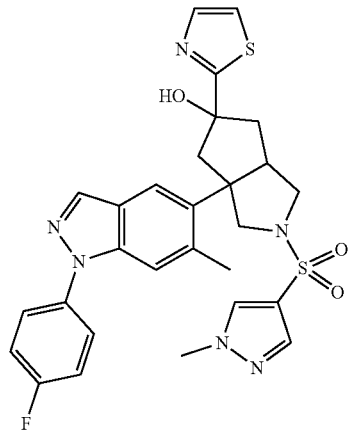 [SMILES: COC1(c2nccs2)CC2CN(S(=O)(=O)c3cnn(C)c3)CC2(c2cc3cnn(-c4ccc(F)cc4)c3cc2C)C1]
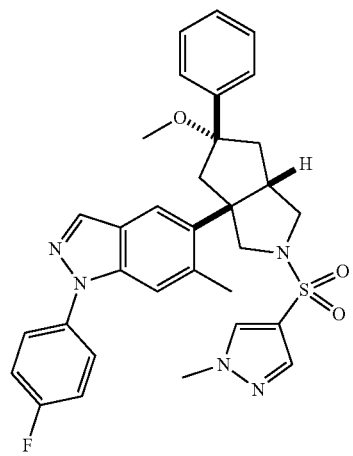
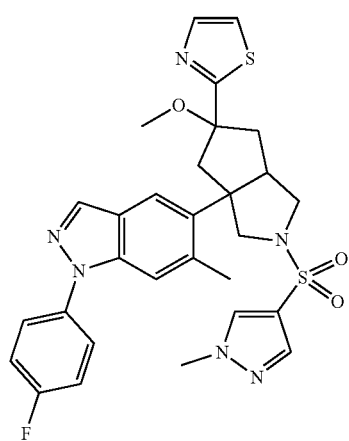
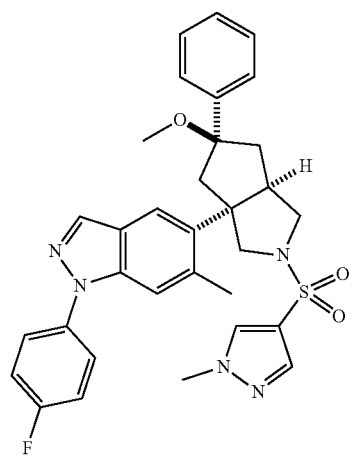
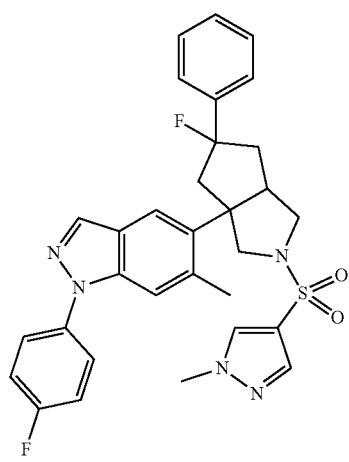
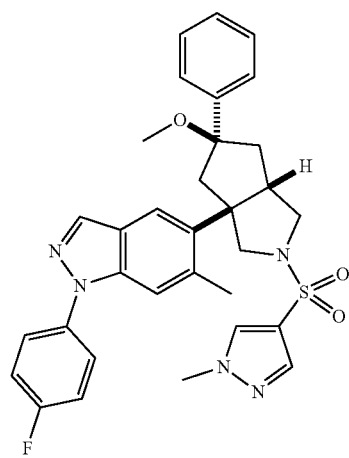

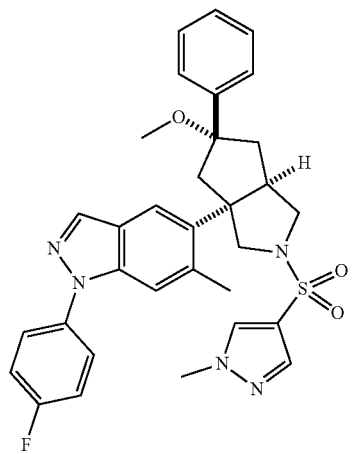
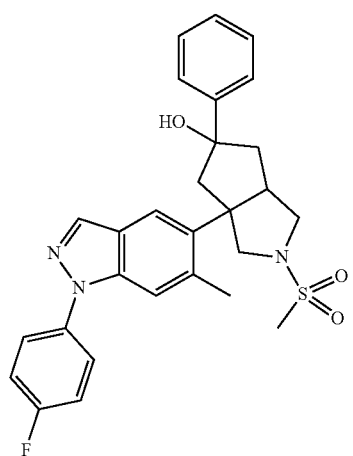 [SMILES: Cc1cc2c(cnn2-c2ccc(F)cc2)cc1C12CN(S(C)(=O)=O)CC1CC(O)(c1ccccc1)C2]
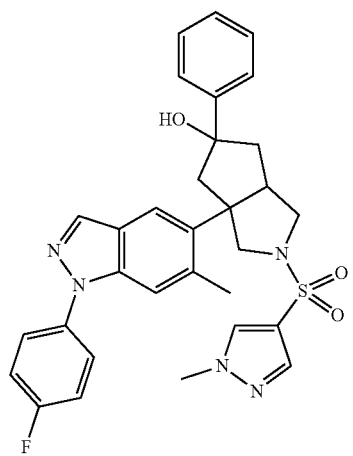 [SMILES: Cc1cc2c(cnn2-c2ccc(F)cc2)cc1C12CN(S(=O)(=O)c3cnn(C)c3)CC1CC(O)(c1ccccc1)C2]
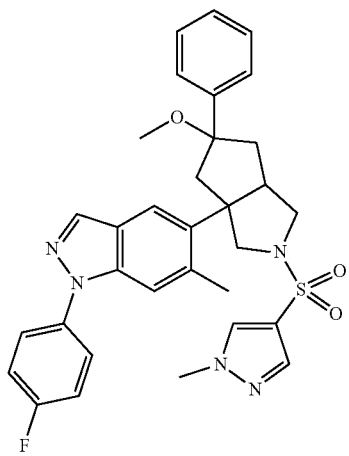 [SMILES: COC1(c2ccccc2)CC2CN(S(=O)(=O)c3cnn(C)c3)CC2(c2cc3cnn(-c4ccc(F)cc4)c3cc2C)C1]
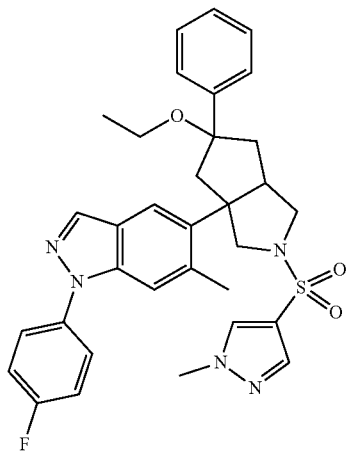 [SMILES: CCOC1(c2ccccc2)CC2CN(S(=O)(=O)c3cnn(C)c3)CC2(c2cc3cnn(-c4ccc(F)cc4)c3cc2C)C1]
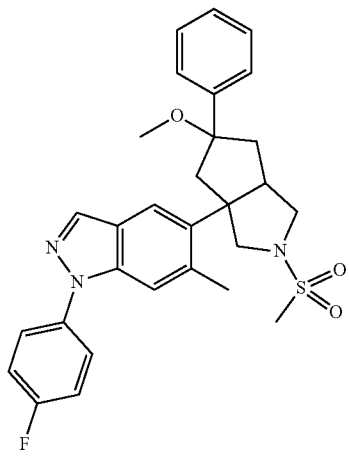 [SMILES: COC1(c2ccccc2)CC2CN(S(C)(=O)=O)CC2(c2cc3cnn(-c4ccc(F)cc4)c3cc2C)C1]

TABLE 1A-continued
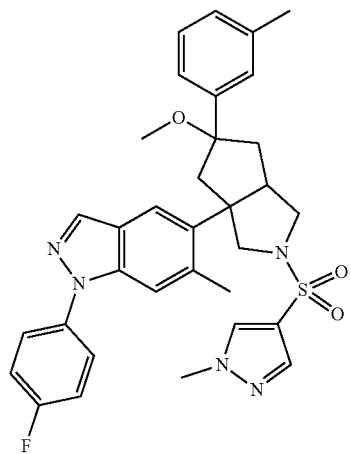 [SMILES: COC1(c2cccc(C)c2)CC2CN(S(=O)(=O)c3cnn(C)c3)CC2(c2cc3cnn(-c4ccc(F)cc4)c3cc2C)C1]
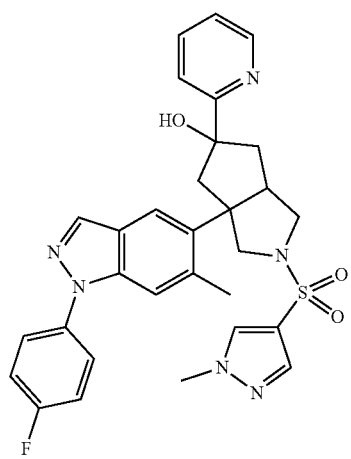 [SMILES: Cc1cc2c(cnn2-c2ccc(F)cc2)cc1C12CN(S(=O)(=O)c3cnn(C)c3)CC1CC(O)(c1ccccn1)C2]
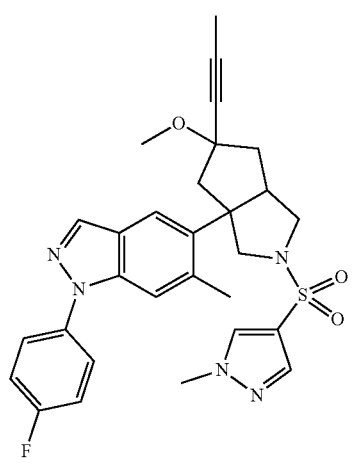 [SMILES: CC#CC1(OC)CC2CN(S(=O)(=O)c3cnn(C)c3)CC2(c2cc3cnn(-c4ccc(F)cc4)c3cc2C)C1]
TABLE 1A-continued
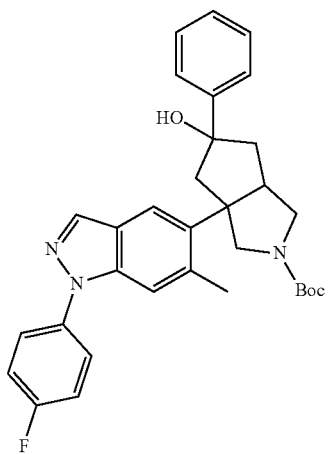 [SMILES: Cc1cc2c(cnn2-c2ccc(F)cc2)cc1C12CN(C(=O)OC(C)(C)C)CC1CC(O)(c1ccccc1)C2]
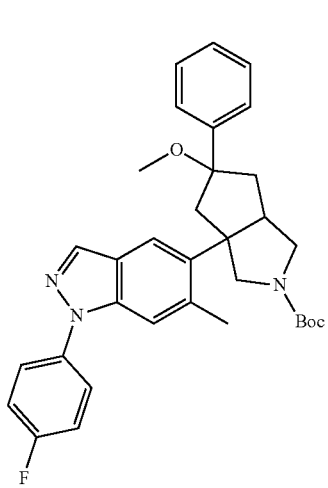 [SMILES: COC1(c2ccccc2)CC2CN(C(=O)OC(C)(C)C)CC2(c2cc3cnn(-c4ccc(F)cc4)c3cc2C)C1]
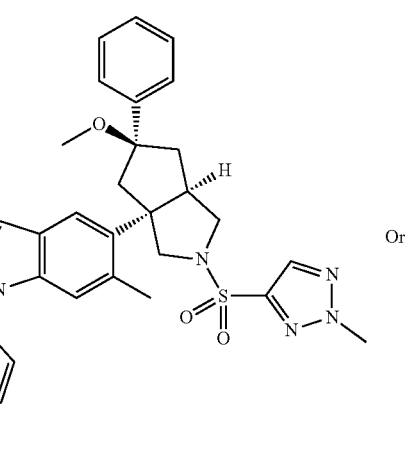
Or TABLE 1A-continued
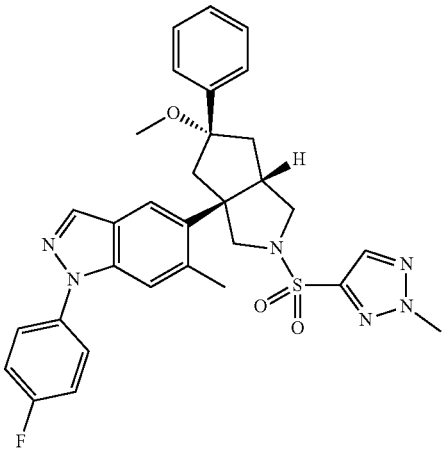 [SMILES: CO[C@]1(c2ccccc2)C[C@@H]2CN(S(=O)(=O)c3cnn(C)n3)C[C@]2(c2cc3cnn(-c4ccc(F)cc4)c3cc2C)C1]
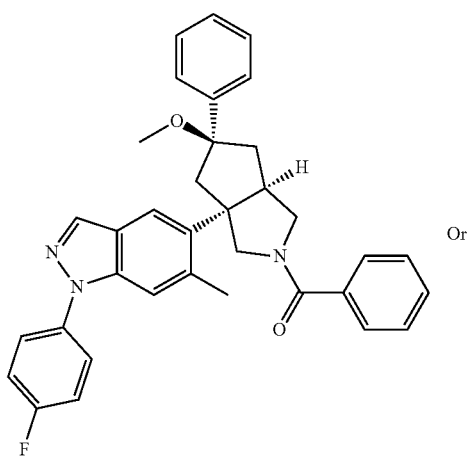 [SMILES: CO[C@@]1(c2ccccc2)C[C@H]2CN(C(=O)c3ccccc3)C[C@@]2(c2cc3cnn(-c4ccc(F)cc4)c3cc2C)C1]
Or
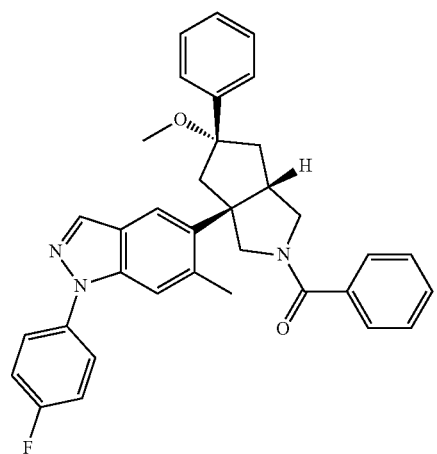 [SMILES: CO[C@]1(c2ccccc2)C[C@@H]2CN(C(=O)c3ccccc3)C[C@]2(c2cc3cnn(-c4ccc(F)cc4)c3cc2C)C1]
TABLE 1A-continued
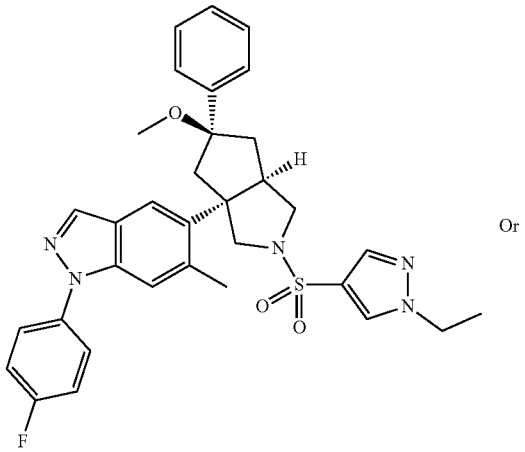 [SMILES: CCn1cc(S(=O)(=O)N2C[C@@H]3C[C@@](OC)(c4ccccc4)C[C@]3(c3cc4cnn(-c5ccc(F)cc5)c4cc3C)C2)cn1]
Or
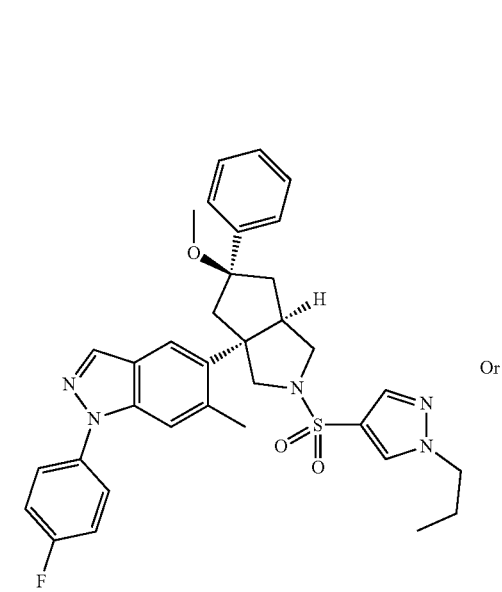 [SMILES: CCCn1cc(S(=O)(=O)N2C[C@@H]3C[C@@](OC)(c4ccccc4)C[C@]3(c3cc4cnn(-c5ccc(F)cc5)c4cc3C)C2)cn1]
Or TABLE 1A-continued
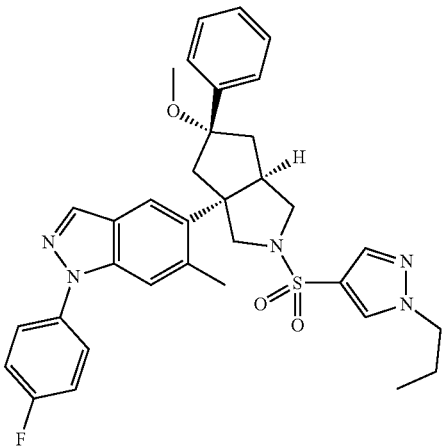 [SMILES: CCCn1cc(S(=O)(=O)N2C[C@@H]3C[C@](OC)(c4ccccc4)C[C@]3(c3cc4cnn(-c5ccc(F)cc5)c4cc3C)C2)cn1]
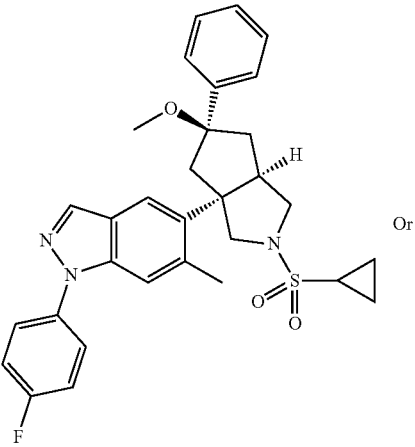
Or
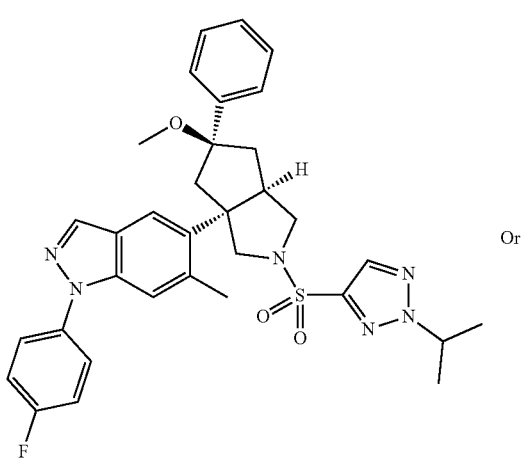 [SMILES: CO[C@@]1(c2ccccc2)C[C@H]2CN(S(=O)(=O)c3cnn(C(C)C)n3)C[C@@]2(c2cc3cnn(-c4ccc(F)cc4)c3cc2C)C1]
Or
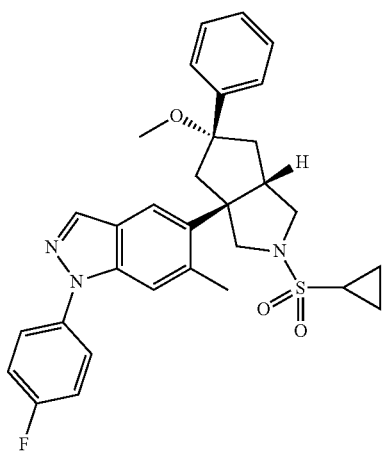
Or
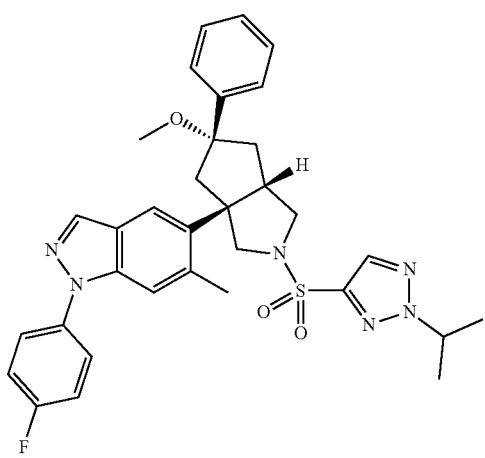 [SMILES: CO[C@]1(c2ccccc2)C[C@@H]2CN(S(=O)(=O)c3cnn(C(C)C)n3)C[C@]2(c2cc3cnn(-c4ccc(F)cc4)c3cc2C)C1]
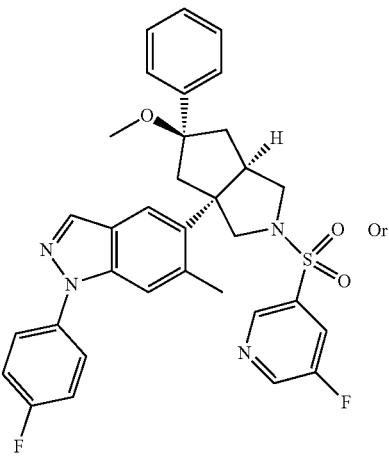 [SMILES: CO[C@@]1(c2ccccc2)C[C@H]2CN(S(=O)(=O)c3cncc(F)c3)C[C@@]2(c2cc3cnn(-c4ccc(F)cc4)c3cc2C)C1]
Or TABLE 1A-continued
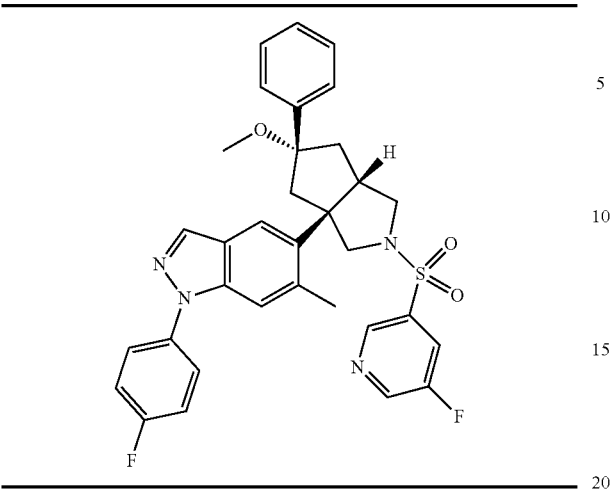
In some embodiments, the compound of Formula I, Ia, Ib, Ib-1, Ib-2, Ic, or Ic-1, or a pharmaceutically acceptable salt thereof, is a compound of Table 11B.
TABLE 1B
TABLE 1B-continued
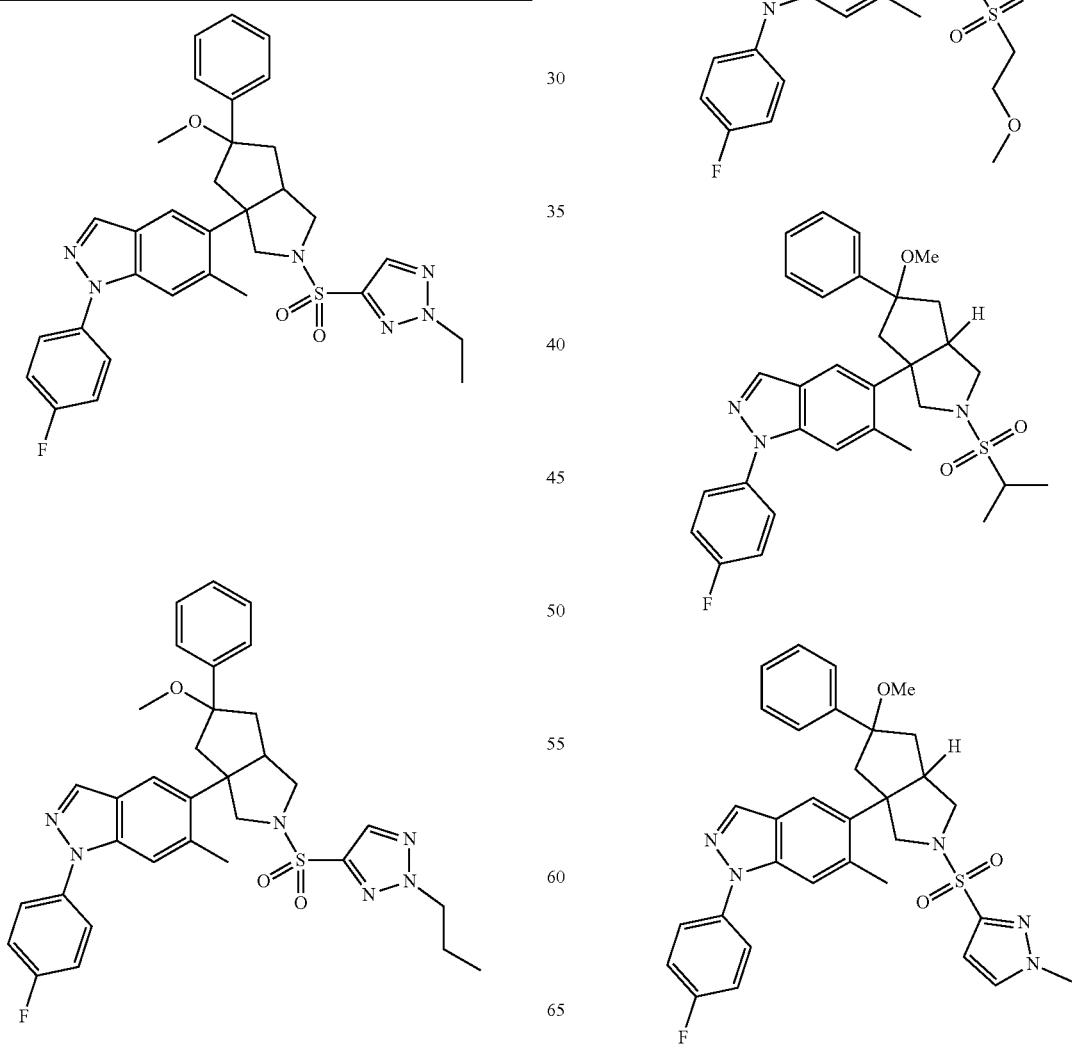

TABLE 1B-continued
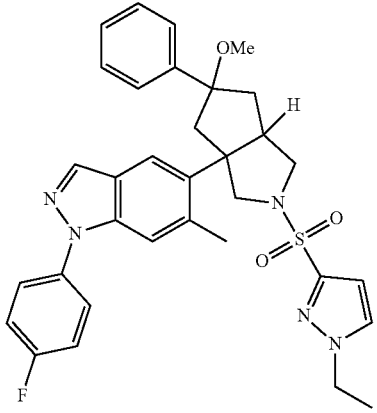 [SMILES: CCn1ccc(S(=O)(=O)N2CC3CC(OC)(c4ccccc4)CC3(c3cc4cnn(-c5ccc(F)cc5)c4cc3C)C2)n1]
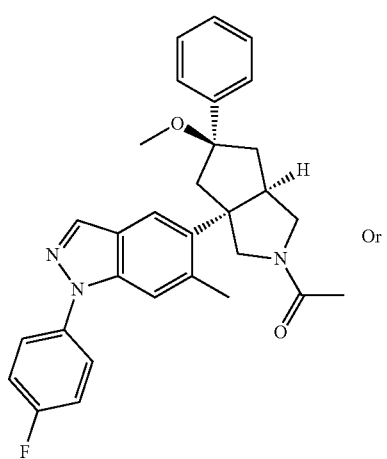 [SMILES: CO[C@@]1(c2ccccc2)C[C@H]2CN(C(C)=O)C[C@@]2(c2cc3cnn(-c4ccc(F)cc4)c3cc2C)C1]
Or
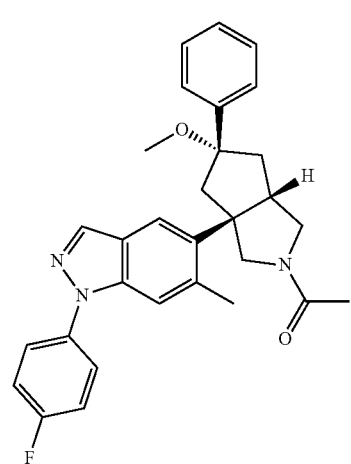 [SMILES: CO[C@]1(c2ccccc2)C[C@@H]2CN(C(C)=O)C[C@]2(c2cc3cnn(-c4ccc(F)cc4)c3cc2C)C1]
TABLE 1B-continued
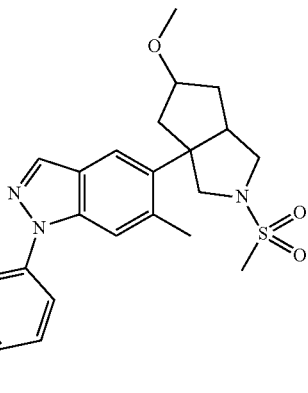
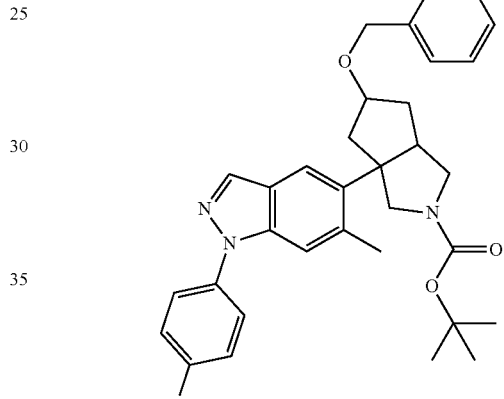
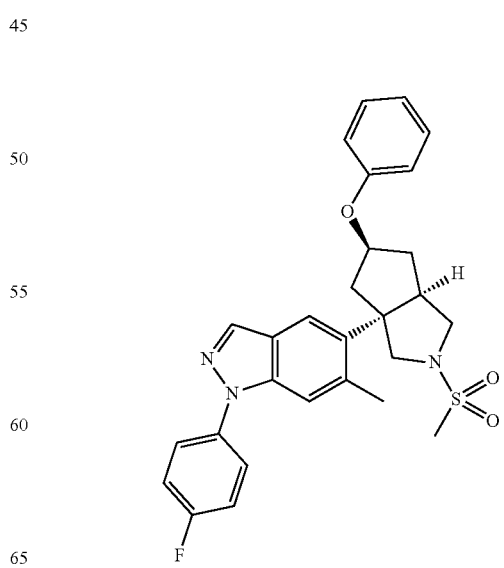

TABLE 1B-continued
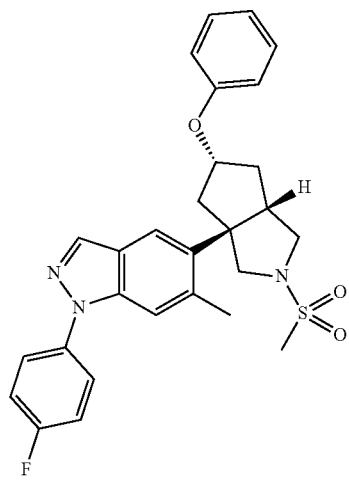 [SMILES: Cc1cc2c(cnn2-c2ccc(F)cc2)cc1[C@@]12C[C@H](Oc3ccccc3)C[C@@H]1CN(S(C)(=O)=O)C2]
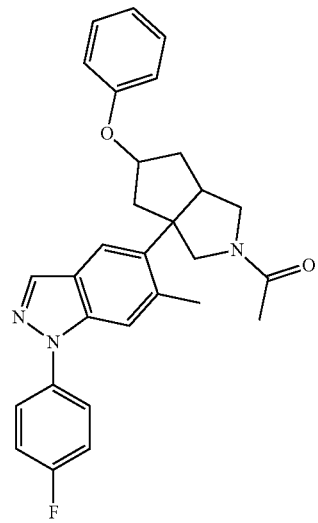 [SMILES: CC(=O)N1CC2CC(Oc3ccccc3)CC2(c2cc3cnn(-c4ccc(F)cc4)c3cc2C)C1]
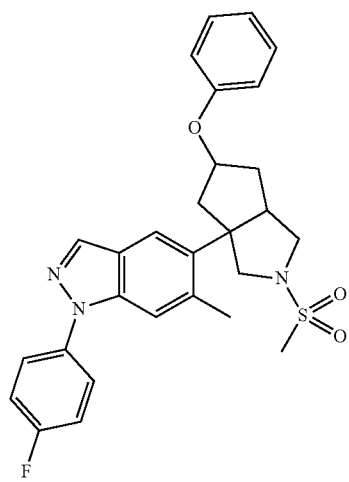
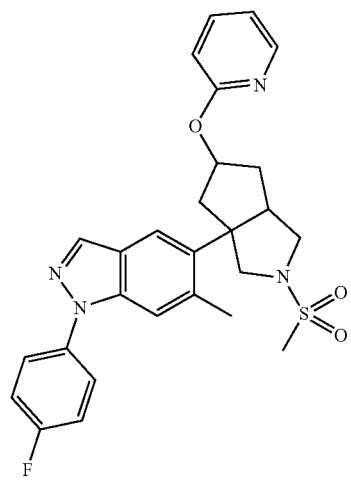 [SMILES: Cc1cc2c(cnn2-c2ccc(F)cc2)cc1C12CC(Oc3ccccn3)CC1CN(S(C)(=O)=O)C2]
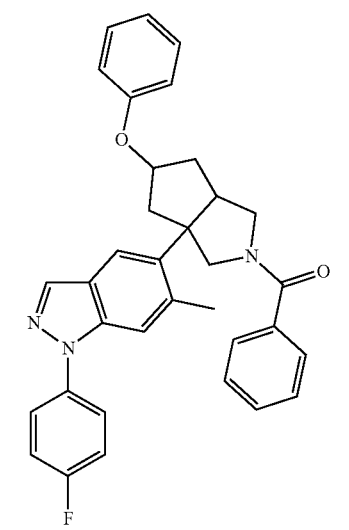
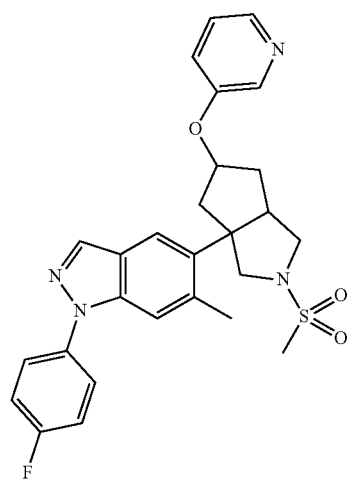 [SMILES: Cc1cc2c(cnn2-c2ccc(F)cc2)cc1C12CC(Oc3cccnc3)CC1CN(S(C)(=O)=O)C2]

TABLE 1B-continued
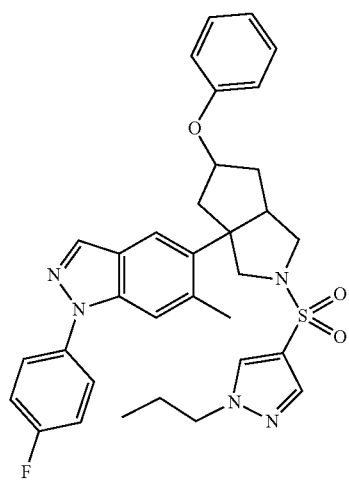 [SMILES: CCCn1cc(S(=O)(=O)N2CC3CC(Oc4ccccc4)CC3(c3cc4cnn(-c5ccc(F)cc5)c4cc3C)C2)cn1]
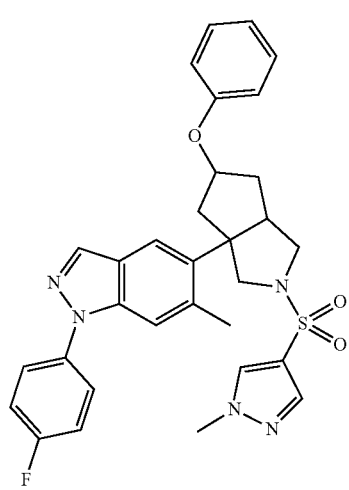 [SMILES: Cc1cc2c(cnn2-c2ccc(F)cc2)cc1C12CC(Oc3ccccc3)CC1CN(S(=O)(=O)c1cnn(C)c1)C2]
TABLE 1B-continued
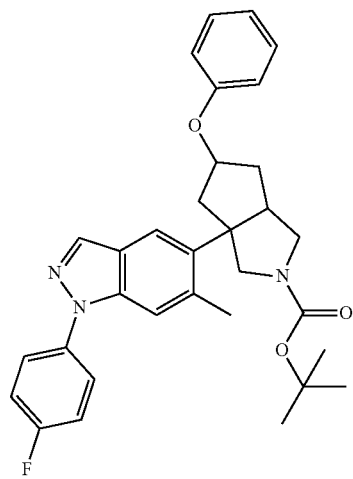 [SMILES: Cc1cc2c(cnn2-c2ccc(F)cc2)cc1C12CC(Oc3ccccc3)CC1CN(C(=O)OC(C)(C)C)C2]
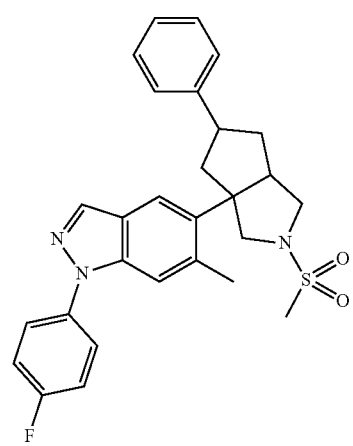 [SMILES: Cc1cc2c(cnn2-c2ccc(F)cc2)cc1C12CC(c3ccccc3)CC1CN(S(C)(=O)=O)C2]
In some embodiments, the compound of Formula L, Ia, Ib, Ib-1, Ib-2, Ic, or Ic-1, or a pharmaceutically acceptable salt thereof, is a compound of Table 1C.
TABLE 1C
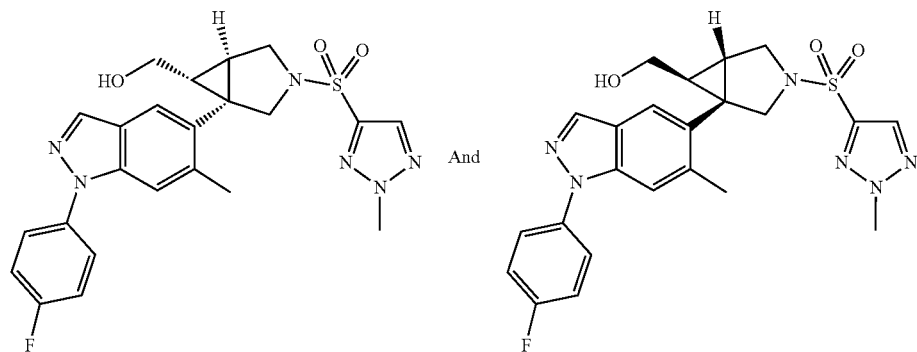 [SMILES: Cc1cc2c(cnn2-c2ccc(F)cc2)cc1[C@@]12CN(S(=O)(=O)c3cnn(C)n3)C[C@@H]1[C@H]2CO ; Cc1cc2c(cnn2-c2ccc(F)cc2)cc1[C@]12CN(S(=O)(=O)c3cnn(C)n3)C[C@H]1[C@@H]2CO]

TABLE 1C-continued
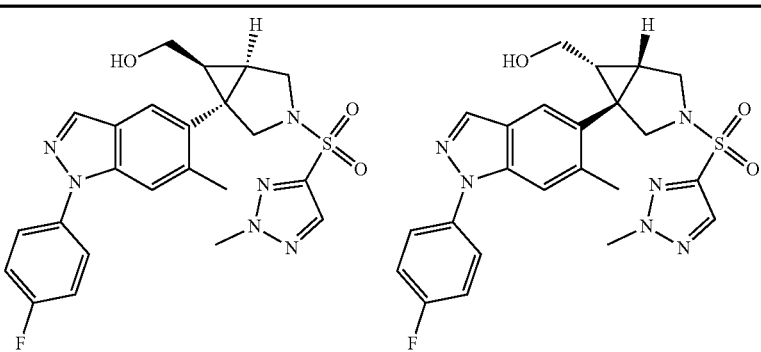
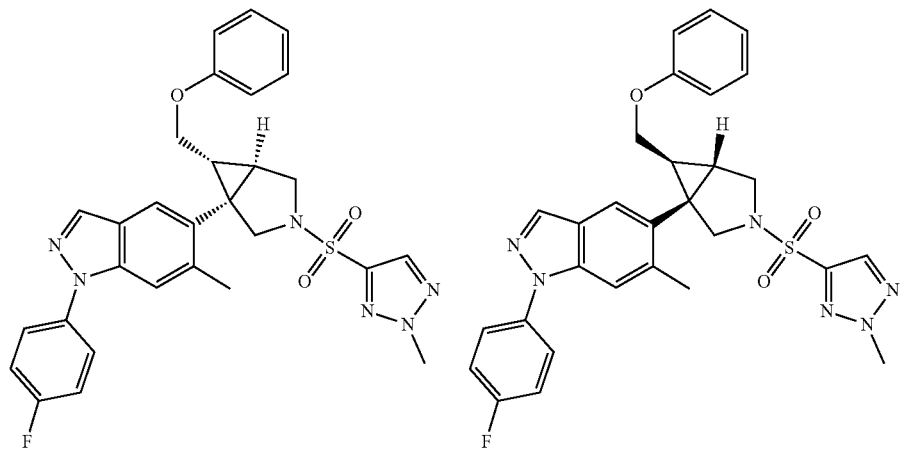
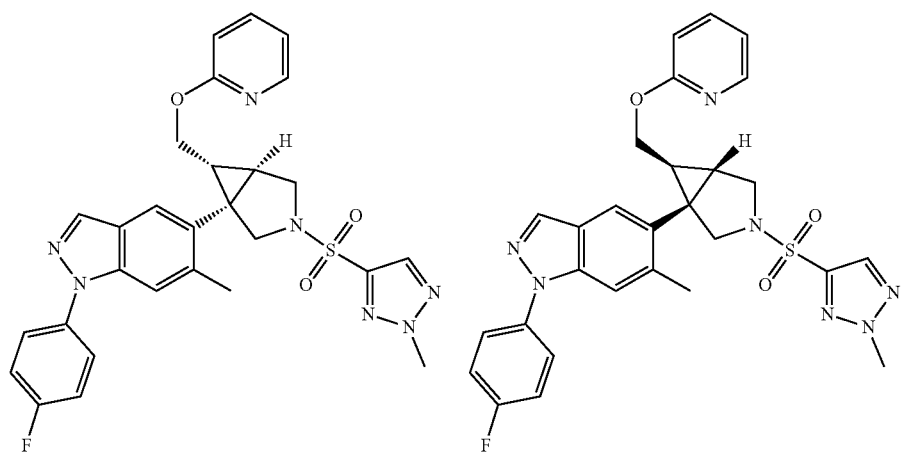

TABLE 1C-continued
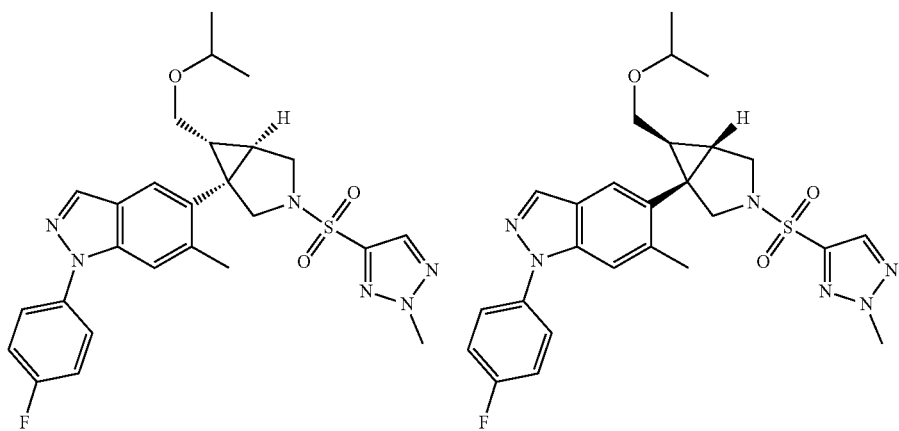
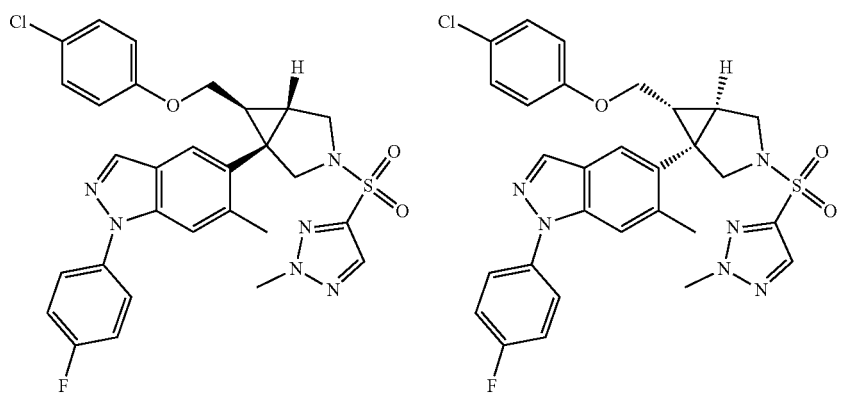 [SMILES: Cc1cc2c(cnn2-c2ccc(F)cc2)cc1[C@]12CN(S(=O)(=O)c3cnn(C)n3)C[C@H]1[C@@H]2COc1ccc(Cl)cc1 ; Cc1cc2c(cnn2-c2ccc(F)cc2)cc1[C@@]12CN(S(=O)(=O)c3cnn(C)n3)C[C@@H]1[C@H]2COc1ccc(Cl)cc1]
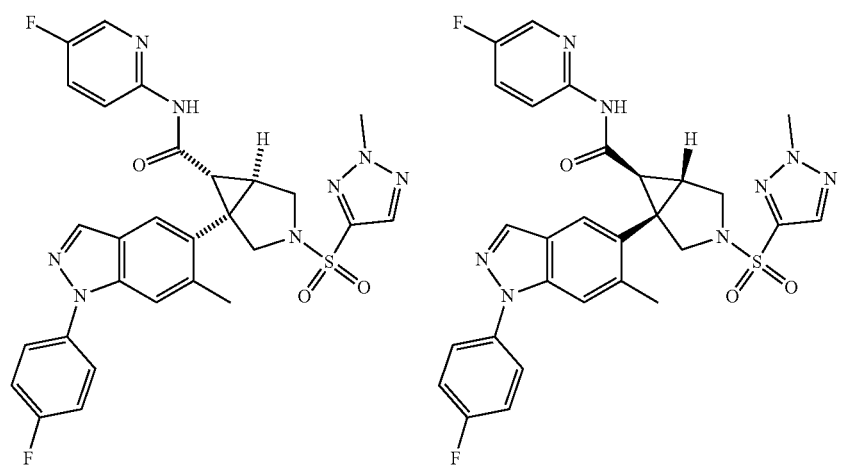

TABLE 1C-continued
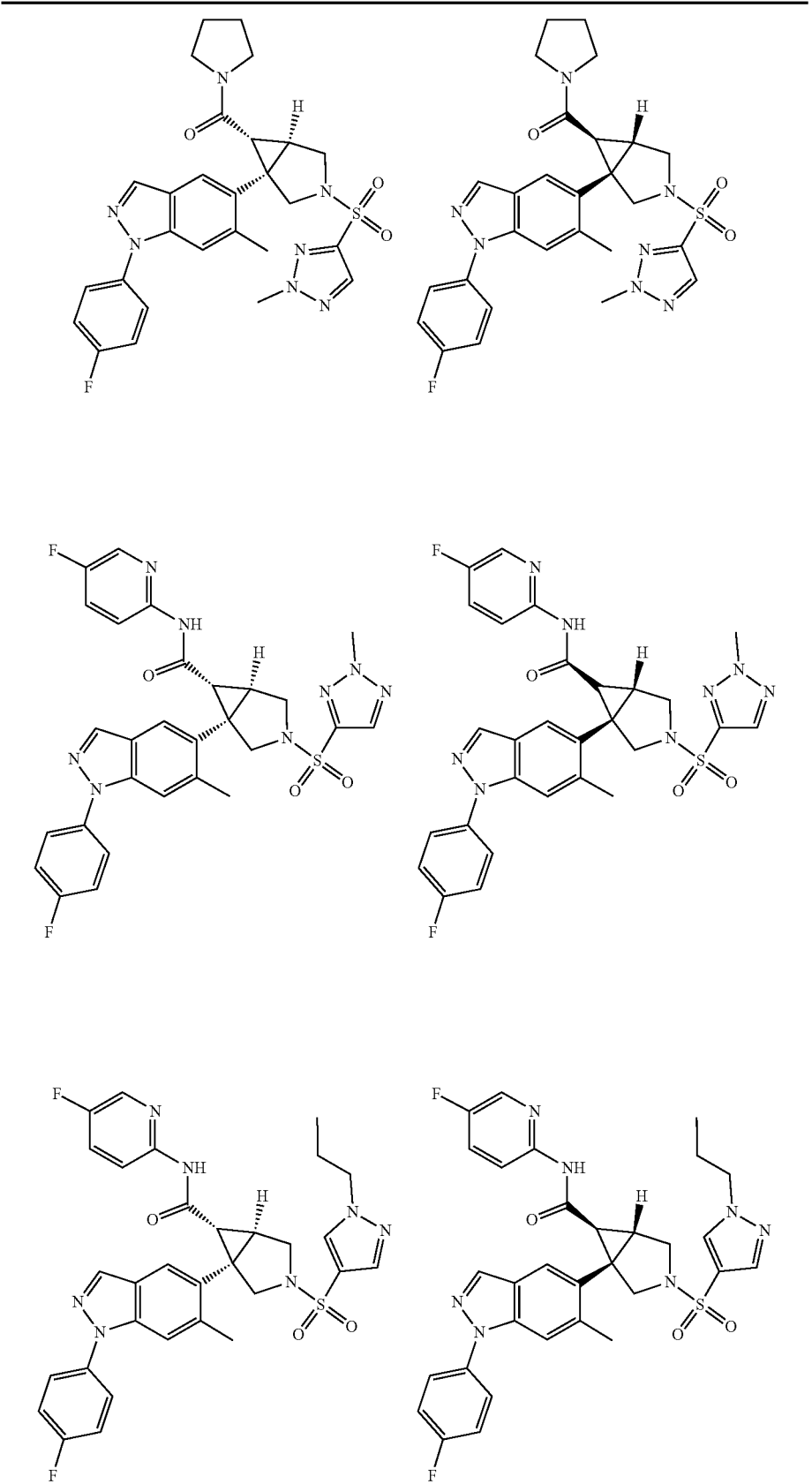

TABLE 1C-continued
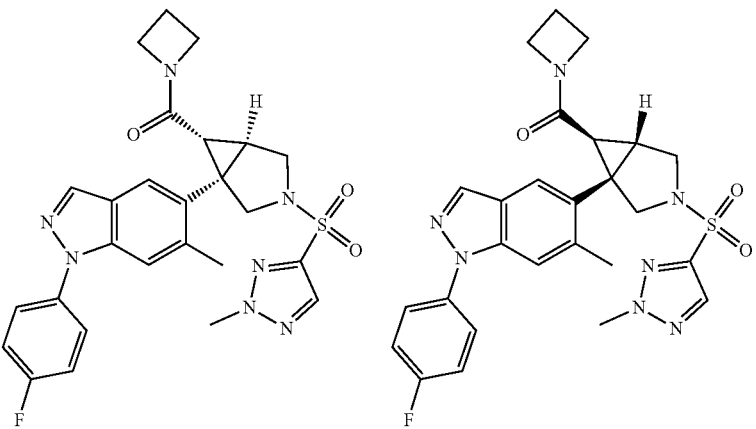
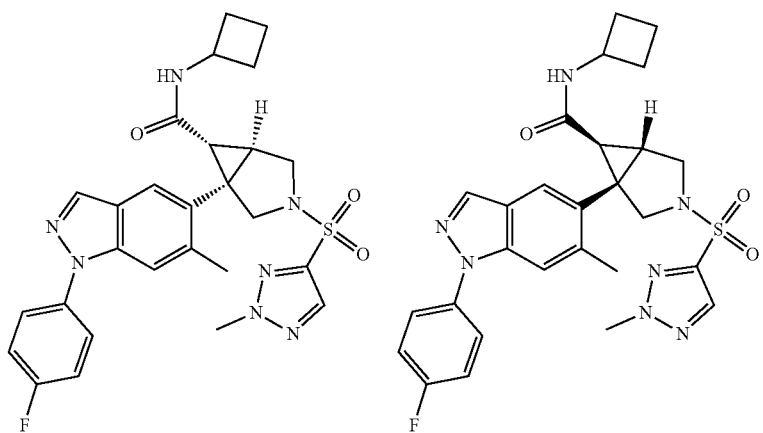
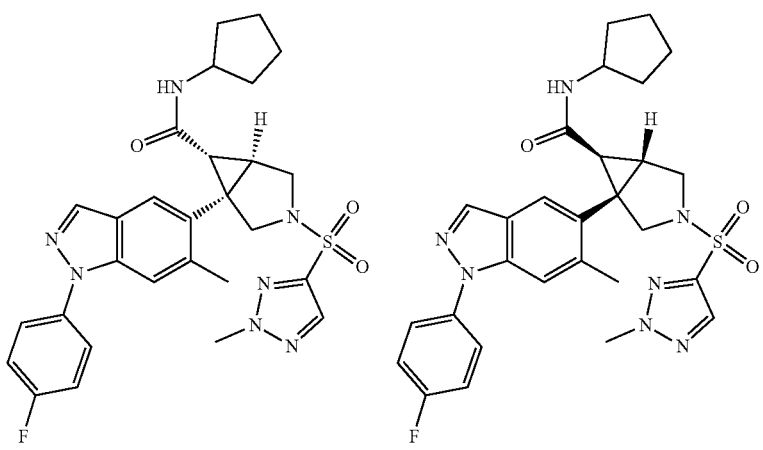 [SMILES: Cc1cc2c(cnn2-c2ccc(F)cc2)cc1[C@@]12CN(S(=O)(=O)c3cnn(C)n3)C[C@@H]1[C@H]2C(=O)NC1CCCC1 ; Cc1cc2c(cnn2-c2ccc(F)cc2)cc1[C@]12CN(S(=O)(=O)c3cnn(C)n3)C[C@H]1[C@@H]2C(=O)NC1CCCC1]

TABLE 1C-continued
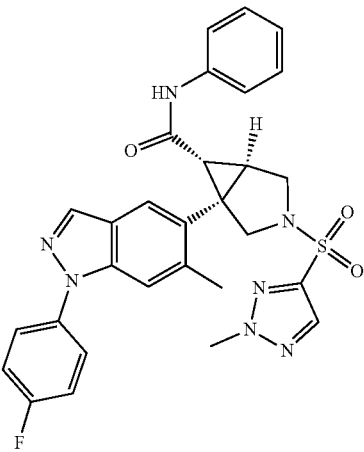 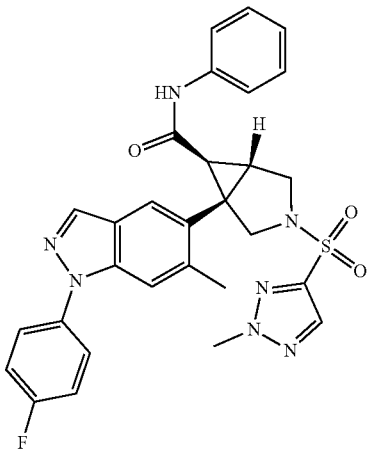
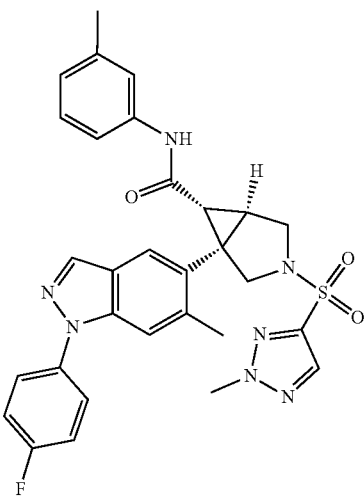 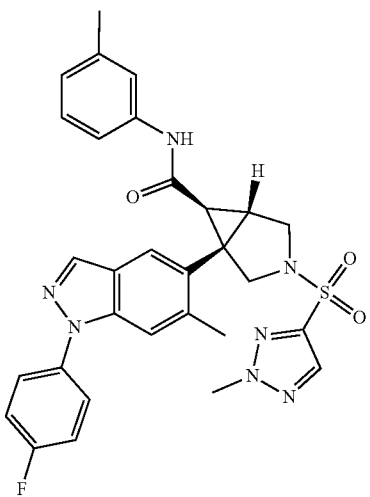
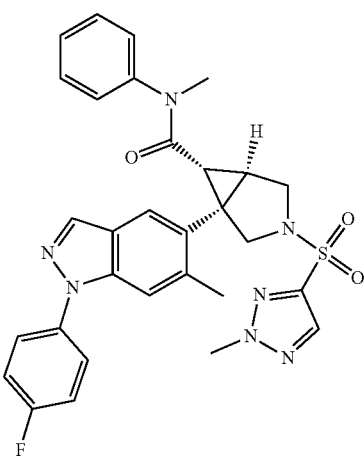 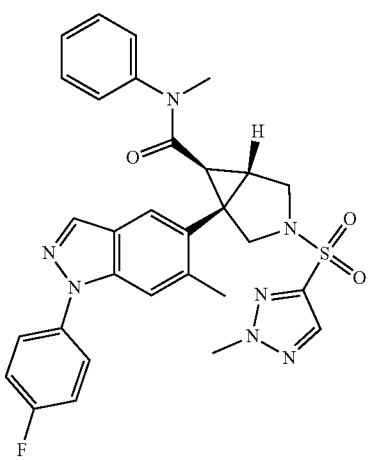

TABLE 1C-continued
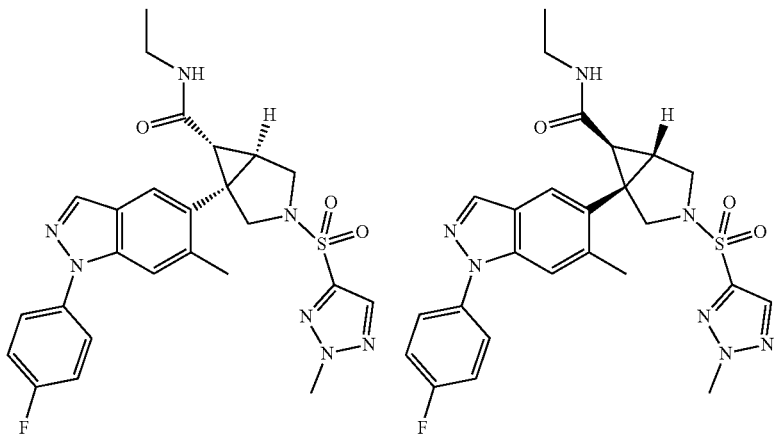
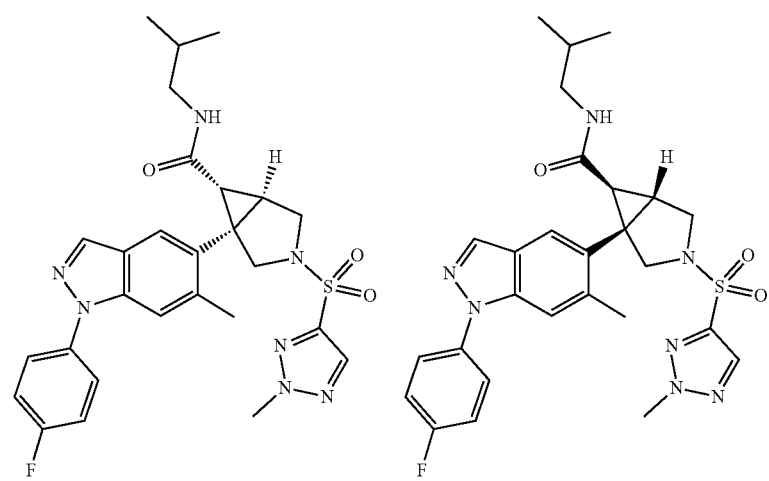 [SMILES: Cc1cc2c(cnn2-c2ccc(F)cc2)cc1[C@@]12CN(S(=O)(=O)c3cnn(C)n3)C[C@@H]1[C@H]2C(=O)NCC(C)C ; Cc1cc2c(cnn2-c2ccc(F)cc2)cc1[C@]12CN(S(=O)(=O)c3cnn(C)n3)C[C@H]1[C@@H]2C(=O)NCC(C)C]
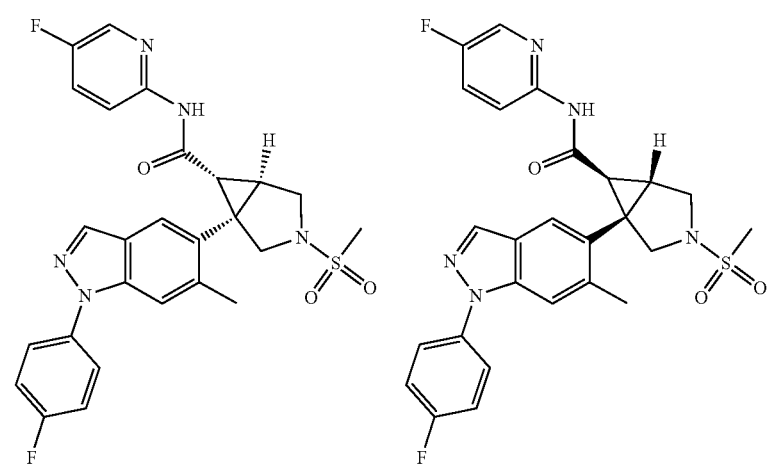 [SMILES: Cc1cc2c(cnn2-c2ccc(F)cc2)cc1[C@@]12CN(S(C)(=O)=O)C[C@@H]1[C@H]2C(=O)Nc1ccc(F)cn1 ; Cc1cc2c(cnn2-c2ccc(F)cc2)cc1[C@]12CN(S(C)(=O)=O)C[C@H]1[C@@H]2C(=O)Nc1ccc(F)cn1]

TABLE 1C-continued
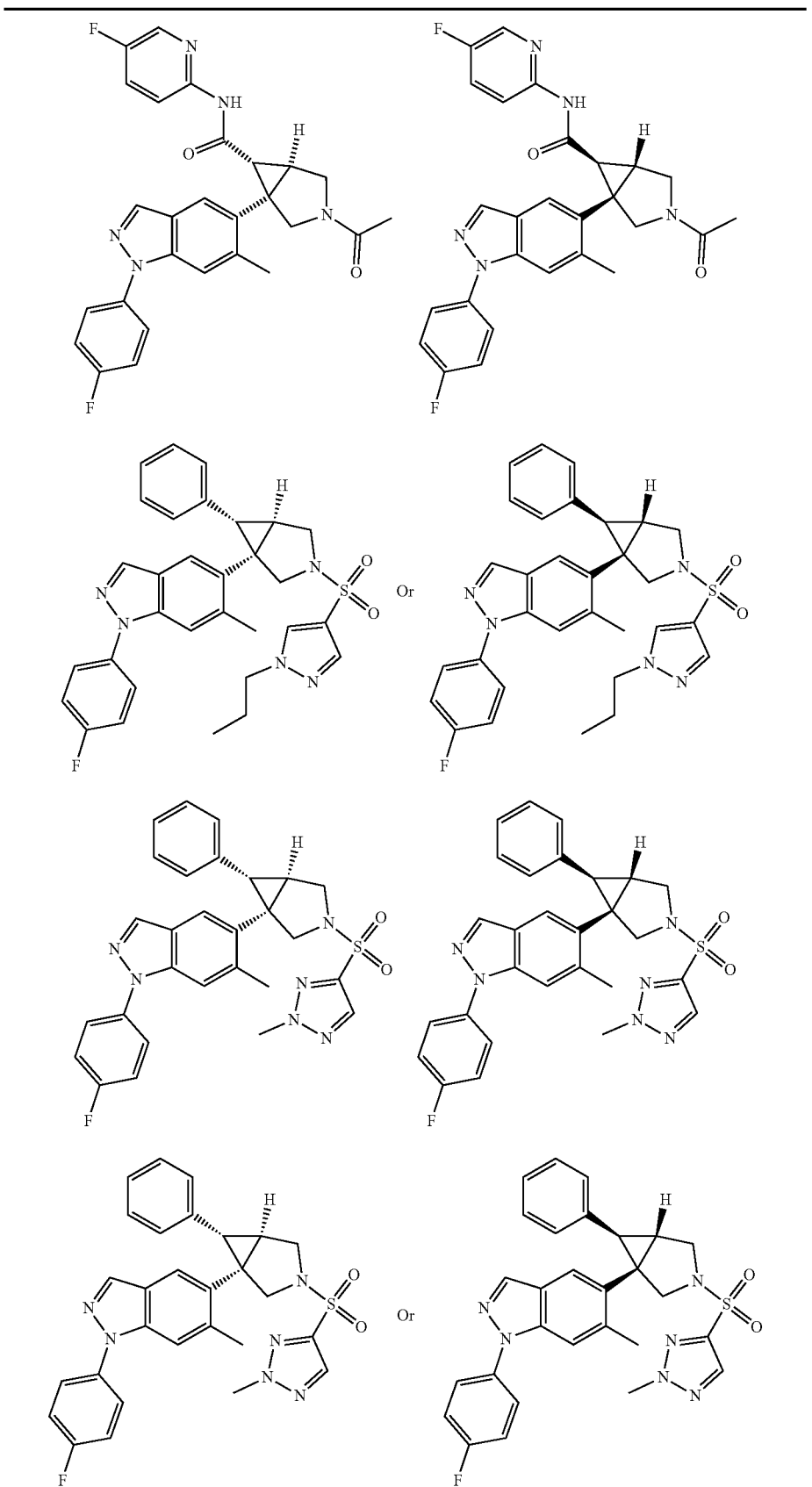

TABLE 1C-continued
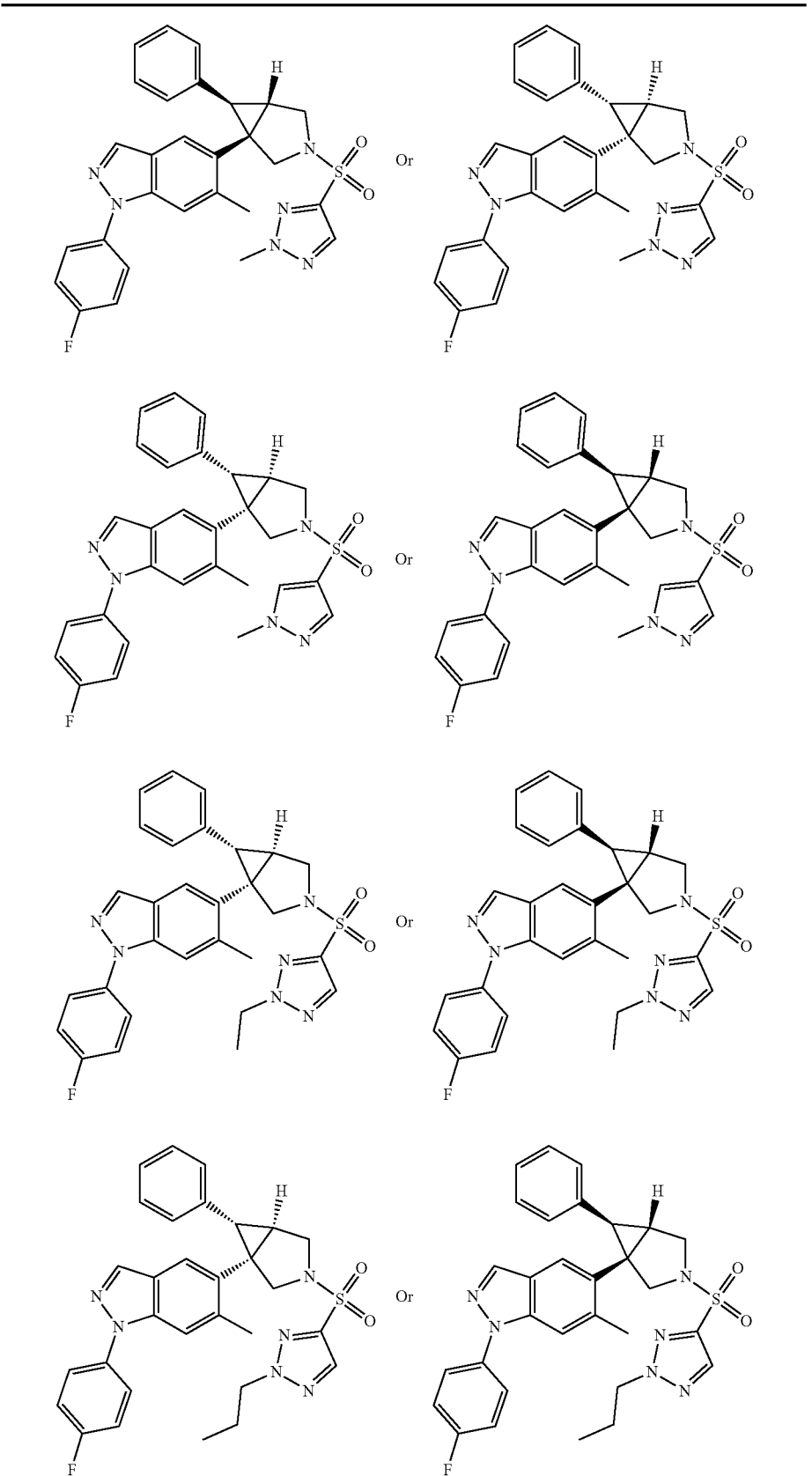

TABLE 1C-continued
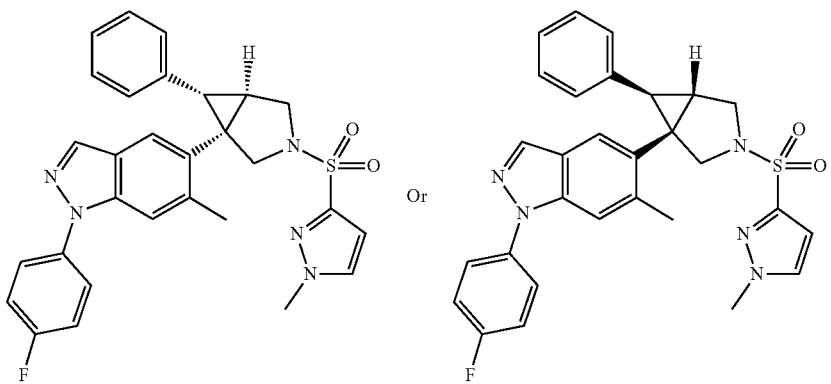
In some embodiments, the compound of Formula I, Ia, Ib, Ib-1, Ib-2, Ic, or Ic-1, or a pharmaceutically acceptable salt thereof, is a compound of Table 1D.
TABLE 1D
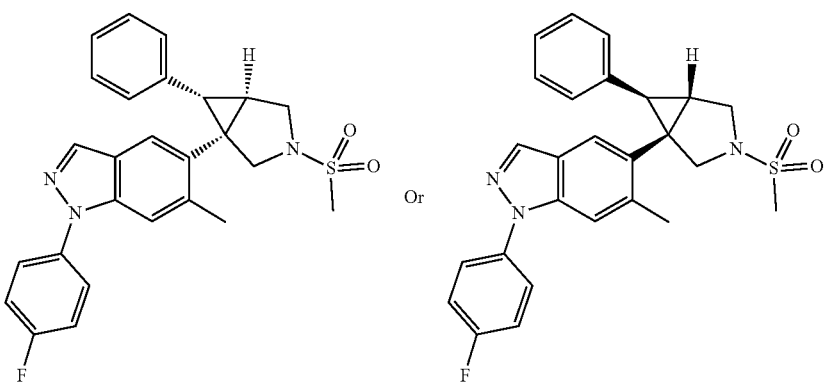 [SMILES: Cc1cc2c(cnn2-c2ccc(F)cc2)cc1[C@@]12CN(S(C)(=O)=O)C[C@@H]1[C@H]2c1ccccc1 ; Cc1cc2c(cnn2-c2ccc(F)cc2)cc1[C@]12CN(S(C)(=O)=O)C[C@H]1[C@@H]2c1ccccc1]
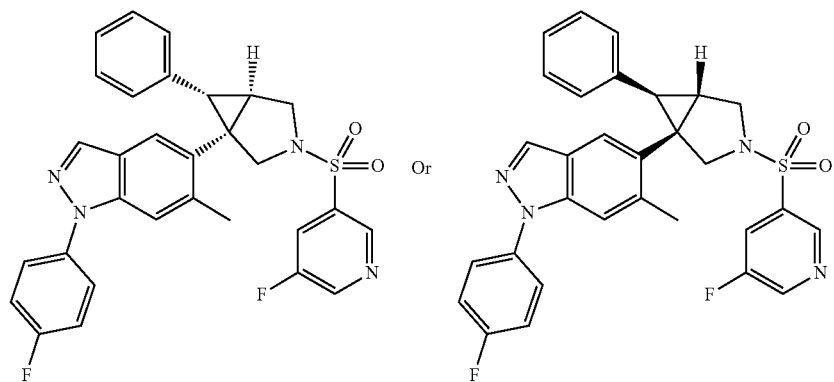

TABLE 1D-continued
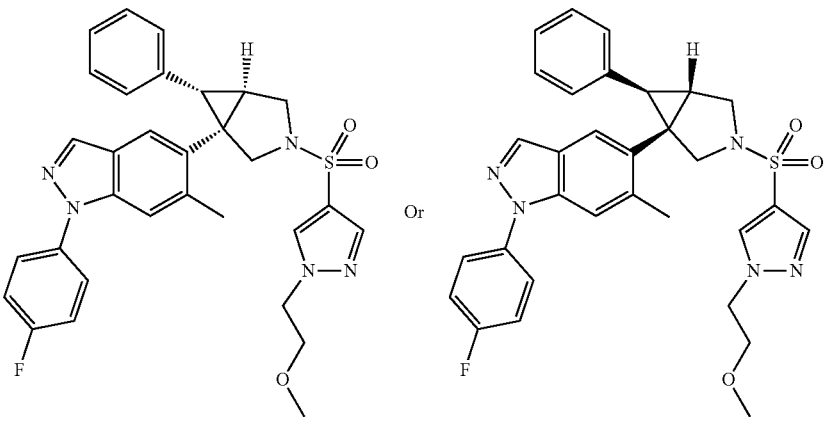 [SMILES: COCCn1cc(S(=O)(=O)N2C[C@@H]3[C@@H](c4ccccc4)[C@]3(c3cc4cnn(-c5ccc(F)cc5)c4cc3C)C2)cn1 ; COCCn1cc(S(=O)(=O)N2C[C@H]3[C@H](c4ccccc4)[C@@]3(c3cc4cnn(-c5ccc(F)cc5)c4cc3C)C2)cn1]
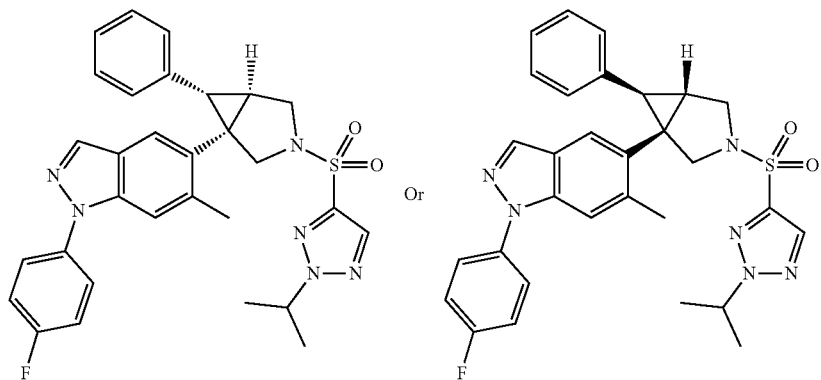
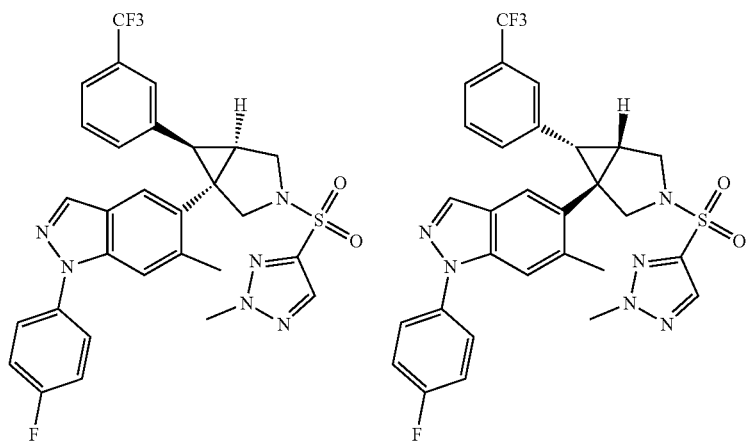 [SMILES: Cc1cc2c(cnn2-c2ccc(F)cc2)cc1[C@@]12CN(S(=O)(=O)c3cnn(C)n3)C[C@@H]1[C@@H]2c1cccc(C(F)(F)F)c1 ; Cc1cc2c(cnn2-c2ccc(F)cc2)cc1[C@]12CN(S(=O)(=O)c3cnn(C)n3)C[C@H]1[C@H]2c1cccc(C(F)(F)F)c1]

TABLE 1D-continued
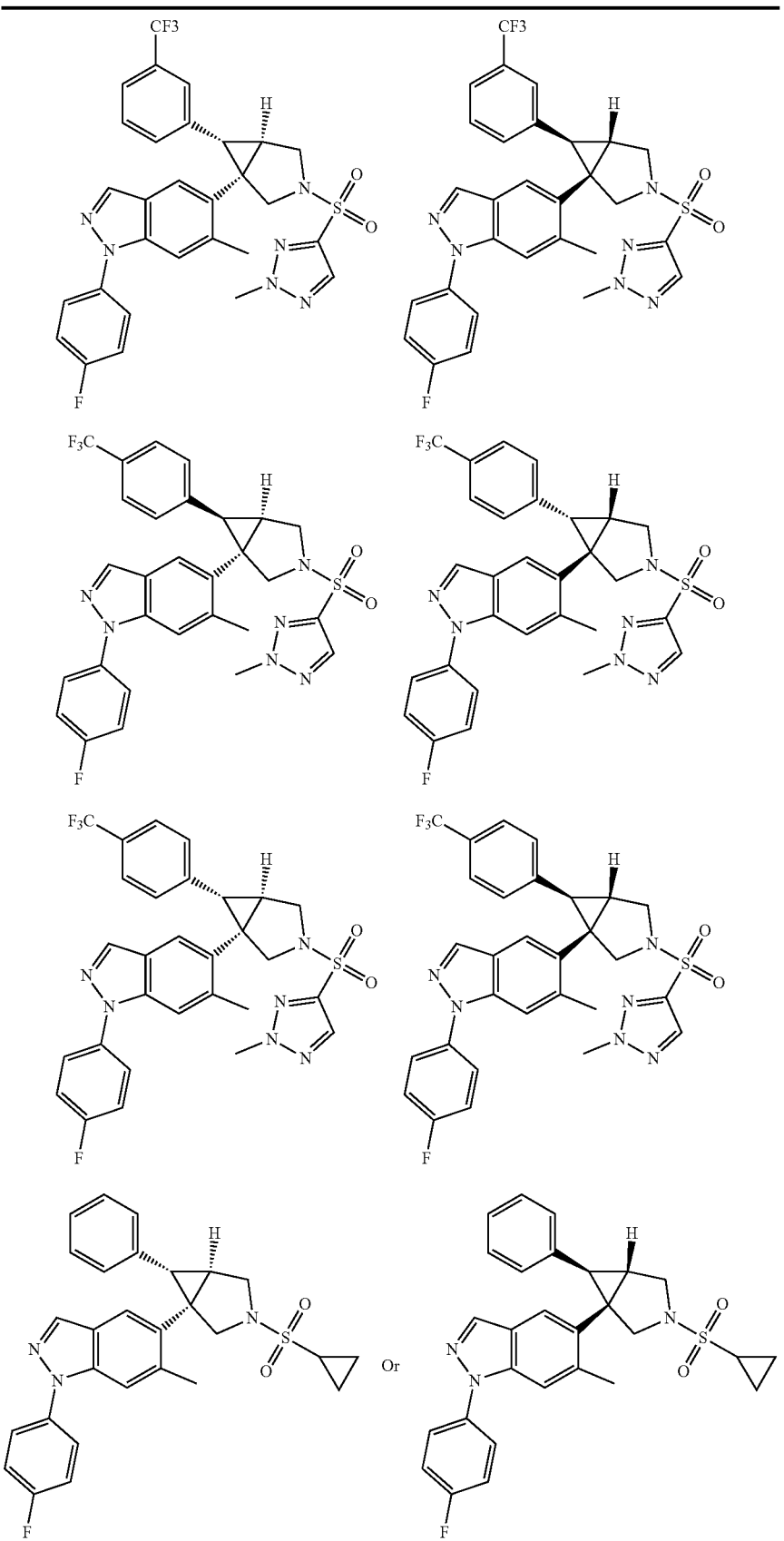

TABLE 1D-continued
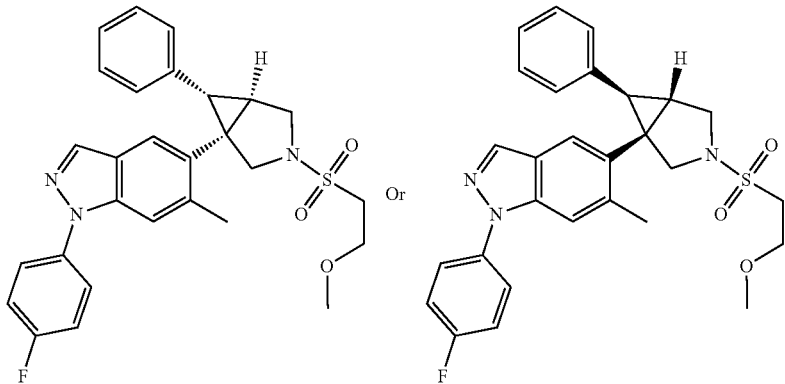 Or 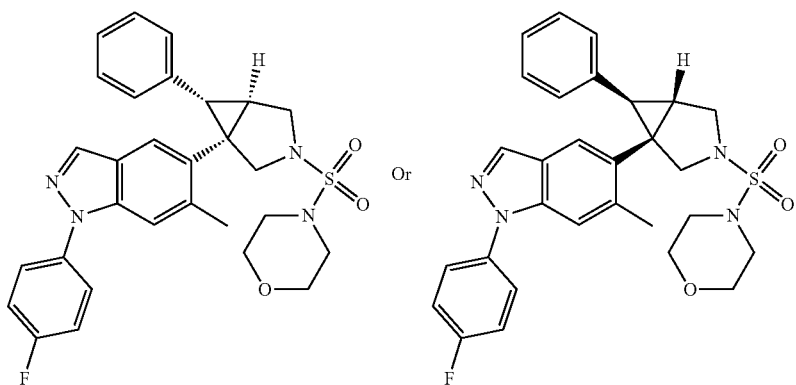 [SMILES: Cc1cc2c(cnn2-c2ccc(F)cc2)cc1[C@@]12CN(S(=O)(=O)N3CCOCC3)C[C@@H]1[C@H]2c1ccccc1 ; Cc1cc2c(cnn2-c2ccc(F)cc2)cc1[C@]12CN(S(=O)(=O)N3CCOCC3)C[C@H]1[C@@H]2c1ccccc1] Or 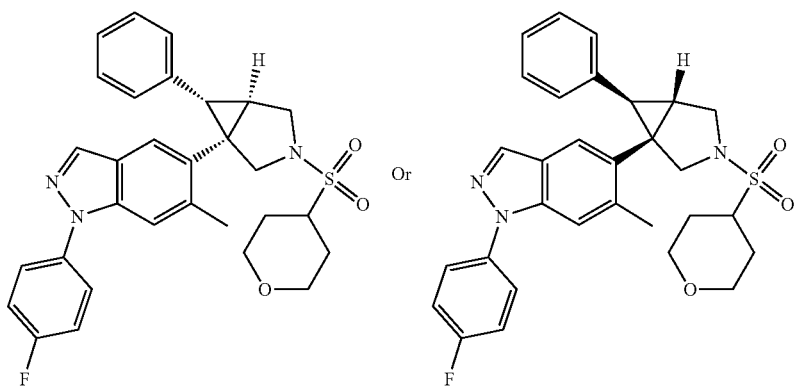 [SMILES: Cc1cc2c(cnn2-c2ccc(F)cc2)cc1[C@@]12CN(S(=O)(=O)C3CCOCC3)C[C@@H]1[C@H]2c1ccccc1 ; Cc1cc2c(cnn2-c2ccc(F)cc2)cc1[C@]12CN(S(=O)(=O)C3CCOCC3)C[C@H]1[C@@H]2c1ccccc1] Or 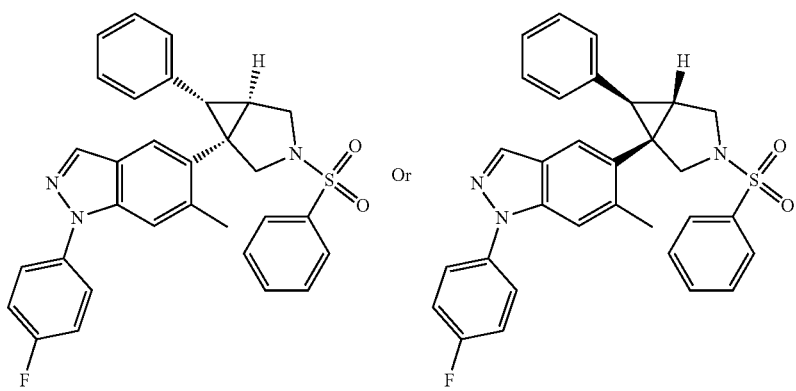 [SMILES: Cc1cc2c(cnn2-c2ccc(F)cc2)cc1[C@@]12CN(S(=O)(=O)c3ccccc3)C[C@@H]1[C@H]2c1ccccc1 ; Cc1cc2c(cnn2-c2ccc(F)cc2)cc1[C@]12CN(S(=O)(=O)c3ccccc3)C[C@H]1[C@@H]2c1ccccc1] Or

TABLE 1D-continued
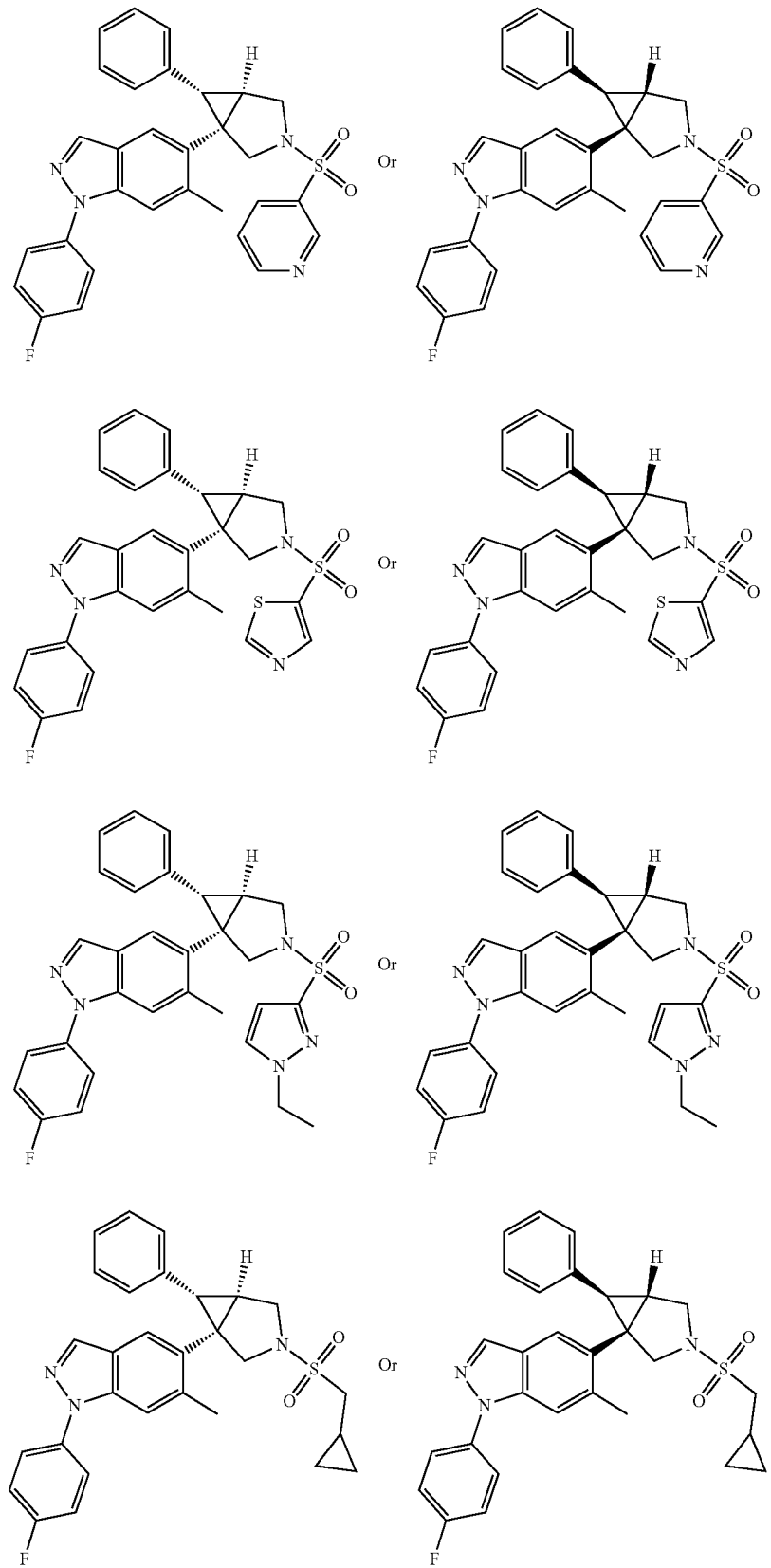

TABLE 1D-continued
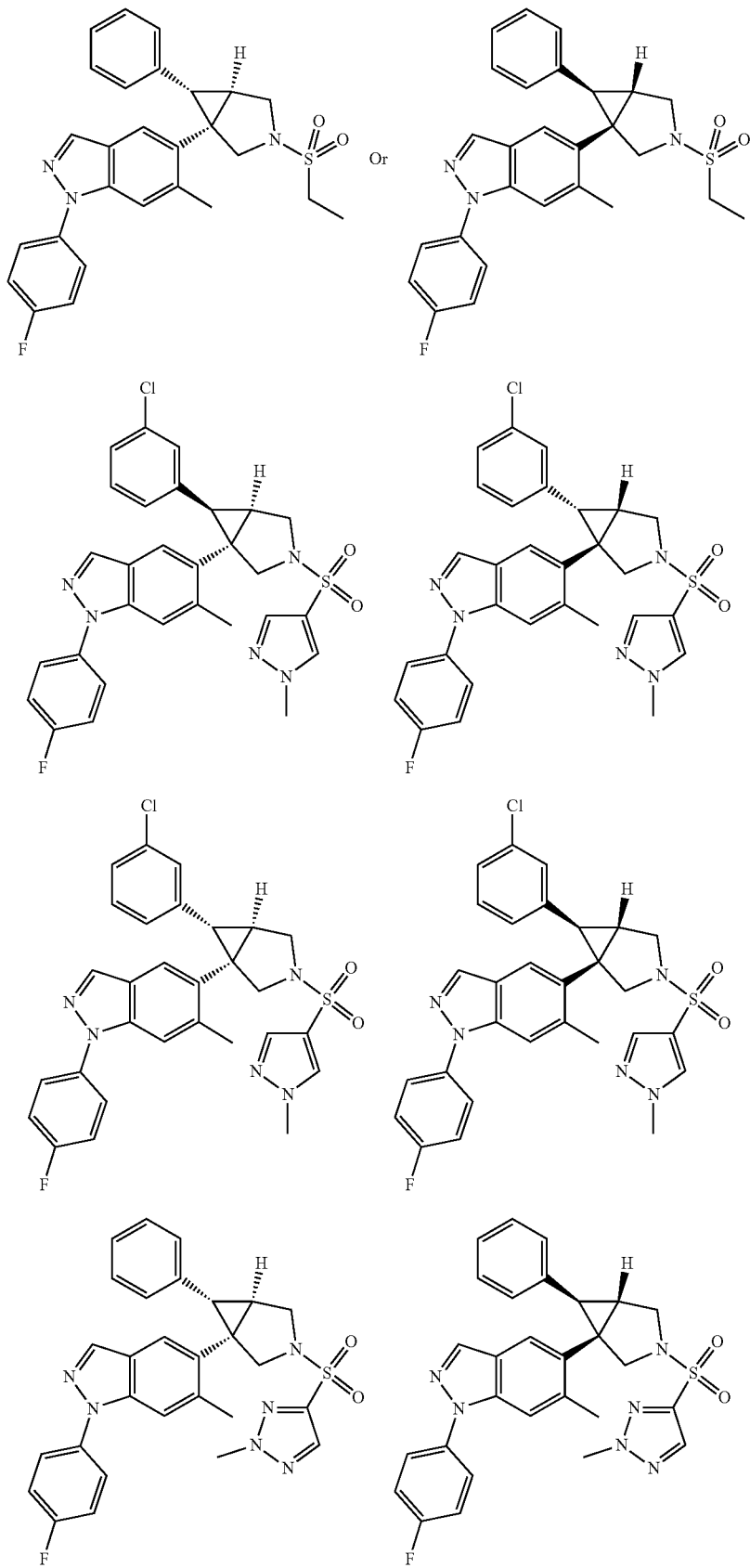

TABLE 1D-continued
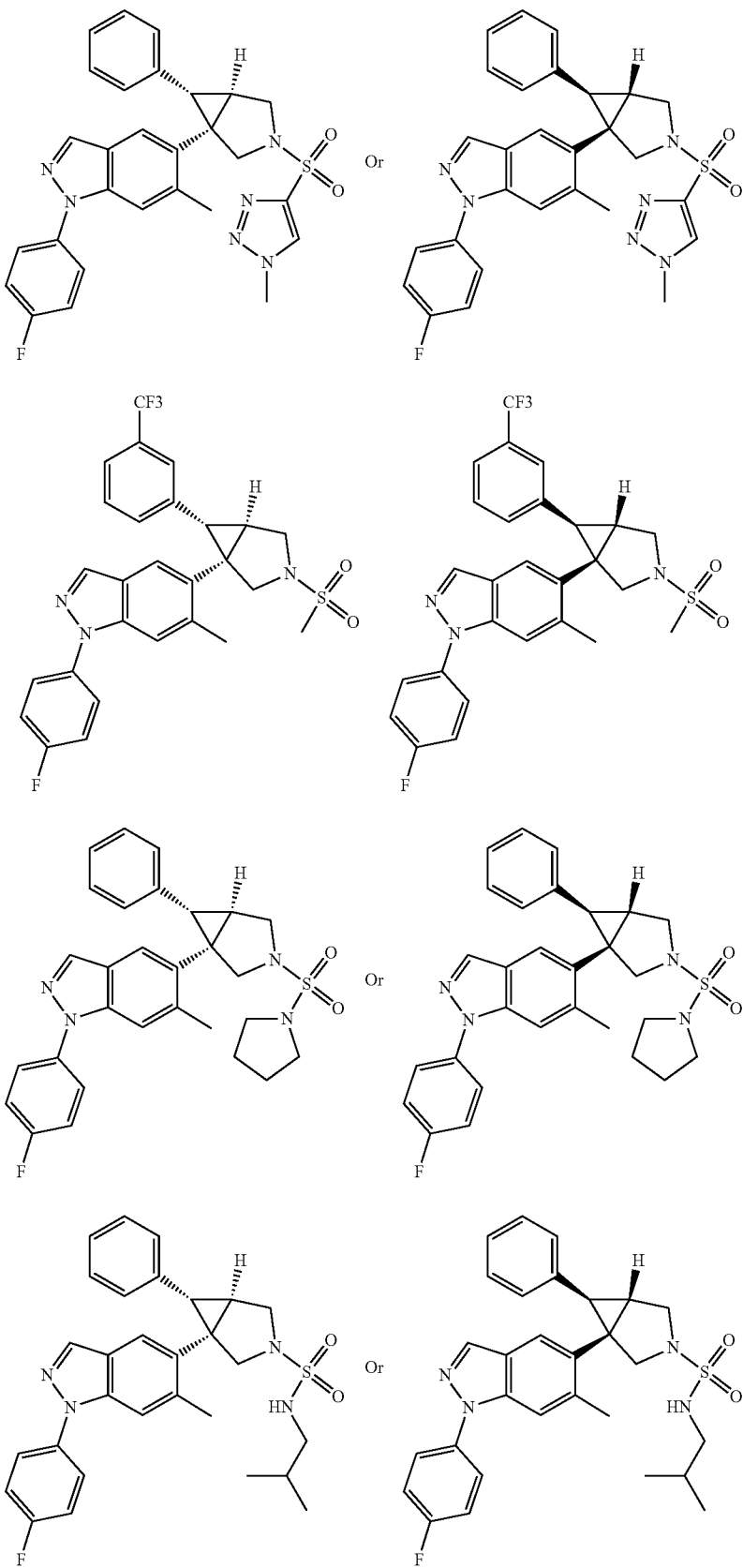

In some embodiments, the compound of Formula I, Ia, Ib, Ib-1, Ib-2, Ic, Ic-1, Id-1, or Id-2, or a pharmaceutically acceptable salt thereof, is a compound of Table 1E.
TABLE 1E
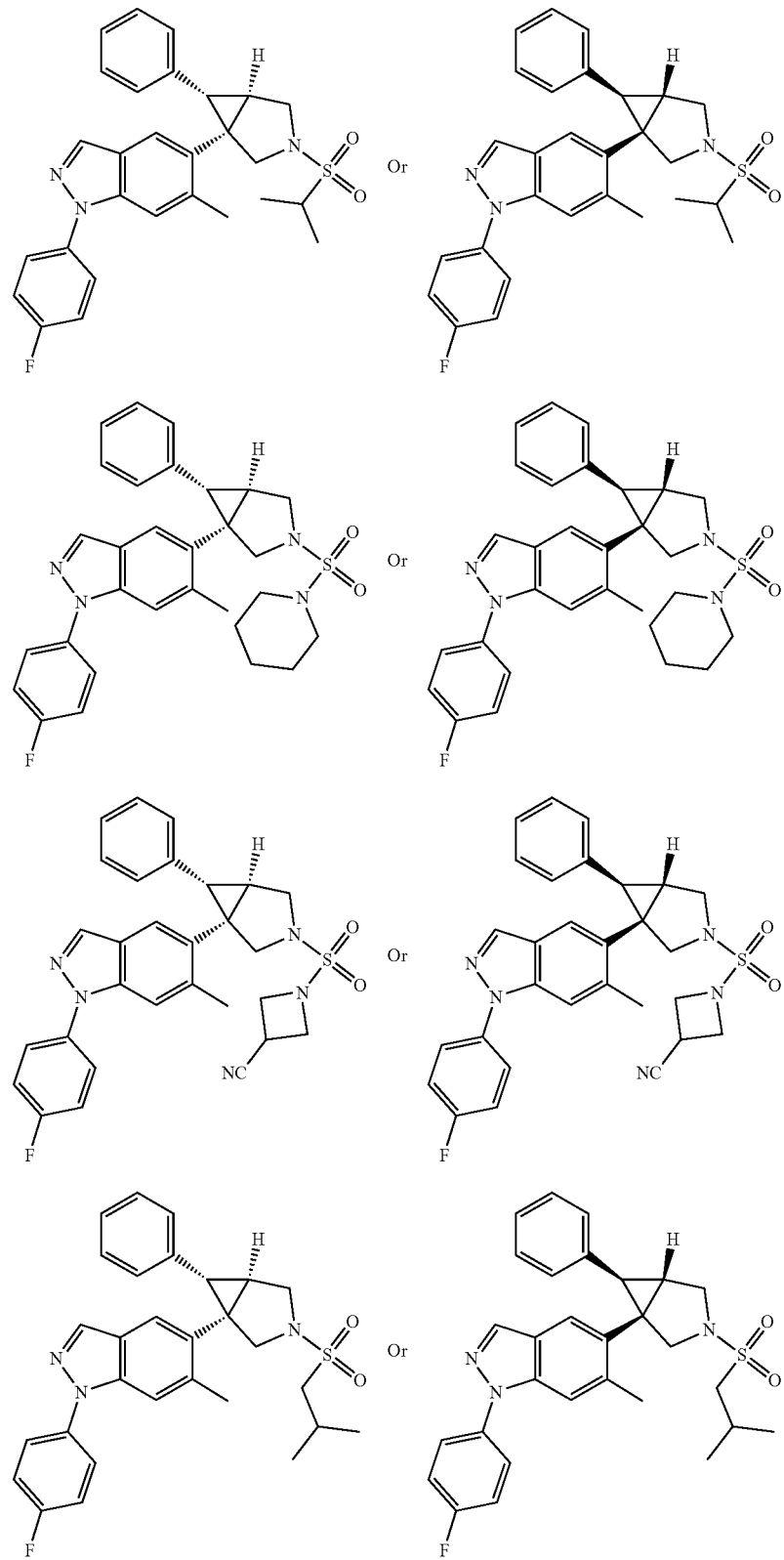

TABLE 1E-continued
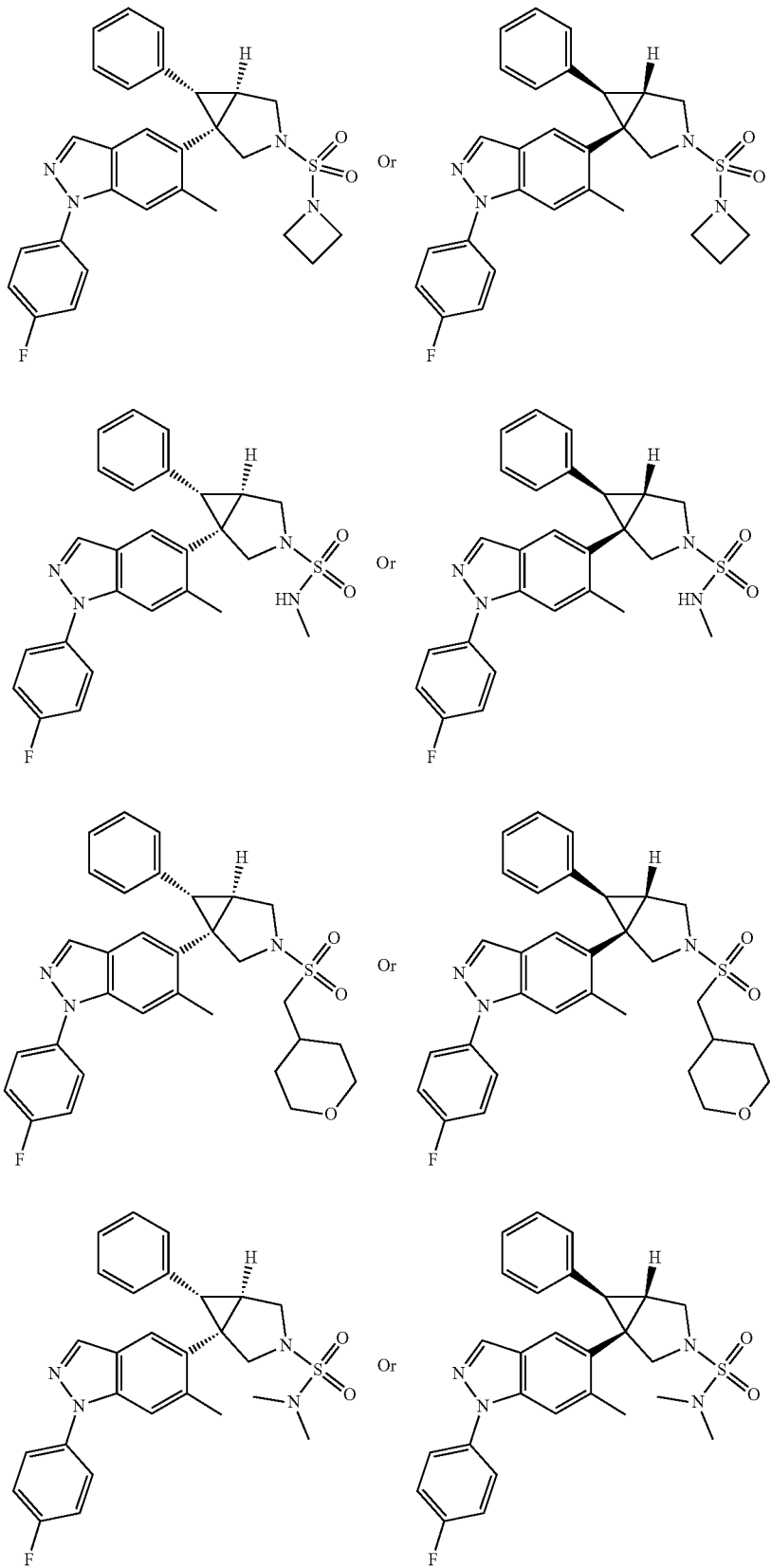

TABLE 1E-continued
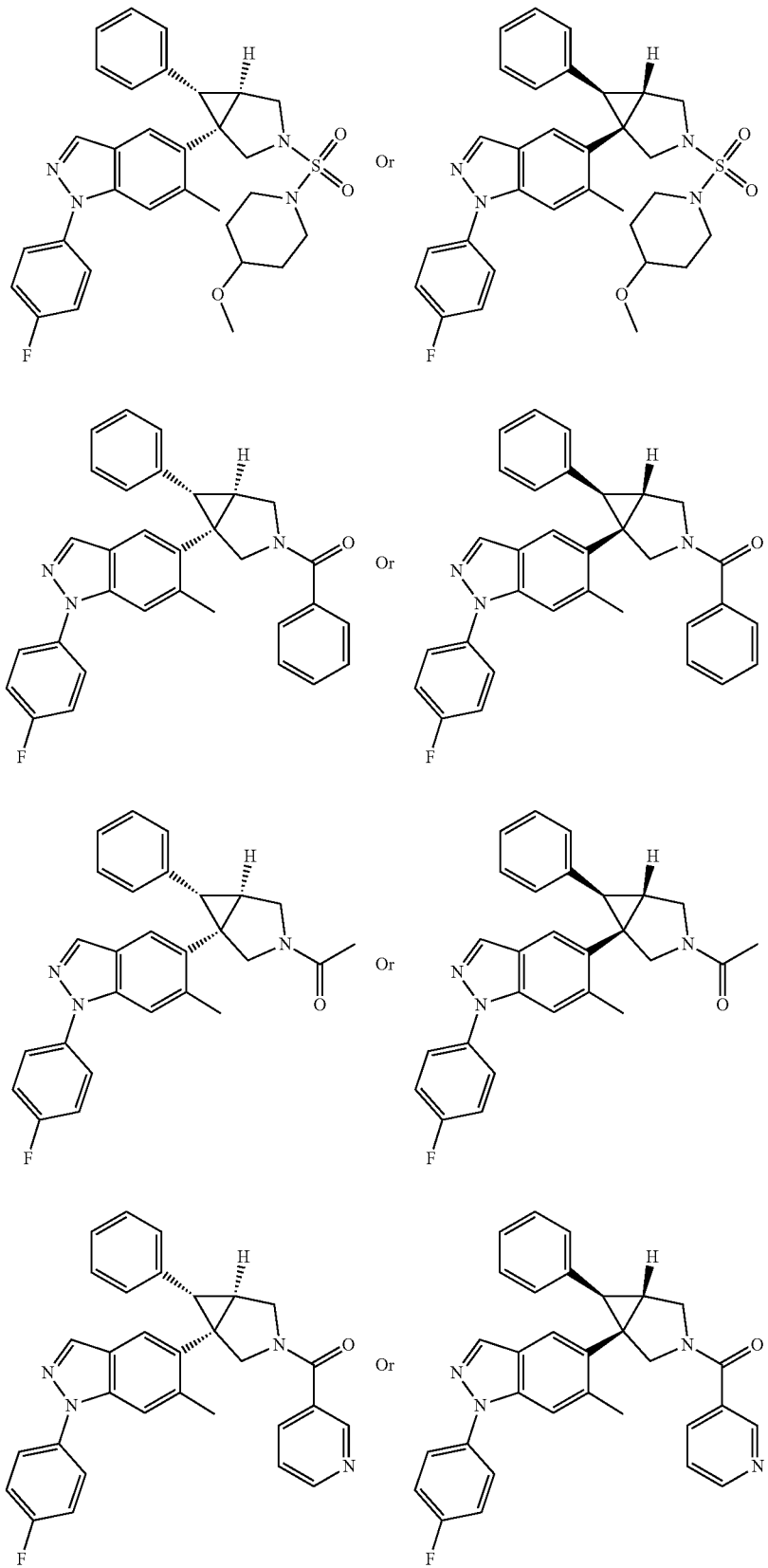

TABLE 1E-continued
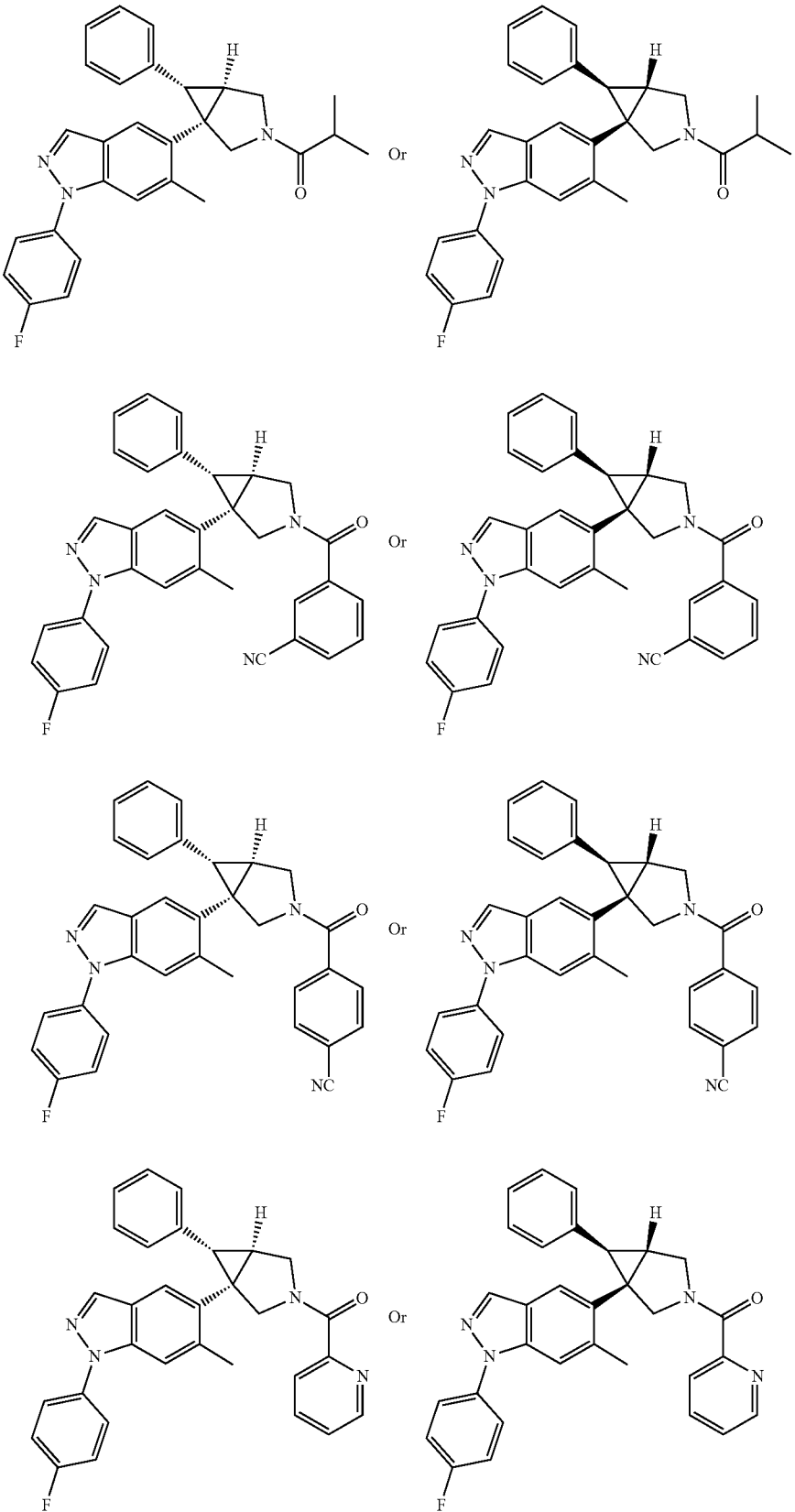

TABLE 1E-continued
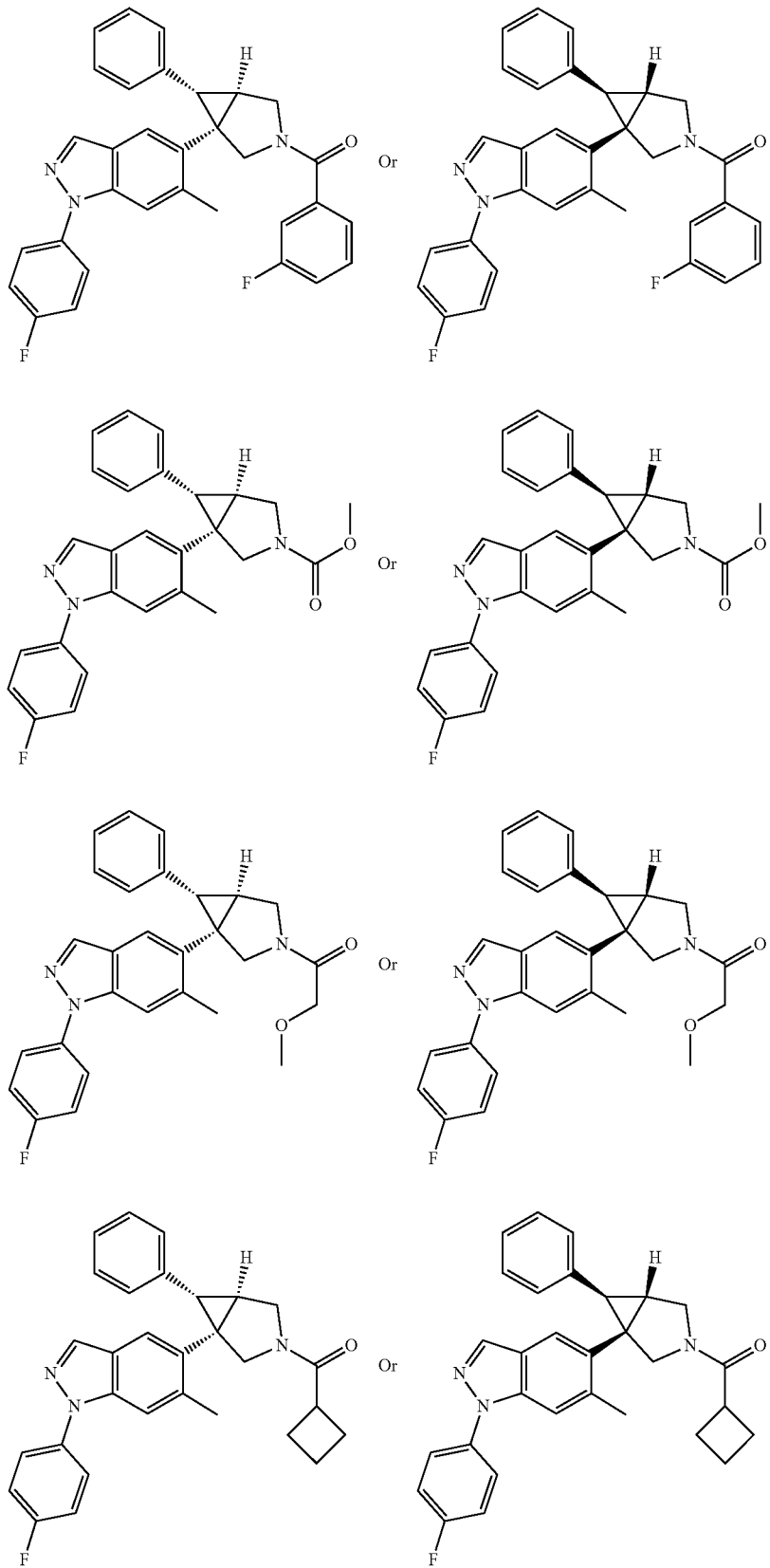

TABLE 1E-continued
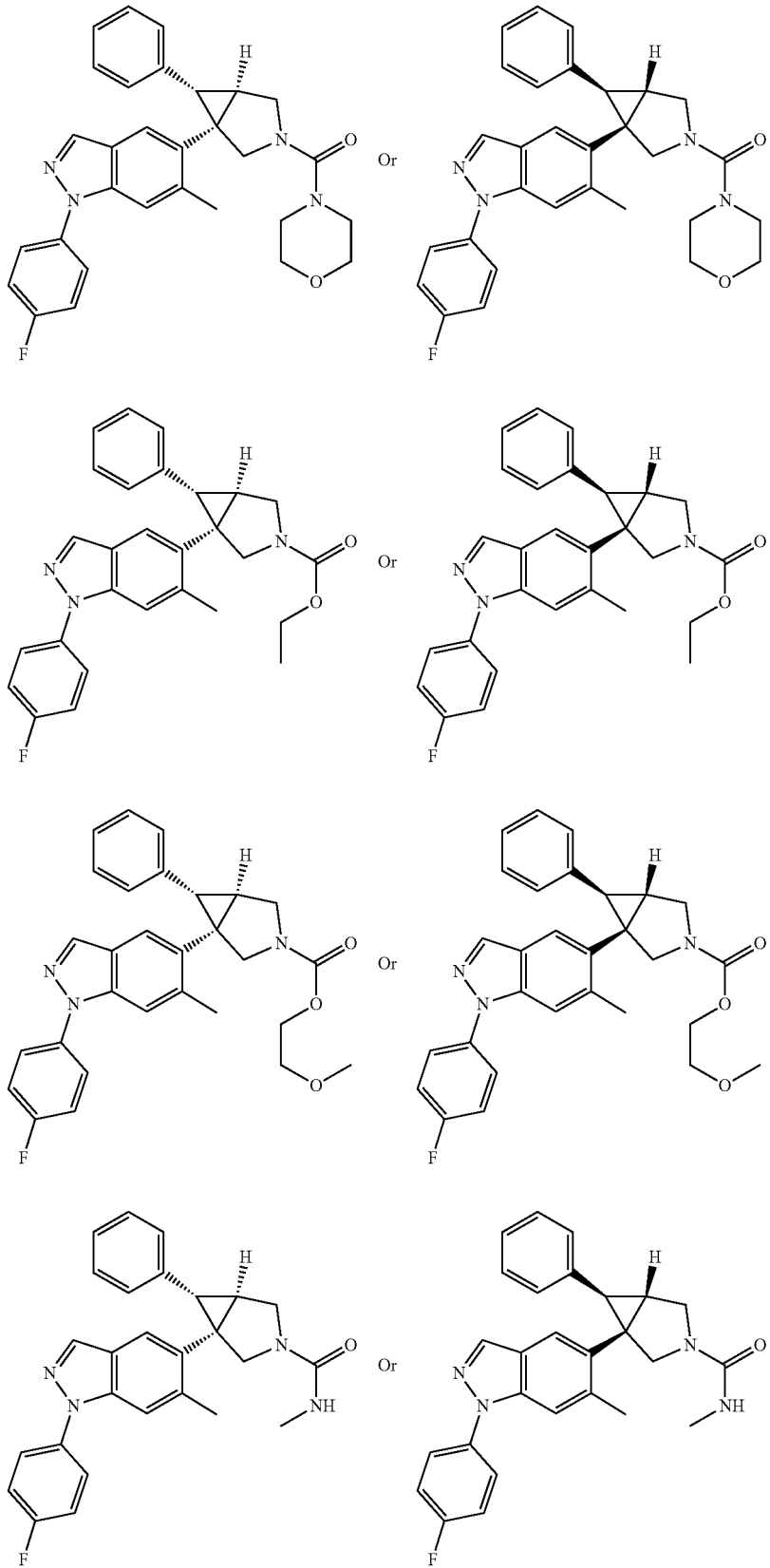

TABLE 1E-continued
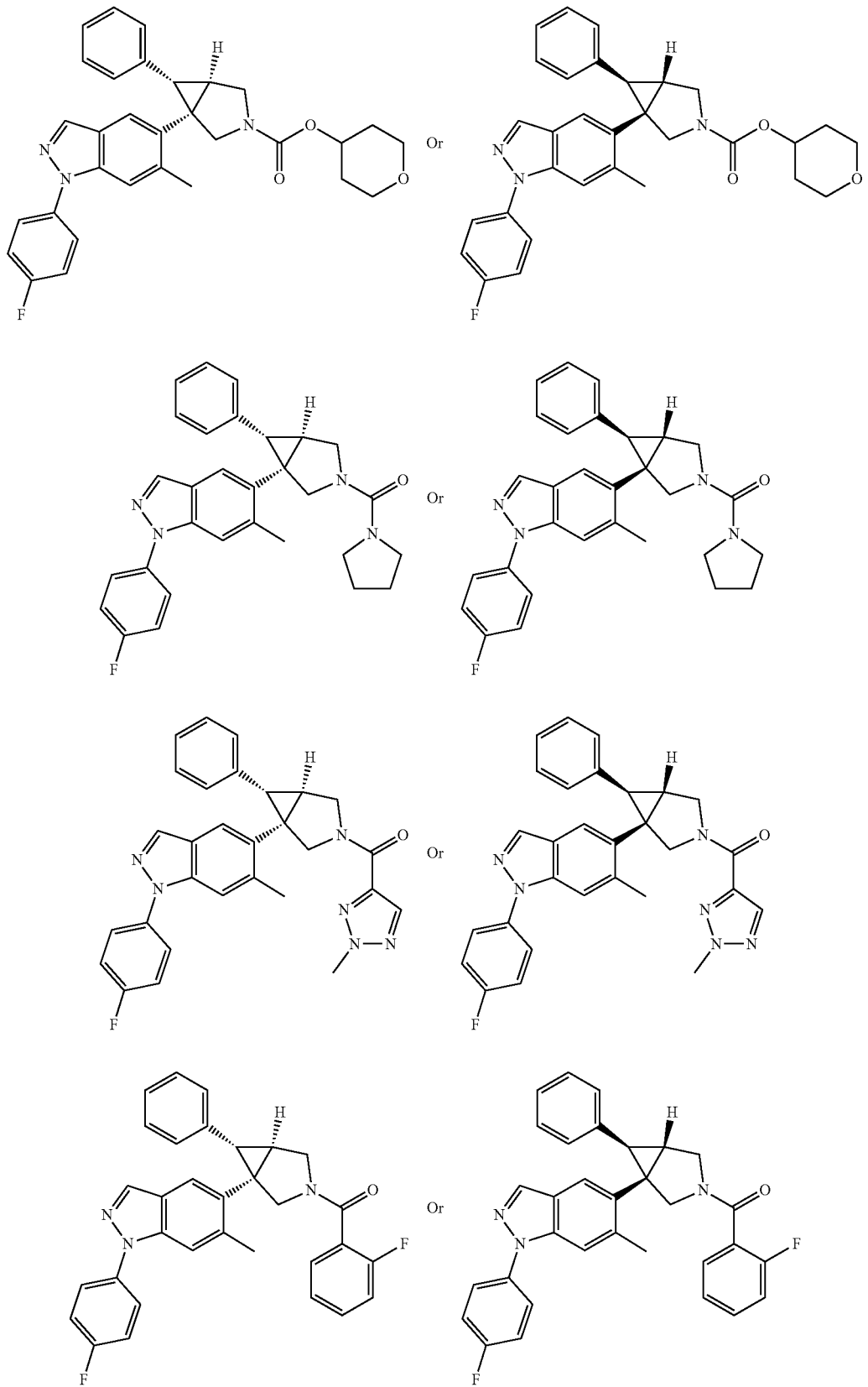

TABLE 1E-continued
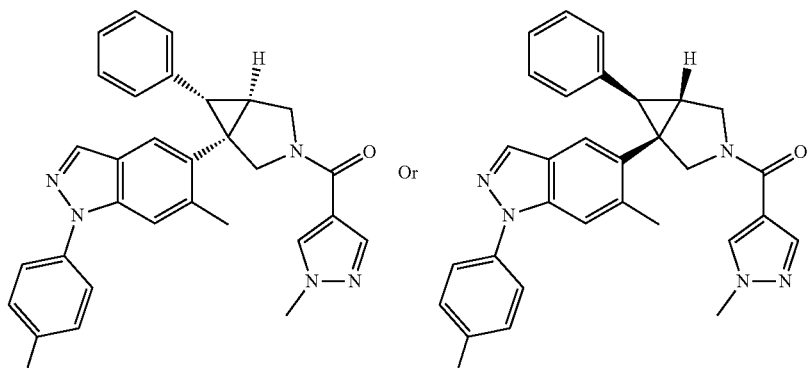
Or
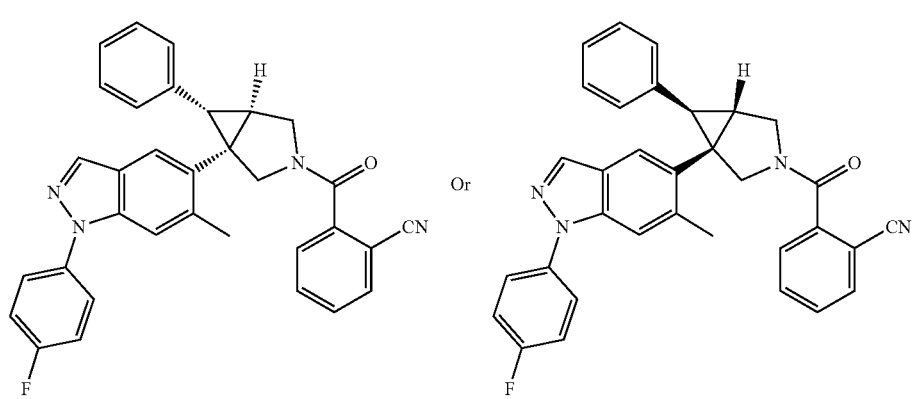 [SMILES: Cc1cc2c(cnn2-c2ccc(F)cc2)cc1[C@@]12CN(C(=O)c3ccccc3C#N)C[C@@H]1[C@H]2c1ccccc1 ; Cc1cc2c(cnn2-c2ccc(F)cc2)cc1[C@]12CN(C(=O)c3ccccc3C#N)C[C@H]1[C@@H]2c1ccccc1]
Or
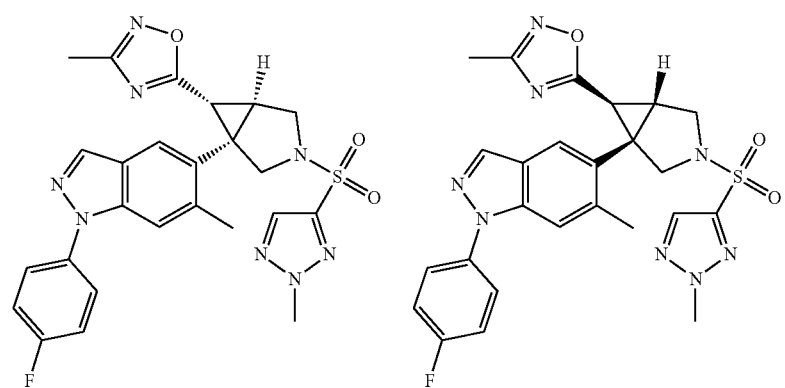 [SMILES: Cc1noc([C@@H]2[C@H]3CN(S(=O)(=O)c4cnn(C)n4)C[C@]32c2cc3cnn(-c4ccc(F)cc4)c3cc2C)n1 ; Cc1noc([C@H]2[C@@H]3CN(S(=O)(=O)c4cnn(C)n4)C[C@@]32c2cc3cnn(-c4ccc(F)cc4)c3cc2C)n1]
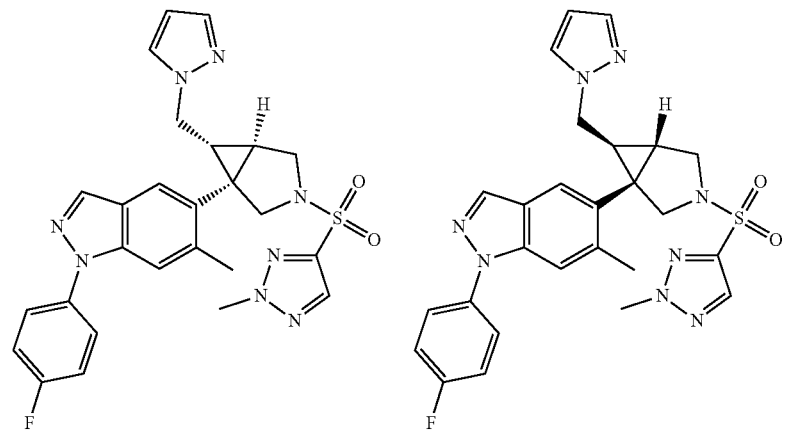 [SMILES: Cc1cc2c(cnn2-c2ccc(F)cc2)cc1[C@@]12CN(S(=O)(=O)c3cnn(C)n3)C[C@@H]1[C@H]2Cn1cccn1 ; Cc1cc2c(cnn2-c2ccc(F)cc2)cc1[C@]12CN(S(=O)(=O)c3cnn(C)n3)C[C@H]1[C@@H]2Cn1cccn1]

TABLE 1E-continued
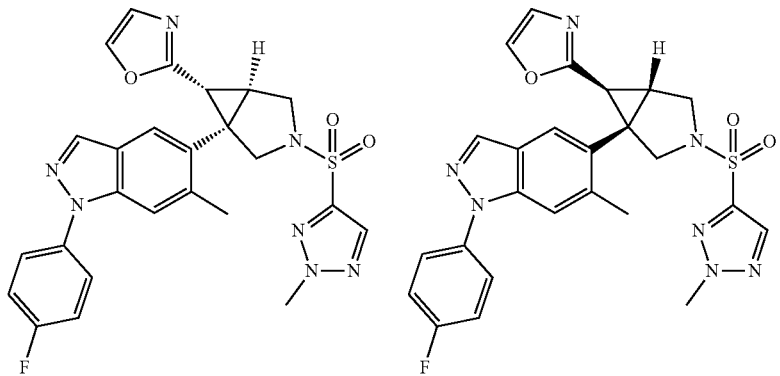 [SMILES: Cc1cc2c(cnn2-c2ccc(F)cc2)cc1[C@@]12CN(S(=O)(=O)c3cnn(C)n3)C[C@@H]1[C@H]2c1ncco1 ; Cc1cc2c(cnn2-c2ccc(F)cc2)cc1[C@]12CN(S(=O)(=O)c3cnn(C)n3)C[C@H]1[C@@H]2c1ncco1]
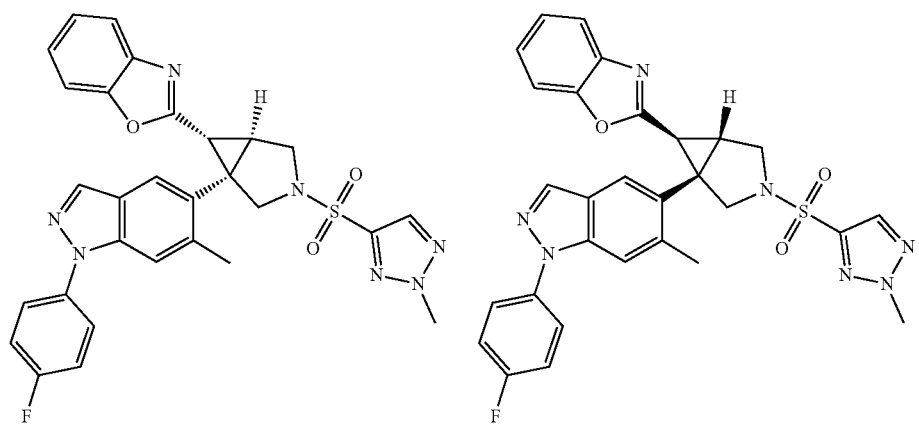
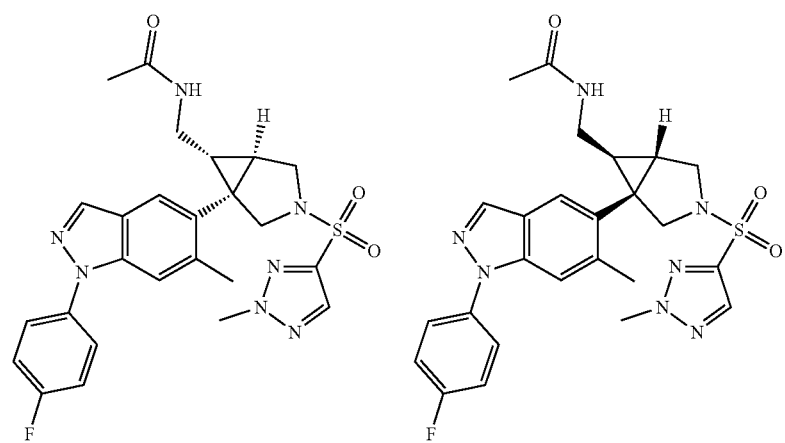 [SMILES: CC(=O)NC[C@@H]1[C@H]2CN(S(=O)(=O)c3cnn(C)n3)C[C@@]12c1cc2cnn(-c3ccc(F)cc3)c2cc1C ; CC(=O)NC[C@H]1[C@@H]2CN(S(=O)(=O)c3cnn(C)n3)C[C@]12c1cc2cnn(-c3ccc(F)cc3)c2cc1C]

In some embodiments, the compound of Formula I, Ia, Ib, Ib-1, Ib-2, Ic, Ic-1, Id-1, or Id-2, or a pharmaceutically acceptable salt thereof, is a compound of Table 1F.
TABLE 1F
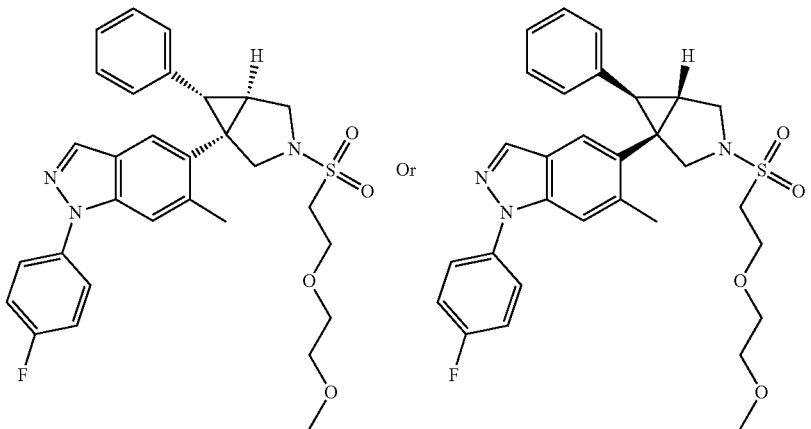 [SMILES: COCCOCCS(=O)(=O)N1C[C@@H]2[C@@H](c3ccccc3)[C@]2(c2cc3cnn(-c4ccc(F)cc4)c3cc2C)C1 ; COCCOCCS(=O)(=O)N1C[C@H]2[C@H](c3ccccc3)[C@@]2(c2cc3cnn(-c4ccc(F)cc4)c3cc2C)C1]
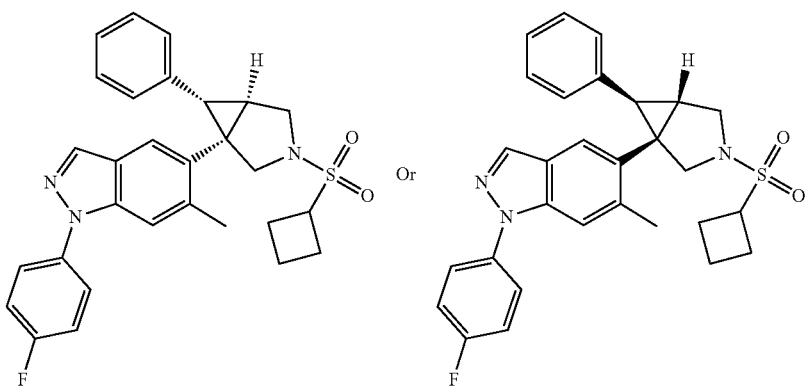 [SMILES: Cc1cc2c(cnn2-c2ccc(F)cc2)cc1[C@@]12CN(S(=O)(=O)C3CCC3)C[C@@H]1[C@H]2c1ccccc1 ; Cc1cc2c(cnn2-c2ccc(F)cc2)cc1[C@]12CN(S(=O)(=O)C3CCC3)C[C@H]1[C@@H]2c1ccccc1]
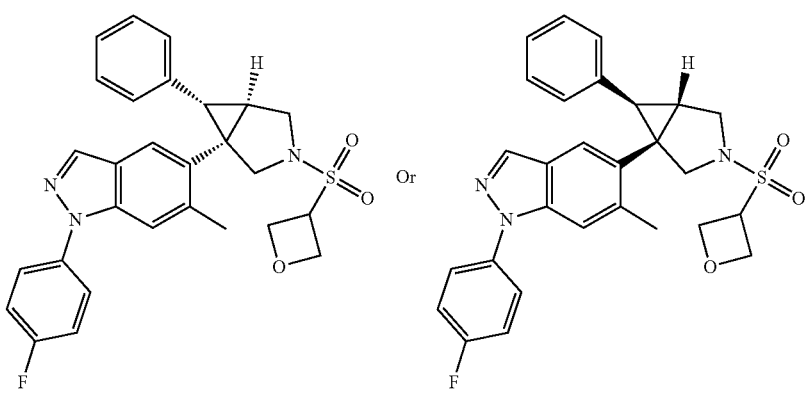 [SMILES: Cc1cc2c(cnn2-c2ccc(F)cc2)cc1[C@@]12CN(S(=O)(=O)C3COC3)C[C@@H]1[C@H]2c1ccccc1 ; Cc1cc2c(cnn2-c2ccc(F)cc2)cc1[C@]12CN(S(=O)(=O)C3COC3)C[C@H]1[C@@H]2c1ccccc1]

TABLE 1F-continued
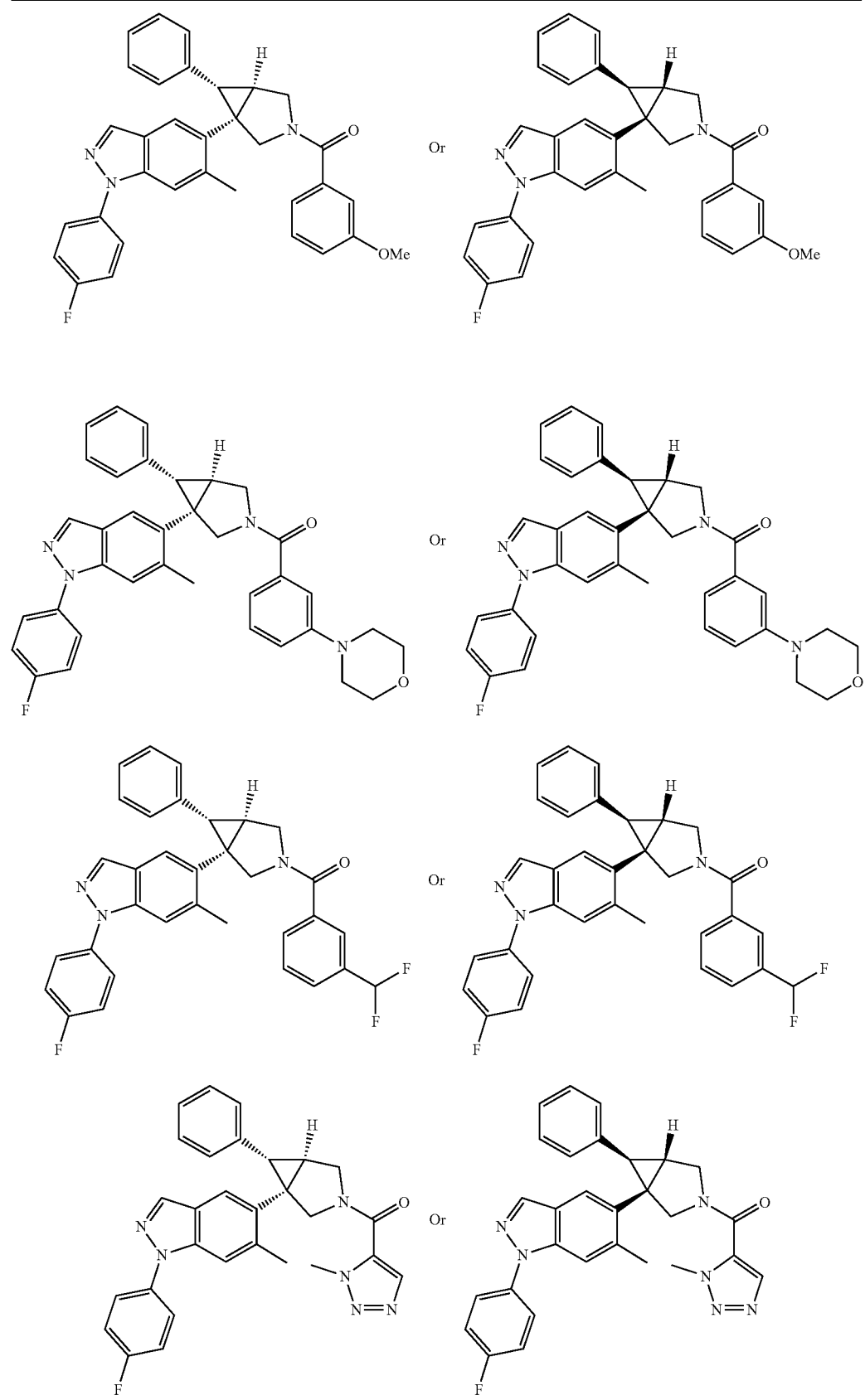

TABLE 1F-continued
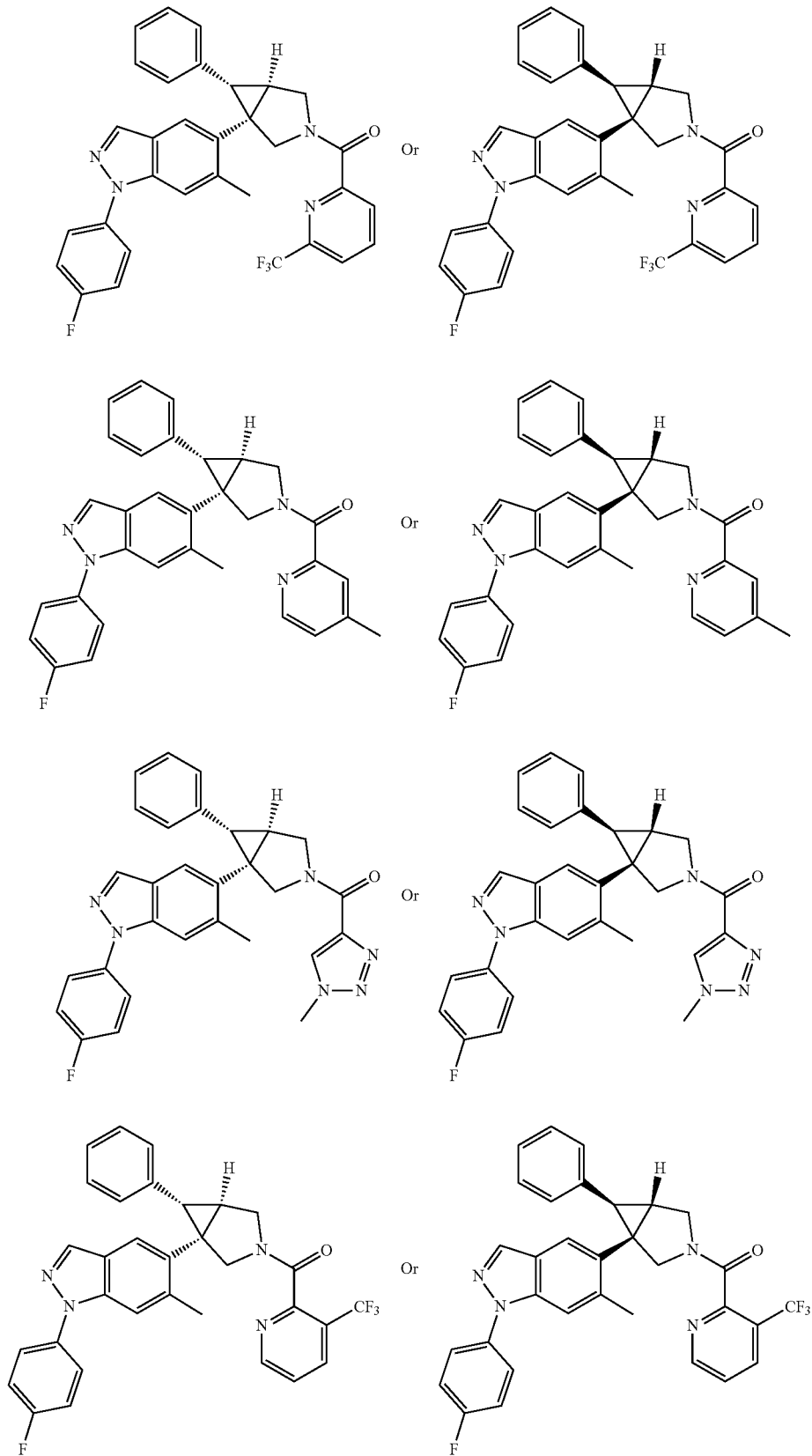

TABLE 1F-continued
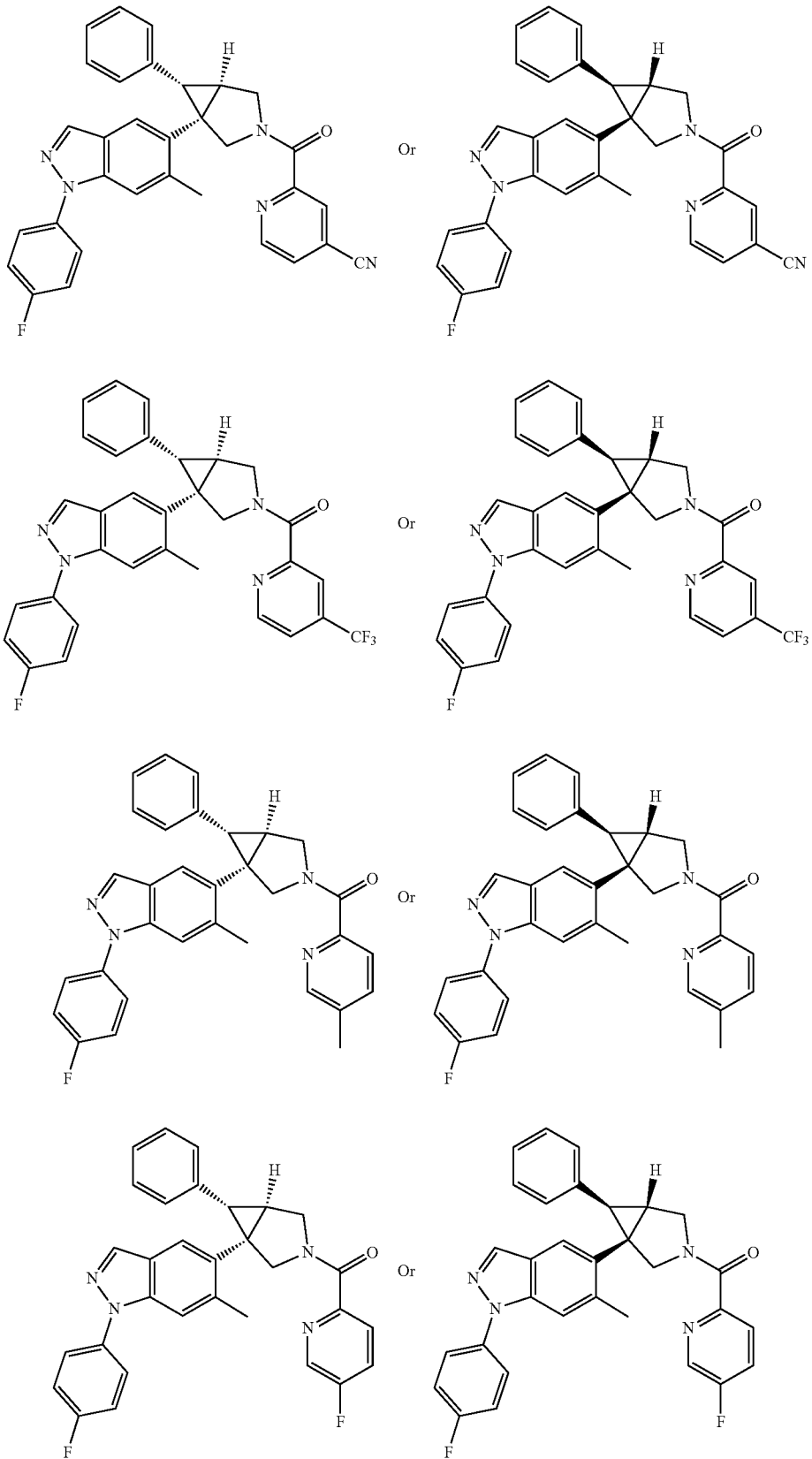

TABLE 1F-continued
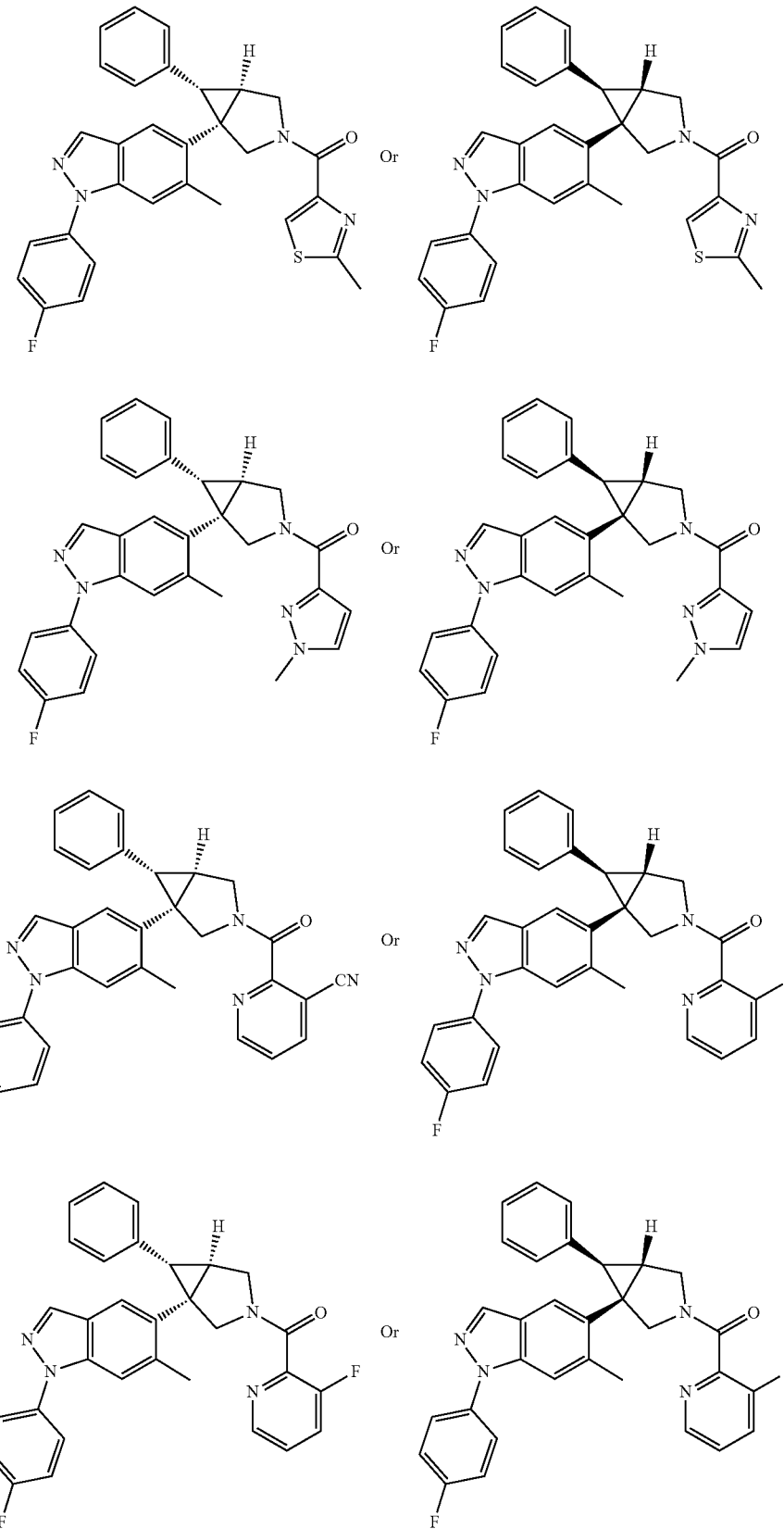

TABLE 1F-continued
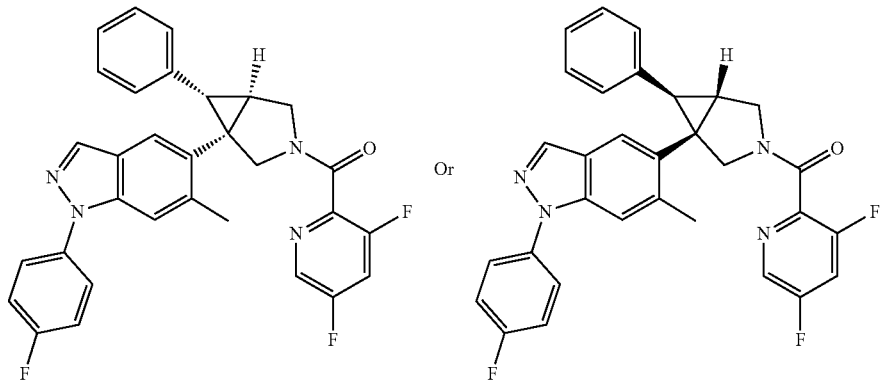 [SMILES: Cc1cc2c(cnn2-c2ccc(F)cc2)cc1[C@@]12CN(C(=O)c3ncc(F)cc3F)C[C@@H]1[C@H]2c1ccccc1 ; Cc1cc2c(cnn2-c2ccc(F)cc2)cc1[C@]12CN(C(=O)c3ncc(F)cc3F)C[C@H]1[C@@H]2c1ccccc1]
Or
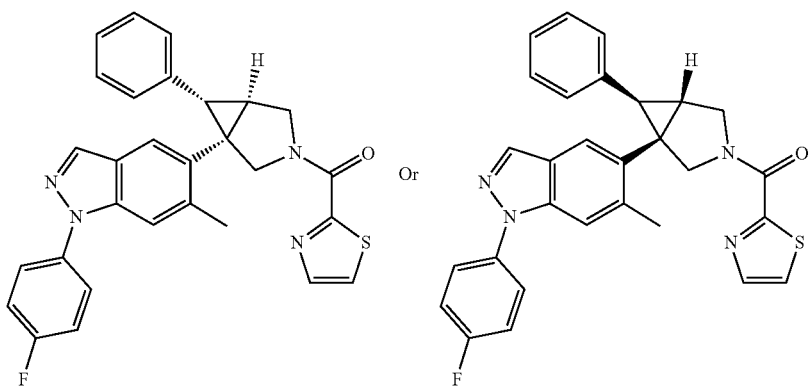 [SMILES: Cc1cc2c(cnn2-c2ccc(F)cc2)cc1[C@@]12CN(C(=O)c3nccs3)C[C@@H]1[C@H]2c1ccccc1 ; Cc1cc2c(cnn2-c2ccc(F)cc2)cc1[C@]12CN(C(=O)c3nccs3)C[C@H]1[C@@H]2c1ccccc1]
Or
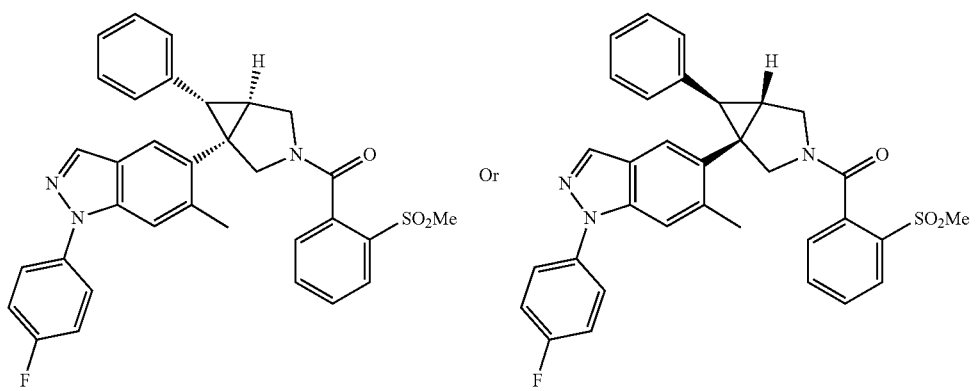 [SMILES: Cc1cc2c(cnn2-c2ccc(F)cc2)cc1[C@@]12CN(C(=O)c3ccccc3S(C)(=O)=O)C[C@@H]1[C@H]2c1ccccc1 ; Cc1cc2c(cnn2-c2ccc(F)cc2)cc1[C@]12CN(C(=O)c3ccccc3S(C)(=O)=O)C[C@H]1[C@@H]2c1ccccc1]
Or
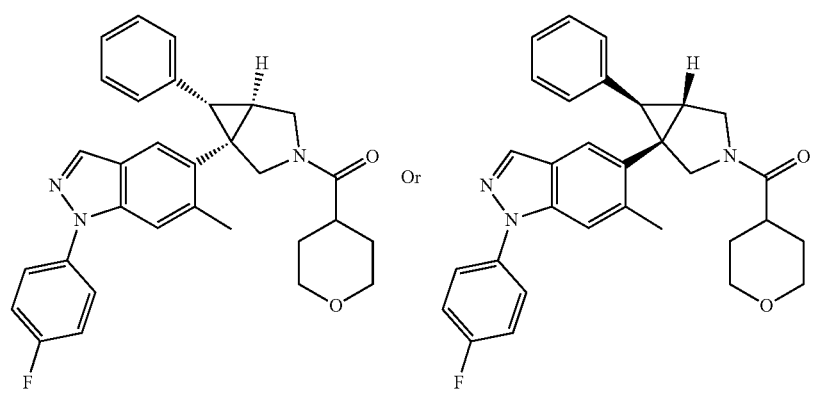 [SMILES: Cc1cc2c(cnn2-c2ccc(F)cc2)cc1[C@@]12CN(C(=O)C3CCOCC3)C[C@@H]1[C@H]2c1ccccc1 ; Cc1cc2c(cnn2-c2ccc(F)cc2)cc1[C@]12CN(C(=O)C3CCOCC3)C[C@H]1[C@@H]2c1ccccc1]
Or

TABLE 1F-continued
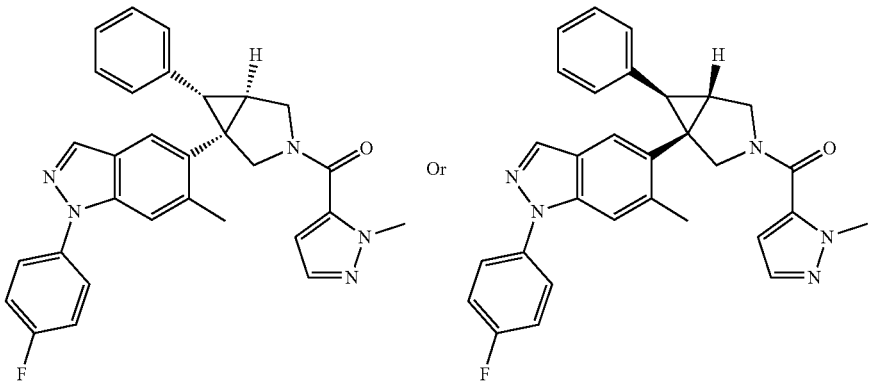 [SMILES: Cc1cc2c(cnn2-c2ccc(F)cc2)cc1[C@@]12CN(C(=O)c3ccnn3C)C[C@@H]1[C@H]2c1ccccc1 ; Cc1cc2c(cnn2-c2ccc(F)cc2)cc1[C@]12CN(C(=O)c3ccnn3C)C[C@H]1[C@@H]2c1ccccc1]
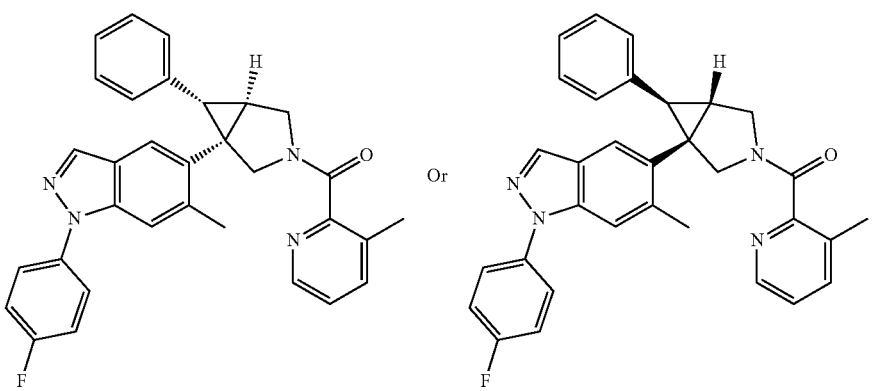 [SMILES: Cc1cc2c(cnn2-c2ccc(F)cc2)cc1[C@@]12CN(C(=O)c3ncccc3C)C[C@@H]1[C@H]2c1ccccc1 ; Cc1cc2c(cnn2-c2ccc(F)cc2)cc1[C@]12CN(C(=O)c3ncccc3C)C[C@H]1[C@@H]2c1ccccc1]
In some embodiments, the compound of Formula I, Ia, Ib, Ib-1, Ib-2, Ic, Ic-1, Id-1, or Id-2, or a pharmaceutically acceptable salt thereof, is a compound of Table 1G.
TABLE 1G
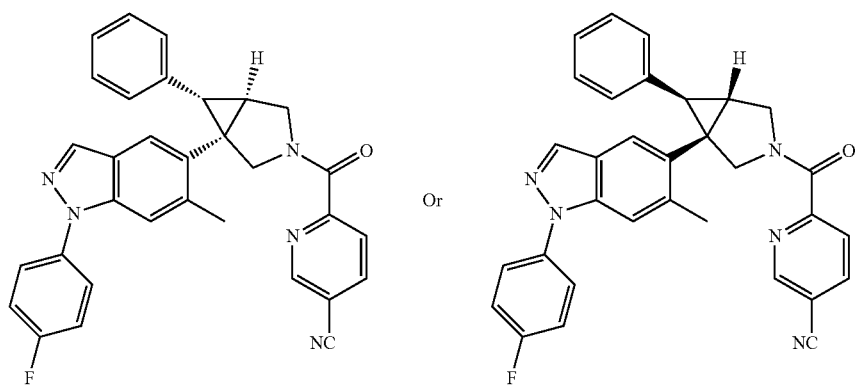 [SMILES: Cc1cc2c(cnn2-c2ccc(F)cc2)cc1[C@@]12CN(C(=O)c3ccc(C(F)(F)F)cn3)C[C@@H]1[C@H]2c1ccccc1 ; Cc1cc2c(cnn2-c2ccc(F)cc2)cc1[C@]12CN(C(=O)c3ccc(C(F)(F)F)cn3)C[C@H]1[C@@H]2c1ccccc1]

TABLE 1G-continued
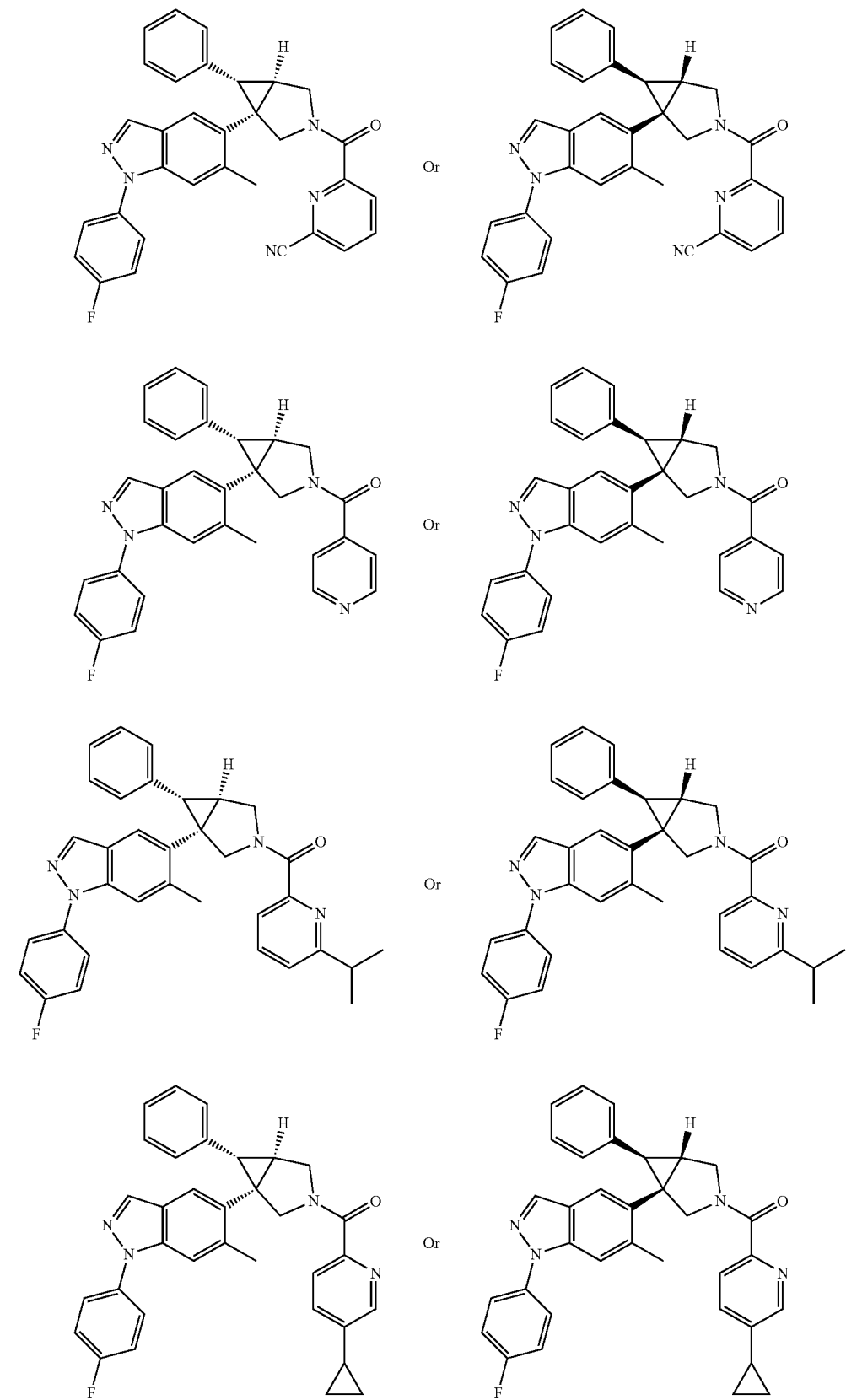

TABLE 1G-continued
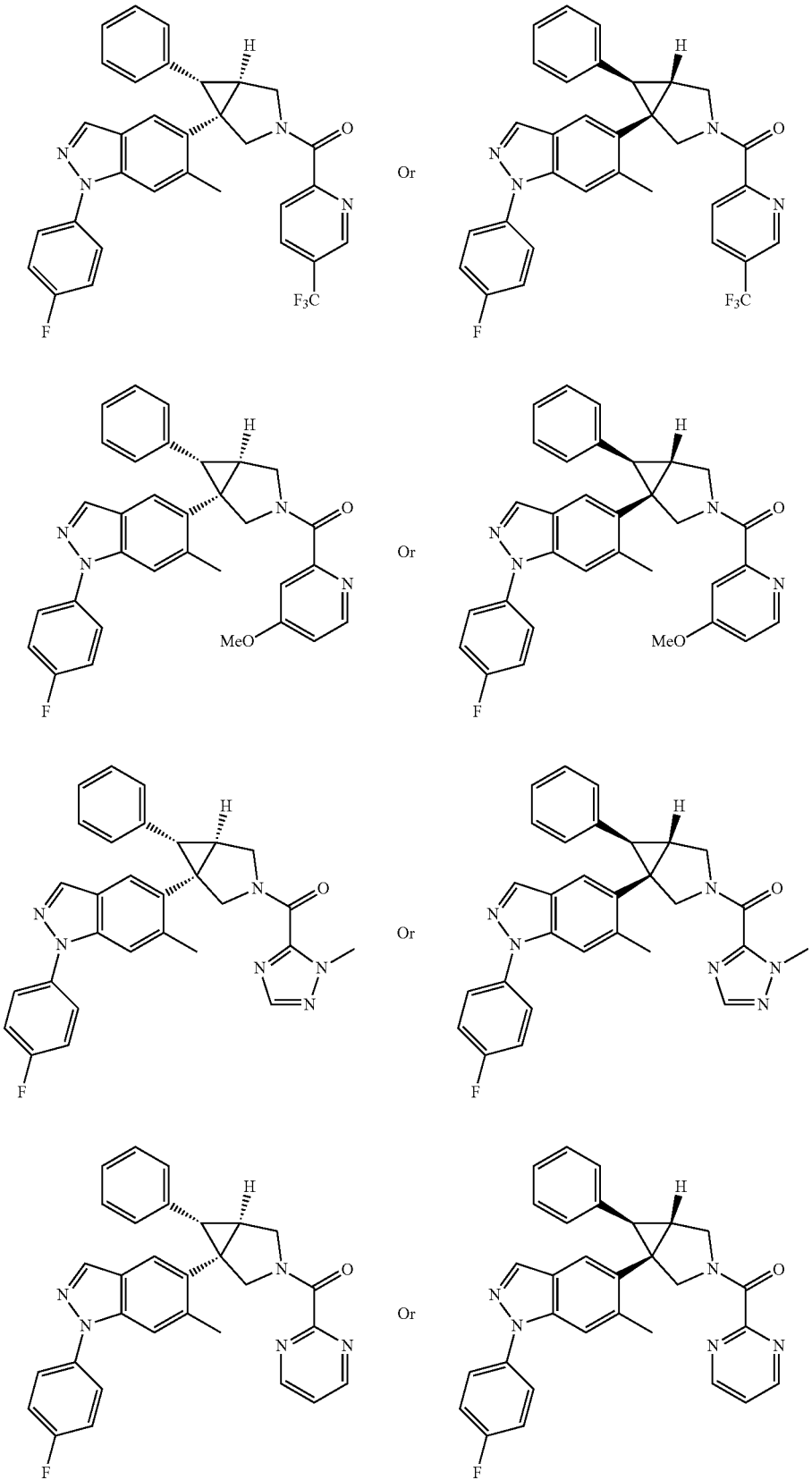

TABLE 1G-continued
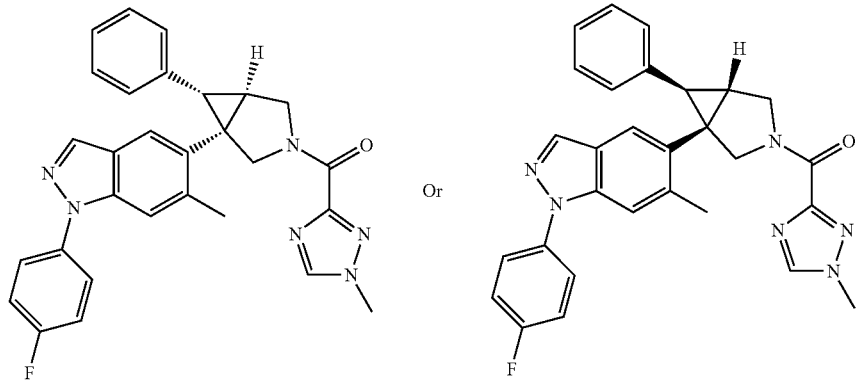 [SMILES: Cc1cc2c(cnn2-c2ccc(F)cc2)cc1[C@@]12CN(C(=O)c3ncn(C)n3)C[C@@H]1[C@H]2c1ccccc1 ; Cc1cc2c(cnn2-c2ccc(F)cc2)cc1[C@]12CN(C(=O)c3ncn(C)n3)C[C@H]1[C@@H]2c1ccccc1]
Or
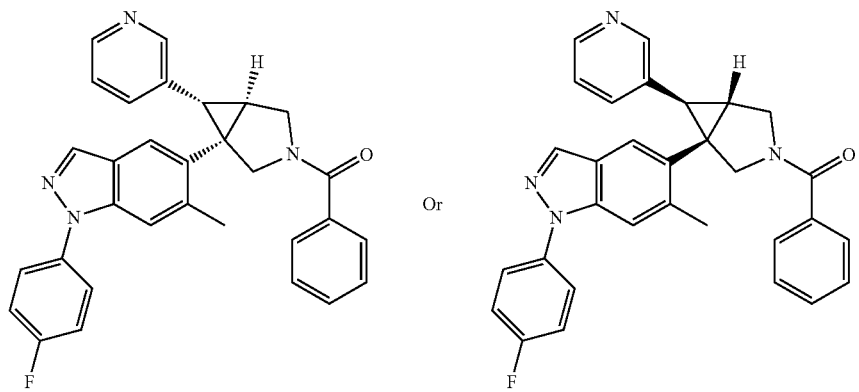 [SMILES: Cc1cc2c(cnn2-c2ccc(F)cc2)cc1[C@@]12CN(C(=O)c3ccccc3)C[C@@H]1[C@H]2c1cccnc1 ; Cc1cc2c(cnn2-c2ccc(F)cc2)cc1[C@]12CN(C(=O)c3ccccc3)C[C@H]1[C@@H]2c1cccnc1]
Or
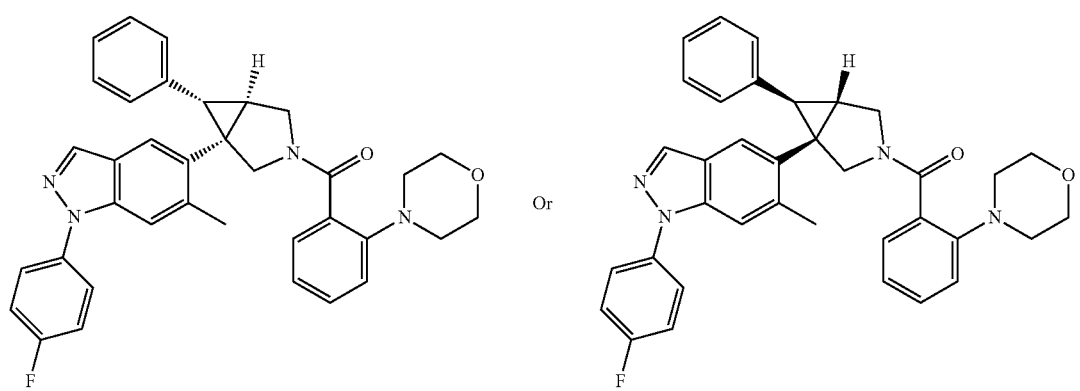 [SMILES: Cc1cc2c(cnn2-c2ccc(F)cc2)cc1[C@@]12CN(C(=O)c3ccccc3N3CCOCC3)C[C@@H]1[C@H]2c1ccccc1 ; Cc1cc2c(cnn2-c2ccc(F)cc2)cc1[C@]12CN(C(=O)c3ccccc3N3CCOCC3)C[C@H]1[C@@H]2c1ccccc1]
Or
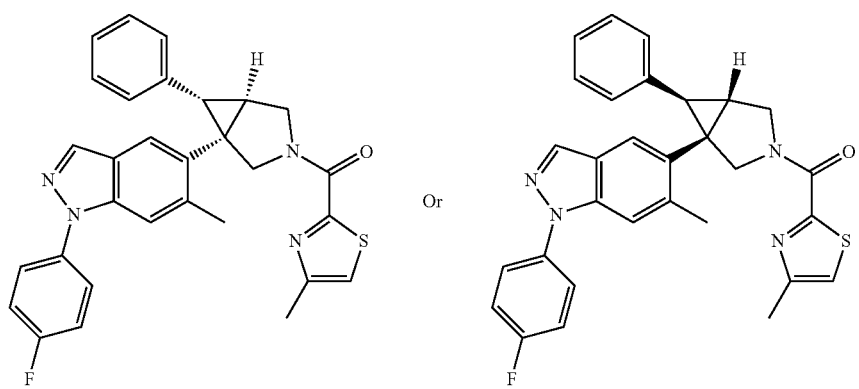 [SMILES: Cc1csc(C(=O)N2C[C@@H]3[C@@H](c4ccccc4)[C@]3(c3cc4cnn(-c5ccc(F)cc5)c4cc3C)C2)n1 ; Cc1csc(C(=O)N2C[C@H]3[C@H](c4ccccc4)[C@@]3(c3cc4cnn(-c5ccc(F)cc5)c4cc3C)C2)n1]
Or

TABLE 1G-continued
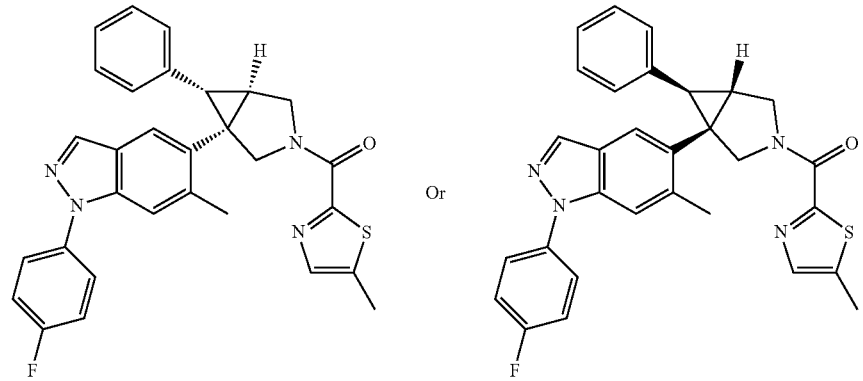 [SMILES: Cc1cnc(C(=O)N2C[C@@H]3[C@@H](c4ccccc4)[C@]3(c3cc4cnn(-c5ccc(F)cc5)c4cc3C)C2)s1 ; Cc1cnc(C(=O)N2C[C@H]3[C@H](c4ccccc4)[C@@]3(c3cc4cnn(-c5ccc(F)cc5)c4cc3C)C2)s1]
Or
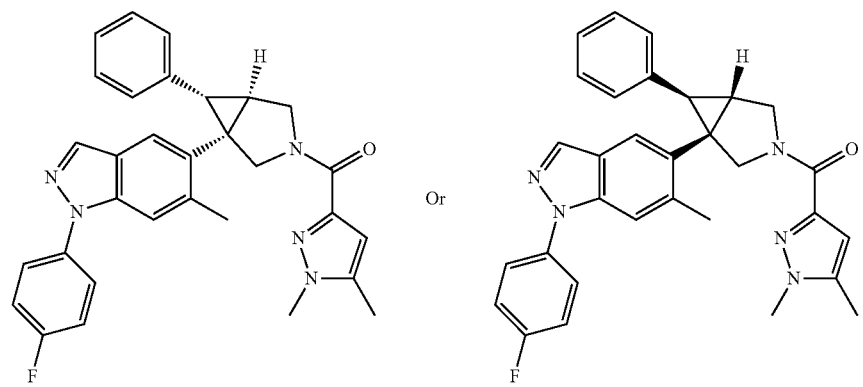 [SMILES: Cc1cc2c(cnn2-c2ccc(F)cc2)cc1[C@@]12CN(C(=O)c3cc(C)n(C)n3)C[C@@H]1[C@H]2c1ccccc1 ; Cc1cc2c(cnn2-c2ccc(F)cc2)cc1[C@]12CN(C(=O)c3cc(C)n(C)n3)C[C@H]1[C@@H]2c1ccccc1]
Or
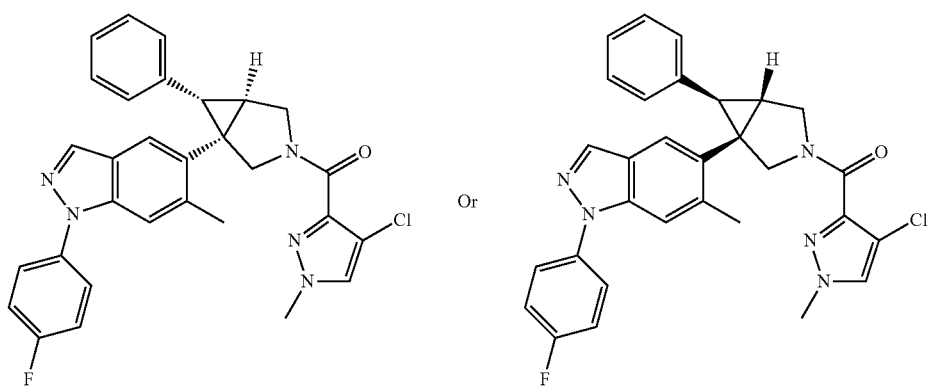 [SMILES: Cc1cc2c(cnn2-c2ccc(F)cc2)cc1[C@@]12CN(C(=O)c3nn(C)cc3Cl)C[C@@H]1[C@H]2c1ccccc1 ; Cc1cc2c(cnn2-c2ccc(F)cc2)cc1[C@]12CN(C(=O)c3nn(C)cc3Cl)C[C@H]1[C@@H]2c1ccccc1]
Or
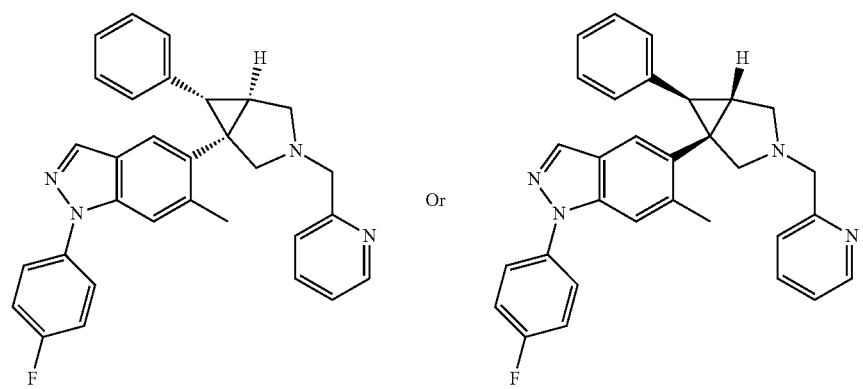 [SMILES: Cc1cc2c(cnn2-c2ccc(F)cc2)cc1[C@@]12CN(Cc3ccccn3)C[C@@H]1[C@H]2c1ccccc1 ; Cc1cc2c(cnn2-c2ccc(F)cc2)cc1[C@]12CN(Cc3ccccn3)C[C@H]1[C@@H]2c1ccccc1]

TABLE 1G-continued
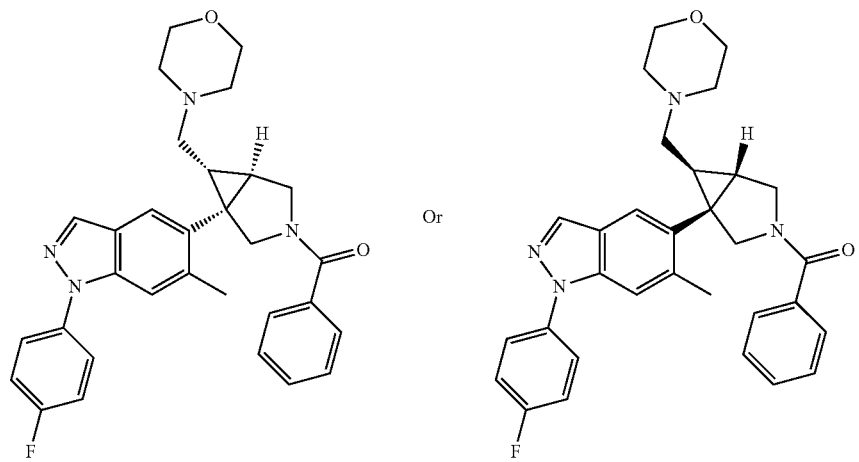 [SMILES: Cc1cc2c(cnn2-c2ccc(F)cc2)cc1[C@@]12CN(C(=O)c3ccccc3)C[C@@H]1[C@H]2CN1CCOCC1 ; Cc1cc2c(cnn2-c2ccc(F)cc2)cc1[C@]12CN(C(=O)c3ccccc3)C[C@H]1[C@@H]2CN1CCOCC1]
Or
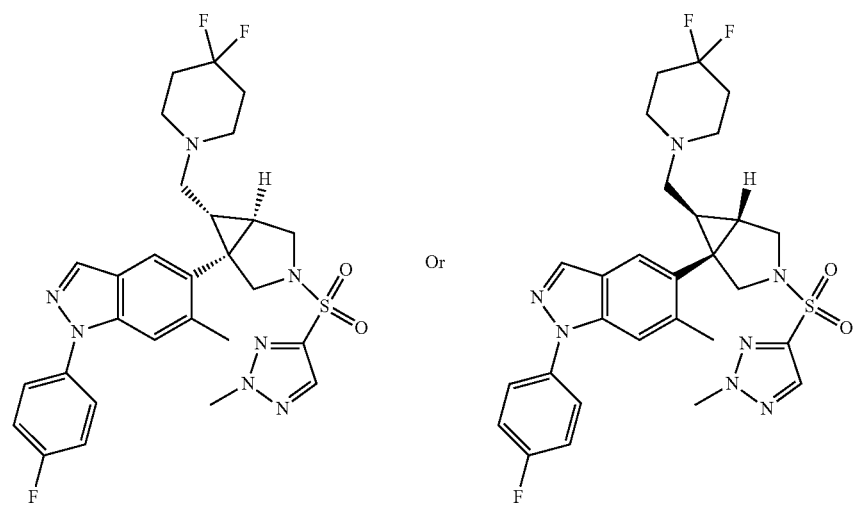 [SMILES: Cc1cc2c(cnn2-c2ccc(F)cc2)cc1[C@@]12CN(S(=O)(=O)c3cnn(C)n3)C[C@@H]1[C@H]2CN1CCC(F)(F)CC1 ; Cc1cc2c(cnn2-c2ccc(F)cc2)cc1[C@]12CN(S(=O)(=O)c3cnn(C)n3)C[C@H]1[C@@H]2CN1CCC(F)(F)CC1]
Or
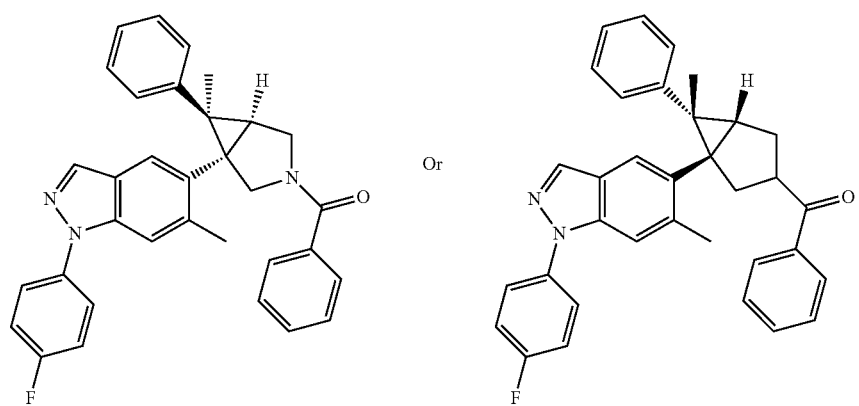 [SMILES: Cc1cc2c(cnn2-c2ccc(F)cc2)cc1[C@@]12CN(C(=O)c3ccccc3)C[C@@H]1[C@]2(C)c1ccccc1 ; Cc1cc2c(cnn2-c2ccc(F)cc2)cc1[C@]12CC(C(=O)c3ccccc3)C[C@H]1[C@@]2(C)c1ccccc1]
Or

TABLE 1G-continued
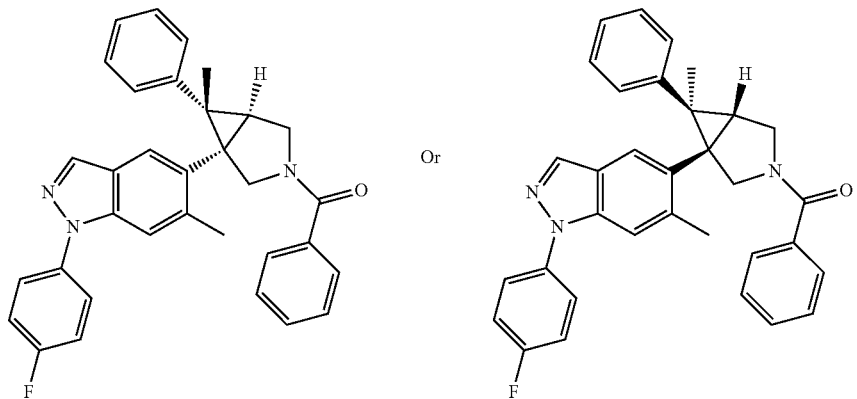 [SMILES: Cc1cc2c(cnn2-c2ccc(F)cc2)cc1[C@@]12CN(C(=O)c3ccccc3)C[C@@H]1[C@@]2(C)c1ccccc1 ; Cc1cc2c(cnn2-c2ccc(F)cc2)cc1[C@]12CN(C(=O)c3ccccc3)C[C@H]1[C@]2(C)c1ccccc1]
Or
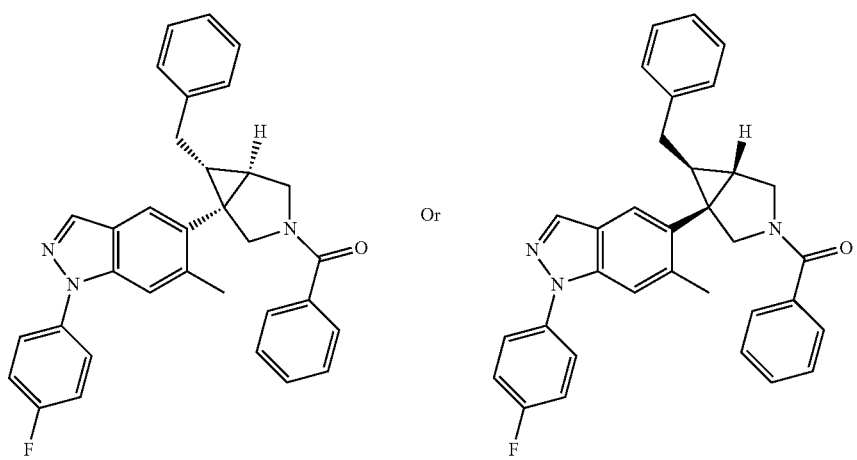 [SMILES: Cc1cc2c(cnn2-c2ccc(F)cc2)cc1[C@@]12CN(C(=O)c3ccccc3)C[C@@H]1[C@H]2Cc1ccccc1 ; Cc1cc2c(cnn2-c2ccc(F)cc2)cc1[C@]12CN(C(=O)c3ccccc3)C[C@H]1[C@@H]2Cc1ccccc1]
Or
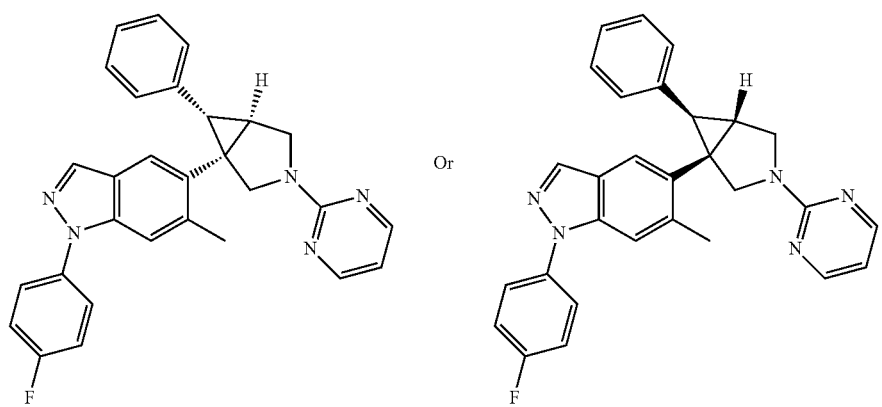 [SMILES: Cc1cc2c(cnn2-c2ccc(F)cc2)cc1[C@@]12CN(c3ncccn3)C[C@@H]1[C@H]2c1ccccc1 ; Cc1cc2c(cnn2-c2ccc(F)cc2)cc1[C@]12CN(c3ncccn3)C[C@H]1[C@@H]2c1ccccc1]
Or

TABLE 1G-continued

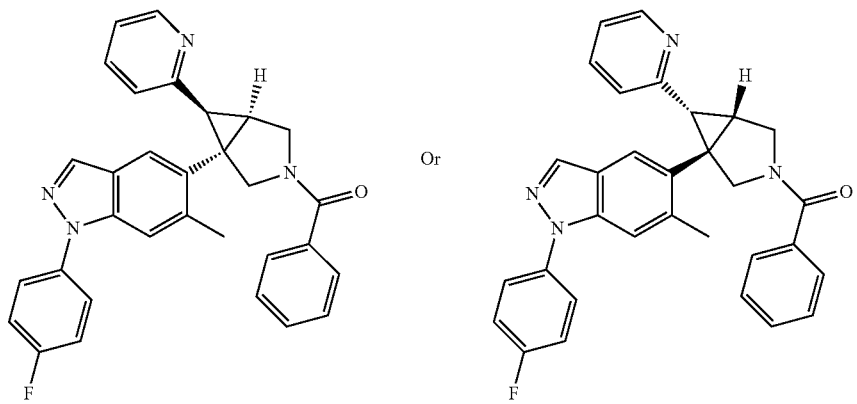 [SMILES: Cc1cc2c(cnn2-c2ccc(F)cc2)cc1[C@@]12CN(C(=O)c3ccccc3)C[C@@H]1[C@@H]2c1ccccn1 ; Cc1cc2c(cnn2-c2ccc(F)cc2)cc1[C@]12CN(C(=O)c3ccccc3)C[C@H]1[C@H]2c1ccccn1]

Or

In some embodiments, the compound of Formula I, Ia, Ib, Ib-1, Ib-2, Ic, Ic-1, Id-1, or Id-2, or a pharmaceutically acceptable salt thereof, is a compound of Table 1A, Table 1B, Table 1C, Table 1D, Table 1E, Table 1F or Table 1G. In some embodiments, the compound of Formula I, Ia, Ib, Ib-1, Ib-2, Ic, Ic-1, Id-1, or Id-2, or a pharmaceutically acceptable salt thereof, is a compound of Table 1A, Table 1B, Table 1C, Table 1D or Table 1E. In some embodiments, the compound of Formula I, Ia, Ic, or Ic-1, or a pharmaceutically acceptable salt thereof, is a compound of Table 1A, or Table 1B. In some embodiments, the compound of Formula I, Ia, Ic, or Ic-1, or a pharmaceutically acceptable salt thereof, is a compound of Table 1A. In some embodiments, the compound of Formula I, Ia, Ic, or Ic-1, or a pharmaceutically acceptable salt thereof, is a compound of Table 1B.

In some embodiments, the compound of Formula I, Ia, Ib, Ib-1, Ib-2, Ic, Ic-1, Id-1, or Id-2 is a compound of Table 1A, Table 1B, Table 1C, Table 1D, Table 1E, Table 1F or Table 1G. In some embodiments, the compound of Formula I, Ia, Ib, Ib-1, Ib-2, Ic, Ic-1, Id-1, or Id-2 is a compound of Table 1A, Table 1B, Table 1C, Table 1D or Table 1E. In some embodiments, the compound of Formula I, Ia, Ic, or Ic-1 is a compound of Table 1A, or Table 1B. In some embodiments, the compound of Formula I, Ia, Ic, or Ic-1 is a compound of Table 1A. In some embodiments, the compound of Formula I, Ia, Ic, or Ic-1 is a compound of Table 1B.

In some embodiments, the compound of Formula I, Ia, Ib, Ib-1, Ib-2, Id-1, or Id-2, or a pharmaceutically acceptable salt thereof, is a compound of Table 1C, Table 1D or Table 1E, Table 1F or Table 1G. In some embodiments, the compound of Formula I, Ia, Ib, Ib-1, Ib-2, Id-1, or Id-2, or a pharmaceutically acceptable salt thereof, is a compound of Table 1C, Table 1D or Table 1E. In some embodiments, the compound of Formula I, Ia, Ib, Ib-1, Ib-2, Id-1, or Id-2, or a pharmaceutically acceptable salt thereof, is a compound of Table 1C. In some embodiments, the compound of Formula I, Ia, Ib, Ib-1, Ib-2, Id-1, or Id-2, or a pharmaceutically acceptable salt thereof, is a compound of Table 1D. In some embodiments, the compound of Formula I, Ia, Ib, Ib-1, Ib-2, Id-1, or Id-2, or a pharmaceutically acceptable salt thereof, is a compound of Table 1E. In some embodiments, the compound of Formula I, Ia, Ib, Ib-1, Ib-2, Id-1, or Id-2, or a pharmaceutically acceptable salt thereof, is a compound of Table 1F. In some embodiments, the compound of Formula I, Ia, Ib, Ib-1, Ib-2, Id-1, or Id-2, or a pharmaceutically acceptable salt thereof, is a compound of Table 1G.

In some embodiments, the compound of Formula I, Ia, Ib, Ib-1, Ib-2, Id-1, or Id-2 is a compound of Table 1C, Table 1D or Table 1E, Table 1F or Table 1G. In some embodiments, the compound of Formula I, Ia, Ib, Ib-1, Ib-2, Id-1, or Id-2 is a compound of Table 1C, Table 1D or Table 1E. In some embodiments, the compound of Formula I, Ia, Ib, Ib-1, Ib-2, Id-1, or Id-2 is a compound of Table 1C. In some embodiments, the compound of Formula I, Ia, Ib, Ib-1, Ib-2, Id-1, or Id-2 is a compound of Table 1D. In some embodiments, the compound of Formula I, Ia, Ib, Ib-1, Ib-2, Id-1, or Id-2 is a compound of Table 1E. In some embodiments, the compound of Formula I, Ia, Ib, Ib-1, Ib-2, Id-1, or Id-2 is a compound of Table 1F. In some embodiments, the compound of Formula I, Ia, Ib, Ib-1, Ib-2, Id-1, or Id-2 is a compound of Table 1G.

In some embodiments, the compound of Formula I, Ia, Ib, Ib-1, Ib-2, Id-1, or Id-2, or a pharmaceutically acceptable salt thereof, is a compound having the structure of

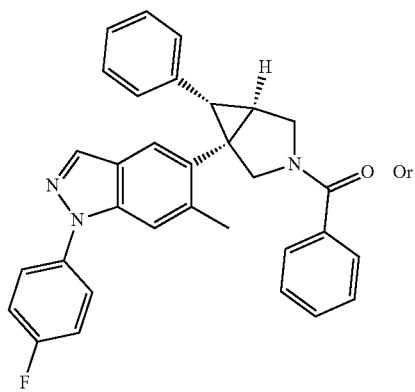

Or

169
-continued
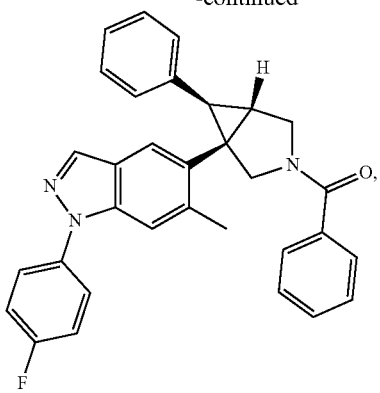
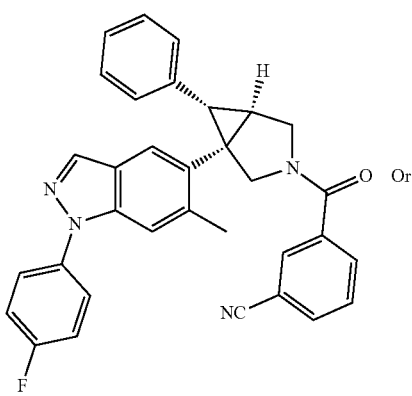  Or
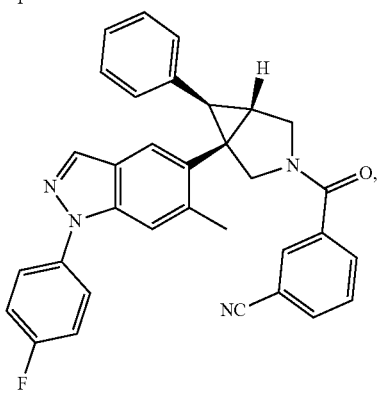
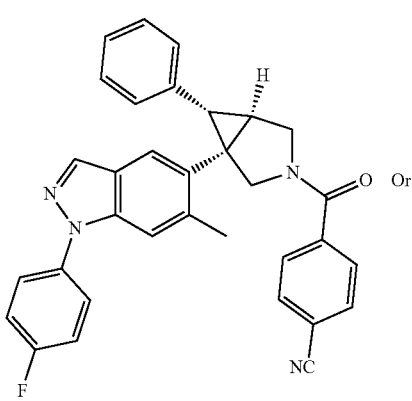  Or
170
-continued
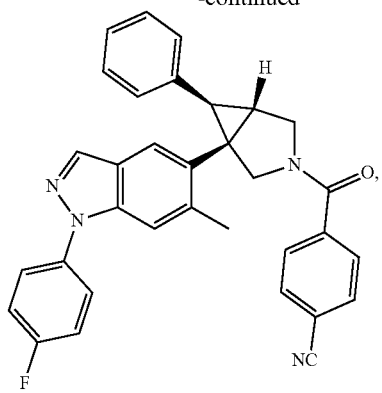
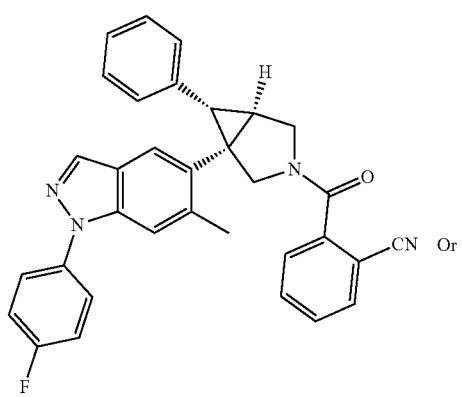  Or
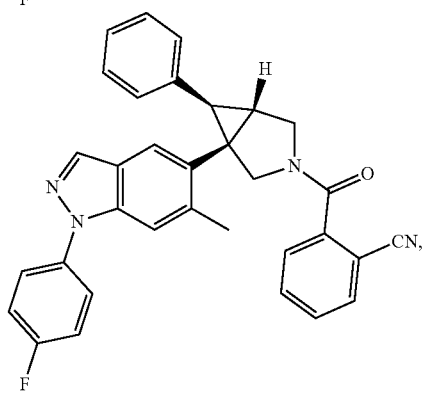
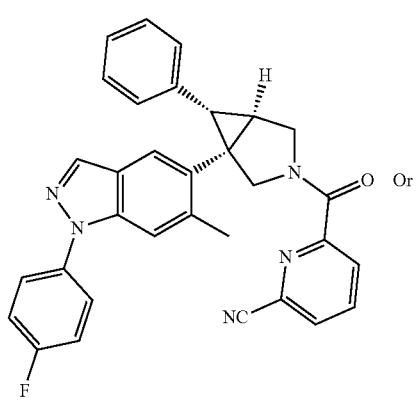  Or 171
-continued
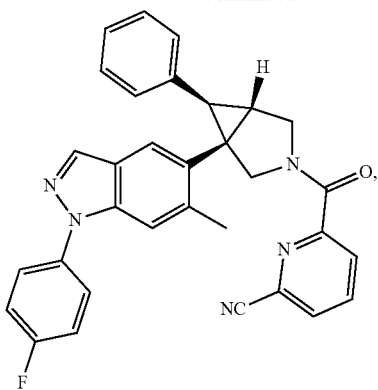
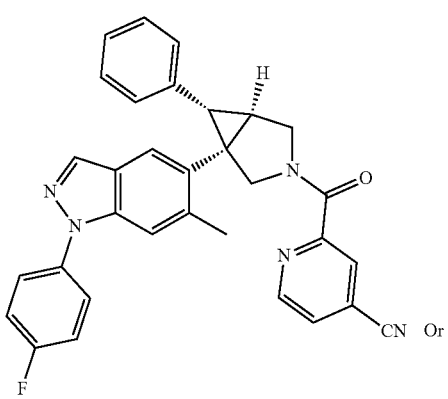
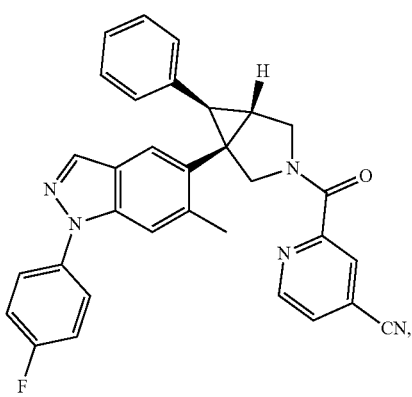
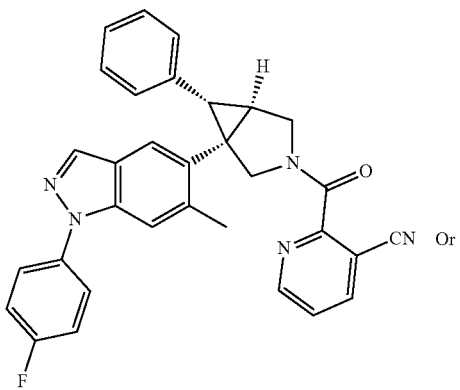
172
-continued
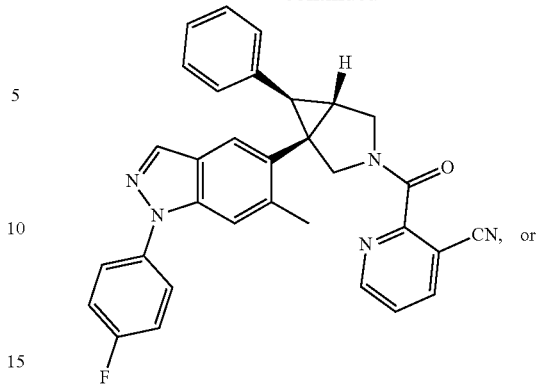
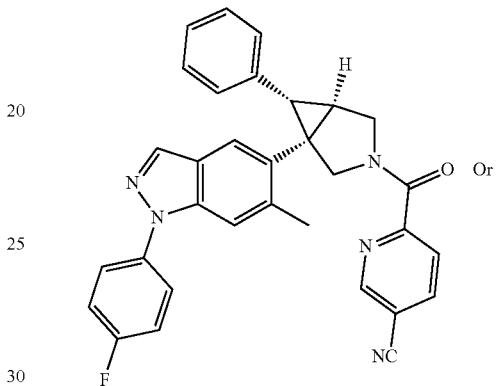
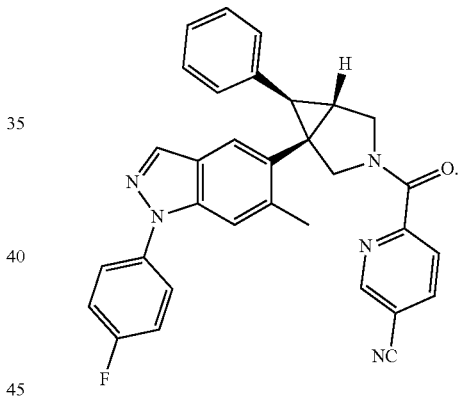
In some embodiments, the compound of Formula I, Ia, Ib, Ib-1, Ib-2, Id-1, or Id-2, or a pharmaceutically acceptable salt thereof, is a compound having the structure of
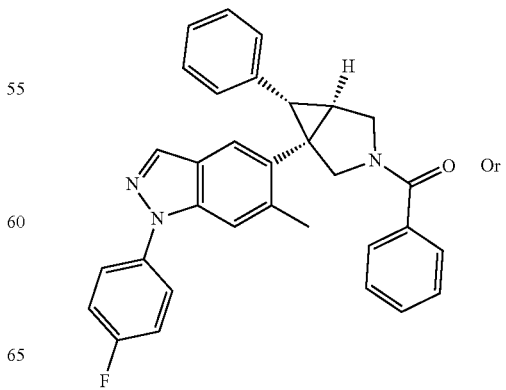

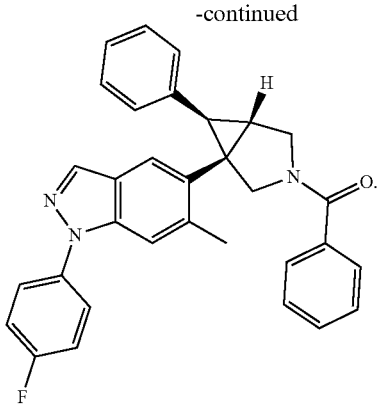

In some embodiments, the compound of Formula I, Ia, Ib, Ib-1, Ib-2, Id-1, or Id-2, or a pharmaceutically acceptable salt thereof, is a compound having the structure of

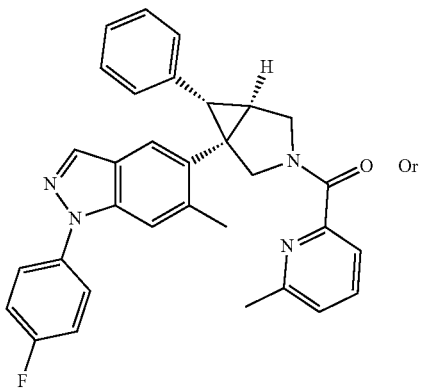 Or

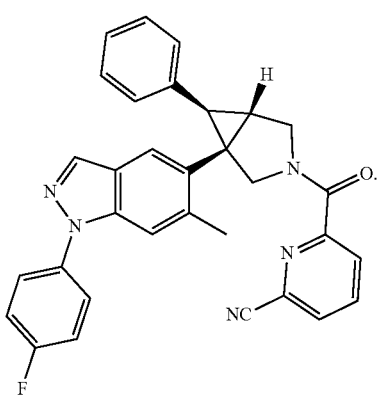

In some embodiments, the compound of Formula I, Ia, Ib, Ib-1, Ib-2, Id-1, or Id-2, or a pharmaceutically acceptable salt thereof, is a compound having the structure of

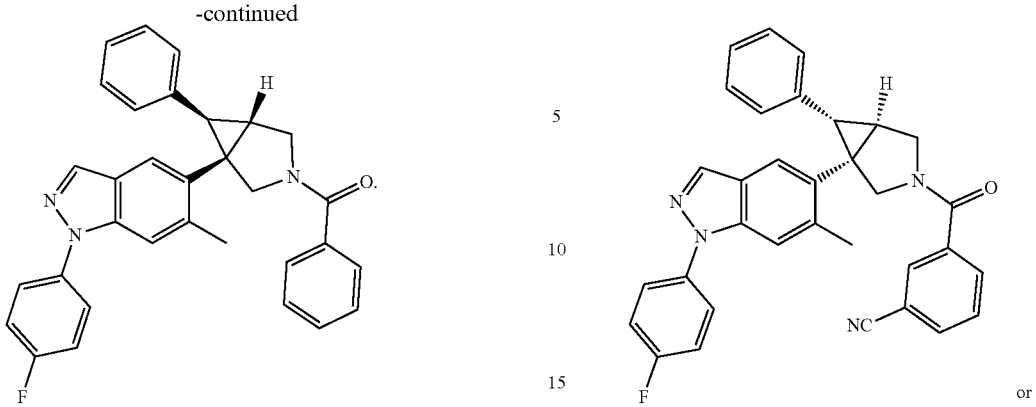

or

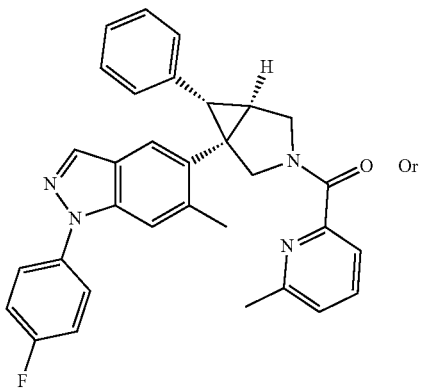

In some embodiments, the compound of Formula I, Ia, Ib, Ib-1, Ib-2, Id-1, or Id-2, or a pharmaceutically acceptable salt thereof, is a compound having the structure of

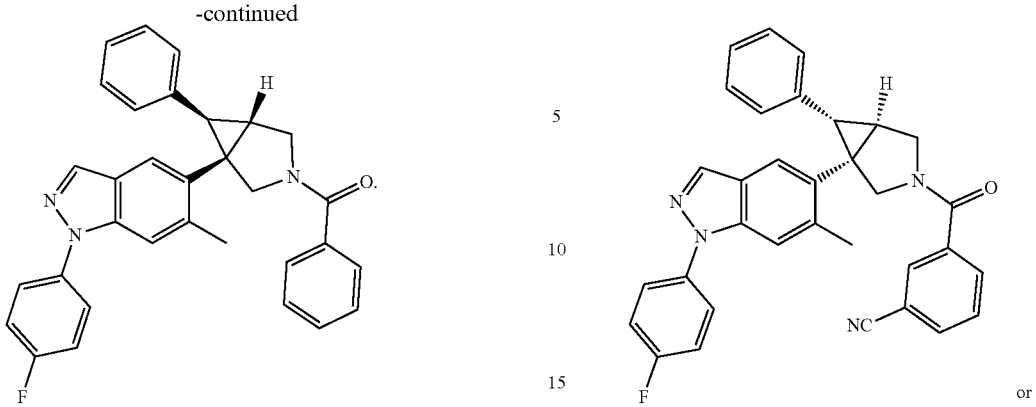

or

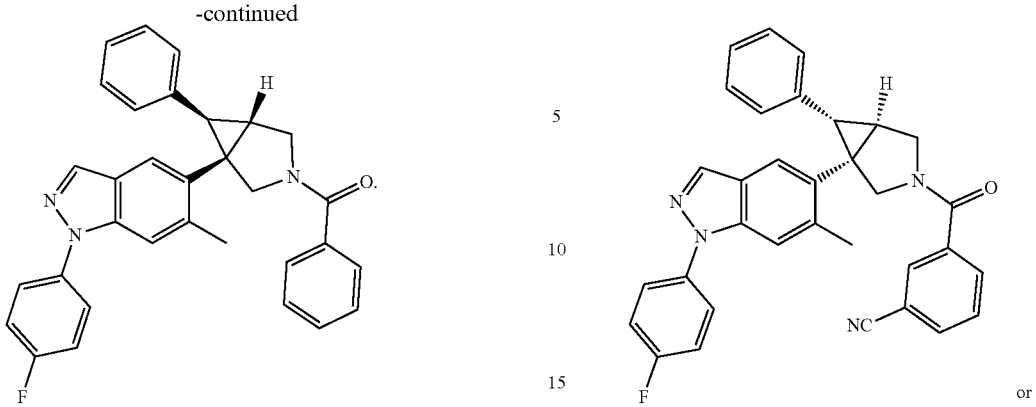

In some embodiments, the compound of Formula I, Ia, Ib, Ib-1, Ib-2, Id-1, or Id-2, or a pharmaceutically acceptable salt thereof, is a compound having the structure of

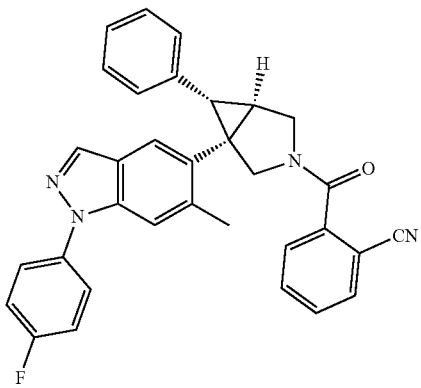

or

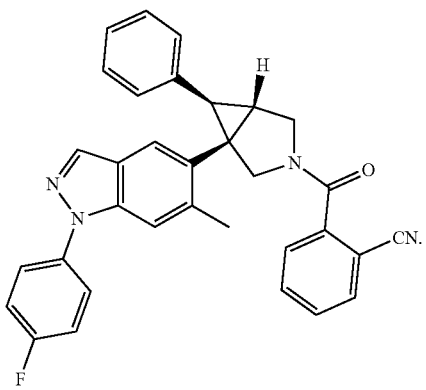

In some embodiments, the compound of Formula I, Ia, Ib, Ib-1, Ib-2, Id-1, or Id-2, or a pharmaceutically acceptable salt thereof, is a compound having the structure of

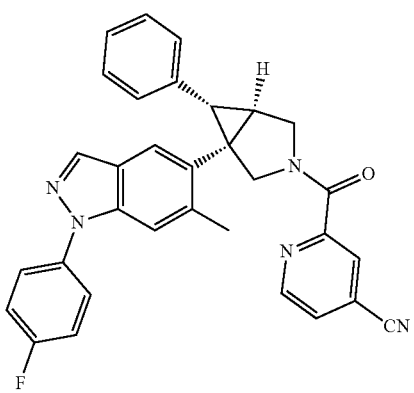

or

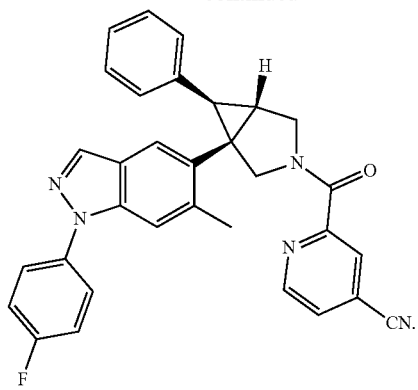

In some embodiments, the compound of Formula I, Ia, Ib, Ib-1, Ib-2, Id-1, or Id-2, or a pharmaceutically acceptable salt thereof, is a compound having the structure of

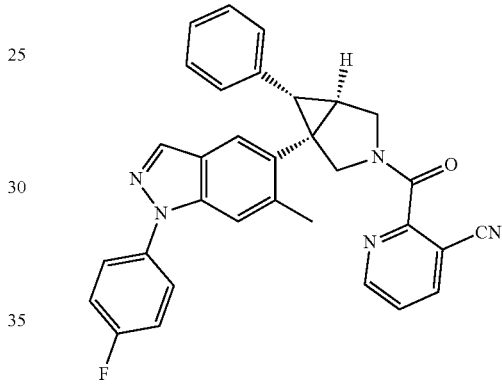

or

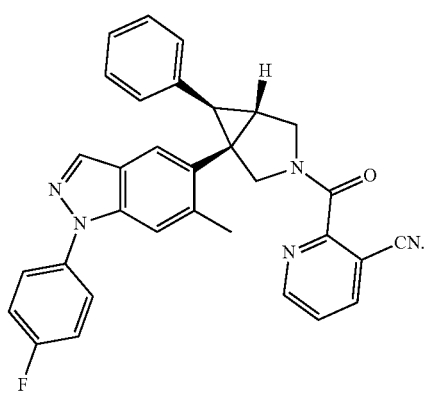

In some embodiments, the compound of Formula I, Ia, Ib, Ib-1, Ib-2, Id-1, or Id-2, or a pharmaceutically acceptable salt thereof, is a compound having the structure of

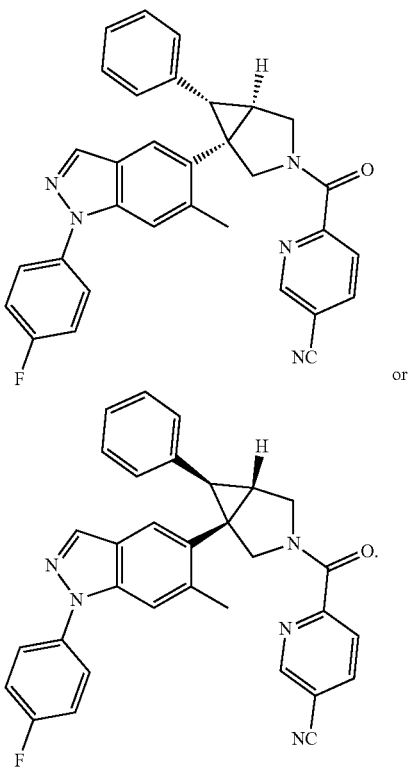

or

The compounds of the present invention may exist as salts. The present invention includes such salts, which can be pharmaceutically acceptable salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Compositions

In some embodiments, the present invention provides a pharmaceutical composition comprising a compound of any one of the compounds of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of Formula I, Ia, Ib, Ib-1, Ib-2, Ic, Ic-1, Id-1, and Id-2 of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including one or more pharmaceutically acceptable carriers and/or excipients and either a compound of Formula I, Ia, Ib, Ib-1, Ib-2, Ic, Ic-1, Id-1, and Id-2, or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excipients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of Formula I, Ia, Ib, Ib-1, Ib-2, Ic, Ic-1, Id-1, and Id-2 mixed with a filler or binders such as lactose or starches, lubricants such as talc or magnesium stearate, and, optionally, stabilizers. In soft capsules, the compounds of Formula I, Ia, Ib, Ib-1, Ib-2, Ic, Ic-1, Id-1, and Id-2 may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of Formula I, Ia, Ib, Ib-1, Ib-2, Ic, Ic-1, Id-1, and Id-2 in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of Formula I, Ia, Ib, Ib-1, Ib-2, Ic, Ic-1, Id-1, and Id-2 of the invention can be delivered by transdermally, by a topical route, formulated as applicator sticks, solutions, suspensions, emulsions, gels, creams, ointments, pastes, jellies, paints, powders, and aerosols.

The compounds of Formula I, Ia, Ib, Ib-1, Ib-2, Ic, Ic-1, Id-1, and Id-2 and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the compounds of Formula I, Ia, Ib, Ib-1, Ib-2, Ic, Ic-1, Id-1, and Id-2 of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The pharmaceutical formulations of the compounds of Formula I, Ia, Ib, Ib-1, Ib-2, Ic, Ic-1, Id-1, and Id-2 of the invention can be provided as a salt and can be formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

In some embodiments, the formulations of the compounds of Formula I, Ia, Ib, Ib-1, Ib-2, Ic, Ic-1, Id-1, and Id-2 of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69;

Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compound of Formula I, Ia, Ib, Ib-1, Ib-2, Ic, Ic-1, Id-1, and Id-2 formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of Formula I, Ia, Ib, Ib-1, Ib-2, Ic, Ic-1, Id-1, and Id-2 is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing formulations including the compound of Formula I, Ia, Ib, Ib-1, Ib-2, Ic, Ic-1, Id-1, and Id-2 for parenteral administration are known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of Formula I, Ia, Ib, Ib-1, Ib-2, Ic, Ic-1, Id-1, and Id-2 of the invention has been formulated in one or more acceptable carriers, it can be placed in an appropriate container and labeled for treatment of an indicated condition. For administration of the compounds of Formula I, Ia, Ib, Ib-1, Ib-2, Ic, Ic-1, Id-1, and Id-2, such labeling would include, e.g., instructions concerning the amount, frequency and method of administration.

In some embodiments, the compositions of the present invention are useful for parenteral administration, such as intravenous (IV) administration or administration into a body cavity or lumen of an organ. The formulations for administration will commonly comprise a solution of the compositions of the present invention dissolved in one or more pharmaceutically acceptable carriers. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, tonicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

V. Methods & Use

In some embodiments, the present invention provides a method of treating a disorder or condition through modulating a glucocorticoid receptor, the method comprising administering to a subject in need of such treatment, a therapeutically effective amount of any one of the compounds of the present invention, or a pharmaceutical composition of the present invention, thereby treating the disorder or condition.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In some embodiments, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR), aldosterone receptor (AR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR). In another exemplary embodiment, the specific glucocorticoid antagonist binds preferentially to GR rather than to the aldosterone receptor (AR).

In some embodiments, the specific glucocorticoid receptor antagonist binds to the GR with an association constant (Kd) that is at least 10-fold less than the Kd for any other NR. In some embodiments, the specific glucocorticoid receptor antagonist binds to the GR with an association constant (Kd) that is at least 100-fold less than the Kd for any other NR. In some embodiments, the specific glucocorticoid receptor antagonist binds to the GR with an association constant (Kd) that is at least 1000-fold less than the Kd for any other NR.

In some embodiments, the present invention provides a method of treating a disorder or condition through antagonizing a glucocorticoid receptor, the method comprising administering to a subject in need of such treatment, an effective amount of any one of the compounds of the present invention, or a pharmaceutical composition of the present invention.

In some embodiments, the disorder or condition is selected from the group consisting of Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the disorder or condition can be ovarian cancer, breast cancer, non-small cell lung cancer or prostate cancer.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor. In some embodiments, the second agent is an agent for treating Alzheimer's disease, amyotrophic lateral sclerosis (ALS), antipsychotic induced weight gain, cancer, Cushing Disease, Cushing's Syndrome, major psychotic depression, Nonalcoholic steatohepatitis, and obesity. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating cancer. In some embodiments, the second agent is an anticancer agent. In some embodiments, the second agent is a chemotherapeutic.

In some embodiments, any one of the compounds of the present invention, or a pharmaceutical composition of the present invention can be used for a method of treating a disorder or condition through modulating a glucocorticoid receptor.

In some embodiments, any one of the compounds of the present invention, or a pharmaceutical composition of the present invention can be used for a method of treating a disorder or condition through antagonizing a glucocorticoid receptor.

In some embodiments, any one of the compounds of the present invention, or a pharmaceutical composition of the present invention, can be used in the manufacture of a medicament for treating a disorder or condition through modulating a glucocorticoid receptor.

In some embodiments, any one of the compounds of the present invention, or a pharmaceutical composition of the present invention, can be used in the manufacture of a medicament for treating a disorder or condition through antagonizing a glucocorticoid receptor.

VI. Compound Examples

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 µm) cartridges using the amount indicated. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography. Prep HPLC was performed using UV detection at 215 and 254 nm with either a Waters X-Select Prep-C18, 5 µm, 19×50 mm column eluting with a $H_2O$-MeCN gradient containing 0.1% v/v formic acid over 10 min (Method A), or a Waters X-Bridge Prep-C18, 5 µm, 19×50 mm column eluting with a $H_2O$-MeCN gradient containing 0.1% ammonium bicarbonate over 10 min (Method B).

4-(benzylthio)-2-methyl-2H-1,2,3-triazole

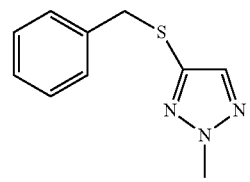

Preparation of 4-(benzylthio)-2-methyl-2H-1,2,3-triazole was performed according to the procedure described for Example 1 in U.S. Pat. No. 10,494,349, which is incorporated herein in its entirety for all purposes.

2-methyl-2H-1,2,3-triazole-4-sulfonyl chloride

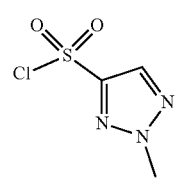

Preparation of 2-methyl-2H-1,2,3-triazole-4-sulfonyl chloride was performed according to the procedure described for Intermediate 5A in U.S. Pat. No. 10,047,082, which is incorporated herein in its entirety for all purposes.

4-(benzylthio)-2-isopropyl-2H-1,2,3-triazole

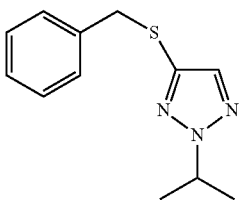 [SMILES: CC(C)n1ncc(SCc2ccccc2)n1]

Preparation of 4-(benzylthio)-2-isopropyl-2H-1,2,3-triazole was performed according to the procedure described for Example 2 in U.S. Pat. No. 10,494,349, which is incorporated herein in its entirety for all purposes.

2-isopropyl-2H-1,2,3-triazol-4-yl)sulfonyl

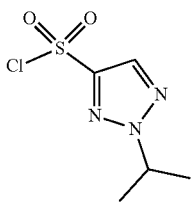

Preparation of 2-isopropyl-2H-1,2,3-triazole-4-sulfonyl chloride was performed according to the procedure described for Intermediate 5D in U.S. Pat. No. 10,494,349, which is incorporated herein in its entirety for all purposes.

Analytical Methods

Reverse Phase High Performance Liquid Chromatography. Method 1: Waters XSelect CSH UPLC C18 1.7 μm (2.1×30 mm) at 40° C.; flow rate 0.77 mL·min$^{-1}$ eluted with a $H_2O$-MeCN gradient containing 0.1% v/v formic acid over 3 min employing UV detection between 210 and 400 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 2: Waters XSelect CSH C18 2.5 μm (4.6×30 mm) at 40° C.; flow rate 2.5-4.5 mL min$^{-1}$ eluted with a $H_2O$-MeCN gradient containing 0.1% v/v formic acid over 4 min employing UV detection at 254 and 215 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

Method 3: Waters XBridge BEH C18, 1.7 μm (2.1×30 mm) at 40° C.; flow rate 2.5-4.5 mL min$^{-1}$ eluted with a $H_2O$-MeCN gradient containing 10 mM ammonium bicarbonate over 4 min employing UV detection at 254 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 4: Waters XSelect BEH C18 1.7 μm (2.1×30 mm) at 40° C.; flow rate 0.77 mL·min$^{-1}$ eluted with a $H_2O$-MeCN gradient containing 10 mM ammonium bicarbonate over 3 min employing UV detection between 210 and 400 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 5: Waters XSelect CSH UPLC C18 1.7 μm (2.1×30 mm) at 40° C.; flow rate 0.77 mL·min$^{-1}$ eluted with a $H_2O$-MeCN gradient containing 0.1% v/v formic acid over 10 min employing UV detection between 210 and 400 nm. Gradient information: 0-9.52 min ramped from 95% $H_2O$-5% MeCN to 5% $H_2O$-95% MeCN; 9.52-9.93 min, held at 5% $H_2O$-95% MeCN, 9.93-10.00 min, ramped from 5% $H_2O$-95% MeCN to 95% $H_2O$-5% MeCN; 10.00-10.20 min, held at 95% $H_2O$-5% MeCN Method 6: Waters HClass; Binary Solvent Pump, SM-FTN, CMA, PDA: 210-400 nm, QDa: ACQ-QDa ESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile.

Method 7: Waters HClass; Quaternary Solvent Pump, SM-FTN, CMA, PDA: 210-400 nm, QDa: ACQ-QDa ESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile.

Method 8: UPLC_Basic, Apparatus: Waters HClass; Binary Solvent Pump, SM-FTN, CMA, PDA: 210-400 nm, QDa: ACQ-QDa ESI; Column: Waters BEH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% NH3 in water, Eluent B: Acetonitrile.

Method 9: LCMS_Acidic, Apparatus: Agilent 1260; Binary Pump, HiP Sampler, Column Compartment, DAD: 260+/−90 nm, G6150 MSD: ESI; Column: Waters Cortecs C18, 30×2.1 mm, 2.7 μm, Temp: 40° C., Flow: 1.35 mL/min, Gradient: t0=5% B, t2.5 min=100% B, t3.0 min=100% B, Eluent A: 0.1% Formic in water, Eluent B: acetonitrile.

NMR spectra were recorded using either a Bruker Avance III HD 500 MHz instrument or a Bruker Avance Neo 400 MHz, using either residual non-deuterated solvent, or tetra-methylsilane as reference or Varian Y 400 MHz instrument, using tetra-methylsilane as reference, or a QOne AS400 400 MHz spectrometer using either residual non-deuterated solvent, or tetra-methylsilane as reference.

All chemical names have been generated using ChemDraw.

Abbreviations

COMU=1-Cyano-2-ethoxy-2-oxoethylidenaminooxy)di-methylamino-morpholino-carbenium hexafluorophosphate
DBU=diazabicyclo[5.4.0]undec-7-ene
DCM=dichloromethane
DIAD=diisopropyl azadicarboxylate
DIBAL-H—diisobutylaluminium hydride
DIPEA=diisopropylethylamine
DMF=dimethylformamide DMSO=dimethyl sulfoxide
EtOAc=ethyl acetate
EtOH=ethanol
H, hr, HR, Hr=hours
HATU=Hexafluorophosphate azabenzotriazole tetramethyl uronium
MeCN=acetonitrile
MeOH=methanol
min=minutes
MgSO$_4$=magnesium sulfate
NaHCO$_3$=sodium hydrogen carbonate
NaOH=sodium hydroxide
Na$_2$SO$_4$=sodium sulfate
NH$_4$Cl=ammonium chloride
RT, rt=room temperature
sat.=saturated
SFC=supercritical fluid chromatography
TBME=t-butylmethylether
THF=tetrahydrofuran
Wt=weight Example 1: tert-butyl 3a-(1-(4-fluorophenyl)-6-methyl-1H-indazol-5-yl)-5-oxohexahydrocyclopenta[c]pyrrole-2(1H)-carboxylate Intermediate A:
5-bromo-1-(4-fluorophenyl)-6-methyl-1H-indazole

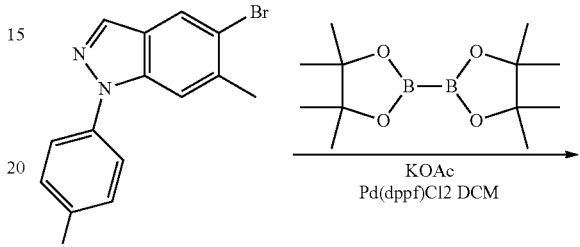

Pyridine (18.7 g, 19.1 mL, 237 mmol) was added to a solution of 5-bromo-6-methyl-1H-indazole (25.0 g, 118 mmol), (4-fluorophenyl)boronic acid (33.1 g, 237 mmol) and copper (II) acetate (21.5 g, 118 mmol) in DCM (500 mL). The reaction mixture was stirred at 20° C. for 21 hours. The reaction mixture was concentrated under reduced pressure, redissolved in EtOAc (500 mL) and washed with water (200 mL), 1N HCl (200 mL), saturated sodium hydrogen carbonate (2×200 mL) and brine (100 mL). The organic layer was concentrated, dried using MgSO$_4$, filtered, and the filtrate was concentrated under reduced pressure. The crude product was purified by chromatography on silica gel (330 g cartridge, 0-10% EtOAc/isohexane) to afford 5-bromo-1-(4-fluorophenyl)-6-methyl-1H-indazole (Intermediate A) (34.2 g, 0.11 mol, 81% yield) as a yellow solid; R$^t$ 2.33 min (Method 7); m/z 305.3 and 307.5 (M+H)$^+$ (ES$^+$); δ$_H$ (DMSO-d6, 400 MHz) δ 8.30 (d, J=0.9 Hz, 1H), 8.16 (s, 1H), 7.81 (s, 1H), 7.80-7.76 (m, 2H), 7.50-7.38 (m, 2H), 2.50 (s, 3H).

Alternatively, 5-bromo-1-(4-fluorophenyl)-6-methyl-1H-indazole can be prepared according to the method for Intermediate C in PCT Publication No. WO2021/262587.

Intermediate B: 1-(4-fluorophenyl)-6-methyl-5-(4,4,5,5-tetramethyl-1,3,2-dioxaborolan-2-yl)-1H-indazole

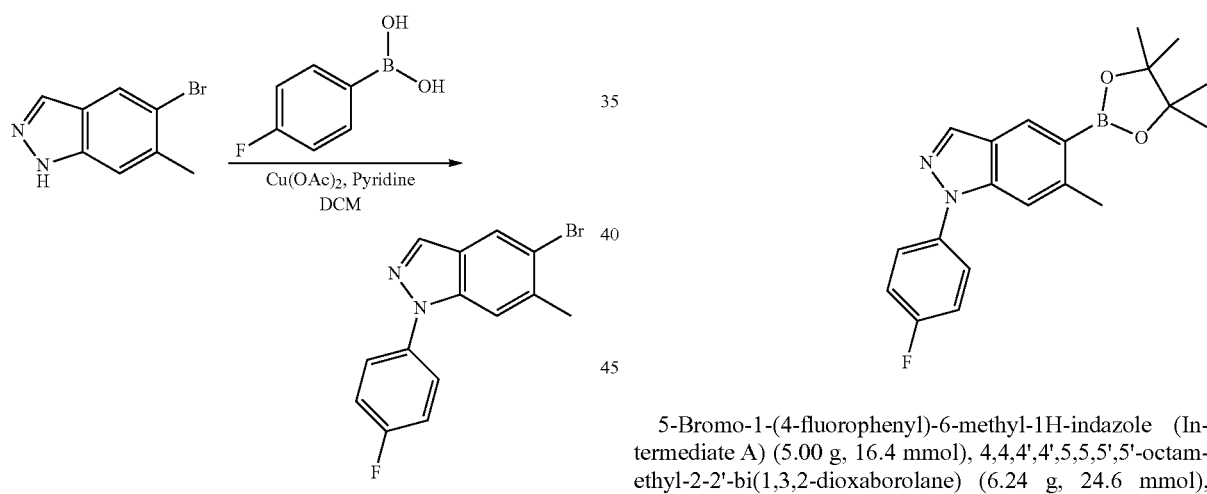

5-Bromo-1-(4-fluorophenyl)-6-methyl-1H-indazole (Intermediate A) (5.00 g, 16.4 mmol), 4,4,4',4',5,5,5',5'-octamethyl-2-2'-bi(1,3,2-dioxaborolane) (6.24 g, 24.6 mmol), potassium acetate (8.04 g, 81.9 mmol) and Pd(dppf)Cl$_2$·DCM (1.34 g, 1.64 mmol) were suspended in 1,4-Dioxane (30 mL). The mixture was evacuated and back filled with nitrogen (3×) then heated to 80° C. for 16 h. The mixture was cooled to rt then filtered through Celite eluting with EtOAc (50 mL). The filtrate was washed with water (2×50 mL) and brine (50 mL) then dried (Na$_2$SO$_4$), filtered and concentrated in vacuo. The crude product was purified by chromatography on silica gel (80 g cartridge, 0-50% EtOAc/isohexane) to afford 1-(4-fluorophenyl)-6-methyl-5-(4,4,5,5-tetramethyl-1,3,2-dioxaborolan-2-yl)-1H-indazole (Intermediate B) (6.8 g, 13 mmol, 79% yield) as a pale yellow crystalline solid; R$^t$ 2.05 min (Method 1); m/z 353.4 (M+H)$^+$ (ES$^+$); δ$_H$ (DMSO-d6, 500 MHz) δ 8.35 (d, J=0.9 Hz, 1H), 8.22 (s, 1H), 7.83-7.76 (m, 2H), 7.58 (br. d, J=0.9 Hz, 1H), 7.46-7.40 (m, 2H), 2.62 (d, J=0.9 Hz, 3H), 1.33 (s, 12H).

Example 1: tert-butyl 3a-(1-(4-fluorophenyl)-6-methyl-1H-indazol-5-yl)-5-oxohexahydrocyclopenta[c]pyrrole-2(1H)-carboxylate

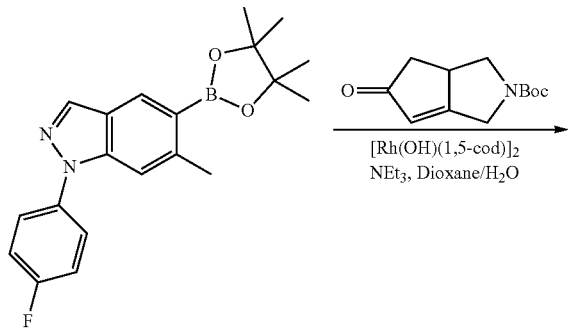

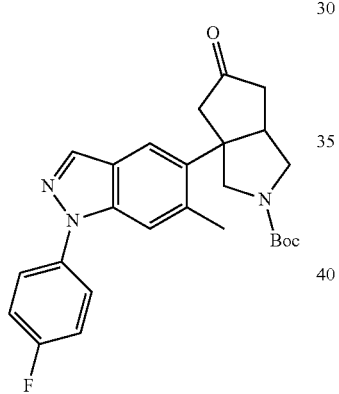

A solution of 1-(4-fluorophenyl)-6-methyl-5-(4,4,5,5-tetramethyl-1,3,2-dioxaborolan-2-yl)-1H-indazole (Intermediate B, 3.82 g, 10.3 mmol), 6-methoxy-5-(4,4,5,5-tetramethyl-1,3,2-dioxaborolan-2-yl)-1-((2-(trimethylsilyl)ethoxy)methyl)-1H-indazole (3.86 g, 9.86 mmol) and triethylamine (4.08 g, 5.62 mL, 40.3 mmol) in 1,4-dioxane (22.5 mL) and water (2.50 mL) was sparged with $N_2$ for 10 min. Hydroxy(cyclooctadiene)rhodium(I) dimer (461 mg, 1.01 mmol) was added and the solution was sparged with $N_2$ for 5 min and then heated to 80° C. and stirred for 5 hours. The reaction mixture was allowed to cool to RT and allowed to stand over the weekend. The reaction mixture was diluted with sat. aqueous $NH_4Cl$ (50 mL), the layers were separated and the aqueous layer extracted with EtOAc (4×50 mL). The combined organics were dried over $MgSO_4$, filtered and concentrated onto silica. The crude product was purified by chromatography on silica gel (220 g cartridge, 0-20% EtOAc/DCM) to afford tert-butyl 3a-(1-(4-fluorophenyl)-6-methyl-1H-indazol-5-yl)-5-oxohexahydrocyclopenta[c]pyrrole-2(1H)-carboxylate (6.32 g, 13 mmol, 63%) as a thick yellow oil; $R^t$ 1.72 min (Method 1); m/z 450.4 $(M+H)^+$ $(ES^+)$.

Example 2: 3a-(1-(4-fluorophenyl)-6-methyl-1H-indazol-5-yl)-2-((1-methyl-1H-pyrazol-4-yl)sulfonyl)-5-(thiazol-2-yl)octahydrocyclopenta[c]pyrrol-5-ol

Intermediate C: 3a-(1-(4-fluorophenyl)-6-methyl-1H-indazol-5-yl)hexahydrocyclopenta[c]pyrrol-5(1H)-one

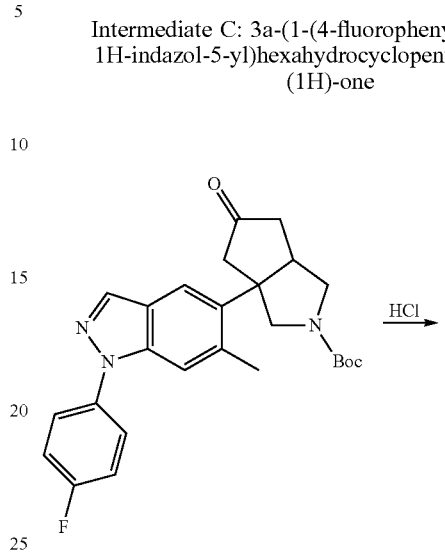

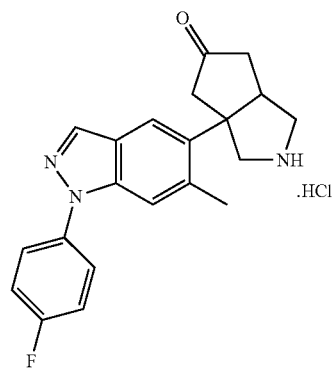

To a solution of tert-butyl 3a-(1-(4-fluorophenyl)-6-methyl-1H-indazol-5-yl)-5-oxohexahydrocyclopenta[c]pyrrole-2(1H)-carboxylate (Example 1) (3.0 g, 6.7 mmol) in 1,4-dioxane (30 mL) was added 4 M in 1,4-dioxane (2.4 g, 17 mL, 67 mmol). The resultant yellow solution was heated at 50° C. for 18 h. The solvent was removed under reduced pressure to afford a grey solid. The solid was triturated in TBME (10 mL), sonicated, filtered, and washed with TBME (2×5 mL) to afford 3a-(1-(4-fluorophenyl)-6-methyl-1H-indazol-5-yl)hexahydrocyclopenta[c]pyrrol-5(1H)-one, HCl (Intermediate C) (1.80 g, 4.61 mmol 69% yield) as a grey solid; $R^t$ 0.66 min (Method 2); m/z 350.2 $(M+H)^+$ $(ES^+)$.

Intermediate D: 3a-(1-(4-fluorophenyl)-6-methyl-1H-indazol-5-yl)-2-((1-methyl-1H-pyrazol-4-yl)sulfonyl)hexahydrocyclopenta[c]pyrrol-5(1H)-one

Example 2: 3a-(1-(4-fluorophenyl)-6-methyl-1H-indazol-5-yl)-2-((1-methyl-1H-pyrazol-4-yl)sulfonyl)-5-(thiazol-2-yl)octahydrocyclopenta[c]pyrrol-5-ol

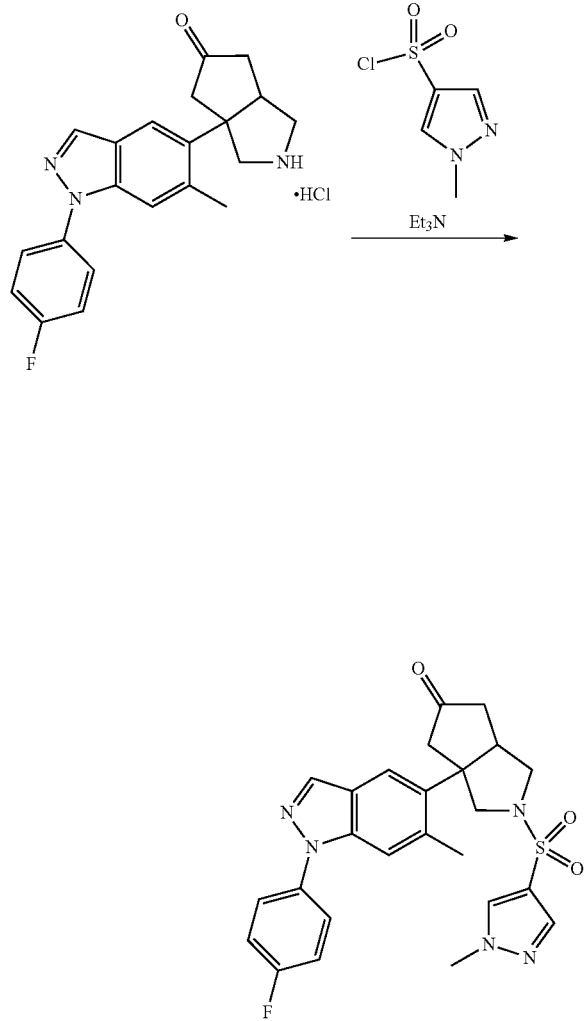

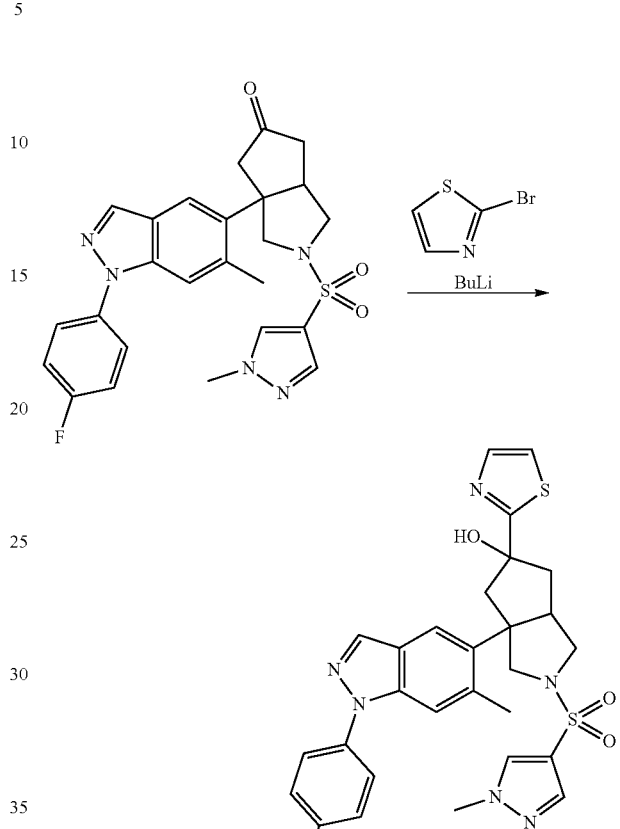

To a solution of 3a-(1-(4-fluorophenyl)-6-methyl-1H-indazol-5-yl)hexahydrocyclopenta[c]pyrrol-5(1H)-one, HCl (Intermediate C) (1.70 g, 4.41 mmol) and 1-methyl-1H-pyrazole-4-sulfonyl chloride (1.59 g, 8.81 mmol) in DCM (60 mL) at 0° C. was added triethylamine (1.23 mL, 8.81 mmol) dropwise. The resultant dark orange solution was stirred at 0° C. for 2 h and was allowed to warm up to rt and stirred for 18 h. The reaction mixture was concentrated onto silica and purified by chromatography on silica gel (80 g, cartridge, 0-100% EtOAc/isohexane, product eluted at 100%) to afford 3a-(1-(4-fluorophenyl)-6-methyl-1H-indazol-5-yl)-2-((1-methyl-1H-pyrazol-4-yl)sulfonyl)hexahydrocyclopenta[c]pyrrol-5(1H)-one (1.52 g, 3.06 mmol, 69.4% yield) (Intermediate D) as a white solid; R$^t$ 1.23 min (Method 2); m/z 494.2 (M+H)$^+$ (ES$^+$). $\delta_H$ (DMSO-d6, 400 MHz) δ 8.21 (d, J=0.9 Hz, 1H), 8.12 (s, 1H), 7.82-7.76 (m, 2H), 7.67-7.62 (m, 3H), 7.48-7.40 (m, 2H), 3.78 (d, J=11.1 Hz, 1H), 3.71 (dd, J=10.3, 7.2 Hz, 1H), 3.64-3.57 (m, 1H), 3.55 (s, 3H), 3.50 (d, J=11.0 Hz, 1H), 3.27 (dd, J=10.3, 4.2 Hz, 1H), 2.88 (d, J=18.6 Hz, 1H), 2.65 (dd, J=18.9, 8.2 Hz, 1H), 2.47-2.44 (m, 3H), 2.43-2.36 (m, 1H), 2.20 (dd, J=18.8, 6.5 Hz, 1H).

To a solution of 2-bromothiazole (66.5 mg, 36.5 µL, 405 µmol) in THF (2 mL) at −78° C. was added butyllithium (2.5 M in hexane) (26.0 mg, 162 µL, 405 µmol) dropwise. The yellow solution was stirred at −78° C. for 30 min before a solution of 3a-(1-(4-fluorophenyl)-6-methyl-1H-indazol-5-yl)-2-((1-methyl-1H-pyrazol-4-yl)sulfonyl)hexahydrocyclopenta[c]pyrrol-5(1H)-one (Intermediate D) (100 mg, 203 µmol) in THF (4 mL) was added dropwise. The reaction was stirred at −78° C. for 2 h and was allowed to warm up to rt and stirred for 18 h. The reaction mixture was quenched with a saturated solution of NaHCO$_3$ (10 mL) and extracted with EtOAc (3×15 mL). The organic layers were combined, dried over MgSO$_4$ and filtered. The solvent was removed under reduced pressure to afford a colourless oil. The crude product was purified by chromatography on silica gel (12 g cartridge, 0-100% EtOAc/isohexane, eluted at 100%) to afford 3a-(1-(4-fluorophenyl)-6-methyl-1H-indazol-5-yl)-2-((1-methyl-1H-pyrazol-4-yl)sulfonyl)-5-(thiazol-2-yl)octahydrocyclopenta[c]pyrrol-5-ol (18 mg, 31 µmol, 15% yield) (Example 2) as a white crystalline solid; R$^t$ 1.29 min (Method 3); m/z 579.2 (M+H)$^+$ (ES$^+$); $\delta_H$ (DMSO-d6, 400 MHz) δ 8.21 (d, J=0.9 Hz, 1H), 8.03 (s, 1H), 7.83-7.76 (m, 2H), 7.64 7.58 (m, 3H), 7.55 (d, J=3.2 Hz, 1H), 7.52 (d, J=3.2 Hz, 1H), 7.47-7.40 (m, 2H), 6.31 (s, 1H), 3.84 (d, J=10.4 Hz, 1H), 3.77-3.67 (m, 1H), 3.59 (dd, J=10.1, 7.6 Hz, 2H), 3.50 (s, 3H), 3.35 (dd, J=10.1, 3.0 Hz, 2H), 2.85 (d, J=14.1 Hz, 1H), 2.47-2.40 (m, 4H), 2.01 (dd, J=13.3, 8.4 Hz, 1H).

Example 3: 2-(3a-(1-(4-fluorophenyl)-6-methyl-H-indazol-5-yl)-5-methoxy-2-((1-methyl-1H-pyrazol-4-yl)sulfonyl)octahydrocyclopenta[c]pyrrol-5-yl)thiazole

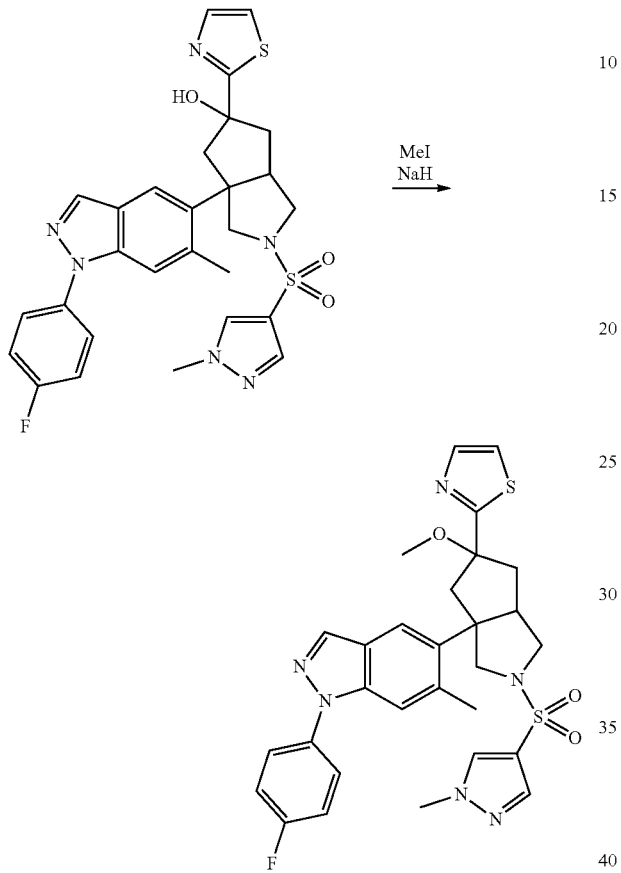

To a solution of 3a-(1-(4-fluorophenyl)-6-methyl-1H-indazol-5-yl)-2-((1-methyl-1H-pyrazol-4-yl)sulfonyl)-5-(thiazol-2-yl)octahydrocyclopenta[c]pyrrol-5-ol (15 mg, 26 μmol) (Example 2) in THF (2 mL) at 0° C. was added sodium hydride (1.6 mg, 60% Wt, 39 μmol). The resultant yellow solution was stirred at 0° C. for 30 min before iodomethane (7.4 mg, 3.2 μL, 52 μmol) was added. The reaction mixture was stirred at 0° C. for 1.5 h and was allowed to warm up to rt and stirred for 18 h. The reaction mixture was quenched with a saturated solution of NaHCO₃ (10 mL) and extracted with EtOAc (3×10 mL). The organic layers were combined, dried over MgSO₄ and filtered. The solvent was removed under reduced pressure to afford a yellow oil. The crude product was purified by chromatography on silica gel (4 g cartridge, 0-100% EtOAc/isohexane) to afford 2-(3a-(1-(4-fluorophenyl)-6-methyl-1H-indazol-5-yl)-5-methoxy-2-((1-methyl-1H-pyrazol-4-yl)sulfonyl)octahydrocyclopenta[c]pyrrol-5-yl)thiazole (10 mg, 16 μmol, 63% yield) (Example 3) as a white solid; R$^t$ 1.47 min (Method 4); m/z 593.2 (M+H)$^+$ (ES$^+$); $\delta_H$ (DMSO-d6, 400 MHz) δ 8.16 (d, J=0.9 Hz, 1H), 8.13 (s, 1H), 7.81-7.76 (m, 2H), 7.68-7.66 (m, 2H), 7.62 (s, 1H), 7.59 (d, J=3.2 Hz, 1H), 7.54 (s, 1H), 7.46-7.38 (m, 2H), 3.70 (d, J=10.4 Hz, 1H), 3.58 (s, 3H), 3.56-3.48 (m, 3H), 3.30 (1H, underneath water signal), 3.00 (s, 3H), 2.95 (d, J=14.2 Hz, 1H), 2.59 (dd, J=13.1, 6.9 Hz, 1H), 2.50 (4H, underneath DMSO signal), 2.05-1.98 (m, 1H).

Example 4: 5-(5-fluoro-2-((1-methyl-1H-pyrazol-4-yl)sulfonyl)-5-phenylhexahydrocyclopenta[c]pyrrol-3a(1H)-yl)-1-(4-fluorophenyl)-6-methyl-1H-indazole To a solution of diethylaminosulfur trifluoride (11 mg, 9.0 μL, 70 μmol) in THF (1 mL) at −78° C. was added a solution of 3a-(1-(4-fluorophenyl)-6-methyl-1H-indazol-5-yl)-2-((1-methyl-1H-pyrazol-4-yl)sulfonyl)-5-phenyloctahydrocyclopenta[c]pyrrol-5-ol (20 mg, 35 μmol) (Example 10) in THF (1 mL). The resultant colourless solution was stirred at −78° C. for 2 h. The reaction mixture was quenched with a saturated solution of NaHCO₃ (10 mL) and extracted with EtOAc (3×10 mL). The organic layers were combined, dried over MgSO₄ and filtered. The solvent was removed under reduced pressure to afford a yellow oil. The crude product was purified by chromatography on silica gel (4 g cartridge, 0-100% EtOAc/isohexane) to afford 5-(5-fluoro-2-((1-methyl-1H-pyrazol-4-yl)sulfonyl)-5-phenylhexahydrocyclopenta[c]pyrrol-3a(1H)-yl)-1-(4-fluorophenyl)-6-methyl-1H-indazole (4.5 mg, 7.8 μmol, 22%) (Example 5) as a white solid; R$^t$ 1.88 min (Method 5); m/z 574.2 (M+H)$^+$ (ES$^+$); $\delta_H$ (400 MHz, Methanol-d4) δ 8.16 (d, J=0.9 Hz, 1H), 7.82-7.76 (m, 3H), 7.61 (d, J=9.7 Hz, 2H), 7.52 (d, J=0.7 Hz, 1H), 7.48-7.33 (m, 7H), 3.95-3.85 (m, 2H), 3.76 (d, J=11.2 Hz, 1H), 3.66-3.62 (m, 2H), 3.43 (s, 3H), 2.97 (dd, J=36.3, 15.3 Hz, 1H), 2.64-2.53 (m, 2H), 2.51 (d, J=0.8 Hz, 3H), 2.35-2.16 (m, 1H).

Example 5: 1-(4-fluorophenyl)-5-((3aR,5R,6aS)-5-methoxy-2-((1-methyl-1H-pyrazol-4-yl)sulfonyl)-5-phenylhexahydrocyclopenta[c]pyrrol-3a(1H)-yl)-6-methyl-1H-indazole Example 6: 1-(4-fluorophenyl)-5-((3aS,5S,6aR)-5-methoxy-2-((1-methyl-1H-pyrazol-4-yl)sulfonyl)-5-phenylhexahydrocyclopenta[c]pyrrol-3a(1H)-yl)-6-methyl-1H-indazole Example 7: 1-(4-fluorophenyl)-5-((3aR,5S,6aS)-5-methoxy-2-((1-methyl-1H-pyrazol-4-yl)sulfonyl)-5-phenylhexahydrocyclopenta[c]pyrrol-3a(1H)-yl)-6-methyl-1H-indazole Example 8: 1-(4-fluorophenyl)-5-((3aS,5R,6aR)-5-methoxy-2-((1-methyl-1H-pyrazol-4-yl)sulfonyl)-5-phenylhexahydrocyclopenta[c]pyrrol-3a(1H)-yl)-6-methyl-1H-indazole Example 5

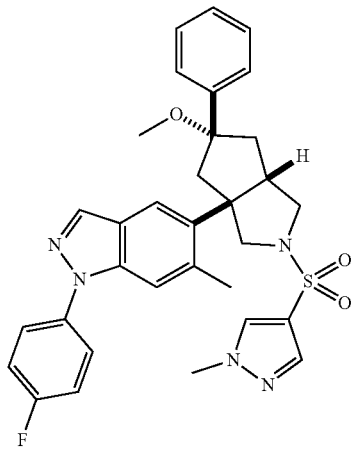

Example 6

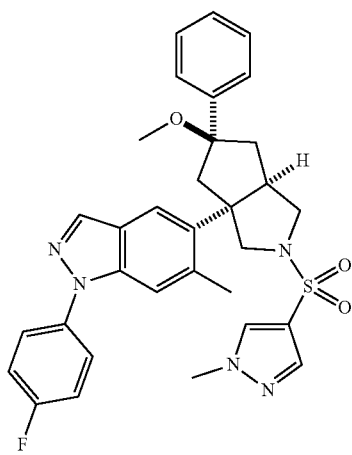

Example 7

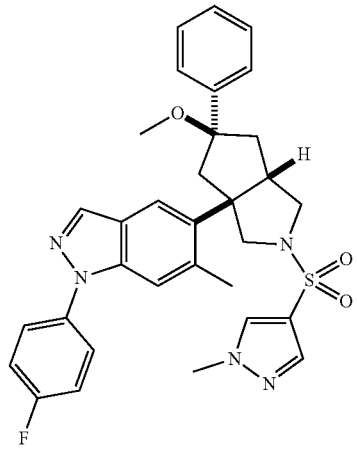

Example 8

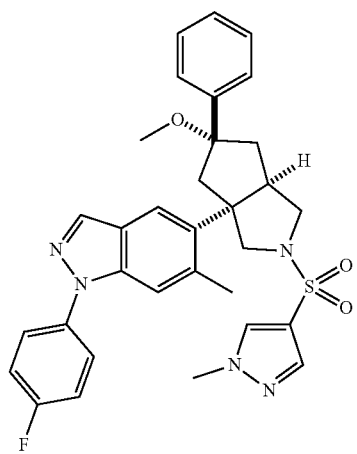

1-(4-Fluorophenyl)-5-(5-methoxy-2-((1-methyl-1H-pyrazol-4-yl)sulfonyl)-5-phenylhexahydrocyclopenta[c]pyrrol-3a(1H)-yl)-6-methyl-1H-indazole (512 mg, 0.88 mmol) (Example 11) was dissolved to 41 mg/mL in MeOH with sonication, filtered and was then separated by chiral SFC on a Waters prep 15 with UV detection by DAD at 210-400 nm, 40° C., 120 bar. The column was Chiralpak IH 10×250 mm, 5um, flow rate 15 mL/min at 40% MeOH (0.1% Ammonia), 60% $CO_2$ to isolate major peaks and then 35% EtOH (0.1% Ammonia), 65% $CO_2$ to isolate minor peaks. The clean fractions were pooled, rinsed with methanol and concentrated to dryness using a rotary evaporator to afford 1-(4-fluorophenyl)-5-((3aR,5R,6aS)-5-methoxy-2-((1-methyl-1H-pyrazol-4-yl)sulfonyl)-5-phenylhexahydrocyclopenta[c]pyrrol-3a(1H)-yl)-6-methyl-1H-indazole (158 mg, 270 µmol, 30.8%) (Example 5) as a white solid; $R^t$ 1.77 min (Method 6); m/z 586.3 (M+H)$^+$ (ES$^+$); $\delta_H$ NMR (400 MHz, DMSO-d6) δ 8.19 (d, J=0.9 Hz, 1H), 8.17 (s, 1H), 7.83-7.77 (m, 2H), 7.70 (s, 1H), 7.65 (d, J=7.1 Hz, 2H), 7.47-7.39 (m, 2H), 7.28-7.22 (m, 2H), 7.19 (d, J=7.2 Hz, 3H), 3.67 (d, J=10.1 Hz, 1H), 3.63 (s, 4H), 3.59-3.53 (m, 1H), 3.52-3.44 (m, 1H), 3.22 (dd, J=9.7, 3.7 Hz, 1H), 2.94 (d, J=14.3 Hz, 1H), 2.74 (s, 3H), 2.54 (s, 3H), 2.35-2.26 (m, 1H), 2.22 (d, J=14.2 Hz, 1H), 2.05 (dd, J=13.4, 7.5 Hz, 1H).

1-(4-fluorophenyl)-5-((3aS,5S,6aR)-5-methoxy-2-((1-methyl-1H-pyrazol-4-yl)sulfonyl)-5-phenylhexahydrocyclopenta[c]pyrrol-3a(1H)-yl)-6-methyl-1H-indazole (156 mg, 266 µmol, 30.5%) (Example 6) as a white solid; $R^t$ 1.77 min (Method 6); m/z 586.3 (M+H)$^+$ (ES$^+$); $\delta_H$ NMR (400

MHz, DMSO-d6) δ 8.19 (d, J=0.9 Hz, 1H), 8.17 (s, 1H), 7.83 7.77 (m, 2H), 7.70 (s, 1H), 7.66 (s, 1H), 7.64 (s, 1H), 7.47-7.39 (m, 2H), 7.28-7.22 (m, 2H), 7.19 (d, J=7.2 Hz, 3H), 3.68 (d, J=10.1 Hz, 1H), 3.63 (s, 4H), 3.60-3.53 (m, 1H), 3.53-3.44 (m, 1H), 3.22 (dd, J=9.7, 3.7 Hz, 1H), 2.94 (d, J=14.2 Hz, 1H), 2.74 (s, 3H), 2.54 (s, 3H), 2.35-2.26 (m, 1H), 2.22 (d, J=14.2 Hz, 1H), 2.05 (dd, J=13.4, 7.6 Hz, 1H).

1-(4-fluorophenyl)-5-((3aR,5S,6aS)-5-methoxy-2-((1-methyl-1H-pyrazol-4-yl)sulfonyl)-5-phenylhexahydrocyclopenta[c]pyrrol-3a(1H)-yl)-6-methyl-1H-indazole (1.4 mg, 2.3 μmol, 0.26%) (Example 7) as a white solid; R$^t$ 1.77 min (Method 6); m/z 586.3 (M+H)$^+$ (ES$^+$); δ$_H$ NMR (400 MHz, Methanol-d4) δ 8.16 (s, 1H), 7.82-7.76 (m, 3H), 7.64 (s, 1H), 7.61 (s, 1H), 7.53 (s, 1H), 7.44-7.34 (m, 6H), 7.34-7.28 (m, 1H), 3.82-3.75 (m, 2H), 3.64-3.51 (m, 3H), 3.47 (s, 3H), 2.80 (s, 3H), 2.72-2.66 (m, 2H), 2.58 (dd, J=14.2, 2.7 Hz, 1H), 2.54 (s, 3H), 2.15-2.06 (m, 1H).

1-(4-fluorophenyl)-5-((3aS,5R,6aR)-5-methoxy-2-((1-methyl-1H-pyrazol-4-yl)sulfonyl)-5-phenylhexahydrocyclopenta[c]pyrrol-3a(1H)-yl)-6-methyl-1H-indazole (2.2 mg, 3.6 μmol, 0.41%) (Example 8) as a white solid; R$^t$ 1.77 min (Method 6); m/z 586.4 (M+H)$^+$ (ES$^+$); δ$_H$ NMR (400 MHz, Methanol-d4) δ 8.16 (s, 1H), 7.82-7.77 (m, 3H), 7.64 (s, 1H), 7.61 (s, 1H), 7.53 (s, 1H), 7.43-7.30 (m, 7H), 3.79 (d, J=10.9 Hz, 2H), 3.65-3.50 (m, 3H), 3.47 (s, 3H), 2.80 (s, 3H), 2.74-2.67 (m, 2H), 2.58 (d, J=16.5 Hz, 1H), 2.54 (s, 3H), 2.15-2.05 (m, 1H).

Examples 9 to 16

TABLE 2

The examples shown in the table below were prepared by similar methods to those described for Example 1 and 2.

| Example | Structure | LC-MS Analysis |
|---|---|---|
| 9 | 3a-(1-(4-fluorophenyl)-6-methyl-1H-indazol-5-yl)-2-(methylsulfonyl)-5-phenyloctahydrocyclopenta[c]pyrrol-5-ol | R$^t$ 1.60 min (Method 1); m/z 506.41 (M + H)$^+$ (ES$^+$) |
| 10 | 3a-(1-(4-fluorophenyl)-6-methyl-1H-indazol-5-yl)-2-((1-methyl-1H-pyrazol-4-yl)sulfonyl)-5-phenyloctahydrocyclopenta[c]pyrrol-5-ol | R$^t$ 1.51 and 1.55 min (Method 1); m/z 572.4 (M + H)$^+$ (ES$^+$) |

TABLE 2-continued

The examples shown in the table below were prepared by similar methods to those described for Example 1 and 2.

| Example | Structure | LC-MS Analysis |
|---------|-----------|----------------|
| 11 | 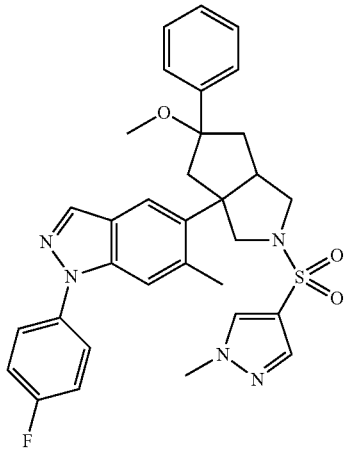<br>1-(4-fluorophenyl)-5-(5-methoxy-2-((1-methyl-1H-pyrazol-4-yl)sulfonyl)-5-phenylhexahydrocyclopenta[c]pyrrol-3a(1H-yl)-6-methyl-1H-indazole | $R^t$ 1.76 min (Method 6); m/z 586.5 $(M + H)^+$ $(ES^+)$ |
| 12 | 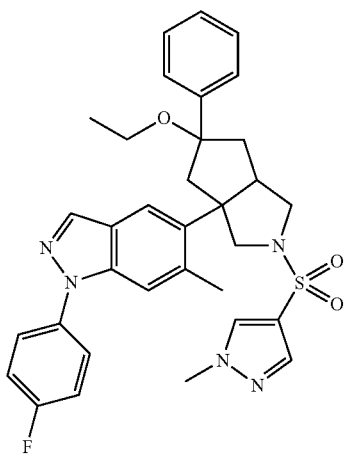<br>5-(5-ethoxy-2-((1-methyl-1H-pyrazol-4-yl)sulfonyl)-5-phenylhexahydrocyclopenta[c]pyrrol-3a(1H-yl)-1-(4-fluorophenyl)-6-methyl-1H-indazole | $R^t$ 2.46 min (Method 1); m/z 600.2 $(M + H)^+$ $(ES^+)$ |

TABLE 2-continued

The examples shown in the table below were prepared by similar methods to those described for Example 1 and 2.

| Example | Structure | LC-MS Analysis |
|---|---|---|
| 13 | 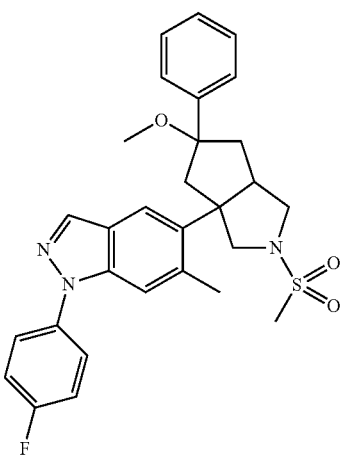<br>1-(4-fluorophenyl)-5-(5-methoxy-2-(methylsulfonyl)-5-phenylhexahydrocyclopenta[c]pyrrol-3a(1H-yl)-6-methyl-1H-indazole | $R^t$ 1.71 min (Method 4); m/z 520.2 $(M + H)^+$ $(ES^+)$ |
| 14 | 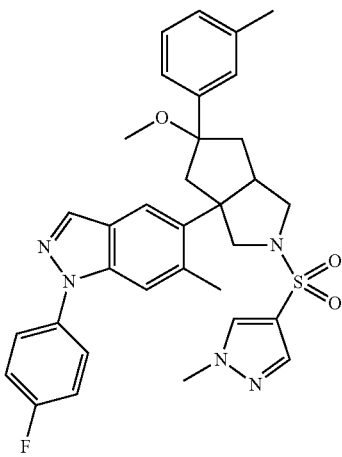<br>1-(4-fluorophenyl)-5-(5-methoxy-2-((1-methyl-1H-pyrazol-4-yl)sulfonyl)-5-(m-tolyl)hexahydrocyclopenta[c]pyrrol-3a(1H)-yl)-6-methyl-1H-indazole | $R^t$ 1.77 min (Method 2); m/z 600.2 $(M + H)^+$ $(ES^+)$ |

TABLE 2-continued

The examples shown in the table below were prepared by similar methods to those described for Example 1 and 2.

| Example | Structure | LC-MS Analysis |
|---|---|---|
| 15 | 3a-(1-(4-fluorophenyl)-6-methyl-1H-indazol-5-yl)-2-((1-methyl-1H-pyrazol-4-yl)sulfonyl)-5-(pyridin-2-yl)octahydrocyclopenta[c]pyrrol-5-ol | $R^t$ 1.03 min (Method 1); m/z 573.2 $(M + H)^+$ $(ES^+)$ |
| 16 | 1-(4-fluorophenyl)-5-(5-methoxy-2-((1-methyl-1H-pyrazol-4-yl)sulfonyl)-5-(prop-1-yn-1-yl)hexahydrocyclopenta[c]pyrrol-3a(1H)-yl)-6-methyl-1H-indazole | $R^t$ 1.54 min (Method 1); m/z 548.2 $(M + H)^+$ $(ES^+)$ |

Example 17: tert-butyl 3a-(1-(4-fluorophenyl)-6-methyl-1H-indazol-5-yl)-5-hydroxy-5-phenylhexahydrocyclopenta[c]pyrrole-2(1H)-carboxylate

Example 18: tert-butyl 3a-(1-(4-fluorophenyl)-6-methyl-1H-indazol-5-yl)-5-methoxy-5-phenylhexahydrocyclopenta[c]pyrrole-2(1H)-carboxylate

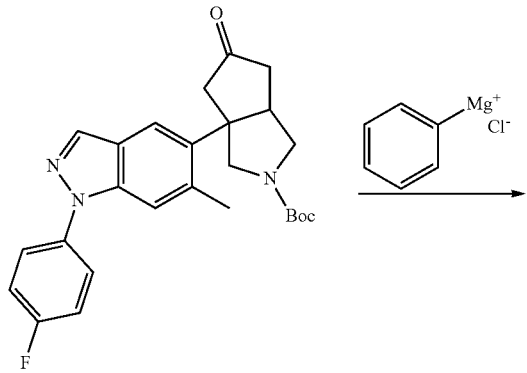

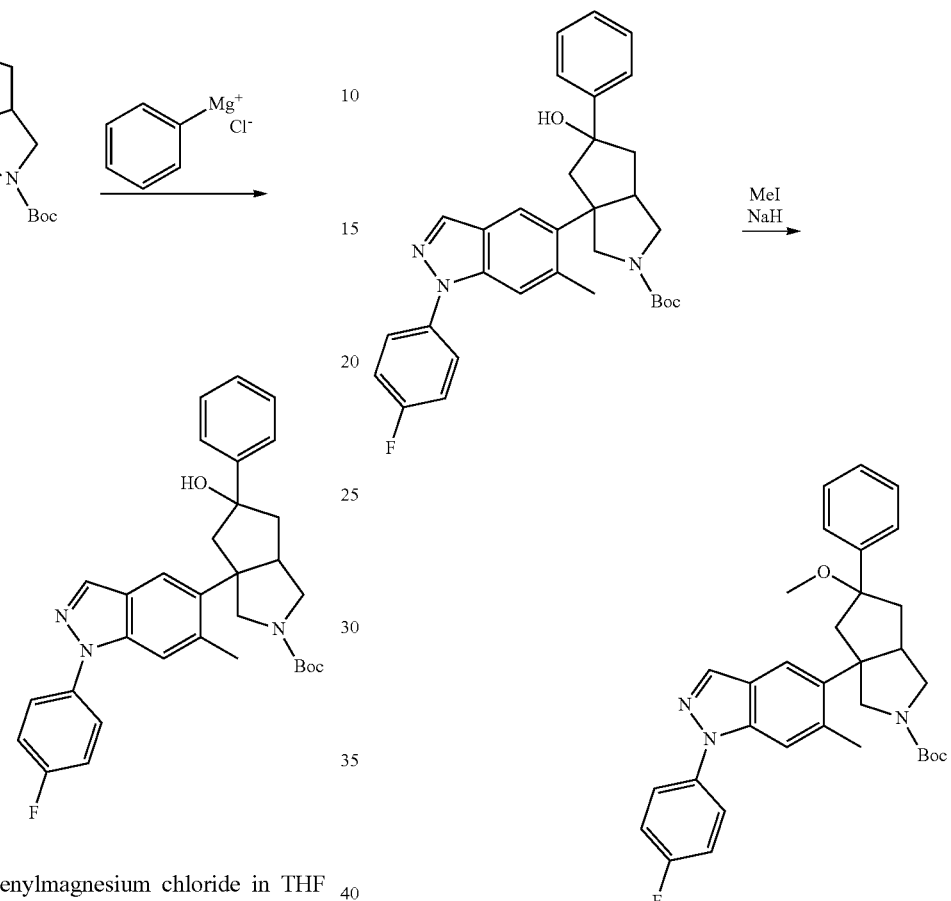

A 2 M solution of phenylmagnesium chloride in THF (8.28 mL, 16.6 mmol) was added to a solution of tert-butyl 3a-(1-(4-fluorophenyl)-6-methyl-1H-indazol-5-yl)-5-oxohexahydrocyclopenta[c]pyrrole-2(1H)-carboxylate (Example 1) (1.55 g, 2.76 mmol) at 0° C. in THF (10 mL). The reaction was stirred at 0° C. for 30 min then phenylmagnesium chloride (2 M in THF) (2.76 mL, 5.52 mmol) was added and the reaction mixture was stirred at 0° C. for 30 min. The reaction mixture was quenched with a saturated solution of NH$_4$Cl (25 mL), the layers were separated and then the aqueous layer was extracted with EtOAc (3×25 mL). The combined organic phase was washed with brine (25 mL), dried over MgSO$_4$, filtered and concentrated in vacuo. The crude product was concentrated onto silica and purified by chromatography on silica gel (80 g cartridge, 0-60% EtOAc/isohexane) to afford tert-butyl 3a-(1-(4-fluorophenyl)-6-methyl-1H-indazol-5-yl)-5-hydroxy-5-phenylhexahydrocyclopenta[c]pyrrole-2(1H)-carboxylate (Example 17) (1.34 g, 2.54 mmol, 53.1% yield) as a colourless oil; R$^t$ 2.32 min (Method 6); m/z 528.4 (M+H)$^+$ (ES$^+$); $\delta_H$ NMR (400 MHz, DMSO-d6) δ 8.26 (s, 1H), 7.85-7.78 (m, 3H), 7.70 (s, 1H), 7.45-7.40 (m, 2H), 7.29-7.24 (m, 2H), 7.23-7.18 (m, 2H), 7.15-7.11 (m, 1H), 5.40 (s, 1H), 4.08 (d, J 11.0, 1H), 3.78-3.70 (m, 1H), 3.68 (d, J 11.0, 1H), 3.54-3.49 (m, 1H), 3.49-3.42 (m, 1H), 2.89 (d, J 14.1, 1H), 2.48 (s, 3H), 2.39-2.32 (m, 1H), 2.18-2.10 (m, 1H), 1.38-1.27 (m, 9H).

To a solution of tert-butyl 3a-(1-(4-fluorophenyl)-6-methyl-1H-indazol-5-yl)-5-hydroxy-5-phenylhexahydrocyclopenta[c]pyrrole-2(1H)-carboxylate (1.34 g, 2.54 mmol) (Example 17) in THF (15 mL) at 0° C. was added sodium hydride (305 mg, 60% Wt, 7.62 mmol). The resultant yellow solution was stirred at 0° C. for 30 min before methyl iodide (1.44 g, 635 μL, 10.2 mmol) was added. The reaction mixture was allowed to warm up to 20° C. and stirred for 17 hours. The reaction mixture was quenched with sat. aqueous NH$_4$Cl (25 mL), the layers were separated and then the aqueous layer was extracted with EtOAc (3×25 mL). The combined organic phase was washed with brine (25 mL), dried over MgSO$_4$, filtered and concentrated in vacuo. The crude product was redissolved in DCM, concentrated onto silica, and purified by chromatography on silica gel (40 g Gold cartridge, 0-20% (3:1 EtOAc/EtOH)/isohexane) to afford tert-butyl 3a-(1-(4-fluorophenyl)-6-methyl-1H-indazol-5-yl)-5-methoxy-5-phenylhexahydrocyclopenta[c]pyrrole-2(1H)-carboxylate (1.30 g, 2.4 mmol, 79% yield) (Example 18) as a pale yellow solid; R$^t$ 2.55 min (Method 6); m/z 542.5 (M+H)$^+$ (ES$^+$). δ 8.22 (s, 1H), 7.79 (dd, J=8.7, 4.9 Hz, 2H), 7.71 (d, J=13.0 Hz, 2H), 7.42 (t, J=8.8 Hz, 2H), 7.31-7.15 (m, 5H), 3.91 (d, J=11.5 Hz, 1H), 3.71 (d, J=11.1

Hz, 2H), 3.45 (d, J=10.1 Hz, 1H), 2.98 (d, J=14.2 Hz, 1H), 2.92 (s, 3H), 2.55 (s, 3H), 2.47-2.38 (m, 3H), 2.29-2.17 (m, 1H), 1.39-1.24 (m, 9H).

Example 19: 1-(4-fluorophenyl)-5-(5-methoxy-2-((2-methyl-2H-1,2,3-triazol-4-yl)sulfonyl)-5-phenyl-hexahydrocyclopenta[c]pyrrol-3a(1H)-yl)-6-methyl-1H-indazole Intermediate E: 1-(4-fluorophenyl)-5-(5-methoxy-5-phenylhexahydrocyclopenta[c]pyrrol-3a(1H)-yl)-6-methyl-1H-indazole

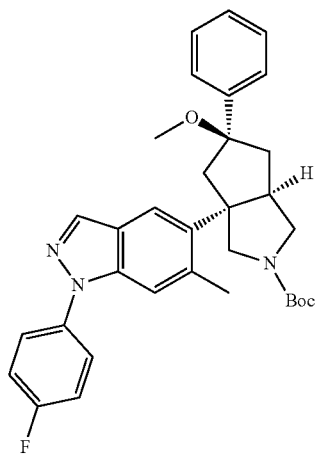

Or

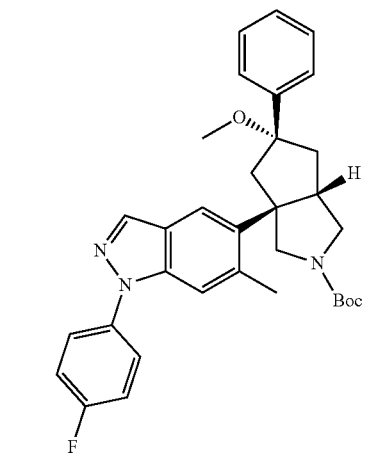

Tert-butyl 3a-(1-(4-fluorophenyl)-6-methyl-1H-indazol-5-yl)-5-methoxy-5-phenylhexahydrocyclopenta[c]pyrrole-2(1H)-carboxylate (1.30 g, 2.4 mmol) (Example 18) was separated by chiral SFC: Waters prep 100 with UV detection across all wavelengths with PDA as well as a QDA, 40° C., 120 bar. The column was a Phenomenex Lux® 5 µM Amylose-1 LC Column 250×50 mm, AXIA™ packed flow rate 65 mL/min of 25% MeOH/MeCN (0.03% ammonia, 75% $CO_2$) to afford tert-butyl 3a-(1-(4-fluorophenyl)-6-methyl-1H-indazol-5-yl)-5-methoxy-5-phenylhexahydrocyclopenta[c]pyrrole-2(1H)-carboxylate (535 mg, 988 µmol, 32.8%) (Intermediate E) as an off-white partial-solid; R'2.58 min (Method 6); m/z 542.5 (M+H)$^+$ (ES$^+$).

Intermediate F: 1-(4-fluorophenyl)-5-(5-methoxy-5-phenylhexahydrocyclopenta[c]pyrrol-3a(1H)-yl)-6-methyl-1H-indazole 211
-continued

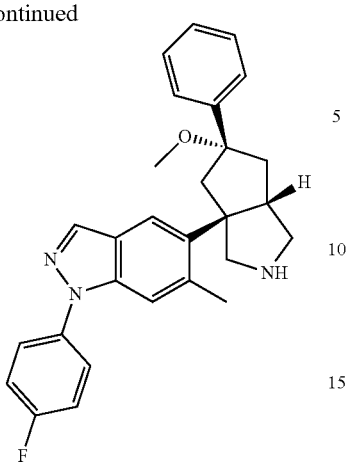

212
-continued

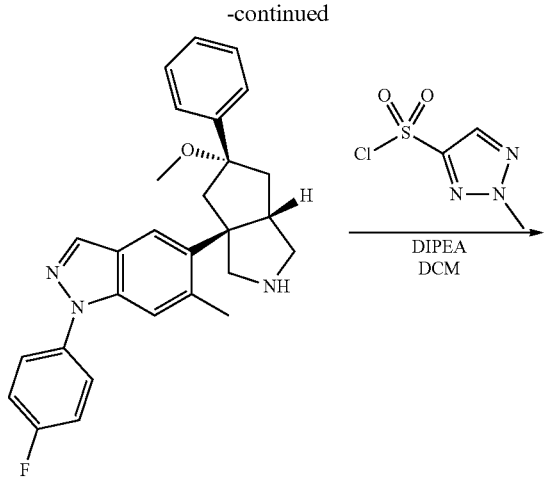

Zinc bromide (2.440 g, 10.83 mmol) was added to a solution of tert-butyl 3a-(1-(4-fluorophenyl)-6-methyl-1H-indazol-5-yl)-5-methoxy-5-phenylhexahydrocyclopenta[c]pyrrole-2(1H)-carboxylate (1630 mg, 2.708 mmol) in DCM (60 mL) (Intermediate E). The suspension was sonicated for 1 min and then the cloudy reaction mixture was vigorously stirred at 20° C. for 7 hours with intermittent sonication. The reaction mixture was treated with DCM (30 mL) and excess saturated sodium hydrogen carbonate solution (60 mL 0.9M). The mixture was agitated by sonication, spatula and stirring to ensure all the reaction precipitate had dissolved. This mixture was passed through a phase separation cartridge directly onto a SCX column prewetted with DCM, the mixture was assisted onto the column by vacuum. Once loaded the column was washed with MeOH (100 mL) and eluted using 0.7 M ammonia in MeOH. The eluted liquid was concentrated under reduced pressure to give 1-(4-fluorophenyl)-5-(5-methoxy-5-phenylhexahydrocyclopenta[c]pyrrol-3a(1H)-yl)-6-methyl-1H-indazole 54 mg, 1.9 mmol, 71%) (Intermediate F) as a brown gum; $R^t$ 1.56 min (Method 6); m/z 442.5 (M+H)$^+$ (ES$^+$).

Examples 19: 1-(4-fluorophenyl)-5-(5-methoxy-2-((2-methyl-2H-1,2,3-triazol-4-yl)sulfonyl)-5-phenyl-hexahydrocyclopenta[c]pyrrol-3a(1H)-yl)-6-methyl-1H-indazole

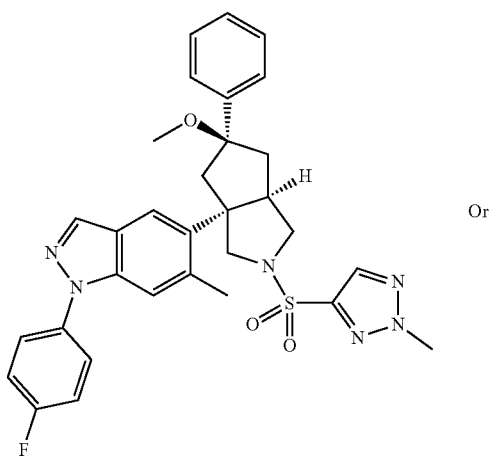

Or

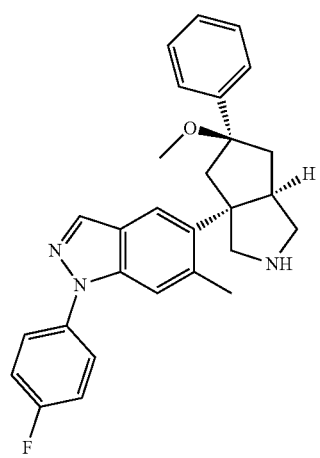

Or

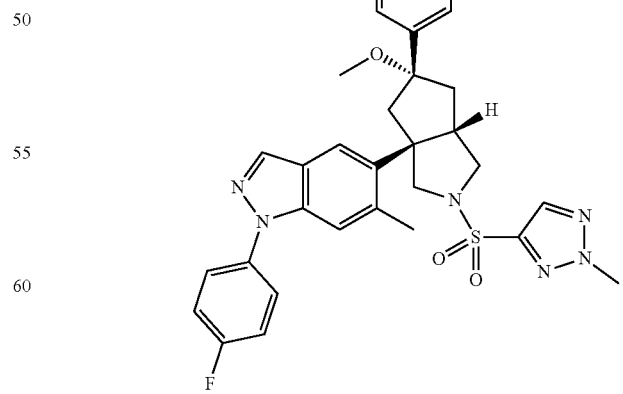

To a solution of 1-(4-fluorophenyl)-5-(5-methoxy-5-phenylhexahydrocyclopenta[c]pyrrol-3a(1H)-yl)-6-methyl-1H-indazole (Intermediate F) (19.0 mg, 33.6 μmol) in DCM (0.50 mL) was added N-ethyl-N-isopropylpropan-2-amine (30.0 μL, 172 μmol) followed by 2-methyl-2H-1,2,3-triazole-4-sulfonyl chloride (12.2 mg, 67.1 μmol). The reaction mixture was stirred at 20° C. for 2 hours. The reaction mixture was quenched with sat. aqueous NaHCO$_3$ (1 mL). The layers were separated and the aqueous layer was extracted with DCM (3×3 mL). The combined organic phase was dried by hydrophobic frit and concentrated in vacuo. The crude product was purified by preparative HPLC (Waters, Basic (0.1% ammonia in water), Basic, Waters XBridge BEH C18 ODB prep column, 50-80% MeCN in Water). The fractions were dissolved in MeCN, concentrated in vacuo and dried in the desiccator for 1 h to afford 1-(4-fluorophenyl)-5-(5-methoxy-2-((2-methyl-2H-1,2,3-triazol-4-yl)sulfonyl)-5-phenylhexahydrocyclopenta[c]pyrrol-3a(1H)-yl)-6-methyl-1H-indazole (Example 19) (11 mg, 18 μmol, 53% yield) as an off-white solid; R$^t$2.23 min (Method 6); m/z 587.3 (M+H)$^+$ (ES$^+$); δ$_H$ (DMSO-d6, 400 MHz) δ 8.20 (d, J=0.9 Hz, 1H), 8.08 (s, 1H), 7.84-7.77 (m, 2H), 7.65 (s, 1H), 7.57 (s, 1H), 7.48-7.40 (m, 2H), 7.30-7.22 (m, 2H), 7.22-7.16 (m, 3H), 3.92-3.69 (m, 6H), 3.52-3.36 (m, 2H), 2.96 (d, J=14.4 Hz, 1H), 2.80 (s, 3H), 2.52 (s, 3H), 2.41-2.31 (m, 1H), 2.23 (d, J=14.3 Hz, 1H), 2.11 (dd, J=13.3, 8.7 Hz, 1H) rotamers evident.

Example 20: (3a-(1-(4-fluorophenyl)-6-methyl-1H-indazol-5-yl)-5-methoxy-5-phenylhexahydrocyclopenta[c]pyrrol-2(1H)-yl)(phenyl)methanone

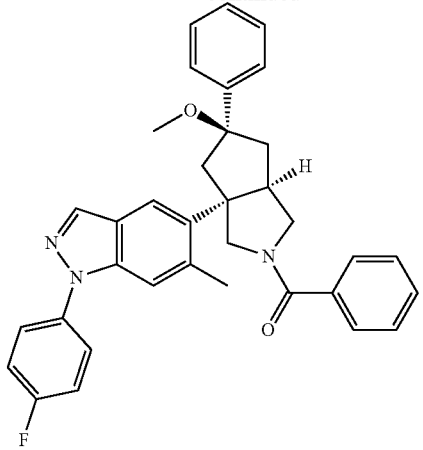

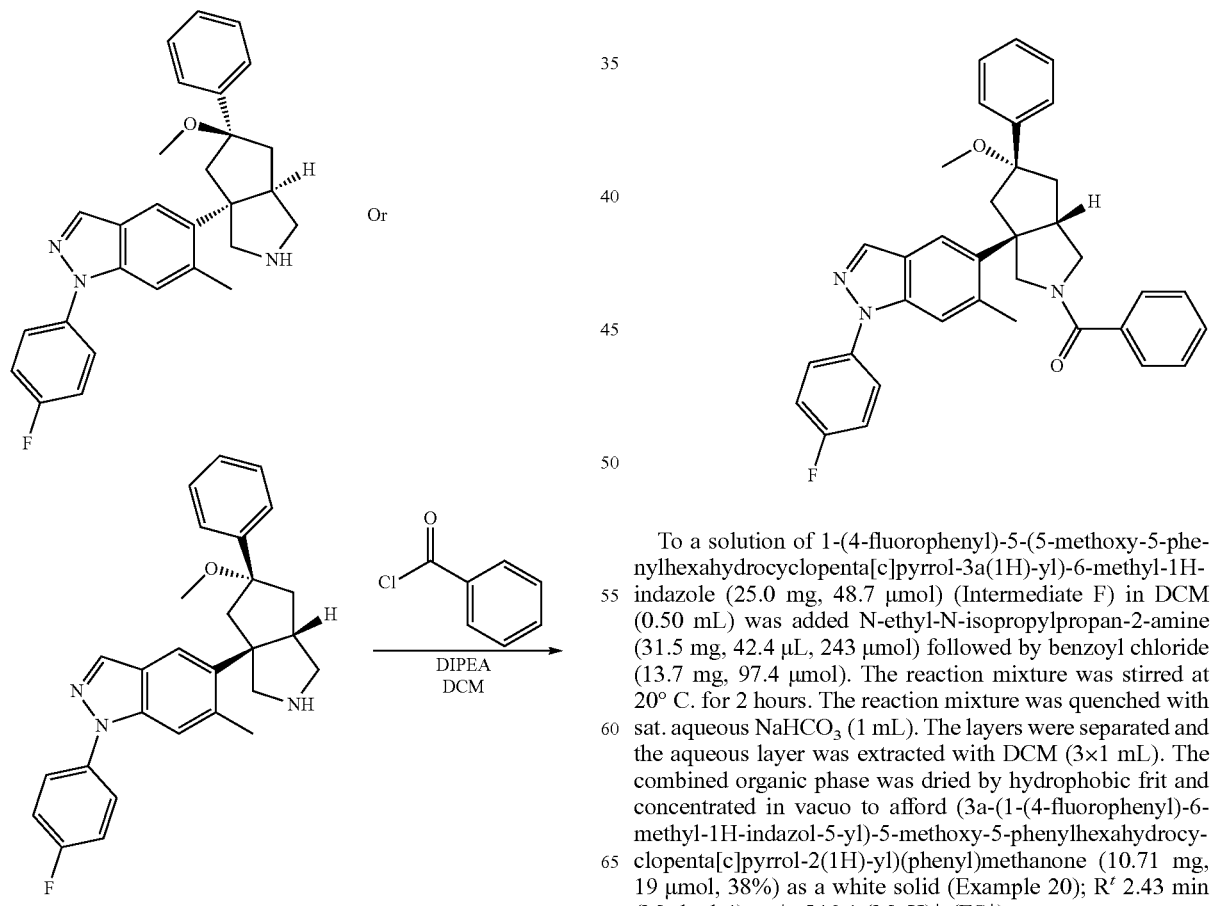

To a solution of 1-(4-fluorophenyl)-5-(5-methoxy-5-phenylhexahydrocyclopenta[c]pyrrol-3a(1H)-yl)-6-methyl-1H-indazole (25.0 mg, 48.7 μmol) (Intermediate F) in DCM (0.50 mL) was added N-ethyl-N-isopropylpropan-2-amine (31.5 mg, 42.4 μL, 243 μmol) followed by benzoyl chloride (13.7 mg, 97.4 μmol). The reaction mixture was stirred at 20° C. for 2 hours. The reaction mixture was quenched with sat. aqueous NaHCO$_3$ (1 mL). The layers were separated and the aqueous layer was extracted with DCM (3×1 mL). The combined organic phase was dried by hydrophobic frit and concentrated in vacuo to afford (3a-(1-(4-fluorophenyl)-6-methyl-1H-indazol-5-yl)-5-methoxy-5-phenylhexahydrocyclopenta[c]pyrrol-2(1H)-yl)(phenyl)methanone (10.71 mg, 19 μmol, 38%) as a white solid (Example 20); R$^t$ 2.43 min (Method 4); m/z 546.4 (M+H)$^+$ (ES$^+$).

Examples 21 to 33

TABLE 3

The examples shown in the table below were prepared by similar methods to those described for Example 19 and Example 20.

| Example | Structure | LC-MS Analysis |
|---|---|---|
| 21 | *Or* 5-(2-((1-ethyl-1H-pyrazol-4-yl)sulfonyl)-5-methoxy-5-phenylhexahydrocyclopenta[c]pyrrol-3a(1H)-yl)-1-(4-fluorophenyl)-6-methyl-1H-indazole | $R^t$ 2.33 min (Method 4); m/z 600.2 $(M + H)^+$ $(ES^+)$ |
| 22 | *Or* 11-(4-fluorophenyl)-5-(5-methoxy-5-phenyl-2-((1-propyl-1H-pyrazol-4-yl)sulfonyl)hexahydrocyclopenta[c]pyrrol-3a(1H)-yl)-6-methyl-1H-indazole | $R^t$ 2.44 min (Method 4); m/z 614.3 $(M + H)^+$ $(ES^+)$ |

TABLE 3-continued

The examples shown in the table below were prepared by similar methods to those described for Example 19 and Example 20.

| Example | Structure | LC-MS Analysis |
|---|---|---|
| 23 | 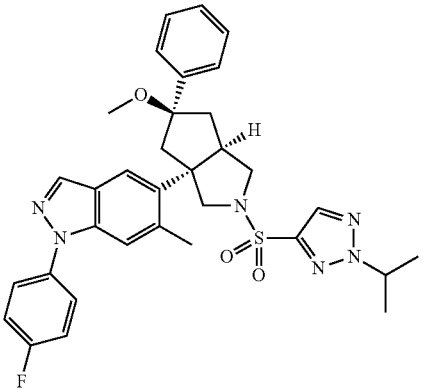 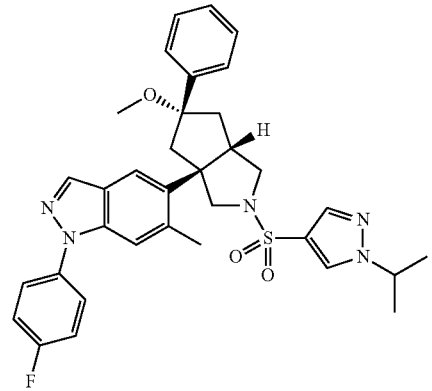   Or<br>1-(4-fluorophenyl)-5-(2-((2-isopropyl-2H-1,2,3-triazol-4-yl)sulfonyl)-5-methoxy-5-phenylhexahydrocyclopenta[c]pyrrol-3a(1H)-yl)-6-methyl-1H-indazole | $R^t$ 2.55 min (Method 4); m/z 615.2 $(M + H)^+$ $(ES^+)$ |
| 24 | 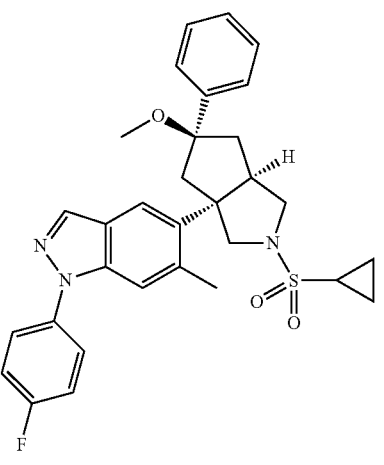 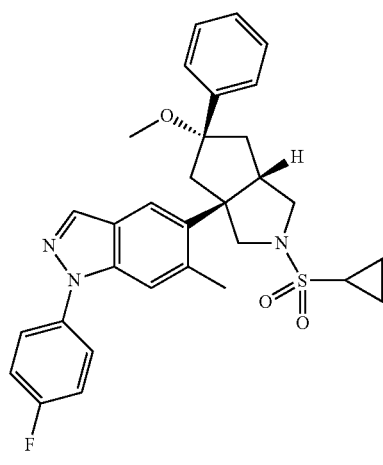   Or<br>5-(2-(cyclopropylsulfonyl)-5-methoxy-5-phenylhexahydrocyclopenta[c]pyrrol-3a(1H)-yl)-1-(4-fluorophenyl)-6-methyl-1H-indazole | $R^t$ 2.37 min (Method 4); m/z 546.2 $(M + H)^+$ $(ES^+)$ |

TABLE 3-continued

The examples shown in the table below were prepared by similar methods to those described for Example 19 and Example 20.

| Example | Structure | LC-MS Analysis |
|---|---|---|
| 25 | 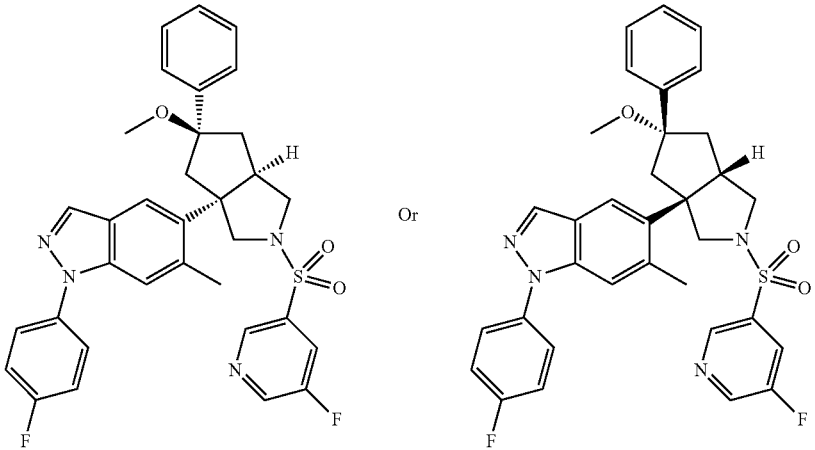<br>1-(4-fluorophenyl)-5-(2-((5-fluoropyridin-3-yl)sulfonyl)-5-methoxy-5-phenylhexahydrocyclopenta[c]pyrrol-3a(1H)-yl)-6-methyl-1H-indazole | $R^t$ 2.28 min (Method 4); m/z 601.2 (M + H)$^+$ (ES$^+$) |
| 26 | 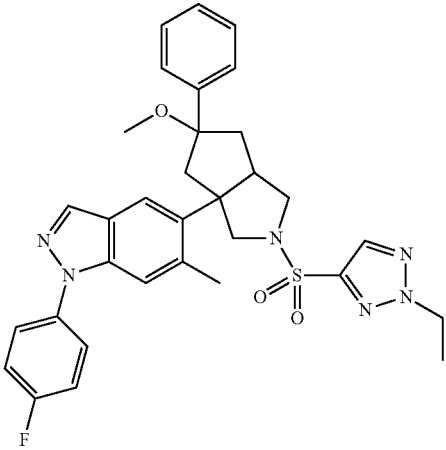<br>5-(2-((2-ethyl-2H-1,2,3-triazol-4-yl)sulfonyl)-5-methoxy-5-phenylhexahydrocyclopenta[c]pyrrol-3a(1H)-yl)-1-(4-fluorophenyl)-6-methyl-1H-indazole | $R^t$ 2.11 min (Method 7); m/z 601.3 (M + H)$^+$ (ES$^+$) |

TABLE 3-continued

The examples shown in the table below were prepared by similar methods to those described for Example 19 and Example 20.

| Example | Structure | LC-MS Analysis |
| --- | --- | --- |
| 27 | 1-(4-fluorophenyl)-5-(5-methoxy-5-phenyl-2-((2-propyl-2H-1,2,3-triazol-4-yl)sulfonyl)hexahydrocyclopenta[c]pyrrol-3a(1H)-yl)-6-methyl-1H-indazole | $R^t$ 2.16 min (Method 7); m/z 615.4 $(M + H)^+$ $(ES^+)$ |
| 28 | 1-(4-fluorophenyl)-5-(5-methoxy-2-((1-methylcyclopropyl)sulfonyl)-5-phenylhexahydrocyclopenta[c]pyrrol-3a(1H)-yl)-6-methyl-1H-indazole | $R^t$ 2.39 min (Method 7); m/z 560.3 $(M + H)^+$ $(ES^+)$ |

TABLE 3-continued

The examples shown in the table below were prepared by similar methods to those described for Example 19 and Example 20.

| Example | Structure | LC-MS Analysis |
|---|---|---|
| 29 | 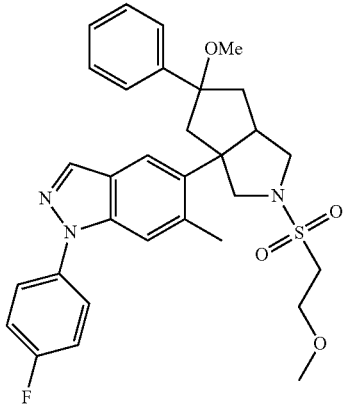<br>1-(4-fluorophenyl)-5-(5-methoxy-2-((2-methoxyethyl)sulfonyl)-5-phenylhexahydrocyclopenta[c]pyrrol-3a(1H)-yl)-6-methyl-1H-indazole | $R^t$ 2.13 min (Method 1); m/z 484.2 $(M + H)^+ (ES^+)$ |
| 30 | 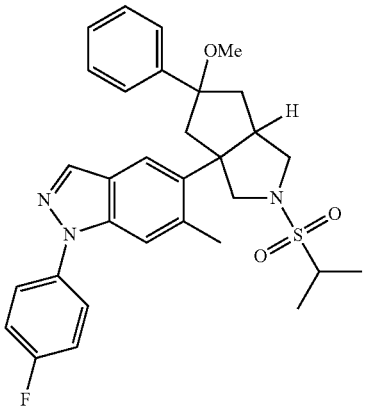<br>1-(4-fluorophenyl)-5-(2-(isopropylsulfonyl)-5-methoxy-5-phenylhexahydrocyclopenta[c]pyrrol-3a(1H)-yl)-6-methyl-1H-indazole | $R^t$ 2.54 min (Method 7); m/z 548.4 $(M + H)^+ (ES^+)$ |

TABLE 3-continued

The examples shown in the table below were prepared by similar methods to those described for Example 19 and Example 20.

| Example | Structure | LC-MS Analysis |
|---|---|---|
| 31 | 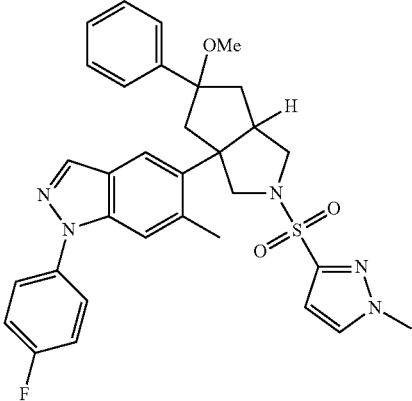<br>1-(4-fluorophenyl)-5-(5-methoxy-2-((1-methyl-1H-pyrazol-3-yl)sulfonyl)-5-phenylhexahydrocyclopenta[c]pyrrol-3a(1H)-yl)-6-methyl-1H-indazole | $R^t$ 2.23 min (Method 7); m/z 586.43 $(M + H)^+$ $(ES^+)$ |
| 32 | 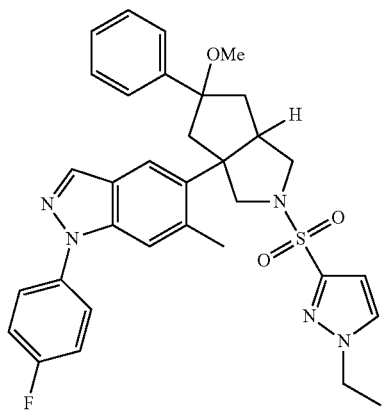<br>5-(2-((1-ethyl-1H-pyrazol-3-yl)sulfonyl)-5-methoxy-5-phenylhexahydrocyclopenta[c]pyrrol-3a(1H)-yl)-1-(4-fluorophenyl)-6-methyl-1H-indazole | $R^t$ 2.30 min (Method 7); m/z 600.65 (M + H+) (ES+) |

TABLE 3-continued

The examples shown in the table below were prepared by similar methods to those described for Example 19 and Example 20.

| Example | Structure | LC-MS Analysis |
|---|---|---|
| 33 | 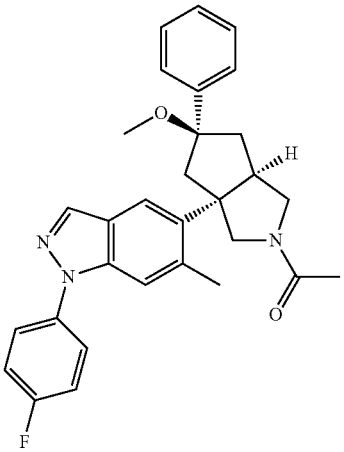 Or 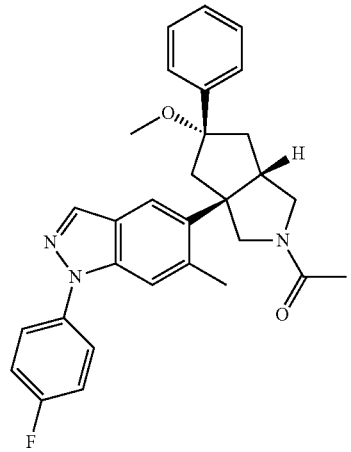<br>1-(3a-(1-(4-fluorophenyl)-6-methyl-1H-indazol-5-yl)-5-methoxy-5-phenylhexahydrocyclopenta[c]pyrrol-2(1H)-yl)ethan-1-one | $R^t$ 2.13 min (Method 4); m/z 484.2 $(M + H)^+$ $(ES^+)$ |

Example 34: 1-(4-fluorophenyl)-5-(5-methoxy-2-(methylsulfonyl)hexahydrocyclopenta[c]pyrrol-3a(1H)-yl)-6-methyl-1H-indazole

Intermediate G: 3a-(1-(4-fluorophenyl)-6-methyl-1H-indazol-5-yl)-2-(methylsulfonyl)octahydrocyclopenta[c]pyrrol-5-ol

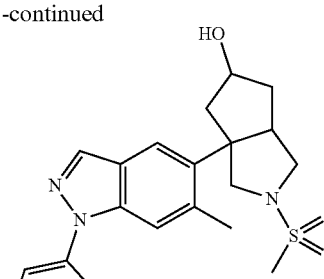 NaBH₄ MeOH → 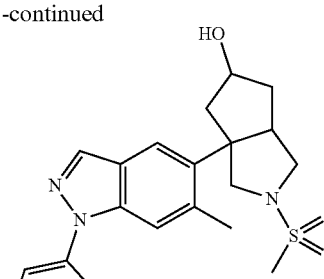

Sodium borohydride (2.7 mg, 70 µmol) was added to a solution of 3a-(1-(4-fluorophenyl)-6-methyl-1H-indazol-5-yl)-2-(methylsulfonyl)hexahydrocyclopenta[c]pyrrol-5(1H)-one (Prepared using the same method as Example 2) (20 mg, 47 µmol) in DCM (1 mL) and the reaction stirred overnight. The reaction mixture was quenched with 1 M HCl (10 mL) and the aqueous layer was extracted with EtOAc (3×20 mL). The combined organics were dried over MgSO₄, filtered and concentrated in vacuo. The crude product was purified by chromatography on silica gel (12 g cartridge, 0-80% EtOAc/isohexane) to afford an 89:11 diastereomeric mixture of 3a-(1-(4-fluorophenyl)-6-methyl-1H-indazol-5-yl)-2-(methylsulfonyl)octahydrocyclopenta[c]pyrrol-5-ol (Intermediate G) (20 mg, 46 µmol, 99% yield) as a white solid as a major and minor pair of diastereoisomers; $R^t$ 1.30 min (major) and 1.27 min (minor) (Method 1); m/z 430.7 $(M+H)^+$ $(ES^+)$.

Example 34: 1-(4-fluorophenyl)-5-(5-methoxy-2-(methylsulfonyl)hexahydrocyclopenta[c]pyrrol-3a(1H)-yl)-6-methyl-1H-indazole

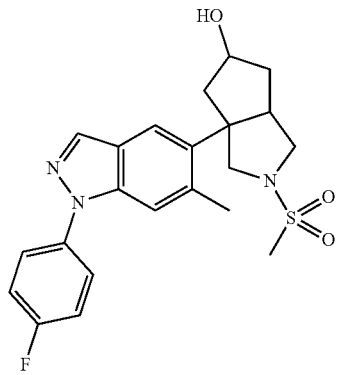

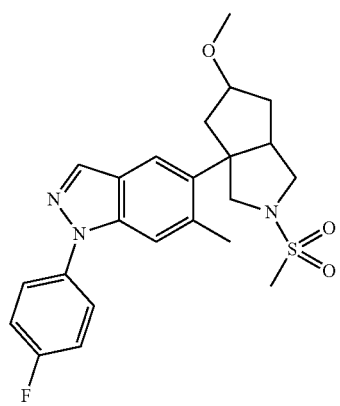

Sodium hydride (2.8 mg, 60% Wt, 70 µmol) was added to a solution of 3a-(1-(4-fluorophenyl)-6-methyl-1H-indazol-5-yl)-2-(methylsulfonyl)octahydrocyclopenta[c]pyrrol-5-ol (Intermediate G) (20 mg, 47 µmol) in THF (1 mL) at 0° C. and the mixture stirred for 30 minutes. Methyl iodide (7.9 mg, 3.5 µL, 56 µmol) was added and the reaction mixture stirred overnight at RT. The mixture was then quenched with water (10 mL). The aqueous phase was extracted with EtOAc (3×15 mL) and the combined organics dried over MgSO$_4$, filtered and concentrated in vacuo. The crude product was purified by chromatography on silica gel (12 g cartridge, 0-50% EtOAc/isohexane) to afford a 9:1 diastereomeric mixture of 1-(4-fluorophenyl)-5-(5-methoxy-2-(methylsulfonyl)hexahydrocyclopenta[c]pyrrol-3a(1H)-yl)-6-methyl-1H-indazole (Example 34) (7.0 mg, 15 µmol, 33% yield) as a white solid; R$^t$ 1.53 min (major) and 1.50 min (minor) (Method 1); m/z 444.4 (M+H)$^+$ (ES$^+$); δH (DMSO-d6, 500 MHz) (Data for major diastereomer) 8.27 (d, J 0.9, 1H), 7.82-7.77 (m, 3H), 7.69 (s, 1H), 7.45-7.40 (m, 2H), 3.86 (d, J 9.9, 1H), 3.74 (p, J 7.2, 1H), 3.63 (dd, J 9.7, 7.5, 1H), 3.41 (d, J 10.0, 2H), 3.30 (d, J 4.4, 1H), 3.20 (s, 3H), 2.81 (s, 3H), 2.52 (s, 3H), 2.42 (dt, J 13.9, 7.3, 1H), 2.31 (dd, J 13.4, 7.3, 1H), 2.22 (dd, J 13.4, 7.2, 1H), 1.64 (dt, J 13.0, 7.4, 1H).

Example 35: tert-butyl 5-(benzyloxy)-3a-(1-(4-fluorophenyl)-6-methyl-1H-indazol-5-yl)hexahydrocyclopenta[c]pyrrole-2(1H)-carboxylate

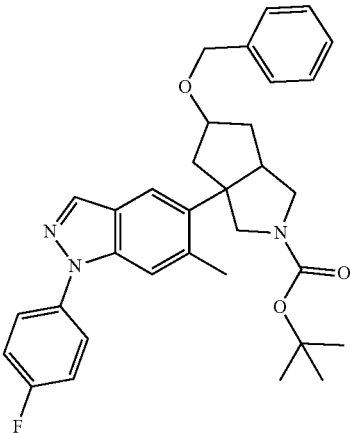 [SMILES: Cc1cc2c(cnn2-c2ccc(F)cc2)cc1C12CC(OCc3ccccc3)CC1CN(C(=O)OC(C)(C)C)C2]

The compound was prepared by similar methods to those described for Example 34 to afford tert-butyl 5-(benzyloxy)-3a-(1-(4-fluorophenyl)-6-methyl-1H-indazol-5-yl)hexahydrocyclopenta[c]pyrrole-2(1H)-carboxylate (6 mg, 0.01 mmol, 20%) (Example 35) as a white solid; Rt 2.44 min (Method 4); m/z 542.4 (M+H)$^+$ (ES$^+$). δH (DMSO-d6, 500 MHz) δ 8.25 (s, 1H), 7.82-7.76 (m, 2H), 7.73 (s, 1H), 7.67 (s, 1H), 7.42 (t, J 8.8, 2H), 7.32 (m, 4H), 7.27 (td, J 6.0, 2.5, 1H), 4.44 (s, 2H), 4.01 (p, J 7.0, 1H), 3.91-3.85 (m, 1H), 3.74-3.69 (m, 1H), 3.58-3.51 (m, 1H), 3.44-3.34 (m, 1H), 3.30-3.21 (m, 1H), 2.44 (dt, J 13.8, 7.2, 1H), 2.31 (d, J 7.1, 2H), 1.74-1.64 (m, 1H), 1.40-1.25 (br. m, 9H). CH$_3$ peak under DMSO-d6 signal.

Example 36 and 37: 1-(4-fluorophenyl)-6-methyl-5-(2-(methylsulfonyl)-5-phenoxyhexahydrocyclopenta[c]pyrrol-3a(1H)-yl)-1H-indazole Intermediate H: tert-butyl 3a-(1-(4-fluorophenyl)-6-methyl-1H-indazol-5-yl)-5-phenoxyhexahydrocyclopenta[c]pyrrole-2(1H)-carboxylate

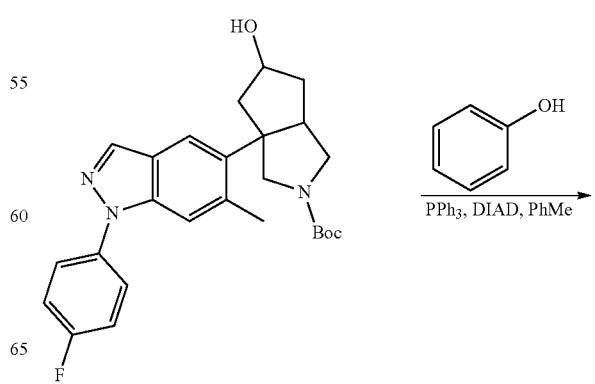

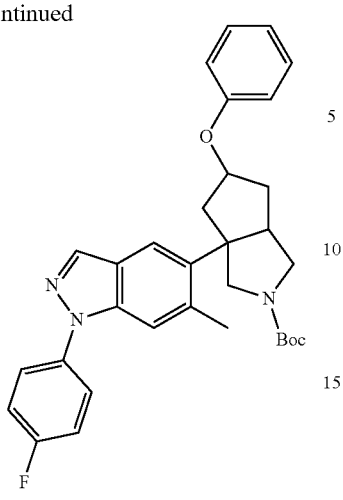

DIAD (104 µL, 536 µmol) was added to a solution of tert-butyl 3a-(1-(4-fluorophenyl)-6-methyl-1H-indazol-5-yl)-5-hydroxyhexahydrocyclopenta[c]pyrrole-2(1H)-carboxylate (220 mg, 487 µmol) (Prepared using the same method as Intermediate G using Intermediate A), phenol (59.6 mg, 633 µmol) and triphenylphosphine (153 mg, 585 µmol) in toluene (3 mL) at 0° C. and the mixture stirred at RT overnight. Phenol (59.6 mg, 633 µmol), DIAD (104 µL, 536 µmol), and triphenylphosphine (153 mg, 585 µmol) were added and the reaction stirred for 2 hours. The reaction mixture was partitioned between EtOAc (10 mL) and water (10 mL), the layers were separated and the aqueous layer extracted with EtOAc (2×10 mL). The combined organics were washed with sat. $NaHCO_{3(aq)}$ (20 mL), dried over $MgSO_4$, filtered and concentrated in vacuo. The crude product was purified by chromatography on silica gel (12 g cartridge, 0-30% EtOAc/isohexane) to afford a 93:7 diastereomeric mixture of tert-butyl 3a-(1-(4-fluorophenyl)-6-methyl-1H-indazol-5-yl)-5-phenoxyhexahydrocyclopenta[c]pyrrole-2(1H)-carboxylate (Intermediate H) (309 mg, 0.48 mmol, 99% yield) as an off white solid; $R^t$ 2.09 min (major) and 2.14 min (minor); (Method 1); m/z 528.8 $(M+H)^+$ $(ES^+)$.

Example 36: 1-(4-fluorophenyl)-6-methyl-5-(2-(methylsulfonyl)-5-phenoxyhexahydrocyclopenta[c]pyrrol-3a(1H)-yl)-1H-indazole Example 37: 1-(4-fluorophenyl)-6-methyl-5-(2-(methylsulfonyl)-5-phenoxyhexahydrocyclopenta[c]pyrrol-3a(1H)-yl)-1H-indazole

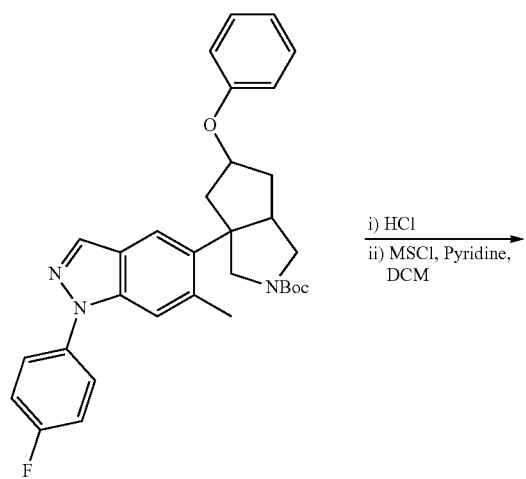

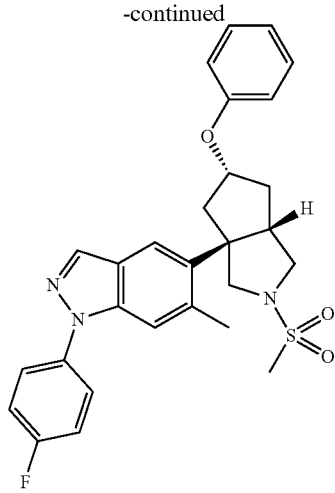

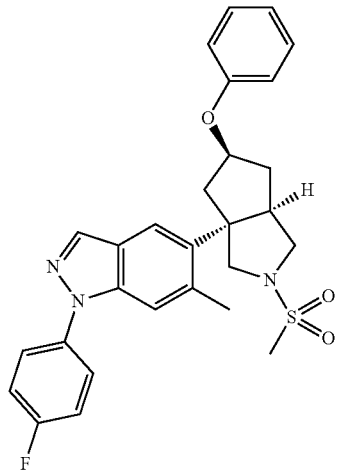

HCl (4 molar, 0.19 mL, 0.76 mmol) was added to a solution of tert-butyl 3a-(1-(4-fluorophenyl)-6-methyl-1H-indazol-5-yl)-5-phenoxyhexahydrocyclopenta[c]pyrrole-2(1H)-carboxylate (137 mg, 260 µmol) (Intermediate H) in 1,4-dioxane (4 mL) and the reaction mixture stirred for 1 h. The reaction was concentrated in vacuo and the residue taken up in pyridine (0.1 mL, 1.3 mmol) and DCM (3 mL). Methanesulfonyl chloride (44.6 mg, 30.1 µL, 389 µmol) was added and the mixture was stirred for 2 h at room temperature. Water (10 mL) and DCM (10 mL) were added and the layers were separated and the organic layer was washed with water (10 mL), dried over $MgSO_4$, filtered and concentrated in vacuo. The crude product was purified by chromatography on silica gel (12 g cartridge, 0-50% EtOAc/isohexane) to afford 1-(4-fluorophenyl)-6-methyl-5-(2-(methylsulfonyl)-5-phenoxyhexahydrocyclopenta[c]pyrrol-3a(1H)-yl)-1H-indazole (28 mg, 54 µmol, 21%) which was dissolved to 50 mg/mL in DCM: MeOH with sonication, filtered and was then separated by chiral SFC on a Waters prep 15 with UV detection by DAD at 210-400 nm, 40° C., 120 bar. The column was IH 10×250 mm, 5 um, flow rate 15 mL/min at 40% MeOH (neutral), 60% $CO_2$. The clean fractions were pooled, rinsed with methanol and concentrated to dryness using a rocket evaporator at 40° C. The residues were re-dissolved in methanol: DCM, transferred into final vials and evaporated on a Biotage V10. The samples were then further dried in a vacuum oven at 30° C./5 mbar over night to afford isomer 1 1-(4-fluorophenyl)-6-methyl-5-(2-(methylsulfonyl)-5-phenoxyhexahydrocyclopenta[c]pyrrol-3a(1H)-yl)-1H-indazole (3.3 mg) (Example 36) $R^t$ 1.86 min (Method 5); m/z 506.4 $(M+H)^+$ $(ES^+)$; and 1-(4-fluorophenyl)-6-methyl-5-(2-(methylsulfonyl)-5-phenoxyhexahydro-cyclopenta[c]pyrrol-3a(1H)-yl)-1H-indazole 3.4 mg) (Example 37) as white powders R$^t$ 1.86 min (Method 5); m/z 506.4 (M+H)$^+$ (ES$^+$)

Examples 38 to 45

TABLE 4

The examples shown in the table below were prepared by similar methods to those described for Example 36 and Example 37.

| Example | Structure | LC-MS Analysis |
|---|---|---|
| 38 | 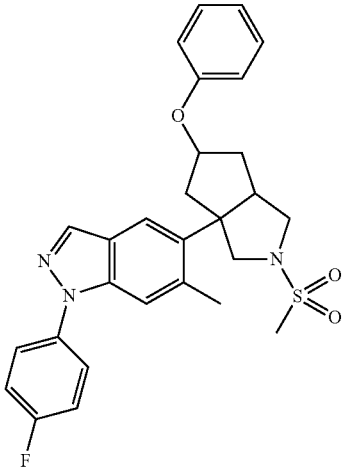<br>1-(4-fluorophenyl)-6-methyl-5-(2-(methylsulfonyl)-5-phenoxyhexahydrocyclopenta[c]pyrrol-3a(1H)-yl)-1H-indazole | R$^t$ 2.54 min (Method 1); m/z 506.35 (M + H)$^+$ (ES$^+$) |
| 39 | 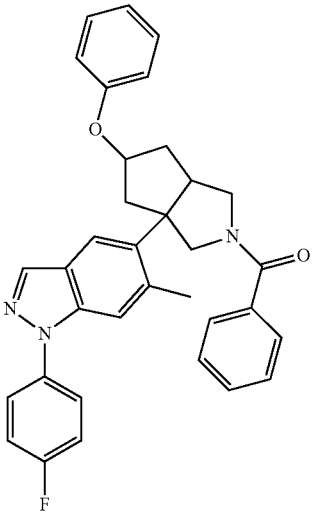<br>(3a-(1-(4-fluorophenyl)-6-methyl-1H-indazol-5-yl)-5-phenoxyhexahydrocyclopenta[c]pyrrol-2(1H)-yl)(phenyl)methanone | R$^t$ 1.86 min (Method 4); m/z 532.5 (M + H)$^+$ (ES$^+$) |

TABLE 4-continued

The examples shown in the table below were prepared by similar methods to those described for Example 36 and Example 37.

| Example | Structure | LC-MS Analysis |
|---------|-----------|----------------|
| 40 | 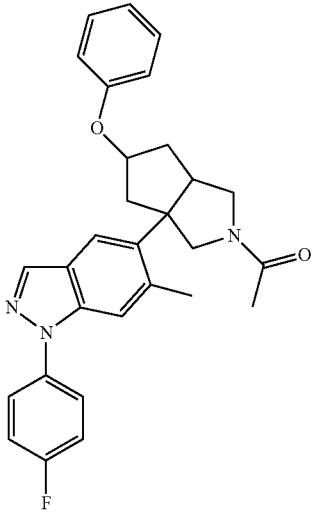 1-(3a-(1-(4-fluorophenyl)-6-methyl-1H-indazol-5-yl)-5-phenoxyhexahydrocyclopenta[c]pyrrol-2(1H)-yl)ethan-1-one | $R^t$ 1.66 min (Method 4); m/z 470.50 $(M + H)^+$ $(ES^+)$ |
| 41 | 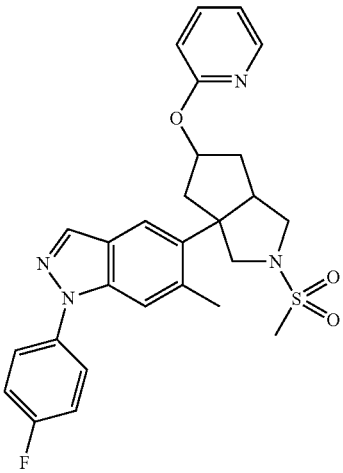 1-(4-fluorophenyl)-6-methyl-5-(2-(methylsulfonyl)-5-(pyridin-2-yloxy)hexahydrocyclopenta[c]pyrrol-3a(1H)-yl)-1H-indazole | $R^t$ 1.63 min (Method 1); m/z 507.35 $(M + H)^+$ $(ES^+)$ |

TABLE 4-continued

The examples shown in the table below were prepared by similar methods to those described for Example 36 and Example 37.

| Example | Structure | LC-MS Analysis |
|---|---|---|
| 42 | 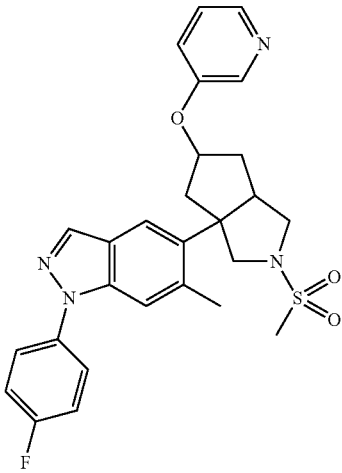 1-(4-fluorophenyl)-6-methyl-5-(2-(methylsulfonyl)-5-(pyridin-3-yloxy)hexahydrocyclopenta[c]pyrrol-3a(1H)-yl)-1H-indazole | $R^t$ 1.19 min (Method 1); m/z 507.38 (M + H)$^+$ (ES$^+$) |
| 43 | 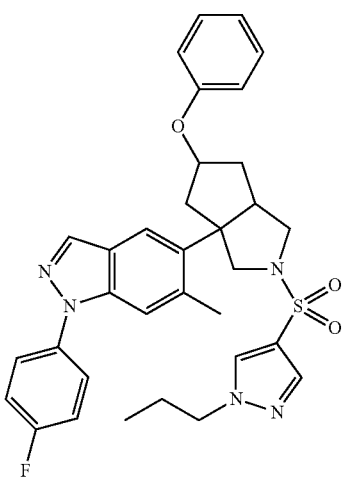 1-(4-fluorophenyl)-6-methyl-5-(2-((1-methyl-1H-pyrazol-4-yl)sulfonyl)-5-phenoxyhexahydrocyclopenta[c]pyrrol-3a(1H)-yl)-1H-indazole | $R^t$ 1.86 min (Method 1); m/z 600.5 (M + H)$^+$ (ES$^+$) |

TABLE 4-continued

The examples shown in the table below were prepared by similar methods to those described for Example 36 and Example 37.

| Example | Structure | LC-MS Analysis |
|---------|-----------|----------------|
| 44 | 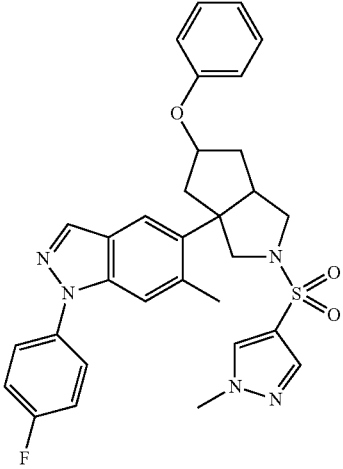<br>1-(4-fluorophenyl)-6-methyl-5-(5-phenoxy-2-((1-propyl-1H-pyrazol-4-yl)sulfonyl)hexahydrocyclopenta[c]pyrrol-3a(1H)-yl)-1H-indazole | R$^t$ 1.75 min (Method 1); m/z 572.7 (M + H)$^+$ (ES$^+$) |
| 45 | 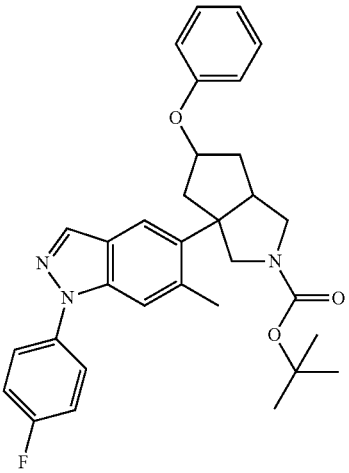<br>tert-butyl 3a-(1-(4-fluorophenyl)-6-methyl-1H-indazol-5-yl)-5-phenoxyhexahydrocyclopenta[c]pyrrole-2(1H)-carboxylate | R$^t$ 2.08 min (Method 1); m/z 528.4 (M + H)$^+$ (ES$^+$) |

Example 46: 1-(4-fluorophenyl)-6-methyl-5-(2-(methylsulfonyl)-5-phenylhexahydrocyclopenta[c]pyrrol-3a(1H)-yl)-1H-indazole Intermediate I: 3a-(1-(4-fluorophenyl)-6-methyl-1H-indazol-5-yl)-2-(methylsulfonyl)-5-phenyloctahydrocyclopenta[c]pyrrol-5-ol

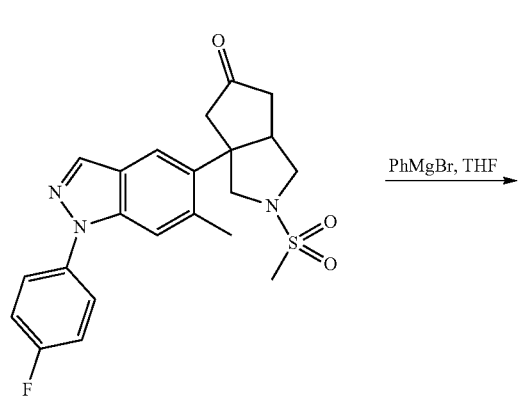

PhMgBr, THF

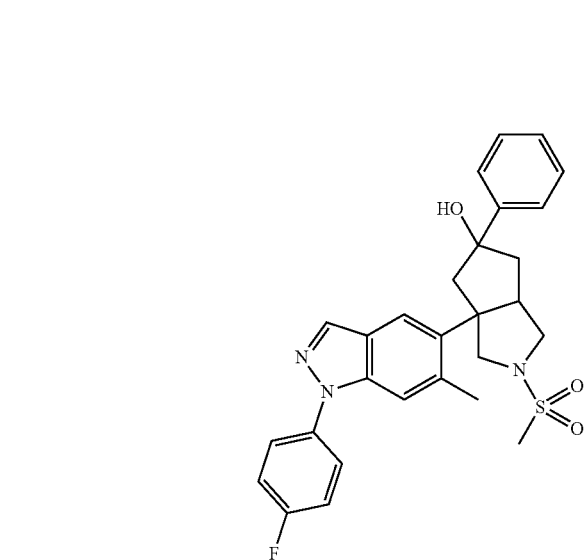

Phenylmagnesium chloride (2M in THF) (38.4 mg, 140 µL, 281 µmol) was added to a solution of 3a-(1-(4-fluorophenyl)-6-methyl-1H-indazol-5-yl)-2-(methylsulfonyl)hexahydrocyclopenta[c]pyrrol-5(1H)-one (100 mg, 234 µmol) (Prepared using the same method as Example 2) in THF (1 mL) at 0° C. The reaction was allowed to warm to RT and stirred overnight. The reaction was quenched with H$_2$O (10 mL) and the layers separated. The aqueous phase was extracted with DCM (3×10 mL) and the combined organics dried over MgSO$_4$, filtered and concentrated in vacuo. The crude product was purified by chromatography on silica gel (12 g cartridge, 0-50% EtOAc/isohexane) to afford a 96.5:3.55 diastereomeric mixture of 3a-(1-(4-fluorophenyl)-6-methyl-1H-indazol-5-yl)-2-(methylsulfonyl)-5-phenyloctahydrocyclopenta[c]pyrrol-5-ol (34 mg, 65 µmol, 28%) (Intermediate I) as a colourless gum; R$^t$ 1.86 min (Method 5); m/z 506.4 (M+H)$^+$ (ES$^+$).

Intermediate J: A mixture of 1-(4-fluorophenyl)-6-methyl-5-(2-(methylsulfonyl)-5-phenyl-2,3,6,6a-tetrahydrocyclopenta[c]pyrrol-3a(1H)-yl)-1H-indazole and 1-(4-fluorophenyl)-6-methyl-5-(2-(methylsulfonyl)-5-phenyl-2,3,4,6a-tetrahydrocyclopenta[c]pyrrol-3a(1H)-yl)-1H-indazole

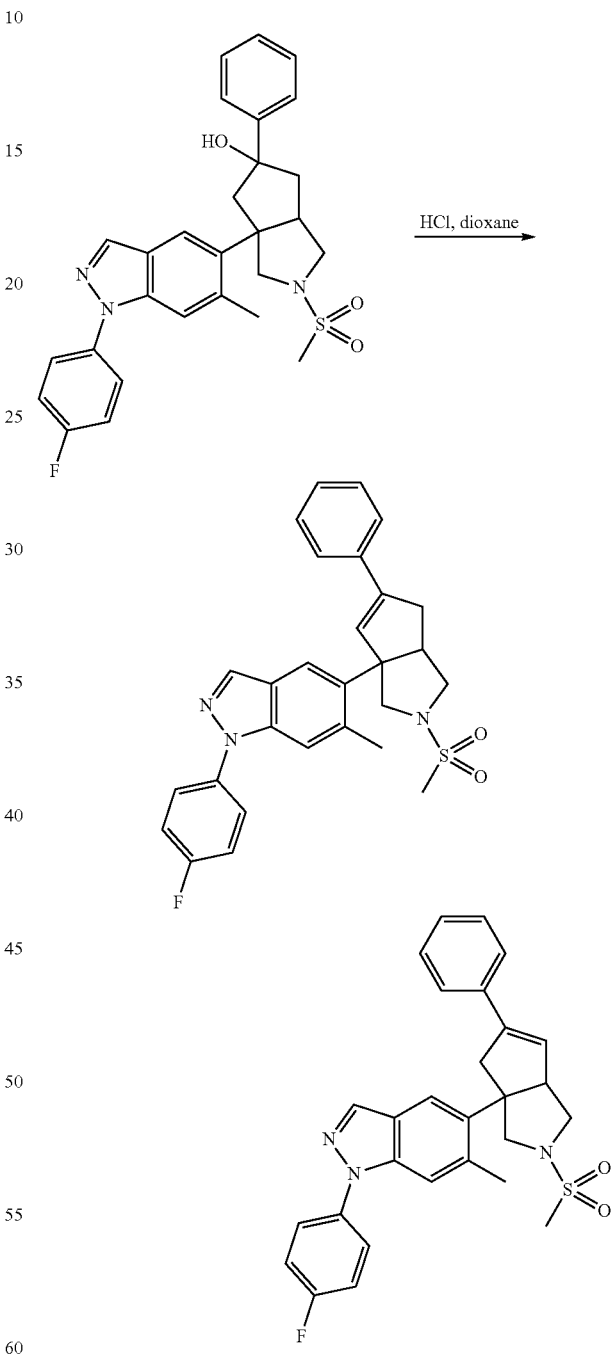

HCl, dioxane

HCl (4 M in dioxane) (25 mg, 0.17 mL, 4.00 molar, 0.67 mmol) was added to a solution of 3a-(1-(4-fluorophenyl)-6-methyl-1H-indazol-5-yl)-2-(methylsulfonyl)-5-phenyloctahydrocyclopenta[c]pyrrol-5-ol (34 mg, 67 µmol) (Intermediate I) in 1,4-dioxane (0.5 mL) and the reaction stirred for 2 h. The reaction was concentrated in vacuo and the crude product was purified by chromatography on silica gel (12 g cartridge, 0-50% EtOAc/isohexane) to afford an inseparable mixture of 1-(4-fluorophenyl)-6-methyl-5-(2-(methylsulfonyl)-5-phenyl-2,3,6,6a-tetrahydrocyclopenta[c]pyrrol-3a(1H)-yl)-1H-indazole and 1-(4-fluorophenyl)-6-methyl-5-(2-(methylsulfonyl)-5-phenyl-2,3,4,6a-tetrahydrocyclopenta[c]pyrrol-3a(1H)-yl)-1H-indazole (30 mg, 29 µmol, 43%) (Intermediate J) as a colourless glass; R$^t$ 1.86 and 1.86 min (Method 1); m/z 488.8 (M+H)$^+$ (ES$^+$).

Example 46: 1-(4-fluorophenyl)-6-methyl-5-(2-(methylsulfonyl)-5-phenylhexahydrocyclopenta[c]pyrrol-3a(1H)-yl)-1H-indazole 10% Palladium on carbon (15 mg, 5.5 µmol) was added to a solution of a mixture of 1-(4-fluorophenyl)-6-methyl-5-(2-(methylsulfonyl)-5-phenyl-2,3,6,6a-tetrahydrocyclopenta[c]pyrrol-3a(1H)-yl)-1H-indazole and 1-(4-fluorophenyl)-6-methyl-5-(2-(methylsulfonyl)-5-phenyl-2,3,4,6a-tetrahydrocyclopenta[c]pyrrol-3a(1H)-yl)-1H-indazole (27 mg, 28 µmol) in EtOH (1 mL) and the reaction mixture was stirred overnight under an atmosphere of hydrogen (5 bar). The reaction was filtered through celite and concentrated in vacuo to give a 1:1 diastereomeric mixture of 1-(4-fluorophenyl)-6-methyl-5-(2-(methylsulfonyl)-5-phenylhexahydrocyclopenta[c]pyrrol-3a(1H)-yl)-1H-indazole (24 mg, 47 µmol, 84%) as an off white foam; R$^t$ 1.84 and 1.85 min (Method 1); m/z 506.4 (M+H)$^+$ (ES$^+$).

Example 47: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol Intermediate K: 1-benzyl-3-(1-(4-fluorophenyl)-6-methyl-1H-indazol-5-yl)-1H-pyrrole-2,5-dione

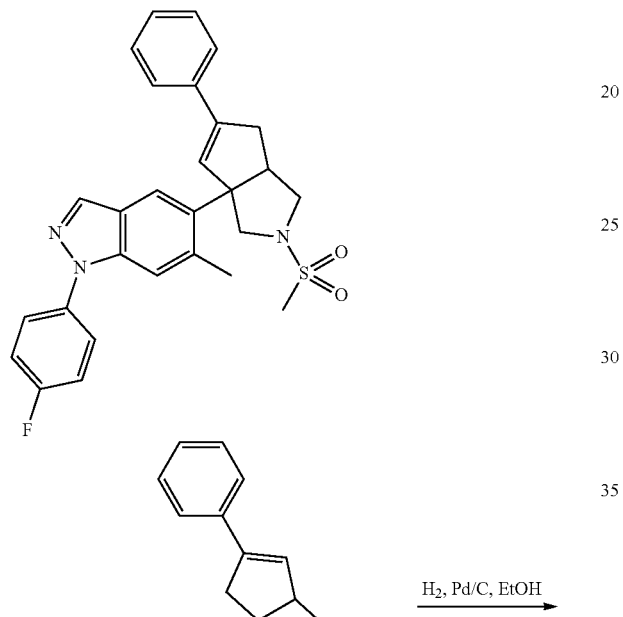

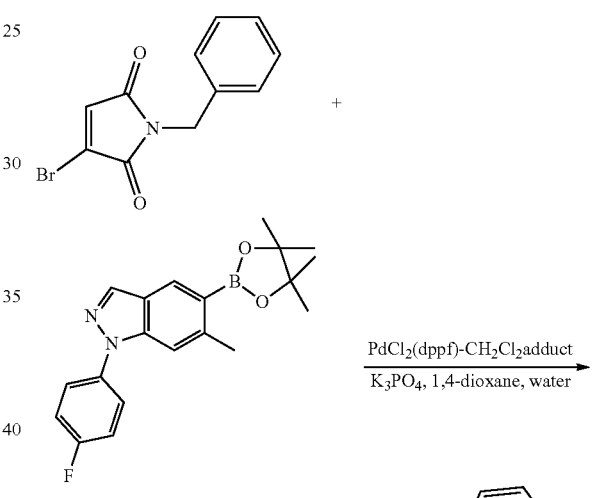

1-benzyl-3-bromo-1H-pyrrole-2,5-dione (2.11 g, 7.94 mmol), 1-(4-fluorophenyl)-6-methyl-5-(4,4,5,5-tetramethyl-1,3,2-dioxaborolan-2-yl)-1H-indazole (2.33 g, 6.62 mmol) (Intermediate B) and tripotassium phosphate (2.81 g, 13.2 mmol) was dissolved in 1,4-dioxane (30 mL) and water (6 mL). The mixture was purged with nitrogen for 5 mins. PdCl$_2$(dppf)-CH$_2$Cl$_2$adduct (270 mg, 331 µmol) was added, and the mixture was purged with nitrogen for a further 5 mins, before heating to 80° C. overnight. The reaction was cooled and diluted with EtOAc (60 mL), washed with water (30 mL) and brine (30 mL). The organic layer was dried using sodium sulphate and concentrated to a dark brown oil. The crude product was purified by chromatography on silica gel (80 g cartridge, 0-30% EtOAc/isohexane) to afford 1-benzyl-3-(1-(4-fluorophenyl)-6-methyl-1H-indazol-5-yl)-1H-pyrrole-2,5-dione (1.44 g, 3.3 mmol, 50%) as a bright yellow solid; Rt 2.19 min (Method 7); m/z 412.2 (M+H)$^+$ (ES$^+$). $\delta_H$ (400 MHz, DMSO-$d_6$) 8.44 (d, J=0.9 Hz, 1H), 8.07 (s, 1H), 7.87-7.78 (m, 2H), 7.76 (s, 1H), 7.50-7.25 (m, 7H), 7.13 (s, 1H), 4.71 (s, 2H), 2.52 (s, 3H).

Intermediate L: ethyl 3-benzyl-1-(1-(4-fluorophenyl)-6-methyl-1H-indazol-5-yl)-2,4-dioxo-3-azabicyclo[3.1.0]hexane-6-carboxylate

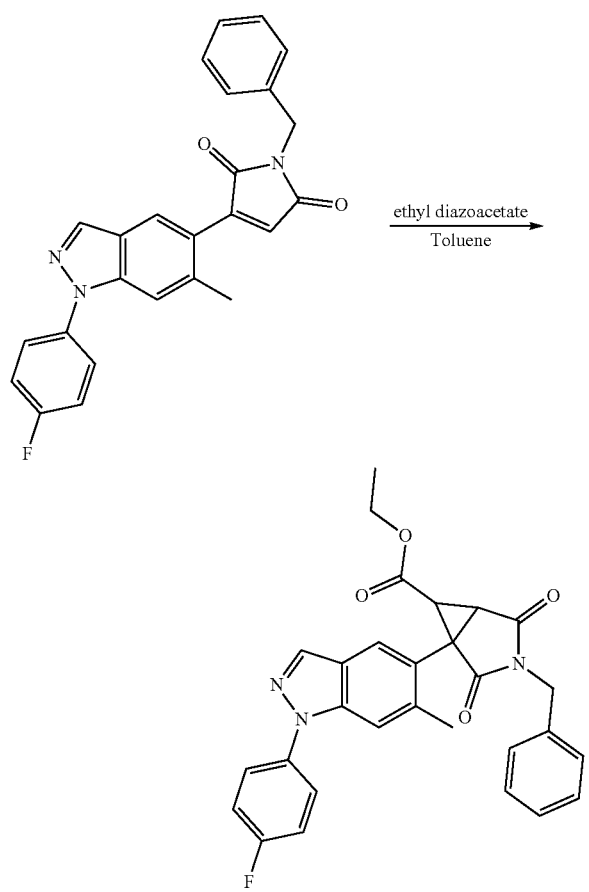

To a solution of 1-benzyl-3-(1-(4-fluorophenyl)-6-methyl-1H-indazol-5-yl)-1H-pyrrole-2,5-dione (1444 mg, 3.51 mmol) in toluene (25 mL) was added 15% ethyl 2-diazoacetate solution in toluene (8.1 g, 8.9 mL, 10.53 mmol) and the reaction was heated to 100° C. for 18 hrs. The solvent was removed in vacuo and the residual solid purified by chromatography on silica gel (80 g cartridge, 0-25% EtOAc/isohexane) to afford ethyl 3-benzyl-1-(1-(4-fluorophenyl)-6-methyl-1H-indazol-5-yl)-2,4-dioxo-3-azabicyclo [3.1.0]hexane-6-carboxylate (1210 mg, 2.3 mmol, 64%) as a yellow solid; Rt 2.26 min (Method 7); m/z 498.2 (M+H)$^+$ (ES$^+$).

Intermediate M: (3-benzyl-1-(1-(4-fluorophenyl)-6-methyl-1H-indazol-5-yl)-3-azabicyclo[3.1.0]hexan-6-yl)methanol Intermediate N: (3-benzyl-1-(1-(4-fluorophenyl)-6-methyl-1H-indazol-5-yl)-3-azabicyclo[3.1.0]hexan-6-yl)methanol

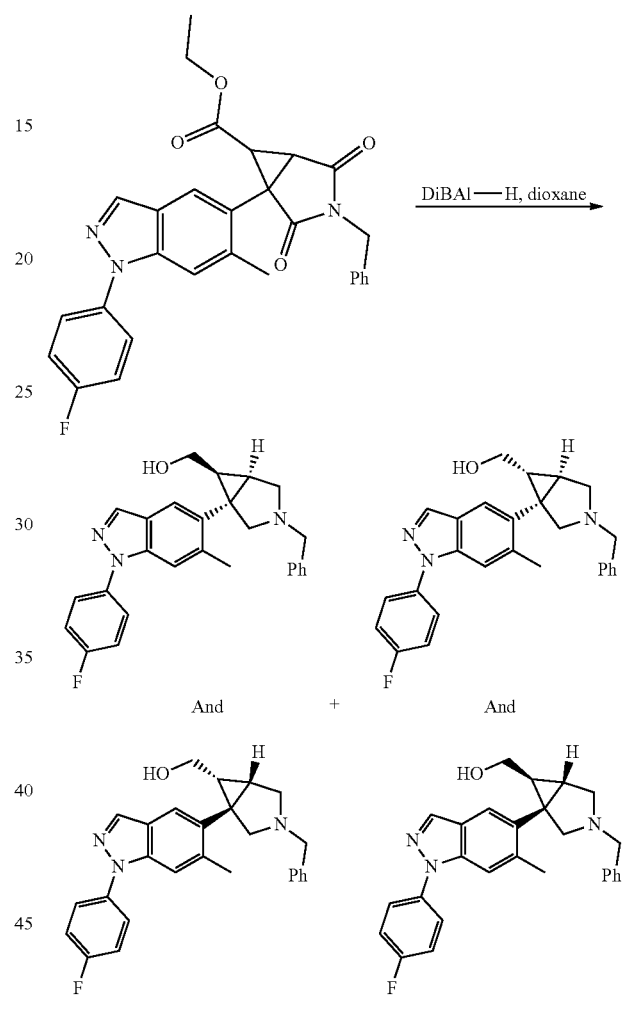

To a solution of ethyl 3-benzyl-1-(1-(4-fluorophenyl)-6-methyl-1H-indazol-5-yl)-2,4-dioxo-3-azabicyclo[3.1.0] hexane-6-carboxylate (3.54 g, 5.62 mmol) in 1,4-dioxane (50 mL) at 0° C. was added DIBAL-H (1 M in hexane) (8.5 g, 60 mL, 60 mmol) slowly. The reaction mixture was stirred with warming to room temperature overnight. The reaction mixture was cooled to 0° C. and quenched with 2 M NaOH solution (5 mL), followed by water (6 mL). The reaction mixture was stirred with warming to room temperature for 15 min. Na$_2$SO$_4$ was added, and stirring was continued for 15 min. The reaction mixture was filtered and the filtrate was concentrated under reduced pressure. The crude product was purified by chromatography on silica gel (80 g cartridge, 0-10% (0.7 M Ammonia/MeOH)/DCM) to afford two separate enantiomeric pairs; (3-benzyl-1-(1-(4-fluorophenyl)-6-methyl-1H-indazol-5-yl)-3-azabicyclo[3.1.0]hexan-6-yl) methanol (437 mg, 0.61 mmol, 11%) (Intermediate M) as an off-white solid Rt 1.35 min (Method 7); m/z 428.4 (M+H)$^+$ (ES⁺) and (3-benzyl-1-(1-(4-fluorophenyl)-6-methyl-1H-indazol-5-yl)-3-azabicyclo[3.1.0]hexan-6-yl)methanol (1.33 g, 2.8 mmol, 50%) (Intermediate N) as an off-white solid. Rt 1.3 min (Method 7); m/z 428.3 (M+H)⁺ (ES⁺), δ$_H$ (400 MHz, DMSO-d₆) δ 8.24-8.19 (m, 1H), 7.80 7.74 (m, 2H), 7.70 (s, 1H), 7.61-7.54 (m, 1H), 7.41 (t, J=8.8 Hz, 2H), 7.34-7.19 (m, 5H), 4.32 (t, J=5.1 Hz, 1H), 3.68-3.52 (m, 2H), 3.37 (d, J=8.7 Hz, 1H), 3.19-3.08 (m, 1H), 3.03 (d, J=8.6 Hz, 1H), 2.96-2.78 (m, 1H), 2.70-2.56 (m, 1H), 2.45 (s, 1H), 2.23 (d, J=8.5 Hz, 1H), 1.95-1.85 (m, 1H), 1.78-1.71 (m, 1H)—one CH obscured by DMSO, and OH not observed.

Intermediate O: (1-(1-(4-fluorophenyl)-6-methyl-1H-indazol-5-yl)-3-azabicyclo[3.1.0]hexan-6-yl)methanol

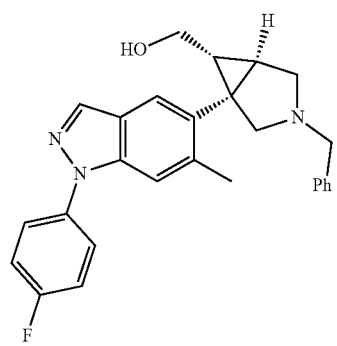

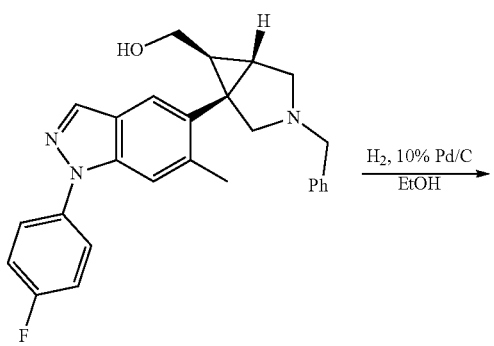

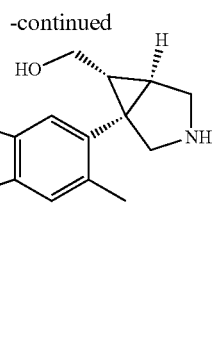

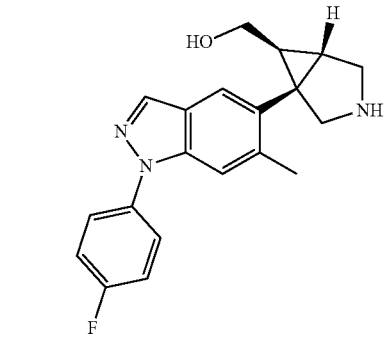

(3-Benzyl-1-(1-(4-fluorophenyl)-6-methyl-1H-indazol-5-yl)-3-azabicyclo[3.1.0]hexan-6-yl)methanol (535 mg, 1.25 mmol) (Intermediate N) was dissolved in EtOH (20 mL) and treated with 10% palladium on carbon (133 mg, 1.25 mmol). The mixture was purged with nitrogen (×3) then hydrogen (×3) before being hydrogenated at 5 atmospheres for 4 hrs. The reaction was heated to 60° C. and stirred overnight. The sample was cooled and stirring under hydrogen continued for a further 48 hrs. The catalyst was removed by filtration, washing with EtOH (20 mL). The solvent was removed in vacuo to give (1-(1-(4-fluorophenyl)-6-methyl-1H-indazol-5-yl)-3-azabicyclo[3.1.0]hexan-6-yl)methanol (428 mg, 1.27 mmol, 101%) as a cloudy glass; Rt 1.07 (90%) and 1.12 (10%) min (Method 7); m/z 428.3 (M+H)⁺ (ES⁺).

Example 47: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol Intermediate P: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl 2-methyl-2H-1,2,3-triazole-4-sulfonate

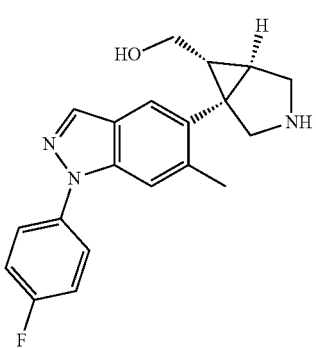 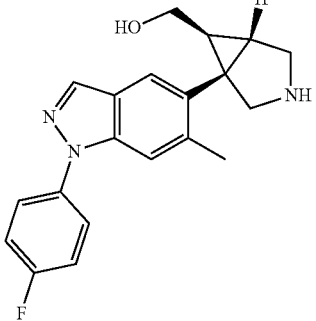 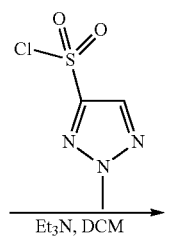

-continued

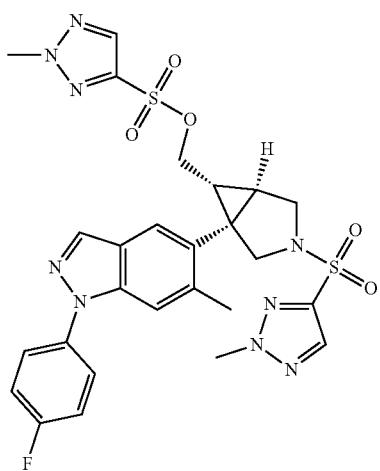

And

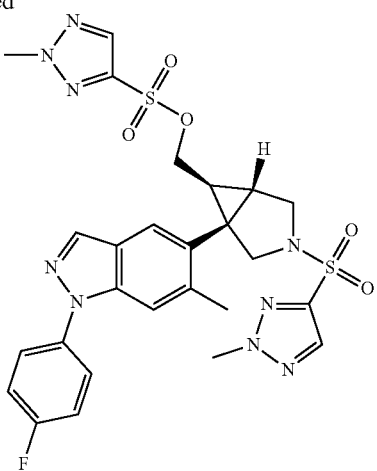

+

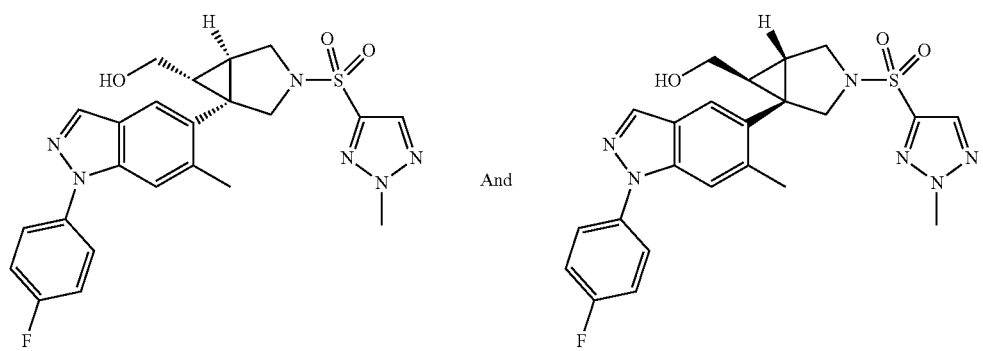

And (1-(1-(4-Fluorophenyl)-6-methyl-1H-indazol-5-yl)-3-azabicyclo[3.1.0]hexan-6-yl)methanol (425 mg, 1.26 mmol) in DCM (10 mL) was treated with triethylamine (191 mg, 263 µL, 1.89 mmol) and 2-methyl-2H-1,2,3-triazole-4-sulfonyl chloride (274 mg, 1.51 mmol). The reaction was stirred for 60 mins. The reaction was diluted with DCM (10 mL) and water (2 mL) and the phases separated. The aqueous layer was washed with DCM (10 mL) and the combined organic layers concentrated in vacuo to give a colourless glass. The crude product was purified by chromatography on silica gel (4 g cartridge, 0-100% EtOAc/isohexane) to afford (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol (350 mg, 700 µmol, 55.6%, 96.5% Purity) (Example 47) as colourless gum; Rt 1.79 min (Method 7); m/z 483.3 (M+H)+ (ES+). δH (400 MHz, DMSO-d6, VT90) δ 8.20 (m, 2H), 7.80-7.62 (m, 3H), 7.62-7.55 (m, 1H), 7.45-7.33 (m, 2H), 4.35-4.13 (m, 3H), 3.96 (m, 1H), 3.65 (m, 2H), 3.17 (m, 2H), 2.93 (m, 1H), 2.52 (m, 3H), 2.26 (m, 1H), 2.05 (m, 1H), 1.38 (m, 1H), and (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl 2-methyl-2H-1,2,3-triazole-4-sulfonate (75 mg, 96 µmol, 7.6%) (Intermediate P) as colourless gum; Rt 2.04 min (Method 7); m/z 627.2 (M+H)+ (ES+).

Example 48: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-el)methanol

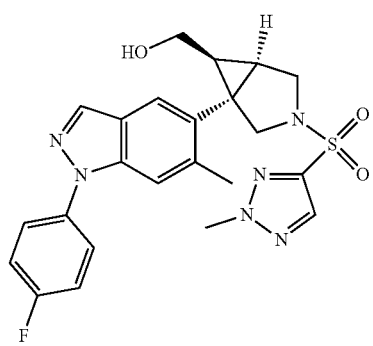

251
-continued

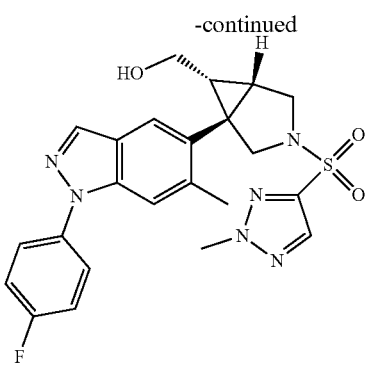

The compound was prepared by similar methods to those described for Example 47 using Intermediate M to afford (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol (4.3 mg, 8.5 μmol, 14%) (Example 48); Rt 1.81 min (Method 7); m/z 483.6 (M+H)$^+$ (ES$^+$). δH (DMSO-d6, 400 MHz) δ 8.22-8.20 (m, 2H), 7.79-7.70 (m, 3H), 7.54 (s, 1H), 7.38 (t, J=8.8 Hz, 2H), 4.51 (t, J=5.3 Hz, 1H), 4.28 (s, 3H), 3.88-3.73 (m, 4H), 3.62 (m, 1H), 3.37 (m, 1H), 2.30 (s, 3H), 2.08 (dd, J=8.7, 5.1 Hz, 1H), 1.55-1.45 (m, 1H).

Example 49: 1-(4-fluorophenyl)-6-methyl-5-(3-((2-methyl-2H-1,2,3-triazol-4-yl)sulfonyl)-6-(phenoxymethyl)-3-azabicyclo[3.1.0]hexan-1-yl)-1H-indazole

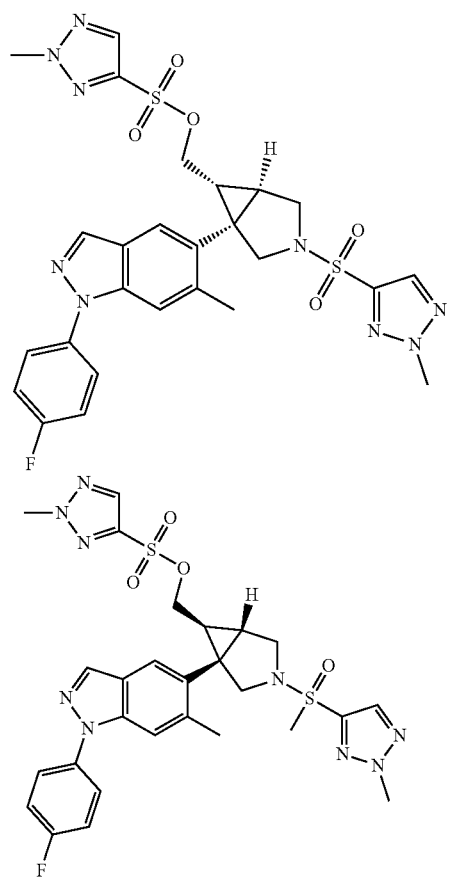

252
-continued

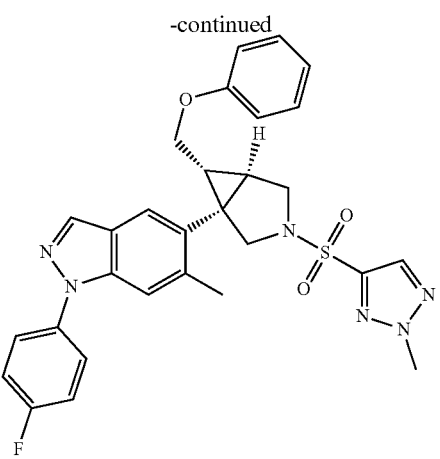

(1-(1-(4-Fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl 2-methyl-2H-1,2,3-triazole-4-sulfonate (80 mg, 0.13 mmol) (Intermediate P) in THF (3 mL) was treated with sodium phenolate (30 mg, 0.25 mmol) and stirred at RT for 24 hrs. The reaction was heated to 60° C. for 18 hrs. The reaction was diluted with DCM (15 mL) and water (5 mL). The phases were separated and the organic phase concentrated to dryness. The crude product was purified by chromatography on silica gel (4 g cartridge, 0-100% EtOAc/isohexane) to afford 1-(4-fluorophenyl)-6-methyl-5-(3-((2-methyl-2H-1,2,3-triazol-4-yl)sulfonyl)-6-(phenoxymethyl)-3-azabicyclo[3.1.0]hexan-1-yl)-1H-indazole (16 mg, 29 μmol, 22%) as a white solid; Rt 2.30 min (Method 7); m/z 559.3 (M+H)$^+$ (ES$^+$). δ$_H$ (400 MHz, DMSO-d$_6$, VT90) 8.20 (m, 2H), 8.01-7.65 (m, 3H), 7.57 (s, 1H), 7.46-7.31 (m, 2H), 7.18 (m, 2H), 6.79 (m, 3H), 4.26 (s, 3H), 4.05 (m, 1H), 3.88 (m, 1H), 3.70 (s, 3H), 3.54 (m, 1H), 3.24 (m, 1H), 3.04 (m, 1H), 2.59 (m, 1H), 2.28 (m, 1H), 1.66 (s, 1H).

Example 50: 1-(4-fluorophenyl)-6-methyl-5-(3-((2-methyl-2H-1,2,3-triazol-4-yl)sulfonyl)-6-((pyridin-2-yloxy)methyl)-3-azabicyclo[3.1.0]hexan-1-yl)-1H-indazole Intermediate Q: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl methanesulfonate A solution of (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol (150 mg, 311 μmol) (Intermediate N) was dissolved in DCM (8 mL) and cooled to 0° C. before the addition of triethylamine (94.4 mg, 130 μL, 933 μmol) and methanesulfonyl chloride (107 mg, 72.7 μL, 933 μmol). The reaction was allowed to warm to room temperature overnight. The reaction was diluted with DCM (10 mL) and washed with water before being passed through a phase separator cartridge. The organic phase was concentrated to dryness to give (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl methanesulfonate (160 mg, 285 μmol, 91.8%) (Intermediate Q) as a colourless gum; Rt 1.92 min (Method 7); m/z 561.3 (M+H)$^+$ (ES$^+$).

Example 50: 1-(4-fluorophenyl)-6-methyl-5-(3-((2-methyl-2H-1,2,3-triazol-4-yl)sulfonyl)-6-((pyridin-2-yloxy)methyl)-3-azabicyclo[3.1.0]hexan-1-yl)-1H-indazole

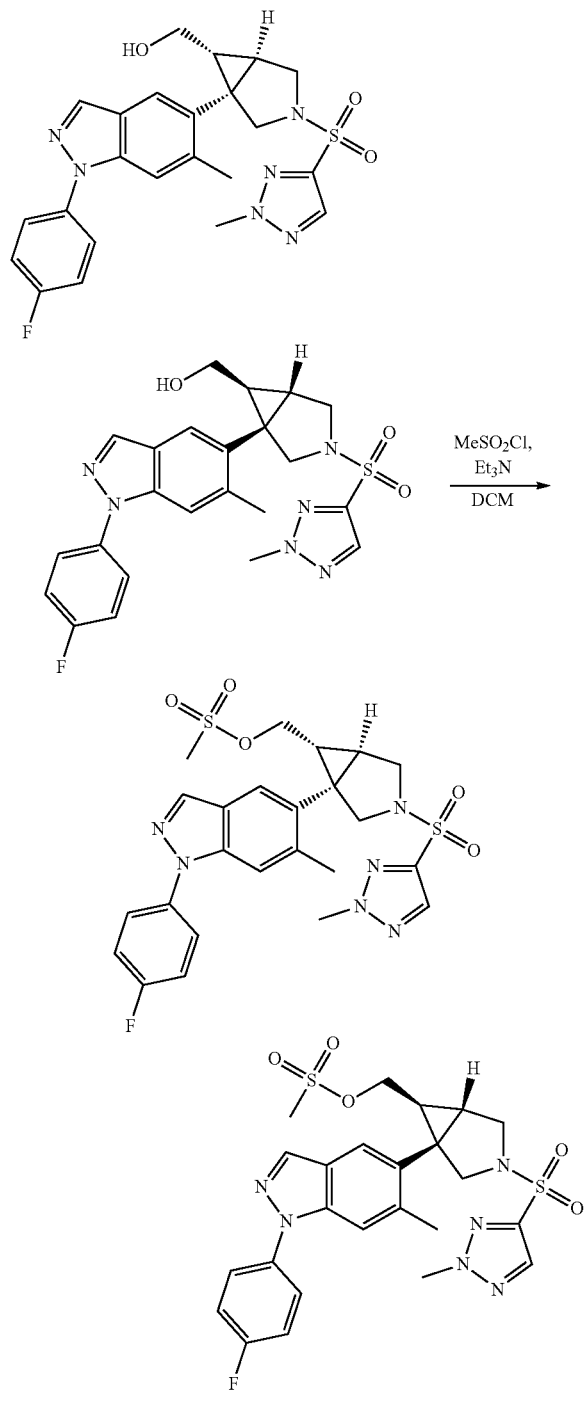

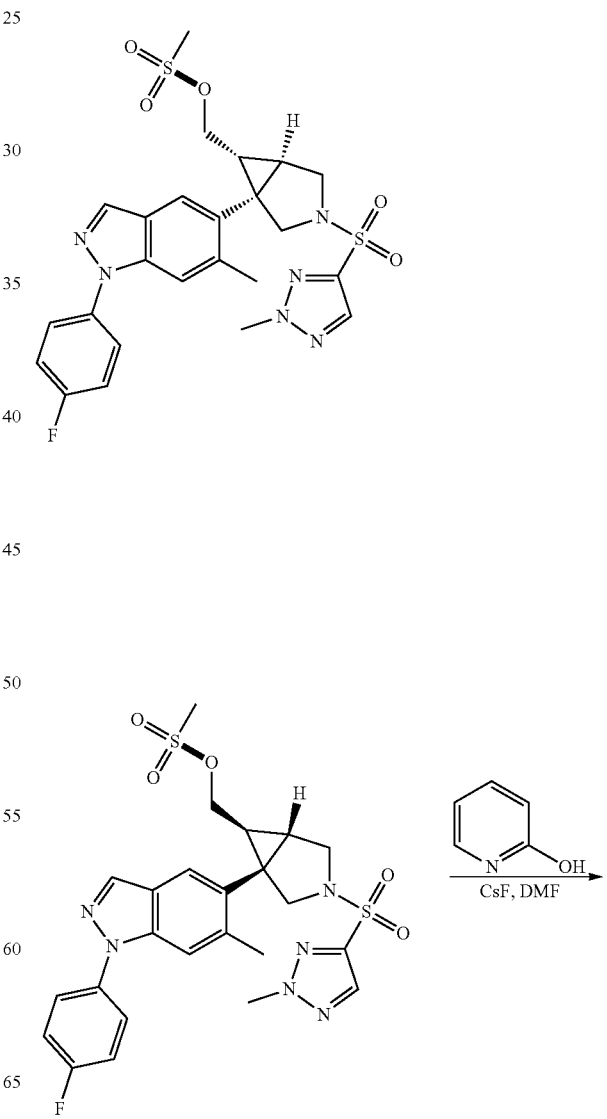

-continued

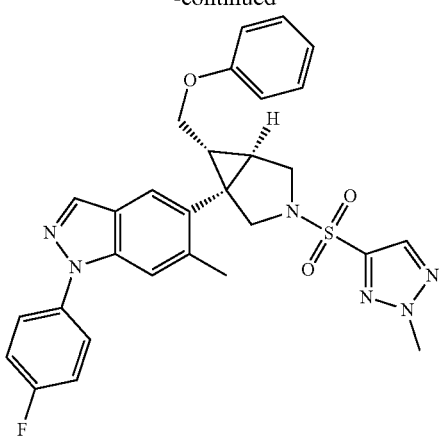

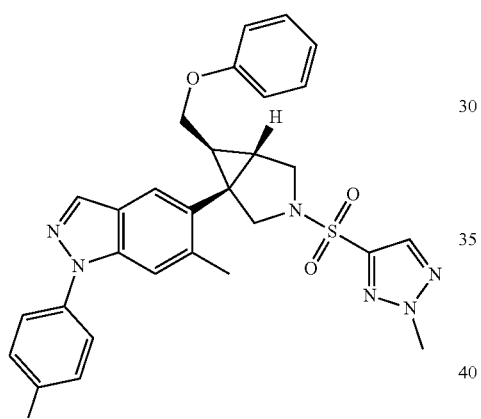

(1-(1-(4-Fluorophenyl)-6-methyl-1H-indazol-5-yl)-3-((2-methyl-2H-1,2,3-triazol-4-yl)sulfonyl)-3-azabicyclo[3.1.0] hexan-6-yl)methyl methanesulfonate (90 mg, 0.16 mmol) (Intermediate Q) in DMF (3 mL) was treated with cesium fluoride (80 mg, 0.53 mmol) and pyridin-2-ol (31 mg, 0.32 mmol) stirred at RT for 24 hrs. The reaction was heated to 50° C. for 16 hrs. The reaction was treated with pyridin-2-ol (31 mg, 0.32 mmol) and cesium fluoride (80 mg, 0.53 mmol) and stirring continued at 80° C. for 4 hrs. The reaction was cooled, diluted with water (10 mL) and the solid was collected by filtration to give a cream solid. The crude product was purified by chromatography on silica gel (4 g cartridge, 0-100% EtOAc/isohexane) to afford 1-(4-fluorophenyl)-6-methyl-5-(3-((2-methyl-2H-1,2,3-triazol-4-yl) sulfonyl)-6-((pyridin-2-yloxy)methyl)-3-azabicyclo[3.1.0] hexan-1-yl)-1H-indazole (6 mg, 0.01 mmol, 7%) as a white solid; Rt 1.84 min (Method 7); m/z 560.1 (M+H)$^+$ (ES$^+$). δH (400 MHz, DMSO-d$_6$, VT90) 8.25 (d, J=0.9 Hz, 1H), 8.18 (s, 1H), 7.83-7.71 (m, 3H), 7.62 (s, 1H), 7.46-7.31 (m, 3H), 7.26 (m, 1H), 6.34 (m, 1H), 6.13 (m, 1H), 4.26 (s, 3H), 4.00 (m, 1H), 3.76 (m, 1H), 3.64 (m, 1H), 3.56 (m, 1H), 3.20 (m, 2H), 2.50 (s, 3H), 2.35 (m, 1H), 1.66 (m, 1H).

Example 51: 1-(4-fluorophenyl)-5-(6-(isopropoxymethyl)-3-((2-methyl-2H-1,2,3-triazol-4-yl)sulfonyl)-3-azabicyclo[3.1.0]hexan-1-yl)-6-methyl-1H-indazole

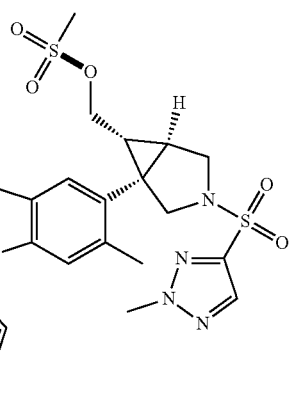

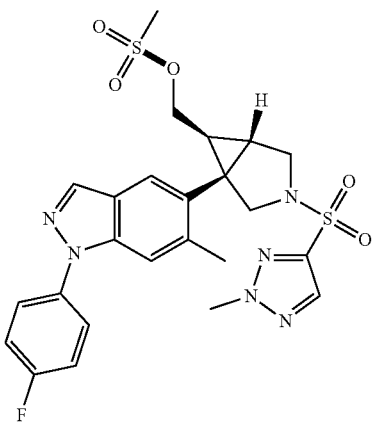

iPrONa, THF

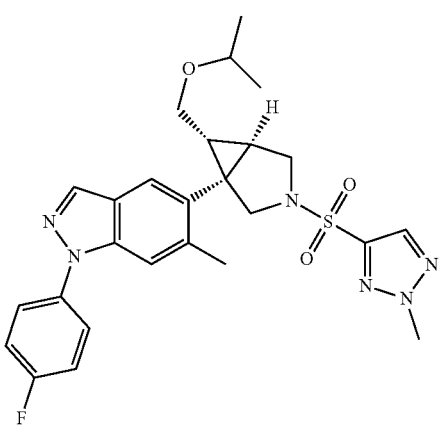

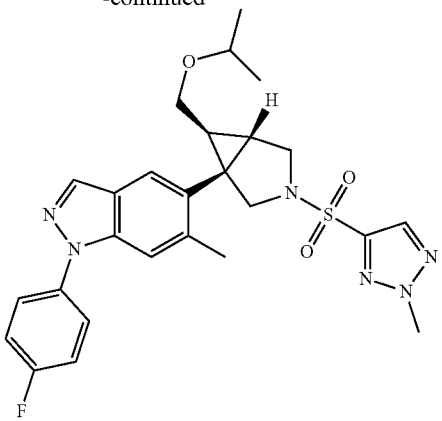

(1-(1-(4-Fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl methanesulfonate (85 mg, 0.15 mmol) (Intermediate Q) in THF (3 mL) was treated with sodium propan-2-olate (0.12 g, 1.5 mmol) and stirred at RT for 24 hrs. The reaction was heated to 60° C. for 4 hrs. DMF (2 mL) was added, and the reaction heated to 70° C. overnight. The temperature was increased to 100° C. and stirring continued overnight. The reaction was cooled, diluted with water (10 mL) and the solid was collected by filtration to give a cream solid. The crude product was purified by chromatography on silica gel (4 g cartridge, 0-100% EtOAc/isohexane) to afford 1-(4-fluorophenyl)-5-(6-(isopropoxymethyl)-3-((2-methyl-2H-1,2,3-triazol-4-yl)sulfonyl)-3-azabicyclo[3.1.0]hexan-1-yl)-6-methyl-1H-indazole (10 mg, 19 μmol, 13%) as a white solid; Rt 2.04 min (Method 7); m/z 525.1 (M+H)⁺ (ES⁺).

Example 52: 5-(6-((4-chlorophenoxy)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole Example 53: 5-(6-((4-chlorophenoxy)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole

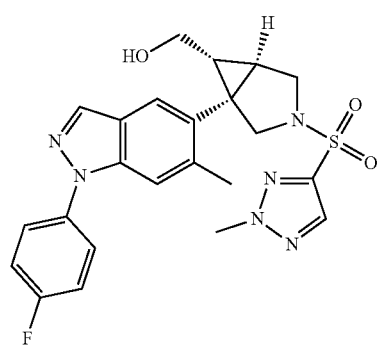

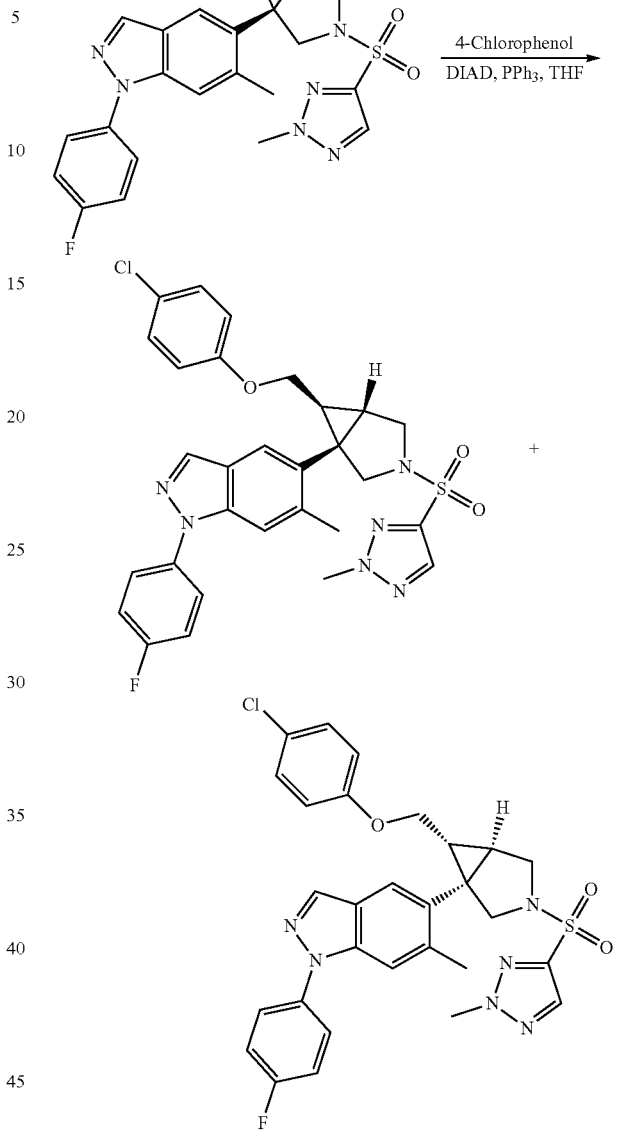

A solution of (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanol (90 mg, 0.19 mmol) (Intermediate N) in THF (4 mL) was treated with 4-chlorophenol (36 mg, 0.28 mmol), triphenylphosphine (73 mg, 0.28 mmol) and then DIAD (57 mg, 54 μL, 0.28 mmol) and the mixture was stirred for 16 hrs. The mixture was diluted with DCM (10 mL) and washed with water (5 mL). The organic phase was concentrated in vacuo to give a colorless gum. The crude product was purified by chromatography on silica gel (12 g cartridge, 0-20% EtOAc/isohexane) before being dissolved to 12 mg/mL in MeOH/THF, filtered and was then separated by chiral SFC on a Waters prep 15 with UV detection by DAD at 210-400 nm, 40° C., 120 bar. The column was A1 10×250 mm, 5um, flow rate 15 mL/min at 45% IPA (0.03% Ammonia), 55% CO₂. The clean fractions were pooled, rinsed with MeOH/THF and concentrated to dryness using a rotary evaporator. The residues were re-dissolved in MeOH/THF transferred into final vials and evaporated on a Biotage V10. The samples were then further dried in a vacuum oven at 30° C./5 mbar over night to afford 5-(6-((4-chlorophenoxy)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole (11 mg, 18 µmol, 9.8%) (Example 52) as a colorless glass; Rt 2.42 min (Method 7); m/z 593.7 (M+H)+ (ES+); 5-(6-((4-chlorophenoxy)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole (12 mg, 20 µmol, 11%) (Example 53) as a colorless glass; Rt 2.42 min (Method 7); m/z 593.7 (M+H)+ (ES+).

Example 54: 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide Intermediate R: 3-benzyl-1-(1-(4-fluorophenyl)-6-methyl-1H-indazol-5-yl)-3-azabicyclo[3.1.0]hexane-6-carboxylic acid

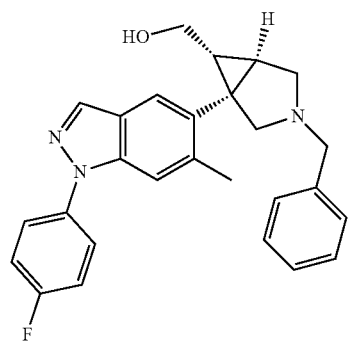

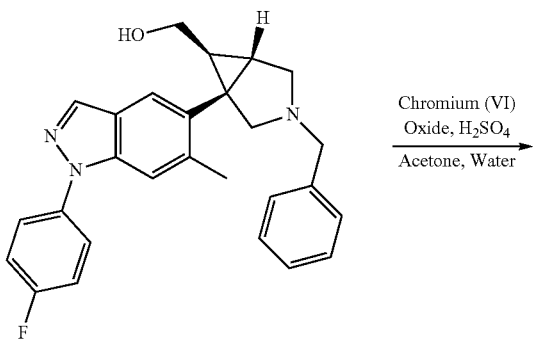

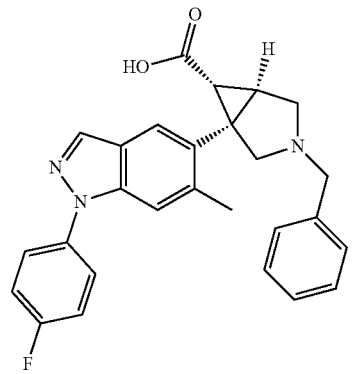

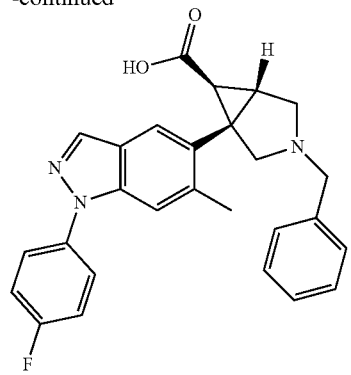

To a solution of (3-benzyl-1-(1-(4-fluorophenyl)-6-methyl-1H-indazol-5-yl)-3-azabicyclo[3.1.0]hexan-6-yl)methanol (1.25 g, 59%, 1.73 mmol) (Intermediate N) in acetone (10.5 mL) at 0° C. was added a solution of chromium (VI) oxide (690 mg 6.90 mmol) and sulfuric acid (1.18 g, 644 µL, 12.1 mmol) in water (6.5 mL). The reaction mixture was stirred with warming to room temperature overnight. The reaction mixture was quenched with saturated aqueous NaHCO₃ solution, and the excess chromium was removed by filtration, washing with EtOAc (50 mL) and water (50 mL). The filtrate was transferred to a separating funnel, and the layers were separated. The aqueous layer was further extracted with EtOAc (2×50 mL). The combined organic layers were dried using MgSO₄, filtered, and concentrated under reduced pressure. The aqueous layer was reacidified with 1 M HCl solution and was further extracted with EtOAc (3×50 mL). The combined organic layers were dried using MgSO₄, filtered, and concentrated under reduced pressure. The crude product was combined and purified by chromatography on silica gel (24 g cartridge, 0-10% MeOH/DCM) to afford 3-benzyl-1-(1-(4-fluorophenyl)-6-methyl-1H-indazol-5-yl)-3-azabicyclo[3.1.0]hexane-6-carboxylic acid (349 mg, 0.71 mmol, 41%) as a yellow glass; Rt 1.33 min (Method 7); m/z 442.4 (M+H)+ (ES+).

Intermediate S: 3-benzyl-1-(1-(4-fluorophenyl)-6-methyl-1H-indazol-5-yl)-N-(5-fluoropyridin-2-yl)-3-azabicyclo[3.1.0]hexane-6-carboxamide

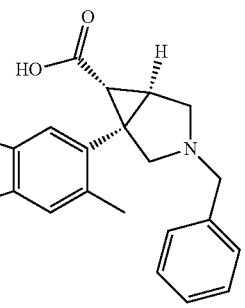

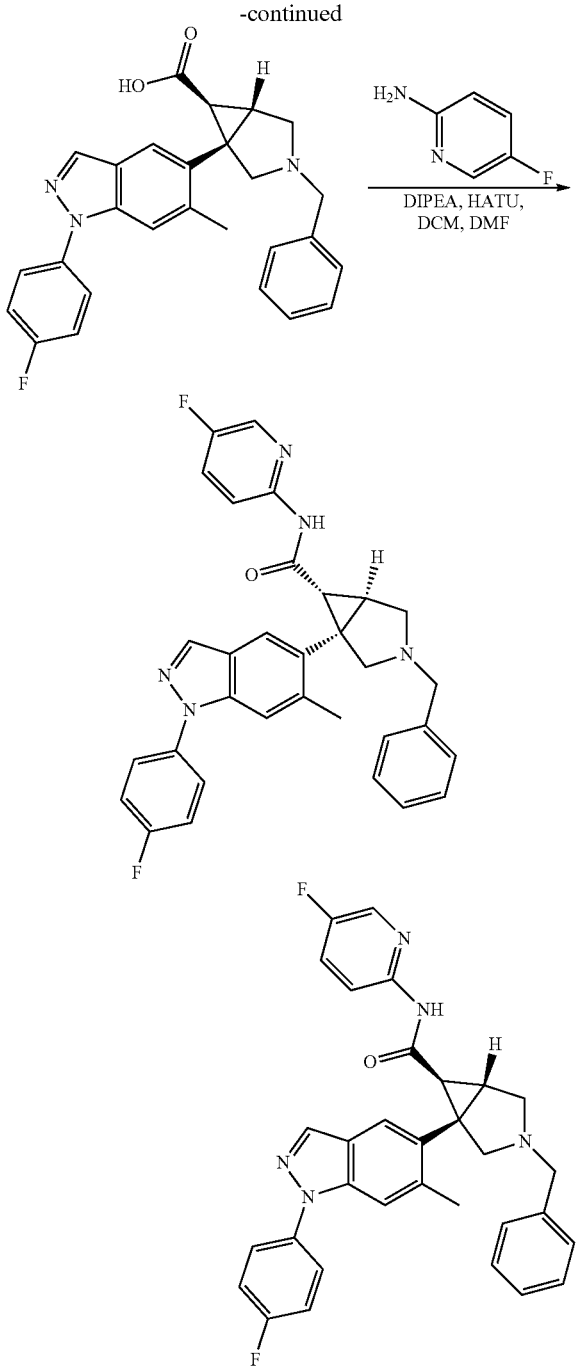
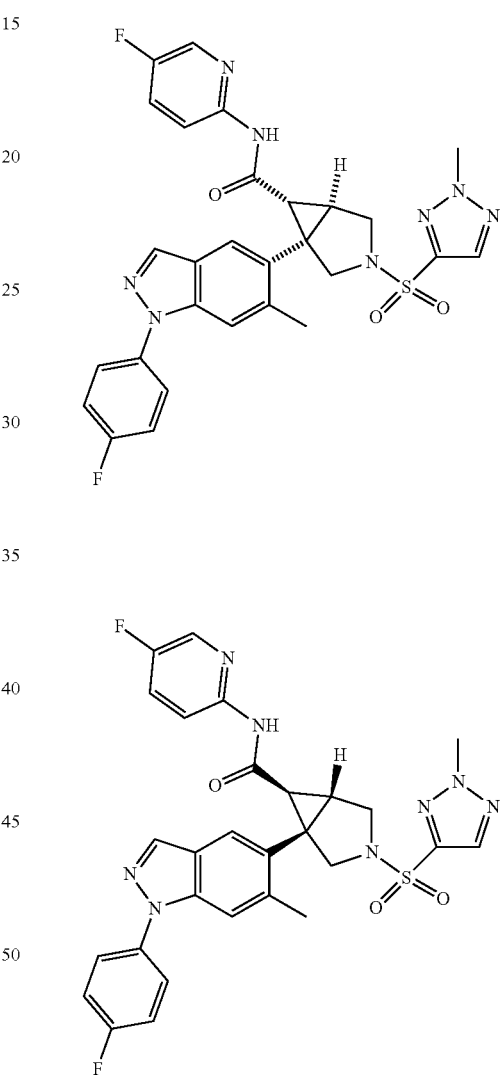

phy on silica gel (12 g cartridge, 0-100% EtOAc/isohexane) to afford 3-benzyl-1-(1-(4-fluorophenyl)-6-methyl-1H-indazol-5-yl)-N-(5-fluoropyridin-2-yl)-3-azabicyclo[3.1.0] hexane-6-carboxamide (117 mg, 0.19 mmol, 61%) as a yellow solid; Rt 1.48 min (Method 7); m/z 536.4 (M+H)$^+$ (ES$^+$).

Example 54: 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide To a solution of 3-benzyl-1-(1-(4-fluorophenyl)-6-methyl-1H-indazol-5-yl)-3-azabicyclo[3.1.0]hexane-6-carboxylic acid (157 mg, 320 μmol) in DCM (2 mL) was added HATU (134 mg, 352 μmol) and DIPEA (137 mg, 184 μL, 1.06 mmol), and the reaction mixture was stirred at room temperature for 5 min. 5-Fluoropyridin-2-amine (43 mg, 0.38 mmol) was then added, and stirring was continued for 2 h. The DCM was removed under reduced pressure, and the crude material was redissolved in DMF (2 mL). The reaction mixture was heated at 60° C. for 18 h. The reaction mixture was diluted with DCM (10 mL) and washed with water (3×10 mL) and brine (10 mL). The organic layer was dried using MgSO$_4$, filtered, and concentrated under reduced pressure. The crude product was purified by chromatogra- The compound was prepared by similar methods to those described for Example 47 using Intermediate S to afford 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide (28.03 mg, 45 μmol, 67%) (Example 54); Rt 2.03 min (Method 7); m/z 591.6 (M+H)$^+$ (ES$^+$). δH (DMSO-d6, 400 MHz) δ 11.14-10.79 (m, 1H), 8.46-8.05 (m, 3H), 7.86-7.65 (m, 4H), 7.63-7.31 (m, 4H), 4.39-4.20 (m, 3H), 4.12-3.95 (m, 1H), 3.87 3.47 (m, 2H), 3.18-3.04 (m, 1H), 2.92-2.61 (m, 2H), 2.48-2.45 (m, 2H), 2.18-2.07 (m, 1H).

Example 55: (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)(pyrrolidin-1-yl)methanone

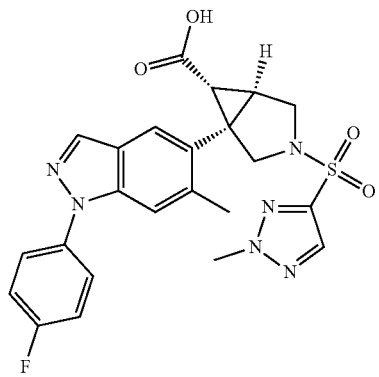

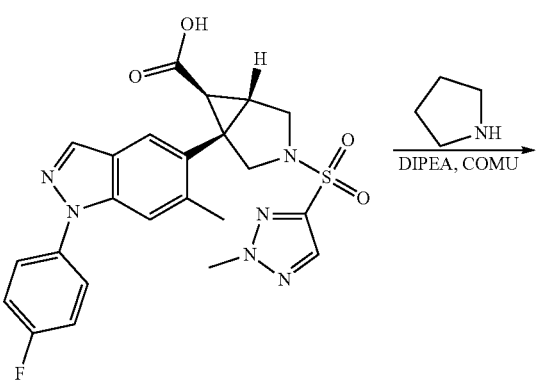

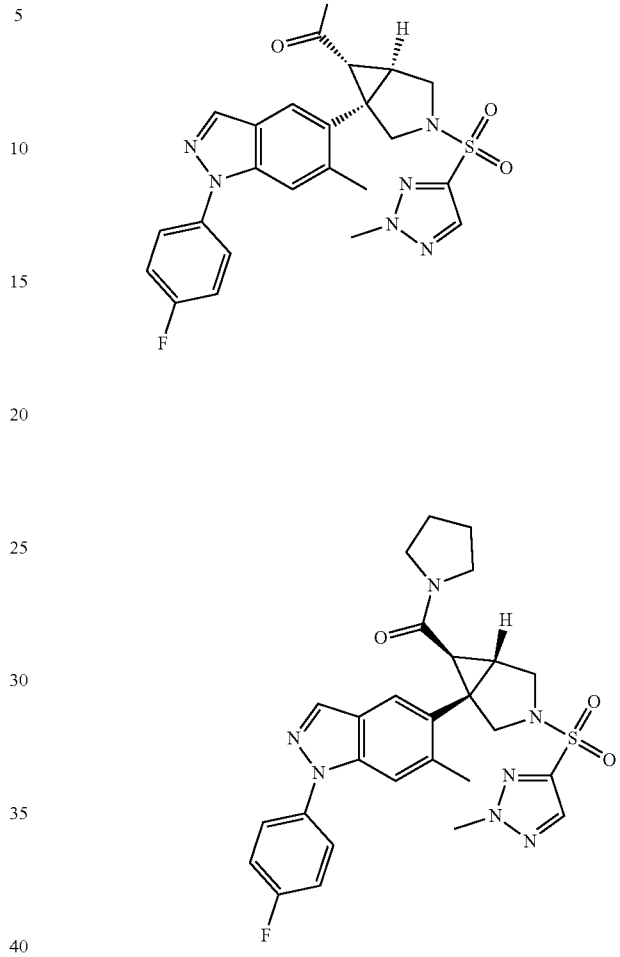

To a solution of 1-(1-(4-fluorophenyl)-6-methyl-1H-indazol-5-yl)-3-((2-methyl-2H-1,2,3-triazol-4-yl)sulfonyl)-3-azabicyclo[3.1.0]hexane-6-carboxylic acid (30 mg, 52 μmol) (prepared using a similar method to those described for Example 47 using Intermediate R) and DIPEA (13 mg, 18 μL, 0.10 mmol) in DCM (0.5 mL) was added COMU (27 mg, 62 μmol). The reaction mixture was stirred at room temperature for 5 min, then pyrrolidine (4.1 mg, 4.8 μL, 57 μmol) was added. The reaction mixture was stirred at room temperature for 2 h. The reaction mixture was concentrated onto silica gel and purified by chromatography on silica gel (4 g cartridge, 0-100% EtOAc/isohexane) to afford (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)(pyrrolidin-1-yl)methanone (6.65 mg, 11 μmol, 22%) as a white solid; Rt 1.98 min (Method 7); m/z 550.2 (M+H)$^+$ (ES$^+$). δH (DMSO-d6, 400 MHz) δ 8.24 (s, 1H), 8.18 (d, J=1.0 Hz, 1H), 7.78-7.70 (m, 2H), 7.55-7.48 (m, 2H), 7.38 (t, J=8.8 Hz, 2H), 4.28 (s, 3H), 3.97 (d, J=10.4 Hz, 1H), 3.81-3.71 (m, 3H), 3.63-3.49 (m, 1H), 3.32 (d, J=10.2 Hz, 1H), 3.24-3.13 (m, 1H), 2.62-2.57 (m, 1H), 2.35-2.29 (m, 4H), 2.10 (d, J=4.0 Hz, 1H), 2.04-1.94 (m, 2H), 1.86-1.73 (m, 2H).

Example 56: 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide

Example 57: 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide

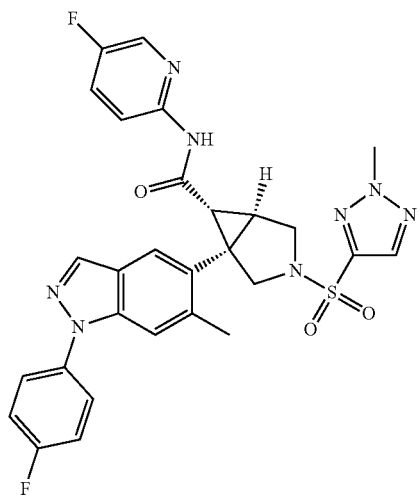 [SMILES: Cc1cc2c(cnn2-c2ccc(F)cc2)cc1[C@]12CN(S(=O)(=O)c3cnn(C)n3)C[C@H]1[C@@H]2C(=O)Nc1ccc(F)cn1]

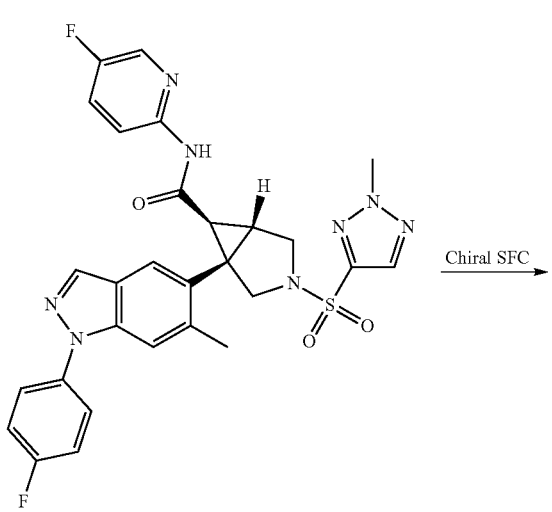

Chiral SFC →

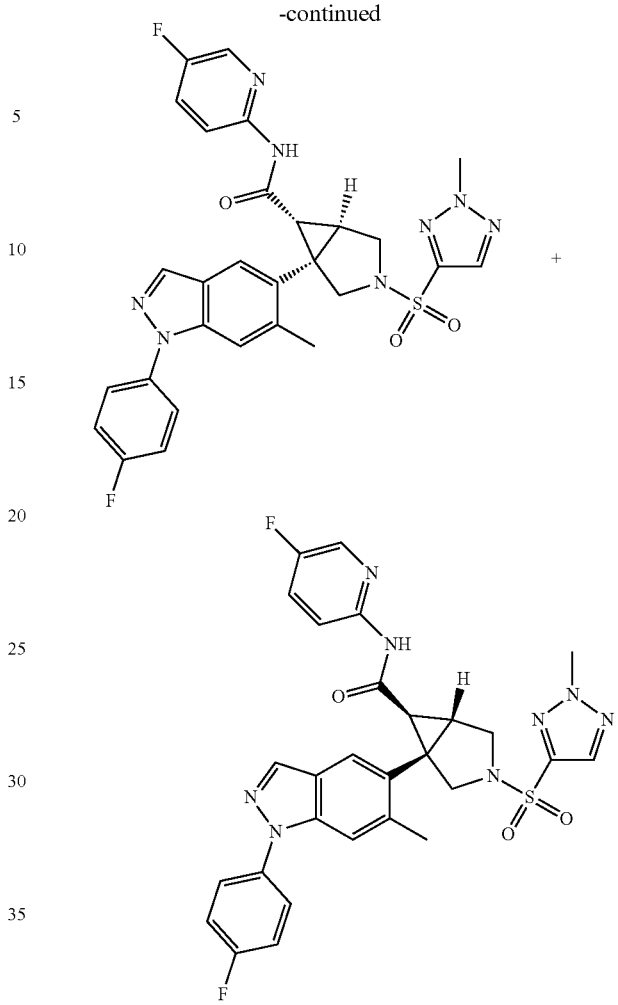

1-(1-(4-Fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide (75 mg, 42 µmol) (Example 54) was dissolved to 11 mg/mL in DCM/MeOH/DMSO with sonication, filtered and was then separated by chiral SFC on a Sepiatec with UV detection by DAD at 220 nm, 40° C., 120 bar. The column was Chiralpak IC 10×250 mm, 5 um, flow rate 20 mL/min at 55% MeOH/(0.1% Ammonia), 45% $CO_2$. The clean fractions were pooled, rinsed with methanol/DCM and concentrated to dryness using a rocket evaporator at 40° C. The residues were re-dissolved in methanol/DCM transferred into final vials and evaporated on a Biotage V10. The samples were then further dried in a vacuum oven at 30° C./5 mbar over night to afford 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide (0.99 mg, 1.6 µmol, 3.0%) Example 56 as a colorless gum; Rt 2.02 min (Method 7); m/z 591.5 (M+H)$^+$ (ES$^+$). δH (400 MHz, MeOD) δ 8.28-7.99 (m, 3H), 7.88-7.64 (m, 4H), 7.58-7.27 (m, 4H), 4.38-4.27 (m, 3H), 4.23 (d, J=9.7 Hz, 1H), 3.96-3.79 (m, 2H), 3.76-3.42 (m, 1H), 3.28 (d, J=9.8 Hz, 1H), 2.90-2.62 (m, 2H), 2.57 (s, 2H), 2.32 (s, 1H); and 1-(1-(4-fluorophenyl)-6-methyl-1H-indazol-5-yl)-N-(5-fluoropyridin-2-yl)-3-((2-methyl-2H-1,2,3-triazol-4-yl)sulfonyl)-3-azabicyclo[3.1.0]hexane-6-carboxamide (2.24 mg, 3.0 µmol, 5.7%) Example 57 as an off white solid; Rt 2.02 min (Method 7); m/z 591.6 (M+H)⁺ (ES⁺); 6H (400 MHz, MeOD) δ 8.28-7.99 (m, 3H), 7.88-7.64 (m, 4H), 7.58-7.27 (m, 4H), 4.38-4.27 (m, 3H), 4.23 (d, J=9.7 Hz, 1H), 3.96-3.79 (m, 2H), 3.76-3.42 (m, 1H), 3.28 (d, J=9.8 Hz, 1H), 2.90-2.62 (m, 2H), 2.57 (s, 2H), 2.32 (s, 1H)

Examples 58-67

TABLE 5

The examples shown in the table below were prepared by similar methods to those described for Example 54 or Example 55.

| Example | Structure | LC-MS Analysis |
|---|---|---|
| 58 | 1-(1-(4-fluorophenyl)-6-methyl-1H-indazol-5-yl)-N-(5-fluoropyridin-2-yl)-3-((1-propyl-1H-pyrazol-4-yl)sulfonyl)-3-azabicyclo[3.1.0]hexane-6-carboxamide | R$^t$ 2.08 min (Method 7); m/z 618.6 (M + H)⁺ (ES⁺) |
| 59 | azetidin-1-yl(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanone | R$^t$ 1.88 min (Method 9); m/z 536.2 (M + H)⁺ (ES⁺) |

TABLE 5-continued

The examples shown in the table below were prepared by similar methods to those described for Example 54 or Example 55.

| Example | Structure | LC-MS Analysis |
|---|---|---|
| 60 | N-cyclobutyl-1-(1-(4-fluorophenyl)-6-methyl-1H-indazol-5-yl)-3-((2-methyl-2H-1,2,3-triazol-4-yl)sulfonyl)-3-azabicyclo[3.1.0]hexane-6-carboxamide | $R^t$ 2.02 min (Method 9); m/z 550.2 $(M + H)^+$ $(ES^+)$ |
| 61 | N-cyclopentyl-1-[1-(4-fluorophenyl)-6-methyl-indazol-5-yl]-3-(2-methyltriazol-4-yl)sulfonyl-3-azabicyclo[3.1.0]hexane-6-carboxamide | $R^t$ 2.00 min (Method 9); m/z 564.2 $(M + H)^+$ $(ES^+)$ |

TABLE 5-continued

The examples shown in the table below were prepared by similar methods to those described for Example 54 or Example 55.

| Example | Structure | LC-MS Analysis |
|---|---|---|
| 62 | 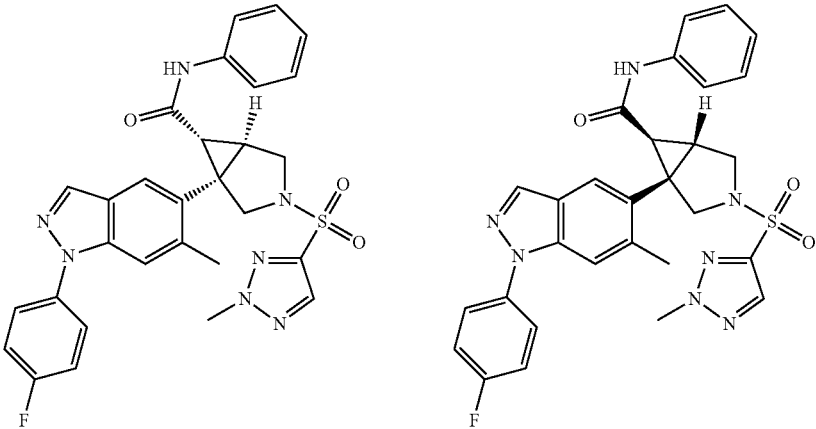<br>1-[1-(4-fluorophenyl)-6-methyl-indazol-5-yl]-3-(2-methyltriazol-4-yl)sulfonyl-N-phenyl-3-azabicyclo[3.1.0]hexane-6-carboxamide | $R^t$ 2.13 min (Method 9); m/z 572.2 (M + H)$^+$ (ES$^+$) |
| 63 | 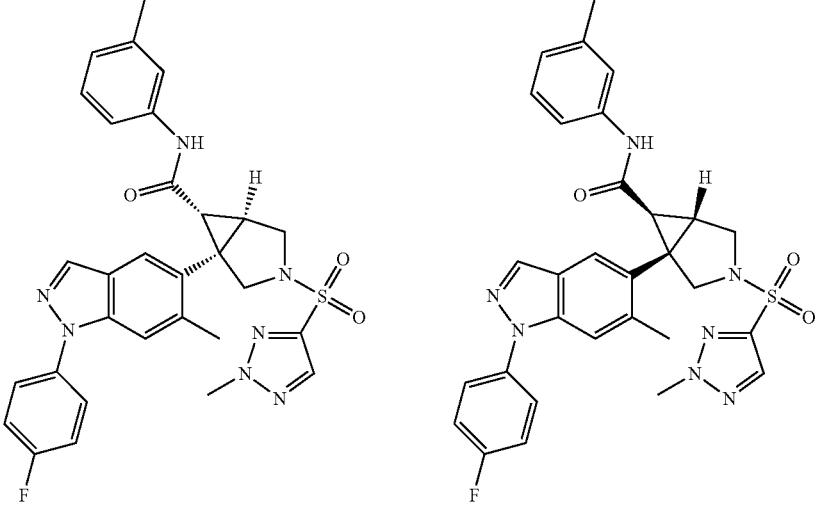<br>1-[1-(4-fluorophenyl)-6-methyl-indazol-5-yl]-3-(2-methyltriazol-4-yl)sulfonyl-N-(m-tolyl)-3-azabicyclo[3.1.0]hexane-6-carboxamide | $R^t$ 2.27 min (Method 9); m/z 586.2 (M + H)$^+$ (ES$^+$) |

TABLE 5-continued

The examples shown in the table below were prepared by similar methods to those described for Example 54 or Example 55.

| Example | Structure | LC-MS Analysis |
|---|---|---|
| 64 | 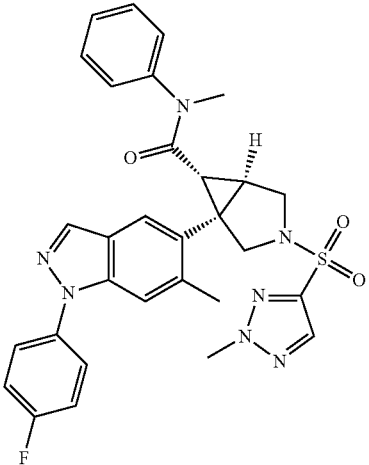  1-[1-(4-fluorophenyl)-6-methyl-indazol-5-yl]-N-methyl-3-(2-methyltriazol-4-yl)sulfonyl-N-phenyl-3-azabicyclo[3.1.0]hexane-6-carboxamide | R$^t$ 2.15 min (Method 9); m/z 586.1 (M + H)$^+$ (ES$^+$) |
| 65 | 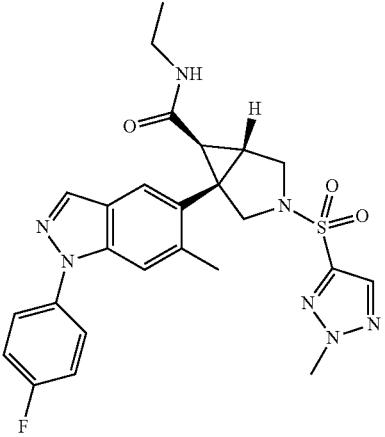  N-ethyl-1-[1-(4-fluorophenyl)-6-methyl-indazol-5-yl]-3-(2-methyltriazol-4-yl)sulfonyl-3-azabicyclo[3.1.0]hexane-6-carboxamide | R$^t$ 1.81 min (Method 7); m/z 524.5 (M + H)$^+$ (ES$^+$) |

TABLE 5-continued

The examples shown in the table below were prepared by similar methods to those described for Example 54 or Example 55.

| Example | Structure | LC-MS Analysis |
|---|---|---|
| 66 | 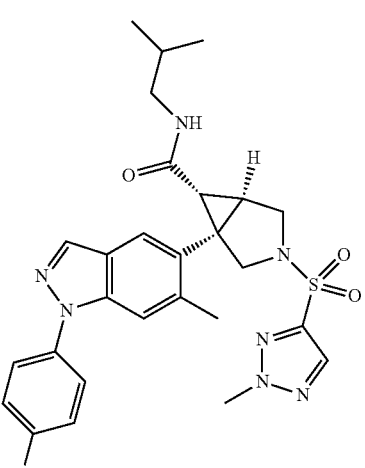<br>1-[1-(4-fluorophenyl)-6-methyl-indazol-5-yl]-N-isobutyl-3-(2-methyltriazol-4-yl)sulfonyl-3-azabicyclo[3.1.0]hexane-6-carboxamide | $R^t$ 1.98 min (Method 7); m/z 552.3 (M + H)$^+$ (ES$^+$) |
| 67 | 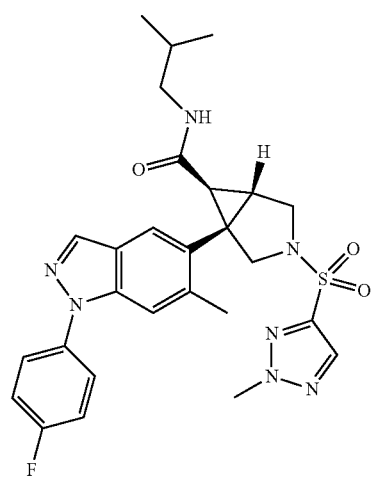<br>1-(1-(4-fluorophenyl)-6-methyl-1H-indazol-5-yl)-N-(5-fluoropyridin-2-yl)-3-(methylsulfonyl)-3-azabicyclo[3.1.0]hexane-6-carboxamide | $R^t$ 1.89 min (Method 7); m/z 524.3 (M + H)$^+$ (ES$^+$) |

Example 68: 3-acetyl-1-(1-(4-fluorophenyl)-6-methyl-1H-indazol-5-yl)-N-(5-fluoropyridin-2-yl)-3-azabicyclo[3.1.0]hexane-6-carboxamide

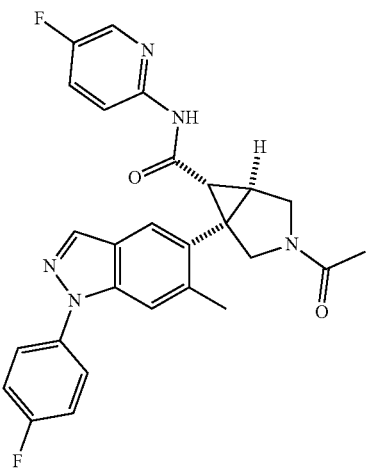

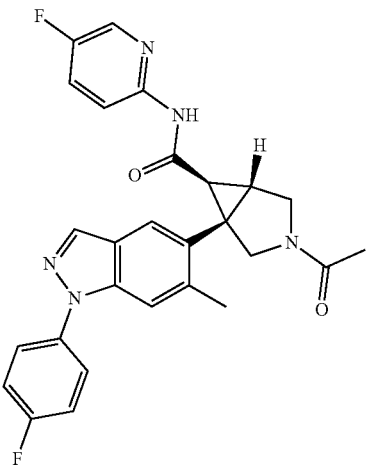

The compound was prepared by similar methods to those described for Example 20 using Intermediate S to afford 3-acetyl-1-(1-(4-fluorophenyl)-6-methyl-1H-indazol-5-yl)-N-(5-fluoropyridin-2-yl)-3-azabicyclo[3.1.0]hexane-6-carboxamide (11.59 mg, 23 μmol); R'1.74 min (Method 7); m/z 488.4 (M+H)$^+$ (ES$^+$).

Example 69: 1-(4-fluorophenyl)-6-methyl-5-(6-phenyl-3-((1-propyl-1H-pyrazol-4-yl)sulfonyl)-3-azabicyclo[3.1.0]hexan-1-yl)-1H-indazole Intermediate T: 3-benzyl-1-(1-(4-fluorophenyl)-6-methyl-1H-indazol-5-yl)-6-phenyl-3-azabicyclo[3.1.0]hexane-2,4-dione

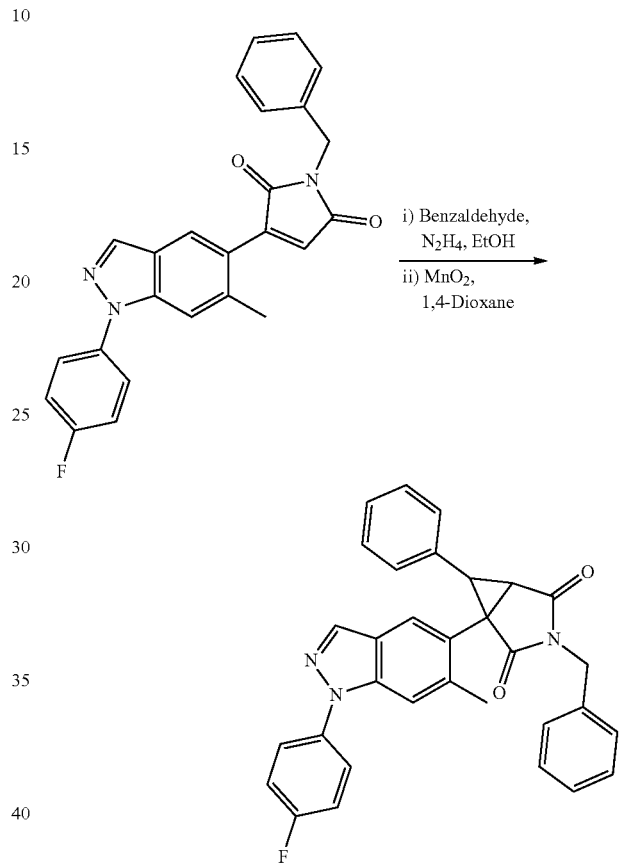

A solution of hydrazine, monohydrate (4.25 g, 4.16 mL, 84.8 mmol) in EtOH (30 mL) was treated with benzaldehyde (3.00 g, 2.87 mL, 28.3 mmol) dropwise over 10 minutes. The mixture was stirred for 60 mins and treated with water (20 mL). The ethanol was removed under reduced pressure. The aqueous phase was extracted with DCM (3×40 mL). Combined organics were dried using sodium sulfate and concentrated in vacuo to give (Z)-benzylidenehydrazine (3 g, 0.02 mol, 90%) as a pale yellow oil. A solution of benzylidenehydrazine (5.00 g, 41.6 mmol) in 1,4-dioxane (200 mL) was cooled to 15° C. and treated with manganese (IV) oxide (14.5 g, 166 mmol) portion wise over 10 mins. The cooling was removed, and the reaction warmed to 20° C. over approximately 30 mins and once warming to 20° C. was complete the reaction was filtered through a glass fibre filter pad into a cooled receiver flask (ice bath) to give a dark red/orange solution. 1-Benzyl-3-(1-(4-fluorophenyl)-6-methyl-1H-indazol-5-yl)-1H-pyrrole-2,5-dione (6.85 g, 16.6 mmol) (Intermediate T) was added and the reaction stirred overnight. The reaction was concentrated under vacuum and the crude product was purified by chromatography on silica gel (220 g cartridge, 0-40% EtOAc/isohexane) to afford 3-benzyl-1-(1-(4-fluorophenyl)-6-methyl-1H-indazol-5-yl)-6-phenyl-3-azabicyclo[3.1.0]hexane-2,4-dione (7.87 g, 15 mmol, 90%) as an off white solid; Rt 2.35 min (80%) 2.38 min (20%) (Method 7); m/z 502.5 (M+H)+ (ES+) as a mixture of major and minor enantiomeric pairs.

Intermediate U: 5-(3-benzyl-6-phenyl-3-azabicyclo[3.1.0]hexan-1-yl)-1-(4-fluorophenyl)-6-methyl-1H-indazole Intermediate V: 5-(3-benzyl-6-phenyl-3-azabicyclo[3.1.0]hexan-1-yl)-1-(4-fluorophenyl)-6-methyl-1H-indazole

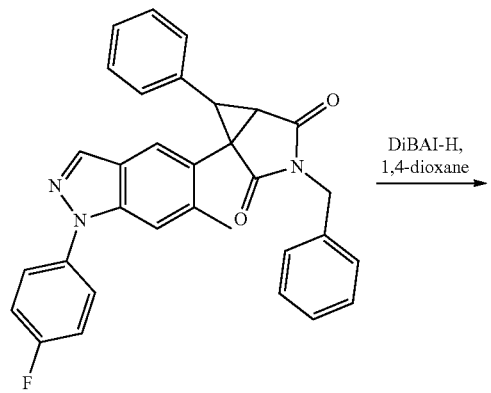

DiBAl-H, 1,4-dioxane

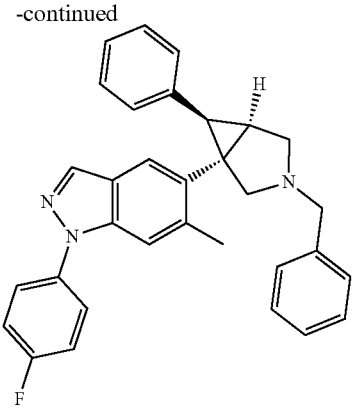

And

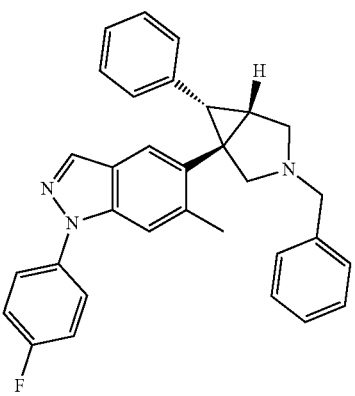

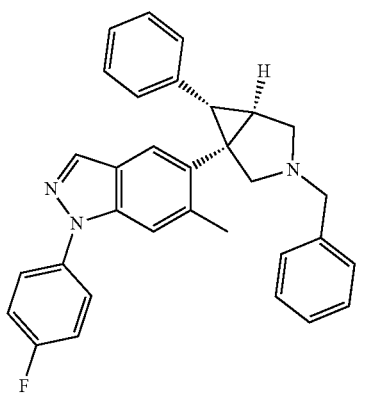

And +

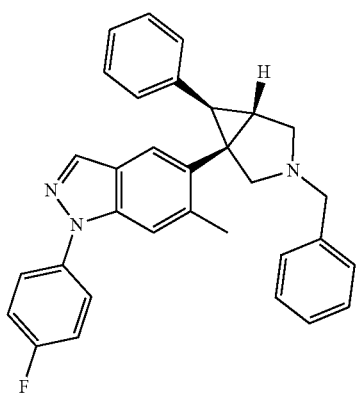

To a solution of 3-benzyl-1-(1-(4-fluorophenyl)-6-methyl-1H-indazol-5-yl)-6-phenyl-3-azabicyclo[3.1.0]hexane-2,4-dione (3.81 g, 7.60 mmol) and 3-benzyl-1-(1-(4-fluorophenyl)-6-methyl-1H-indazol-5-yl)-6-phenyl-3-azabicyclo[3.1.0]hexane-2,4-dione (4.07 g, 8.11 mmol) in 1,4-dioxane (100 mL) at 0° C. was added DIBAL-H (1 molar in heptane) (14.2 g, 100 mL, 100 mmol) slowly. The resulting mixture was stirred with warming to room temperature overnight. The reaction mixture was cooled to 0° C. and quenched with 2 M NaOH solution (8 mL) followed by water (10 mL). The reaction mixture was allowed to stir at room temperature for 15 min and was then dried with $Na_2SO_4$. After stirring at room temperature for 15 min, the mixture was filtered, and the filtrate was concentrated under reduced pressure. The crude product was purified by chromatography on silica gel (120 g gold cartridge, 0-50% EtOAc/isohexane) to afford 5-(3-benzyl-6-phenyl-3-azabicyclo[3.1.0]hexan-1-yl)-1-(4-fluorophenyl)-6-methyl-1H-indazole (1.61 g, 3.3 mmol, 21%) (Intermediate V) as a white solid; Rt 1.77 min (Method 7); m/z 474.5 (M+H)+ (ES+). 8.29 (s, 1H), 7.98 (s, 1H), 7.86-7.76 (m, 2H), 7.63 (s, 1H), 7.50-7.28 (m, 7H), 7.12-6.99 (m, 3H), 6.52-6.40 (m, 2H), 3.36 (d, J=3.3 Hz, 2H), 3.10 (d, J=9.3 Hz, 1H), 3.01 (d, J=9.2 Hz, 1H), 2.90 (dd, J=9.3, 3.7 Hz, 1H), 2.64 (s, 3H), 2.61 (d, J=9.2 Hz, 1H), 2.40 (d, J=8.4 Hz, 1H), 2.12 (dd, J=8.5, 3.5 Hz, 1H) and 5-(3-benzyl-6-phenyl-3-azabicyclo[3.1.0]hexan-1-yl)-1-(4-fluorophenyl)-6-methyl-1H-indazole (3.41 g, 6.8 mmol, 44%) (Intermediate U) as a white solid; Rt 1.63 min (Method 7); m/z 474.1 (M+H)+ (ES+). 6H (DMSO-d6, 400 MHz) δ 8.28 (s, 1H), 7.96 (s, 1H), 7.76-7.67 (m, 2H), 7.44-7.30 (m, 8H), 7.29-7.23 (m, 1H), 7.00-6.88 (m, 2H), 6.84-6.77 (m, 2H), 3.78-3.61 (m, 2H), 3.51 (d, J=8.9 Hz, 1H), 3.20 (d, J=8.8 Hz, 1H), 2.91 (d, J=3.9 Hz, 1H), 2.83-2.75 (m, 1H), 2.40 (d, J=8.4 Hz, 2H), 2.13 (s, 3H).

Intermediate W: 1-(4-fluorophenyl)-6-methyl-5-(6-phenyl-3-azabicyclo[3.1.0]hexan-1-yl)-1H-indazole

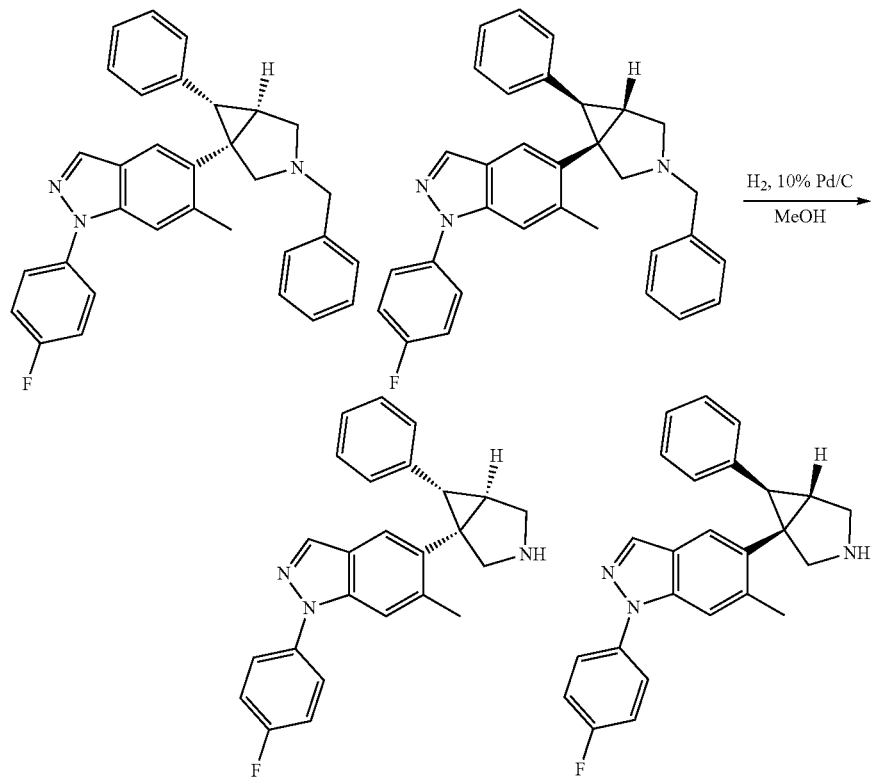

To a solution of 5-(3-benzyl-6-phenyl-3-azabicyclo[3.1.0]hexan-1-yl)-1-(4-fluorophenyl)-6-methyl-1H-indazole (3.41 g, 6.8 mmol) (Intermediate U) in methanol (50 mL) was added palladium on carbon (766 mg, 10% Wt, 720 μmol). The reaction mixture was heated at 50° C. under an atmosphere of hydrogen (5 bar) for 3 h. The catalyst was removed by filtration through a glass-fibre filter paper, and the filtrate was concentrated under reduced pressure to afford 1-(4-fluorophenyl)-6-methyl-5-(6-phenyl-3-azabicyclo[3.1.0]hexan-1-yl)-1H-indazole (2.66 g, 6.2 mmol, 87%) as a white solid; Rt 1.39 min (Method 7); m/z 384.5 (M+H)$^+$ (ES$^+$). δH (DMSO-d6, 400 MHz) δ 8.27 (s, 1H), 7.95 (s, 1H), 7.77-7.67 (m, 2H), 7.44-7.29 (m, 3H), 7.01-6.88 (m, 3H), 6.83-6.75 (m, 2H), 3.47 (d, J=11.2 Hz, 1H), 3.21 3.10 (m, 2H), 2.66 (d, J=11.1 Hz, 1H), 2.56-2.52 (m, 1H), 2.45 (d, J=4.2 Hz, 1H), 2.31 2.25 (m, 1H), 2.15 (s, 3H).

Intermediate X: 1-(4-fluorophenyl)-6-methyl-5-(6-phenyl-3-azabicyclo[3.1.0]hexan-1-yl)-1H-indazole Intermediate Y: 1-(4-fluorophenyl)-6-methyl-5-(6-phenyl-3-azabicyclo[3.1.0]hexan-1-yl)-1H-indazole

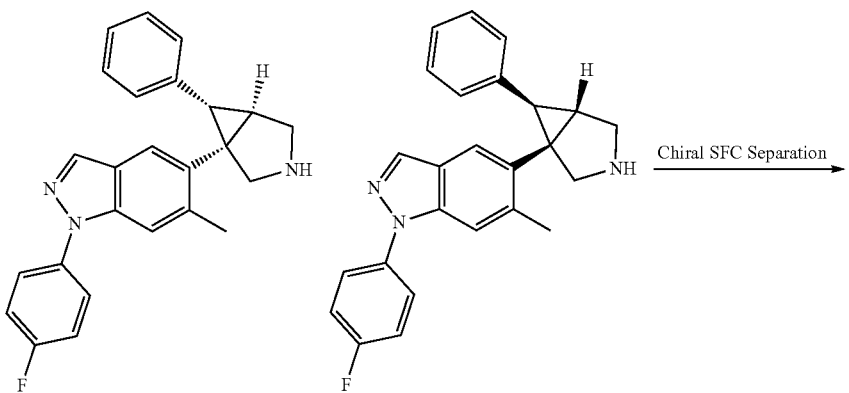

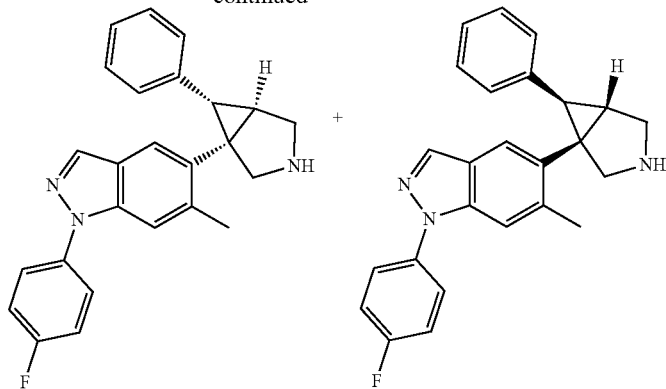

1-(4-Fluorophenyl)-6-methyl-5-(6-phenyl-3-azabicyclo[3.1.0]hexan-1-yl)-1H-indazole (2.66 g) was dissolved in MeOH (12 mL), filtered and was then separated by chiral SFC on a Waters prep 15 with UV detection by DAD at 210-400 nm, 40° C., 120 bar. The column was a C4 10×250 mm, 5 μM, flow rate 15 mL/min at 55% MeOH (0.03% ammonia), 45% $CO_2$. The clean fractions were pooled, rinsed with methanol and concentrated to dryness using a rotary evaporator. The residues were re-dissolved in methanol transferred into final vials and evaporated on a Biotage V10. The samples were then further dried in a vacuum oven at 30° C./5 mbar over night to afford 1-(4-fluorophenyl)-6-methyl-5-(6-phenyl-3-azabicyclo[3.1.0]hexan-1-yl)-1H-indazole (1.28 g, 3.34 mmol, 46.4%) Intermediate X; Rt 1.39 min (Method 7); m/z 384.5 (M+H)$^+$ (ES$^+$). δH (DMSO-d6, 400 MHz) δ 8.27 (s, 1H), 7.95 (s, 1H), 7.77-7.67 (m, 2H), 7.44-7.29 (m, 3H), 7.01-6.88 (m, 3H), 6.83-6.75 (m, 2H), 3.47 (d, J=11.2 Hz, 1H), 3.21-3.10 (m, 2H), 2.66 (d, J=11.1 Hz, 1H), 2.56-2.52 (m, 1H), 2.45 (d, J=4.2 Hz, 1H), 2.31-2.25 (m, 1H), 2.15 (s, 3H), and 1-(4-fluorophenyl)-6-methyl-5-(6-phenyl-3-azabicyclo[3.1.0]hexan-1-yl)-1H-indazole (1.09 g, 2.84 mmol, 39.5%) Intermediate Y; Data consistent with those recorded above.

Example 69: 1-(4-fluorophenyl)-6-methyl-5-(6-phenyl-3-((1-propyl-1H-pyrazol-4-yl)sulfonyl)-3-azabicyclo[3.1.0]hexan-1-yl)-1H-indazole

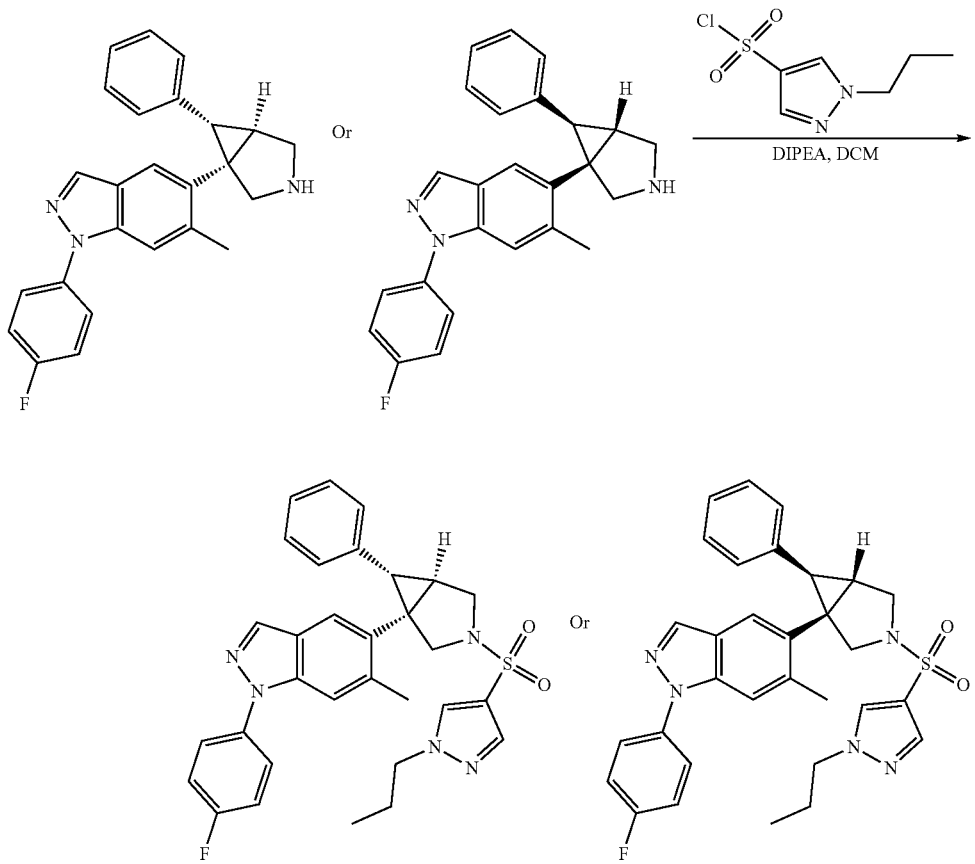

To a solution of 1-(4-fluorophenyl)-6-methyl-5-(6-phenyl-3-azabicyclo[3.1.0]hexan-1-yl)-1H-indazole (20 mg, 52 µmol) Intermediate X in DCM (0.5 mL) was added N-ethyl-N-isopropylpropan-2-amine (20 mg, 27 µL, 0.16 mmol) followed by 1-propyl-1H-pyrazole-4-sulfonyl chloride (13 mg, 63 µmol). The reaction mixture was stirred at room temperature for 45 min. The reaction mixture was concentrated onto silica gel and purified by chromatography on silica gel (4 g cartridge, 0-100% EtOAc/isohexane) to afford 1-(4-fluorophenyl)-6-methyl-5-(6-phenyl-3-((1-propyl-1H-pyrazol-4-yl)sulfonyl)-3-azabicyclo[3.1.0]hexan-1-yl)-1H-indazole (27.37 mg, 47 µmol, 90%) as a white solid; Rt 2.30 min (Method 7); m/z 556.2 (M+H)$^+$ (ES$^+$). δH (DMSO-d6, 400 MHz) δ 8.57-8.46 (m, 1H), 8.24 (s, 1H), 7.98-7.92 (m, 1H), 7.86 (s, 1H), 7.70 (dd, J=8.9, 4.9 Hz, 2H), 7.41-7.31 (m, 3H), 7.11-6.89 (m, 3H), 6.76 (d, J=6.8 Hz, 2H), 4.14 (t, J=6.9 Hz, 2H), 4.03 (d, J=9.7 Hz, 1H), 3.71 (d, J=9.7 Hz, 1H), 3.54-3.41 (m, 1H), 3.12-2.92 (m, 1H), 2.69-2.60 (m, 1H), 2.39 (d, J=4.4 Hz, 1H), 2.15 (s, 3H), 1.88-1.69 (m, 2H), 0.90-0.70 (m, 3H).

Examples 70-109

TABLE 6

The examples shown in the table below were prepared by similar methods to those described for Example 69

| Example | Structure | LC-MS analysis |
|---|---|---|
| 70 | 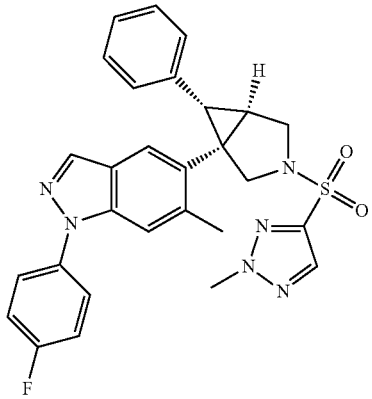 1-(4-fluorophenyl)-6-methyl-5-(3-((2-methyl-2H-1,2,3-triazol-4-yl)sulfonyl)-6-phenyl-3-azabicyclo[3.1.0]hexan-1-yl)-1H-indazole | R$^t$ 2.38 min (Method 7); m/z 529.2 (M + H)$^+$ (ES$^+$) |
| 71 | 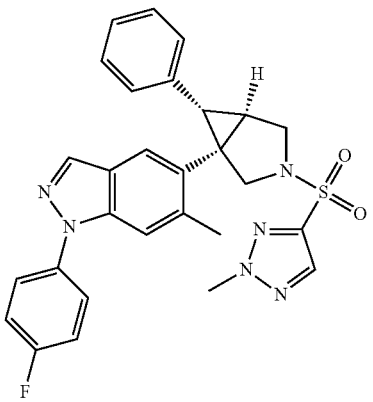 Or 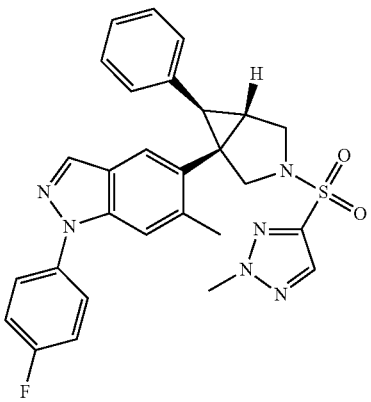 1-(4-fluorophenyl)-6-methyl-5-(3-((2-methyl-2H-1,2,3-triazol-4-yl)sulfonyl)-6-phenyl-3-azabicyclo[3.1.0]hexan-1-yl)-1H-indazole | R$^t$ 2.32 min (Method 9); m/z 529.2 (M + H)$^+$ (ES$^+$) |

TABLE 6-continued

The examples shown in the table below were prepared by similar methods to those described for Example 69

| Example | Structure | LC-MS analysis |
|---|---|---|
| 72 | 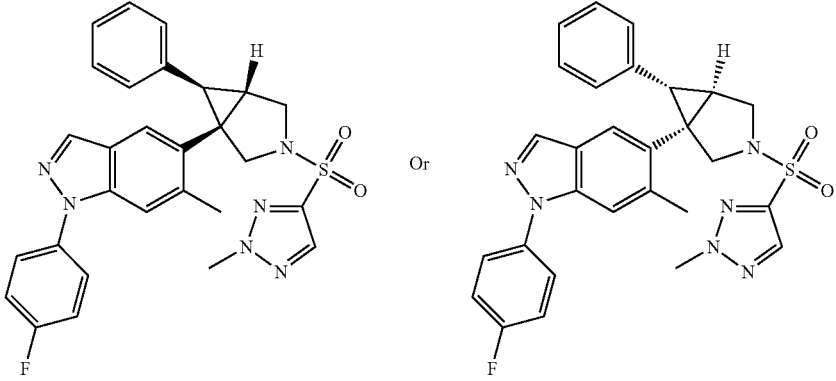<br>1-(4-fluorophenyl)-6-methyl-5-(3-((2-methyl-2H-1,2,3-triazol-4-yl)sulfonyl)-6-phenyl-3-azabicyclo[3.1.0]hexan-1-yl)-1H-indazole | $R^t$ 2.33 min (Method 1); m/z 529.4 $(M + H)^+$ $(ES^+)$ |
| 73 | 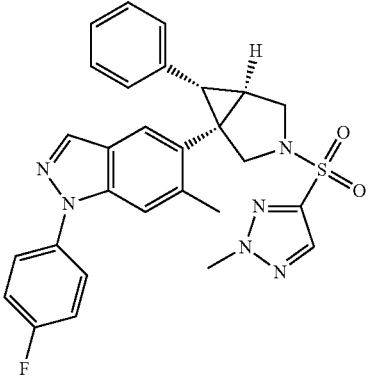<br>1-(4-fluorophenyl)-6-methyl-5-(3-((1-methyl-1H-pyrazol-4-yl)sulfonyl)-6-phenyl-3-azabicyclo[3.1.0]hexan-1-yl)-1H-indazole | $R^t$ 2.15 min (Method 7); m/z 528.4 $(M + H)^+$ $(ES^+)$ |
| 74 | 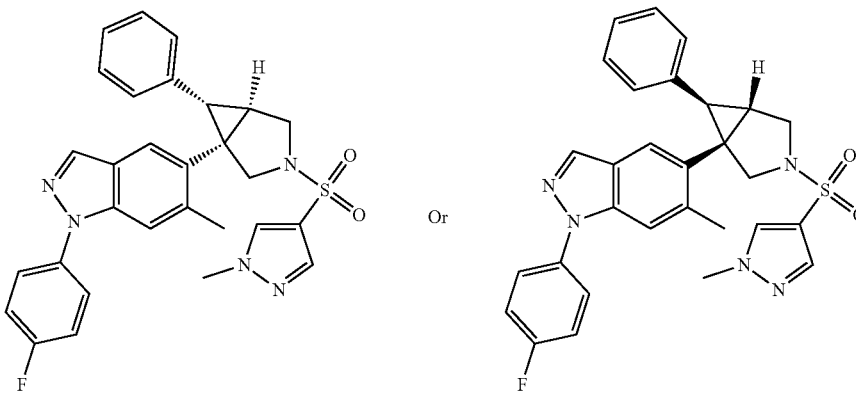<br>5-(3-((2-ethyl-2H-1,2,3-triazol-4-yl)sulfonyl)-6-phenyl-3-azabicyclo[3.1.0]hexan-1-yl)-1-(4-fluorophenyl)-6-methyl-1H-indazole | $R^t$ 2.33 min (Method 7); m/z 543.4 $(M + H)^+$ $(ES^+)$ |

TABLE 6-continued

The examples shown in the table below were prepared by similar methods to those described for Example 69

| Example | Structure | LC-MS analysis |
|---|---|---|
| 75 | 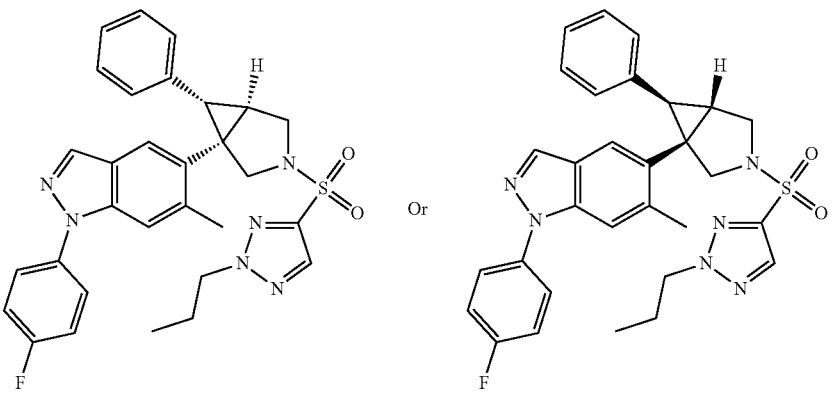<br>1-(4-fluorophenyl)-6-methyl-5-(6-phenyl-3-((2-propyl-2H-1,2,3-triazol-4-yl)sulfonyl)-3-azabicyclo[3.1.0]hexan-1-yl)-1H-indazole | $R^t$ 2.39 min (Method 7); m/z 557.1 $(M + H)^+$ $(ES^+)$ |
| 76 | 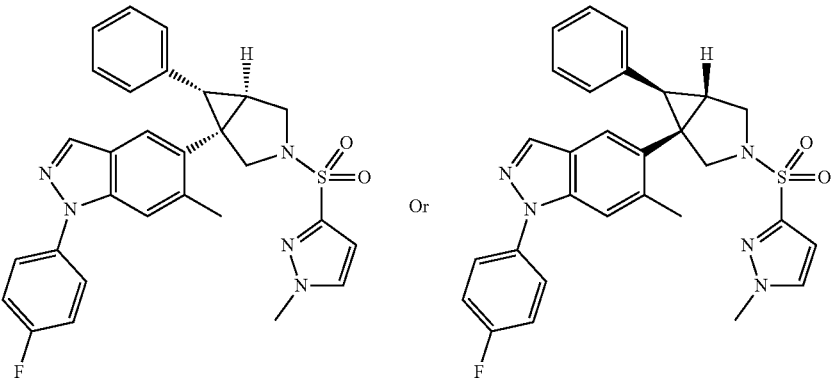<br>1-(4-fluorophenyl)-6-methyl-5-(3-((1-methyl-1H-pyrazol-3-yl)sulfonyl)-6-phenyl-3-azabicyclo[3.1.0]hexan-1-yl)-1H-indaozole | $R^t$ 2.33 min (Method 9); m/z 528.2 $(M + H)^+$ $(ES^+)$ |
| 77 | 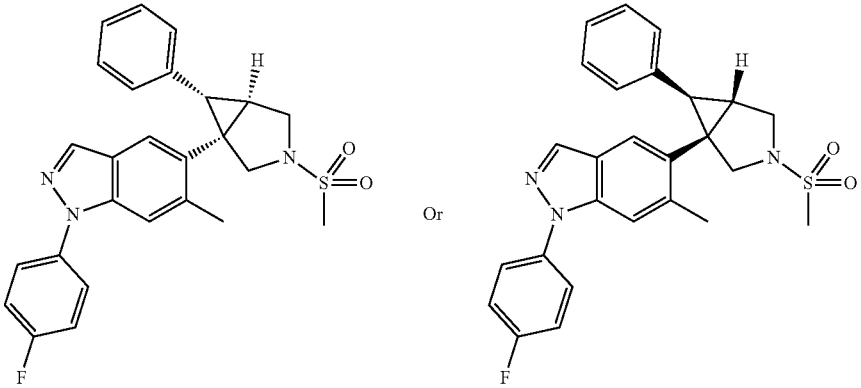<br>1-(4-fluorophenyl)-6-methyl-5-(3-(methylsulfonyl)-6-phenyl-3-azabicyclo[3.1.0]hexan-1-yl)-1H-indazole | $R^t$ 2.14 min (Method 7); m/z 462.2 $(M + H)^+$ $(ES^+)$ |

TABLE 6-continued

The examples shown in the table below were prepared by similar methods to those described for Example 69

| Example | Structure | LC-MS analysis |
|---|---|---|
| 78 | 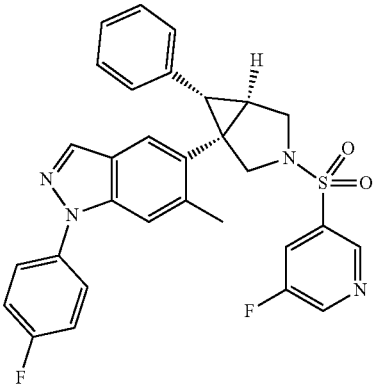 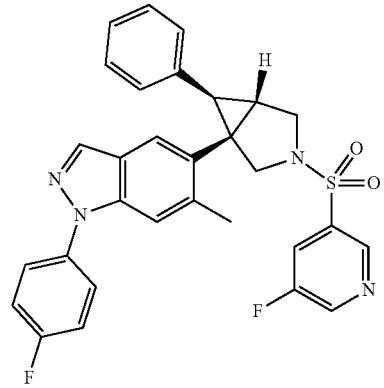<br>1-(4-fluorophenyl)-5-(3-((5-fluoropyridin-3-yl)sulfonyl)-6-phenyl-3-azabicyclo[3.1.0]hexan-1-yl)-6-methyl-1H-indazole | R$^t$ 2.49 min (Method 9); m/z 543.2 (M + H)$^+$ (ES$^+$) |
| 79 | 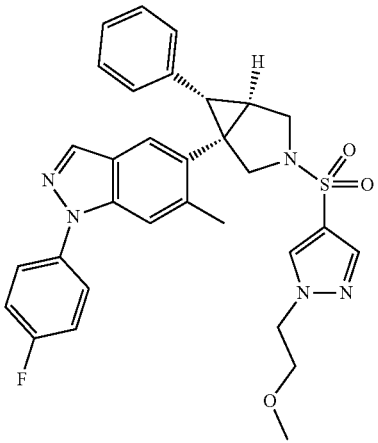 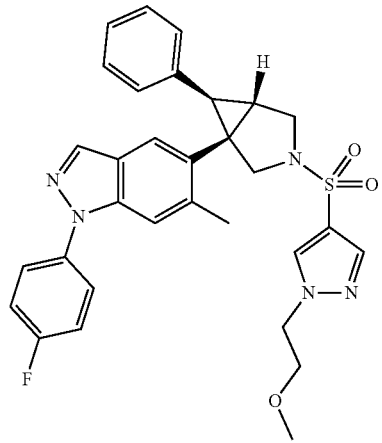<br>1-(4-fluorophenyl)-5-(3-((1-(2-methoxyethyl)-1H-pyrazol-4-yl)sulfonyl)-6-phenyl-3-azabicyclo[3.1.0]hexan-1-yl)-6-methyl-1H-indazole | R$^t$ 2.19 min (Method 7); m/z 572.5 (M + H)$^+$ (ES$^+$) |

TABLE 6-continued

The examples shown in the table below were prepared by similar methods to those described for Example 69

| Example | Structure | LC-MS analysis |
|---|---|---|
| 80 | | R$^t$ 2.52 min (Method 9); m/z 557.2 (M + H)$^+$ (ES$^+$) |

1-(4-fluorophenyl)-5-(3-((2-isopropyl-2H-1,2,3-triazol-4-yl)sulfonyl)-6-phenyl-3-azabicyclo[3.1.0]hexan-1-yl)-6-methyl-1H-indazole

| | | |
|---|---|---|
| 81 | | R$^t$ 2.37 min (Method 7); m/z 597.4 (M + H)$^+$ (ES$^+$) |

1-(4-fluorophenyl)-6-methyl-5-(3-((2-methyl-2H-1,2,3-triazol-4-yl)sulfonyl)-6-(3-(trifluoromethyl)phenyl)-3-azabicyclo[3.1.0]hexan-1-yl)-1H-indazole TABLE 6-continued The examples shown in the table below were prepared by similar methods to those described for Example 69

| Example | Structure | LC-MS analysis |
|---|---|---|
| 82 | 1-(4-fluorophenyl)-6-methyl-5-(3-((2-methyl-2H-1,2,3-triazol-4-yl)sulfonyl)-6-(3-(trifluoromethyl)phenyl)-3-azabicyclo[3.1.0]hexan-1-yl)-1H-indazole | R' 2.34 min (Method 7); m/z 597.4 (M + H)⁺ (ES⁺) |
| 83 | 1-(4-fluorophenyl)-6-methyl-5-(3-((2-methyl-2H-1,2,3-triazol-2-yl)sulfonyl)-6-(4-(trifluoromethyl)phenyl)-3-azabicyclo[3.1.0]hexan-1-yl)-1H-indazole | R' 2.38 min (Method 7); m/z 597.6 (M + H)⁺ (ES⁺) |

TABLE 6-continued

The examples shown in the table below were prepared by similar methods to those described for Example 69

| Example | Structure | LC-MS analysis |
|---|---|---|
| 84 | 1-(4-fluorophenyl)-6-methyl-5-(3-((2-methyl-2H-1,2,3-triazol-4-yl)sulfonyl)-6-(4-(trifluoromethyl)phenyl)-3-azabicyclo[3.1.0]hexan-1-yl)-1H-indazole | $R^t$ 2.35 min (Method 7); m/z 597.4 $(M + H)^+$ $(ES^+)$ |
| 85 | 5-(3-(cyclopropylsulfonyl)-6-phenyl-3-azabicyclo[3.1.0]hexan-1-yl)-1-(4-fluorophenyl)-6-methyl-1H-indazole | $R^t$ 2.37 min (Method 9); m/z 488.3 $(M + H)^+$ $(ES^+)$ |
| 86 | 1-(4-fluorophenyl)-5-(3-((2-methoxyethyl)sulfonyl)-6-phenyl-3-azabicyclo[3.1.0]hexan-1-yl)-6-methyl-1H-indazole | $R^t$ 2.33 min (Method 9); m/z 506.2 $(M + H)^+$ $(ES^+)$ |

TABLE 6-continued

The examples shown in the table below were prepared by similar methods to those described for Example 69

| Example | Structure | LC-MS analysis |
|---|---|---|
| 87 | 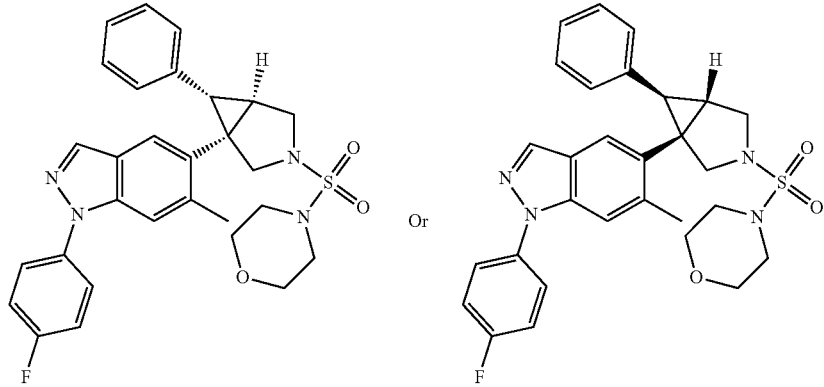 Or 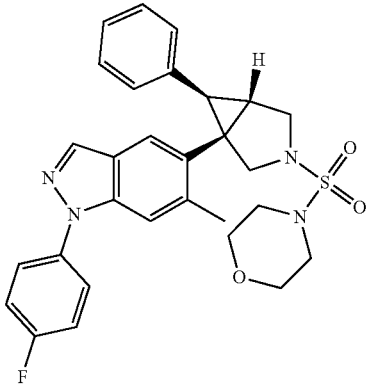<br>4-((1-(1-(4-fluorophenyl)-6-methyl-1H-indazol-5-yl)-6-phenyl-3-azabicyclo[3.1.0]hexan-3-yl)sulfonyl)morpholine | R$^t$ 2.38 min (Method 9); m/z 533.2 (M + H)$^+$ (ES$^+$) |
| 88 | 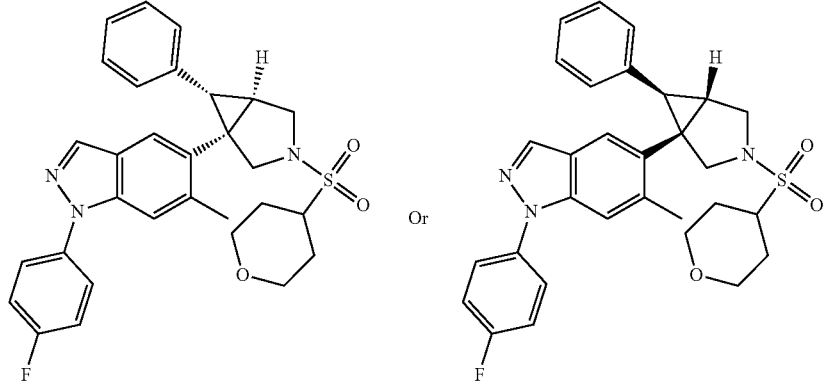 Or 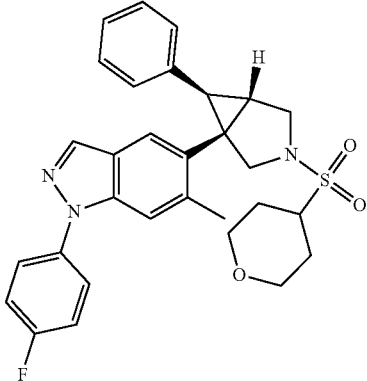<br>1-(4-fluorophenyl)-6-methyl-5-(6-phenyl-3-((tetrahydro-2H-pyran-4-yl)sulfonyl)-3-azabicyclo[3.1.0]hexan-1-yl)-1H-indazole | R$^t$ 2.33 min (Method 9); m/z 532.2 (M + H)$^+$ (ES$^+$) |
| 89 | 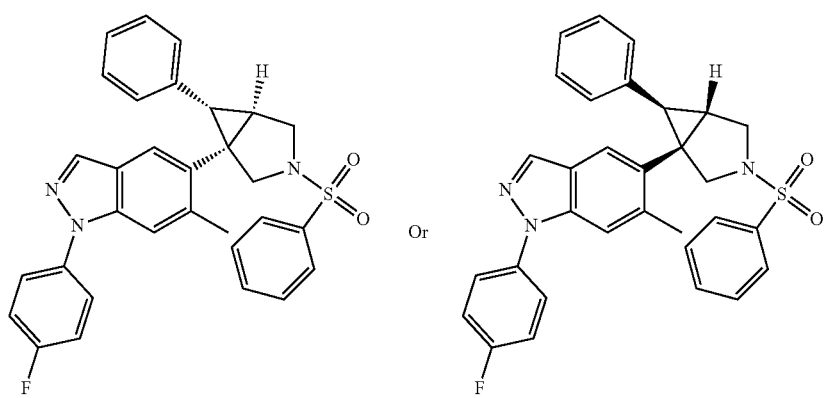 Or 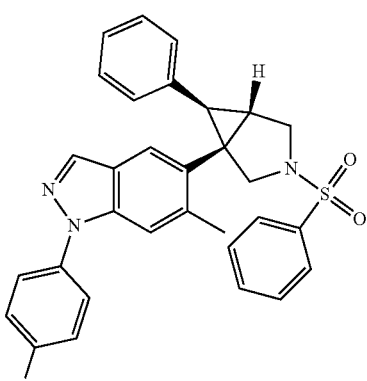<br>1-(4-fluorophenyl)-6-methyl-5-(6-phenyl-3-(phenylsulfonyl)-3-azabicyclo[3.1.0]hexan-1-yl)-1H-indazole | R$^t$ 2.54 min (Method 9); m/z 524.2 (M + H)$^+$ (ES$^+$) |

TABLE 6-continued

The examples shown in the table below were prepared by similar methods to those described for Example 69

| Example | Structure | LC-MS analysis |
|---|---|---|
| 90 | 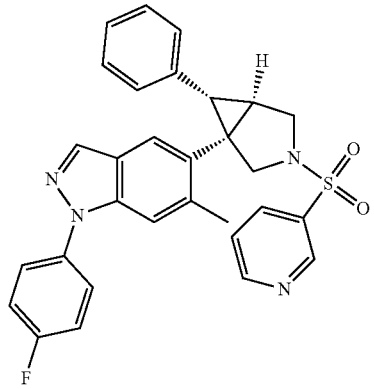<br>1-(4-fluorophenyl)-6-methyl-5-(6-phenyl-3-(pyridin-3-ylsulfonyl)-3-azabicyclo[3.1.0]hexan-1-yl)-1H-indazole | R$^t$ 2.35 min (Method 9); m/z 525.2 (M + H)$^+$ (ES$^+$) |
| 91 | 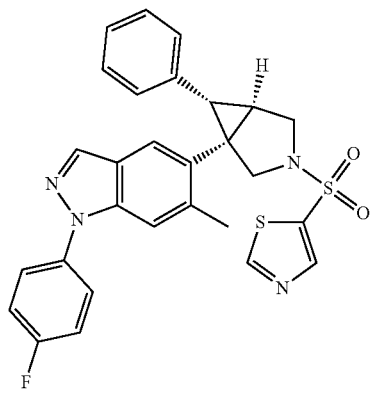<br>5-((1-(1-(4-fluorophenyl)-6-methyl-1H-indazol-5-yl)-6-phenyl-3-azabicyclo[3.1.0]hexan-3-yl)sulfonyl)thiazole | R$^t$ 2.39 min (Method 9); m/z 531.1 (M + H)$^+$ (ES$^+$) |
| 92 | 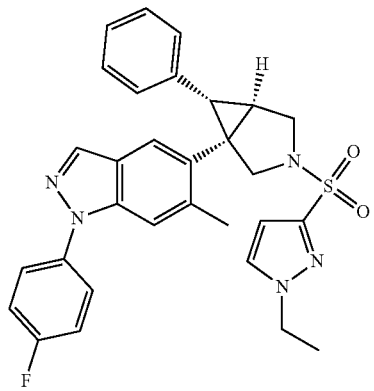<br>5-(3-((1-ethyl-1H-pyrazol-3-yl)sulfonyl)-6-phenyl-3-azabicyclo[3.1.0]hexan-1-yl)-1-(4-fluorophenyl)-6-methyl-1H-indazol | R$^t$ 2.39 min (Method 9); m/z 542.2 (M + H)$^+$ (ES$^+$) |

TABLE 6-continued

The examples shown in the table below were prepared by similar methods to those described for Example 69

| Example | Structure | LC-MS analysis |
|---|---|---|
| 93 | 5-(3-((cyclopropylmethyl)sulfonyl)-6-phenyl-3-azabicyclo[3.1.0]hexan-1-yl)-1-(4-fluorophenyl)-6-methyl-1H-indazole | R$^t$ 2.44 min (Method 9); m/z 502.3 (M + H)$^+$ (ES$^+$) |
| 94 | 5-(3-(ethylsulfonyl)-6-phenyl-3-azabicyclo[3.1.0]hexan-1-yl)-1-(4-fluorophenyl)-6-methyl-1H-indazole | R$^t$ 2.21 min (Method 7); m/z 476.4 (M + H)$^+$ (ES$^+$) |
| 95 | 5-(6-(3-chlorophenyl)-3-((1-methyl-1H-pyrazol-4-yl)sulfonyl)-3-azabicyclo[3.1.0]hexan-1-yl)-1-(4-fluorophenyl)-6-methyl-1H-indazole | R$^t$ 2.28 min (Method 7); m/z 562.4 (M + H)$^+$ (ES$^+$) |

TABLE 6-continued

The examples shown in the table below were prepared by similar methods to those described for Example 69

| Example | Structure | LC-MS analysis |
|---|---|---|
| 96 | 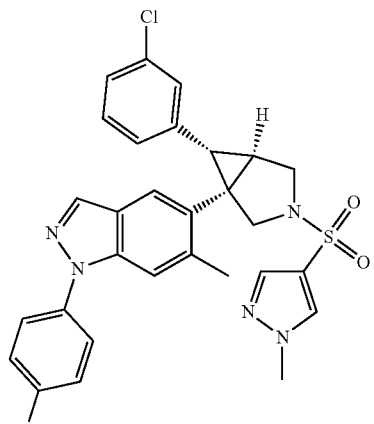<br>5-(6-(3-chlorophenyl)-3-((1-methyl-1H-pyrazol-4-yl)sulfonyl)-3-azabicyclo[3.1.0]hexan-1-yl)-1-(4-fluorophenyl)-6-methyl-1H-indazole | R$^t$ 2.24 min (Method 7); m/z 562.5 (M + H)$^+$ (ES$^+$) |
| 97 | 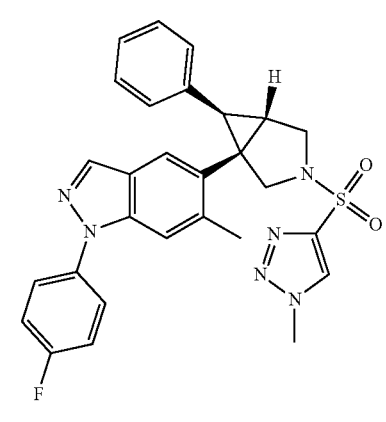<br>1-(4-fluorophenyl)-6-methyl-5-(3-((1-methyl-1H-1,2,3-triazol-4-yl)sulfonyl)-6-phenyl-3-azabicyclo[3.1.0]hexan-1-yl)-1H-indazole | R$^t$ 2.24 min (Method 9); m/z 529.1 (M + H)$^+$ (ES$^+$) |

TABLE 6-continued

The examples shown in the table below were prepared by similar methods to those described for Example 69

| Example | Structure | LC-MS analysis |
|---|---|---|
| 98 | 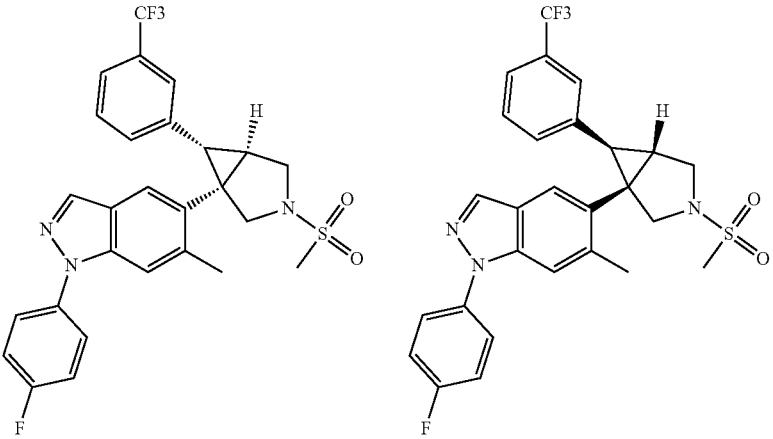<br>1-(4-fluorophenyl)-6-methyl-5-(3-(methylsulfonyl)-6-(3-(trifluoromethyl)phenyl)-3-azabicyclo[3.1.0]hexan-1-yl)-1H-indazole | R$^t$ 2.34 min (Method 9); m/z 530.1 (M + H)$^+$ (ES$^+$) |
| 99 | 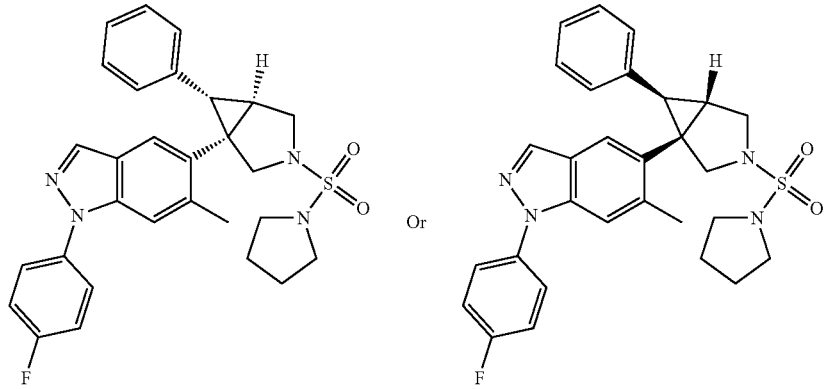<br>1-(4-fluorophenyl)-6-methyl-5-(6-phenyl-3-(pyrrolidin-1-ylsulfonyl)-3-azabicyclo[3.1.0]hexan-1-yl)-1H-indazole | R$^t$ 2.45 min (Method 9); m/z 517.1 (M + H)$^+$ (ES$^+$) |
| 100 | 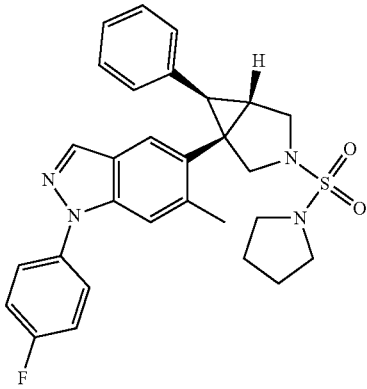<br>1-(1-(4-fluorophenyl)-6-methyl-1H-indazol-5-yl)-N-isobutyl-6-phenyl-3-azabicyclo[3.1.0]hexane-3-sulfonamide | R$^t$ 2.47 min (Method 9); m/z 519.2 (M + H)$^+$ (ES$^+$) |

TABLE 6-continued

The examples shown in the table below were prepared by similar methods to those described for Example 69

| Example | Structure | LC-MS analysis |
|---|---|---|
| 101 | 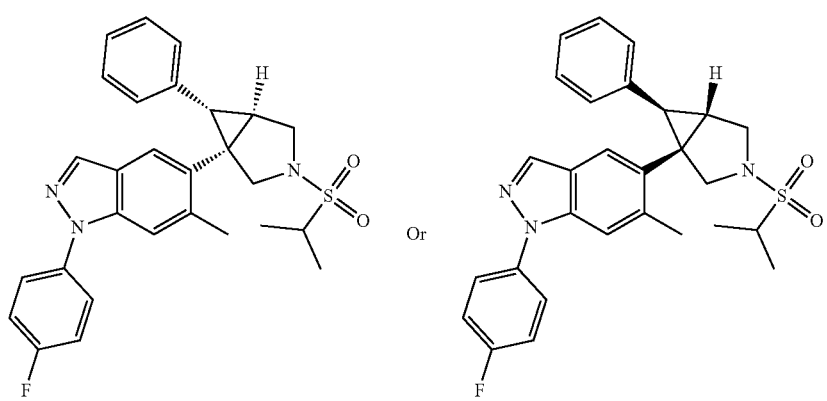<br>1-(4-fluorophenyl)-5-(3-(isopropylsulfonyl)-6-phenyl-3-azabicyclo[3.1.0]hexan-1-yl)-6-methyl-1H-indazole | R$^t$ 2.30 min (Method 7); m/z 490.4 (M + H)$^+$ (ES$^+$) |
| 102 | 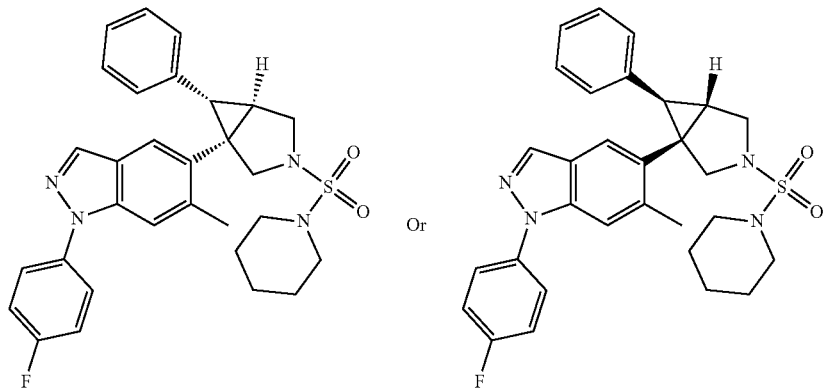<br>1-(4-fluorophenyl)-6-methyl-5-(6-phenyl-3-(piperidin-1-ylsulfonyl)-3-azabicyclo[3.1.0]hexan-1-yl)-1H-indazole | R$^t$ 2.58 min (Method 9); m/z 531.1 (M + H)$^+$ (ES$^+$) |
| 103 | 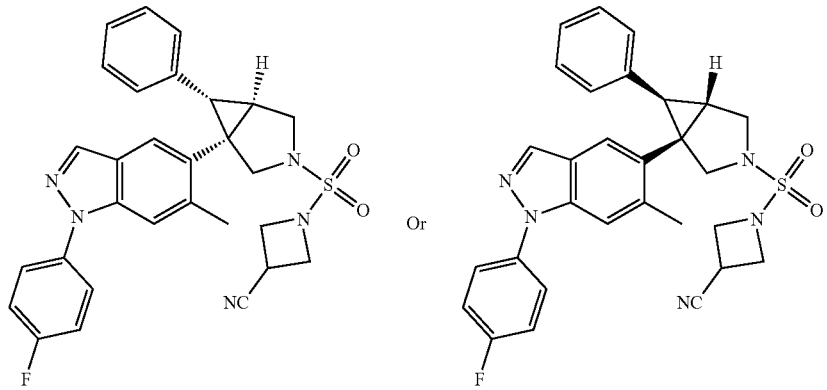<br>1-((1-(1-(4-fluorophenyl)-6-methyl-1H-indazol-5-yl)-6-phenyl-3-azabicyclo[3.1.0]hexan-3-yl)sulfonyl)azetidine-3-carbonitrile | R$^t$ 2.22 min (Method 7); m/z 528.4 (M + H)$^+$ (ES$^+$) |

TABLE 6-continued

The examples shown in the table below were prepared by similar methods to those described for Example 69

| Example | Structure | LC-MS analysis |
|---|---|---|
| 104 | 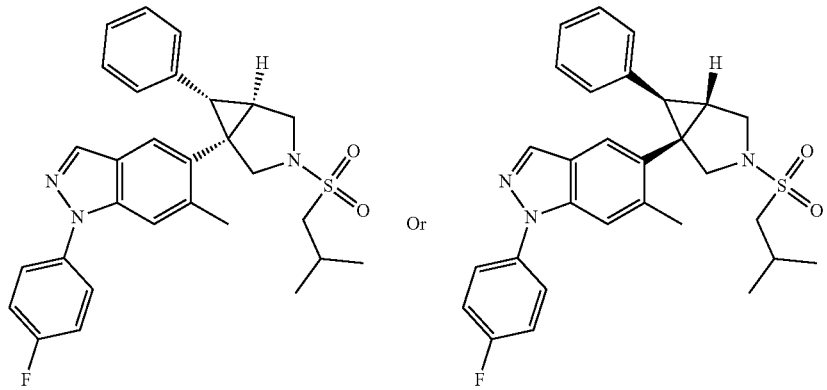<br>1-(4-fluorophenyl)-5-(3-(isobutylsulfonyl)-6-phenyl-3-azabicyclo[3.1.0]hexan-1-yl)-6-methyl-1H-indazole | R$^t$ 2.38 min (Method 7); m/z 504.2 (M + H)$^+$ (ES$^+$) |
| 105 | 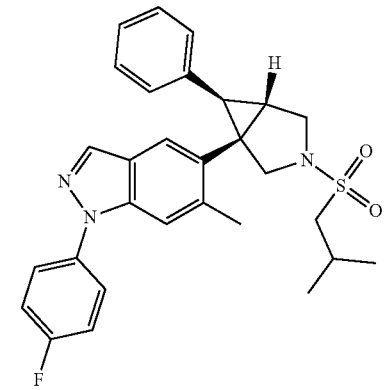<br>5-(3-(azetidin-1-ylsulfonyl)-6-phenyl-3-azabicyclo[3.1.0]hexan-1-yl)-1-(4-fluorophenyl)-6-methyl-1H-indazole | R$^t$ 2.29 min (Method 7); m/z 503.4 (M + H)$^+$ (ES$^+$) |
| 106 | 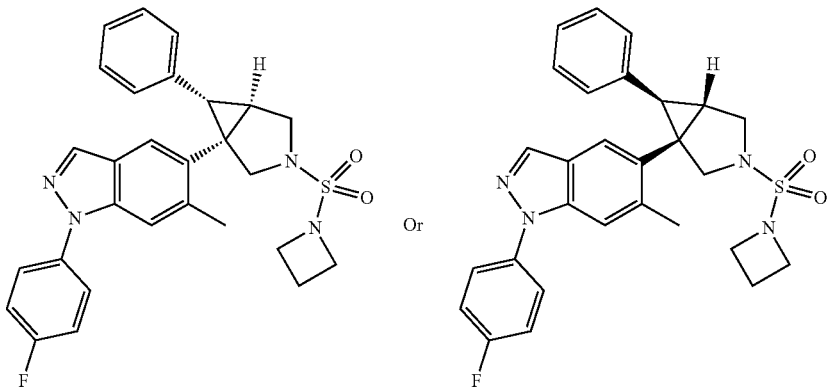<br>1-(1-(4-fluorophenyl)-6-methyl-1H-indazol-5-yl)-N-methyl-6-phenyl-3-azabicyclo[3.1.0]hexane-3-sulfonamide | R$^t$ 2.21 min (Method 9); m/z 477.1 (M + H)$^+$ (ES$^+$) |

TABLE 6-continued

The examples shown in the table below were prepared by similar methods to those described for Example 69

| Example | Structure | LC-MS analysis |
|---|---|---|
| 107 | 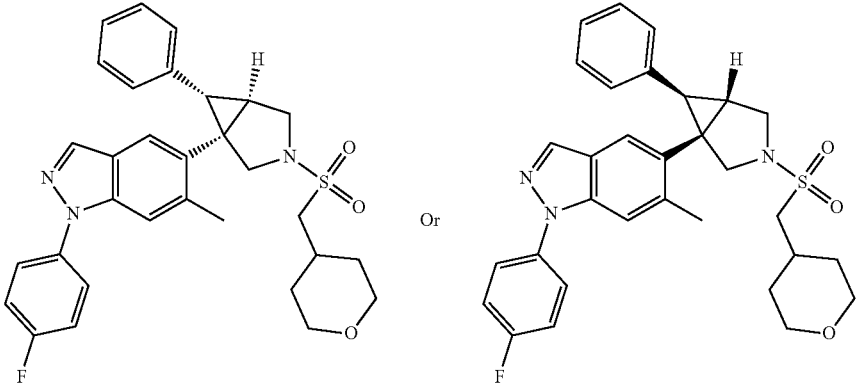<br>1-(4-fluorophenyl)-6-methyl-5-(6-phenyl-3-(((tetrahydro-2H-pyran-4-yl)methyl)sulfonyl)-3-azabicyclo[3.1.0]hexan-1-yl)-1H-indazole | R$^t$ 2.33 min (Method 9); m/z 546.1 (M + H)$^+$ (ES$^+$) |
| 108 | 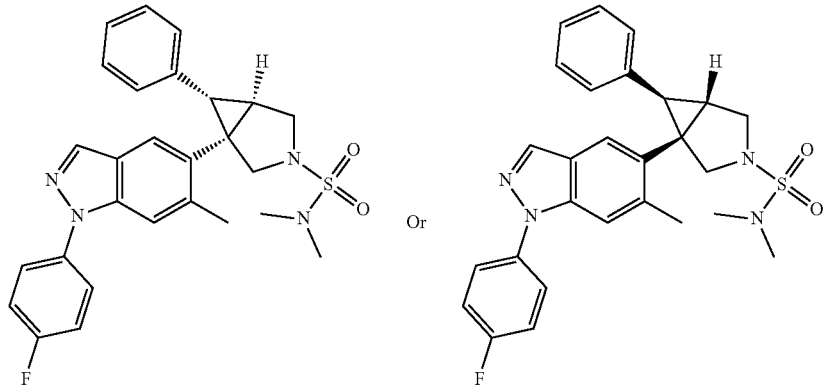<br>1-(1-(4-fluorophenyl)-6-methyl-1H-indazol-5-yl)-N,N-dimethyl-6-phenyl-3-azabicyclo[3.1.0]hexane-3-sulfonamide | R$^t$ 2.37 min (Method 9); m/z 491.1 (M + H)$^+$ (ES$^+$) |
| 109 | 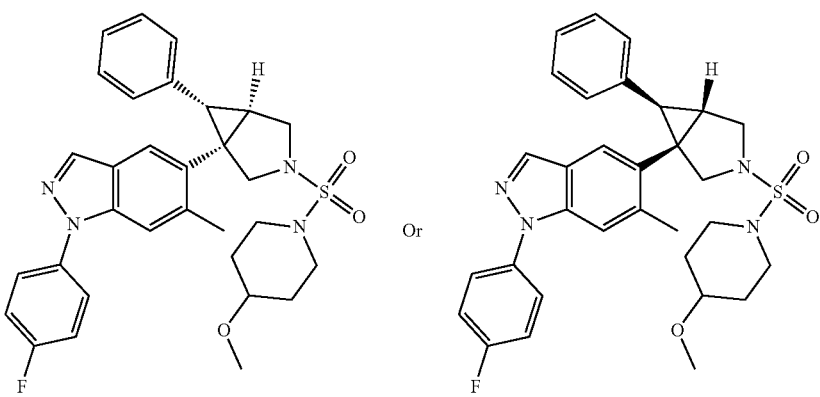<br>1-(4-fluorophenyl)-5-(3-((4-methoxypiperidin-1-yl)sulfonyl)-6-phenyl-3-azabicyclo[3.1.0]hexan-1-yl)-6-methyl-1H-indazole | R$^t$ 2.34 min (Method 7); m/z 561.5 (M + H)$^+$ (ES$^+$) |

Example 110: (1-(1-(4-fluorophenyl)-6-methyl-1H-indazol-5-yl)-6-phenyl-3-azabicyclo[3.1.0]hexan-3-yl)(phenyl)methanone
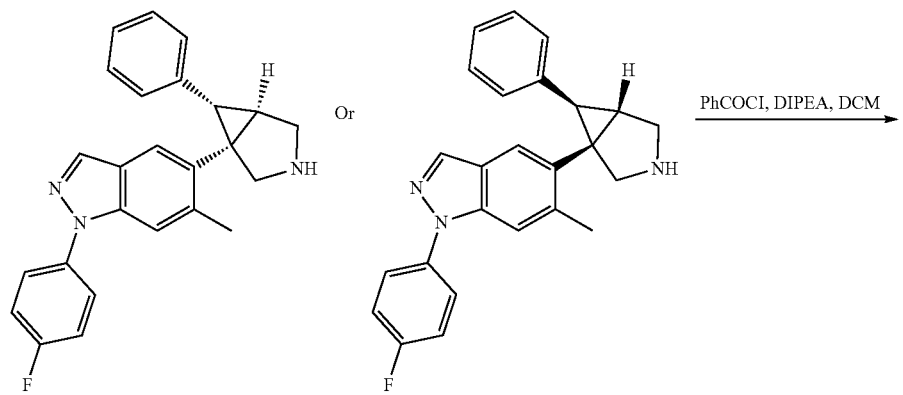
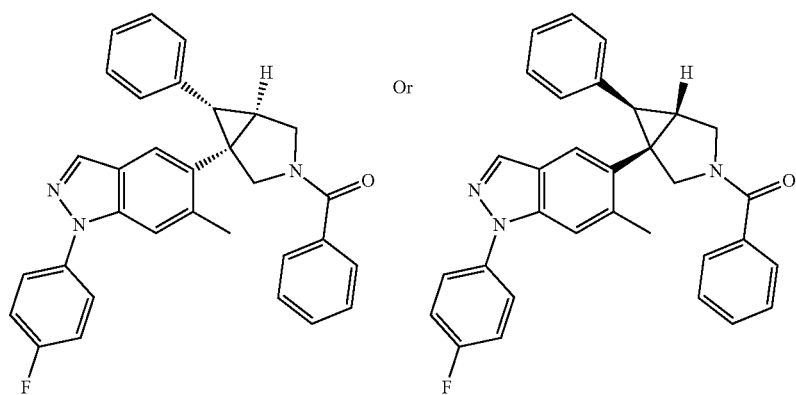

To a solution of 1-(4-fluorophenyl)-6-methyl-5-(6-phenyl-3-azabicyclo[3.1.0]hexan-1-yl)-1H-indazole (20 mg, 52 µmol) (Intermediate X) in DCM (0.5 mL) was added N-ethyl-N-isopropylpropan-2-amine (20 mg, 27 µL, 0.16 mmol) followed by benzoyl chloride (8.8 mg, 7.3 µL, 63 µmol). The reaction mixture was stirred at room temperature for 45 min. The reaction mixture was concentrated onto silica gel and purified by chromatography on silica gel (4 g cartridge, 0-100% EtOAc/isohexane) to afford (1-(1-(4-fluorophenyl)-6-methyl-1H-indazol-5-yl)-6-phenyl-3-azabicyclo[3.1.0]hexan-3-yl)(phenyl)methanone (23.10 mg, 45 µmol, 86%) as a white solid; Rt 2.28 min (Method 7); m/z 488.4 (M+H)+ (ES+).

Examples 111-130

TABLE 7

The examples shown in the table below were prepared by similar methods to those described for Example 110

| Example | Structure | LC-MS Analysis |
|---|---|---|
| 111 | 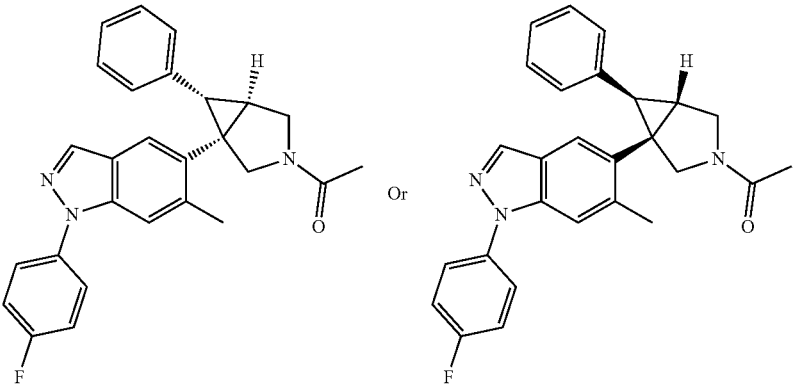 [SMILES: CC(=O)N1C[C@@H]2[C@@H](c3ccccc3)[C@]2(c2cc3cnn(-c4ccc(F)cc4)c3cc2C)C1 ; CC(=O)N1C[C@H]2[C@H](c3ccccc3)[C@@]2(c2cc3cnn(-c4ccc(F)cc4)c3cc2C)C1] 1-(1-(1-(4-fluorophenyl)-6-methyl-1H-indazol-5-yl)-6-phenyl-3-azabicyclo[3.1.0]hexan-3-yl)ethan-1-one | $R^t$ 2.01 min (Method 7); m/z 426.5 (M + H)+ (ES+) |
| 112 | 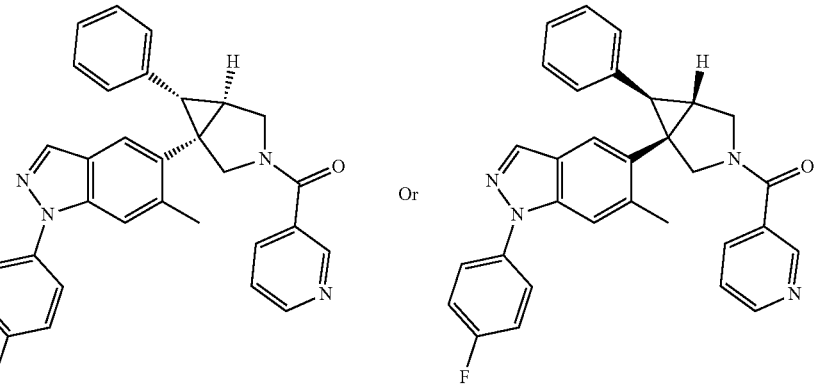 (1-(1-(4-fluorophenyl)-6-methyl-1H-indazol-5-yl)-6-phenyl-3-azabicyclo[3.1.0]hexan-3-yl)(pyridin-3-yl)methanone | $R^t$ 1.98 min (Method 7); m/z 489.4 (M + H)+ (ES+) |

TABLE 7-continued

The examples shown in the table below were prepared by similar methods to those described for Example 110

| Example | Structure | LC-MS Analysis |
|---|---|---|
| 113 | 1-(1-(1-(4-fluorophenyl)-6-methyl-1H-indazol-5-yl)-6-phenyl-3-azabicyclo[3.1.0]hexan-3-yl)-2-methylpropan-1-one | R' 2.22 min (Method 7); m/z 454.5 (M + H)+ (ES+) |
| 114 | 3-(1-(1-(4-fluorophenyl)-6-methyl-1H-indazol-5-yl)-6-phenyl-3-azabicyclo[3.1.0]hexane-3-carbonyl)benzonitrile | R' 2.34 min (Method 9); m/z 513.2 (M + H)+ (ES+) |
| 115 | 4-(1-(1-(4-fluorophenyl)-6-methyl-1H-indazol-5-yl)-6-phenyl-3-azabicyclo[3.1.0]hexane-3-carbonyl)benzonitrile | R' 2.34 min (Method 9); m/z 513.2 (M + H)+ (ES+) |

TABLE 7-continued

The examples shown in the table below were prepared by similar methods to those described for Example 110

| Example | Structure | LC-MS Analysis |
|---|---|---|
| 116 | 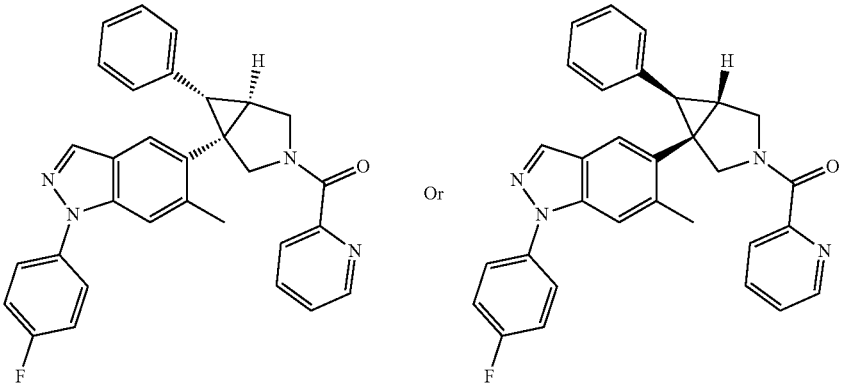 [SMILES: Cc1cc2c(cnn2-c2ccc(F)cc2)cc1[C@@]12CN(C(=O)c3ccccn3)C[C@@H]1[C@H]2c1ccccc1 ; Cc1cc2c(cnn2-c2ccc(F)cc2)cc1[C@]12CN(C(=O)c3ccccn3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(pyridin-2-yl)methanone | R$^t$ 2.26 min (Method 9); m/z 489.2 (M + H)$^+$ (ES$^+$) |
| 117 | 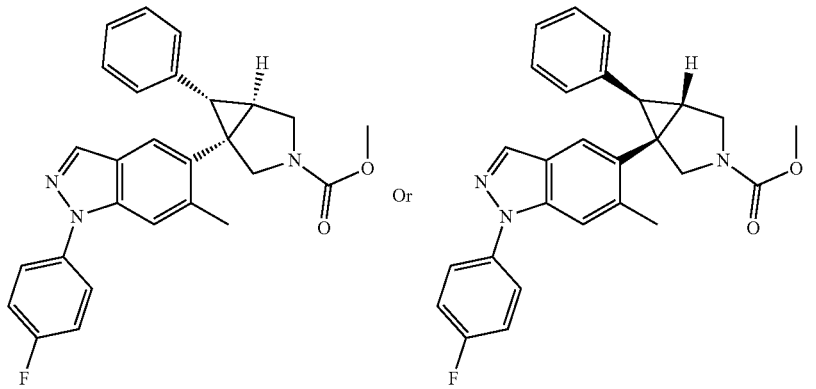 [SMILES: COC(=O)N1C[C@@H]2[C@@H](c3ccccc3)[C@]2(c2cc3cnn(-c4ccc(F)cc4)c3cc2C)C1 ; COC(=O)N1C[C@H]2[C@H](c3ccccc3)[C@@]2(c2cc3cnn(-c4ccc(F)cc4)c3cc2C)C1]<br>(3-fluorophenyl)(1-(1-(4-fluorophenyl)-6-methyl-1H-indazol-5-yl)-6-phenyl-3-azabicyclo[3.1.0]hexan-3-yl)methanone | R$^t$ 2.43 min (Method 7); m/z 506.2 (M + H)$^+$ (ES$^+$) |
| 118 | 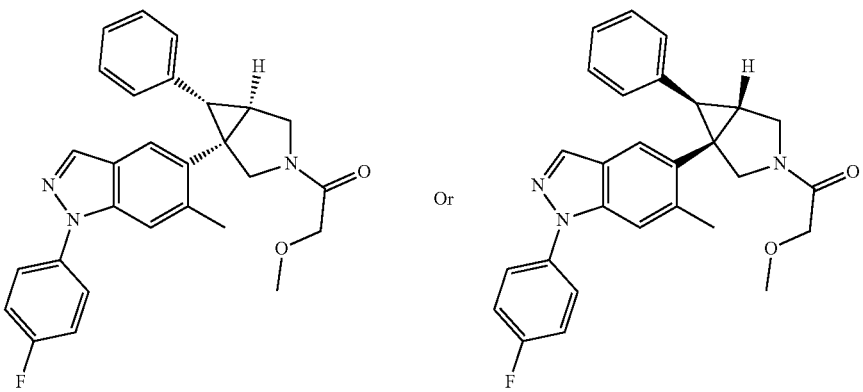 [SMILES: COCC(=O)N1C[C@@H]2[C@@H](c3ccccc3)[C@]2(c2cc3cnn(-c4ccc(F)cc4)c3cc2C)C1 ; COCC(=O)N1C[C@H]2[C@H](c3ccccc3)[C@@]2(c2cc3cnn(-c4ccc(F)cc4)c3cc2C)C1]<br>methyl 1-(1-(4-fluorophenyl)-6-methyl-1H-indazol-5-yl)-6-phenyl-3-azabicyclo[3.1.0]hexane-3-carboxylate | R$^t$ 2.25 min (Method 7); m/z 442.2 (M + H)$^+$ (ES$^+$) |

TABLE 7-continued

The examples shown in the table below were prepared by similar methods to those described for Example 110

| Example | Structure | LC-MS Analysis |
|---|---|---|
| 119 | 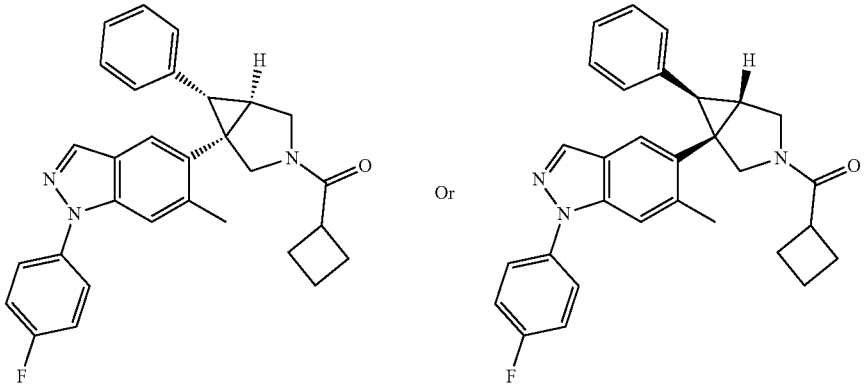 [SMILES: Cc1cc2c(cnn2-c2ccc(F)cc2)cc1[C@@]12CN(C(=O)C3CCC3)C[C@@H]1[C@H]2c1ccccc1 ; Cc1cc2c(cnn2-c2ccc(F)cc2)cc1[C@]12CN(C(=O)C3CCC3)C[C@H]1[C@@H]2c1ccccc1] Or 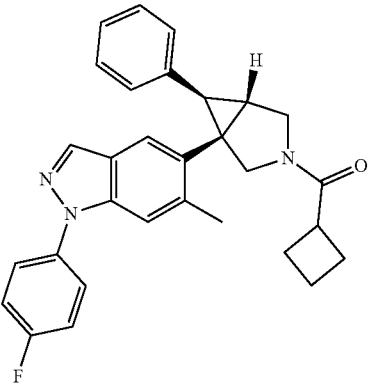<br>1-(1-(1-(4-fluorophenyl)-6-methyl-1H-indazol-5-yl)-6-phenyl-3-azabicyclo[3.1.0]hexan-3-yl)-2-methoxyethan-1-one | $R^t$ 2.11 min (Method 9); m/z 456.2 $(M + H)^+$ $(ES^+)$ |
| 120 | 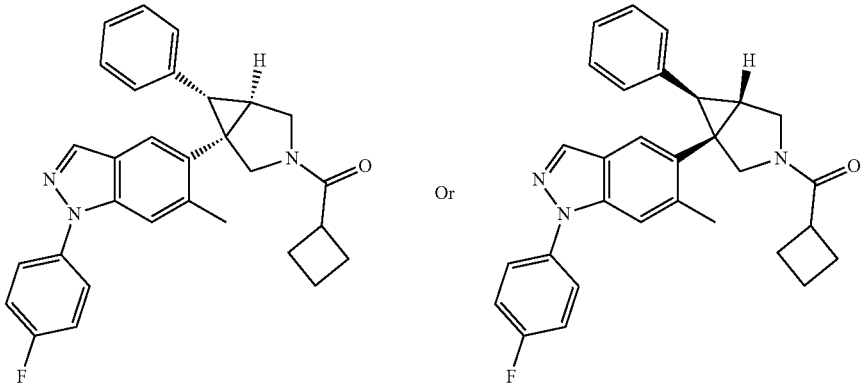 [SMILES: Cc1cc2c(cnn2-c2ccc(F)cc2)cc1[C@@]12CN(C(=O)C3CCC3)C[C@@H]1[C@H]2c1ccccc1 ; Cc1cc2c(cnn2-c2ccc(F)cc2)cc1[C@]12CN(C(=O)C3CCC3)C[C@H]1[C@@H]2c1ccccc1] Or 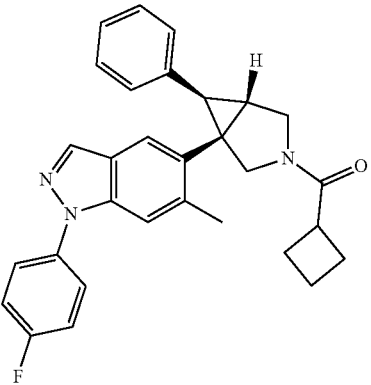<br>cyclobutyl(1-(1-(4-fluorophenyl)-6-methyl-1H-indazol-5-yl)-6-phenyl-3-azabicyclo[3.1.0]hexan-3-yl)methanone | $R^t$ 2.40 min (Method 9); m/z 466.2 $(M + H)^+$ $(ES^+)$ |
| 121 | 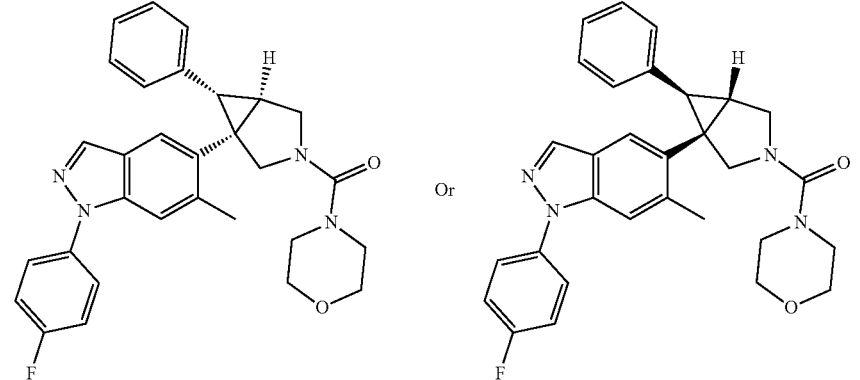 [SMILES: Cc1cc2c(cnn2-c2ccc(F)cc2)cc1[C@@]12CN(C(=O)N3CCOCC3)C[C@@H]1[C@H]2c1ccccc1 ; Cc1cc2c(cnn2-c2ccc(F)cc2)cc1[C@]12CN(C(=O)N3CCOCC3)C[C@H]1[C@@H]2c1ccccc1] Or 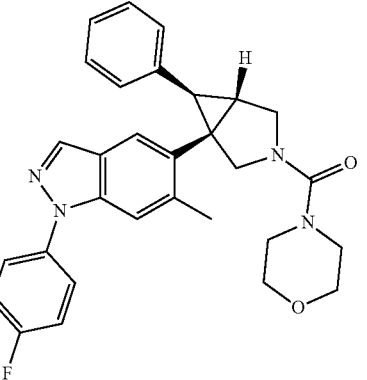<br>(1-(1-(4-fluorophenyl)-6-methyl-1H-indazol-5-yl)-6-phenyl-3-azabicyclo[3.1.0]hexan-3-yl)(morpholino)methanone | $R^t$ 2.08 min (Method 7); m/z 497.5 $(M + H)^+$ $(ES^+)$ |

TABLE 7-continued

The examples shown in the table below were prepared by similar methods to those described for Example 110

| Example | Structure | LC-MS Analysis |
|---|---|---|
| 122 | 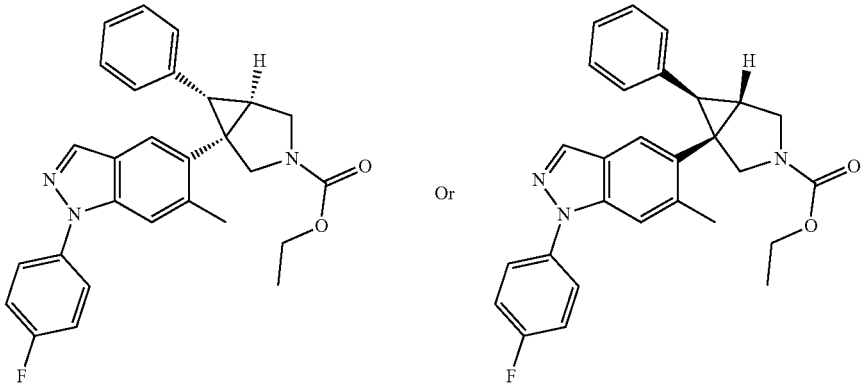 [SMILES: CCOC(=O)N1C[C@@H]2[C@@H](c3ccccc3)[C@]2(c2cc3cnn(-c4ccc(F)cc4)c3cc2C)C1 ; CCOC(=O)N1C[C@H]2[C@H](c3ccccc3)[C@@]2(c2cc3cnn(-c4ccc(F)cc4)c3cc2C)C1]<br>ethyl 1-(1-(4-fluorophenyl)-6-methyl-1H-indazol-5-yl)-6-phenyl-3-azabicyclo[3.1.0]hexane-3-carboxylate | $R^t$ 2.46 min (Method 9); m/z 456.2 $(M + H)^+$ $(ES^+)$ |
| 123 | 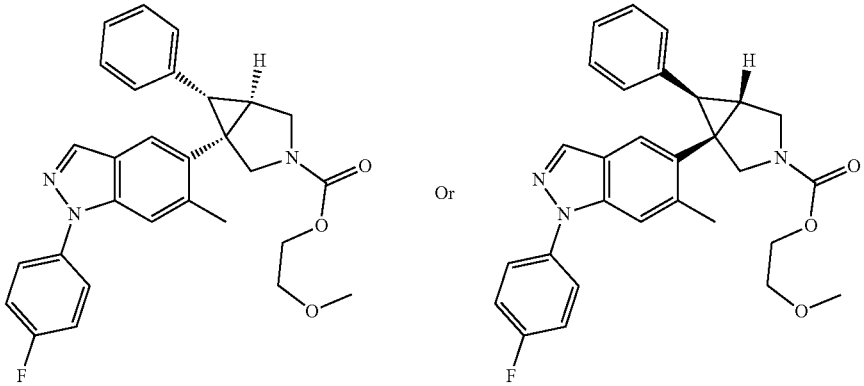 [SMILES: COCCOC(=O)N1C[C@@H]2[C@@H](c3ccccc3)[C@]2(c2cc3cnn(-c4ccc(F)cc4)c3cc2C)C1 ; COCCOC(=O)N1C[C@H]2[C@H](c3ccccc3)[C@@]2(c2cc3cnn(-c4ccc(F)cc4)c3cc2C)C1]<br>2-methoxyethyl 1-(1-(4-fluorophenyl)-6-methyl-1H-indazol-5-yl)-6-phenyl-3-azabicyclo[3.1.0]hexane-3-carboxylate | $R^t$ 2.30 min (Method 9); m/z 486.2 $(M + H)^+$ $(ES^+)$ |
| 124 | 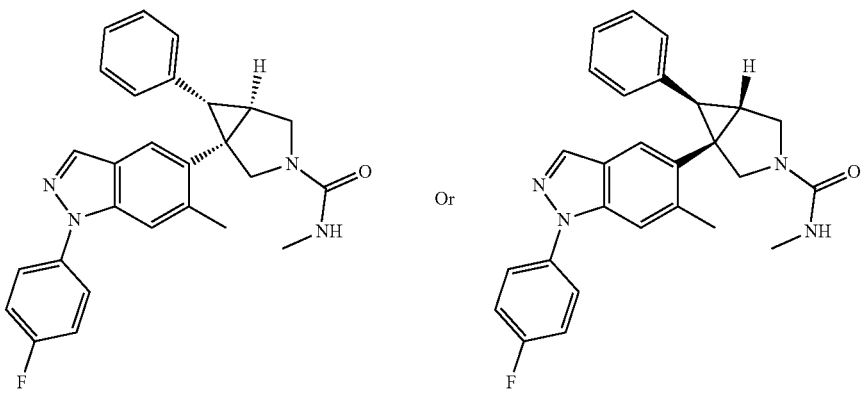 [SMILES: CNC(=O)N1C[C@@H]2[C@@H](c3ccccc3)[C@]2(c2cc3cnn(-c4ccc(F)cc4)c3cc2C)C1 ; CNC(=O)N1C[C@H]2[C@H](c3ccccc3)[C@@]2(c2cc3cnn(-c4ccc(F)cc4)c3cc2C)C1]<br>1-(1-(4-fluorophenyl)-6-methyl-1H-indazol-5-yl)-N-methyl-6-phenyl-3-azabicyclo[3.1.0]hexane-3-carboxamide | $R^t$ 2.06 min (Method 9); m/z 441.1 $(M + H)^+$ $(ES^+)$ |

TABLE 7-continued

The examples shown in the table below were prepared by similar methods to those described for Example 110

| Example | Structure | LC-MS Analysis |
|---|---|---|
| 125 | 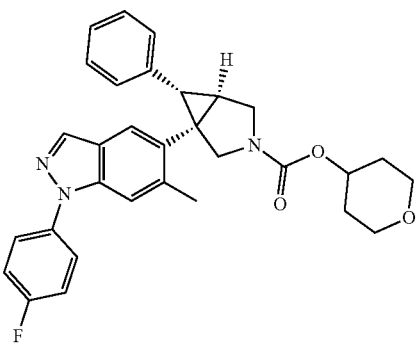 Or 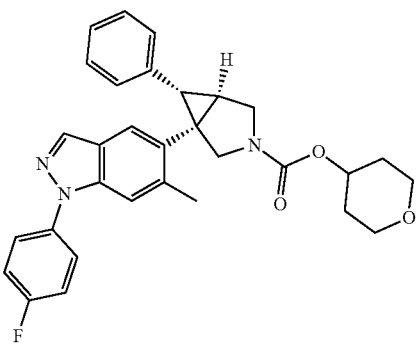<br>tetrahydro-2H-pyran-4-yl 1-(1-(4-fluorophenyl)-6-methyl-1H-indazol-5-yl)-6-phenyl-3-azabicyclo[3.1.0]hexane-3-carboxylate | R$^t$ 2.39 min (Method 7); m/z 512.2 (M + H)$^+$ (ES$^+$) |
| 126 | 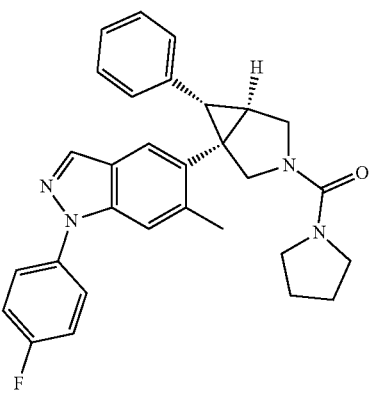 Or 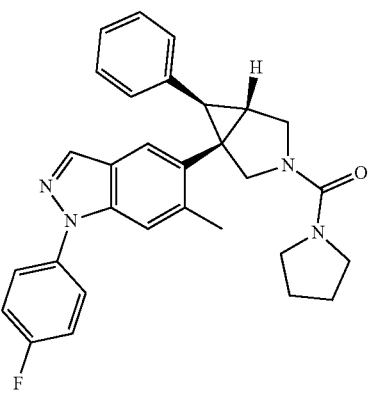<br>(1-(1-(4-fluorophenyl)-6-methyl-1H-indazol-5-yl)-6-phenyl-3-azabicyclo[3.1.0]hexan-3-yl)(pyrrolidin-1-yl)methanone | R$^t$ 2.37 min (Method 7); m/z 481.3 (M + H)$^+$ (ES$^+$) |
| 127 | 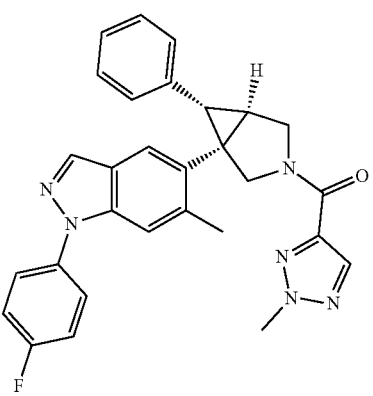 Or 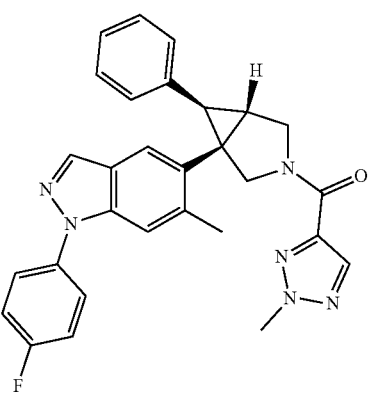<br>(1-(1-(4-fluorophenyl)-6-methyl-1H-indazol-5-yl)-6-phenyl-3-azabicyclo[3.1.0]hexan-3-yl)(2-methyl-2H-1,2,3-triazol-4-yl)methanone | R$^t$ 2.13 min (Method 7); m/z 493.3 (M + H)$^+$ (ES$^+$) |

TABLE 7-continued

The examples shown in the table below were prepared by similar methods to those described for Example 110

| Example | Structure | LC-MS Analysis |
|---|---|---|
| 128 | 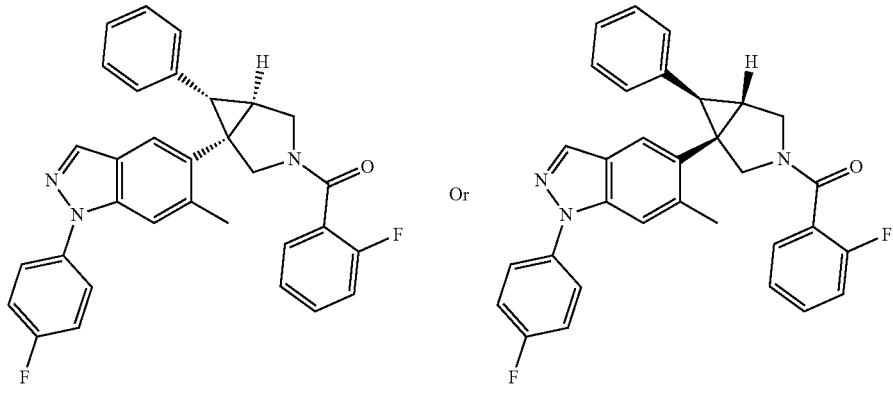 [SMILES: Cc1cc2c(cnn2-c2ccc(F)cc2)cc1[C@@]12CN(C(=O)c3ccccc3F)C[C@@H]1[C@H]2c1ccccc1 ; Cc1cc2c(cnn2-c2ccc(F)cc2)cc1[C@]12CN(C(=O)c3ccccc3F)C[C@H]1[C@@H]2c1ccccc1]<br>(2-fluorophenyl)(1-(1-(4-fluorophenyl)-6-methyl-1H-indazol-5-yl)-6-phenyl-3-azabicyclo[3.1.0]hexan-3-yl)methanone | $R^t$ 2.29 min (Method 7); m/z 506.1 $(M + H)^+$ $(ES^+)$ |
| 129 | 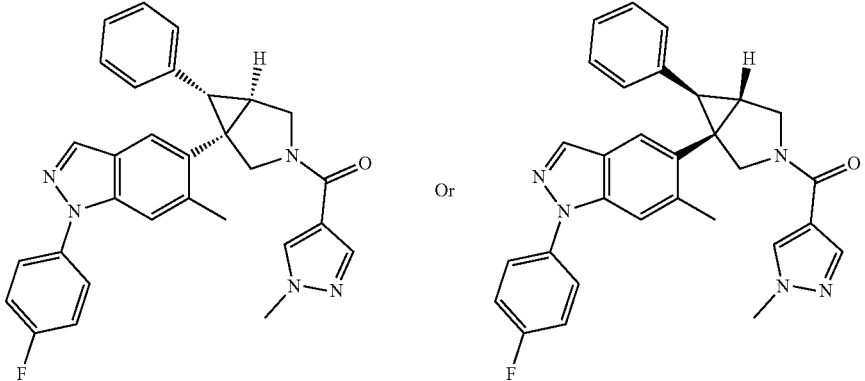 [SMILES: Cc1cc2c(cnn2-c2ccc(F)cc2)cc1[C@@]12CN(C(=O)c3cnn(C)c3)C[C@@H]1[C@H]2c1ccccc1 ; Cc1cc2c(cnn2-c2ccc(F)cc2)cc1[C@]12CN(C(=O)c3cnn(C)c3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(1-methyl-1H-pyrazol-4-yl)methanone | $R^t$ 1.98 min (Method 7); m/z 492.3 $(M + H)^+$ $(ES^+)$ |
| 130 | 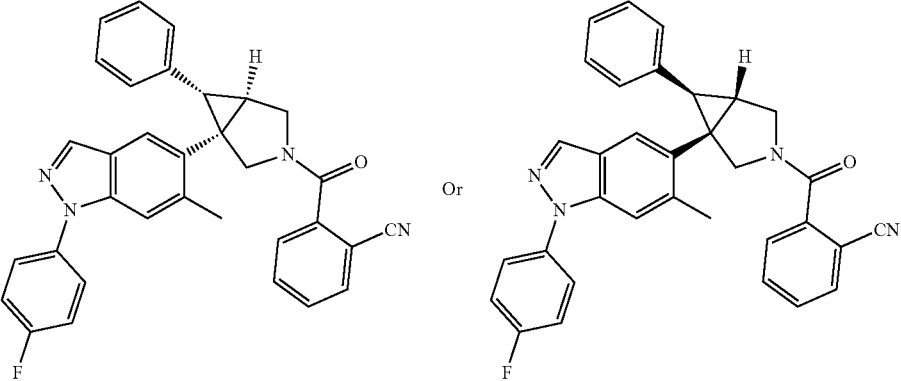 [SMILES: Cc1cc2c(cnn2-c2ccc(F)cc2)cc1[C@@]12CN(C(=O)c3ccccc3C#N)C[C@@H]1[C@H]2c1ccccc1 ; Cc1cc2c(cnn2-c2ccc(F)cc2)cc1[C@]12CN(C(=O)c3ccccc3C#N)C[C@H]1[C@@H]2c1ccccc1]<br>2-(1-(1-(4-fluorophenyl)-6-methyl-1H-indazol-5-yl)-6-phenyl-3-azabicyclo[3.1.0]hexane-3-carbonyl)benzonitrile | $R^t$ 2.21 min (Method 7); m/z 513.1 $(M + H)^+$ $(ES^+)$ |

Example 131: 5-(1-(1-(4-fluorophenyl)-6-methyl-1H-indazol-5-yl)-3-((?2-methyl-2H-1,2,3-triazol-4-yl)sulfonyl)-3-azabicyclo[3.1.0]hexan-6-yl)-3-methyl-1,2,4-oxadiazole

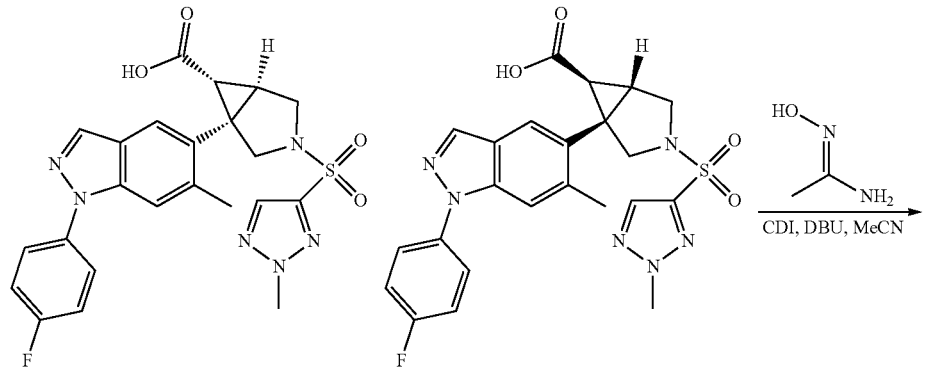

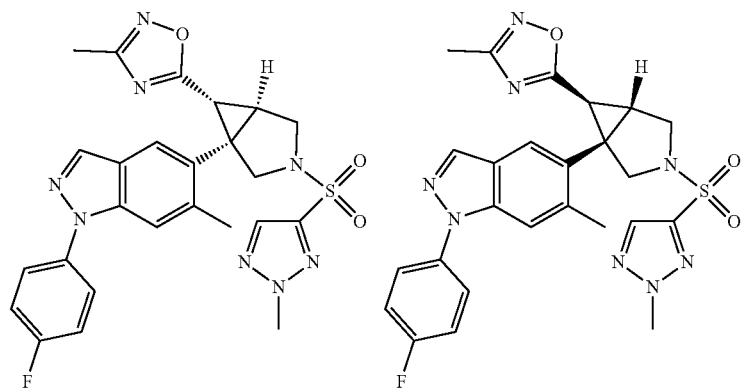

To a solution of 1-(1-(4-fluorophenyl)-6-methyl-1H-indazol-5-yl)-3-((2-methyl-2H-1,2,3-triazol-4-yl)sulfonyl)-3-azabicyclo[3.1.0]hexane-6-carboxylic acid (50 mg, 87 µmol) (Intermediate R) and carbodiimide (28 mg, 0.17 mmol) in acetonitrile (2 mL) was added (E)-N'-hydroxyacetimidamide (16 mg, 0.22 mmol). The reaction mixture was stirred at room temperature overnight. A further portion of carbodiimide (28 mg, 0.17 mmol) was added, and the reaction mixture was stirred for 15 min at room temperature. N-hydroxyacetimidamide (16 mg, 0.22 mmol) was then added, and stirring was continued for 1 hr. DBU (111 mg, 110 µL, 730 µmol) was added, and stirring was continued at 80° C. for 3 h. The reaction mixture was diluted with water (10 mL) and extracted into DCM (3×10 mL). The combined organic layers were dried using MgSO$_4$, filtered, and concentrated under reduced pressure. The crude product was purified by chromatography on silica gel (4 g cartridge, 0-100% EtOAc/isohexane) to afford 5-(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)-3-methyl-1,2,4-oxadiazole (21.49 mg, 38 µmol, 44%) as a yellow solid; Rt 1.98 min (Method 7); m/z 535.5 (M+H)$^+$ (ES$^+$). δH (DMSO-d6, 400 MHz) δ 8.26 (s, 1H), 8.19 (s, 1H), 7.77-7.70 (m, 2H), 7.50 (s, 1H), 7.41-7.32 (m, 2H), 4.29 (s, 3H), 4.12 (br. s, 1H), 3.94-3.76 (m, 2H), 3.42-3.31 (m, 1H), 2.98-2.93 (m, 1H), 2.82-2.76 (m, 1H), 2.33 (s, 3H), 2.06 (s, 3H)—one ArH not observed due to broadening of peaks).

Example 132: 5-(6-(((1H-pyrazol-1-yl)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole

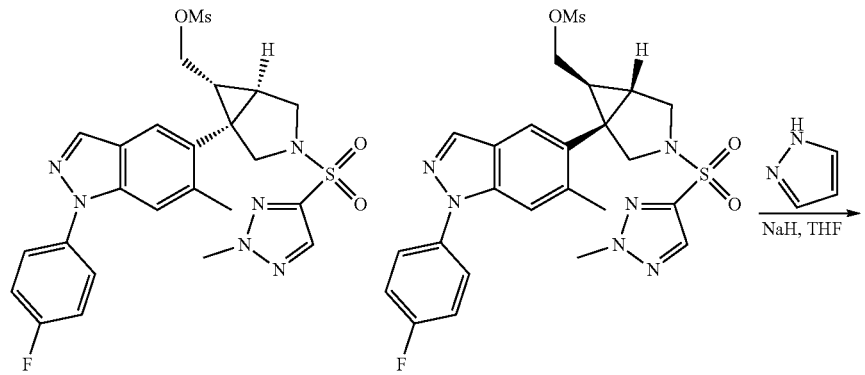

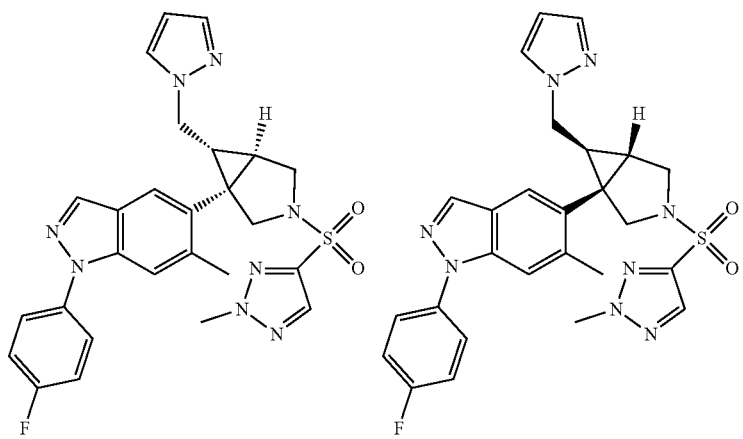

To a solution of 1H-pyrazole (10 mg, 0.15 mmol) in THF (0.5 mL) at 0° C. was added sodium hydride (7.1 mg, 60% Wt, 0.18 mmol). The reaction mixture was stirred at this temperature for 15 min, and then 1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl methanesulfonate (40 mg, 71 µmol) (Intermediate Q) was added. The reaction mixture was heated to reflux and stirred overnight. The reaction mixture was quenched with water (10 mL) and extracted into DCM (3×10 mL). The combined organic layers were dried using MgSO$_4$, filtered, and concentrated under reduced pressure. The crude product was purified by chromatography on silica gel (4 g cartridge, 0-60% EtOAc/isohexane), to afford 5-(6-(((1H-pyrazol-1-yl)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole (7.79 mg, 14 µmol, 19%) as a white solid; Rt 1.98 min (Method 7); m/z 533.1 (M+H)$^+$ (ES$^+$). δH 8.22 (s, 1H), 8.19 (s, 1H), 7.79-7.73 (m, 3H), 7.60 (s, 1H), 7.46-7.34 (m, 4H), 6.18 (s, 1H), 4.25 (s, 3H), 4.10-3.88 (m, 2H), 3.71-3.36 (m, 4H), 3.28-3.18 (m, 1H), 2.36 (s, 3H), 1.78-1.60 (m, 1H).

Example 133: 2-(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)oxazole

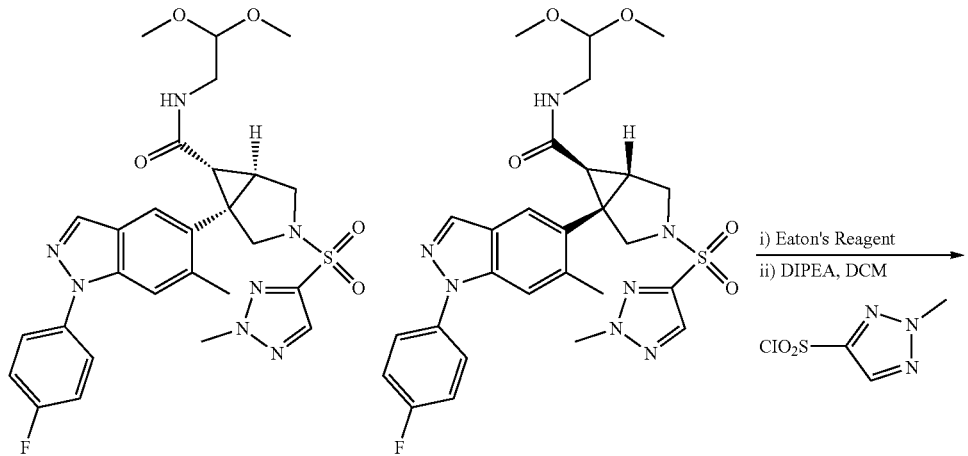

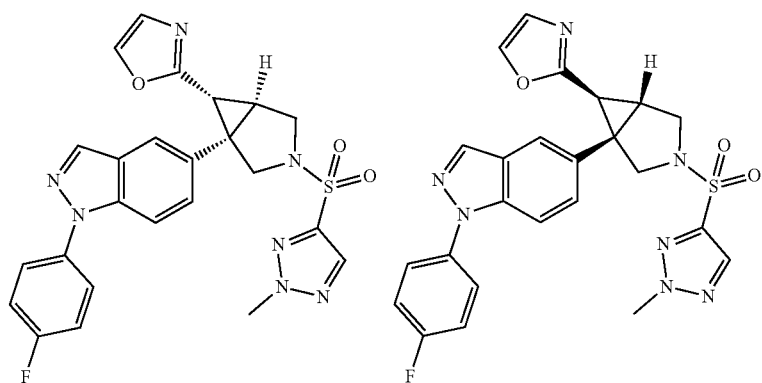

A solution of N-(2,2-dimethoxyethyl)-1-(1-(4-fluorophenyl)-6-methyl-1H-indazol-5-yl)-3-((2-methyl-2H-1,2,3-triazol-4-yl)sulfonyl)-3-azabicyclo[3.1.0]hexane-6-carboxamide (75 mg, 90 μmol) (prepared by a similar method to Example 55) in Eaton's reagent (0.83 g, 0.55 mL, 0.45 mmol) was heated at 135° C. for 18 h. A further portion of Eaton's reagent (0.83 g, 0.55 mL, 0.45 mmol) was added, and stirring was continued for a further 18 h. The reaction mixture was quenched carefully with saturated aqueous NaHCO$_3$ solution (50 mL) and extracted into DCM (3×20 mL). The combined organic layers were dried using MgSO$_4$, filtered and concentrated under reduced pressure to give 2-(1-(1-(4-fluorophenyl)-6-methyl-1H-indazol-5-yl)-3-azabicyclo[3.1.0]hexan-6-yl)oxazole (48 mg, 71%). This material was re-dissolved in DCM (1 mL) and DIPEA (29.5 mg, 39.8 μL, 229 μmol) was added, followed by 2-methyl-2H-1,2,3-triazole-4-sulfonyl chloride (16.6 mg, 91.4 μmol). The reaction mixture was stirred at room temperature for 20 min. The reaction mixture was concentrated onto silica gel and purified by chromatography on silica gel (4 g cartridge, 0-100% EtOAc/isohexane) to afford 2-(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)oxazole (1.54 mg, 2.8 μmol, 6.2%) as a white solid; Rt 2.06 min (Method 7); m/z 520.1 (M+H)$^+$ (ES$^+$). δH 8.22-7.92 (m, 2H), 7.87-7.58 (m, 3H), 7.57-7.44 (m, 1H), 7.40-7.18 (m, 3H), 7.00-6.75 (m, 1H), 4.41-4.17 (m, 4H), 4.03-3.43 (m, 3H), 3.05-2.71 (m, 2H), 2.47-2.29 (m, 3H).

Example 134: 2-(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)benzo[d]oxazole

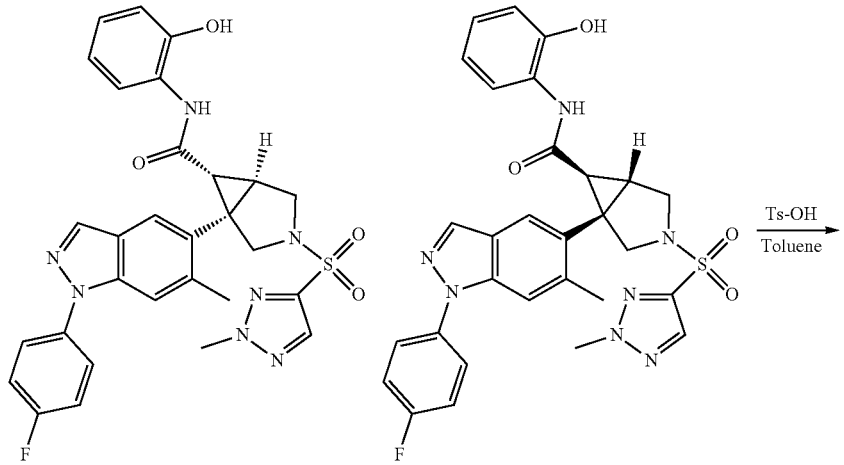

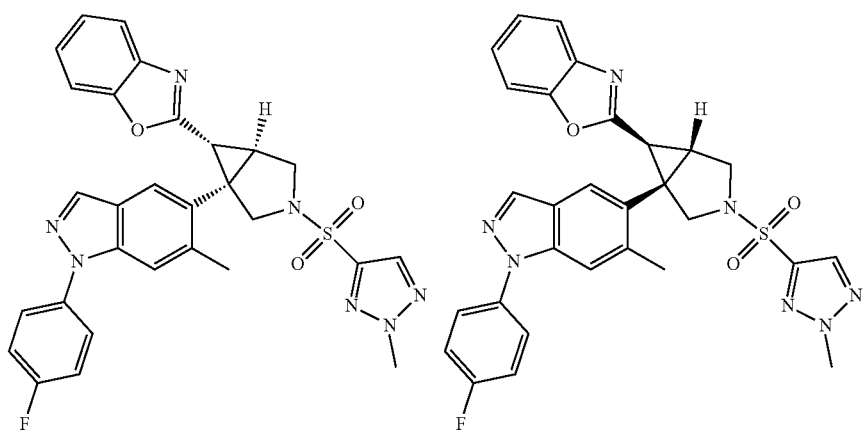

To a solution of 1-(1-(4-fluorophenyl)-6-methyl-1H-indazol-5-yl)-N-(2-hydroxyphenyl)-3-((2-methyl-2H-1,2,3-triazol-4-yl)sulfonyl)-3-azabicyclo[3.1.0]hexane-6-carboxamide (24 mg, 35 μmol) (prepared by a similar method to Example 55) in toluene (1 mL) was added tosic acid, monohydrate (1.4 mg, 6.9 μmol). The reaction mixture was heated under reflux overnight. The reaction mixture was cooled to room temperature and quenched with saturated aqueous NaHCO$_3$ solution. The reaction mixture was extracted into DCM (3×20 mL). The combined organic layers were dried using MgSO$_4$, filtered, and concentrated under reduced pressure. The crude product was purified by chromatography on silica gel (4 g cartridge, 0-100% EtOAc/isohexane) to afford 2-(1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)benzo[d]oxazole (6.96 mg, 12 μmol, 33%) as an off-white solid; Rt 2.23 min (Method 7); m/z 570.1 (M+H)$^+$ (ES$^+$). δH 8.27 (s, 1H), 8.23-7.75 (m, 2H), 7.76-7.59 (m, 2H), 7.54-7.37 (m, 3H), 7.32 (t, J=8.8 Hz, 2H), 7.25-7.10 (m, 2H), 4.31 (s, 3H), 4.27-4.03 (m, 1H), 4.00-3.78 (m, 2H), 3.40 (d, J=10.3 Hz, 1H), 3.13-3.03 (m, 1H), 2.78 (d, J=4.2 Hz, 1H), 2.37 (s, 3H).

Example 135: N-((1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl)acetamide

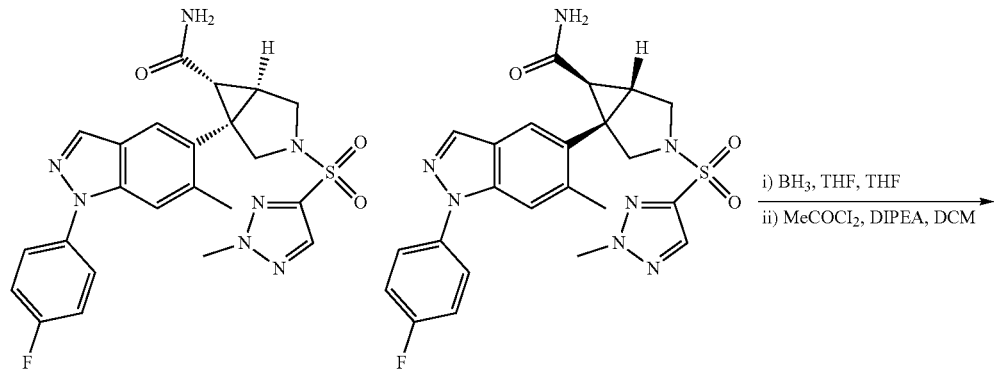

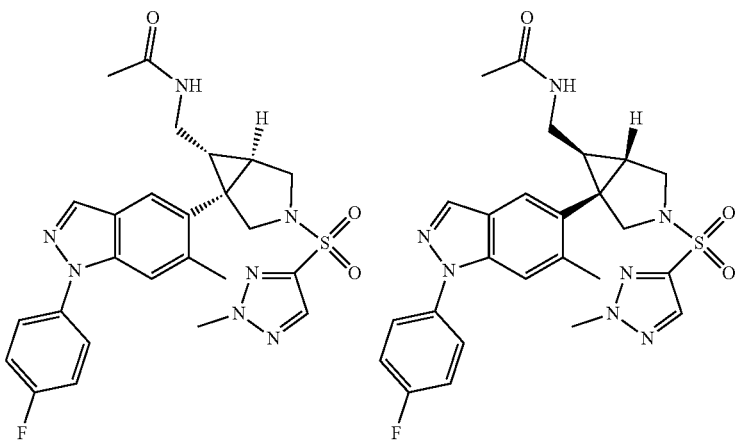

To a solution of 1-(1-(4-fluorophenyl)-6-methyl-1H-indazol-5-yl)-3-((2-methyl-2H-1,2,3-triazol-4-yl)sulfonyl)-3-azabicyclo[3.1.0]hexane-6-carboxamide (33 mg, 67 μmol) (prepared using a similar method to Example 55) in THF (1 mL) at 0° C. was added borane·THF complex (23 mg, 0.27 mL, 1 molar THF). The reaction mixture was stirred with warming to room temperature for 4 hr. A further portion of borane·THF (23 mg, 0.27 mL, 1 molar THF) was added, and stirring was continued for 72 hr. The reaction mixture was quenched by the addition of Na$_2$SO$_4$·10H$_2$O and stirred at room temperature until effervescence ceased. The solids were removed by filtration, washing with THF (2×10 mL), and the filtrate was concentrated under reduced pressure and purified by chromatography on silica gel (4 g cartridge, 0-10% (0.7 M Ammonia/MeOH)/DCM) to afford (1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methanamine (11 mg, 21 μmol, 24%) as a white solid. This material was dissolved in DCM (0.5 mL) and DIPEA (8.2 mg, 11 μL, 64 μmol) was added, followed by acetyl chloride (2.0 mg, 1.8 μL, 25 μmol). The reaction mixture was stirred with warming to room temperature overnight. The reaction mixture was concentrated onto silica gel and purified by chromatography on silica gel (4 g cartridge, 0-10% (0.7 M Ammonia/MeOH)/DCM) to afford N-((1-(1-(4-fluorophenyl)-6-methyl-1H-indazol-5-yl)-3-((2-methyl-2H-1,2,3-triazol-4-yl)sulfonyl)-3-azabicyclo[3.1.0]hexan-6-yl)methyl)acetamide (8.31 mg, 15 μmol, 71%) as a white solid; Rt 1.74 min (Method 7); m/z 524.3 (M+H)$^+$ (ES$^+$). δH 8.38-8.28 (m, 1H), 8.28-8.20 (m, 1H), 8.04-7.82 (m, 1H), 7.81-7.58 (m, 4H), 7.47-7.35 (m, 2H), 4.34-4.19 (m, 3H), 4.02-3.86 (m, 1H), 3.70-3.49 (m, 2H), 3.14 2.89 (m, 3H), 2.23-1.99 (m, 3H), 1.86-1.67 (m, 3H), 1.52-1.34 (m, 1H)—one proton obscured by DMSO.

Examples 138-140

TABLE 8

The examples shown in the table below were prepared by similar methods to those described for Example 69

| Example | Structure | LC-MS analysis |
|---|---|---|
| 138 | 1-(4-fluorophenyl)-5-(3-((2-(2-methoxyethoxy)ethyl)sulfonyl)-6-phenyl-3-azabicyclo[3.1.0]hexan-1-yl)-6-methyl-1H-indazole | R$^t$ 2.27 min (Method 7); m/z 550.2 (M + H)$^+$ (ES$^+$) |
| 139 | 5-(3-(cyclobutylsulfonyl)-6-phenyl-3-azabicyclo[3.1.0]hexan-1-yl)-1-(4-fluorophenyl)-6-methyl-1H-indazole | R$^t$ 2.33 min (Method 7); m/z 502.4 (M + H)$^+$ (ES$^+$) |
| 140 | 5-(3-(oxetan-3-ylsulfonyl)-6-phenyl-3-azabicyclo[3.1.0]hexan-1-yl)-1-(4-fluorophenyl)-6-methyl-1H-indazole | R$^t$ 2.14 min (Method 7); m/z 504.3 (M + H)$^+$ (ES$^+$) |

Examples 141-163

TABLE 9

The examples shown in the table below were prepared by similar methods to those described for Example 110

| Example | Structure | LC-MS analysis |
|---|---|---|
| 141 | 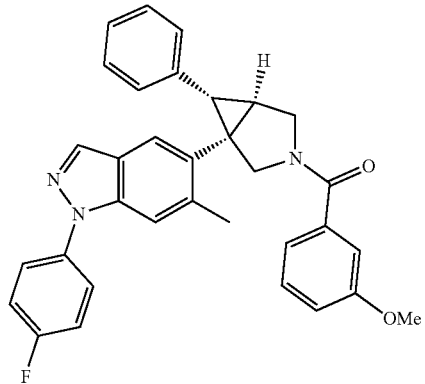 (1-(1-(4-fluorophenyl)-6-methyl-1H-indazol-5-yl)-6-phenyl-3-azabicyclo[3.1.0]hexan-3-yl)(3-methoxyphenyl)methanone | $R^t$ 2.30 min (Method 7); m/z 518.2 $(M + H)^+$ $(ES^+)$ |
| 142 | 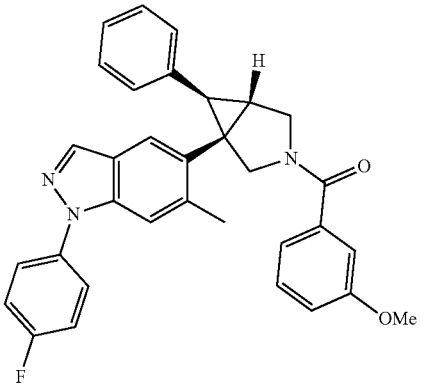 (1-(1-(4-fluorophenyl)-6-methyl-1H-indazol-5-yl)-6-phenyl-3-azabicyclo[3.1.0]hexan-3-yl)(3-morpholinophenyl)methanone | $R^t$ 2.24 min (Method 7); m/z 573.8 $(M + H)^+$ $(ES^+)$ |
| 143 | 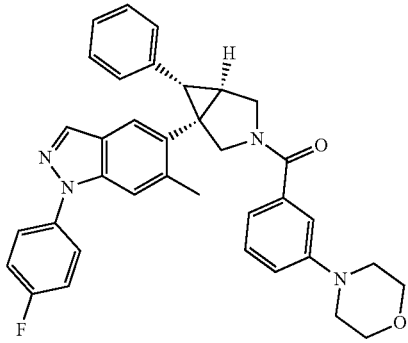 (3-(difluoromethyl)phenyl)(1-(1-(4-fluorophenyl)-6-methyl-1H-indazol-5-yl)-6-phenyl-3-azabicyclo[3.1.0]hexan-3-yl)methanone | $R^t$ 2.28 min (Method 7); m/z 538.2 $(M + H)^+$ $(ES^+)$ |

345 346

TABLE 9-continued

The examples shown in the table below were prepared by similar methods to those described for Example 110

| Example | Structure | LC-MS analysis |
|---|---|---|
| 144 | 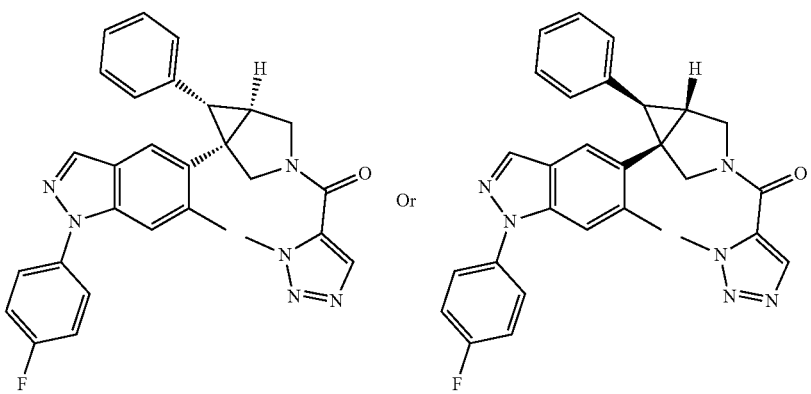 [SMILES: Cc1cc2c(cnn2-c2ccc(F)cc2)cc1[C@@]12CN(C(=O)c3cnnn3C)C[C@@H]1[C@H]2c1ccccc1 ; Cc1cc2c(cnn2-c2ccc(F)cc2)cc1[C@]12CN(C(=O)c3cnnn3C)C[C@H]1[C@@H]2c1ccccc1] Or 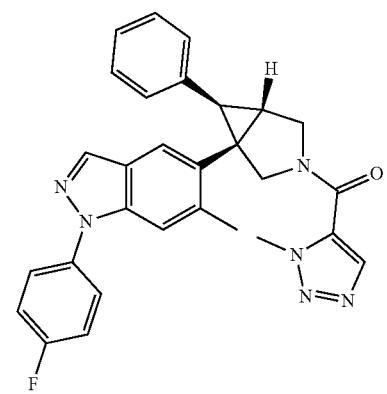<br>(1-(1-(4-fluorophenyl)-6-methyl-1H-indazol-5-yl)-6-phenyl-3-azabicyclo[3.1.0]hexan-3-yl)(1-methyl-1H-1,2,3-triazol-5-yl)methanone | $R^t$ 2.17 min (Method 9); m/z 493.1 $(M + H)^+$ $(ES^+)$ |
| 145 | 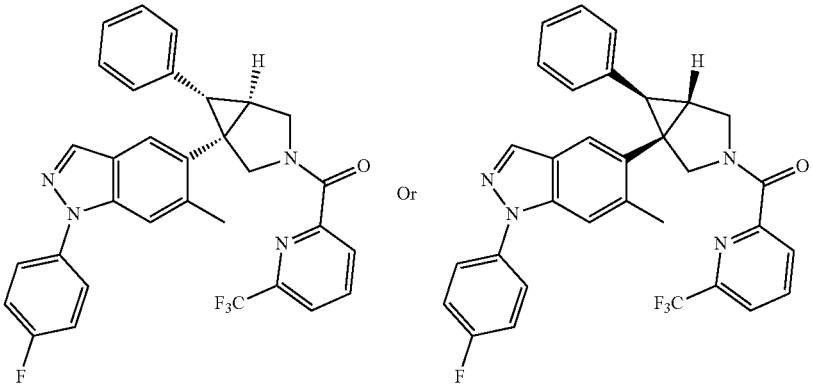 [SMILES: Cc1cc2c(cnn2-c2ccc(F)cc2)cc1[C@@]12CN(C(=O)c3cccc(C(F)(F)F)n3)C[C@@H]1[C@H]2c1ccccc1 ; Cc1cc2c(cnn2-c2ccc(F)cc2)cc1[C@]12CN(C(=O)c3cccc(C(F)(F)F)n3)C[C@H]1[C@@H]2c1ccccc1] Or 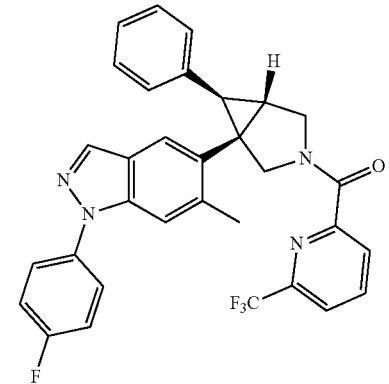<br>(1-(1-(4-fluorophenyl)-6-methyl-1H-indazol-5-yl)-6-phenyl-3-azabicyclo[3.1.0]hexan-3-yl)(6-(trifluoromethyl)pyridin-2-yl)methanone | $R^t$ 2.37 min (Method 9); m/z 557.2 $(M + H)^+$ $(ES^+)$ |
| 146 | 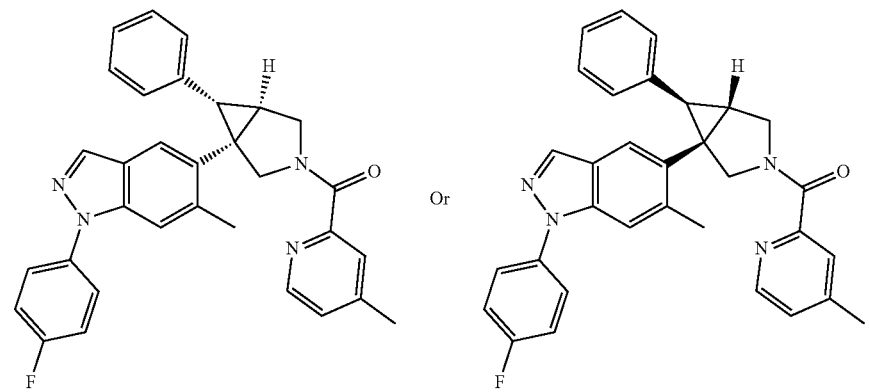 [SMILES: Cc1ccnc(C(=O)N2C[C@@H]3[C@@H](c4ccccc4)[C@]3(c3cc4cnn(-c5ccc(F)cc5)c4cc3C)C2)c1 ; Cc1ccnc(C(=O)N2C[C@H]3[C@H](c4ccccc4)[C@@]3(c3cc4cnn(-c5ccc(F)cc5)c4cc3C)C2)c1] Or 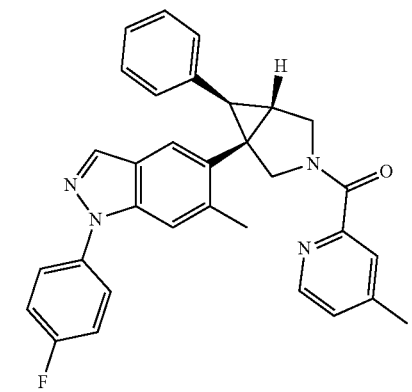<br>(1-(1-(4-fluorophenyl)-6-methyl-1H-indazol-5-yl)-6-phenyl-3-azabicyclo[3.1.0]hexan-3-yl)(4-methylpyridin-2-yl)methanone | $R^t$ 2.36 min (Method 9); m/z 503.2 $(M + H)^+$ $(ES^+)$ |

TABLE 9-continued

The examples shown in the table below were prepared by similar methods to those described for Example 110

| Example | Structure | LC-MS analysis |
|---|---|---|
| 147 | 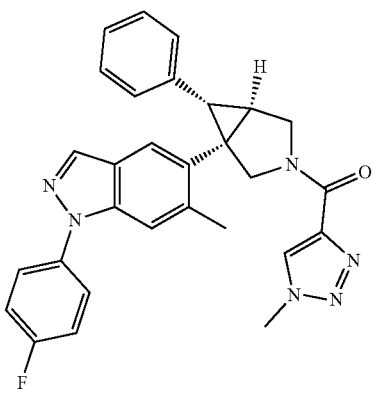<br>(1-(1-(4-fluorophenyl)-6-methyl-1H-indazol-5-yl)-6-phenyl-3-azabicyclo[3.1.0]hexan-3-yl)(1-methyl-1H-1,2,3-triazol-4-yl)methanone | R$^t$ 2.01 min (Method 7); m/z 493.1 (M + H)$^+$ (ES$^+$) |
| 148 | 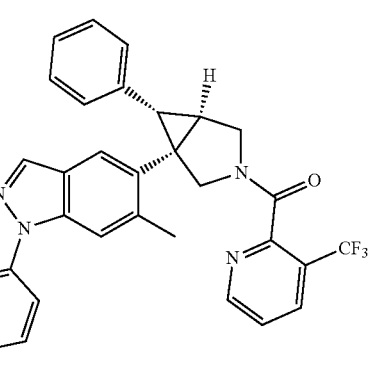<br>(1-(1-(4-fluorophenyl)-6-methyl-1H-indazol-5-yl)-6-phenyl-3-azabicyclo[3.1.0]hexan-3-yl)(3-(trifluoromethyl)pyridin-2-yl)methanone | R$^t$ 2.25 min (Method 7); m/z 557.3 (M + H)$^+$ (ES$^+$) |
| 149 | 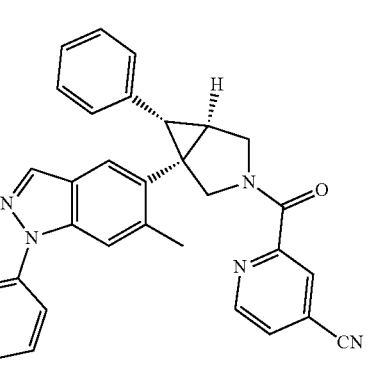<br>2-(1-(1-(4-fluorophenyl)-6-methyl-1H-indazol-5-yl)-6-phenyl-3-azabicyclo[3.1.0]hexane-3-carbonyl)isonicotinonitrile | R$^t$ 2.35 min (Method 9); m/z 514.1 (M + H)$^+$ (ES$^+$) |

TABLE 9-continued

The examples shown in the table below were prepared by similar methods to those described for Example 110

| Example | Structure | LC-MS analysis |
|---------|-----------|----------------|
| 150 | 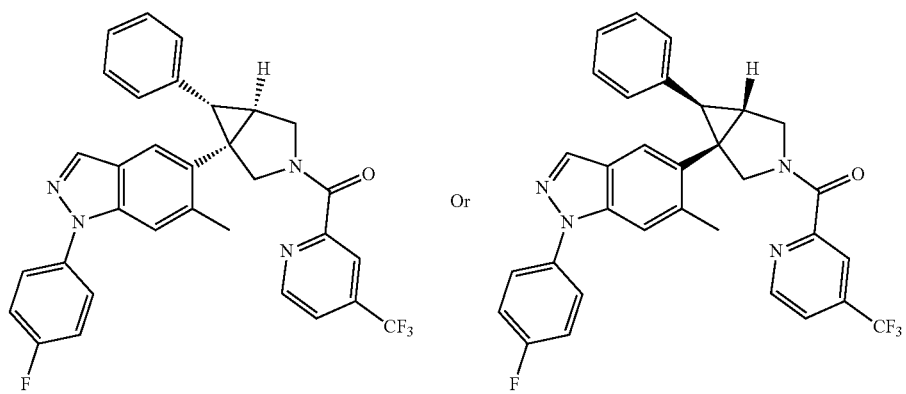 [SMILES: Cc1cc2c(cnn2-c2ccc(F)cc2)cc1[C@@]12CN(C(=O)c3cc(C(F)(F)F)ccn3)C[C@@H]1[C@H]2c1ccccc1 ; Cc1cc2c(cnn2-c2ccc(F)cc2)cc1[C@]12CN(C(=O)c3cc(C(F)(F)F)ccn3)C[C@H]1[C@@H]2c1ccccc1] (1-(1-(4-fluorophenyl)-6-methyl-1H-indazol-5-yl)-6-phenyl-3-azabicyclo[3.1.0]hexan-3-yl)(4-(trifluoromethyl)pyridin-2-yl)methanone | $R^t$ 2.55 min (Method 9); m/z 557.1 $(M + H)^+$ $(ES^+)$ |
| 151 | 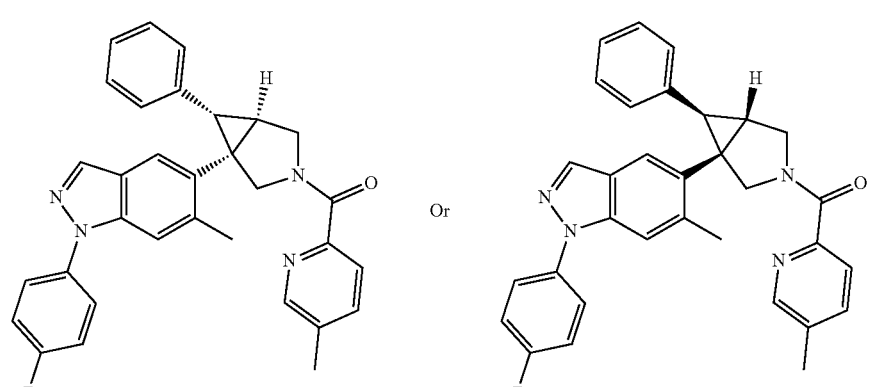 (1-(1-(4-fluorophenyl)-6-methyl-1H-indazol-5-yl)-6-phenyl-3-azabicyclo[3.1.0]hexan-3-yl)(5-methylpyridin-2-yl)methanone | $R^t$ 2.23 min (Method 7); m/z 503.3 $(M + H)^+$ $(ES^+)$ |
| 152 | 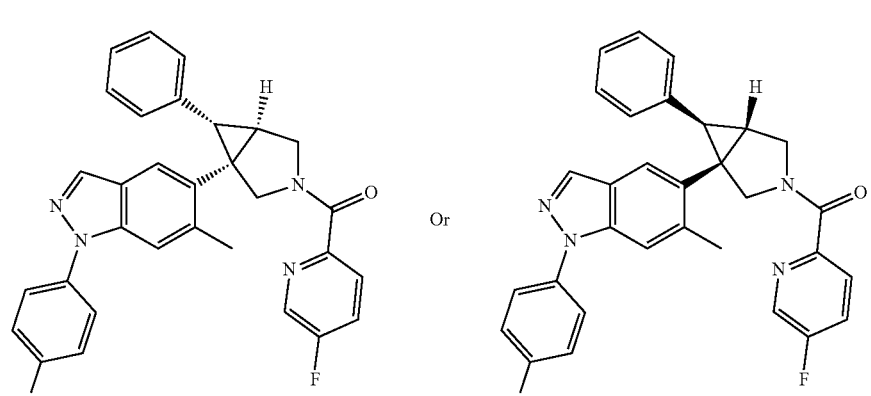 (1-(1-(4-fluorophenyl)-6-methyl-1H-indazol-5-yl)-6-phenyl-3-azabicyclo[3.1.0]hexan-3-yl)(5-fluoropyridin-2-yl)methanone | $R^t$ 2.24 min (Method 7); m/z 507.4 $(M + H)^+$ $(ES^+)$ |

TABLE 9-continued

The examples shown in the table below were prepared by similar methods to those described for Example 110

| Example | Structure | LC-MS analysis |
|---|---|---|
| 153 | 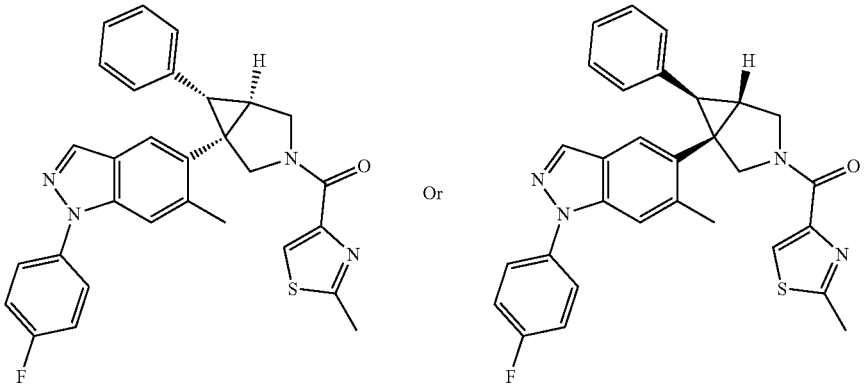 [SMILES: Cc1nc(C(=O)N2C[C@@H]3[C@@H](c4ccccc4)[C@]3(c3cc4cnn(-c5ccc(F)cc5)c4cc3C)C2)cs1 ; Cc1nc(C(=O)N2C[C@H]3[C@H](c4ccccc4)[C@@]3(c3cc4cnn(-c5ccc(F)cc5)c4cc3C)C2)cs1]<br>(1-(1-(4-fluorophenyl)-6-methyl-1H-indazol-5-yl)-6-phenyl-3-azabicyclo[3.1.0]hexan-3-yl)(2-methylthiazol-4-yl)methanone | R$^t$ 2.21 min (Method 9); m/z 509.2 (M + H)$^+$ (ES$^+$) |
| 154 | 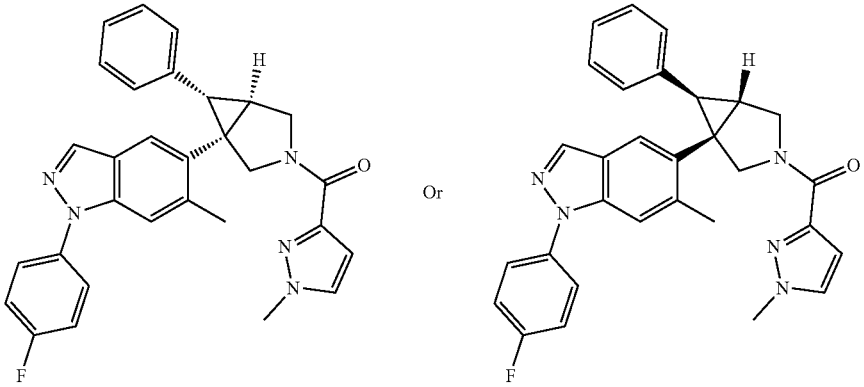 [SMILES: Cc1cc2c(cnn2-c2ccc(F)cc2)cc1[C@@]12CN(C(=O)c3ccn(C)n3)C[C@@H]1[C@H]2c1ccccc1 ; Cc1cc2c(cnn2-c2ccc(F)cc2)cc1[C@]12CN(C(=O)c3ccn(C)n3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(1-methyl-1H-pyrazol-3-yl)methanone | R$^t$ 2.09 min (Method 9); m/z 492.2 (M + H)$^+$ (ES$^+$) |
| 155 | 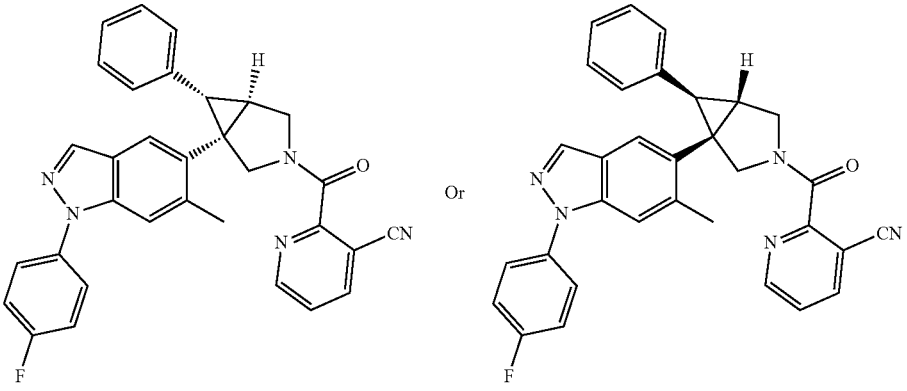<br>2-(1-(1-(4-fluorophenyl)-6-methyl-1H-indazol-5-yl)-6-phenyl-3-azabicyclo[3.1.0]hexane-3-carbonyl)nicotinonitrile | R$^t$ 2.22 min (Method 9); m/z 514.1 (M + H)$^+$ (ES$^+$) |

TABLE 9-continued

The examples shown in the table below were prepared by similar methods to those described for Example 110

| Example | Structure | LC-MS analysis |
|---|---|---|
| 156 | 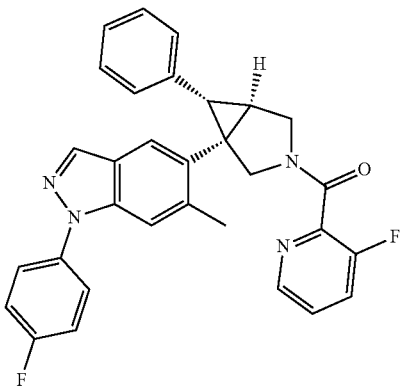<br>(1-(1-(4-fluorophenyl)-6-methyl-1H-indazol-5-yl)-6-phenyl-3-azabicyclo[3.1.0]hexan-3-yl)(3-fluoropyridin-2-yl)methanone | R$^t$ 2.22 min (Method 9); m/z 507.1 (M + H)$^+$ (ES$^+$) |
| 157 | 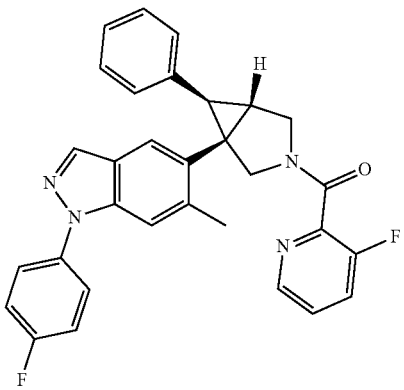<br>(3,5-difluoropyridin-2-yl)(1-(1-(4-fluorophenyl)-6-methyl-1H-indazol-5-yl)-6-phenyl-3-azabicyclo[3.1.0]hexan-3-yl)methanone | R$^t$ 2.30 min (Method 9); m/z 525.1 (M + H)$^+$ (ES$^+$) |
| 158 | 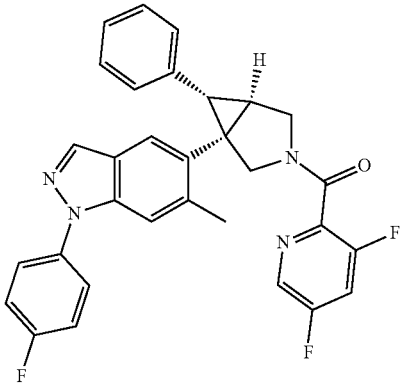<br>(1-(1-(4-fluorophenyl)-6-methyl-1H-indazol-5-yl)-6-phenyl-3-azabicyclo[3.1.0]hexan-3-yl)(thiazol-2-yl)methanone | R$^t$ 2.41 min (Method 9); m/z 495.0 (M + H)$^+$ (ES$^+$) |

TABLE 9-continued

The examples shown in the table below were prepared by similar methods to those described for Example 110

| Example | Structure | LC-MS analysis |
|---|---|---|
| 159 | 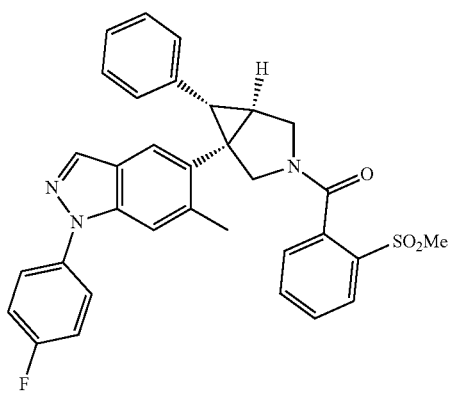<br>(1-(1-(4-fluorophenyl)-6-methyl-1H-indazol-5-yl)-6-phenyl-<br>3-azabicyclo[3.1.0]hexan-3-yl)(2-<br>(methylsulfonyl)phenyl)methanone | R$^t$ 2.26 min (Method 9); m/z 566.1 (M + H)$^+$ (ES$^+$) |
| 160 | 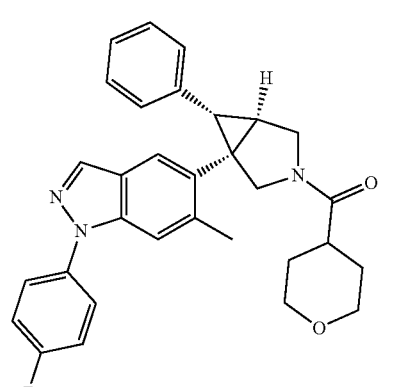<br>(1-(1-(4-fluorophenyl)-6-methyl-1H-indazol-5-yl)-6-phenyl-<br>3-azabicyclo[3.1.0]hexan-3-yl)(tetrahydro-2H-pyran-4-<br>yl)methanone | R$^t$ 2.07 min (Method 7); m/z 496.3 (M + H)$^+$ (ES$^+$) |
| 161 | 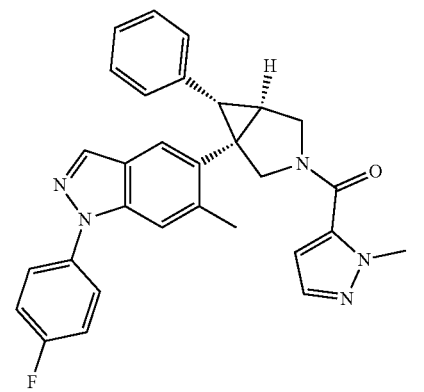<br>(1-(1-(4-fluorophenyl)-6-methyl-1H-indazol-5-yl)-6-phenyl-<br>3-azabicyclo[3.1.0]hexan-3-yl)(1-methyl-1H-pyrazol-5-<br>yl)methanone | R$^t$ 2.11 min (Method 7); m/z 492.2 (M + H)$^+$ (ES$^+$) |

TABLE 9-continued

The examples shown in the table below were prepared by similar methods to those described for Example 110

| Example | Structure | LC-MS analysis |
|---|---|---|
| 162 | 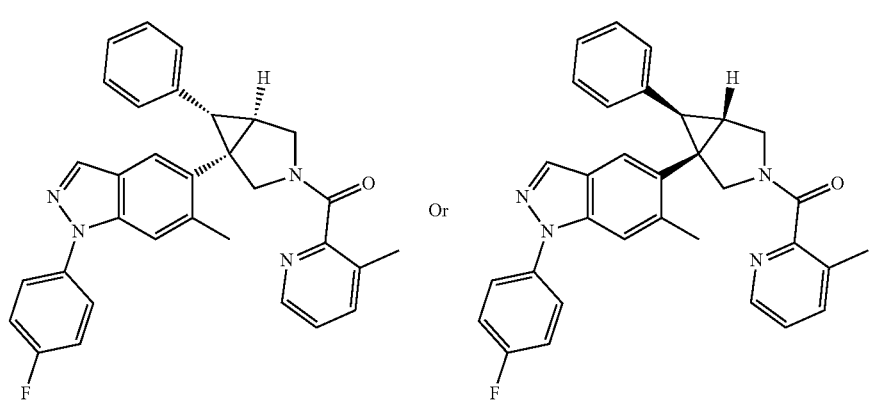 [SMILES: Cc1cc2c(cnn2-c2ccc(F)cc2)cc1[C@@]12CN(C(=O)c3ncccc3C)C[C@@H]1[C@H]2c1ccccc1 ; Cc1cc2c(cnn2-c2ccc(F)cc2)cc1[C@]12CN(C(=O)c3ncccc3C)C[C@H]1[C@@H]2c1ccccc1] Or 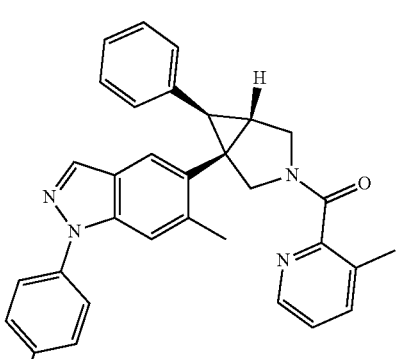<br>(1-(1-(4-fluorophenyl)-6-methyl-1H-indazol-5-yl)-6-phenyl-3-azabicyclo[3.1.0]hexan-3-yl)(3-methylpyridin-2-yl)methanone | $R^t$ 2.12 min (Method 7); m/z 503.4 $(M + H)^+$ $(ES^+)$ |
| 163 | 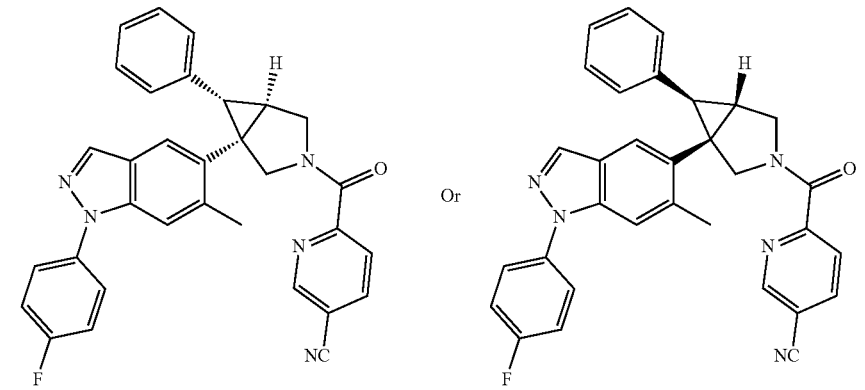 [SMILES: Cc1cc2c(cnn2-c2ccc(F)cc2)cc1[C@@]12CN(C(=O)c3ccc(C#N)cn3)C[C@@H]1[C@H]2c1ccccc1 ; Cc1cc2c(cnn2-c2ccc(F)cc2)cc1[C@]12CN(C(=O)c3ccc(C#N)cn3)C[C@H]1[C@@H]2c1ccccc1] Or 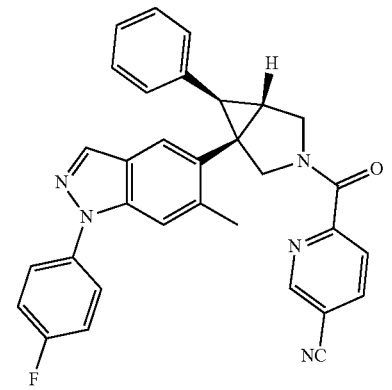<br>6-(1-(1-(4-fluorophenyl)-6-methyl-1H-indazol-5-yl)-6-phenyl-3-azabicyclo[3.1.0]hexane-3-carbonyl)nicotinonitrile | $R^t$ 2.18 min (Method 7); m/z 514.5 $(M + H)^+$ $(ES^+)$ |

Example 164: 6-(1-(1-(4-fluorophenyl)-6-methyl-1H-indazol-5-yl)-6-phenyl-3-azabicyclo[3.1.0]hexane-3-carbonyl)picolinonitrile
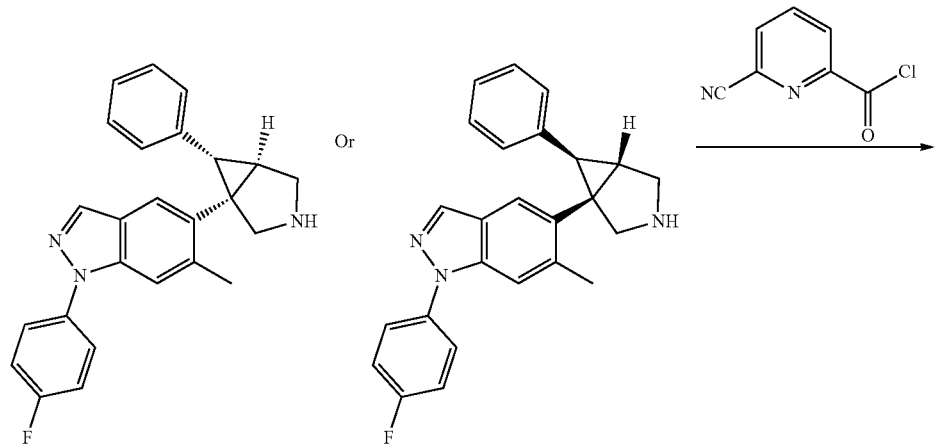
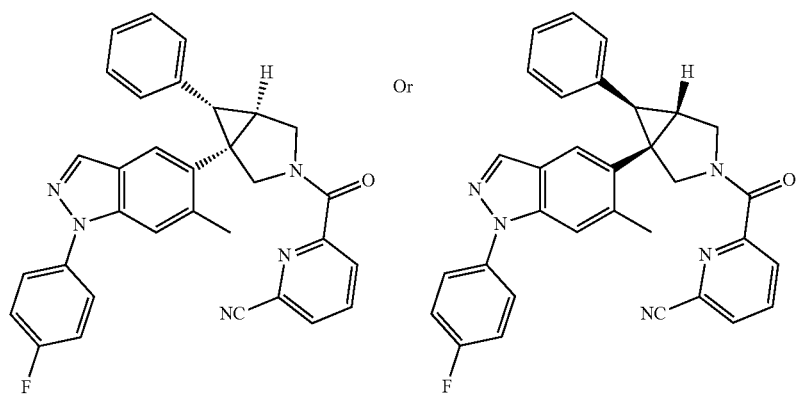

DCM (150 mL) was charged to an agitated reactor under nitrogen at rt followed by the addition of 1-(4-fluorophenyl)-6-methyl-5-(6-phenyl-3-azabicyclo[3.1.0]hexan-1-yl)-1H-indazole (Intermediate X, 7.5 g, 0.02 mol), 6-cyano-2-pyridinecarbonyl chloride (3.3 g, 0.02 mol), N-(3-Dimethylaminopropyl)-N'-ethylcarbodiimide hydrochloride (5.8 g, 0.03 mol) and 1-hydroxybenzotriazole (2.7 g, 0.02 mol). The reaction mixture was stirred for at least 2 hr at rt, filtered and the filter cake washed with DCM (23 ml). The combined filtrates were washed with 5% aqueous HCl (75 mL), 5% aqueous NaHCO$_3$ (75 mL), 5% aqueous NaCl (75 mL) and then concentrated under reduced pressure. The resulting residue was purified by silica chromatography to provide 6-(1-(1-(4-fluorophenyl)-6-methyl-1H-indazol-5-yl)-6-phenyl-3-azabicyclo[3.1.0]hexane-3-carbonyl)picolinonitrile as an off-white solid in 35% yield and a purity of >97% by HPLC. R$^t$ 2.19 min (Method 7). m/z 514.3 (M+H)$^+$ (ES$^+$). δH NMR (300 MHz, DMSO) δ 8.33-7.97 (m, 5H), 7.75-7.68 (m, 2H), 7.41-7.33 (m, 3H), 7.08-6.84 (m, 5H), 4.70-4.43 (m, 1H), 4.32-4.03 (m, 2H), 4.00-3.50 (m, 1H), 2.75-2.36 (m, 3H), 2.42 (s, 1H) and 2.09 (s, 1H).

Examples 165-178

TABLE 10

The examples shown in the table below were prepared by similar methods to those described for Example 110

| Example | Structure | LC-MS analysis |
|---|---|---|
| 165 | 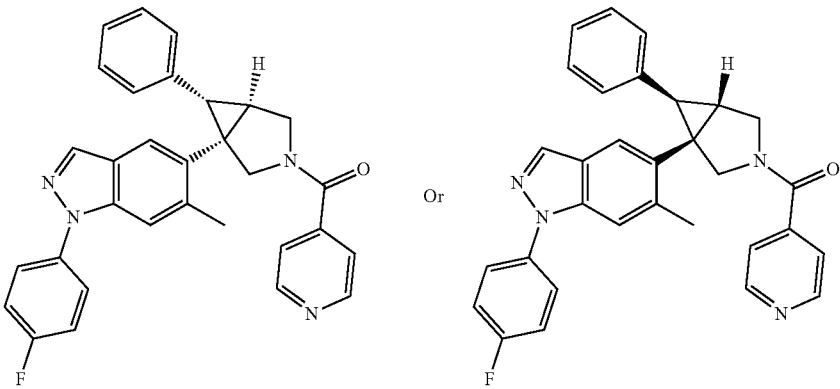 [SMILES: Cc1cc2c(cnn2-c2ccc(F)cc2)cc1[C@@]12CN(C(=O)c3ccncc3)C[C@@H]1[C@H]2c1ccccc1 ; Cc1cc2c(cnn2-c2ccc(F)cc2)cc1[C@]12CN(C(=O)c3ccncc3)C[C@H]1[C@@H]2c1ccccc1] (1-(1-(4-fluorophenyl)-6-methyl-1H-indazol-5-yl)-6-phenyl-3-azabicyclo[3.1.0]hexan-3-yl)(pyridin-4-yl)methanone | R$^t$ 2.06 min (Method 9); m/z 489.1 (M + H)$^+$ (ES$^+$) |
| 166 | 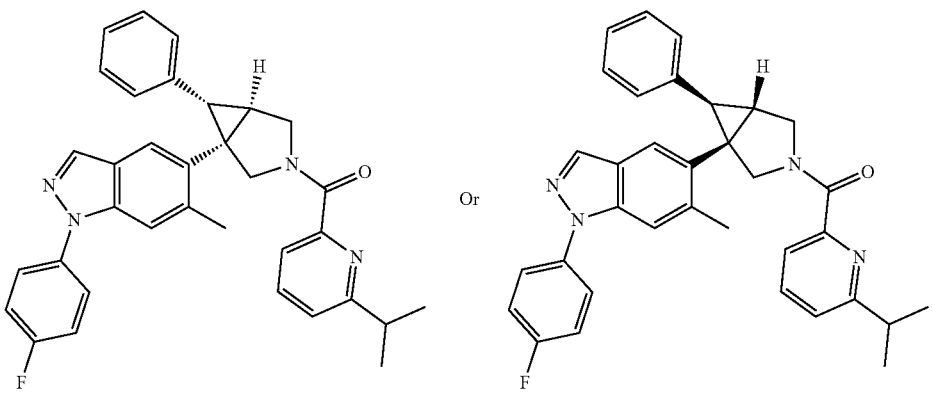 [SMILES: Cc1cc2c(cnn2-c2ccc(F)cc2)cc1[C@@]12CN(C(=O)c3cccc(C(C)C)n3)C[C@@H]1[C@H]2c1ccccc1 ; Cc1cc2c(cnn2-c2ccc(F)cc2)cc1[C@]12CN(C(=O)c3cccc(C(C)C)n3)C[C@H]1[C@@H]2c1ccccc1] (1-(1-(4-fluorophenyl)-6-methyl-1H-indazol-5-yl)-6-phenyl-3-azabicyclo[3.1.0]hexan-3-yl)(6-isopropylpyridin-2-yl)methanone | R$^t$ 2.45 min (Method 7); m/z 531.5 (M + H)$^+$ (ES$^+$) |

TABLE 10-continued

The examples shown in the table below were prepared by similar methods to those described for Example 110

| Example | Structure | LC-MS analysis |
|---|---|---|
| 167 | 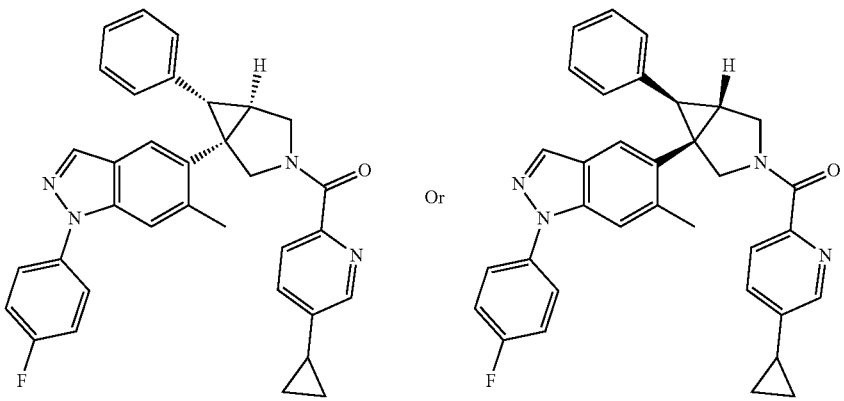 [SMILES: Cc1cc2c(cnn2-c2ccc(F)cc2)cc1[C@@]12CN(C(=O)c3ccc(C4CC4)cn3)C[C@@H]1[C@H]2c1ccccc1 ; Cc1cc2c(cnn2-c2ccc(F)cc2)cc1[C@]12CN(C(=O)c3ccc(C4CC4)cn3)C[C@H]1[C@@H]2c1ccccc1]<br>(5-cyclopropylpyridin-2-yl)(1-(1-(4-fluorophenyl)-6-methyl-1H-indazol-5-yl)-6-phenyl-3-azabicyclo[3.1.0]hexan-3-yl)methanone | $R^t$ 2.34 min (Method 7); m/z 529.4 $(M + H)^+$ $(ES^+)$ |
| 168 | 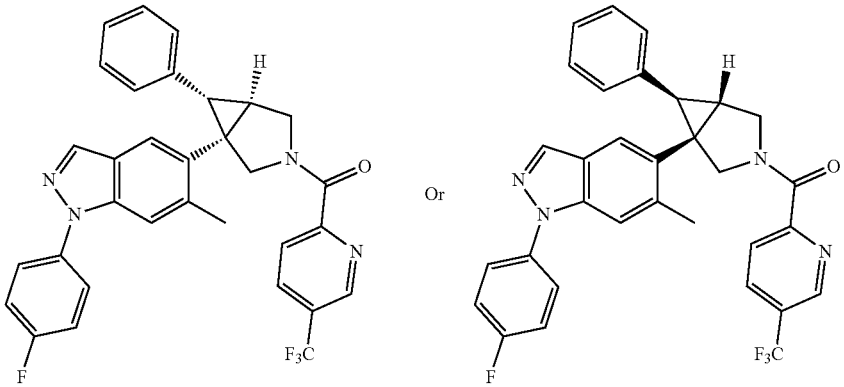 [SMILES: Cc1cc2c(cnn2-c2ccc(F)cc2)cc1[C@@]12CN(C(=O)c3ccc(C(F)(F)F)cn3)C[C@@H]1[C@H]2c1ccccc1 ; Cc1cc2c(cnn2-c2ccc(F)cc2)cc1[C@]12CN(C(=O)c3ccc(C(F)(F)F)cn3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(5-(trifluoromethyl)pyridin-2-yl)methanone | $R^t$ 2.38 min (Method 7); m/z 557.2 $(M + H)^+$ $(ES^+)$ |
| 169 | 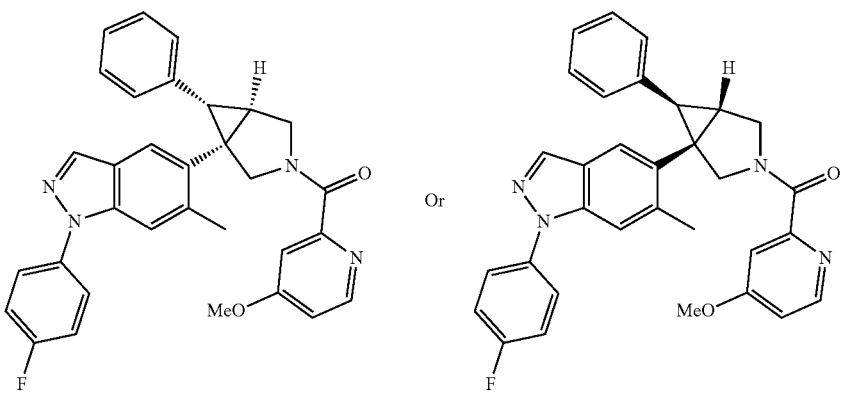 [SMILES: COc1ccnc(C(=O)N2C[C@@H]3[C@@H](c4ccccc4)[C@]3(c3cc4cnn(-c5ccc(F)cc5)c4cc3C)C2)c1 ; COc1ccnc(C(=O)N2C[C@H]3[C@H](c4ccccc4)[C@@]3(c3cc4cnn(-c5ccc(F)cc5)c4cc3C)C2)c1]<br>(1-(1-(4-fluorophenyl)-6-methyl-1H-indazol-5-yl)-6-phenyl-3-azabicyclo[3.1.0]hexan-3-yl)(4-methoxypyridin-2-yl)methanone | $R^t$ 2.12 min (Method 7); m/z 519.1 $(M + H)^+$ $(ES^+)$ |

TABLE 10-continued

The examples shown in the table below were prepared by similar methods to those described for Example 110

| Example | Structure | LC-MS analysis |
|---|---|---|
| 170 | 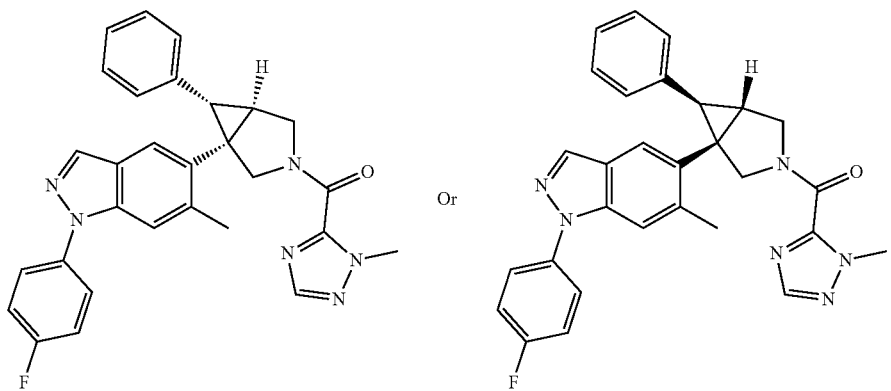 [SMILES: Cc1cc2c(cnn2-c2ccc(F)cc2)cc1[C@@]12CN(C(=O)c3ncnn3C)C[C@@H]1[C@H]2c1ccccc1 ; Cc1cc2c(cnn2-c2ccc(F)cc2)cc1[C@]12CN(C(=O)c3ncnn3C)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(1-methyl-1H-1,2,4-triazol-5-yl)methanone | R$^t$ 2.11 min (Method 7); m/z 493.4 (M + H)$^+$ (ES$^+$) |
| 171 | 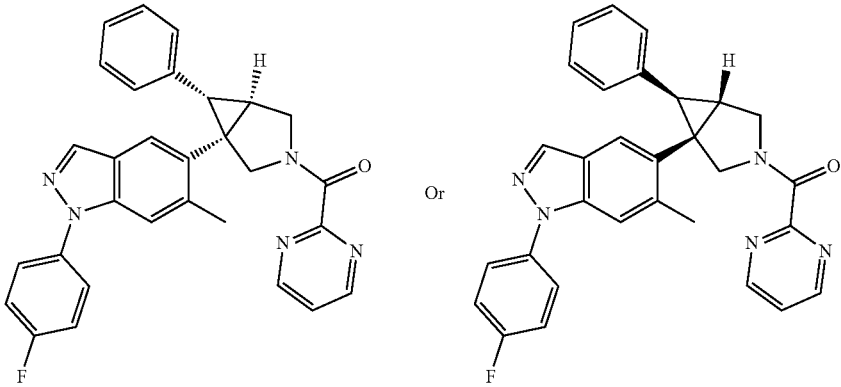 [SMILES: Cc1cc2c(cnn2-c2ccc(F)cc2)cc1[C@@]12CN(C(=O)c3ncccn3)C[C@@H]1[C@H]2c1ccccc1 ; Cc1cc2c(cnn2-c2ccc(F)cc2)cc1[C@]12CN(C(=O)c3ncccn3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(pyrimidin-2-yl)methanone | R$^t$ 1.99 min (Method 7); m/z 490.4 (M + H)$^+$ (ES$^+$) |
| 172 | 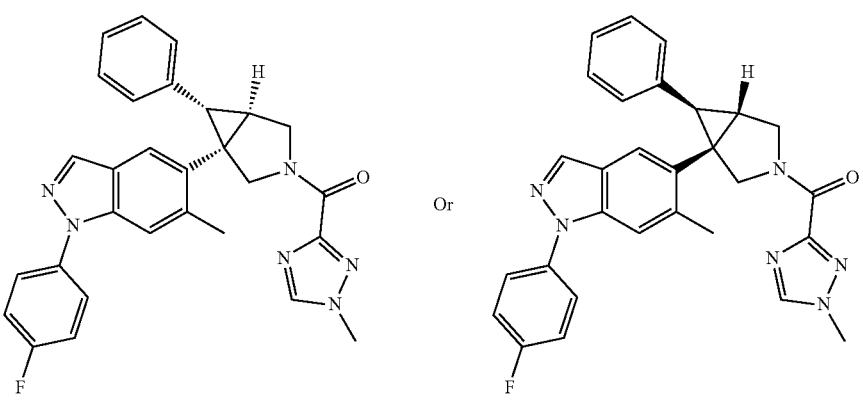 [SMILES: Cc1cc2c(cnn2-c2ccc(F)cc2)cc1[C@@]12CN(C(=O)c3ncn(C)n3)C[C@@H]1[C@H]2c1ccccc1 ; Cc1cc2c(cnn2-c2ccc(F)cc2)cc1[C@]12CN(C(=O)c3ncn(C)n3)C[C@H]1[C@@H]2c1ccccc1]<br>(1-(1-(4-fluorophenyl)-6-methyl-1H-indazol-5-yl)-6-phenyl-3-azabicyclo[3.1.0]hexan-3-yl)(1-methyl-1H-1,2,4-triazol-3-yl)methanone | R$^t$ 1.95 min (Method 7); m/z 493.3 (M + H)$^+$ (ES$^+$) |

TABLE 10-continued

The examples shown in the table below were prepared by similar methods to those described for Example 110

| Example | Structure | LC-MS analysis |
|---|---|---|
| 173 | 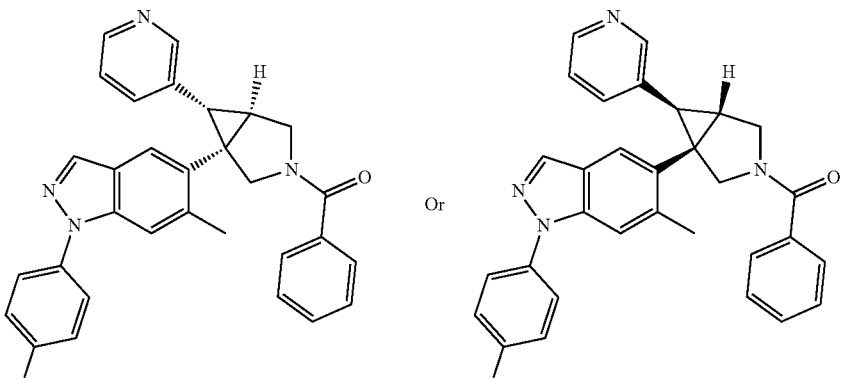<br>(1-(1-(4-fluorophenyl)-6-methyl-1H-indazol-5-yl)-6-(pyridin-3-yl)-3-azabicyclo[3.1.0]hexan-3-yl)(phenyl)methanone | R$^t$ 1.54 min (Method 7); m/z 489.4 (M + H)$^+$ (ES$^+$) |
| 174 | 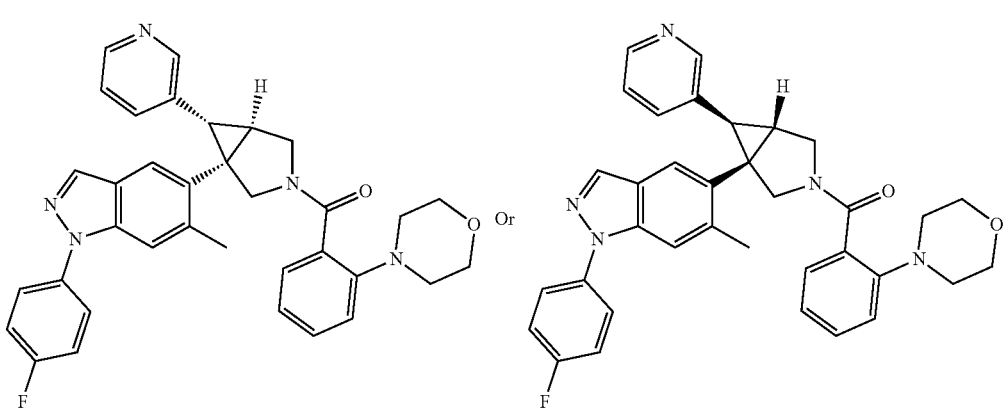 [SMILES: Cc1cc2c(cnn2-c2ccc(F)cc2)cc1[C@@]12CN(C(=O)c3ccccc3N3CCOCC3)C[C@@H]1[C@H]2c1cccnc1 ; Cc1cc2c(cnn2-c2ccc(F)cc2)cc1[C@]12CN(C(=O)c3ccccc3N3CCOCC3)C[C@H]1[C@@H]2c1cccnc1]<br>(1-(1-(4-fluorophenyl)-6-methyl-1H-indazol-5-yl)-6-phenyl-3-azabicyclo[3.1.0]hexan-3-yl)(2-morpholinophenyl)methanone | R$^t$ 2.27 min (Method 7); m/z 573.6 (M + H)$^+$ (ES$^+$) |
| 175 | 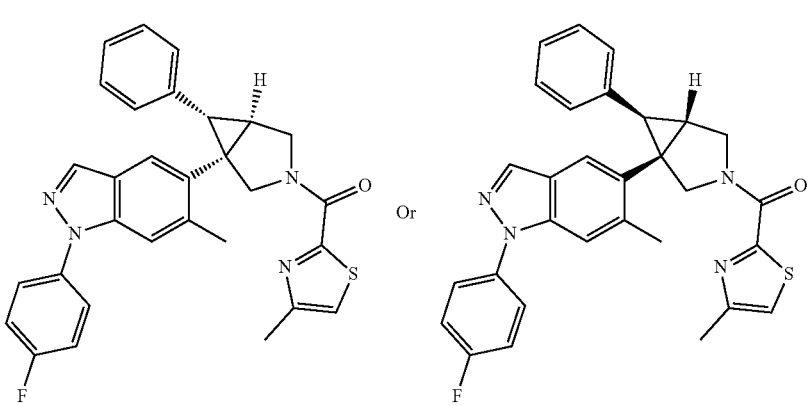 [SMILES: Cc1csc(C(=O)N2C[C@@H]3[C@@H](c4ccccc4)[C@]3(c3cc4cnn(-c5ccc(F)cc5)c4cc3C)C2)n1 ; Cc1csc(C(=O)N2C[C@H]3[C@H](c4ccccc4)[C@@]3(c3cc4cnn(-c5ccc(F)cc5)c4cc3C)C2)n1]<br>(1-(1-(4-fluorophenyl)-6-methyl-1H-indazol-5-yl)-6-phenyl-3-azabicyclo[3.1.0]hexan-3-yl)(4-methylthiazol-2-yl)methanone | R$^t$ 2.40 min (Method 7); m/z 509.4 (M + H)$^+$ (ES$^+$) |

TABLE 10-continued

The examples shown in the table below were prepared by similar methods to those described for Example 110

| Example | Structure | LC-MS analysis |
|---|---|---|
| 176 | 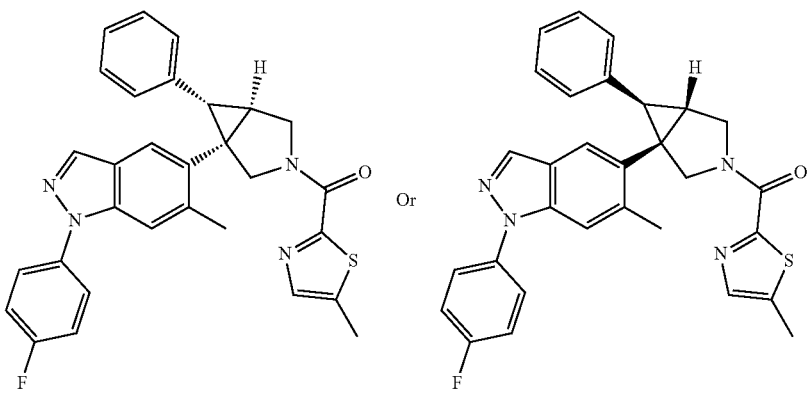 [SMILES: Cc1cnc(C(=O)N2C[C@@H]3[C@@H](c4ccccc4)[C@]3(c3cc4cnn(-c5ccc(F)cc5)c4cc3C)C2)s1 ; Cc1cnc(C(=O)N2C[C@H]3[C@H](c4ccccc4)[C@@]3(c3cc4cnn(-c5ccc(F)cc5)c4cc3C)C2)s1]<br>(1-(1-(4-fluorophenyl)-6-methyl-1H-indazol-5-yl)-6-phenyl-3-azabicyclo[3.1.0]hexan-3-yl)(5-methylthiazol-2-yl)methanone | R$^t$ 2.39 min (Method 7); m/z 509.3 (M + H)$^+$ (ES$^+$) |
| 177 | 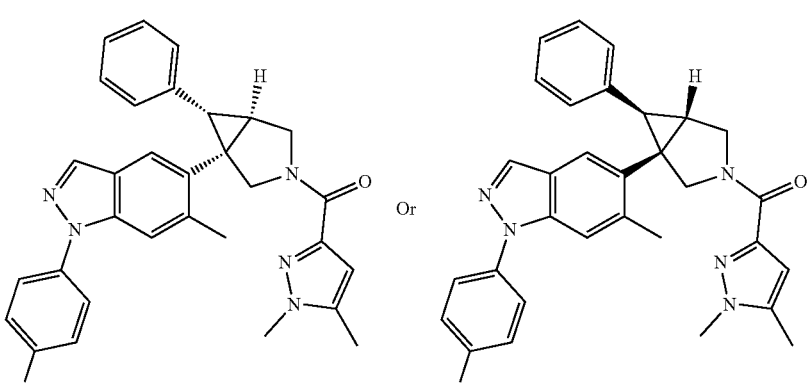<br>(1,5-dimethyl-1H-pyrazol-3-yl)(1-(1-(4-fluorophenyl)-6-methyl-1H-indazol-5-yl)-6-phenyl-3-azabicyclo[3.1.0]hexan-3-yl)methanone | R$^t$ 2.15 min (Method 7); m/z 506.4 (M + H)$^+$ (ES$^+$) |
| 178 | 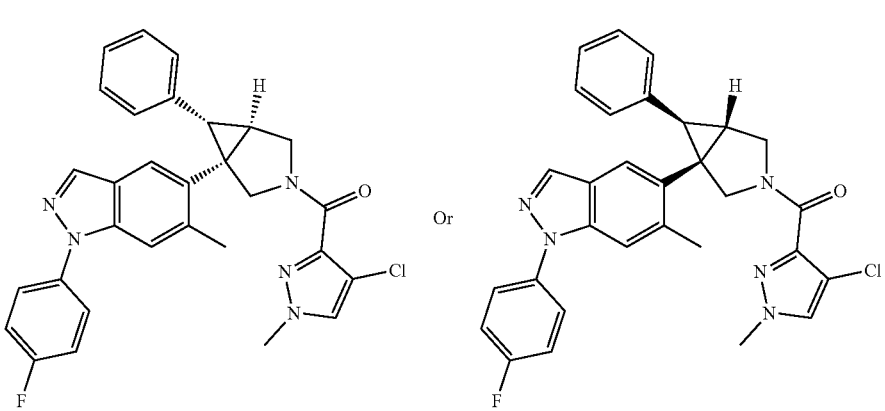 [SMILES: Cc1cc2c(cnn2-c2ccc(F)cc2)cc1[C@@]12CN(C(=O)c3nn(C)cc3Cl)C[C@@H]1[C@H]2c1ccccc1 ; Cc1cc2c(cnn2-c2ccc(F)cc2)cc1[C@]12CN(C(=O)c3nn(C)cc3Cl)C[C@H]1[C@@H]2c1ccccc1]<br>(4-chloro-1-methyl-1H-pyrazol-3-yl)(1-(1-(4-fluorophenyl)-6-methyl-1H-indazol-5-yl)-6-phenyl-3-azabicyclo[3.1.0]hexan-3-yl)methanone | R$^t$ 2.18 min (Method 7); m/z 526.8/528.8 (M + H)$^+$ (ES$^+$) |

Example 179: 1-(4-fluorophenyl)-6-methyl-5-(6-phenyl-3-(pyridin-2-ylmethyl)-3-azabicyclo[3.1.0]hexan-1-yl)-1H-indazole

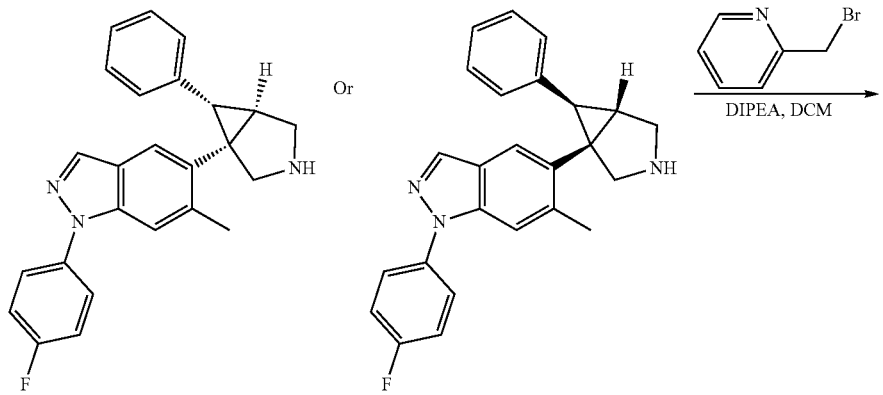

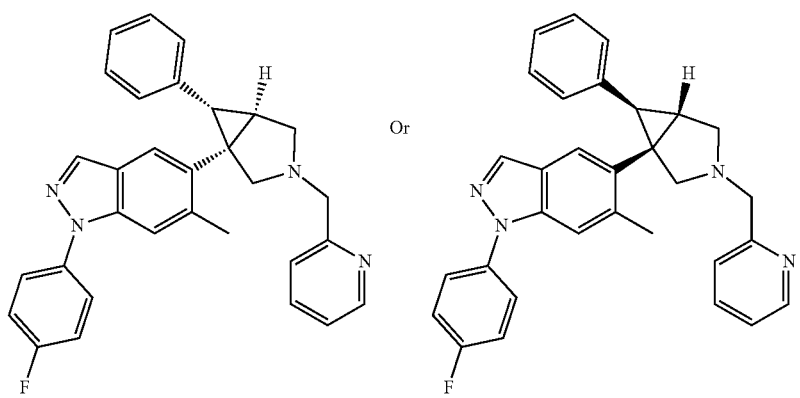

To a solution of 1-(4-fluorophenyl)-6-methyl-5-((1S,5R,6S)-6-phenyl-3-azabicyclo[3.1.0]hexan-1-yl)-1H-indazole (10 mg, 26 μmol) Intermediate X in DCM (0.5 mL) was added N-ethyl-N-isopropylpropan-2-amine (17 mg, 23 μL, 0.13 mmol) followed by 2-(bromomethyl)pyridine, HBr (7.9 mg, 31 μmol). The reaction mixture was stirred at room temperature overnight. The reaction mixture was concentrated onto silica gel and purified by chromatography on silica gel (4 g cartridge, 0-100% EtOAc/isohexane) to afford 1-(4-fluorophenyl)-6-methyl-5-((1S,5R,6S)-6-phenyl-3-(pyridin-2-ylmethyl)-3-azabicyclo[3.1.0]hexan-1-yl)-1H-indazole Example 179 (7.76 mg, 16 μmol, 60%) as a white solid; Rt 1.55 min (Method 9); m/z 475.2 (M+H)$^+$ (ES$^+$). δH (DMSO-d6, 400 MHz) δ 8.49 (dd, J=4.9, 1.3 Hz, 1H), 8.28 (s, 1H), 7.97 (s, 1H), 7.79 (td, J=7.7, 1.8 Hz, 1H), 7.72 (dd, J=8.9, 4.8 Hz, 2H), 7.49 (d, J=7.7 Hz, 1H), 7.43-7.31 (m, 3H), 7.27 (ddd, J=7.5, 4.8, 1.1 Hz, 1H), 7.10-6.87 (m, 3H), 6.87-6.76 (m, 2H), 3.93-3.71 (m, 2H), 3.61-3.50 (m, 1H), 3.29-3.17 (m, 1H), 3.06-2.83 (m, 2H), 2.73-2.54 (m, 1H), 2.42 (s, 1H), 2.15 (s, 3H).

Example 180: (1-(1-(4-fluorophenyl)-6-methyl-1H-indazol-5-yl)-6-(morpholinomethyl)-3-azabicyclo[3.1.0]hexan-3-yl)(phenyl)methanone
Intermediate Y: (1-(1-(4-fluorophenyl)-6-methyl-1H-indazol-5-yl)-6-(hydroxymethyl)-3-azabicyclo[3.1.0]hexan-3-yl)(phenyl)methanone
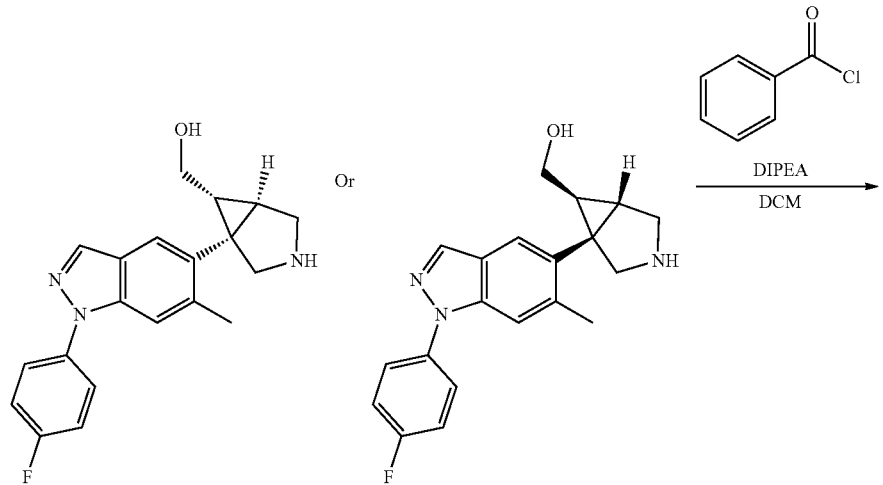
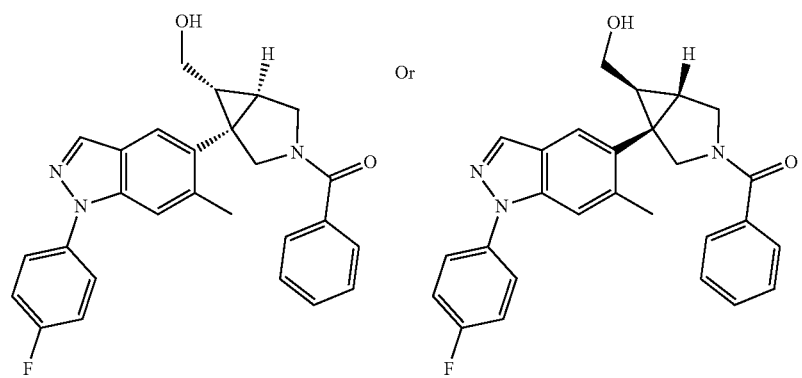

To a solution of (1-(1-(4-fluorophenyl)-6-methyl-1H-indazol-5-yl)-3-azabicyclo[3.1.0]hexan-6-yl)methanol Intermediate O (5.00 g, 82% Wt, 12.2 mmol) in DCM (50 mL) at 0° C. was added DIPEA (4.71 g, 6.35 mL, 36.5 mmol) followed by benzoyl chloride (2.05 g, 1.69 mL, 14.6 mmol). The reaction mixture was stirred with warming to room temperature for 1 h. The reaction mixture was diluted with water and the biphasic mixture was separated using a phase separator. The organic layer was concentrated under reduced pressure and purified by chromatography on silica gel (80 g cartridge, 0-100% EtOAc/isohexane) to afford (1-(1-(4-fluorophenyl)-6-methyl-1H-indazol-5-yl)-6-(hydroxymethyl)-3-azabicyclo[3.1.0]hexan-3-yl)(phenyl)methanone Intermediate Y (4.90 g, 10 mmol, 83%) as a white solid; Rt 1.80 min (Method 7); m/z 442.4 (M+H)⁺ (ES⁺). δH (DMSO-d6, 400 MHz) δ 8.33-8.16 (m, 1H), 8.00-7.72 (m, 3H), 7.72-7.32 (m, 8H), 4.72 4.36 (m, 1H), 4.34-3.95 (m, 1H), 3.91-3.41 (m, 2H), 3.27-2.81 (m, 2H), 2.60 (s, 1H), 2.58-2.52 (m, 1H), 2.41-2.33 (m, 1H), 2.09-1.66 (m, 1H), 1.35-1.23 (m, 1H)—one proton not observed.

Intermediate Z: 3-benzoyl-1-(1-(4-fluorophenyl)-6-methyl-1H-indazol-5-yl)-3-azabicyclo[3.1.0]hexane-6-carbaldehyde

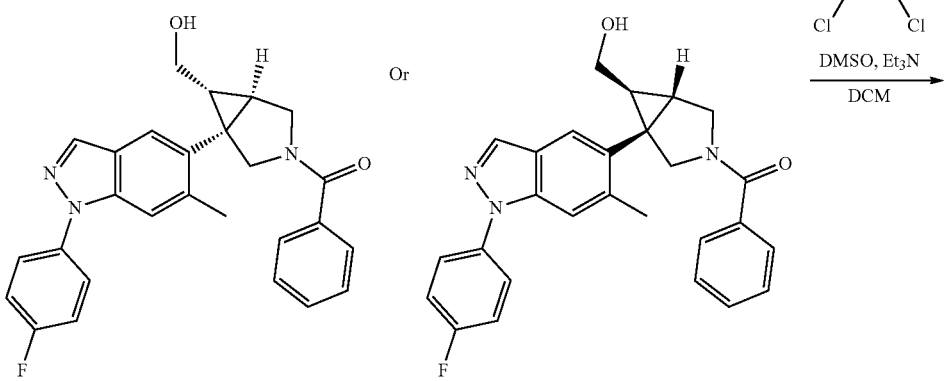

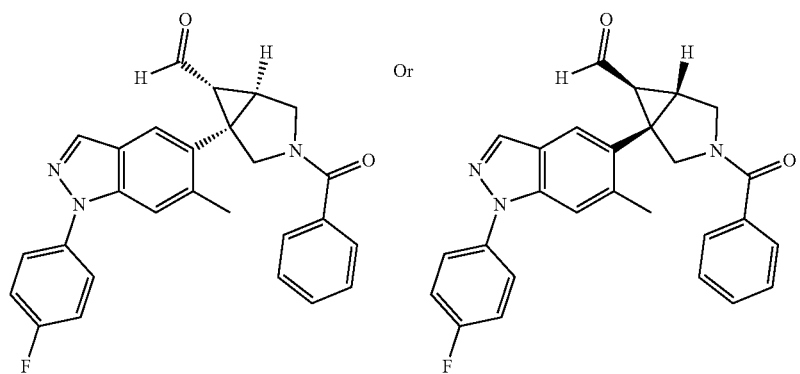

377

To a solution of oxalyl chloride (1.54 g, 1.06 mL, 12.1 mmol) in dry DCM (50 mL) at −78° C. was added DMSO (2.05 g, 1.86 mL, 26.3 mmol) dropwise. The reaction mixture was stirred at this temperature for 10 min, then a solution of (1-(1-(4-fluorophenyl)-6-methyl-1H-indazol-5-yl)-6-(hydroxymethyl)-3-azabicyclo[3.1.0]hexan-3-yl)(phenyl)methanone Intermediate N (4.90 g, 91% Wt, 10.1 mmol) in dry DCM (10 mL) was added. The reaction mixture was stirred at −78° C. for 30 min, then triethylamine (5.11 g, 7.04 mL, 50.5 mmol) was added. The reaction mixture was stirred with warming to room temperature overnight. The reaction mixture was concentrated under reduced pressure and purified by chromatography on silica gel (80 g cartridge,

378

0-100% EtOAc/isohexane) to afford 3-benzoyl-1-(1-(4-fluorophenyl)-6-methyl-1H-indazol-5-yl)-3-azabicyclo[3.1.0]hexane-6-carbaldehyde Intermediate Z (2.87 g, 6.1 mmol, 60%) as a white solid; Rt 1.92 min (Method 7); m/z 440.4 (M+H)⁺ (ES⁺). δH (DMSO-d6, 400 MHz) δ 9.06-8.64 (m, 1H), 8.38-8.18 (m, 1H), 8.10-7.31 (m, 11H), 4.72-4.20 (m, 1H), 4.20-3.81 (m, 1H), 3.81-3.40 (m, 1H), 3.21-2.82 (m, 1H), 2.69-2.57 (m, 1H), 2.49-2.40 (m, 1H), 2.37-2.09 (m, 3H).

Example 180: (1-(1-(4-fluorophenyl)-6-methyl-1H-indazol-5-yl)-6-(morpholinomethyl)-3-azabicyclo[3.1.0]hexan-3-yl)(phenyl)methanone

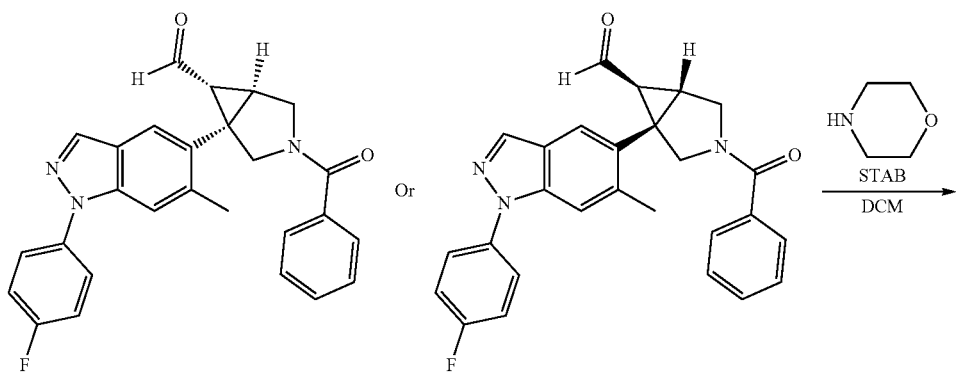

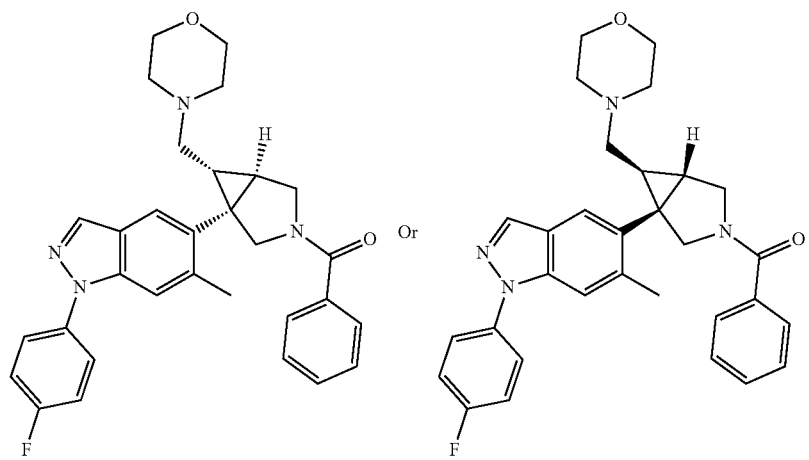

To a solution of (1R,5R,6R)-3-benzoyl-1-(1-(4-fluorophenyl)-6-methyl-1H-indazol-5-yl)-3-azabicyclo[3.1.0]hexane-6-carbaldehyde Intermediate Z (10 mg, 23 μmol) in dry THF (1 mL) was added morpholine (5.9 mg, 5.9 μL, 68 μmol). The reaction mixture was stirred at room temperature for 30 min, then sodium triacetoxyborohydride (9.6 mg, 46 μmol) was added. Stirring was continued at room temperature for 30 min. The reaction mixture was quenched with saturated NaHCO$_3$ aqueous solution (20 mL), and the products were extracted into DCM (3×20 mL). The combined organic layers were dried using MgSO$_4$, filtered, and concentrated under reduced pressure. The crude product was purified by chromatography on silica gel (4 g cartridge, 0-10% (0.7 M Ammonia/MeOH)/DCM) to afford (1-(1-(4-fluorophenyl)-6-methyl-1H-indazol-5-yl)-6-(morpholinomethyl)-3-azabicyclo[3.1.0]hexan-3-yl)(phenyl)methanone Example 180 (12.21 mg, 23 μmol, 100%) as a white solid; Rt 1.50 min (Method 9); m/z 511.2 (M+H)$^+$ (ES$^+$). δH (DMSO-d6, 400 MHz) δ 8.36-8.18 (m, 1H), 7.90-7.72 (m, 3H), 7.71-7.54 (m, 1H), 7.56-7.33 (m, 7H), 4.63-3.96 (m, 2H), 3.94-3.65 (m, 1H), 3.65-3.41 (m, 5H), 2.77-2.57 (m, 2H), 2.40-1.69 (m, 5H), 1.57-1.37 (m, 1H), 1.32-1.17 (m, 1H)—two protons obscured by solvent.

Example 181: 5-(6-((4,4-difluoropiperidin-1-yl)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole

TABLE 11

The example shown in the table below was prepared by similar methods to those described for Example 180

| Example | Structure | LC-MS analysis |
|---------|-----------|----------------|
| 181 | | R$^t$ 1.58 min (Method 9); m/z 545.2 (M + H)$^+$ (ES$^+$) |

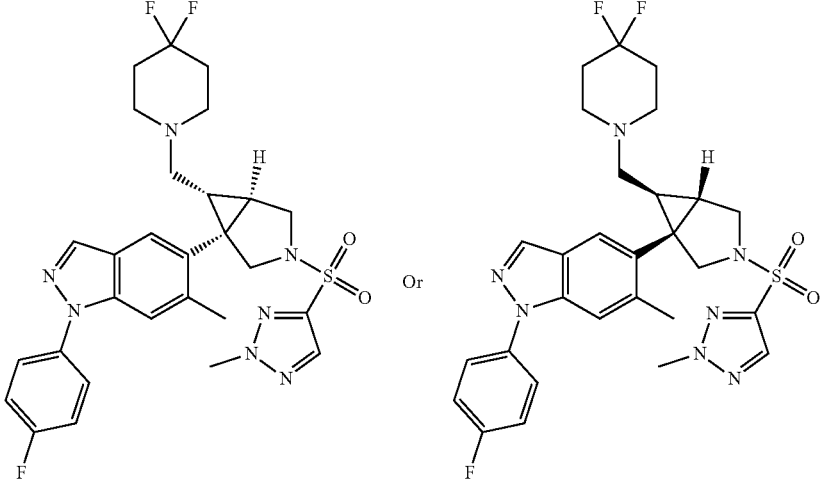 [SMILES: Cc1cc2c(cnn2-c2ccc(F)cc2)cc1[C@@]12CN(S(=O)(=O)c3cnn(C)n3)C[C@@H]1[C@H]2CN1CCC(F)(F)CC1 ; Cc1cc2c(cnn2-c2ccc(F)cc2)cc1[C@]12CN(S(=O)(=O)c3cnn(C)n3)C[C@H]1[C@@H]2CN1CCC(F)(F)CC1]

5-(6-((4,4-difluoropiperidin-1-yl)methyl)-3-((2-methyl-2H-1,2,3-triazol-4-yl)sulfonyl)-3-azabicyclo[3.1.0]hexan-1-yl)-1-(4-fluorophenyl)-6-methyl-1H-indazole Example 182: (1-(1-(4-fluorophenyl)-6-methyl-1H-indazol-5-yl)-6-methyl-6-phenyl-3-azabicyclo[3.1.0]hexan-3-yl)(phenyl)methanone Intermediate AA: 3-benzyl-1-(1-(4-fluorophenyl)-6-methyl-1H-indazol-5-yl)-6-methyl-6-phenyl-3-azabicyclo[3.1.0]hexane-2,4-dione

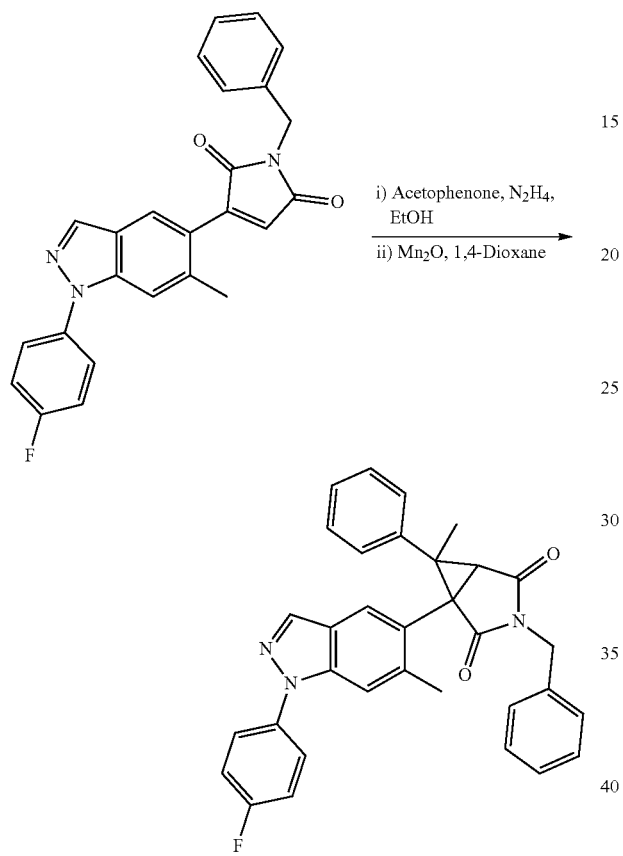

purified by chromatography on silica gel (80 g cartridge, 0-30% EtOAc/isohexane) to afford an inseparable mixture of isomers of 3-benzyl-1-(1-(4-fluorophenyl)-6-methyl-1H-indazol-5-yl)-6-methyl-6-phenyl-3-azabicyclo[3.1.0]hexane-2,4-dione (3.19 g, 5.7 mmol, 94%) as a yellow solid (combined total 92%, 4 isomers). The ratio of isomers is 4:60:25:11 in order of elution on UPLC). Rt 2.36, 2.39, 2.42 and 2.55 min (Method 7); m/z 516.4 (M+H)$^+$ (ES$^+$).

Intermediate AB: 5-(3-benzyl-6-methyl-6-phenyl-3-azabicyclo[3.1.0]hexan-1-yl)-1-(4-fluorophenyl)-6-methyl-1H-indazole Intermediate AC: 5-(3-benzyl-6-methyl-6-phenyl-3-azabicyclo[3.1.0]hexan-1-yl)-1-(4-fluorophenyl)-6-methyl-1H-indazole

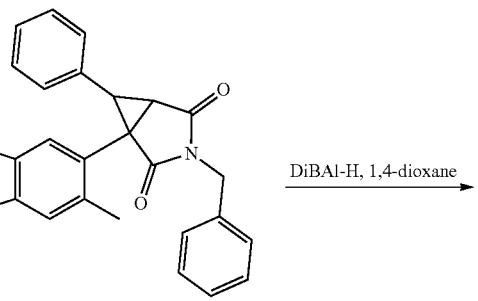

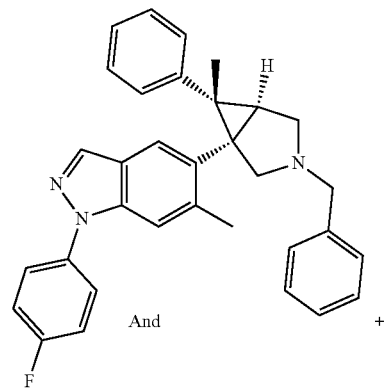

To a solution of hydrazine (1.23 g, 1.20 mL, 38.3 mmol) in EtOH (3 mL) was added acetophenone (1.53 g, 1.49 mL, 12.8 mmol) dropwise. The reaction mixture was stirred at room temperature for 3 h and was then concentrated under reduced pressure. The crude material was diluted with water (25 mL) and extracted into DCM (3×25 mL). The combined organic layers were dried using MgSO$_4$ and concentrated under reduced pressure to afford (E)-(1-phenylethylidene)hydrazine (1.91 g, 12 mmol, 90%) as a colourless oil; Rt 1.50 min (Method 8); m/z 135.4 (M+H)$^+$ (ES$^+$).

(E)-(1-phenylethylidene)hydrazine (1.91 g, 12 mmol) was dissolved in 1,4-dioxane (50 mL) and cooled to −10° C. Manganese(IV) oxide (6.34 g, 72.9 mmol) was added portionwise, keeping the temperature constant. The reaction mixture was stirred with warming to room temperature for 45 min. The reaction mixture was filtered through a glass-fibre filter paper into a cooled receiver flask, washing with dioxane. To the resulting filtrate was added 1-benzyl-3-(1-(4-fluorophenyl)-6-methyl-1H-indazol-5-yl)-1H-pyrrole-2,5-dione (2.50 g, 1 Eq, 6.08 mmol), and the reaction mixture was stirred with warming to room temperature overnight. Acetic acid (1 mL) was added, and the reaction mixture was concentrated under reduced pressure. The crude product was -continued

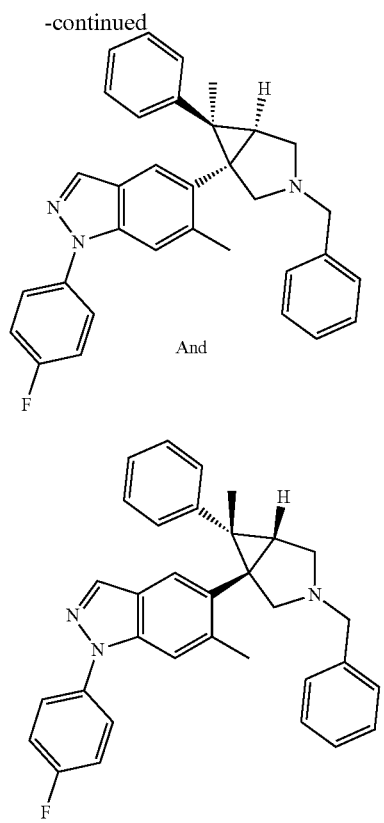

And

To a solution of 3-benzyl-1-(1-(4-fluorophenyl)-6-methyl-1H-indazol-5-yl)-6-methyl-6-phenyl-3-azabicyclo[3.1.0]hexane-2,4-dione (3.19 g, 5.69 mmol) in 1,4-dioxane (50 mL) at 0° C. was added DIBAL-H (1 M in hexane) (7.1 g, 50 mL, 1.00 molar, 50 mmol) dropwise. The reaction mixture was stirred with warming to room temperature overnight. The reaction mixture was cooled to 0° C. and quenched with water (2 mL) followed by 15% NaOH solution (2 mL) followed by water (5 mL). The reaction mixture was stirred with warming to room temperature for 15 min. MgSO$_4$ was added, and stirring was continued for 15 min. The reaction mixture was filtered, washing with EtOAc, and the filtrate was concentrated under reduced pressure. The crude product was purified by chromatography on silica gel (80 g cartridge, 0-20% EtOAc/isohexane) to afford 5-(3-benzyl-6-methyl-6-phenyl-3-azabicyclo[3.1.0]hexan-1-yl)-1-(4-fluorophenyl)-6-methyl-1H-indazole Intermediate AB (93 mg, 0.13 mmol, 2.3%) as a sticky colourless oil; Rt 1.73 min (Method 7); m/z 488.4 (M+H)$^+$ (ES$^+$) and 5-(3-benzyl-6-methyl-6-phenyl-3-azabicyclo[3.1.0]hexan-1-yl)-1-(4-fluorophenyl)-6-methyl-1H-indazole Intermediate AC (1.24 g, 2.3 mmol, 40%) as a sticky colourless oil; Rt 1.59 min (Method 7); m/z 488.4 (M+H)$^+$ (ES$^+$). δH (DMSO-d6, 400 MHz) δ 8.07 (s, 1H), 7.74-7.62 (m, 2H), 7.54 (s, 1H), 7.43-7.26 (m, 7H), 7.27-7.19 (m, 1H), 7.10 (d, J=7.8 Hz, 2H), 6.96 (t, J=7.4 Hz, 2H), 6.92-6.80 (m, 1H), 3.73 (s, 2H), 3.64-3.52 (m, 1H), 3.37-3.24 (m, 1H), 3.23-3.12 (m, 1H), 2.80 (d, J=9.7 Hz, 2H), 2.41 (s, 3H), 1.85 (s, 3H).

Intermediate AD: 1-(4-fluorophenyl)-6-methyl-5-(6-methyl-6-phenyl-3-azabicyclo[3.1.0]hexan-1-yl)-1H-indazole

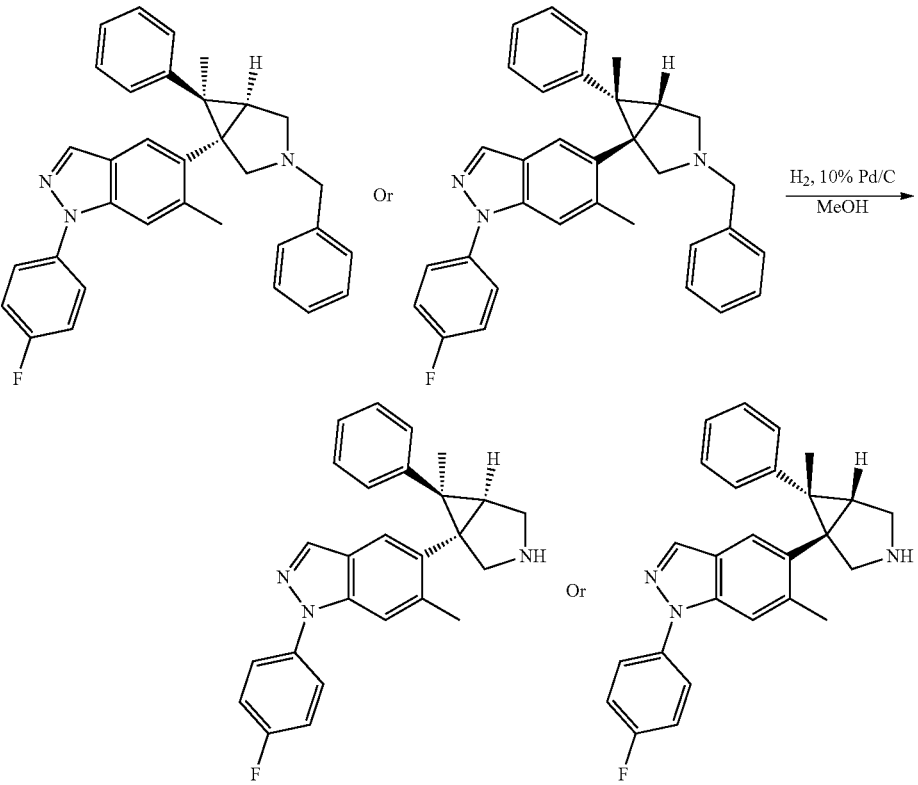

To a solution of 5-(3-benzyl-6-methyl-6-phenyl-3-azabicyclo[3.1.0]hexan-1-yl)-1-(4-fluorophenyl)-6-methyl-1H-indazole Intermediate AB (93 mg, 0.13 mmol) in Methanol (1 mL) was added Pd/C (14 mg, 10% Wt, 13 μmol). The reaction mixture was stirred at room temperature under hydrogen atmosphere (5 bar) over the weekend. The catalyst was removed by filtration through a glass-fibre filter paper, and the filtrate was concentrated under reduced pressure. The crude product was purified by chromatography on silica gel (4 g cartridge, 0-10% (0.7 M Ammonia/MeOH)/DCM) to afford 1-(4-fluorophenyl)-6-methyl-5-(6-methyl-6-phenyl-3-azabicyclo[3.1.0]hexan-1-yl)-1H-indazole Intermediate AD (32 mg, 79 μmol, 59%) as a colourless glass which was scratched to a white solid; Rt 1.45 and 1.48 min (Method 7); m/z 398.4 (M+H)$^+$ (ES$^+$).

Example 182: (1-(1-(4-fluorophenyl)-6-methyl-1H-indazol-5-yl)-6-methyl-6-phenyl-3-azabicyclo[3.1.0]hexan-3-yl)(phenyl)methanone

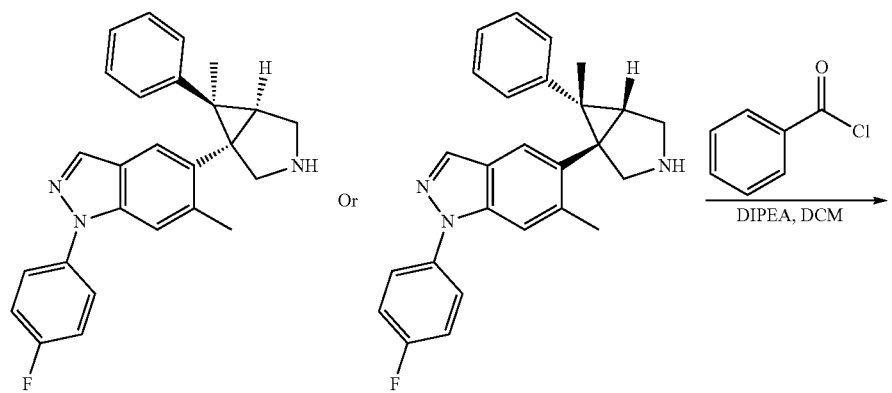

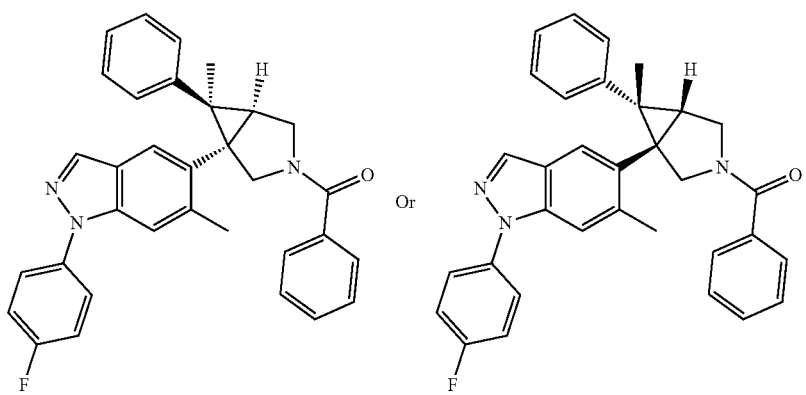

To a solution of 1-(4-fluorophenyl)-6-methyl-5-(6-methyl-6-phenyl-3-azabicyclo[3.1.0]hexan-1-yl)-1H-indazole (32 mg, 79 μmol) in DCM (1 mL) was added DIPEA (31 mg, 41 μL, 0.24 mmol) followed by benzoyl chloride (13 mg, 11 μL, 95 μmol). The reaction mixture was stirred at room temperature overnight. Water (1 mL) was added, and the reaction mixture was passed through a phase separator, washing with DCM (2×1 mL). The reaction mixture was concentrated under reduced pressure. The crude product was purified by chromatography on silica gel (4 g cartridge, 0-100% EtOAc/isohexane) to afford (1-(1-(4-fluorophenyl)-6-methyl-1H-indazol-5-yl)-6-methyl-6-phenyl-3-azabicyclo[3.1.0]hexan-3-yl)(phenyl)methanone (32.12 mg, 61 μmol, 77%) as a white solid; Rt 2.36 min (Method 7); m/z 502.5 (M+H)$^+$ (ES$^+$).

Example 183: (1-(1-(4-fluorophenyl)-6-methyl-1H-indazol-5-yl)-6-methyl-6-phenyl-3-azabicyclo[3.1.0]hexan-3-yl)(phenyl)methanone Intermediate AE: 1-(4-fluorophenyl)-6-methyl-5-(6-methyl-6-phenyl-3-azabicyclo[3.1.0]hexan-1-yl)-1H-indazole

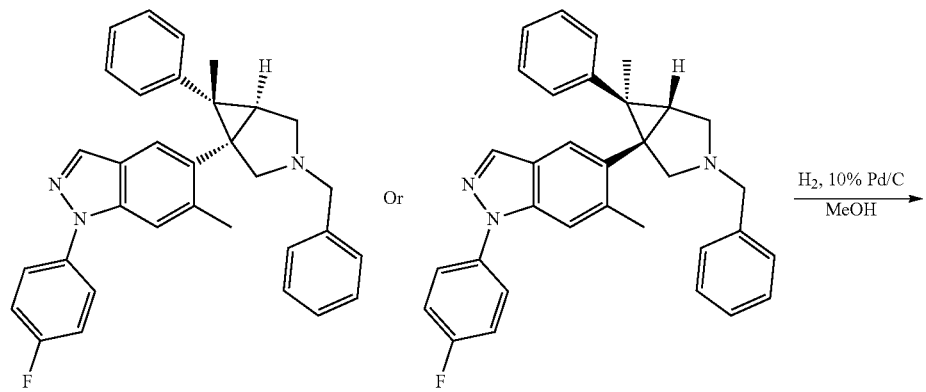

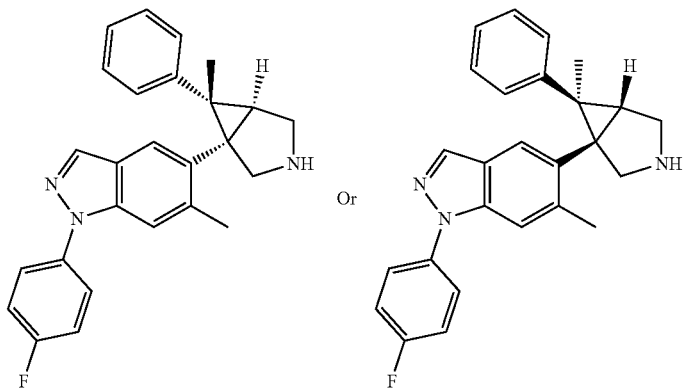

To a solution of 5-(3-benzyl-6-methyl-6-phenyl-3-azabicyclo[3.1.0]hexan-1-yl)-1-(4-fluorophenyl)-6-methyl-1H-indazole (1.24 g, 2.29 mmol) in methanol (12 mL) was added Pd/C (244 mg, 10% Wt, 229 μmol). The reaction mixture was stirred at room temperature under a hydrogen atmosphere (5 bar) over the weekend. The catalyst was removed by filtration through a glass-fibre filter paper, and the filtrate was concentrated under reduced pressure. The crude product was purified by chromatography on silica gel (12 g cartridge, 0-10% (0.7 M Ammonia/MeOH)/DCM) to afford 1-(4-fluorophenyl)-6-methyl-5-(6-methyl-6-phenyl-3-azabicyclo[3.1.0]hexan-1-yl)-1H-indazole Intermediate AE (896 mg, 2.2 mmol, 97%) as a white solid; Rt 1.40 min (Method 7); m/z 398.5 (M+H)$^+$ (ES$^+$).

Example 183: (1-(1-(4-fluorophenyl)-6-methyl-1H-indazol-5-yl)-6-methyl-6-phenyl-3-azabicyclo[3.1.0]hexan-3-yl)(phenyl)methanone

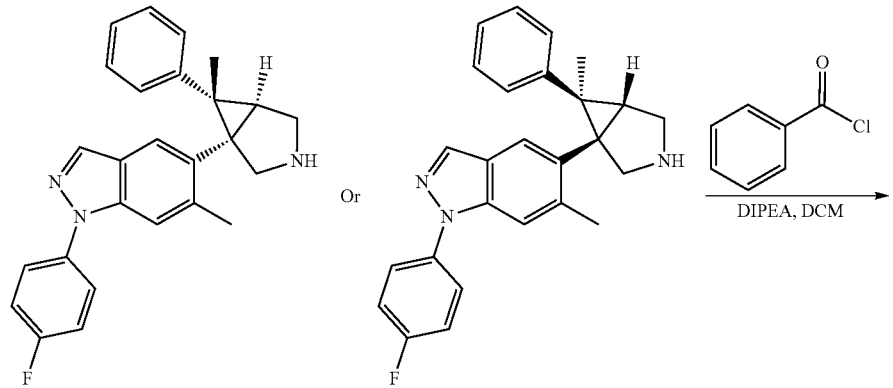

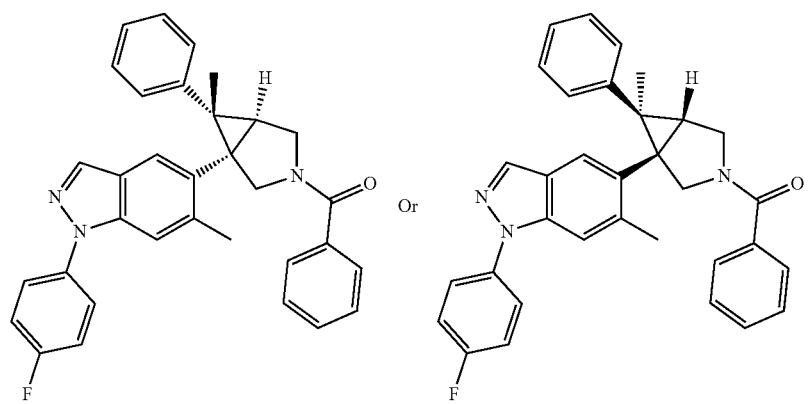

To a solution of 1-(4-fluorophenyl)-6-methyl-5-(6-methyl-6-phenyl-3-azabicyclo[3.1.0]hexan-1-yl)-1H-indazole (32 mg, 79 μmol) (32 mg, 79 μmol) in DCM (1 mL) was added DIPEA (31 mg, 41 μL, 0.24 mmol) followed by benzoyl chloride (13 mg, 11 μL, 95 μmol). The reaction mixture was stirred at room temperature overnight. Water (1 mL) was added, and the reaction mixture was passed through a phase separator, washing with DCM (2×1 mL). The reaction mixture was concentrated under reduced pressure. The crude product was purified by chromatography on silica gel (4 g cartridge, 0-100% EtOAc/isohexane) to afford (1-(1-(4-fluorophenyl)-6-methyl-1H-indazol-5-yl)-6-methyl-6-phenyl-3-azabicyclo[3.1.0]hexan-3-yl)(phenyl)methanone (28.60 mg, 54 μmol, 69%) as a white solid; Rt 2.28 min (Method 7); m/z 502.5 (M+H)$^+$ (ES$^+$).

Example 184: (6-benzyl-1-(1-(4-fluorophenyl)-6-methyl-1H-indazol-5-yl)-3-azabicyclo[3.1.0]hexan-3-yl)(phenyl)methanone Intermediate AF: 3-benzyl-1-(1-(4-fluorophenyl)-6-methyl-1H-indazol-5-yl)-3-azabicyclo[3.1.0]hexane-6-carbaldehyde

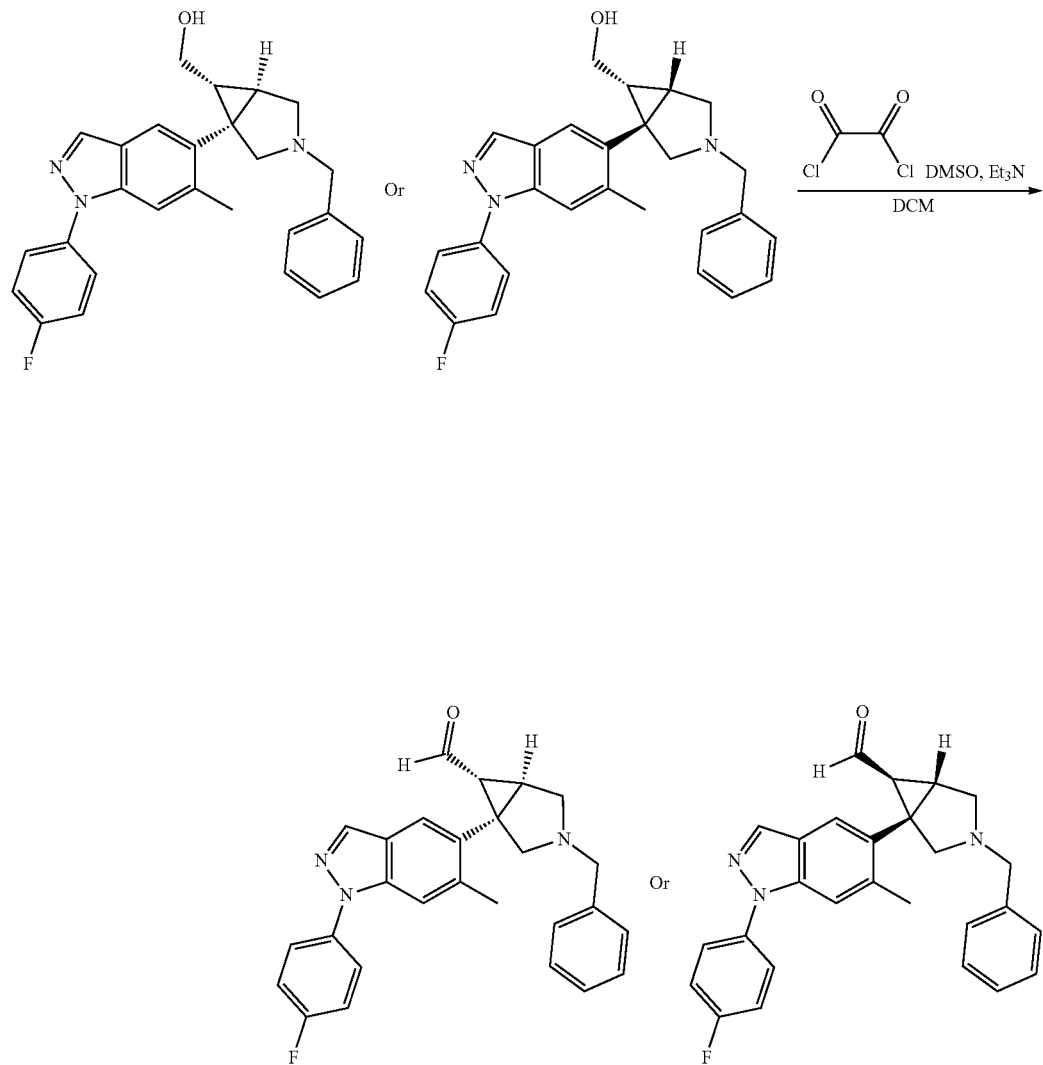

To a solution of oxalyl chloride (338 mg, 233 μL, 2.67 mmol) in dry DCM (10 mL) at −78° C. was added DMSO (451 mg, 410 μL, 5.78 mmol) dropwise. The reaction mixture was stirred at this temperature for 10 min, then a solution of (3-benzyl-1-(1-(4-fluorophenyl)-6-methyl-1H-indazol-5-yl)-3-azabicyclo[3.1.0]hexan-6-yl)methanol Intermediate N (1.00 g, 95% Wt, 2.22 mmol) in dry DCM (2 mL) was added. The reaction mixture was stirred at −78° C. for 30 min, then Et$_3$N (1.12 g, 1.55 mL, 11.1 mmol) was added. The reaction mixture was stirred with warming to room temperature overnight. The reaction mixture was concentrated under reduced pressure to afford 3-benzyl-1-(1-(4-fluorophenyl)-6-methyl-1H-indazol-5-yl)-3-azabicyclo[3.1.0]hexane-6-carbaldehyde (1.09 g, 2.2 mmol, 100%) as an orange oil. The product was used crude with no purification. Rt 1.39 min (Method 7); m/z 426.4 (M+H)$^+$ (ES$^+$).

Intermediate AG: (3-benzyl-1-(1-(4-fluorophenyl)-6-methyl-1H-indazol-5-yl)-3-azabicyclo[3.1.0]hexan-6-yl)(phenyl)methanol

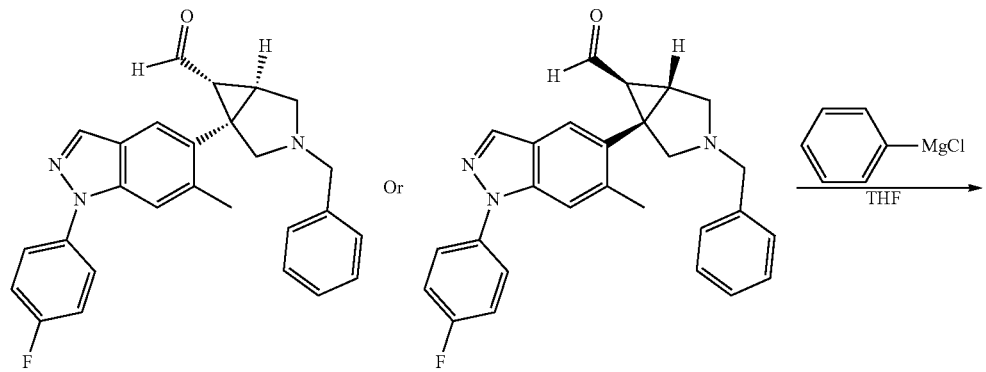

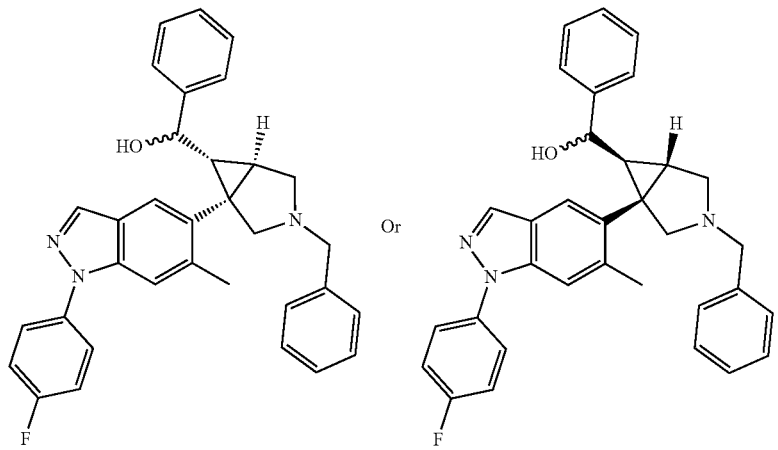

To a solution of 3-benzyl-1-(1-(4-fluorophenyl)-6-methyl-1H-indazol-5-yl)-3-azabicyclo[3.1.0]hexane-6-carbaldehyde (500 mg, 87% Wt, 1.02 mmol) in dry THF (10 mL) at −78° C. was added phenylmagnesium chloride (0.15 g, 0.55 mL, 2 molar, 1.1 mmol) dropwise. The reaction mixture was stirred with warming to room temperature for 90 min. The reaction mixture was quenched with saturated aqueous NH$_4$Cl solution (50 mL) and extracted with DCM (3×50 mL). The combined organic layers were dried using MgSO$_4$, filtered, and concentrated under reduced pressure. The crude product was purified by chromatography on silica gel (24 g cartridge, 0-50% EtOAc/isohexane) to afford (3-benzyl-1-(1-(4-fluorophenyl)-6-methyl-1H-indazol-5-yl)-3-azabicyclo[3.1.0]hexan-6-yl)(phenyl)methanol Intermediate AG (290 mg, 0.55 mmol, 54%) as a white solid; Rt 1.44 min (Method 7); m/z 504.4 (M+H)$^+$ (ES$^+$). δH (DMSO-d6, 400 MHz) δ 8.43-8.19 (m, 1H), 7.90-7.55 (m, 4H), 7.53-6.76 (m, 13H), 5.46-4.75 (m, 1H), 3.82-3.39 (m, 4H), 2.91-2.67 (m, 2H), 2.51 (s, 2H), 2.30-1.70 (m, 3H).

Intermediate AH: (3-benzyl-1-(1-(4-fluorophenyl)-6-methyl-1H-indazol-5-yl)-3-azabicyclo[3.1.0]hexan-6-yl)(phenyl)methyl acetate
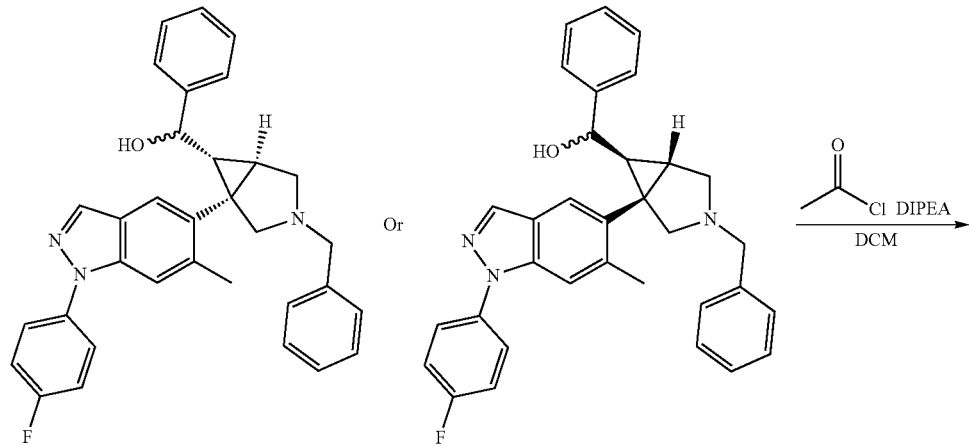
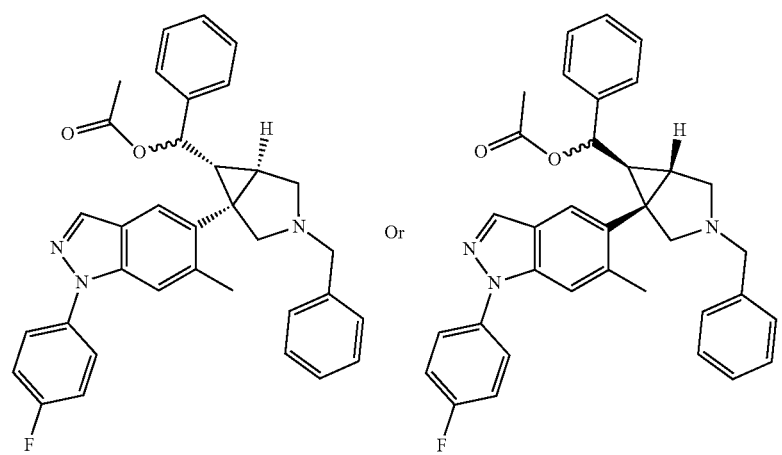

To a solution of (3-benzyl-1-(1-(4-fluorophenyl)-6-methyl-1H-indazol-5-yl)-3-azabicyclo[3.1.0]hexan-6-yl)(phenyl)methanol (50 mg, 99 μmol) in DCM (0.5 mL) was added DIPEA (38 mg, 52 μL, 0.30 mmol) followed by acetyl chloride (9.4 mg, 8.5 μL, 0.12 mmol). The reaction mixture was stirred at room temperature for 2 h. A further portion of DIPEA (38 mg, 52 μL, 0.30 mmol) was added, followed by acetyl chloride (9.4 mg, 8.5 μL, 0.12 mmol). The reaction mixture was stirred at room temperature overnight. Further DIPEA (0.26 g, 0.35 mL, 2.0 mmol) was added, followed by acetyl chloride (39 mg, 35 μL, 0.50 mmol). Stirring was continued for a further 5 days. The reaction mixture was diluted with water (5 mL) and extracted into DCM (3×5 mL). The combined organic layers were dried using $MgSO_4$, filtered, and concentrated under reduced pressure. The crude product was purified by chromatography on silica gel (4 g cartridge, 0-100% EtOAc/isohexane) to afford (3-benzyl-1-(1-(4-fluorophenyl)-6-methyl-1H-indazol-5-yl)-3-azabicyclo[3.1.0]hexan-6-yl)(phenyl)methyl acetate (26.0 mg, 29 μmol, 29%) as a colourless oil; Rt 1.60 and 1.63 min (Method 7); m/z 546.5 (M+H)+ (ES+).

Intermediate AI: 5-(6-benzyl-3-azabicyclo[3.1.0]hexan-1-yl)-1-(4-fluorophenyl)-6-methyl-1H-indazole

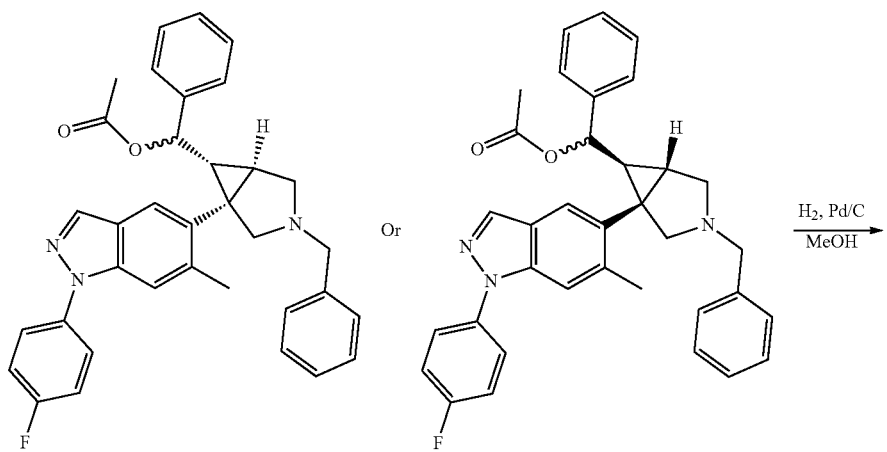

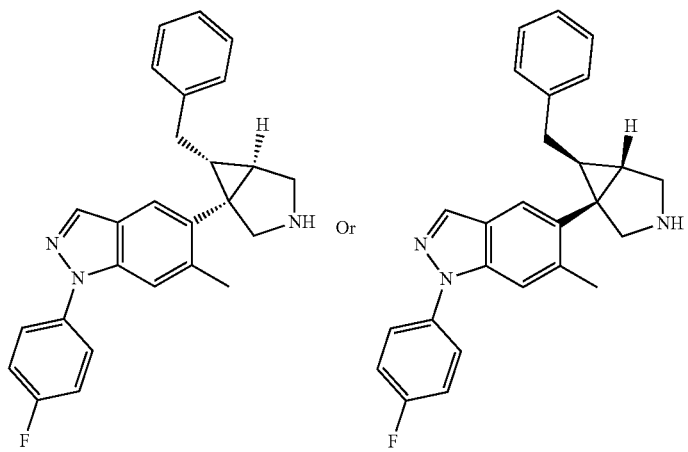

To a solution of (3-benzyl-1-(1-(4-fluorophenyl)-6-methyl-1H-indazol-5-yl)-3-azabicyclo[3.1.0]hexan-6-yl)(phenyl)methyl acetate (26 mg, 61% Wt, 29 μmol) in MeOH (0.5 mL) (plus a few drops of DCM to aid solubility) was added Pd/C (3.1 mg, 10% Wt, 2.9 μmol). The reaction mixture was stirred at room temperature under an atmosphere of hydrogen (5 bar) over the weekend. The catalyst was removed by filtration through a glass-fibre filter paper, and the filtrate was concentrated under reduced pressure. The crude product was purified by chromatography on silica gel (4 g cartridge, 0-10% (0.7 M $NH_3$/MeOH)/DCM) to afford 5-(6-benzyl-3-azabicyclo[3.1.0]hexan-1-yl)-1-(4-fluorophenyl)-6-methyl-1H-indazole (3.0 mg, 6.9 μmol, 24%) as a white solid; Rt 1.49 min (Method 7); m/z 398.4 $(M+H)^+$ $(ES^+)$.

Example 184: (6-benzyl-1-(1-(4-fluorophenyl)-6-methyl-1H-indazol-5-yl)-3-azabicyclo[3.1.0]hexan-3-yl)(phenyl)methanone

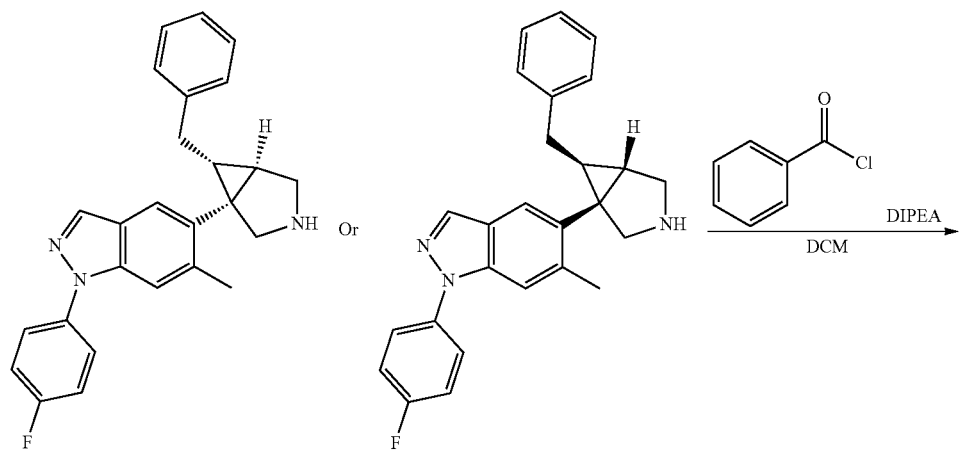

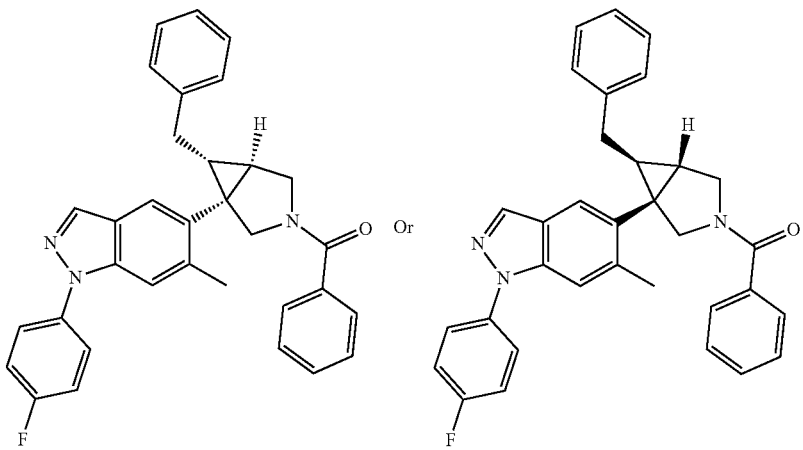

To a solution of 5-(6-benzyl-3-azabicyclo[3.1.0]hexan-1-yl)-1-(4-fluorophenyl)-6-methyl-1H-indazole (3.0 mg, 7.5 µmol) in DCM (0.5 mL) was added DIPEA (1.2 mg, 1.6 µL, 9.1 µmol) followed by benzoyl chloride (3.2 mg, 2.6 µL, 23 µmol). The reaction mixture was stirred at room temperature overnight. Water (0.5 mL) was added, and the reaction mixture was passed through a phase separator, washing with DCM (2×0.5 mL). The reaction mixture was concentrated under reduced pressure. The crude product was purified by chromatography on silica gel (4 g cartridge, 0-100% EtOAc/isohexane) to afford (6-benzyl-1-(1-(4-fluorophenyl)-6-methyl-1H-indazol-5-yl)-3-azabicyclo[3.1.0]hexan-3-yl)(phenyl)methanone (4.13 mg, 7.8 µmol, 100%) as a white solid; Rt 2.41 min (Method 7); m/z 502.4 (M+H)$^+$ (ES$^+$). δH (DMSO-d6, 400 MHz) δ 8.35-8.18 (m, 1H), 7.96-7.57 (m, 4H), 7.57-7.33 (m, 7H), 7.35-7.01 (m, 5H), 4.66-3.97 (m, 2H), 3.93-3.07 (m, 3H), 2.65 2.55 (m, 2H), 2.32-2.26 (m, 1H), 2.18-2.05 (m, 1H), 1.94-1.74 (m, 1H), 1.48-1.32 (m, 1H).

Example 185: 1-(4-fluorophenyl)-6-methyl-5-(6-phenyl-3-(pyrimidin-2-yl)-3-azabicyclo[3.1.0]hexan-1-yl)-1H-indazole

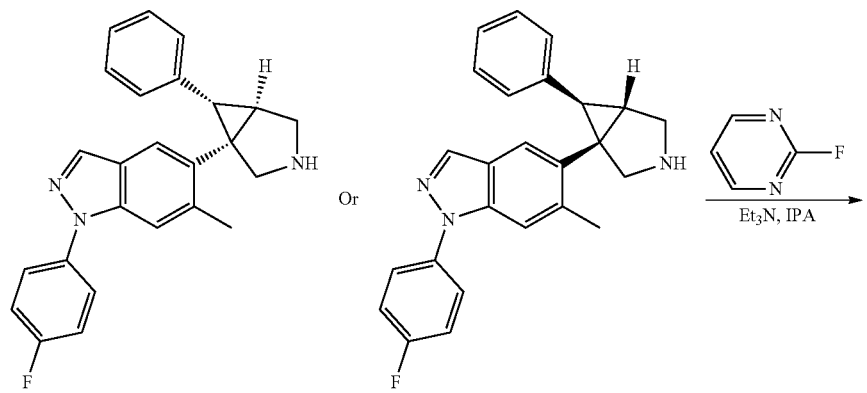

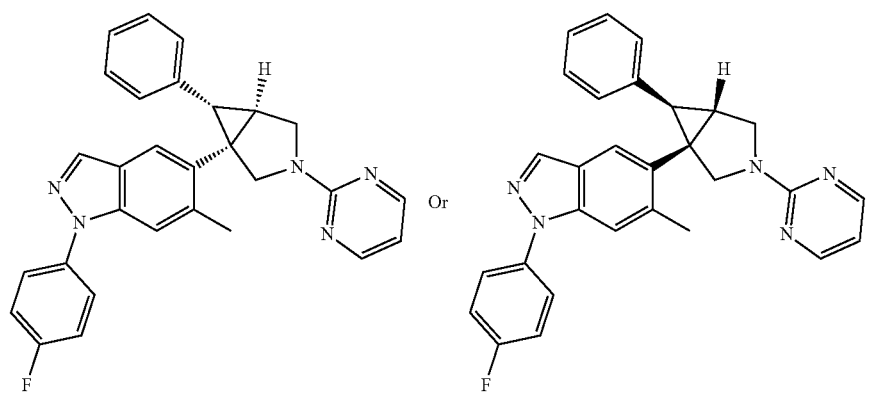

To a solution of 1-(4-fluorophenyl)-6-methyl-5-(6-phenyl-3-azabicyclo[3.1.0]hexan-1-yl)-1H-indazole Intermediate X (10 mg, 26 μmol) and triethylamine (13 mg, 18 μL, 0.13 mmol) in isopropanol (0.5 mL) was added 2-fluoropyrimidine (5.1 mg, 52 μmol). The reaction mixture was stirred in the microwave at 130° C. for 1 hour. The reaction mixture was concentrated under reduced pressure. The crude product was diluted with DCM (1 mL) and water (1 mL), and passed through a phase separator, washing with DCM (1 mL). The combined organic layers were loaded directly onto the column and purified by chromatography on silica gel (4 g cartridge, 0-100% EtOAc/isohexane) to afford 1-(4-fluorophenyl)-6-methyl-5-(6-phenyl-3-(pyrimidin-2-yl)-3-azabicyclo[3.1.0]hexan-1-yl)-1H-indazole Example 185 (7.69 mg, 16 μmol, 61%) as a yellow solid; Rt 2.41 min (Method 9); m/z 462.1 (M+H)+ (ES+). δH (DMSO-d6, 400 MHz) δ 8.37 (d, J=4.8 Hz, 2H), 8.31 (s, 1H), 8.08 (s, 1H), 7.81-7.69 (m, 2H), 7.47-7.32 (m, 3H), 7.11-6.91 (m, 3H), 6.89-6.81 (m, 2H), 6.67 (t, J=4.8 Hz, 1H), 4.58-4.48 (m, 1H), 4.21-4.09 (m, 1H), 3.95 (dd, J=11.2, 4.2 Hz, 1H), 3.51-3.37 (m, 1H), 2.83-2.75 (m, 1H), 2.44-2.39 (m, 1H), 2.24 (s, 3H).

Example 186: (1-(1-(4-fluorophenyl)-6-methyl-1H-indazol-5-yl)-6-(pyridin-2-yl)-3-azabicyclo[3.1.0]hexan-3-yl)(phenyl)methanone Intermediate AJ: 3-benzyl-1-(1-(4-fluorophenyl)-6-methyl-1H-indazol-5-yl)-6-(pyridin-2-yl)-3-azabicyclo[3.1.0]hexane-2,4-dione

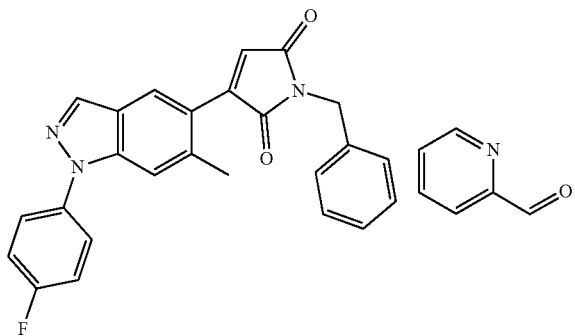
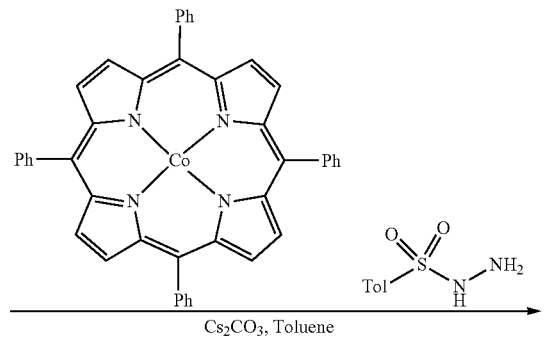
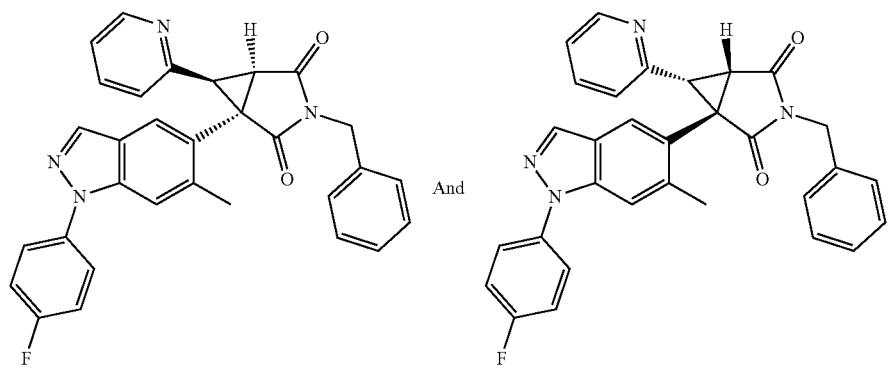

Four identical reactions were set up in parallel. To a microwave vial was added picolinaldehyde (26.0 mg, 23.1 μL, 243 μmol), 4-methylbenzenesulfonohydrazide (54.3 mg, 292 μmol), cesium carbonate (158 mg, 486 μmol), 5,10,15,20-tetraphenyl-21H,23H-porphine cobalt(II) (8.16 mg, 12.2 μmol), 1-benzyl-3-(1-(4-fluorophenyl)-6-methyl-1H-indazol-5-yl)-1H-pyrrole-2,5-dione (100 mg, 243 μmol) and dry toluene (2.00 mL). The vial was purged with nitrogen, sealed, and stirred at 80° C. overnight. The reaction mixtures were combined, concentrated under reduced pressure. EtOAc (10 mL) was added, and the reaction mixture was filtered through a glass fibre filter paper to remove excess inorganics, washing with EtOAc. The filtrate was concentrated under reduced pressure. The crude product was purified by chromatography on silica gel (12 g cartridge, 0-100% EtOAc/isohexane) to afford 3-benzyl-1-(1-(4-fluorophenyl)-6-methyl-1H-indazol-5-yl)-6-(pyridin-2-yl)-3-azabicyclo[3.1.0]hexane-2,4-dione Intermediate AJ (342 mg, 0.67 mmol, 55%) as a brown oil; Rt 2.13 min (Method 7); m/z 503.4 (M+H)$^+$ (ES$^+$).

TABLE 12

The example shown in the table below was prepared by similar methods to those described for Example 110, using Intermediate AJ

| Example | Structure | LC-MS analysis |
|---|---|---|
| 186 | 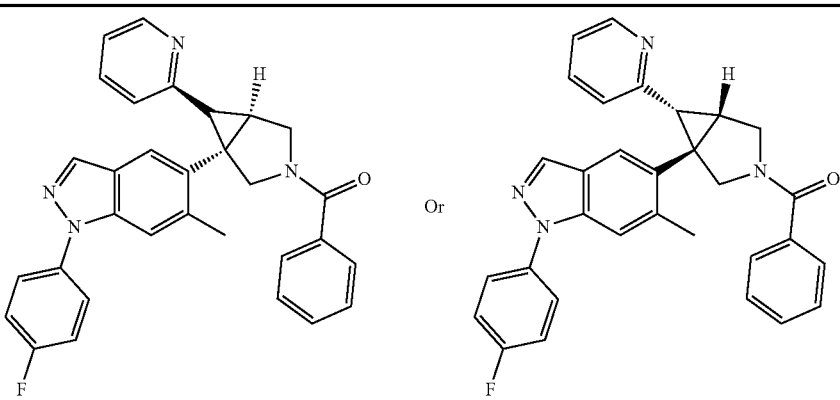 (1-(1-(4-fluorophenyl)-6-methyl-1H-indazol-5-yl)-6-(pyridin-2-yl)-3-azabicyclo[3.1.0]hexan-3-yl)(phenyl)methanone | R$^t$ 1.78 min (Method 7); m/z 489.4 (M + H)$^+$ (ES$^+$) |

VII. Biological Examples

Example 1. GR Binding Assay

Binding of test compounds to the glucocorticoid receptor (GR) is determined using a fluorescence polarisation (FP) assay utilising a recombinant ligand binding domain (LBD) of GR. The test compounds are assessed by their ability to displace a fluorescently tagged ligand and detection of the resulting decrease in fluorescence polarisation. Fluorescence polarisation values are converted to % inhibition using the high (1% DMSO only) and low (1 μM) controls and IC$_{50}$ values are calculated from non-linear regression curves fitted using Dotmatics software.

Example 2. Hep G2 TAT Ki

Glucocorticoid mediated activation of TAT occurs by transactivation of glucocorticoid response elements in the TAT promoter by glucocorticoid receptor-agonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ali et al., J. Med. Chem., 2004, 47, 2441-2452. Dexamethasone induced TAT production with an average EC$_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) CO$_2$/air. The HepG2 cells were counted and adjusted to yield a density of 0.2×10$^6$ cells/ml in RPMI 1640 without phenol red, 10% (v/v) charcoal stripped FBS, 2 mM L-glutamine and seeded at 40,000 cells/well in 200 μl into 96 well, sterile, tissue culture micro titre plates, and incubated at 37° C., 5% CO$_2$ for 24 hours Growth media was removed and replaced with assay media {RPMI 1640 without phenol red, 2 mM L-glutamine+ 10 μM forskolin}. Test compounds were screened against a challenge of 100 nM dexamethasone. Compounds were serially half log diluted in 100% (v/v) dimethylsulphoxide from a 10 mM stock. Then an 8-point half-log dilution curve was generated followed by a 1:100 dilution into assay media to give a 10× final assay [compound]: this resulted in final assay [compound] that ranged 10 to 0.003 μM in 0.1% (v/v) dimethylsulfoxide.

100 nM of dexamethasone was added to the test compounds which were then subsequently incubated for 18-24 hr at 37° C., 5/95 (v/v) $CO_2$/air to allow optimal TAT induction.

HepG2 cells were then lysed with 30 μl of cell lysis buffer containing a protease inhibitor cocktail for 15 minutes at 4° C. 155 μl of substrate mixture was then added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction was terminated by the addition of 15 μl of 10M aqueous potassium hydroxide solution, and the plates incubated for a further 30 minutes at 37° C. The TAT activity product was measured by absorbance at k 340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 13

Activity Data

| Example No. | HepG2 TAT Ki (nM) |
|---|---|
| 1 | 370 |
| 2 | 490 |
| 3 | 290 |
| 4 | 540 |
| 5 | 240 |
| 6 | 44 |
| 7 | 350 |
| 8 | 310 |
| 9 | 130 |
| 10 | 220 |
| 11 | 33 |
| 12 | 170 |
| 13 | 78 |
| 14 | 110 |
| 15 | 330 |
| 16 | 270 |
| 17 | 42 |
| 18 | 44 |
| 19 | 47 |
| 20 | 79 |
| 21 | 37 |
| 22 | 32 |
| 23 | 30 |
| 24 | 32 |
| 25 | 52 |
| 26 | 53 |
| 27 | 78 |
| 28 | 32 |
| 29 | 72 |
| 30 | 32 |
| 31 | 130 |
| 32 | — |
| 33 | 220 |
| 34 | 800 |
| 35 | 160 |
| 36 | 72 |
| 37 | 170 |
| 38 | 97 |
| 39 | 190 |
| 40 | 420 |
| 41 | 110 |
| 42 | 260 |
| 43 | 41 |
| 44 | 370 |
| 45 | 96 |
| 46 | 87 |
| 47 | 270 |
| 48 | 570 |
| 49 | 120 |
| 50 | 680 |
| 51 | 290 |
| 52 | 380 |
| 53 | 110 |
| 54 | 33 |
| 55 | 300 |
| 56 | 38 |
| 57 | 190 |
| 58 | 20 |
| 59 | 360 |
| 60 | 200 |
| 61 | 200 |
| 62 | 38 |
| 63 | 88 |
| 64 | 130 |
| 65 | 430 |
| 66 | 150 |
| 67 | 84 |
| 68 | 90 |
| 69 | 24 |
| 70 | 24 |
| 71 | 15 |
| 72 | 160 |
| 73 | 36 |
| 74 | 15 |
| 75 | 25 |
| 76 | 9.4 |
| 77 | 39 |
| 78 | 25 |
| 79 | 33 |
| 80 | 23 |
| 81 | 30 |
| 82 | 200 |
| 83 | 130 |
| 84 | 50 |
| 85 | 21 |
| 86 | 32 |
| 87 | 20 |
| 88 | 47 |
| 89 | 17 |
| 90 | 14 |
| 91 | 22 |
| 92 | 9.5 |
| 93 | 29 |
| 94 | 31 |
| 95 | — |
| 96 | 110 |
| 97 | 32 |
| 98 | 200 |
| 99 | 28 |
| 100 | 82 |
| 101 | 41 |
| 102 | 26 |
| 103 | 27 |
| 104 | 30 |
| 105 | 14 |
| 106 | 55 |
| 107 | 32 |
| 108 | 16 |
| 109 | 13 |
| 110 | 23 |
| 111 | 52 |
| 112 | 65 |
| 113 | 58 |
| 114 | 26 |
| 115 | 36 |
| 116 | 31 |
| 117 | 34 |
| 118 | 40 |

TABLE 13-continued

Activity Data

| Example No. | HepG2 TAT Ki (nM) |
|---|---|
| 119 | 48 |
| 120 | 52 |
| 121 | 49 |
| 122 | 22 |
| 123 | 27 |
| 124 | 120 |
| 125 | 29 |
| 126 | 34 |
| 127 | 19 |
| 128 | 5.9 |
| 129 | 37 |
| 130 | 5.7 |
| 131 | 240 |
| 132 | 350 |
| 133 | 260 |
| 134 | 55 |
| 135 | 300 |
| 138 | 70 |
| 139 | 45 |
| 140 | 65 |
| 141 | 19 |
| 142 | 15 |
| 143 | 25 |
| 144 | 120 |
| 145 | 48 |
| 146 | 14 |
| 147 | 37 |
| 148 | 9.2 |
| 149 | 13 |
| 150 | 18 |
| 151 | 28 |
| 152 | 20 |
| 153 | 38 |
| 154 | 16 |
| 155 | 19 |
| 156 | 20 |
| 157 | 18 |
| 158 | 12 |
| 159 | 24 |
| 160 | 70 |
| 161 | 61 |
| 162 | 29 |
| 163 | 19 |
| 164 | 7.2 |
| 165 | 84 |
| 166 | 47 |
| 167 | 21 |
| 168 | 39 |
| 169 | 35 |
| 170 | 41 |
| 171 | 36 |
| 172 | 26 |
| 173 | 130 |
| 174 | 39 |
| 175 | 13 |
| 176 | 45 |
| 177 | 23 |
| 178 | 19 |
| 179 | 48 |
| 180 | 600 |
| 181 | 250 |
| 182 | 180 |
| 183 | 37 |
| 184 | 860 |
| 185 | 100 |
| 186 | 630 |

Although the foregoing invention has been described in some detail by way of illustration and Examples for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula I:

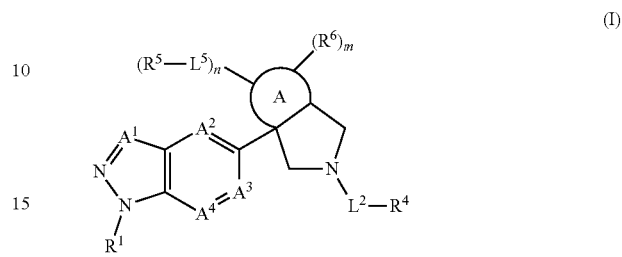

(I)

or a pharmaceutically acceptable salt thereof, wherein $R^1$ is heterocycloalkyl having 3 to 12 ring members and 1 to 4 heteroatoms each N, O or S, phenyl or heteroaryl having 5 to 10 ring members and 1 to 5 heteroatoms each N, O or S, each independently substituted with 0 to 5 $R^{1a}$ groups;

each $R^{1a}$ is independently $C_{1-6}$ alkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 12 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy, $C_{1-6}$ hydroxyalkyl, or —CN;

Ring A is a $C_{3-6}$ cycloalkyl;

$L^2$ is absent, —C(O)—, —C(O)O—, —C(O)N($R^3$)—, —S(O)$_2$— or —S(O)$_2$N($R^3$) —;

$R^3$ is hydrogen or $C_{1-6}$ alkyl;

$R^4$ is $C_{1-6}$ alkyl, $C_{2-6}$ alkenyl, $C_{2-6}$ alkynyl, $C_{2-6}$ alkoxyalkyl, —(CH$_2$CH$_2$O)$_{2-6}$CH$_3$, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 5 $R^{4a}$ groups;

alternatively, $R^3$ and $R^4$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{4a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —OC(O)$R^{4b}$, —OC(O)O$R^{4b}$, —C(O)N($R^{4b}$)($R^{4c}$), —N($R^{4b}$)C(O)$R^{4c}$, —OC(O)N($R^{4b}$)($R^{4c}$), —N($R^{4b}$)C(O)O$R^{4c}$, —S(O)$_2R^{4b}$, —S(O)$_2$N($R^{4b}$)($R^{4c}$), —N($R^{4b}$)S(O)$_2R^{4c}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0, 1 or 2 $C_{1-6}$ alkyl groups;

each $R^{4b}$ and $R^{4c}$ is hydrogen or $C_{1-6}$ alkyl;

each $L^5$ is independently absent or $C_{1-6}$ alkylene;

each $R^5$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OR$^{5a}$, —C(O)R$^{5a}$, —C(O)OR$^{5a}$, —OC(O)R$^{5a}$, —C(O)N(R$^{5a}$)(R$^{5b}$), —N(R$^{5a}$)C(O)R$^{5b}$, —OC(O)N(R$^{5a}$)(R$^{5b}$), —N(R$^{5a}$)C(O)OR$^{5b}$, —S(O)$_2$R$^{5a}$, —S(O)$_2$N(R$^{5a}$)(R$^{5b}$), —N(R$^{5a}$)S(O)$_2$R$^{5b}$, $C_{3-8}$ cycloalkyl, heterocycloalkyl, $C_{6-12}$ aryl, or heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is independently substituted with 0 to 4 $R^{5c}$ groups;

each $R^{5a}$ and $R^{5b}$ is independently hydrogen, $C_{1-6}$ alkyl, $C_{2-6}$ alkenyl, $C_{2-6}$ alkynyl, $C_{2-6}$ alkoxyalkyl, hydroxy, $C_{1-6}$ hydroxyalkyl, $C_{1-6}$ haloalkyl, $C_{1-6}$ haloalkoxy, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each cycloalkyl, heterocycloalkyl, aryl and heteroaryl is substituted with 0 to 4 $R^{5d}$ groups;

alternatively, $R^{5a}$ and $R^{5b}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5c}$ is independently $C_{1-6}$ alkyl, $C_{2-6}$ alkenyl, $C_{2-6}$ alkynyl, $C_{1-6}$ alkoxy, $C_{2-6}$ alkoxyalkyl, hydroxy, $C_{1-6}$ hydroxyalkyl, halogen, $C_{1-6}$ haloalkyl, $C_{1-6}$ haloalkoxy, —CN, oxo, —OH, —C(O)R$^{5c1}$, —C(O)OR$^{5c1}$, —OC(O)R$^{5c1}$, —OC(O)OR$^{5c1}$, —C(O)N(R$^{5c1}$)(R$^{5c2}$), —N(R$^{5c1}$)C(O)R$^{5c2}$, —OC(O)N(R$^{5c1}$)(R$^{5c2}$), —N(R$^{5c1}$)C(O)OR$^{5c2}$, —S(O)$_2$R$^{5c1}$, —S(O)$_2$N(R$^{5c1}$)(R$^{5c2}$), —N(R$^{5c1}$)S(O)$_2$R$^{5c2}$, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

each $R^{5c1}$ and $R^{5c2}$ is independently hydrogen, $C_{1-6}$ alkyl, $C_{2-6}$ alkenyl, $C_{2-6}$ alkynyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl independently has 3 to 12 ring members and 1 to 3 heteroatoms each independently N, O or S, wherein each heteroaryl independently has 5 to 10 ring members and 1 to 4 heteroatoms each independently N, O or S, and wherein each heterocycloalkyl and heteroaryl is substituted with 0, 1 or 2 $C_{1-6}$ alkyl groups;

alternatively, $R^{5c1}$ and $R^{5c2}$ are combined with the atoms to which they are attached to form a heterocycloalkyl having 3 to 12 ring members and 1 to 3 additional heteroatoms each independently N, O or S, wherein the heterocycloalkyl is substituted with 0, 1 or 2 $C_{1-6}$ alkyl groups;

each $R^{5d}$ is independently $C_{1-6}$ alkyl or halogen;

each $R^6$ is independently $C_{1-6}$ alkoxy, hydroxy, $C_{1-6}$ hydroxyalkyl, halogen, $C_{1-6}$ haloalkyl, or $C_{1-6}$ haloalkoxy;

subscript m is 0, 1, 2, 3, 4 or 5; and subscript n is 1 or 2.

2. The compound of claim 1, or a pharmaceutically acceptable salt thereof, wherein $R^1$ is

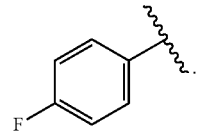

3. The compound of claim 1, or a pharmaceutically acceptable salt thereof, wherein $A^1$, $A^2$ and $A^4$ are each =CH—; and $A^3$ is =CH— or =C(Me)-.

4. The compound of claim 1, or a pharmaceutically acceptable salt thereof, having the structure of Formula Ib:

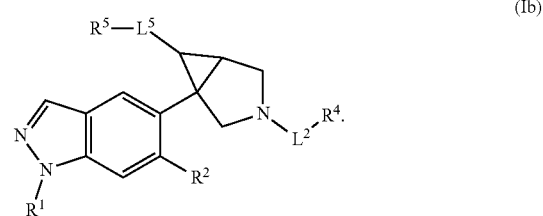

(Ib)

5. The compound of claim 1, or a pharmaceutically acceptable salt thereof, having the structure of Formula Ib-1:

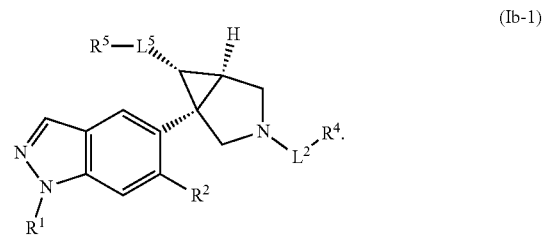

(Ib-1)

6. The compound of claim 1, or a pharmaceutically acceptable salt thereof, having the structure of Formula Ib-2:

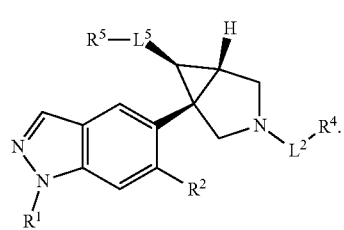
(Ib-2)
7. The compound of claim 1, or a pharmaceutically acceptable salt thereof, wherein L² is —C(O)—.
8. The compound of claim 1, or a pharmaceutically acceptable salt thereof, wherein
R⁴ is methyl, ethyl, iso-propyl, iso-butyl, t-butyl, methoxymethyl, methoxyethyl, —(CH₂CH₂O)₂CH₃,
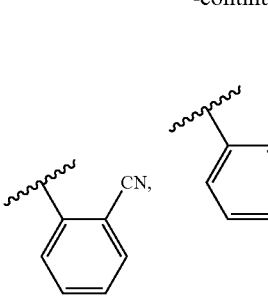
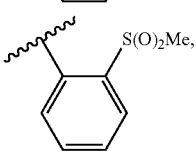
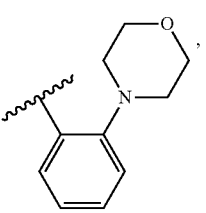
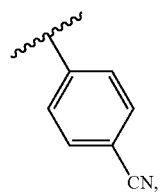
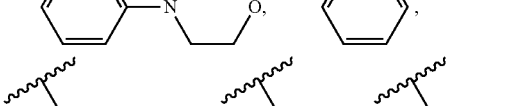
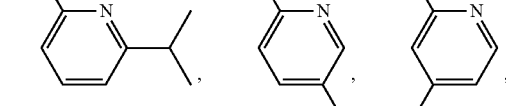
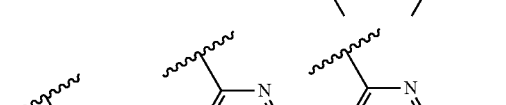
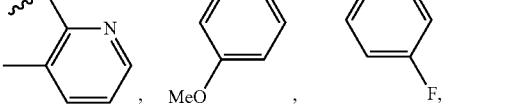
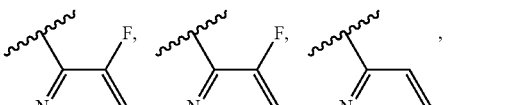
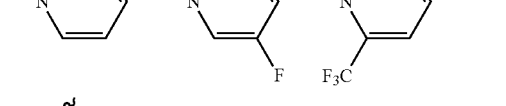
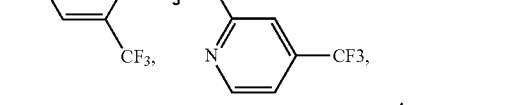
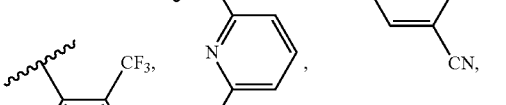
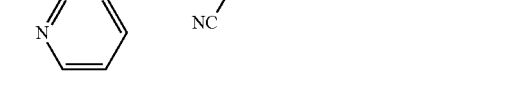

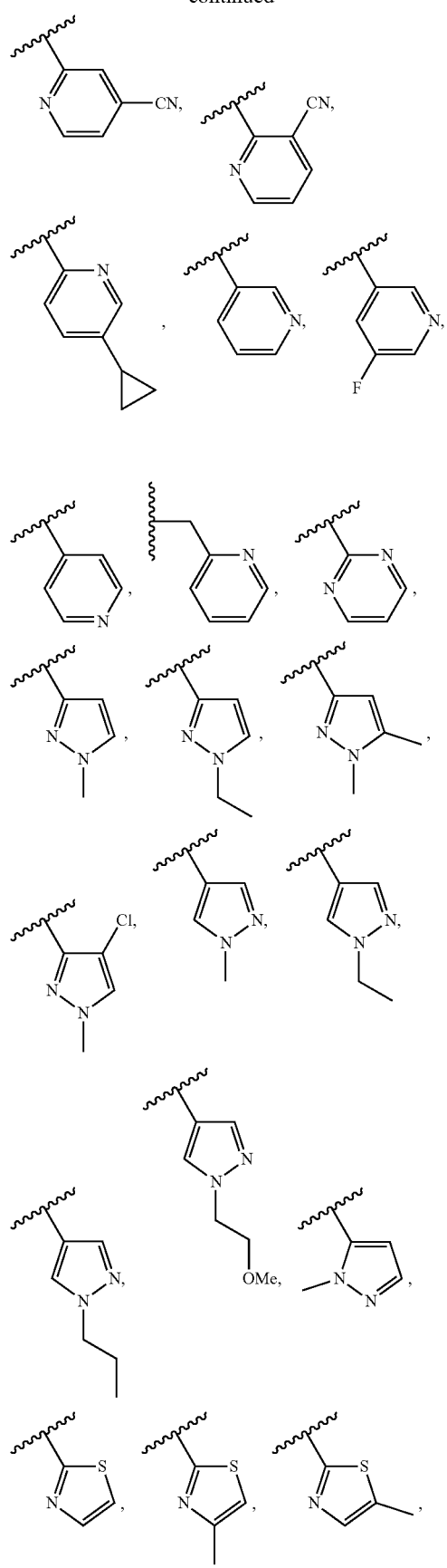
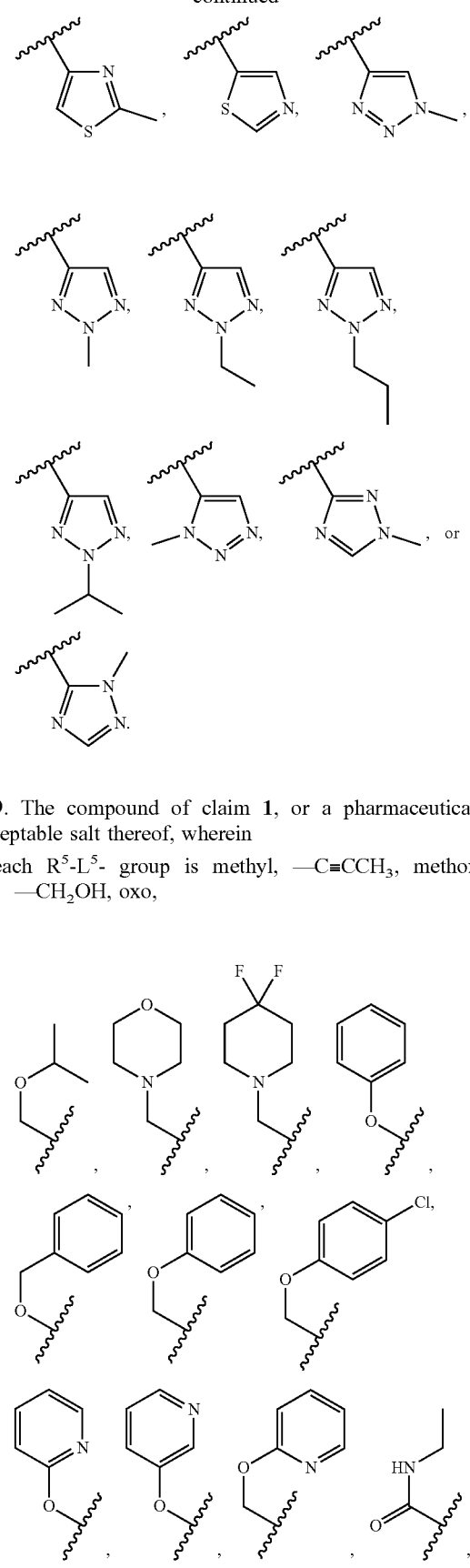
9. The compound of claim 1, or a pharmaceutically acceptable salt thereof, wherein
each $R^5$-$L^5$- group is methyl, —C≡CCH$_3$, methoxy, —CH$_2$OH, oxo, 10. The compound of claim 1, or a pharmaceutically acceptable salt thereof, wherein
R¹ is $A^1$, $A^2$ and $A^4$ are each =CH—;
$A^3$ is =CH— or —C(Me)—;
Ring A is a $C_3$ cycloalkyl or a $C_5$ cycloalkyl;
$L^2$ is absent, —C(O)—, —C(O)O—, —S(O)$_2$— or —S(O)$_2$N($R^3$)—;
$R^3$ is hydrogen or methyl;
$R^4$ is methyl, ethyl, iso-propyl, iso-butyl, t-butyl, methoxymethyl, methoxyethyl, CH$_2$(CH$_2$OCH$_2$)$_2$H,

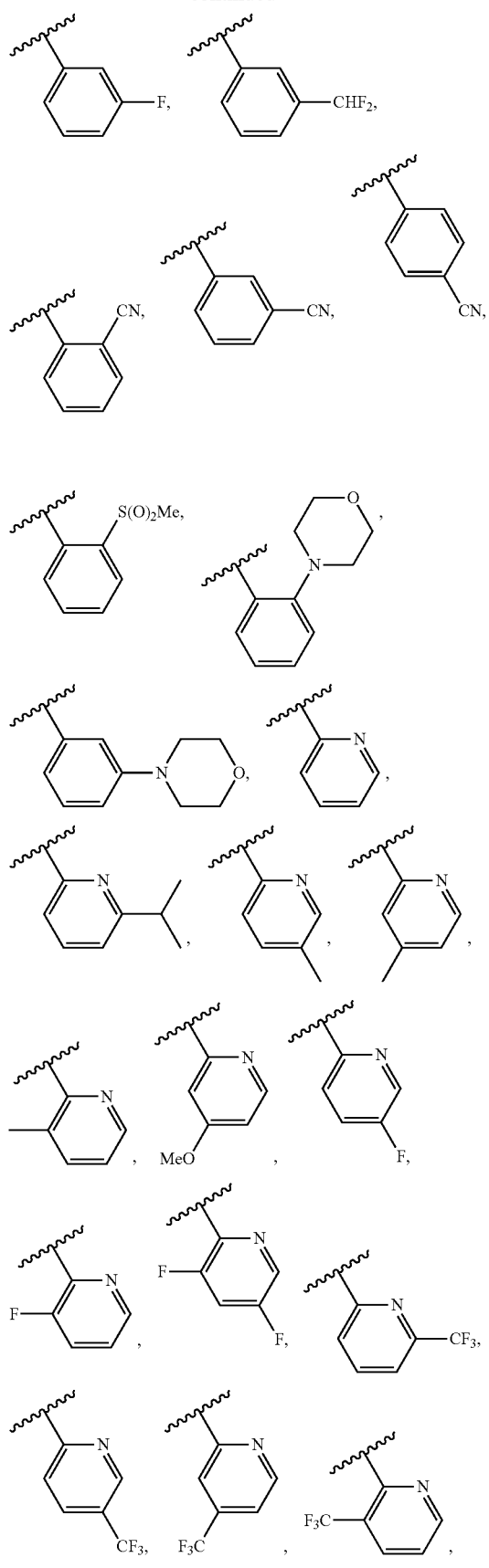
-continued
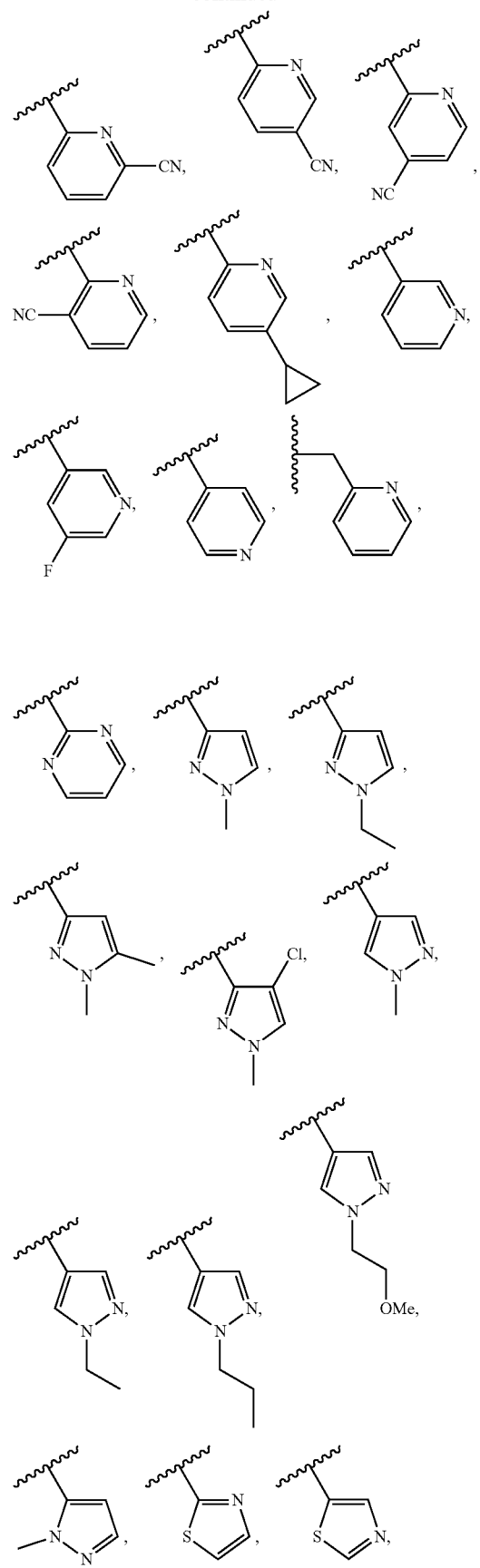
-continued

421
-continued
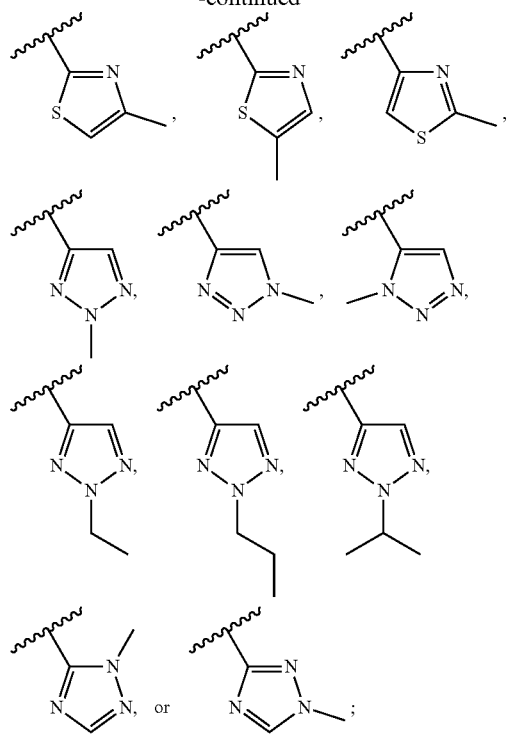
each R⁵-L⁵- group is methyl, —C≡CCH₃, methoxy, —CH₂OH, oxo,
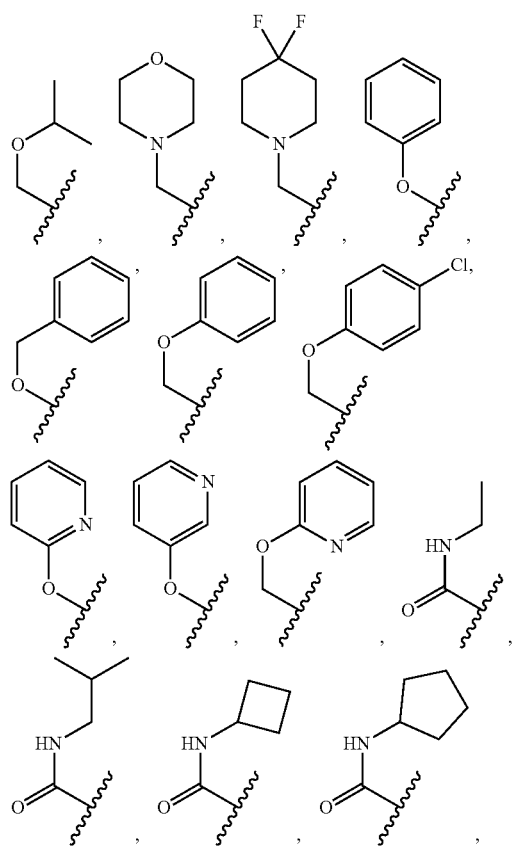
422
-continued
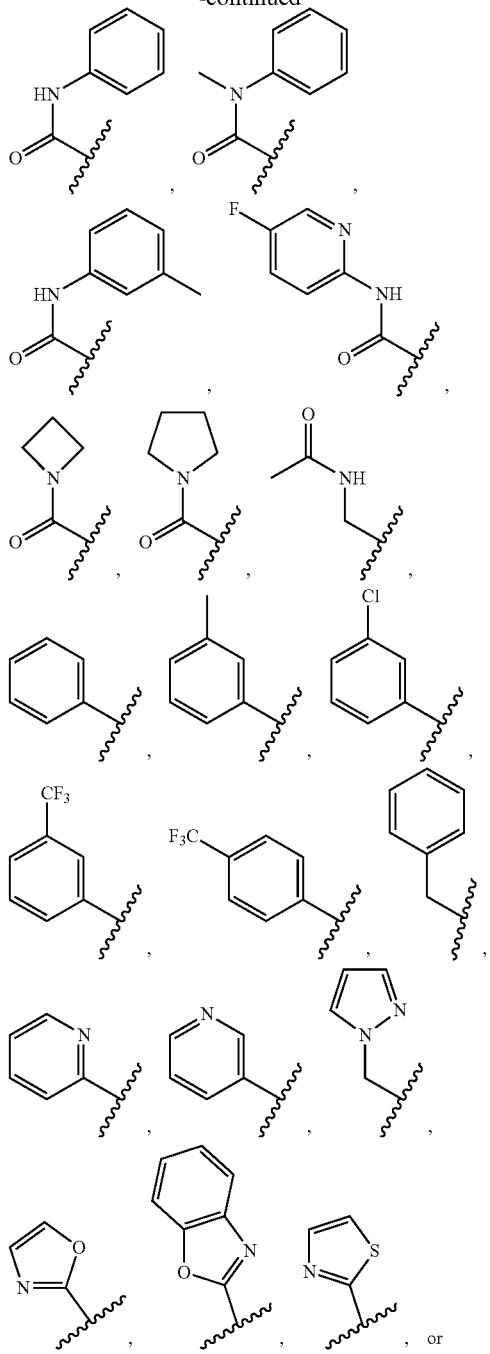
each $R^6$ is independently —OMe, —OEt, hydroxy, or F;
subscript m is 0 or 1; and
subscript n is 1.
11. The compound of claim 1, or a pharmaceutically acceptable salt thereof, wherein
$R^4$ is methyl, ethyl, iso-propyl, iso-butyl, methoxymethyl, methoxyethyl, $CH_2(CH_2OCH_2)_2H$,

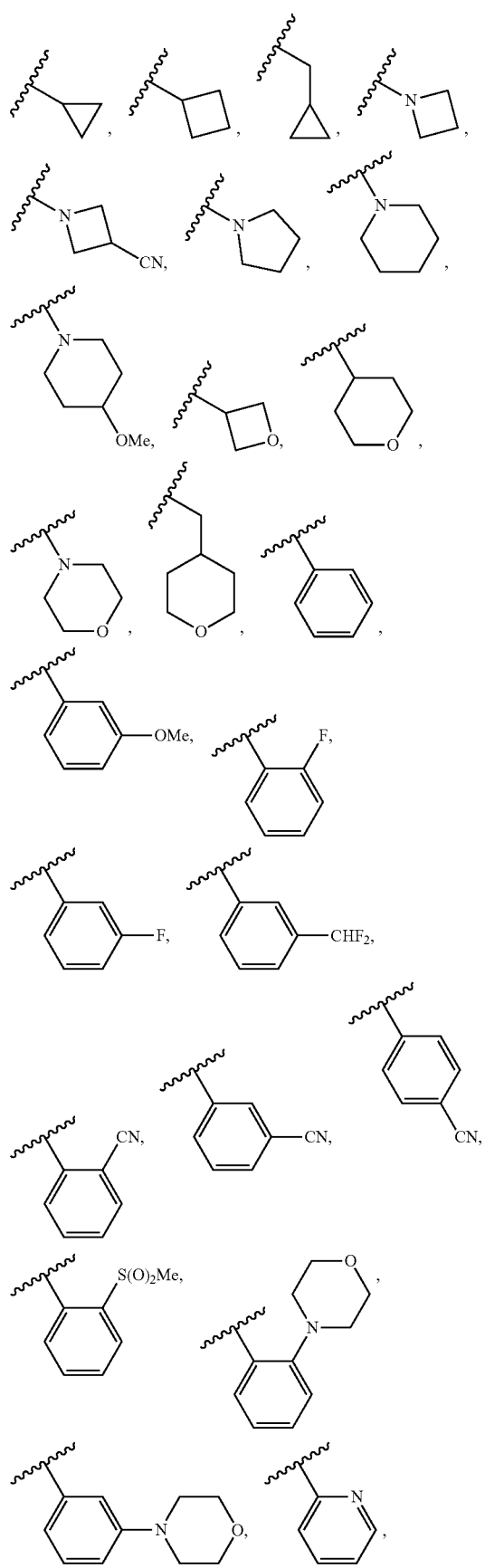
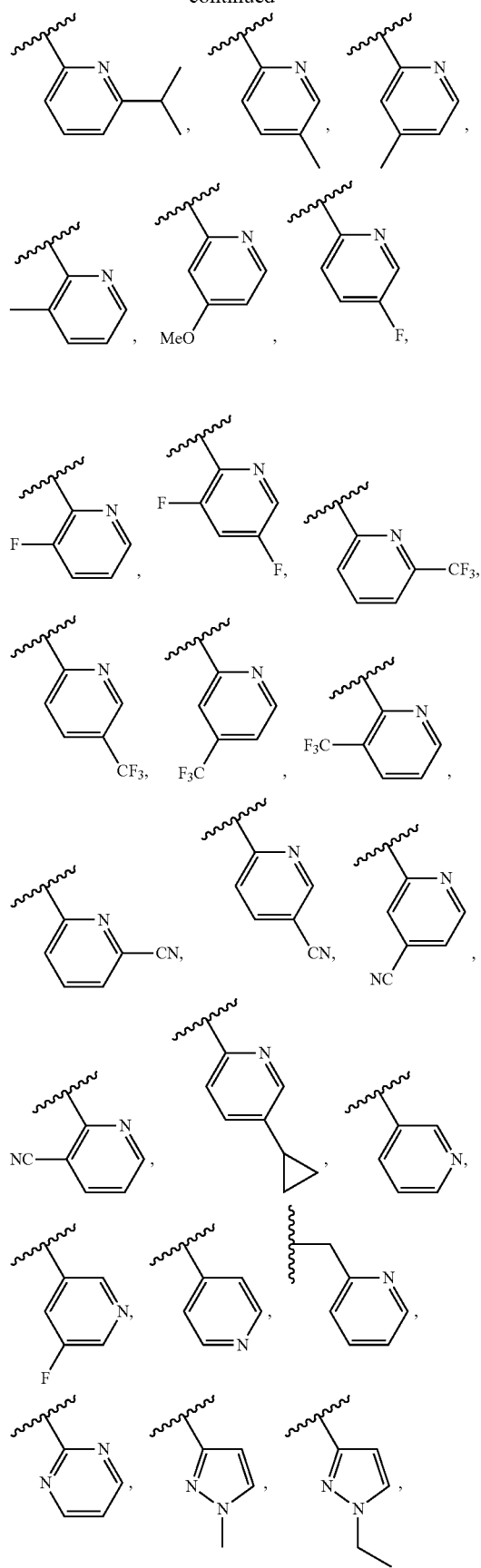

425
-continued
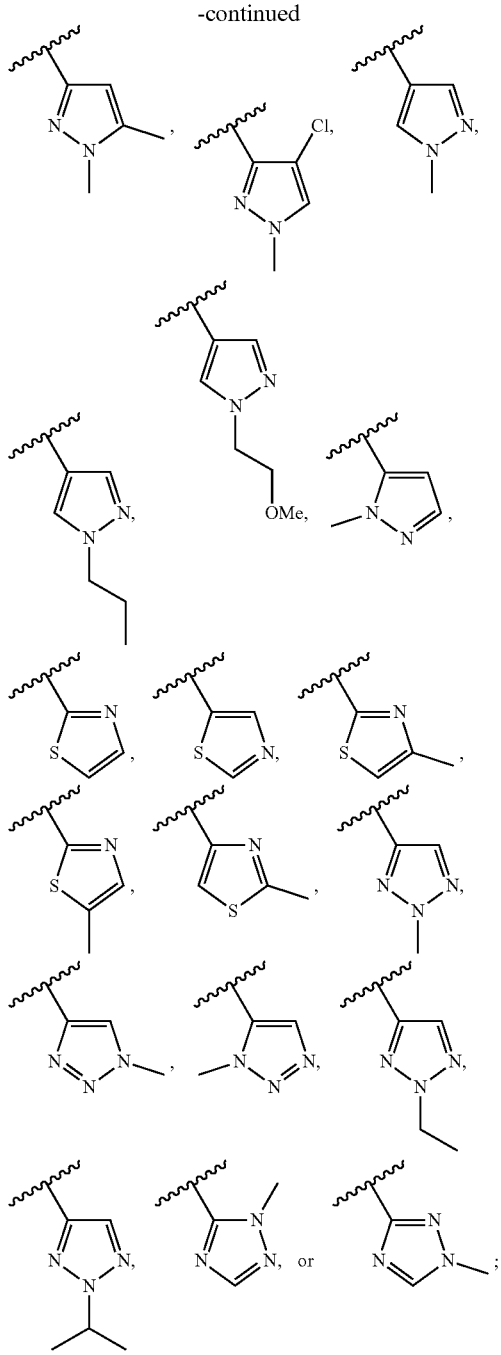
and
each R⁵-L⁵- group is methyl, —CH₂OH,
426
-continued
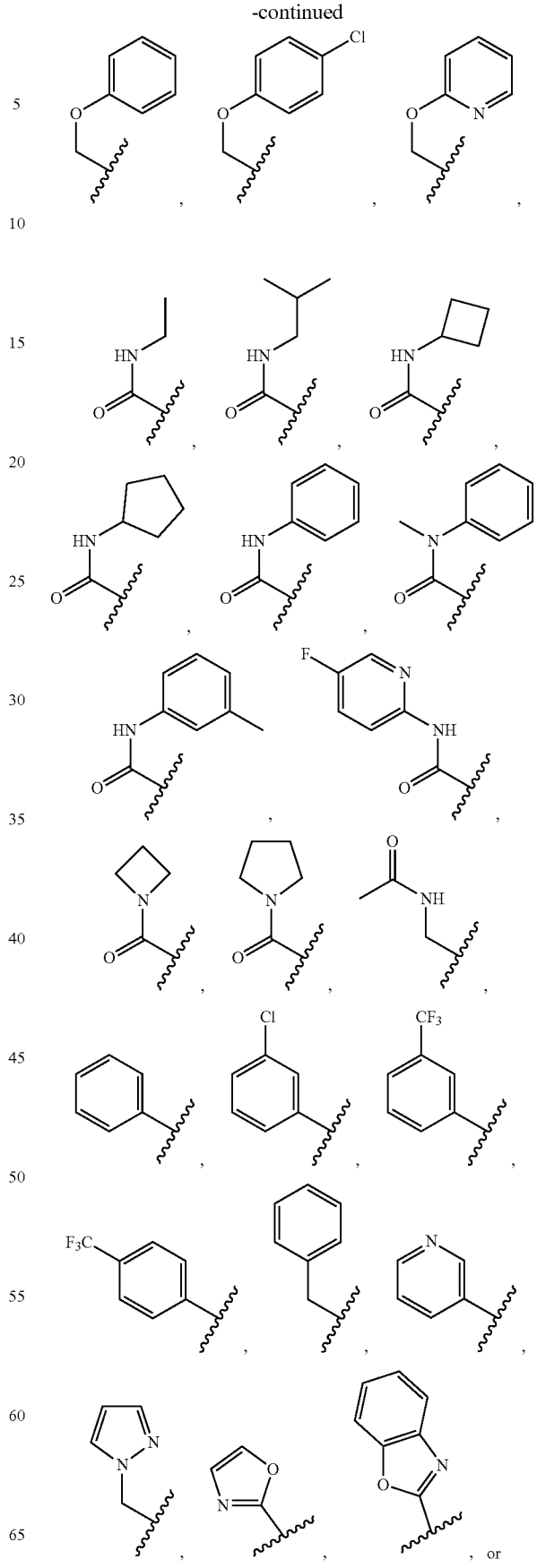

-continued

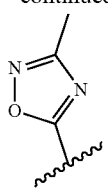

12. The compound of claim 1, or a pharmaceutically acceptable salt thereof, having the structure of Formula Id-1 or Id-2:

(Id-1)

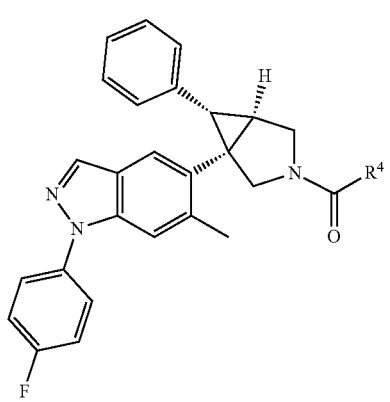

or (Id-2)

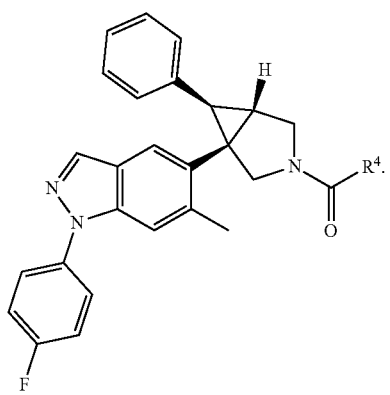

13. The compound of claim 1, or a pharmaceutically acceptable salt thereof, wherein
- $R^4$ is $C_{6-12}$ aryl, or heteroaryl having 5 to 6 ring members and 1 to 4 heteroatoms each independently N, O or S, and wherein aryl and heteroaryl are independently substituted with 0 to 3 $R^{4a}$ groups;
- each $R^{4a}$ is independently $C_{1-3}$ alkyl, $C_{1-3}$ alkoxy, halogen, $C_{1-3}$ haloalkyl, —CN, —S(O)$_2$R$^{4b}$, $C_{3-6}$ cycloalkyl, and heterocycloalkyl, wherein each heterocycloalkyl independently has 5 to 6 ring members and 1 to 2 heteroatoms each independently N, O or S; and
- each $R^{4b}$ is $C_{1-3}$ alkyl.

14. The compound of claim 1, or a pharmaceutically acceptable salt thereof, wherein
$R^4$ is

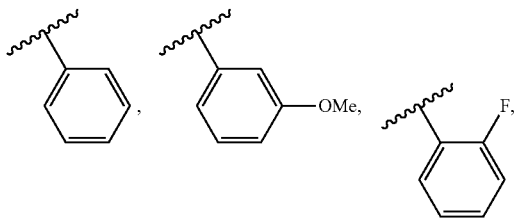

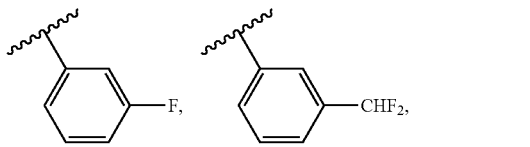

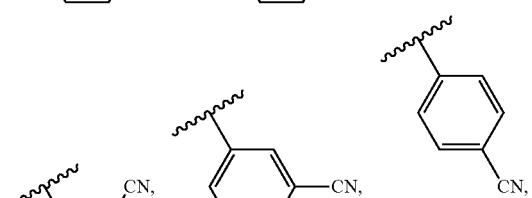

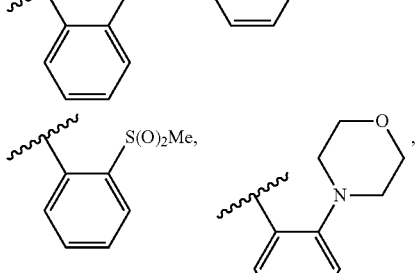

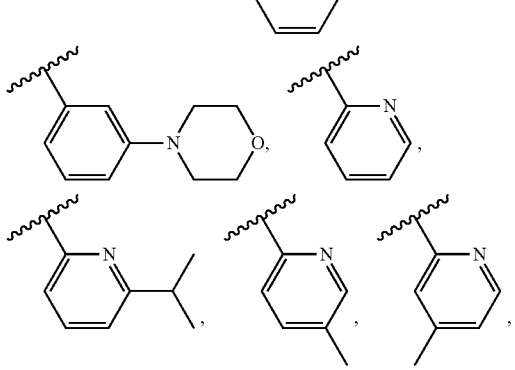

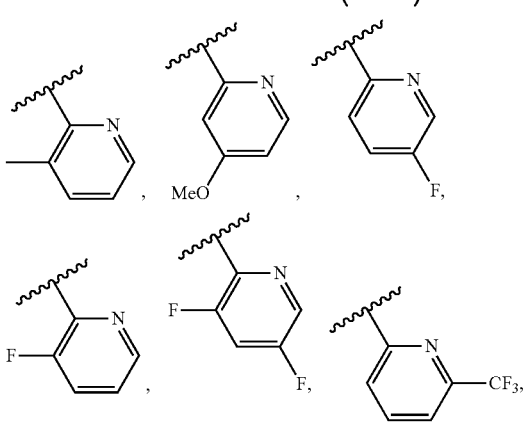

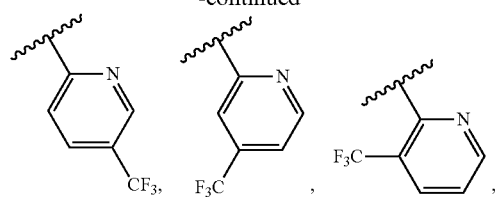
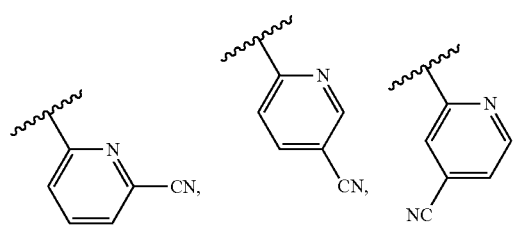
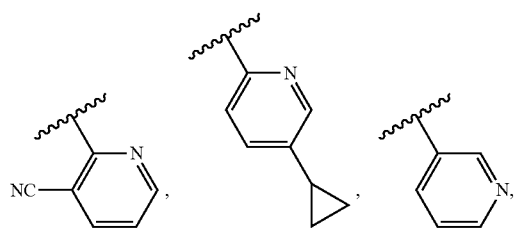
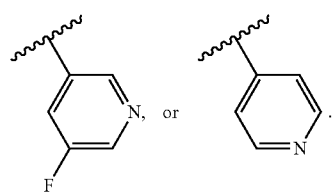
15. The compound of claim 1, or a pharmaceutically acceptable salt thereof, having the structure of
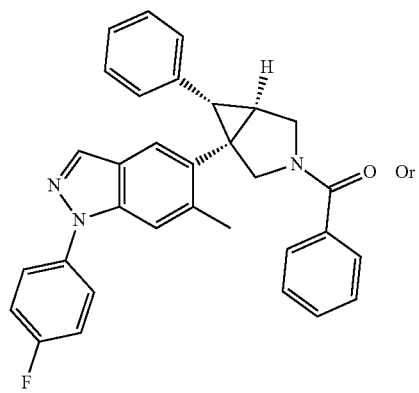
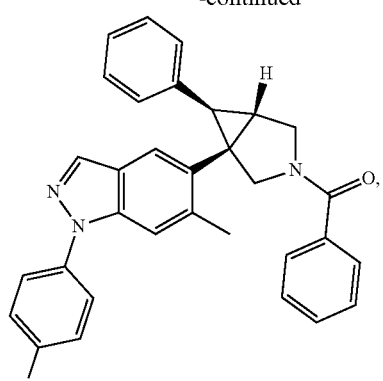
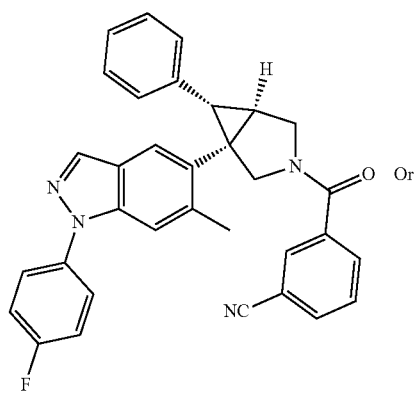
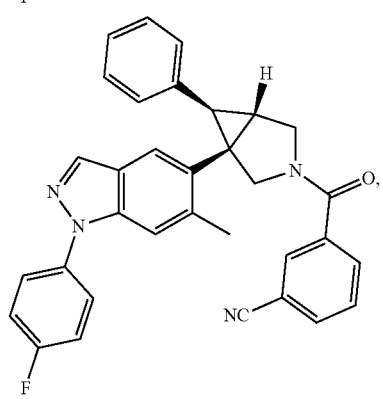
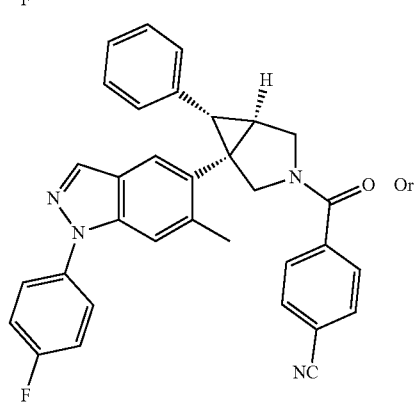

431
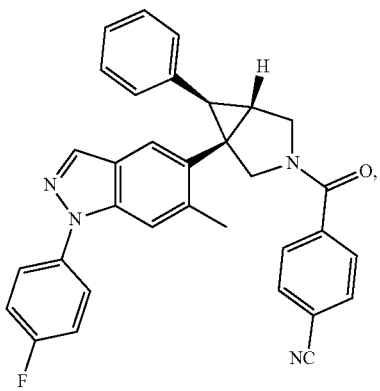
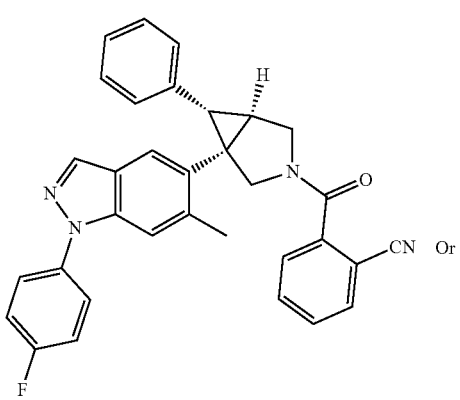 Or
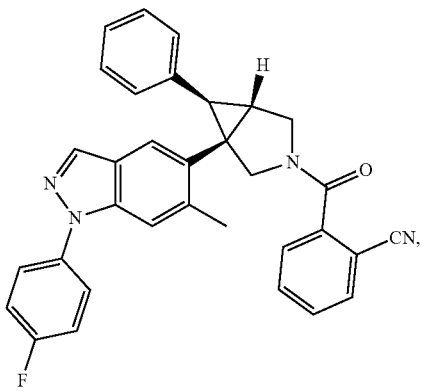,
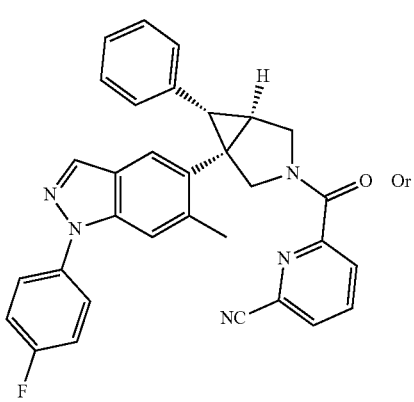 Or
432
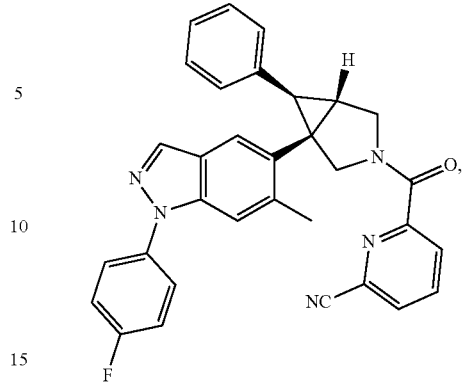
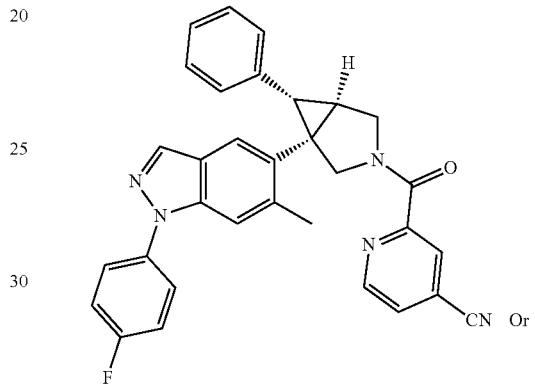 Or
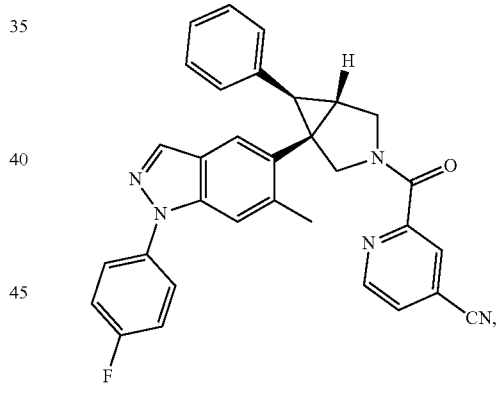,
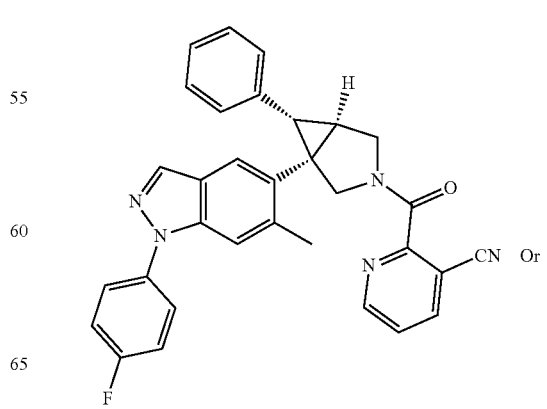 Or 433
-continued
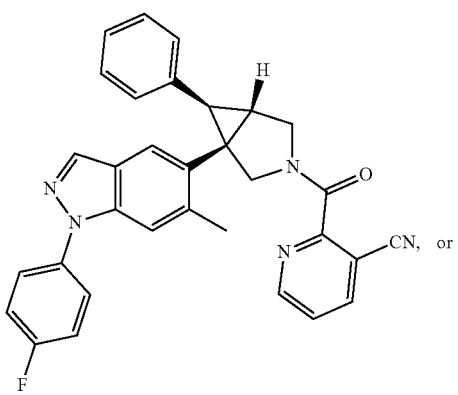
434
-continued
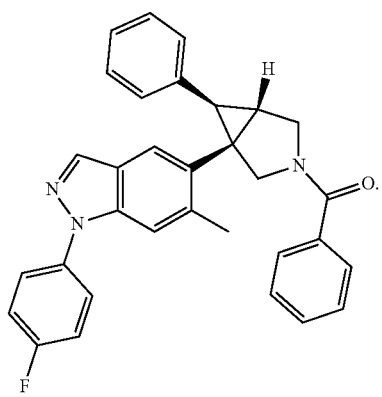
17. The compound of claim 1, or a pharmaceutically acceptable salt thereof, having the structure:
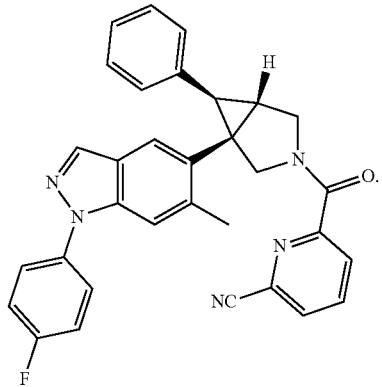
16. The compound of claim 1, or a pharmaceutically acceptable salt thereof, having the structure:
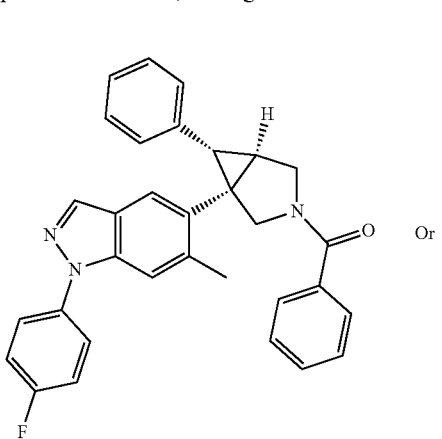

18. The compound of claim 1, or a pharmaceutically acceptable salt thereof, having the structure:

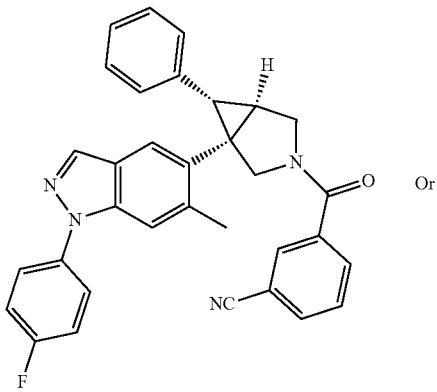

Or

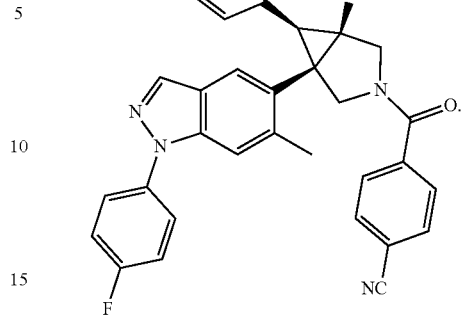

19. The compound of claim 1, or a pharmaceutically acceptable salt thereof, having the structure:

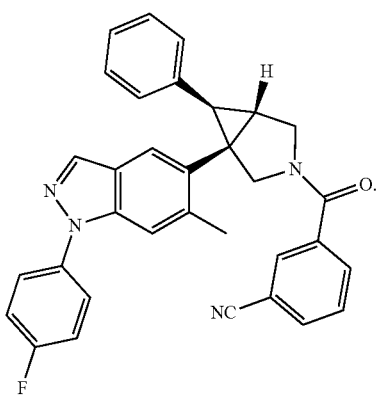

Or

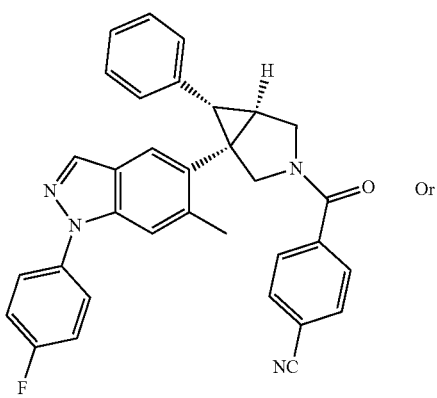

20. The compound of claim 1, or a pharmaceutically acceptable salt thereof, having the structure:

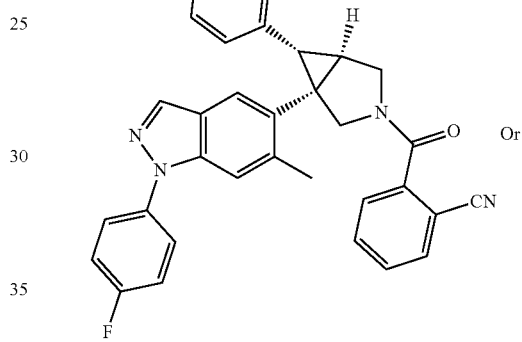

Or

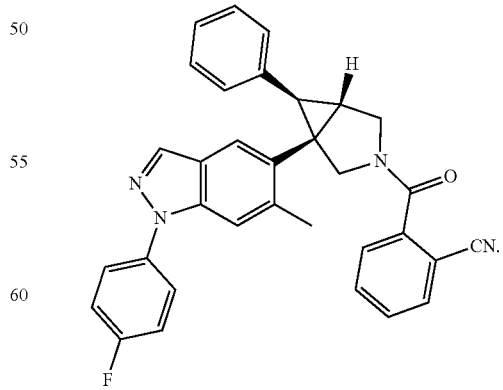

21. The compound of claim 1, or a pharmaceutically acceptable salt thereof, having the structure:

23. The compound of claim 1, or a pharmaceutically acceptable salt thereof, having the structure:

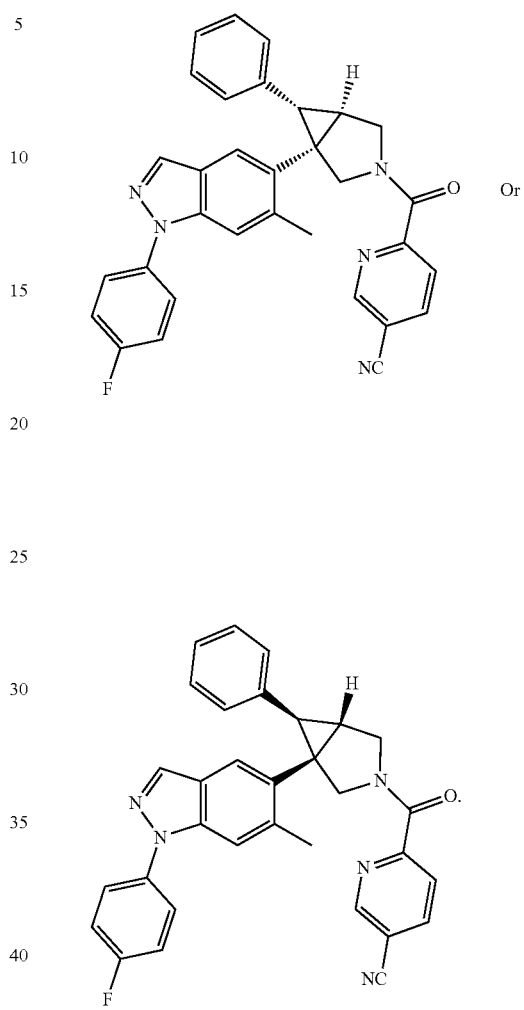

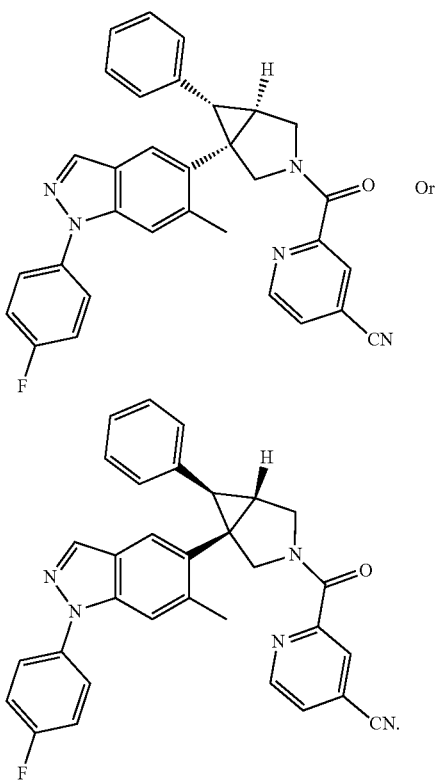

22. The compound of claim 1, or a pharmaceutically acceptable salt thereof, having the structure:

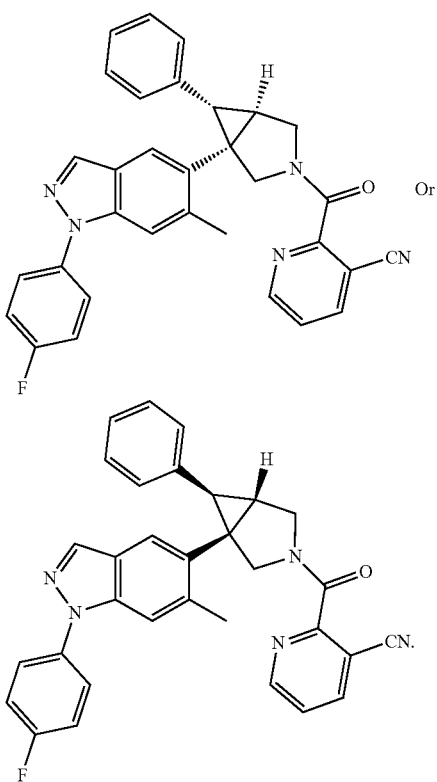

24. A pharmaceutical composition comprising a compound of claim 1, or a pharmaceutically acceptable salt thereof, and a pharmaceutically acceptable excipient.

25. A method of treating a disorder or condition through modulating a glucocorticoid receptor, the method comprising administering to a subject in need of such treatment, a therapeutically effective amount of a compound of claim 1, or a pharmaceutically acceptable salt thereof, thereby treating the disorder or condition.

26. A method of treating a disorder or condition through antagonizing a glucocorticoid receptor, the method comprising administering to a subject in need of such treatment, an effective amount of the compound of claim 1, or a pharmaceutically acceptable salt thereof.

27. The method of claim 25, wherein the disorder or condition is selected from the group consisting of Alzheimer's disease, amyotrophic lateral sclerosis (ALS), antipsychotic induced weight gain, cancer, Cushing Disease, Cushing's Syndrome, major psychotic depression, nonalcoholic steatohepatitis, and obesity.

* * * * *